US011548872B2

(12) United States Patent
KC et al.

(10) Patent No.: US 11,548,872 B2
(45) Date of Patent: Jan. 10, 2023

(54) ISOQUINOLIN-3-YL CARBOXAMIDES AND PREPARATION AND USE THEREOF

(71) Applicant: BioSplice Therapeutics, Inc., San Diego, CA (US)

(72) Inventors: Sunil Kumar KC, San Diego, CA (US); Chi Ching Mak, San Diego, CA (US); Brian Walter Eastman, San Diego, CA (US); Jianguo Cao, San Diego, CA (US); Venkataiah Bollu, San Diego, CA (US); Gopi Kumar Mittapalli, San Diego, CA (US); Chandramouli Chiruta, San Diego, CA (US)

(73) Assignee: BioSplice Therapeutics, Inc., San Diego, CA (US)

( * ) Notice: Subject to any disclaimer, the term of this patent is extended or adjusted under 35 U.S.C. 154(b) by 0 days.

(21) Appl. No.: 17/155,577

(22) Filed: Jan. 22, 2021

(65) Prior Publication Data
US 2022/0332698 A1    Oct. 20, 2022

Related U.S. Application Data

(63) Continuation of application No. 16/703,321, filed on Dec. 4, 2019, now Pat. No. 10,947,217, which is a continuation of application No. 16/130,842, filed on Sep. 13, 2018, now Pat. No. 10,544,128, which is a continuation of application No. 15/499,013, filed on Apr. 27, 2017, now Pat. No. 10,106,527.

(60) Provisional application No. 62/328,255, filed on Apr. 27, 2016.

(51) Int. Cl.
| | |
|---|---|
| A61K 31/4725 | (2006.01) |
| C07D 401/14 | (2006.01) |
| C07D 471/10 | (2006.01) |
| C07D 417/04 | (2006.01) |
| C07D 413/14 | (2006.01) |
| C07D 405/14 | (2006.01) |
| C07D 409/14 | (2006.01) |
| C07D 487/08 | (2006.01) |
| C07D 401/04 | (2006.01) |
| C07D 491/048 | (2006.01) |
| C07D 417/14 | (2006.01) |
| C07D 487/04 | (2006.01) |
| C07D 471/08 | (2006.01) |

(52) U.S. Cl.
CPC ......... *C07D 401/14* (2013.01); *C07D 401/04* (2013.01); *C07D 405/14* (2013.01); *C07D 409/14* (2013.01); *C07D 413/14* (2013.01); *C07D 417/04* (2013.01); *C07D 417/14* (2013.01); *C07D 471/08* (2013.01); *C07D 471/10* (2013.01); *C07D 487/04* (2013.01); *C07D 487/08* (2013.01); *C07D 491/048* (2013.01)

(58) Field of Classification Search
CPC ...... A61K 31/4725; A61P 19/08; A61P 43/00; A61P 19/00; A61P 19/02
USPC ....................................................... 514/310
See application file for complete search history.

(56) References Cited

U.S. PATENT DOCUMENTS

| | | | |
|---|---|---|---|
| 4,164,559 | A | 8/1979 | Miyata et al. |
| 4,474,752 | A | 10/1984 | Haslam et al. |
| 6,093,730 | A | 7/2000 | Weidmann et al. |
| 6,120,484 | A | 9/2000 | Silverstein |
| 6,377,849 | B1 | 4/2002 | Lenarz et al. |
| 6,440,102 | B1 | 8/2002 | Arenberg et al. |
| 6,648,873 | B2 | 11/2003 | Arenberg et al. |
| 6,911,211 | B2 | 6/2005 | Eini et al. |
| 7,998,878 | B2 | 8/2011 | Levy et al. |
| 7,998,978 | B2 | 8/2011 | Huang et al. |
| 8,088,793 | B2 | 1/2012 | Qian et al. |
| 8,697,887 | B2 | 4/2014 | Hood et al. |
| 9,090,613 | B2 | 7/2015 | Hood et al. |
| 9,221,793 | B2 | 12/2015 | Hood et al. |
| 9,557,993 | B2 | 1/2017 | Sanghai et al. |
| 9,745,271 | B2 | 8/2017 | Hood et al. |
| 9,951,048 | B1 | 4/2018 | KC et al. |
| 10,947,217 | B2 | 3/2021 | KC et al. |
| 11,174,244 | B2 | 11/2021 | KC et al. |
| 2006/0264897 | A1 | 11/2006 | Lobl |
| 2007/0142428 | A1 | 6/2007 | Seiler |

(Continued)

FOREIGN PATENT DOCUMENTS

| | | |
|---|---|---|
| EA | 021225 | 5/2015 |
| JP | H 11302257 | 11/1999 |

(Continued)

OTHER PUBLICATIONS

U.S. Appl. No. 15/884,112, filed Jan. 30, 2018, Kumar KC et al.

(Continued)

*Primary Examiner* — Charanjit Aulakh
(74) *Attorney, Agent, or Firm* — Fish & Richardson P.C.

(57) ABSTRACT

Isoquinoline compounds for treating various diseases and pathologies are disclosed. More particularly, the present invention concerns the use of an isoquinoline compound or analogs thereof, in the treatment of disorders characterized by the activation of Wnt pathway signaling (e.g., cancer, abnormal cellular proliferation, angiogenesis, fibrotic disorders, bone or cartilage diseases, and osteoarthritis), the modulation of cellular events mediated by Wnt pathway signaling, as well as genetic diseases and neurological conditions/disorders/diseases due to mutations or dysregulation of the Wnt pathway and/or of one or more of Wnt signaling components. Also provided are methods for treating Wnt-related disease states.

37 Claims, No Drawings

(56) References Cited

U.S. PATENT DOCUMENTS

| | | |
|---|---|---|
| 2011/0190290 A1 | 8/2011 | Hood et al. |
| 2012/0035194 A1 | 2/2012 | Huang et al. |
| 2013/0096119 A1 | 4/2013 | Bur et al. |
| 2014/0088076 A1 | 3/2014 | Lyssikatos et al. |
| 2017/0313681 A1 | 11/2017 | KC et al. |
| 2017/0313682 A1 | 11/2017 | KC et al. |
| 2018/0155323 A1 | 6/2018 | KC et al. |
| 2020/0299263 A1 | 9/2020 | KC et al. |
| 2022/0062240 A1 | 3/2022 | Tam et al. |

FOREIGN PATENT DOCUMENTS

| | | |
|---|---|---|
| JP | 2006-525976 | 11/2006 |
| JP | 2009-535393 | 10/2009 |
| JP | 2010-536752 | 12/2010 |
| JP | 2013-501792 | 1/2013 |
| JP | 2014-502601 | 2/2014 |
| JP | 2014-526510 | 10/2014 |
| WO | WO 1987/005297 | 9/1987 |
| WO | WO 2001/053268 | 7/2001 |
| WO | WO 2005/009997 | 2/2005 |
| WO | WO 2005/012256 | 2/2005 |
| WO | WO 2007/125405 | 11/2007 |
| WO | WO 2009/085226 | 7/2009 |
| WO | WO 2011/121555 | 10/2011 |
| WO | WO 2013/169793 | 11/2013 |
| WO | WO 2016/046530 | 3/2016 |
| WO | WO 2017/189823 | 11/2017 |
| WO | WO 2018/064545 | 4/2018 |
| WO | WO 2020/150545 | 7/2020 |

OTHER PUBLICATIONS

Bharath Rao et al., "Evaluation of Myofibroblasts by Expression of Alpha Smooth Muscle Actin: A Marker in Fibrosis, Dysplasia and Carcinoma," Journal of Clinical and Diagnostic Research, Apr. 2014, 4(4):ZC14-ZC17.

Bollong et al., "Small molecule-mediated inhibition of myofibroblast transdifferentiation for the treatment of fibrosis," PNAS, May 2017, 114(18):4679-4684.

Carpino et al., "Alpha-SMA expression in hepatic stellate cells and quantitative analysis of hepatic fibrosis in cirrhosis and in recurrent chronic hepatitis after liver transplantation," Digestive and Liver Disease, May 2005, 37(5):349-356.

Chou et al., "Quantitative analysis of dose-effect relationships: the combined effects of multiple drugs or enzyme inhibitors," Advances in enzyme regulation, Jan. 1, 1984, 22:27-55.

Cisternas et al., "Role of Wnt Signaling in Tissue Fibrosis, Lessons from Skeletal Muscle and Kidney," Current Molecular Medicine, 2014, 14(4):510-522.

Clevers et al., "Wnt/β-catenin signaling and disease," Cell, Jun. 2012, 149(6):1192-1205.

Datta et al., "Novel therapeutic approaches for pulmonary fibrosis," Br J Pharmacol., 163(1):141-172, May 2011.

Extended European Search Report in European Appln. No. 21159576.4, dated Aug. 16, 2021, 8 pages.

Guo et al., "Wnt/β-Catenin Signaling: a Promising New Target for Fibrosis Diseases," Physiol. Res., 2012, 61:337-346.

He et al., "Synthesis and SAR of novel quinazolines as potent and brain-penetrant c-jun N-terminal kinase (JNK) Inhibitors," Bioorganic & Medicinal Chemistiy Letters, 2011, 21(6), 1719-1723.

Ionescu et al., "DYRK1A kinase inhibitors with emphasis on cancer," Mid-Reviews in Medicinal Chemistiy, Nov. 2012, 12(13):1315-1329.

Kim et al., "Blockade of the Wnt/B-Catenin Pathway Attenuates Bleomycin-Induced Pulmonary Fibrosis," Tohoku J. Exp, Med., 2011, 223:45-54.

King et al., "BUILD-3: a randomized, controlled trial of bosentan in idiopathic pulmonary fibrosis," Am J Respir Crit Care Med., 184(1):92-99, Epub Apr. 2011.

Leyns et al., "Frzb-1 is a Secreted Antagonist of Wnt Signaling Expressed in the Spemann Organizer," Cell, Mar. 21, 1997, 88(6):747-756.

Lin et al., "The Effects and Possible Mechanisms of Puerarin to Treat Uterine Fibrosis Induced by Ischemia-Reperfusion Injury in Rats," Medical Science monitor, 2017, 23:3404-3411.

Liu, et.al., "Fibrotic lung fibroblasts show blunted inhibition by cAMP due to deficient cAMP response element-binding protein phosphorylation," J Pharmacol Exp Ther., 315(2):678-687, Epub Aug. 3, 2005.

Non-Final Office Action for U.S. Appl. No. 15/884,112, dated Mar. 8, 2018, 7 pages.

Non-Final Office Action for U.S. Appl. No. 15/498,990, dated Jun. 14, 2018, 13 pages.

Non-Final Office Action for U.S. Appl. No. 15/499,013, dated Jan. 26, 2018, 10 pages.

Non-Final Office Action for U.S. Appl. No. 15/925,157, dated Aug. 8, 2018, 11 pages.

Non-Final Office Action for U.S. Appl. No. 15/943,864, dated Aug. 9, 2018, 11 pages.

PCT International Search Report and Written Opinion in International Application No. PCT/US2017/29805, dated Jul. 31, 2017, 9 pages.

PCT International Search Report and Written Opinion in International Application No. PCT/US2017/029797, dated Dec. 29, 2017, 10 pages.

PCT Invitation to Pay Additional Fees in International Application No. PCT/US2017/029797, dated Jun. 26, 2017, 2 pages.

PUBCHEM. Substance Record for SID 162584226. Deposit Date: May 22, 2013. [retrieved on Jun. 13, 2017], Retrieved from the Internet. <URL: https://pubchem.ncbi.nlm.nih.gov/substance/162584226#sectio>, 5 pages.

RU Office Action in Russian Appln. No. 2018141379, dated Aug. 13, 2020, 20 pages (with English translation).

Stotani et al., "DYRK1A inhibition as potential treatment for Alzheimer's disease," Future Medicinal Chemistiy, Apr. 2016, 8(6):681-696.

Surendran, "Wnt-Dependent B-Catenin Signaling is Activated after Unilateral Ureteral Obstruction, and Recombinant Secreted Frizzled-Related Protein 4 Alters the Progression of Renal Fibrosis," J. Am. Soc. Nephrol., 2005, 2373-2384.

Watts et.al., "RhoA signaling modulates cyclin D1 expression in human lung fibroblasts; implications for idiopathic pulmonary fibrosis," Respir Res., 7(1):88, Jun. 15, 2006.

Wei et al., "Canonical Wnt Signaling Induces Skin Fibrosis and Subcutaneous Lipoatrophy," Arthritis & Rheumatism, Jun. 2011, 63(6):1707-1717.

Wu et al., "Design and synthesis of novel substituted naphthyridines as potential c-Met kinase inhibitors based on MK-2461," Bioorganic & medicinal chemistry letters. Aug. 15, 2015, 25(16):3251-3255.

Wynn et al., "Mechanisms of fibrosis: therapeutic translation for fibrotic disease," Nature Medicine, Jul. 2012, 18(7):1028-1040.

Zhang et al., "Research progress of dual specificity tyrosine-phosphorylation-regulated kinase 1A," Xiandai Zhongliu Yixue (2015), 23(15):2223-2226 (abstract only).

Extended European Search Report in European Appln. No. 21181038.7, dated Dec. 3, 2021, 11 pages.

Iwai et al., "Anti-tumor efficacy of a novel CLK inhibitor via targeting RNA splicing and MYC-dependent vulnerability," EMBO molecular medicine, Jun. 2018, 10(6):e8289, 15 pages.

Supplementary European Search Report in European Appln. No. 19824758.7, dated Jun. 24, 2022, 13 pages.

clinicaltrials.gov [online] "A Long-Term Safety and Efficacy Study of Lorecivivint in Subjects With Osteoarthritis of the Knee" dated Aug. 20, 2020, retrieved on Aug. 17, 2022, retrieved from URL<https://clinicaltrials.gov/ct2/show/NCT04520607>, 11 pages.

Deshmukh et al., "A small-molecule inhibitor of the Wnt pathway, lorecivivint (SM04690), as a potential disease-modifying agent for the treatment of degenerative disc disease," The Spine Journal, Sep. 1, 2020, 20(9):1492-1502.

Hiyama et al., "A complex interaction between Wnt signaling and TNF-α in nucleus pulposus cells," Arthritis research & therapy, Dec. 2013, 15(6):1-11.

(56) References Cited

OTHER PUBLICATIONS

Staines et al., "Cartilage development and degeneration: a Wnt Wnt situation," Cell biochemistry and function, Dec. 2012, 30(8):633-642.

Yazici et al., "A Phase 2b randomized trial of lorecivivint, a novel intra-articular CLK2/DYRK1A inhibitor and Wnt pathway modulator for knee osteoarthritis," Osteoarthritis and cartilage, May 1, 2021, 29(5):654-666.

ISOQUINOLIN-3-YL CARBOXAMIDES AND PREPARATION AND USE THEREOF

RELATED APPLICATIONS

This application is a continuation of U.S. application Ser. No. 16/703,321, filed Dec. 4, 2019, which is a continuation of U.S. application Ser. No. 16/130,842, filed Sep. 13, 2018 (now U.S. Pat. No. 10,544,128), which is a continuation of U.S. application Ser. No. 15/499,013, filed Apr. 27, 2017 (now U.S. Pat. No. 10,106,527), and claims the benefit of U.S. Provisional Application No. 62/328,255, filed Apr. 27, 2016, which are incorporated herein by reference in their entirety.

BACKGROUND

Technical Field

This disclosure relates to inhibitors of one or more proteins in the Wnt pathway, including inhibitors of one or more Wnt proteins, and compositions comprising the same. More particularly, it concerns the use of an isoquinoline compound or salts or analogs thereof, in the treatment of disorders characterized by the activation of Wnt pathway signaling (e.g., cancer, abnormal cellular proliferation, angiogenesis, fibrotic disorders, bone or cartilage diseases, and osteoarthritis), the modulation of cellular events mediated by Wnt pathway signaling, as well as genetic diseases and neurological conditions/disorders/diseases due to mutations or dysregulation of the Wnt pathway and/or of one or more of Wnt signaling components. Also provided are methods for treating Wnt-related disease states.

Background

The Wnt growth factor family includes more than 10 genes identified in the mouse and at least 19 genes identified in the human. Members of the Wnt family of signaling molecules mediate many short- and long-range patterning processes during invertebrate and vertebrate development. The Wnt signaling pathway is known for its role in the inductive interactions that regulate growth and differentiation, and it also plays roles in the homeostatic maintenance of post-embryonic tissue integrity. Wnt stabilizes cytoplasmic β-catenin, which stimulates the expression of genes including c-myc, c jun, fra-1, and cyclin D1. In addition, misregulation of Wnt signaling can cause developmental defects and is implicated in the genesis of several human cancers. The Wnt pathway has also been implicated in the maintenance of stem or progenitor cells in a growing list of adult tissues including skin, blood, gut, prostate, muscle, and the nervous system.

SUMMARY

The present disclosure provides methods and reagents, involving contacting a cell with an agent, such as an isoquinoline compound, in a sufficient amount to antagonize a Wnt activity, e.g., to reverse or control an aberrant growth state or correct a genetic disorder due to mutations in Wnt signaling components.

Some embodiments disclosed herein include Wnt inhibitors containing an isoquinoline core. Other embodiments disclosed herein include pharmaceutical compositions and methods of treatment using these compounds.

One embodiment disclosed herein includes a compound having the structure of Formula I:

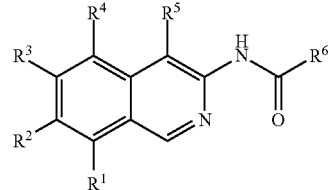

as well as prodrugs and pharmaceutically acceptable salts thereof.

In some embodiments of Formula (I):

$R^1$, $R^2$, $R^4$, and $R^5$ are independently selected from the group consisting of H, halide, unsubstituted —($C_{1-3}$ haloalkyl), and unsubstituted —($C_{1-3}$ alkyl);

$R^3$ is a 5-membered heteroaryl optionally substituted with 1-4 $R^{45}$;

$R^6$ is selected from the group consisting of -aryl substituted with 1-5 $R^{36}$ and a 6-membered heteroaryl optionally substituted with 1-6 $R^{37}$;

each $R^{36}$ is independently selected from the group consisting of halide, unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), —$XR^{42}$, —$C(O)N(R^{47})_2$, —($C_{1-4}$ alkylene)$_p$heterocyclyl optionally substituted with 1-10 $R^{43}$, and —($C_{1-4}$ alkylene)$_p$carbocyclyl optionally substituted with 1-12 $R^{44}$; wherein each —($C_{1-4}$ alkylene) is, independently, optionally substituted with one or more substituents as defined anywhere herein;

each $R^{37}$ is independently selected from the group consisting of halide, unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), —$XR^{42}$, —$C(O)N(R^{47})_2$, —($C_{1-4}$ alkylene)$_p$heterocyclyl optionally substituted with 1-10 $R^{43}$, and —($C_{1-4}$ alkylene)$_p$carbocyclyl optionally substituted with 1-12 $R^{44}$; wherein each —($C_{1-4}$ alkylene) is, independently, optionally substituted with one or more substituents as defined anywhere herein;

each $R^{38}$ is independently selected from the group consisting of halide, unsubstituted —($C_{1-5}$ alkyl), unsubstituted —($C_{2-5}$ alkenyl), unsubstituted —($C_{2-5}$ alkynyl), unsubstituted —($C_{1-5}$ haloalkyl), —CN, and —($C_{1-4}$ alkylene)$_p$carbocyclyl optionally substituted with 1-12 $R^{44}$; wherein each —($C_{1-4}$ alkylene) is, independently, optionally substituted with one or more substituents as defined anywhere herein;

each $R^{39}$ is independently selected from the group consisting of halide, unsubstituted —($C_{1-5}$ alkyl), unsubstituted —($C_{2-5}$ alkenyl), unsubstituted —($C_{2-5}$ alkynyl), unsubstituted —($C_{1-5}$ haloalkyl), —CN, and —($C_{1-4}$ alkylene)$_p$carbocyclyl optionally substituted with 1-12 $R^{44}$; wherein each —($C_{1-4}$ alkylene) is, independently, optionally substituted with one or more substituents as defined anywhere herein;

each $R^{40}$ is independently selected from the group consisting of halide, unsubstituted —($C_{1-5}$ alkyl), unsubstituted —($C_{2-5}$ alkenyl), unsubstituted —($C_{2-5}$ alkynyl), unsubstituted —($C_{1-5}$ haloalkyl), —CN, and —($C_{1-4}$ alkylene)$_p$carbocyclyl optionally substituted with 1-12 $R^{44}$; wherein each —($C_{1-4}$ alkylene) is, independently, optionally substituted with one or more substituents as defined anywhere herein;

each $R^{41}$ is independently selected from the group consisting of halide, unsubstituted —($C_{1-5}$ alkyl), unsubstituted —(C$_{2-5}$ alkenyl), unsubstituted —(C$_{2-5}$ alkynyl), unsubstituted —(C$_{1-5}$ haloalkyl), and —CN;

each R$^{42}$ is independently selected from the group consisting of unsubstituted —(C$_{1-5}$ alkyl), unsubstituted —(C$_{2-5}$ alkenyl), unsubstituted —(C$_{2-5}$ alkynyl), unsubstituted —(C$_{1-5}$ haloalkyl), —(C$_{1-4}$ alkylene)$_p$aryl optionally substituted with 1-10 R$^{46}$, —(C$_{1-4}$ alkylene)$_p$heterocyclyl optionally substituted with 1-12 R$^{43}$, and —(C$_{1-4}$ alkylene)$_p$carbocyclyl optionally substituted with 1-12 R$^{44}$; wherein each —(C$_{1-4}$ alkylene) is, independently, optionally substituted with one or more substituents as defined anywhere herein;

each R$^{43}$ is independently selected from the group consisting of halide, unsubstituted —(C$_{1-5}$ alkyl), unsubstituted —(C$_{2-5}$ alkenyl), unsubstituted —(C$_{2-5}$ alkynyl), unsubstituted —(C$_{1-5}$ haloalkyl), —CN, and —(C$_{1-4}$ alkylene)$_p$carbocyclyl optionally substituted with 1-12 R$^{44}$; wherein each —(C$_{1-4}$ alkylene) is, independently, optionally substituted with one or more substituents as defined anywhere herein;

each R$^{44}$ is independently selected from the group consisting of halide, unsubstituted —(C$_{1-5}$ alkyl), unsubstituted —(C$_{2-5}$ alkenyl), unsubstituted —(C$_{2-5}$ alkynyl), unsubstituted —(C$_{1-5}$ haloalkyl), and —CN;

each R$^{45}$ is independently selected from the group consisting of unsubstituted —(C$_{1-9}$ alkyl), unsubstituted —(C$_{2-9}$ alkenyl), unsubstituted —(C$_{2-9}$ alkynyl), unsubstituted —(C$_{1-9}$ haloalkyl), —(C$_{1-4}$ alkylene)$_p$heterocyclyl optionally substituted with 1-10 R$^{38}$, and -carbocyclyl optionally substituted with 1-12 R$^{39}$; wherein each —(C$_{1-4}$ alkylene) is, independently, optionally substituted with one or more substituents as defined anywhere herein;

alternatively, two adjacent R$^{45}$ taken together form a ring which is selected from the group consisting of -heterocyclyl optionally substituted with 1-10 R$^{40}$ and -carbocyclyl optionally substituted with 1-12 R$^{41}$;

each R$^{46}$ is independently selected from the group consisting of halide, unsubstituted —(C$_{1-5}$ alkyl), unsubstituted —(C$_{2-5}$ alkenyl), unsubstituted —(C$_{2-5}$ alkynyl), unsubstituted —(C$_{1-5}$ haloalkyl), and —CN;

each R$^{47}$ is independently selected from the group consisting of unsubstituted —(C$_{1-5}$ alkyl), unsubstituted —(C$_{2-5}$ alkenyl), unsubstituted —(C$_{2-5}$ alkynyl), and unsubstituted —(C$_{1-5}$ haloalkyl);

each X is selected from the group consisting of O, S, and NH; and each p is independently 0 or 1.

In another embodiment of Formula (I):

R$^1$, R$^2$, R$^4$, and R$^5$ are independently selected from the group consisting of H, halide, unsubstituted —(C$_{1-3}$ haloalkyl), and unsubstituted —(C$_{1-3}$ alkyl);

R$^3$ is selected from the group consisting of:

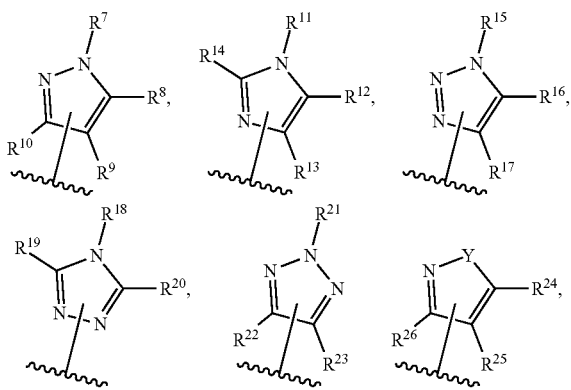

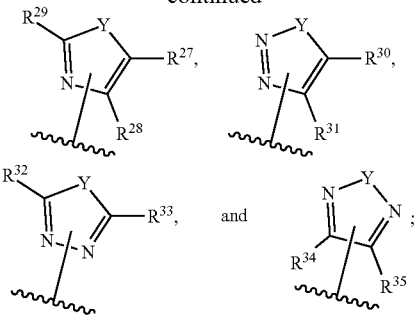

wherein each of R$^7$-R$^{35}$ is, independently, a substituent as defined anywhere herein or a single bond connecting R$^3$ to the isoquinoline ring; wherein only one of R$^7$-R$^{10}$ (when present) is a bond, only one of R$^{11}$-R$^{14}$ (when present) is a bond, only one of R$^{15}$-R$^{17}$ (when present) is a bond, only one of R$^{18}$-R$^{20}$ (when present) is a bond, only one of R$^{21}$-R$^{23}$ (when present) is a bond, only one of R$^{24}$-R$^{26}$ (when present) is a bond, only one of R$^{27}$-R$^{29}$ (when present) is a bond, only one of R$^{30}$-R$^{31}$ (when present) is a bond, only one of R$^{32}$-R$^{33}$ (when present) is a bond, and only one of R$^{34}$-R$^{35}$ (when present) is a bond; for purposes of clarification, any one of the nitrogen atoms attached to R$^7$, R$^{11}$, R$^{15}$, R$^{18}$, or R$^{21}$ can serve as the point of attachment of R$^3$ to the isoquinoline ring; likewise, any one of the carbon atoms attached to R$^8$, R$^9$, R$^{10}$, R$^{12}$, R$^{13}$, R$^{14}$, R$^{16}$, R$^{17}$, R$^{19}$, R$^{20}$, R$^{22}$, R$^{23}$, R$^{24}$, R$^{25}$, R$^{26}$, R$^{27}$, R$^{28}$, R$^{29}$, R$^{30}$, R$^{31}$, R$^{32}$, R$^{33}$, R$^{34}$, or R$^{35}$ can serve as the point of attachment of R$^3$ to the isoquinoline ring; so that:

when the nitrogen atom to which R$^7$ is attached serves as the point of attachment of R$^3$ to the isoquinoline ring, then R$^7$ is a single bond connecting R$^3$ to the isoquinoline ring;

when the carbon atom to which R$^8$ is attached serves as the point of attachment of R$^3$ to the isoquinoline ring, then R$^8$ is a single bond connecting R$^3$ to the isoquinoline ring;

when the carbon atom to which R$^9$ is attached serves as the point of attachment of R$^3$ to the isoquinoline ring, then R$^9$ is a single bond connecting R$^3$ to the isoquinoline ring;

when the carbon atom to which R$^{10}$ is attached serves as the point of attachment of R$^3$ to the isoquinoline ring, then R$^{10}$ is a single bond connecting R$^3$ to the isoquinoline ring;

when the nitrogen atom to which R$^{11}$ is attached serves as the point of attachment of R$^3$ to the isoquinoline ring, then R$^{11}$ is a single bond connecting R$^3$ to the isoquinoline ring;

when the carbon atom to which R$^{12}$ is attached serves as the point of attachment of R$^3$ to the isoquinoline ring, then R$^{12}$ is a single bond connecting R$^3$ to the isoquinoline ring;

when the carbon atom to which R$^{13}$ is attached serves as the point of attachment of R$^3$ to the isoquinoline ring, then R$^{13}$ is a single bond connecting R$^3$ to the isoquinoline ring;

when the carbon atom to which R$^{14}$ is attached serves as the point of attachment of R$^3$ to the isoquinoline ring, then R$^{14}$ is a single bond connecting R$^3$ to the isoquinoline ring;

when the nitrogen atom to which R$^{15}$ is attached serves as the point of attachment of R$^3$ to the isoquinoline ring, then R$^{15}$ is a single bond connecting R$^3$ to the isoquinoline ring;

when the carbon atom to which R$^{16}$ is attached serves as the point of attachment of R$^3$ to the isoquinoline ring, then R$^{16}$ is a single bond connecting R$^3$ to the isoquinoline ring;

when the carbon atom to which R$^{17}$ is attached serves as the point of attachment of R$^3$ to the isoquinoline ring, then R$^{77}$ is a single bond connecting R$^3$ to the isoquinoline ring;

when the nitrogen atom to which R⁻is attached serves as the point of attachment of $R^3$ to the isoquinoline ring, then R⁻is a single bond connecting $R^3$ to the isoquinoline ring;

when the carbon atom to which $R^{19}$ is attached serves as the point of attachment of $R^3$ to the isoquinoline ring, then $R^{19}$ is a single bond connecting $R^3$ to the isoquinoline ring;

when the carbon atom to which $R^{20}$ is attached serves as the point of attachment of $R^3$ to the isoquinoline ring, then $R^{20}$ is a single bond connecting $R^3$ to the isoquinoline ring;

when the nitrogen atom to which $R^{21}$ is attached serves as the point of attachment of $R^3$ to the isoquinoline ring, then $R^{21}$ is a single bond connecting $R^3$ to the isoquinoline ring;

when the carbon atom to which $R^{22}$ is attached serves as the point of attachment of $R^3$ to the isoquinoline ring, then $R^{22}$ is a single bond connecting $R^3$ to the isoquinoline ring;

when the carbon atom to which $R^{23}$ is attached serves as the point of attachment of $R^3$ to the isoquinoline ring, then $R^{23}$ is a single bond connecting $R^3$ to the isoquinoline ring;

when the carbon atom to which $R^{24}$ is attached serves as the point of attachment of $R^3$ to the isoquinoline ring, then $R^{24}$ is a single bond connecting $R^3$ to the isoquinoline ring;

when the carbon atom to which $R^{25}$ is attached serves as the point of attachment of $R^3$ to the isoquinoline ring, then $R^{25}$ is a single bond connecting $R^3$ to the isoquinoline ring;

when the carbon atom to which $R^{26}$ is attached serves as the point of attachment of $R^3$ to the isoquinoline ring, then $R^{26}$ is a single bond connecting $R^3$ to the isoquinoline ring;

when the carbon atom to which $R^{27}$ is attached serves as the point of attachment of $R^3$ to the isoquinoline ring, then $R^{27}$ is a single bond connecting $R^3$ to the isoquinoline ring;

when the carbon atom to which $R^{28}$ is attached serves as the point of attachment of $R^3$ to the isoquinoline ring, then $R^{28}$ is a single bond connecting $R^3$ to the isoquinoline ring;

when the carbon atom to which $R^{29}$ is attached serves as the point of attachment of $R^3$ to the isoquinoline ring, then $R^{29}$ is a single bond connecting $R^3$ to the isoquinoline ring;

when the carbon atom to which $R^{30}$ is attached serves as the point of attachment of $R^3$ to the isoquinoline ring, then $R^{30}$ is a single bond connecting $R^3$ to the isoquinoline ring;

when the carbon atom to which $R^{31}$ is attached serves as the point of attachment of $R^3$ to the isoquinoline ring, then $R^{31}$ is a single bond connecting $R^3$ to the isoquinoline ring;

when the carbon atom to which $R^{32}$ is attached serves as the point of attachment of $R^3$ to the isoquinoline ring, then $R^{32}$ is a single bond connecting $R^3$ to the isoquinoline ring;

when the carbon atom to which $R^{33}$ is attached serves as the point of attachment of $R^3$ to the isoquinoline ring, then $R^{33}$ is a single bond connecting $R^3$ to the isoquinoline ring;

when the carbon atom to which $R^{34}$ is attached serves as the point of attachment of $R^3$ to the isoquinoline ring, then $R^{34}$ is a single bond connecting $R^3$ to the isoquinoline ring;

when the carbon atom to which $R^{35}$ is attached serves as the point of attachment of $R^3$ to the isoquinoline ring, then $R^{35}$ is a single bond connecting $R^3$ to the isoquinoline ring;

$R^6$ is selected from the group consisting of -aryl substituted with 1-5 $R^{36}$ and a 6-membered heteroaryl optionally substituted with 1-6 $R^{37}$;

$R^7$ is selected from the group consisting of a single bond, H, unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), —($C_{1-4}$ alkylene)$_p$heterocyclyl optionally substituted with 1-10 $R^{38}$, and -carbocyclyl optionally substituted with 1-12 $R^{39}$; wherein —($C_{1-4}$ alkylene) is optionally substituted with one or more substituents as defined anywhere herein;

$R^8$, $R^9$, and $R^{10}$ are independently selected from the group consisting of a single bond, H, halide, unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), —($C_{1-4}$ alkylene)$_p$heterocyclyl optionally substituted with 1-10 $R^{38}$, and -carbocyclyl optionally substituted with 1-12 $R^9$; wherein each —($C_{1-4}$ alkylene) is, independently, optionally substituted with one or more substituents as defined anywhere herein; alternatively, one of $R^7$ and $R^8$, $R^8$ and $R^9$, or $R^9$ and $R^{10}$ are taken together to form a ring which is selected from the group consisting of -heterocyclyl optionally substituted with 1-10 $R^{40}$ and -carbocyclyl optionally substituted with 1-12 $R^{41}$;

$R^{11}$ is selected from the group consisting of a single bond, H, unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), —($C_{1-4}$ alkylene)$_p$heterocyclyl optionally substituted with 1-10 $R^{38}$, and -carbocyclyl optionally substituted with 1-12 $R^{39}$; wherein —($C_{1-4}$ alkylene) is optionally substituted with one or more substituents as defined anywhere herein;

$R^{12}$, $R^{13}$, and $R^{14}$ are independently selected from the group consisting of a single bond, H, halide, unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), —($C_{1-4}$ alkylene)$_p$heterocyclyl optionally substituted with 1-10 $R^{38}$, and -carbocyclyl optionally substituted with 1-12 $R^{39}$; wherein each —($C_{1-4}$ alkylene) is, independently, optionally substituted with one or more substituents as defined anywhere herein; alternatively, one of $R^{10}$ and $R^{12}$, $R^{12}$ and $R^{13}$, or $R^{14}$ and $R^{10}$ are taken together to form a ring which is selected from the group consisting of -heterocyclyl optionally substituted with 1-10 $R^{40}$ and -carbocyclyl optionally substituted with 1-12 $R^{41}$;

$R^{15}$ is selected from the group consisting of a single bond, H, unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), —($C_{1-4}$ alkylene)$_p$heterocyclyl optionally substituted with 1-10 $R^{38}$, and -carbocyclyl optionally substituted with 1-12 $R^{39}$; wherein —($C_{1-4}$ alkylene) is optionally substituted with one or more substituents as defined anywhere herein;

$R^{16}$ and $R^{17}$ are independently selected from the group consisting of a single bond, H, halide, unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), —($C_{1-4}$ alkylene)$_p$heterocyclyl optionally substituted with 1-10 $R^{38}$, and -carbocyclyl optionally substituted with 1-12 $R^{39}$; wherein each —($C_{1-4}$ alkylene) is, independently, optionally substituted with one or more substituents as defined anywhere herein; alternatively, one of $R^{15}$ and $R^{16}$ or $R^{16}$ and $R^{17}$ are taken together to form a ring which is selected from the group consisting of -heterocyclyl optionally substituted with 1-10 $R^{40}$ and -carbocyclyl optionally substituted with 1-12 $R^{41}$;

$R^{18}$ is selected from the group consisting of a single bond, H, unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), —($C_{1-4}$ alkylene)$_p$heterocyclyl optionally substituted with 1-10 $R^{38}$, and -carbocyclyl optionally substituted with 1-12 $R^{39}$; wherein —($C_{1-4}$ alkylene) is optionally substituted with one or more substituents as defined anywhere herein;

$R^{19}$ and $R^{20}$ are independently selected from the group consisting of a single bond, H, halide, unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), —($C_{1-4}$ alkylene)$_p$heterocyclyl optionally substituted with 1-10 $R^{38}$, and -carbocyclyl optionally substituted with 1-12 $R^{39}$;

wherein each —($C_{1-4}$ alkylene) is, independently, optionally substituted with one or more substituents as defined anywhere herein;

alternatively, one of $R^{18}$ and $R^{19}$ or $R^{18}$ and $R^{20}$ are taken together to form a heterocyclyl optionally substituted with 1-10 $R^{40}$;

$R^{21}$ is selected from the group consisting of a single bond, H, unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), —($C_{1-4}$ alkylene)$_p$heterocyclyl optionally substituted with 1-10 $R^{38}$, and -carbocyclyl optionally substituted with 1-12 $R^{39}$; wherein —($C_{1-4}$ alkylene) is optionally substituted with one or more substituents as defined anywhere herein;

$R^{22}$ and $R^{23}$ are independently selected from the group consisting of a single bond, H, halide, unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), —($C_{1-4}$ alkylene)$_p$heterocyclyl optionally substituted with 1-10 $R^{38}$, and -carbocyclyl optionally substituted with 1-12 $R^{39}$; wherein each —($C_{1-4}$ alkylene) is, independently, optionally substituted with one or more substituents as defined anywhere herein;

alternatively, $R^{22}$ and $R^{23}$ are taken together to form a ring which is selected from the group consisting of -heterocyclyl optionally substituted with 1-10 $R^{40}$ and -carbocyclyl optionally substituted with 1-12 $R^{41}$;

$R^{24}$, $R^{25}$, and $R^{26}$ are independently selected from the group consisting of a single bond, H, halide, unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), —($C_{1-4}$ alkylene)$_p$heterocyclyl optionally substituted with 1-10 $R^{38}$, and -carbocyclyl optionally substituted with 1-12 $R^{39}$; wherein each —($C_{1-4}$ alkylene) is, independently, optionally substituted with one or more substituents as defined anywhere herein;

alternatively, one of $R^{24}$ and $R^{25}$ or $R^{25}$ and $R^{26}$ are taken together to form a ring which is selected from the group consisting of -heterocyclyl optionally substituted with 1-10 $R^{40}$ and -carbocyclyl optionally substituted with 1-12 $R^{41}$;

$R^{27}$, $R^{28}$, and $R^{29}$ are independently selected from the group consisting of a single bond, H, halide, unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), —($C_{1-4}$ alkylene)$_p$heterocyclyl optionally substituted with 1-10 $R^{38}$, and -carbocyclyl optionally substituted with 1-12 $R^{39}$; wherein each —($C_{1-4}$ alkylene) is, independently, optionally substituted with one or more substituents as defined anywhere herein;

alternatively, $R^{27}$ and $R^{28}$ are taken together to form a ring which is selected from the group consisting of -heterocyclyl optionally substituted with 1-10 $R^{40}$ and -carbocyclyl optionally substituted with 1-12 $R^{41}$;

$R^{30}$ and $R^{31}$ are independently selected from the group consisting of a single bond, H, halide, unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), —($C_{1-4}$ alkylene)$_p$heterocyclyl optionally substituted with 1-10 $R^{38}$, and -carbocyclyl optionally substituted with 1-12 $R^{39}$; wherein each —($C_{1-4}$ alkylene) is, independently, optionally substituted with one or more substituents as defined anywhere herein;

alternatively, $R^{30}$ and $R^{31}$ are taken together to form a ring which is selected from the group consisting of -heterocyclyl optionally substituted with 1-10 $R^{40}$ and -carbocyclyl optionally substituted with 1-12 $R^{41}$;

$R^{32}$ and $R^{33}$ are independently selected from the group consisting of a single bond, H, halide, unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), —($C_{1-4}$ alkylene)$_p$heterocyclyl optionally substituted with 1-10 $R^{38}$, and -carbocyclyl optionally substituted with 1-12 $R^{39}$; wherein each —($C_{1-4}$ alkylene) is, independently, optionally substituted with one or more substituents as defined anywhere herein;

$R^{34}$ and $R^{35}$ are independently selected from the group consisting of a single bond, H, halide, unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), —($C_{1-4}$ alkylene)$_p$heterocyclyl optionally substituted with 1-10 $R^{38}$, and -carbocyclyl optionally substituted with 1-12 $R^{39}$; wherein each —($C_{1-4}$ alkylene) is, independently, optionally substituted with one or more substituents as defined anywhere herein;

alternatively, $R^{34}$ and $R^{35}$ are taken together to form a ring which is selected from the group consisting of -heterocyclyl optionally substituted with 1-10 $R^{40}$ and -carbocyclyl optionally substituted with 1-12 $R^{41}$;

each $R^{36}$ is independently selected from the group consisting of halide, unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), —$XR^{42}$, —C(O)N($R^{47}$)$_2$, —($C_{1-4}$ alkylene)$_p$heterocyclyl optionally substituted with 1-10 $R^{43}$, and —($C_{1-4}$ alkylene)$_p$carbocyclyl optionally substituted with 1-12 $R^{44}$; wherein each —($C_{1-4}$ alkylene) is, independently, optionally substituted with one or more substituents as defined anywhere herein;

each $R^{37}$ is independently selected from the group consisting of halide, unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), —$XR^{42}$, —C(O)N($R^{47}$)$_2$, —($C_{1-4}$ alkylene)$_p$heterocyclyl optionally substituted with 1-10 $R^{43}$, and —($C_{1-4}$ alkylene)$_p$carbocyclyl optionally substituted with 1-12 $R^{44}$; wherein each —($C_{1-4}$ alkylene) is, independently, optionally substituted with one or more substituents as defined anywhere herein;

each $R^{38}$ is independently selected from the group consisting of halide, unsubstituted —($C_{1-5}$ alkyl), unsubstituted —($C_{2-5}$ alkenyl), unsubstituted —($C_{2-5}$ alkynyl), unsubstituted —($C_{1-5}$ haloalkyl), —CN, and —($C_{1-4}$ alkylene)$_p$carbocyclyl optionally substituted with 1-12 $R^{44}$; wherein each —($C_{1-4}$ alkylene) is, independently, optionally substituted with one or more substituents as defined anywhere herein;

each $R^{39}$ is independently selected from the group consisting of halide, unsubstituted —($C_{1-5}$ alkyl), unsubstituted —($C_{2-5}$ alkenyl), unsubstituted —($C_{2-5}$ alkynyl), unsubstituted —($C_{1-5}$ haloalkyl), —CN, and —($C_{1-4}$ alkylene)$_p$carbocyclyl optionally substituted with 1-12 $R^{44}$; wherein each —($C_{1-4}$ alkylene) is, independently, optionally substituted with one or more substituents as defined anywhere herein;

each $R^{40}$ is independently selected from the group consisting of halide, unsubstituted —($C_{1-5}$ alkyl), unsubstituted —($C_{2-5}$ alkenyl), unsubstituted —($C_{2-5}$ alkynyl), unsubstituted —($C_{1-5}$ haloalkyl), —CN, and —($C_{1-4}$ alkylene)$_p$carbocyclyl optionally substituted with 1-12 $R^{44}$; wherein each —($C_{1-4}$ alkylene) is, independently, optionally substituted with one or more substituents as defined anywhere herein;

each $R^{41}$ is independently selected from the group consisting of halide, unsubstituted —($C_{1-5}$ alkyl), unsubstituted —($C_{2-5}$ alkenyl), unsubstituted —($C_{2-5}$ alkynyl), unsubstituted —($C_{1-5}$ haloalkyl), and —CN;

each $R^{42}$ is independently selected from the group consisting of unsubstituted —($C_{1-5}$ alkyl), unsubstituted —($C_{2-5}$ alkenyl), unsubstituted —($C_{2-5}$ alkynyl), unsubstituted —($C_{1-5}$ haloalkyl), —($C_{1-4}$ alkylene)$_p$aryl optionally substituted with 1-10 $R^{46}$, —($C_{1-4}$ alkylene)$_p$heterocyclyl optionally substituted with 1-12 $R^{43}$, and —($C_{1-4}$ alkylene)$_p$carbocyclyl optionally substituted with 1-12 $R^{44}$; wherein each —($C_{1-4}$ alkylene) is, independently, optionally substituted with one or more substituents as defined anywhere herein;

each $R^{43}$ is independently selected from the group consisting of halide, unsubstituted —($C_{1-5}$ alkyl), unsubstituted —($C_{2-5}$ alkenyl), unsubstituted —($C_{2-5}$ alkynyl), unsubstituted —($C_{1-5}$ haloalkyl), —CN, and —($C_{1-4}$ alkylene)$_p$carbocyclyl optionally substituted with 1-12 $R^{44}$; wherein each —($C_{1-4}$ alkylene) is, independently, optionally substituted with one or more substituents as defined anywhere herein;

each $R^{44}$ is selected from the group consisting of halide, unsubstituted —($C_{1-5}$ alkyl), unsubstituted —($C_{2-5}$ alkenyl), unsubstituted —($C_{2-5}$ alkynyl), unsubstituted —($C_{1-5}$ haloalkyl), and —CN;

each $R^{46}$ is independently selected from the group consisting of halide, unsubstituted —($C_{1-5}$ alkyl), unsubstituted —($C_{2-5}$ alkenyl), unsubstituted —($C_{2-5}$ alkynyl), unsubstituted —($C_{1-5}$ haloalkyl), and —CN;

each $R^{47}$ is independently selected from the group consisting of unsubstituted —($C_{1-5}$ alkyl), unsubstituted —($C_{2-5}$ alkenyl), unsubstituted —($C_{2-5}$ alkynyl), and unsubstituted —($C_{1-5}$ haloalkyl);

each X is selected from the group consisting of O, S, and NH;

each Y is selected from the group consisting of O and S; and each p is independently 0 or 1.

In another embodiment of Formula (I):

$R^1$, $R^2$, $R^4$, and $R^5$ are independently selected from the group consisting of H, halide, amino, unsubstituted —($C_{1-3}$ haloalkyl), and unsubstituted —($C_{1-3}$ alkyl);

$R^3$ is a 5-membered heteroaryl optionally substituted with 1-4 $R^{45}$;

$R^6$ is selected from the group consisting of -phenyl substituted with 1-5 $R^{36}$, —($C_{1-3}$ alkylene)$_p$pyridinyl optionally substituted with 1-6 $R^{37}$, and a 6-10 membered heteroaryl optionally substituted with 1-6 $R^{37}$; wherein the carbonyl of Formula I is attached to an aromatic ring of the heteroaryl; wherein —($C_{1-3}$ alkylene) is optionally substituted with one or more substituents as defined anywhere herein;

each $R^{36}$ is independently selected from the group consisting of halide, unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), —XR$^{42}$, —C(=O)N(R$^{47}$)$_2$, —($C_{1-4}$ alkylene)$_p$N(R$^{50}$)$_2$, —($C_{1-4}$ alkylene)$_p$heterocyclyl optionally substituted with 1-10 $R^{43}$, and —($C_{1-4}$ alkylene)$_p$carbocyclyl optionally substituted with 1-12 $R^{44}$; wherein each —($C_{1-4}$ alkylene) is, independently, optionally substituted with one or more substituents as defined anywhere herein;

each $R^{37}$ is independently selected from the group consisting of halide, unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), —XR$^{42}$, —C(=O)N(R$^{47}$)$_2$, —($C_{1-4}$ alkylene)$_p$N(R$^{50}$)$_2$, —($C_{1-4}$ alkylene)$_p$heterocyclyl optionally substituted with 1-10 $R^{43}$, and —($C_{1-4}$ alkylene)$_p$carbocyclyl optionally substituted with 1-12 $R^{44}$; wherein each —($C_{1-4}$ alkylene) is, independently, optionally substituted with one or more substituents as defined anywhere herein;

each $R^{38}$ is independently selected from the group consisting of halide, unsubstituted —($C_{1-5}$ alkyl), unsubstituted —($C_{2-5}$ alkenyl), unsubstituted —($C_{2-5}$ alkynyl), unsubstituted —($C_{1-5}$ haloalkyl), —CN, and —($C_{1-4}$ alkylene)$_p$carbocyclyl optionally substituted with 1-12 $R^{44}$; wherein each —($C_{1-4}$ alkylene) is, independently, optionally substituted with one or more substituents as defined anywhere herein;

each $R^{39}$ is independently selected from the group consisting of halide, unsubstituted —($C_{1-5}$ alkyl), unsubstituted —($C_{2-5}$ alkenyl), unsubstituted —($C_{2-5}$ alkynyl), unsubstituted —($C_{1-5}$ haloalkyl), —CN, and —($C_{1-4}$ alkylene)$_p$carbocyclyl optionally substituted with 1-12 $R^{44}$; wherein each —($C_{1-4}$ alkylene) is, independently, optionally substituted with one or more substituents as defined anywhere herein;

each $R^{40}$ is independently selected from the group consisting of halide, unsubstituted —($C_{1-5}$ alkyl), unsubstituted —($C_{2-5}$ alkenyl), unsubstituted —($C_{2-5}$ alkynyl), unsubstituted —($C_{1-5}$ haloalkyl), —CN, and —($C_{1-4}$ alkylene)$_p$carbocyclyl optionally substituted with 1-12 $R^{44}$; wherein each —($C_{1-4}$ alkylene) is, independently, optionally substituted with one or more substituents as defined anywhere herein;

each $R^{41}$ is independently selected from the group consisting of halide, unsubstituted —($C_{1-5}$ alkyl), unsubstituted —($C_{2-5}$ alkenyl), unsubstituted —($C_{2-5}$ alkynyl), unsubstituted —($C_{1-5}$ haloalkyl), and —CN;

each $R^{42}$ is independently selected from the group consisting of H, unsubstituted —($C_{1-5}$ alkyl), unsubstituted —($C_{2-5}$ alkenyl), unsubstituted —($C_{2-5}$ alkynyl), unsubstituted —($C_{1-5}$ haloalkyl), —($C_{1-4}$ alkylene)N(R$^{48}$)$_2$, —($C_{1-4}$ alkylene)$_p$aryl optionally substituted with 1-10 $R^{46}$, —($C_{1-4}$ alkylene)$_p$heterocyclyl optionally substituted with 1-12 $R^{43}$, and —($C_{1-4}$ alkylene)$_p$carbocyclyl optionally substituted with 1-12 $R^{44}$; wherein each —($C_{1-4}$ alkylene) is, independently, optionally substituted with one or more substituents as defined anywhere herein;

each $R^{43}$ is independently selected from the group consisting of halide, unsubstituted —($C_{1-5}$ alkyl), unsubstituted —($C_{2-5}$ alkenyl), unsubstituted —($C_{2-5}$ alkynyl), unsubstituted —($C_{1-5}$ haloalkyl), —CN, —OH, —C(=O)R$^{51}$, —N(R$^{50}$)$_2$, and —($C_{1-4}$ alkylene)$_p$carbocyclyl optionally substituted with 1-12 $R^{44}$; wherein each —($C_{1-4}$ alkylene) is, independently, optionally substituted with one or more substituents as defined anywhere herein;

each $R^{44}$ is independently selected from the group consisting of halide, unsubstituted —($C_{1-5}$ alkyl), unsubstituted —($C_{2-5}$ alkenyl), unsubstituted —($C_{2-5}$ alkynyl), unsubstituted —($C_{1-5}$ haloalkyl), and —CN;

each $R^{45}$ is independently selected from the group consisting of halide, unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), —($C_{1-4}$ alkylene)$_p$N(R$^{48}$)$_2$, —($C_{1-4}$ alkylene)$_p$OR$^{49}$, —C(=O)N(R$^{48}$)$_2$, —($C_{1-4}$ alkylene)$_p$heterocyclyl optionally substituted with 1-10 $R^{38}$, and -carbocyclyl optionally substituted with 1-12 $R^{39}$; wherein each —($C_{1-4}$ alkylene) is, independently, optionally substituted with one or more substituents as defined anywhere herein;

alternatively, two adjacent $R^{45}$ taken together form a ring which is selected from the group consisting of -heterocyclyl optionally substituted with 1-10 $R^{40}$ and -carbocyclyl optionally substituted with 1-12 $R^{41}$;

each $R^{46}$ is independently selected from the group consisting of halide, unsubstituted —($C_{1-5}$ alkyl), unsubstituted —($C_{2-5}$ alkenyl), unsubstituted —($C_{2-5}$ alkynyl), unsubstituted —($C_{1-5}$ haloalkyl), and —CN;

each $R^{47}$ is independently selected from the group consisting of H, unsubstituted —($C_{1-5}$ alkyl), unsubstituted —($C_{2-5}$ alkenyl), unsubstituted —($C_{2-5}$ alkynyl), and unsubstituted —($C_{1-5}$ haloalkyl);

each $R^{48}$ is independently selected from the group consisting of H, unsubstituted —($C_{1-5}$ alkyl), unsubstituted —($C_{2-5}$ alkenyl), unsubstituted —($C_{2-5}$ alkynyl), and unsubstituted —($C_{1-5}$ haloalkyl);

each $R^{49}$ is independently selected from the group consisting of H, unsubstituted —($C_{1-5}$ alkyl), unsubstituted —($C_{2-5}$ alkenyl), unsubstituted —($C_{2-5}$ alkynyl), and unsubstituted —($C_{1-5}$ haloalkyl);

each $R^{50}$ is independently selected from the group consisting of H, unsubstituted —($C_{1-5}$ alkyl), unsubstituted —($C_{2-5}$ alkenyl), unsubstituted —($C_{2-5}$ alkynyl), unsubstituted —($C_{1-5}$ haloalkyl), and —($C_{1-4}$ alkylene)N($R^{48}$)$_2$; wherein —($C_{1-4}$ alkylene) is optionally substituted with one or more substituents as defined anywhere herein;

each $R^{51}$ is a heteroaryl optionally substituted with 1-6 $R^{52}$;

each $R^{52}$ is a -heterocyclyl optionally substituted with 1-10 $R^{46}$;

each X is selected from the group consisting of O, S, and $NR^{48}$; and each p is independently 0 or 1.

In another embodiment of Formula (I):

$R^1$, $R^2$, $R^4$, and $R^5$ are independently selected from the group consisting of H, halide, amino, unsubstituted —($C_{1-3}$ haloalkyl), and unsubstituted —($C_{1-3}$ alkyl);

$R^3$ is selected from the group consisting of:

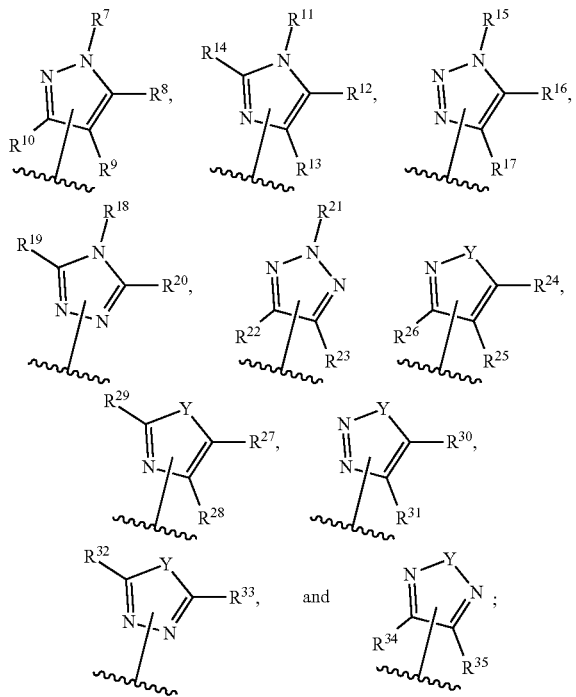

wherein each of $R^7$-$R^{35}$ is, independently, a substituent as defined anywhere herein or a single bond connecting $R^3$ to the isoquinoline ring; wherein only one of $R^7$-$R^{10}$ (when present) is a bond, only one of $R^{11}$-$R^{14}$ (when present) is a bond, only one of $R^{15}$-$R^{17}$ (when present) is a bond, only one of $R^{18}$-$R^{20}$ (when present) is a bond, only one of $R^{21}$-$R^{23}$ (when present) is a bond, only one of $R^{24}$-$R^{26}$ (when present) is a bond, only one of $R^{27}$-$R^{29}$ (when present) is a bond, only one of $R^{30}$-$R^{31}$ (when present) is a bond, only one of $R^{32}$-$R^{33}$ (when present) is a bond, and only one of $R^{34}$-$R^{35}$ (when present) is a bond; for purposes of clarification, any one of the nitrogen atoms attached to $R^7$, $R^{11}$, $R^{15}$, $R^{18}$, or $R^{21}$ can serve as the point of attachment of $R^3$ to the isoquinoline ring; likewise, any one of the carbon atoms attached to $R^8$, $R^9$, $R^{10}$, $R^{12}$, $R^{13}$, $R^{14}$, $R^{16}$, $R^{17}$, $R^{19}$, $R^{20}$, $R^{22}$, $R^{23}$, $R^{24}$, $R^{25}$, $R^{26}$, $R^{27}$, $R^{28}$, $R^{29}$, $R^{30}$, $R^{31}$, $R^{32}$, $R^{33}$, $R^{34}$, or $R^{35}$ can serve as the point of attachment of $R^3$ to the isoquinoline ring; so that:

when the nitrogen atom to which $R^7$ is attached serves as the point of attachment of $R^3$ to the isoquinoline ring, then $R^7$ is a single bond connecting $R^3$ to the isoquinoline ring;

when the carbon atom to which $R^8$ is attached serves as the point of attachment of $R^3$ to the isoquinoline ring, then $R^8$ is a single bond connecting $R^3$ to the isoquinoline ring;

when the carbon atom to which $R^9$ is attached serves as the point of attachment of $R^3$ to the isoquinoline ring, then $R^9$ is a single bond connecting $R^3$ to the isoquinoline ring;

when the carbon atom to which $R^{10}$ is attached serves as the point of attachment of $R^3$ to the isoquinoline ring, then $R^{10}$ is a single bond connecting $R^3$ to the isoquinoline ring;

when the nitrogen atom to which $R^{11}$ is attached serves as the point of attachment of $R^3$ to the isoquinoline ring, then $R^{11}$ is a single bond connecting $R^3$ to the isoquinoline ring;

when the carbon atom to which $R^{12}$ is attached serves as the point of attachment of $R^3$ to the isoquinoline ring, then $R^{12}$ is a single bond connecting $R^3$ to the isoquinoline ring;

when the carbon atom to which $R^{13}$ is attached serves as the point of attachment of $R^3$ to the isoquinoline ring, then $R^{13}$ is a single bond connecting $R^3$ to the isoquinoline ring;

when the carbon atom to which $R^{14}$ is attached serves as the point of attachment of $R^3$ to the isoquinoline ring, then $R^{14}$ is a single bond connecting $R^3$ to the isoquinoline ring;

when the nitrogen atom to which $R^{15}$ is attached serves as the point of attachment of $R^3$ to the isoquinoline ring, then $R^{15}$ is a single bond connecting $R^3$ to the isoquinoline ring;

when the carbon atom to which $R^{16}$ is attached serves as the point of attachment of $R^3$ to the isoquinoline ring, then $R^{16}$ is a single bond connecting $R^3$ to the isoquinoline ring;

when the carbon atom to which $R^{17}$ is attached serves as the point of attachment of $R^3$ to the isoquinoline ring, then $R^{17}$ is a single bond connecting $R^3$ to the isoquinoline ring;

when the nitrogen atom to which $R^{18}$ is attached serves as the point of attachment of $R^3$ to the isoquinoline ring, then $R^{18}$ is a single bond connecting $R^3$ to the isoquinoline ring;

when the carbon atom to which $R^{19}$ is attached serves as the point of attachment of $R^3$ to the isoquinoline ring, then $R^{19}$ is a single bond connecting $R^3$ to the isoquinoline ring;

when the carbon atom to which $R^{20}$ is attached serves as the point of attachment of $R^3$ to the isoquinoline ring, then $R^{20}$ is a single bond connecting $R^3$ to the isoquinoline ring;

when the nitrogen atom to which $R^{21}$ is attached serves as the point of attachment of $R^3$ to the isoquinoline ring, then $R^{21}$ is a single bond connecting $R^3$ to the isoquinoline ring;

when the carbon atom to which $R^{22}$ is attached serves as the point of attachment of $R^3$ to the isoquinoline ring, then $R^{22}$ is a single bond connecting $R^3$ to the isoquinoline ring;

when the carbon atom to which $R^{23}$ is attached serves as the point of attachment of $R^3$ to the isoquinoline ring, then $R^{23}$ is a single bond connecting $R^3$ to the isoquinoline ring;

when the carbon atom to which $R^{24}$ is attached serves as the point of attachment of $R^3$ to the isoquinoline ring, then $R^{24}$ is a single bond connecting $R^3$ to the isoquinoline ring;

when the carbon atom to which $R^{25}$ is attached serves as the point of attachment of $R^3$ to the isoquinoline ring, then $R^{25}$ is a single bond connecting $R^3$ to the isoquinoline ring;

when the carbon atom to which $R^{26}$ is attached serves as the point of attachment of $R^3$ to the isoquinoline ring, then $R^{26}$ is a single bond connecting $R^3$ to the isoquinoline ring;

when the carbon atom to which $R^{27}$ is attached serves as the point of attachment of $R^3$ to the isoquinoline ring, then $R^{27}$ is a single bond connecting $R^3$ to the isoquinoline ring;

when the carbon atom to which $R^{28}$ is attached serves as the point of attachment of $R^3$ to the isoquinoline ring, then $R^{28}$ is a single bond connecting $R^3$ to the isoquinoline ring;

when the carbon atom to which $R^{29}$ is attached serves as the point of attachment of $R^3$ to the isoquinoline ring, then $R^{29}$ is a single bond connecting $R^3$ to the isoquinoline ring;

when the carbon atom to which $R^{30}$ is attached serves as the point of attachment of $R^3$ to the isoquinoline ring, then $R^{30}$ is a single bond connecting $R^3$ to the isoquinoline ring;

when the carbon atom to which $R^{31}$ is attached serves as the point of attachment of $R^3$ to the isoquinoline ring, then $R^{31}$ is a single bond connecting $R^3$ to the isoquinoline ring;

when the carbon atom to which $R^{32}$ is attached serves as the point of attachment of $R^3$ to the isoquinoline ring, then $R^{32}$ is a single bond connecting $R^3$ to the isoquinoline ring;

when the carbon atom to which $R^{33}$ is attached serves as the point of attachment of $R^3$ to the isoquinoline ring, then $R^{33}$ is a single bond connecting $R^3$ to the isoquinoline ring;

when the carbon atom to which $R^{34}$ is attached serves as the point of attachment of $R^3$ to the isoquinoline ring, then $R^{34}$ is a single bond connecting $R^3$ to the isoquinoline ring;

when the carbon atom to which $R^{35}$ is attached serves as the point of attachment of $R^3$ to the isoquinoline ring, then $R^{35}$ is a single bond connecting $R^3$ to the isoquinoline ring;

$R^6$ is selected from the group consisting of -phenyl substituted with 1-5 $R^{36}$, —$(C_{1-3}$ alkylene$)_p$pyridinyl optionally substituted with 1-6 $R^{37}$, and a 6-10 membered heteroaryl optionally substituted with 1-6 $R^{37}$; wherein the carbonyl of Formula I is attached to an aromatic ring of the heteroaryl; wherein —$(C_{1-3}$ alkylene) is optionally substituted with one or more substituents as defined anywhere herein;

$R^7$ is selected from the group consisting of a single bond, H, unsubstituted —$(C_{1-9}$ alkyl), unsubstituted —$(C_{2-9}$ alkenyl), unsubstituted —$(C_{2-9}$ alkynyl), unsubstituted —$(C_{1-9}$ haloalkyl), —$(C_{1-4}$ alkylene)$N(R^{48})_2$, —$(C_{1-4}$ alkylene)$OR^{49}$, —$C(=O)N(R^{48})_2$, —$(C_{1-4}$ alkylene)$_p$heterocyclyl optionally substituted with 1-10 $R^{38}$, and -carbocyclyl optionally substituted with 1-12 $R^{39}$; wherein —$(C_{1-4}$ alkylene) is optionally substituted with one or more substituents as defined anywhere herein;

$R^8$, $R^9$, and $R^{10}$ are independently selected from the group consisting of a single bond, H, halide, unsubstituted —$(C_{1-9}$ alkyl), unsubstituted —$(C_{2-9}$ alkenyl), unsubstituted —$(C_{2-9}$ alkynyl), unsubstituted —$(C_{1-9}$ haloalkyl), —$(C_{1-4}$ alkylene)$_p$N(R^{48})_2$, —$(C_{1-4}$ alkylene)$_p$OR$^{49}$, —$C(=O)N(R^{48})_2$, —$(C_{1-4}$ alkylene)$_p$heterocyclyl optionally substituted with 1-10 $R^{38}$, and -carbocyclyl optionally substituted with 1-12 $R^{39}$; wherein each —$(C_{1-4}$ alkylene) is, independently, optionally substituted with one or more substituents as defined anywhere herein;

alternatively, one of $R^7$ and $R^8$, $R^8$ and $R^9$, or $R^9$ and $R^{10}$ are taken together to form a ring which is selected from the group consisting of -heterocyclyl optionally substituted with 1-10 $R^{40}$ and -carbocyclyl optionally substituted with 1-12 $R^{41}$;

$R^{11}$ is selected from the group consisting of a single bond, H, unsubstituted —$(C_{1-9}$ alkyl), unsubstituted —$(C_{2-9}$ alkenyl), unsubstituted —$(C_{2-9}$ alkynyl), unsubstituted —$(C_{1-9}$ haloalkyl), —$(C_{1-4}$ alkylene)$N(R^{48})_2$, —$(C_{1-4}$ alkylene)$OR^{49}$, —$C(=O)N(R^{48})_2$, —$(C_{1-4}$ alkylene)$_p$heterocyclyl optionally substituted with 1-10 $R^{38}$, and -carbocyclyl optionally substituted with 1-12 $R^{39}$; wherein —$(C_{1-4}$ alkylene) is optionally substituted with one or more substituents as defined anywhere herein;

$R^{12}$, $R^{13}$, and $R^{14}$ are independently selected from the group consisting of a single bond, H, halide, unsubstituted —$(C_{1-9}$ alkyl), unsubstituted —$(C_{2-9}$ alkenyl), unsubstituted —$(C_{2-9}$ alkynyl), unsubstituted —$(C_{1-9}$ haloalkyl), —$(C_{1-4}$ alkylene)$_p$N(R^{48})_2$, —$(C_{1-4}$ alkylene)$_p$OR$^{49}$, —$C(=O)N(R^{48})_2$, —$(C_{1-4}$ alkylene)$_p$heterocyclyl optionally substituted with 1-10 $R^{38}$, and -carbocyclyl optionally substituted with 1-12 $R^9$; wherein each —$(C_{1-4}$ alkylene) is, independently, optionally substituted with one or more substituents as defined anywhere herein;

alternatively, one of $R^{11}$ and $R^{12}$, $R^{12}$ and $R^{13}$, or $R^{14}$ and $R^{11}$ are taken together to form a ring which is selected from the group consisting of -heterocyclyl optionally substituted with 1-10 $R^{40}$ and -carbocyclyl optionally substituted with 1-12 $R^{41}$;

$R^{15}$ is selected from the group consisting of a single bond, H, unsubstituted —$(C_{1-9}$ alkyl), unsubstituted —$(C_{2-9}$ alkenyl), unsubstituted —$(C_{2-9}$ alkynyl), unsubstituted —$(C_{1-9}$ haloalkyl), —$(C_{1-4}$ alkylene)$N(R^{48})_2$, —$(C_{1-4}$ alkylene)$OR^{49}$, —$C(=O)N(R^{48})_2$, —$(C_{1-4}$ alkylene)$_p$heterocyclyl optionally substituted with 1-10 $R^{38}$, and -carbocyclyl optionally substituted with 1-12 $R^9$; wherein —$(C_{1-4}$ alkylene) is optionally substituted with one or more substituents as defined anywhere herein;

$R^{16}$ and $R^{17}$ are independently selected from the group consisting of a single bond, H, halide, unsubstituted —$(C_{1-9}$ alkyl), unsubstituted —$(C_{2-9}$ alkenyl), unsubstituted —$(C_{2-9}$ alkynyl), unsubstituted —$(C_{1-9}$ haloalkyl), —$(C_{1-4}$ alkylene)$_p$N(R^{48})_2$, —$(C_{1-4}$ alkylene)$_p$OR$^{49}$, —$C(=O)N(R^{48})_2$, —$(C_{1-4}$ alkylene)$_p$heterocyclyl optionally substituted with 1-10 $R^{38}$, and -carbocyclyl optionally substituted with 1-12 $R^{39}$; wherein each —$(C_{1-4}$ alkylene) is, independently, optionally substituted with one or more substituents as defined anywhere herein;

alternatively, one of $R^{15}$ and $R^{16}$ or $R^{16}$ and $R^{17}$ are taken together to form a ring which is selected from the group consisting of -heterocyclyl optionally substituted with 1-10 $R^{40}$ and -carbocyclyl optionally substituted with 1-12 $R^{41}$;

$R^{18}$ is selected from the group consisting of a single bond, H, unsubstituted —$(C_{1-9}$ alkyl), unsubstituted —$(C_{2-9}$ alkenyl), unsubstituted —$(C_{2-9}$ alkynyl), unsubstituted —$(C_{1-9}$ haloalkyl), —$(C_{1-4}$ alkylene)$N(R^{48})_2$, —$(C_{1-4}$ alkylene)$OR^{49}$, —$C(=O)N(R^{48})_2$, —$(C_{1-4}$ alkylene)$_p$heterocyclyl optionally substituted with 1-10 $R^{38}$, and -carbocyclyl optionally substituted with 1-12 $R^9$; wherein —$(C_{1-4}$ alkylene) is optionally substituted with one or more substituents as defined anywhere herein;

$R^{19}$ and $R^{20}$ are independently selected from the group consisting of a single bond, H, halide, unsubstituted —$(C_{1-9}$ alkyl), unsubstituted —$(C_{2-9}$ alkenyl), unsubstituted —$(C_{2-9}$ alkynyl), unsubstituted —$(C_{1-9}$ haloalkyl), —$(C_{1-4}$ alkylene)$_p$N(R^{48})_2$, —$(C_{1-4}$ alkylene)$_p$OR$^{49}$, —$C(=O)N(R^{48})_2$, —$(C_{1-4}$ alkylene)$_p$heterocyclyl optionally substituted with 1-10 $R^{38}$, and -carbocyclyl optionally substituted with 1-12 $R^9$; wherein each —$(C_{1-4}$ alkylene) is, independently, optionally substituted with one or more substituents as defined anywhere herein;

alternatively, one of $R^{18}$ and $R^{19}$ or $R^{18}$ and $R^{20}$ are taken together to form a heterocyclyl optionally substituted with 1-10 $R^{40}$;

$R^{21}$ is selected from the group consisting of a single bond, H, unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), —($C_{1-4}$ alkylene)N($R^{48}$)$_2$, —($C_{1-4}$ alkylene)$_p$OR$^{49}$, —C(=O)N($R^{48}$)$_2$, —($C_{1-4}$ alkylene)$_p$heterocyclyl optionally substituted with 1-10 $R^{38}$, and -carbocyclyl optionally substituted with 1-12 $R^{39}$; wherein —($C_{1-4}$ alkylene) is optionally substituted with one or more substituents as defined anywhere herein;

$R^{22}$ and $R^{23}$ are independently selected from the group consisting of a single bond, H, halide, unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), —($C_{1-4}$ alkylene)$_p$N($R^{48}$)$_2$, —($C_{1-4}$ alkylene)$_p$OR$^{49}$, —C(=O)N($R^{48}$)$_2$, —($C_{1-4}$ alkylene)$_p$heterocyclyl optionally substituted with 1-10 $R^{38}$, and -carbocyclyl optionally substituted with 1-12 $R^{39}$; wherein each —($C_{1-4}$ alkylene) is, independently, optionally substituted with one or more substituents as defined anywhere herein;

alternatively, $R^{22}$ and $R^{23}$ are taken together to form a ring which is selected from the group consisting of -heterocyclyl optionally substituted with 1-10 $R^{40}$ and -carbocyclyl optionally substituted with 1-12 $R^{41}$;

$R^{24}$, $R^{25}$, and $R^{26}$ are independently selected from the group consisting of a single bond, H, halide, unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), —($C_{1-4}$ alkylene)$_p$N($R^{48}$)$_2$, —($C_{1-4}$ alkylene)$_p$OR$^{49}$, —C(=O)N($R^{48}$)$_2$, —($C_{1-4}$ alkylene)$_p$heterocyclyl optionally substituted with 1-10 $R^{38}$, and -carbocyclyl optionally substituted with 1-12 $R^{39}$; wherein each —($C_{1-4}$ alkylene) is, independently, optionally substituted with one or more substituents as defined anywhere herein;

alternatively, one of $R^{24}$ and $R^{25}$ or $R^{25}$ and $R^{26}$ are taken together to form a ring which is selected from the group consisting of -heterocyclyl optionally substituted with 1-10 $R^{40}$ and -carbocyclyl optionally substituted with 1-12 $R^{41}$;

$R^{27}$, $R^{28}$, and $R^{29}$ are independently selected from the group consisting of a single bond, H, halide, unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), —($C_{1-4}$ alkylene)$_p$N($R^{48}$)$_2$, —($C_{1-4}$ alkylene)$_p$OR$^{49}$, —C(=O)N($R^{48}$)$_2$, —($C_{1-4}$ alkylene)$_p$heterocyclyl optionally substituted with 1-10 $R^{38}$, and -carbocyclyl optionally substituted with 1-12 $R^{39}$; wherein each —($C_{1-4}$ alkylene) is, independently, optionally substituted with one or more substituents as defined anywhere herein;

alternatively, $R^{27}$ and $R^{28}$ are taken together to form a ring which is selected from the group consisting of -heterocyclyl optionally substituted with 1-10 $R^{40}$ and -carbocyclyl optionally substituted with 1-12 $R^{41}$;

$R^{30}$ and $R^{31}$ are independently selected from the group consisting of a single bond, H, halide, unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), —($C_{1-4}$ alkylene)$_p$N($R^{48}$)$_2$, —($C_{1-4}$ alkylene)$_p$OR$^{49}$, —C(=O)N($R^{48}$)$_2$, —($C_{1-4}$ alkylene)$_p$heterocyclyl optionally substituted with 1-10 $R^{38}$, and -carbocyclyl optionally substituted with 1-12 $R^{39}$; wherein each —($C_{1-4}$ alkylene) is, independently, optionally substituted with one or more substituents as defined anywhere herein;

alternatively, $R^{30}$ and $R^{31}$ are taken together to form a ring which is selected from the group consisting of -heterocyclyl optionally substituted with 1-10 $R^{40}$ and -carbocyclyl optionally substituted with 1-12 $R^{41}$;

$R^{32}$ and $R^{33}$ are independently selected from the group consisting of a single bond, H, halide, unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), —($C_{1-4}$ alkylene)$_p$N($R^{48}$)$_2$, —($C_{1-4}$ alkylene)$_p$OR$^{49}$, —C(=O)N($R^{48}$)$_2$, —($C_{1-4}$ alkylene)$_p$heterocyclyl optionally substituted with 1-10 $R^{38}$, and -carbocyclyl optionally substituted with 1-12 $R^{39}$; wherein each —($C_{1-4}$ alkylene) is, independently, optionally substituted with one or more substituents as defined anywhere herein;

$R^{34}$ and $R^{35}$ are independently selected from the group consisting of a single bond, H, halide, unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), —($C_{1-4}$ alkylene)$_p$N($R^{48}$)$_2$, —($C_{1-4}$ alkylene)$_p$OR$^{49}$, —C(=O)N($R^{48}$)$_2$, —($C_{1-4}$ alkylene)$_p$heterocyclyl optionally substituted with 1-10 $R^{38}$, and -carbocyclyl optionally substituted with 1-12 $R^{39}$; wherein each —($C_{1-4}$ alkylene) is, independently, optionally substituted with one or more substituents as defined anywhere herein;

alternatively, $R^{34}$ and $R^{35}$ are taken together to form a ring which is selected from the group consisting of -heterocyclyl optionally substituted with 1-10 $R^{40}$ and -carbocyclyl optionally substituted with 1-12 $R^{41}$;

each $R^{36}$ is independently selected from the group consisting of halide, unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), —XR$^{42}$, —C(=O)N($R^{47}$)$_2$, —($C_{1-4}$ alkylene)$_p$N($R^{50}$)$_2$, —($C_{1-4}$ alkylene)$_p$heterocyclyl optionally substituted with 1-10 $R^{43}$, and —($C_{1-4}$ alkylene)$_p$carbocyclyl optionally substituted with 1-12 $R^{44}$; wherein each —($C_{1-4}$ alkylene) is, independently, optionally substituted with one or more substituents as defined anywhere herein;

each $R^{37}$ is independently selected from the group consisting of halide, unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), —XR$^{42}$, —C(=O)N($R^{47}$)$_2$, —($C_{1-4}$ alkylene)$_p$N($R^{50}$)$_2$, —($C_{1-4}$ alkylene)$_p$heterocyclyl optionally substituted with 1-10 $R^{43}$, and —($C_{1-4}$ alkylene)$_p$carbocyclyl optionally substituted with 1-12 $R^{44}$; wherein each —($C_{1-4}$ alkylene) is, independently, optionally substituted with one or more substituents as defined anywhere herein;

each $R^{38}$ is independently selected from the group consisting of halide, unsubstituted —($C_{1-5}$ alkyl), unsubstituted —($C_{2-5}$ alkenyl), unsubstituted —($C_{2-5}$ alkynyl), unsubstituted —($C_{1-5}$ haloalkyl), —CN, and —($C_{1-4}$ alkylene)$_p$carbocyclyl optionally substituted with 1-12 $R^{44}$; wherein each —($C_{1-4}$ alkylene) is, independently, optionally substituted with one or more substituents as defined anywhere herein;

each $R^{39}$ is independently selected from the group consisting of halide, unsubstituted —($C_{1-5}$ alkyl), unsubstituted —($C_{2-5}$ alkenyl), unsubstituted —($C_{2-5}$ alkynyl), unsubstituted —($C_{1-5}$ haloalkyl), —CN, and —($C_{1-4}$ alkylene)$_p$carbocyclyl optionally substituted with 1-12 $R^{44}$; wherein each —($C_{1-4}$ alkylene) is, independently, optionally substituted with one or more substituents as defined anywhere herein;

each $R^{40}$ is independently selected from the group consisting of halide, unsubstituted —($C_{1-5}$ alkyl), unsubstituted —($C_{2-5}$ alkenyl), unsubstituted —($C_{2-5}$ alkynyl), unsubstituted —($C_{1-5}$ haloalkyl), —CN, and —($C_{1-4}$ alkylene)$_p$carbocyclyl optionally substituted with 1-12 $R^{44}$; wherein each —($C_{1-4}$ alkylene) is, independently, optionally substituted with one or more substituents as defined anywhere herein;

each $R^{41}$ is independently selected from the group consisting of halide, unsubstituted —($C_{1-5}$ alkyl), unsubstituted —($C_{2-5}$ alkenyl), unsubstituted —($C_{2-5}$ alkynyl), unsubstituted —($C_{1-5}$ haloalkyl), and —CN;

each $R^{42}$ is independently selected from the group consisting of H, unsubstituted —($C_{1-5}$ alkyl), unsubstituted —($C_{2-5}$ alkenyl), unsubstituted —($C_{2-5}$ alkynyl), unsubstituted —($C_{1-5}$ haloalkyl), —($C_{1-4}$ alkylene)N($R^{48}$)$_2$, —($C_{1-4}$ alkylene)$_p$aryl optionally substituted with 1-10 $R^{46}$, —($C_{1-4}$ alkylene)$_p$heterocyclyl optionally substituted with 1-12 $R^{43}$, and —($C_{1-4}$ alkylene)$_p$carbocyclyl optionally substituted with 1-12 $R^{44}$; wherein each —($C_{1-4}$ alkylene) is, independently, optionally substituted with one or more substituents as defined anywhere herein;

each $R^{43}$ is independently selected from the group consisting of halide, unsubstituted —($C_{1-5}$ alkyl), unsubstituted —($C_{2-5}$ alkenyl), unsubstituted —($C_{2-5}$ alkynyl), unsubstituted —($C_{1-5}$ haloalkyl), —CN, —OH, —C(=O)$R^{51}$, —N($R^{50}$)$_2$, and —($C_{1-4}$ alkylene)$_p$carbocyclyl optionally substituted with 1-12 $R^{44}$; wherein each —($C_{1-4}$ alkylene) is, independently, optionally substituted with one or more substituents as defined anywhere herein;

each $R^{44}$ is selected from the group consisting of halide, unsubstituted —($C_{1-5}$ alkyl), unsubstituted —($C_{2-5}$ alkenyl), unsubstituted —($C_{2-5}$ alkynyl), unsubstituted —($C_{1-5}$ haloalkyl), and —CN;

each $R^{46}$ is independently selected from the group consisting of halide, unsubstituted —($C_{1-5}$ alkyl), unsubstituted —($C_{2-5}$ alkenyl), unsubstituted —($C_{2-5}$ alkynyl), unsubstituted —($C_{1-5}$ haloalkyl), and —CN;

each $R^{47}$ is independently selected from the group consisting of H, unsubstituted —($C_{1-5}$ alkyl), unsubstituted —($C_{2-5}$ alkenyl), unsubstituted —($C_{2-5}$ alkynyl), and unsubstituted —($C_{1-5}$ haloalkyl);

each $R^{48}$ is independently selected from the group consisting of H, unsubstituted —($C_{1-5}$ alkyl), unsubstituted —($C_{2-5}$ alkenyl), unsubstituted —($C_{2-5}$ alkynyl), and unsubstituted —($C_{1-5}$ haloalkyl);

each $R^{49}$ is independently selected from the group consisting of H, unsubstituted —($C_{1-5}$ alkyl), unsubstituted —($C_{2-5}$ alkenyl), unsubstituted —($C_{2-5}$ alkynyl), and unsubstituted —($C_{1-5}$ haloalkyl);

each $R^{50}$ is independently selected from the group consisting of H, unsubstituted —($C_{1-5}$ alkyl), unsubstituted —($C_{2-5}$ alkenyl), unsubstituted —($C_{2-5}$ alkynyl), unsubstituted —($C_{1-5}$ haloalkyl), and —($C_{1-4}$ alkylene)N($R^{48}$)$_2$; wherein —($C_{1-4}$ alkylene) is optionally substituted with one or more substituents as defined anywhere herein;

each $R^{51}$ is a heteroaryl optionally substituted with 1-6 $R^{52}$;

each $R^{52}$ is a -heterocyclyl optionally substituted with 1-10 $R^{46}$;

each X is selected from the group consisting of O, S, and $NR^{48}$;

each Y is selected from the group consisting of O and S; and each p is independently 0 or 1.

Some embodiments include stereoisomers and pharmaceutically acceptable salts of a compound of Formula (I). Some embodiments include pharmaceutically acceptable salts of a compound of Formula (I).

Some embodiments include pro-drugs of a compound of Formula (I).

Some embodiments of the present disclosure include pharmaceutical compositions comprising a compound of Formula (I) and a pharmaceutically acceptable carrier, diluent, or excipient.

Other embodiments disclosed herein include methods of inhibiting one or more members of the Wnt pathway, including one or more Wnt proteins by administering to a patient affected by a disorder or disease in which aberrant Wnt signaling is implicated, such as cancer and other diseases associated with abnormal angiogenesis, cellular proliferation, cell cycling and mutations in Wnt signaling components, a compound according to Formula (I). Accordingly, the compounds and compositions provided herein can be used to treat cancer, to reduce or inhibit angiogenesis, to reduce or inhibit cellular proliferation and correct a genetic disorder due to mutations in Wnt signaling components.

Non-limiting examples of diseases which can be treated with the compounds and compositions provided herein include a variety of cancers, diabetic retinopathy, pulmonary fibrosis, rheumatoid arthritis, sepsis, ankylosing spondylitis, psoriasis, scleroderma, mycotic and viral infections, osteochondrodysplasia, Alzheimer's disease, lung disease, bone/osteoporotic (wrist, spine, shoulder and hip) fractures, articular cartilage (chondral) defects, degenerative disc disease (or intervertebral disc degeneration), polyposis coli, osteoporosis-pseudoglioma syndrome, familial exudative vitreoretinopathy, retinal angiogenesis, early coronary disease, tetra-amelia syndrome, Müllerian-duct regression and virilization, SERKAL syndrome, diabetes mellitus type 2, Fuhrmann syndrome, Al-Awadi/Raas-Rothschild/Schinzel phocomelia syndrome, odonto-onycho-dermal dysplasia, obesity, split-hand/foot malformation, caudal duplication syndrome, tooth agenesis, Wilms tumor, skeletal dysplasia, focal dermal hypoplasia, autosomal recessive anonychia, neural tube defects, alpha-thalassemia (ATRX) syndrome, fragile X syndrome, ICF syndrome, Angelman syndrome, Prader-Willi syndrome, Beckwith-Wiedemann Syndrome, Norrie disease, and Rett syndrome.

Some embodiments of the present disclosure include methods to prepare compounds of Formula (I).

It is to be understood that both the foregoing general description and the following detailed description are exemplary and explanatory only and are not restrictive of the invention, as claimed.

DETAILED DESCRIPTION

Provided herein are compositions and methods for inhibiting one or more members of the Wnt pathway, including one or more Wnt proteins.

Some embodiments provided herein relate to a method for treating a disease or disorder including, but not limited to, cancers, diabetic retinopathy, pulmonary fibrosis, rheumatoid arthritis, sepsis, ankylosing spondylitis, psoriasis, scleroderma, mycotic and viral infections, bone and cartilage diseases, Alzheimer's disease, lung disease, osteoarthritis, bone/osteoporotic (wrist, spine, shoulder and hip) fractures, articular cartilage (chondral) defects, degenerative disc disease (or intervertebral disc degeneration), polyposis coli, bone density and vascular defects in the eye (Osteoporosis-pseudoglioma Syndrome, OPPG), familial exudative vitreoretinopathy, retinal angiogenesis, early coronary disease, tetra-amelia, Müllerian-duct regression and virilization, SERKAL syndrome, type II diabetes, Fuhrmann syndrome, Al-Awadi/Raas-Rothschild/Schinzel phocomelia syndrome, odonto-onycho-dermal dysplasia, obesity, split-hand/foot malformation, caudal duplication, tooth agenesis, Wilms tumor, skeletal dysplasia, focal dermal hypoplasia, autosomal recessive anonychia, neural tube defects, alpha-thalassemia (ATRX) syndrome, fragile X syndrome, ICF syndrome, Angelman syndrome, Prader-Willi syndrome, Beckwith-Wiedemann Syndrome, Norrie disease, and Rett syndrome.

In some embodiments, non-limiting examples of bone and cartilage diseases which can be treated with the compounds and compositions provided herein include bone spur (osteophytes), craniosynostosis, fibrodysplasia ossificans progressiva, fibrous dysplasia, giant cell tumor of bone, hip labral tear, meniscal tears, bone/osteoporotic (wrist, spine, shoulder and hip) fractures, articular cartilage (chondral) defects, degenerative disc disease (or intervertebral disc degeneration), osteochondritis dissecans, osteochondroma (bone tumor), osteopetrosis, relapsing polychondritis, and Salter-Harris fractures.

In some embodiments, pharmaceutical compositions are provided that are effective for treatment of a disease of an animal, e.g., a mammal, caused by the pathological activation or mutations of the Wnt pathway. The composition includes a pharmaceutically acceptable carrier and a compound as described herein.

Definitions

Unless defined otherwise, all technical and scientific terms used herein have the same meaning as is commonly understood by one of ordinary skill in the art to which this disclosure belongs. All patents, applications, published applications, and other publications are incorporated by reference in their entirety. In the event that there is a plurality of definitions for a term herein, those in this section prevail unless stated otherwise.

As used herein, "alkyl" means a branched, or straight chain chemical group containing only carbon and hydrogen, such as methyl, ethyl, n-propyl, iso-propyl, n-butyl, iso-butyl, sec-butyl, tert-butyl, n-pentyl, iso-pentyl, sec-pentyl and neo-pentyl. Alkyl groups can either be unsubstituted or substituted with one or more substituents. In some embodiments, alkyl groups include 1 to 9 carbon atoms (for example, 1 to 6 carbon atoms, 1 to 4 carbon atoms, or 1 to 2 carbon atoms).

As used herein, "alkenyl" means a straight or branched chain chemical group containing only carbon and hydrogen and containing at least one carbon-carbon double bond, such as ethenyl, 1-propenyl, 2-propenyl, 2-methyl-1-propenyl, 1-butenyl, 2-butenyl, and the like. In various embodiments, alkenyl groups can either be unsubstituted or substituted with one or more substituents. Typically, alkenyl groups will comprise 2 to 9 carbon atoms (for example, 2 to 6 carbon atoms, 2 to 4 carbon atoms, or 2 carbon atoms).

As used herein, "alkynyl" means a straight or branched chain chemical group containing only carbon and hydrogen and containing at least one carbon-carbon triple bond, such as ethynyl, 1-propynyl, 1-butynyl, 2-butynyl, and the like. In various embodiments, alkynyl groups can either be unsubstituted or substituted with one or more substituents. Typically, alkynyl groups will comprise 2 to 9 carbon atoms (for example, 2 to 6 carbon atoms, 2 to 4 carbon atoms, or 2 carbon atoms).

As used herein, "alkylene" means a bivalent branched, or straight chain chemical group containing only carbon and hydrogen, such as methylene, ethylene, n-propylene, iso-propylene, n-butylene, iso-butylene, sec-butylene, tert-butylene, n-pentylene, iso-pentylene, sec-pentylene and neo-pentylene. Alkylene groups can either be unsubstituted or substituted with one or more substituents. Alkylene groups can be saturated or unsaturated (e.g., containing —C=C— or —C≡C— subunits), at one or several positions. In some embodiments, alkylene groups include 1 to 9 carbon atoms (for example, 1 to 6 carbon atoms, 1 to 4 carbon atoms, or 1 to 2 carbon atoms).

As used herein, "alkenylene" means a bivalent branched, or straight chain chemical group containing only carbon and hydrogen and containing at least one carbon-carbon double bond, such as ethenylene, 1-propenylene, 2-propenylene, 2-methyl-1-propenylene, 1-butenylene, 2-butenylene, and the like. In various embodiments, alkenylene groups can either be unsubstituted or substituted with one or more substituents. Typically, alkenylene groups will comprise 2 to 9 carbon atoms (for example, 2 to 6 carbon atoms, 2 to 4 carbon atoms, or 2 carbon atoms).

As used herein, "alkynylene" means a bivalent branched, or straight chain chemical group containing only carbon and hydrogen and containing at least one carbon-carbon triple bond, such as ethynylene, 1-propynylene, 1-butynylene, 2-butynylene, and the like. In various embodiments, alkynylene groups can either be unsubstituted or substituted with one or more substituents. Typically, alkynylene groups will comprise 2 to 9 carbon atoms (for example, 2 to 6 carbon atoms, 2 to 4 carbon atoms, or 2 carbon atoms).

As used herein, "carbocyclyl" means a cyclic ring system containing only carbon atoms in the ring system backbone, such as cyclopropyl, cyclobutyl, cyclopentyl, cyclohexyl, and cyclohexenyl. Carbocyclyls may include multiple fused rings. Carbocyclyls may have any degree of saturation provided that at least one ring in the ring system is not aromatic. Carbocyclyl groups can either be unsubstituted or substituted with one or more substituents. In some embodiments, carbocyclyl groups include 3 to 10 carbon atoms, for example, 3 to 6 carbon atoms.

As used herein, "aryl" means a mono-, bi-, tri- or polycyclic group with only carbon atoms present in the ring backbone having 5 to 14 ring atoms, alternatively 5, 6, 9, or 10 ring atoms; and having 6, 10, or 14 pi electrons shared in a cyclic array; wherein at least one ring in the system is aromatic. Aryl groups can either be unsubstituted or substituted with one or more substituents. Examples of aryl include phenyl, naphthyl, tetrahydronaphthyl, 2,3-dihydro-1H-indenyl, and others. In some embodiments, the aryl is phenyl.

As used herein, "arylalkylene" means an aryl-alkylene-group in which the aryl and alkylene moieties are as previously described. In some embodiments, arylalkylene groups contain a $C_{1-4}$alkylene moiety. Exemplary arylalkylene groups include benzyl and 2-phenethyl.

As used herein, the term "heteroaryl" means a mono-, bi-, tri- or polycyclic group having 5 to 14 ring atoms, alternatively 5, 6, 9, or 10 ring atoms; and having 6, 10, or 14 pi electrons shared in a cyclic array; wherein at least one ring in the system is aromatic, and at least one ring in the system contains one or more heteroatoms independently selected from the group consisting of N, O, and S. Heteroaryl groups can either be unsubstituted or substituted with one or more substituents. Examples of heteroaryl include thienyl, pyridinyl, furyl, oxazolyl, oxadiazolyl, pyrrolyl, imidazolyl, triazolyl, thiodiazolyl, pyrazolyl, isoxazolyl, thiadiazolyl, pyranyl, pyrazinyl, pyrimidinyl, pyridazinyl, triazinyl, thiazolyl benzothienyl, benzoxadiazolyl, benzofuranyl, benzimidazolyl, benzotriazolyl, cinnolinyl, indazolyl, indolyl, isoquinolinyl, isothiazolyl, naphthyridinyl, purinyl, thienopyridinyl, pyrido[2,3-d]pyrimidinyl, pyrrolo[2,3-b]pyridinyl, quinazolinyl, quinolinyl, thieno[2,3-c]pyridinyl, pyrazolo[3,4-b]pyridinyl, pyrazolo[3,4-c]pyridinyl, pyrazolo[4,3-c]pyridine, pyrazolo[4,3-b]pyridinyl, tetrazolyl, chromane, 2,3-dihydrobenzo[b][1,4]dioxine, benzo[d][1,3]dioxole, 2,3-dihydrobenzofuran, tetrahydroquinoline, 2,3-dihydrobenzo[b][1,4]oxathiine, and others. In some embodiments, the heteroaryl is selected from thienyl, pyridinyl, furyl, pyrazolyl, imidazolyl, pyranyl, pyrazinyl, and pyrimidinyl.

As used herein, "halo", "halide" or "halogen" is a chloro, bromo, fluoro, or iodo atom radical. In some embodiments, a halo is a chloro, bromo or fluoro. For example, a halide can be fluoro.

As used herein, "haloalkyl" means a hydrocarbon substituent, which is a linear or branched, alkyl, alkenyl or alkynyl substituted with one or more chloro, bromo, fluoro, and/or iodo atom(s). In some embodiments, a haloalkyl is a fluoroalkyls, wherein one or more of the hydrogen atoms have been substituted by fluoro. In some embodiments, haloalkyls are of 1 to about 3 carbons in length (e.g., 1 to about 2 carbons in length or 1 carbon in length). The term "haloalkylene" means a diradical variant of haloalkyl, and such diradicals may act as spacers between radicals, other atoms, or between a ring and another functional group.

As used herein, "heterocyclyl" means a nonaromatic cyclic ring system comprising at least one heteroatom in the ring system backbone. Heterocyclyls may include multiple fused rings. Heterocyclyls may be substituted or unsubstituted with one or more substituents. In some embodiments, heterocycles have 3-11 members. In six membered monocyclic heterocycles, the heteroatom(s) are selected from one to three of O, N or S, and wherein when the heterocycle is five membered, it can have one or two heteroatoms selected from O, N, or S. Examples of heterocyclyl include azirinyl, aziridinyl, azetidinyl, oxetanyl, thietanyl, 1,4,2-dithiazolyl, dihydropyridinyl, 1,3-dioxanyl, 1,4-dioxanyl, 1,3-dioxolanyl, morpholinyl, thiomorpholinyl, piperazinyl, pyranyl, pyrrolidinyl, tetrahydrofuryl, tetrahydropyridinyl, oxazinyl, thiazinyl, thiinyl, thiazolidinyl, isothiazolidinyl, oxazolidinyl, isoxazolidinyl, piperidinyl, pyrazolidinyl imidazolidinyl, thiomorpholinyl, and others. In some embodiments, the heterocyclyl is selected from azetidinyl, morpholinyl, piperazinyl, pyrrolidinyl, and tetrahydropyridinyl.

As used herein, "monocyclic heterocyclyl" means a single nonaromatic cyclic ring comprising at least one heteroatom in the ring system backbone. Heterocyclyls may be substituted or unsubstituted with one or more substituents. In some embodiments, heterocycles have 3-7 members. In six membered monocyclic heterocycles, the heteroatom(s) are selected from one to three of O, N or S, and wherein when the heterocycle is five membered, it can have one or two heteroatoms selected from O, N, or S. Examples of heterocyclyls include azirinyl, aziridinyl, azetidinyl, oxetanyl, thietanyl, 1,4,2-dithiazolyl, dihydropyridinyl, 1,3-dioxanyl, 1,4-dioxanyl, 1,3-dioxolanyl, morpholinyl, thiomorpholinyl, piperazinyl, pyranyl, pyrrolidinyl, tetrahydrofuryl, tetrahydropyridinyl, oxazinyl, thiazinyl, thiinyl, thiazolidinyl, isothiazolidinyl, oxazolidinyl, isoxazolidinyl, piperidinyl, pyrazolidinyl imidazolidinyl, thiomorpholinyl, and others.

As used herein, "bicyclic heterocyclyl" means a nonaromatic bicyclic ring system comprising at least one heteroatom in the ring system backbone. Bicyclic heterocyclyls may be substituted or unsubstituted with one or more substituents. In some embodiments, bicyclic heterocycles have 4-11 members with the heteroatom(s) being selected from one to five of O, N or S. Examples of bicyclic heterocyclyls include 2-azabicyclo[1.1.0]butane, 2-azabicyclo[2.1.0]pentane, 2-azabicyclo[1.1.1]pentane, 3-azabicyclo[3.1.0]hexane, 5-azabicyclo[2.1.1]hexane, 3-azabicyclo[3.2.0]heptane, octahydrocyclopenta[c]pyrrole, 3-azabicyclo[4.1.0]heptane, 7-azabicyclo[2.2.1]heptane, 6-azabicyclo[3.1.1]heptane, 7-azabicyclo[4.2.0]octane, 2-azabicyclo[2.2.2]octane, and the like.

As used herein, "spirocyclic heterocyclyl" means a nonaromatic bicyclic ring system comprising at least one heteroatom in the ring system backbone and with the rings connected through just one atom. Spirocyclic heterocyclyls may be substituted or unsubstituted with one or more substituents. In some embodiments, spirocyclic heterocycles have 5-11 members with the heteroatom(s) being selected from one to five of O, N or S. Examples of spirocyclic heterocyclyls include 2-azaspiro[2.2]pentane, 4-azaspiro[2.5]octane, 1-azaspiro[3.5]nonane, 2-azaspiro[3.5]nonane, 7-azaspiro[3.5]nonane, 2-azaspiro[4.4]nonane, 6-azaspiro[2.6]nonane, 1,7-diazaspiro[4.5]decane, 2,5-diazaspiro[3.6]decane, and the like.

The term "substituted" refers to moieties having substituents replacing a hydrogen on one or more non-hydrogen atoms of the molecule. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. Substituents can include, for example, —($C_{1-9}$ alkyl) optionally substituted with one or more of hydroxyl, —$NH_2$, —$NH(C_{1-3}$ alkyl), and —$N(C_{1-3}$ alkyl)$_2$; —($C_{1-9}$ haloalkyl); a halide; a hydroxyl; a carbonyl [such as —C(O)OR, and —C(O)R]; a thiocarbonyl [such as —C(S)OR, —C(O)SR, and —C(S)R]; —($C_{1-9}$ alkoxyl) optionally substituted with one or more of halide, hydroxyl, —$NH_2$, —$NH(C_{1-3}$ alkyl), and —$N(C_{1-3}$ alkyl)$_2$; —OPO(OH)$_2$; a phosphonate [such as —PO(OH)$_2$ and —PO(OR')$_2$]; —OPO(OR')R"; —NRR'; —C(O)NRR'; —C(NR)NR'R"; —C(NR')R"; a cyano; a nitro; an azido; —SH; —S—R; —OSO$_2$(OR); a sulfonate [such as —SO$_2$(OH) and —SO$_2$(OR)]; —SO$_2$NR'R"; and —SO$_2$R; in which each occurrence of R, R' and R" are independently selected from H; —($C_{1-9}$ alkyl); $C_{6-10}$ aryl optionally substituted with from 1-3R'"; 5-10 membered heteroaryl having from 1-4 heteroatoms independently selected from N, O, and S and optionally substituted with from 1-3 R'"; $C_{3-7}$ carbocyclyl optionally substituted with from 1-3 R'"; and 3-8 membered heterocyclyl having from 1-4 heteroatoms independently selected from N, O, and S and optionally substituted with from 1-3 R'"; wherein each R'" is independently selected from —($C_{1-6}$ alkyl), —($C_{1-6}$ haloalkyl), a halide (e.g., F), a hydroxyl, —C(O)OR, —C(O)R, —($C_{1-6}$ alkoxy), —NRR', —C(O)NRR', and a cyano, in which each occurrence of R and R' is independently selected from H and —($C_{1-6}$ alkyl). In some embodiments, the substituent is selected from —($C_{1-6}$ alkyl), —($C_{1-6}$ haloalkyl), a halide (e.g., F), a hydroxyl, —C(O)OR, —C(O)R, —($C_{1-6}$ alkoxyl), —NRR', —C(O)NRR', and a cyano, in which each occurrence of R and R' is independently selected from H and —($C_{1-6}$ alkyl).

As used herein, when two groups are indicated to be "linked" or "bonded" to form a "ring", it is to be understood that a bond is formed between the two groups and may involve replacement of a hydrogen atom on one or both groups with the bond, thereby forming a carbocyclyl, heterocyclyl, aryl, or heteroaryl ring. The skilled artisan will recognize that such rings can and are readily formed by routine chemical reactions. In some embodiments, such rings have from 3-7 members, for example, 5 or 6 members.

The skilled artisan will recognize that some structures described herein may be resonance forms or tautomers of compounds that may be fairly represented by other chemical structures, even when kinetically, the artisan recognizes that such structures are only a very small portion of a sample of such compound(s). Such compounds are clearly contemplated within the scope of this disclosure, though such resonance forms or tautomers are not represented herein.

The compounds provided herein may encompass various stereochemical forms. The compounds also encompass diastereomers as well as optical isomers, e.g., mixtures of enantiomers including racemic mixtures, as well as individual enantiomers and diastereomers, which arise as a consequence of structural asymmetry in certain compounds. Separation of the individual isomers or selective synthesis of the individual isomers is accomplished by application of various methods which are well known to practitioners in the art. Unless otherwise indicated, when a disclosed compound is named or depicted by a structure without specifying the stereochemistry and has one or more chiral centers, it is understood to represent all possible stereoisomers of the compound.

The present disclosure includes all pharmaceutically acceptable isotopically labeled compounds of Formula I wherein one or more atoms are replaced by atoms having the same atomic number, but an atomic mass or mass number different from the atomic mass or mass number which predominates in nature. Examples of isotopes suitable for inclusion in the compounds of the disclosure include, but are not limited to, isotopes of hydrogen, such as $^2$H (deuterium) and $^3$H (tritium), carbon, such as $^{11}$C, $^{13}$C and $^{14}$C, chlorine, such as $^{36}$Cl, fluorine, such as $^{18}$F, iodine, such as $^{123}$I and $^{125}$I, nitrogen, such as $^{13}$N and $^{15}$N, oxygen, such as $^{15}$O, $^{17}$O and $^{18}$O, phosphorus, such as $^{32}$P, and sulfur, such as $^{35}$S.

The term "administration" or "administering" refers to a method of providing a dosage of a compound or pharmaceutical composition to a vertebrate or invertebrate, including a mammal, a bird, a fish, or an amphibian, where the method is, e.g., orally, subcutaneously, intravenously, intralymphatic, intranasally, topically, transdermally, intraperitoneally, intramuscularly, intrapulmonarilly, vaginally, rectally, ontologically, neuro-otologically, intraocularly, subconjuctivally, via anterior eye chamber injection, intravitreally, intraperitoneally, intrathecally, intracysticaly, intrapleurally, via wound irrigation, intrabuccally, intraabdominally, intra-articularly, intra-aurally, intrabronchially, intracapsularly, intrameningeally, via inhalation, via endotracheal or endobronchial instillation, via direct instillation into pulmonary cavities, intraspinally, intrasynovially, intrathoracically, via thoracostomy irrigation, epidurally, intratympanically, intracisternally, intravascularly, intraventricularly, intraosseously, via irrigation of infected bone, or via application as part of any admixture with a prosthetic device. The method of administration can vary depending on various factors, e.g., the components of the pharmaceutical composition, the site of the disease, the disease involved, and the severity of the disease.

A "diagnostic" as used herein is a compound, method, system, or device that assists in the identification or characterization of a health or disease state. The diagnostic can be used in standard assays as is known in the art.

The term "mammal" is used in its usual biological sense. Thus, it specifically includes humans, cattle, horses, monkeys, dogs, cats, mice, rats, cows, sheep, pigs, goats, and non-human primates, but also includes many other species.

The term "pharmaceutically acceptable carrier", "pharmaceutically acceptable diluent" or "pharmaceutically acceptable excipient" includes any and all solvents, co-solvents, complexing agents, dispersion media, coatings, isotonic and absorption delaying agents and the like which are not biologically or otherwise undesirable. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions. In addition, various adjuvants such as are commonly used in the art may be included. These and other such compounds are described in the literature, e.g., in the Merck Index, Merck & Company, Rahway, N.J. Considerations for the inclusion of various components in pharmaceutical compositions are described, e.g., in Gilman et al. (Eds.) (2010); *Goodman and Gilman's: The Pharmacological Basis of Therapeutics*, 12th Ed., The McGraw-Hill Companies.

The term "pharmaceutically acceptable salt" refers to salts that retain the biological effectiveness and properties of the compounds provided herein and, which are not biologically or otherwise undesirable. In many cases, the compounds provided herein are capable of forming acid and/or base salts by virtue of the presence of amino and/or carboxyl groups or groups similar thereto. Many such salts are known in the art, for example, as described in WO 87/05297. Pharmaceutically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese, aluminum, and the like; particularly preferred are the ammonium, potassium, sodium, calcium, and magnesium salts. Organic bases from which salts can be derived include, for example, primary, secondary, and tertiary amines, substituted amines including naturally occurring substituted amines, cyclic amines, basic ion exchange resins, and the like, specifically such as isopropylamine, trimethylamine, diethylamine, triethylamine, tripropylamine, and ethanolamine.

"Patient" as used herein, means a human or a non-human mammal, e.g., a dog, a cat, a mouse, a rat, a cow, a sheep, a pig, a goat, a non-human primate, or a bird, e.g., a chicken, as well as any other vertebrate or invertebrate. In some embodiments, the patient is a human.

A "therapeutically effective amount" of a compound as provided herein is one which is sufficient to achieve the desired physiological effect and may vary according to the nature and severity of the disease condition, and the potency of the compound. "Therapeutically effective amount" is also intended to include one or more of the compounds of Formula I in combination with one or more other agents that are effective to treat the diseases and/or conditions described herein. The combination of compounds can be a synergistic combination. Synergy, as described, for example, by Chou and Talalay, *Advances in Enzyme Regulation* (1984), 22, 27-55, occurs when the effect of the compounds when administered in combination is greater than the additive effect of the compounds when administered alone as a single agent. In general, a synergistic effect is most clearly demonstrated at sub-optimal concentrations of the compounds. It will be appreciated that different concentrations may be employed for prophylaxis than for treatment of an active disease. This amount can further depend upon the patient's height, weight, sex, age and medical history.

A therapeutic effect relieves, to some extent, one or more of the symptoms of the disease.

"Treat," "treatment," or "treating," as used herein refers to administering a compound or pharmaceutical composition as provided herein for therapeutic purposes. The term "therapeutic treatment" refers to administering treatment to a patient already suffering from a disease thus causing a therapeutically beneficial effect, such as ameliorating existing symptoms, ameliorating the underlying metabolic causes of symptoms, postponing or preventing the further development of a disorder, and/or reducing the severity of symptoms that will or are expected to develop.

Compounds

The compounds and compositions described herein can be used as anti-proliferative agents, e.g., anti-cancer and anti-angiogenesis agents, and/or as inhibitors of the Wnt signaling pathway, e.g., for treating diseases or disorders associated with aberrant Wnt signaling. In addition, the compounds can be used as inhibitors of one or more kinases, kinase receptors, or kinase complexes. Such compounds and compositions are also useful for controlling cellular proliferation, differentiation, and/or apoptosis.

Some embodiments of the present disclosure include compounds of Formula I:

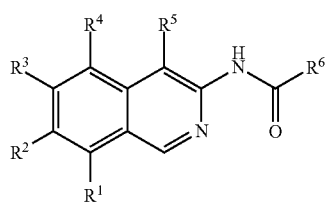

or salts, pharmaceutically acceptable salts, or prodrugs thereof.

In some embodiments, $R^1$, $R^2$, $R^4$, and $R^5$ are independently selected from the group consisting of H, halide, unsubstituted —($C_{1-3}$ haloalkyl), and unsubstituted —($C_{1-3}$ alkyl);

In some embodiments, $R^1$, $R^2$, $R^4$, and $R^5$ are independently selected from the group consisting of H, halide, amino, unsubstituted —($C_{1-3}$ haloalkyl), and unsubstituted —($C_{1-3}$ alkyl).

In some embodiments, $R^1$, $R^2$, $R^4$, and $R^5$ are independently selected from the group consisting of H and halide.

In some embodiments, $R^1$, $R^2$, $R^4$, and $R^5$ are independently selected from the group consisting of H and F.

In some embodiments, $R^1$, $R^2$, $R^4$, and $R^5$ are all H.

In some embodiments, $R^1$ is F, and $R^2$, $R^4$, and $R^5$ are all H.

In some embodiments, $R^2$ is F, and $R^1$, $R^4$, and $R^5$ are all H.

In some embodiments, $R^4$ is F, and $R^1$, $R^2$, and $R^5$ are all H.

In some embodiments, $R^5$ is F, and $R^1$, $R^2$, and $R^4$ are all H.

In some embodiments, $R^3$ is a 5-membered heteroaryl ring optionally substituted as defined anywhere herein.

In some embodiments, $R^3$ is 5-membered heteroaryl ring optionally substituted with 1-4 (e.g., 1-3, 1-2, 1) $R^{45}$;

In some embodiments, $R^3$ is selected from the group consisting of: furanyl optionally substituted with 1-4 (e.g., 1-3, 1-2, 1) $R^{45}$, thiophenyl optionally substituted with 1-4 (e.g., 1-3, 1-2, 1) $R^{45}$, pyrrolyl optionally substituted with 1-4 (e.g., 1-3, 1-2, 1) $R^{45}$,

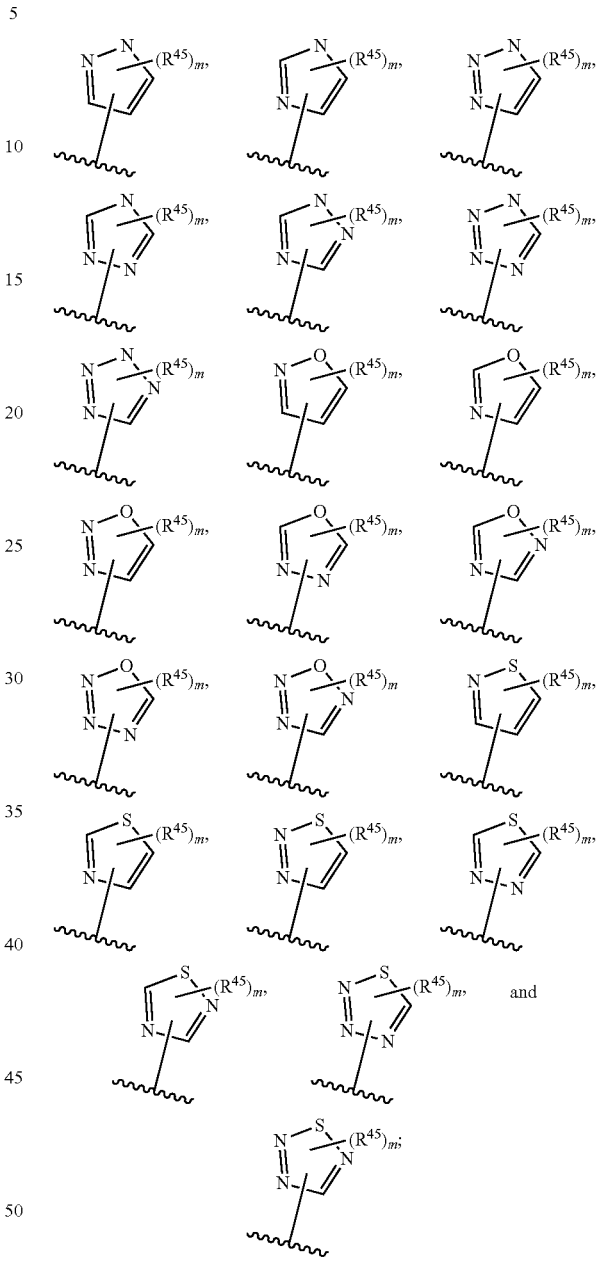

wherein each m is independently 1 to 4 (e.g., 1-3, 1-2, 1).

In some embodiments, $R^3$ is selected from the group consisting of:

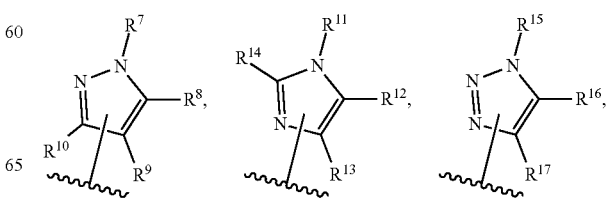

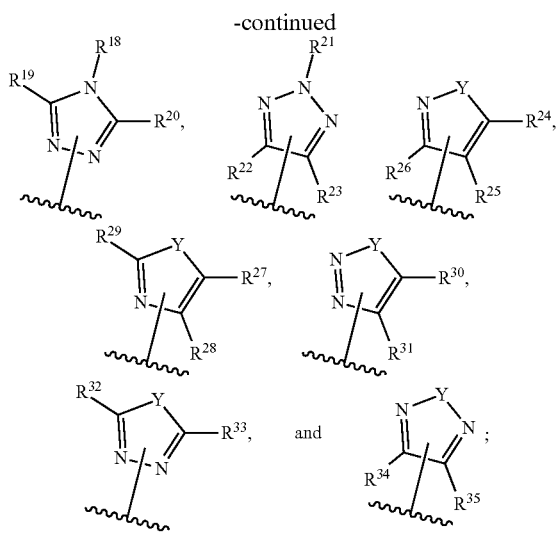

wherein each of $R^7$-$R^{35}$ is, independently, a substituent as defined anywhere herein or a single bond connecting $R^3$ to the isoquinoline ring; wherein only one of $R^7$-$R^{10}$ (when present) is a bond, only one of $R^{11}$-$R^{14}$ (when present) is a bond, only one of $R^{15}$-$R^{17}$ (when present) is a bond, only one of $R^{18}$-$R^{20}$ (when present) is a bond, only one of $R^{21}$-$R^{23}$ (when present) is a bond, only one of $R^{24}$-$R^{26}$ (when present) is a bond, only one of $R^{27}$-$R^{29}$ (when present) is a bond, only one of $R^{30}$-$R^{31}$ (when present) is a bond, only one of $R^{32}$-$R^{33}$ (when present) is a bond, and only one of $R^{34}$-$R^{35}$ (when present) is a bond; for purposes of clarification, any one of the nitrogen atoms attached to $R^7$, $R^{11}$, $R^{15}$, $R^{18}$, or $R^{21}$ can serve as the point of attachment of $R^3$ to the isoquinoline ring; likewise, any one of the carbon atoms attached to $R^8$, $R^9$, $R^{10}$, $R^{12}$, $R^{13}$, $R^{14}$, $R^{16}$, $R^{17}$, $R^{19}$, $R^{20}$, $R^{22}$, $R^{23}$, $R^{24}$, $R^{25}$, $R^{26}$, $R^{27}$, $R^{28}$, $R^{29}$, $R^{30}$, $R^{31}$, $R^{32}$, $R^{33}$, $R^{34}$, or $R^{35}$ can serve as the point of attachment of $R^3$ to the isoquinoline ring.

In some embodiments, $R^6$ is selected from the group consisting of -aryl substituted with 1-5 (e.g., 1-4, 1-3, 1-2, 1) $R^{36}$ and a 6-membered heteroaryl optionally substituted with 1-6 (e.g., 1-5, 1-4, 1-3, 1-2, 1) $R^{37}$.

In some embodiments, $R^6$ is selected from the group consisting of -phenyl substituted with 1-5 $R^{36}$, —$(C_{1-3}$ alkylene$)_p$pyridinyl optionally substituted with 1-6 $R^{37}$, and a 6-10 membered heteroaryl optionally substituted with 1-6 $R^{37}$; wherein the carbonyl of Formula I is attached to an aromatic ring of the heteroaryl; wherein —$(C_{1-3}$ alkylene) is optionally substituted with one or more substituents as defined anywhere herein;

In some embodiments, $R^7$ is selected from the group consisting of a single bond, H, unsubstituted —$(C_{1-9}$ alkyl), unsubstituted —$(C_{2-9}$ alkenyl), unsubstituted —$(C_{2-9}$ alkynyl), unsubstituted —$(C_{1-9}$ haloalkyl), —$(C_{1-4}$ alkylene$)_p$heterocyclyl optionally substituted with 1-10 (e.g., 1-9, 1-8, 1-7, 1-6, 1-5, 1-4, 1-3, 1-2, 1) $R^{38}$, and -carbocyclyl optionally substituted with 1-12 (e.g., 1-11, 1-10, 1-9, 1-8, 1-7, 1-6, 1-5, 1-4, 1-3, 1-2, 1) $R^{39}$; wherein —$(C_{1-4}$ alkylene) is optionally substituted with one or more substituents as defined anywhere herein.

In some embodiments, $R^7$ is selected from the group consisting of a single bond, H, unsubstituted —$(C_{1-9}$ alkyl), unsubstituted —$(C_{2-9}$ alkenyl), unsubstituted —$(C_{2-9}$ alkynyl), unsubstituted —$(C_{1-9}$ haloalkyl), —$(C_{1-4}$ alkylene)N$(R^{48})_2$, —$(C_{1-4}$ alkylene)OR$^{49}$, —C(=O)N$(R^{48})_2$, —$(C_{1-4}$ alkylene$)_p$heterocyclyl optionally substituted with 1-10 $R^{38}$, and -carbocyclyl optionally substituted with 1-12 $R^{39}$; wherein —$(C_{1-4}$ alkylene) is optionally substituted with one or more substituents as defined anywhere herein.

In some embodiments, $R^8$, $R^9$, and $R^{10}$ are independently selected from the group consisting of a single bond, H, halide, unsubstituted —$(C_{1-9}$ alkyl), unsubstituted —$(C_{2-9}$ alkenyl), unsubstituted —$(C_{2-9}$ alkynyl), unsubstituted —$(C_{1-9}$ haloalkyl), —$(C_{1-4}$ alkylene$)_p$heterocyclyl optionally substituted with 1-10 (e.g., 1-9, 1-8, 1-7, 1-6, 1-5, 1-4, 1-3, 1-2, 1) $R^{38}$, and -carbocyclyl optionally substituted with 1-12 (e.g., 1-11, 1-10, 1-9, 1-8, 1-7, 1-6, 1-5, 1-4, 1-3, 1-2, 1) $R^{39}$; wherein each —$(C_{1-4}$ alkylene) is, independently, optionally substituted with one or more substituents as defined anywhere herein.

In some embodiments, $R^8$, $R^9$, and $R^{10}$ are independently selected from the group consisting of a single bond, H, halide, unsubstituted —$(C_{1-9}$ alkyl), unsubstituted —$(C_{2-9}$ alkenyl), unsubstituted —$(C_{2-9}$ alkynyl), unsubstituted —$(C_{1-9}$ haloalkyl), —$(C_{1-4}$ alkylene$)_p$N$(R^{48})_2$, —$(C_{1-4}$ alkylene$)_p$OR$^{49}$, —C(=O)N$(R^{48})_2$, —$(C_{1-4}$ alkylene$)_p$heterocyclyl optionally substituted with 1-10 $R^{38}$, and -carbocyclyl optionally substituted with 1-12 $R^{39}$; wherein each —$(C_{1-4}$ alkylene) is, independently, optionally substituted with one or more substituents as defined anywhere herein.

In some embodiments, one of $R^7$ and $R^8$, $R^8$ and $R^9$, or $R^9$ and $R^{10}$ are taken together to form a ring which is selected from the group consisting of -heterocyclyl optionally substituted with 1-10 (e.g., 1-9, 1-8, 1-7, 1-6, 1-5, 1-4, 1-3, 1-2, 1) $R^{40}$ and -carbocyclyl optionally substituted with 1-12 (e.g., 1-11, 1-10, 1-9, 1-8, 1-7, 1-6, 1-5, 1-4, 1-3, 1-2, 1) $R^{41}$.

In some embodiments, $R^{11}$ is selected from the group consisting of a single bond, H, unsubstituted —$(C_{1-9}$ alkyl), unsubstituted —$(C_{2-9}$ alkenyl), unsubstituted —$(C_{2-9}$ alkynyl), unsubstituted —$(C_{1-9}$ haloalkyl), —$(C_{1-4}$ alkylene$)_p$heterocyclyl optionally substituted with 1-10 (e.g., 1-9, 1-8, 1-7, 1-6, 1-5, 1-4, 1-3, 1-2, 1) $R^{38}$, and -carbocyclyl optionally substituted with 1-12 (e.g., 1-11, 1-10, 1-9, 1-8, 1-7, 1-6, 1-5, 1-4, 1-3, 1-2, 1) $R^{39}$; wherein —$(C_{1-4}$ alkylene) is optionally substituted with one or more substituents as defined anywhere herein.

In some embodiments, $R^{10}$ is selected from the group consisting of a single bond, H, unsubstituted —$(C_{1-9}$ alkyl), unsubstituted —$(C_{2-9}$ alkenyl), unsubstituted —$(C_{2-9}$ alkynyl), unsubstituted —$(C_{1-9}$ haloalkyl), —$(C_{1-4}$ alkylene)N$(R^{48})_2$, —$(C_{1-4}$ alkylene)OR$^{49}$, —C(=O)N$(R^{48})_2$, —$(C_{1-4}$ alkylene$)_p$heterocyclyl optionally substituted with 1-10 $R^{38}$, and -carbocyclyl optionally substituted with 1-12 $R^{39}$; wherein —$(C_{1-4}$ alkylene) is optionally substituted with one or more substituents as defined anywhere herein.

In some embodiments, $R^{12}$, $R^{13}$, and $R^{14}$ are independently selected from the group consisting of a single bond, H, halide, unsubstituted —$(C_{1-9}$ alkyl), unsubstituted —$(C_{2-9}$ alkenyl), unsubstituted —$(C_{2-9}$ alkynyl), unsubstituted —$(C_{1-9}$ haloalkyl), —$(C_{1-4}$ alkylene$)_p$heterocyclyl optionally substituted with 1-10 (e.g., 1-9, 1-8, 1-7, 1-6, 1-5, 1-4, 1-3, 1-2, 1) $R^{38}$, and -carbocyclyl optionally substituted with 1-12 (e.g., 1-11, 1-10, 1-9, 1-8, 1-7, 1-6, 1-5, 1-4, 1-3, 1-2, 1) $R^{39}$; wherein each —$(C_{1-4}$ alkylene) is, independently, optionally substituted with one or more substituents as defined anywhere herein.

In some embodiments, $R^{12}$, $R^{13}$, and $R^{14}$ are independently selected from the group consisting of a single bond, H, halide, unsubstituted —$(C_{1-9}$ alkyl), unsubstituted —$(C_{2-9}$ alkenyl), unsubstituted —$(C_{2-9}$ alkynyl), unsubstituted —$(C_{1-9}$ haloalkyl), —$(C_{1-4}$ alkylene$)_p$N$(R^{48})_2$, —$(C_{1-4}$ alkylene$)_p$OR$^{49}$, —C(=O)N$(R^{48})_2$, —$(C_{1-4}$ alkylene$)_p$heterocyclyl optionally substituted with 1-10 $R^{38}$, and -carbocyclyl optionally substituted with 1-12 $R^9$; wherein each —$(C_{1-4}$ alkylene) is, independently, optionally substituted with one or more substituents as defined anywhere herein.

In some embodiments, one of $R^{11}$ and $R^{12}$, $R^{12}$ and $R^{13}$, or $R^{14}$ and $R^{11}$ are taken together to form a ring which is selected from the group consisting of -heterocyclyl optionally substituted with 1-10 (e.g., 1-9, 1-8, 1-7, 1-6, 1-5, 1-4, 1-3, 1-2, 1) $R^{40}$ and -carbocyclyl optionally substituted with 1-12 (e.g., 1-11, 1-10, 1-9, 1-8, 1-7, 1-6, 1-5, 1-4, 1-3, 1-2, 1) $R^{41}$.

In some embodiments, $R^5$ is selected from the group consisting of a single bond, H, unsubstituted —$(C_{1-9}$ alkyl), unsubstituted —$(C_{2-9}$ alkenyl), unsubstituted —$(C_{2-9}$ alkynyl), unsubstituted —$(C_{1-9}$ haloalkyl), —$(C_{1-4}$ alkylene)$_p$heterocyclyl optionally substituted with 1-10 (e.g., 1-9, 1-8, 1-7, 1-6, 1-5, 1-4, 1-3, 1-2, 1) $R^{38}$, and -carbocyclyl optionally substituted with 1-12 (e.g., 1-11, 1-10, 1-9, 1-8, 1-7, 1-6, 1-5, 1-4, 1-3, 1-2, 1) $R^{39}$; wherein —$(C_{1-4}$ alkylene) is optionally substituted with one or more substituents as defined anywhere herein.

In some embodiments, $R^{15}$ is selected from the group consisting of a single bond, H, unsubstituted —$(C_{1-9}$ alkyl), unsubstituted —$(C_{2-9}$ alkenyl), unsubstituted —$(C_{2-9}$ alkynyl), unsubstituted —$(C_{1-9}$ haloalkyl), —$(C_{1-4}$ alkylene)N$(R^{48})_2$, —$(C_{1-4}$ alkylene)OR$^{49}$, —C(=O)N$(R^{48})_2$, —$(C_{1-4}$ alkylene)$_p$heterocyclyl optionally substituted with 1-10 $R^{38}$, and -carbocyclyl optionally substituted with 1-12 $R^{39}$; wherein —$(C_{1-4}$ alkylene) is optionally substituted with one or more substituents as defined anywhere herein.

In some embodiments, $R^{16}$ and $R^{17}$ are independently selected from the group consisting of a single bond, H, halide, unsubstituted —$(C_{1-9}$ alkyl), unsubstituted —$(C_{2-9}$ alkenyl), unsubstituted —$(C_{2-9}$ alkynyl), unsubstituted —$(C_{1-9}$ haloalkyl), —$(C_{1-4}$ alkylene)$_p$heterocyclyl optionally substituted with 1-10 (e.g., 1-9, 1-8, 1-7, 1-6, 1-5, 1-4, 1-3, 1-2, 1) $R^{38}$, and -carbocyclyl optionally substituted with 1-12 (e.g., 1-11, 1-10, 1-9, 1-8, 1-7, 1-6, 1-5, 1-4, 1-3, 1-2, 1) $R^{39}$; wherein each —$(C_{1-4}$ alkylene) is, independently, optionally substituted with one or more substituents as defined anywhere herein.

In some embodiments, $R^{16}$ and $R^{17}$ are independently selected from the group consisting of a single bond, H, halide, unsubstituted —$(C_{1-9}$ alkyl), unsubstituted —$(C_{2-9}$ alkenyl), unsubstituted —$(C_{2-9}$ alkynyl), unsubstituted —$(C_{1-9}$ haloalkyl), —$(C_{1-4}$ alkylene)$_p$N$(R^{48})_2$, —$(C_{1-4}$ alkylene)$_p$OR$^{49}$, —C(=O)N$(R^{48})_2$, —$(C_{1-4}$ alkylene)$_p$heterocyclyl optionally substituted with 1-10 $R^{38}$, and -carbocyclyl optionally substituted with 1-12 $R^{39}$; wherein each —$(C_{1-4}$ alkylene) is, independently, optionally substituted with one or more substituents as defined anywhere herein.

In some embodiments, one of $R^{15}$ and $R^{16}$ or $R^{16}$ and $R^{17}$ are taken together to form a ring which is selected from the group consisting of -heterocyclyl optionally substituted with 1-10 (e.g., 1-9, 1-8, 1-7, 1-6, 1-5, 1-4, 1-3, 1-2, 1) $R^{40}$ and -carbocyclyl optionally substituted with 1-12 (e.g., 1-11, 1-10, 1-9, 1-8, 1-7, 1-6, 1-5, 1-4, 1-3, 1-2, 1) $R^{41}$.

In some embodiments, $R^{18}$ is selected from the group consisting of a single bond, H, unsubstituted —$(C_{1-9}$ alkyl), unsubstituted —$(C_{2-9}$ alkenyl), unsubstituted —$(C_{2-9}$ alkynyl), unsubstituted —$(C_{1-9}$ haloalkyl), —$(C_{1-4}$ alkylene)$_p$heterocyclyl optionally substituted with 1-10 (e.g., 1-9, 1-8, 1-7, 1-6, 1-5, 1-4, 1-3, 1-2, 1) $R^{38}$, and -carbocyclyl optionally substituted with 1-12 (e.g., 1-11, 1-10, 1-9, 1-8, 1-7, 1-6, 1-5, 1-4, 1-3, 1-2, 1) $R^{39}$; wherein —$(C_{1-4}$ alkylene) is optionally substituted with one or more substituents as defined anywhere herein.

In some embodiments, $R^{18}$ is selected from the group consisting of a single bond, H, unsubstituted —$(C_{1-9}$ alkyl), unsubstituted —$(C_{2-9}$ alkenyl), unsubstituted —$(C_{2-9}$ alkynyl), unsubstituted —$(C_{1-9}$ haloalkyl), —$(C_{1-4}$ alkylene)N$(R^{48})_2$, —$(C_{1-4}$ alkylene)OR$^{49}$, —C(=O)N$(R^{48})_2$, —$(C_{1-4}$ alkylene)$_p$heterocyclyl optionally substituted with 1-10 $R^{38}$, and -carbocyclyl optionally substituted with 1-12 $R^{39}$; wherein —$(C_{1-4}$ alkylene) is optionally substituted with one or more substituents as defined anywhere herein.

In some embodiments, $R^{19}$ and $R^{20}$ are independently selected from the group consisting of a single bond, H, halide, unsubstituted —$(C_{1-9}$ alkyl), unsubstituted —$(C_{2-9}$ alkenyl), unsubstituted —$(C_{2-9}$ alkynyl), unsubstituted —$(C_{1-9}$ haloalkyl), —$(C_{1-4}$ alkylene)$_p$heterocyclyl optionally substituted with 1-10 (e.g., 1-9, 1-8, 1-7, 1-6, 1-5, 1-4, 1-3, 1-2, 1) $R^{38}$, and -carbocyclyl optionally substituted with 1-12 (e.g., 1-11, 1-10, 1-9, 1-8, 1-7, 1-6, 1-5, 1-4, 1-3, 1-2, 1) $R^{39}$; wherein each —$(C_{1-4}$ alkylene) is, independently, optionally substituted with one or more substituents as defined anywhere herein.

In some embodiments, $R^{19}$ and $R^{20}$ are independently selected from the group consisting of a single bond, H, halide, unsubstituted —$(C_{1-9}$ alkyl), unsubstituted —$(C_{2-9}$ alkenyl), unsubstituted —$(C_{2-9}$ alkynyl), unsubstituted —$(C_{1-9}$ haloalkyl), —$(C_{1-4}$ alkylene)$_p$N$(R^{48})_2$, —$(C_{1-4}$ alkylene)$_p$OR$^{49}$, —C(=O)N$(R^{48})_2$, —$(C_{1-4}$ alkylene)$_p$heterocyclyl optionally substituted with 1-10 $R^{38}$, and -carbocyclyl optionally substituted with 1-12 $R^{39}$; wherein each —$(C_{1-4}$ alkylene) is, independently, optionally substituted with one or more substituents as defined anywhere herein.

In some embodiments, one of $R^{18}$ and $R^{19}$ or $R^{18}$ and $R^{20}$ are taken together to form a heterocyclyl optionally substituted with 1-10 (e.g., 1-9, 1-8, 1-7, 1-6, 1-5, 1-4, 1-3, 1-2, 1) $R^{40}$.

In some embodiments, $R^{21}$ is selected from the group consisting of a single bond, H, unsubstituted —$(C_{1-9}$ alkyl), unsubstituted —$(C_{2-9}$ alkenyl), unsubstituted —$(C_{2-9}$ alkynyl), unsubstituted —$(C_{1-9}$ haloalkyl), —$(C_{1-4}$ alkylene)$_p$heterocyclyl optionally substituted with 1-10 (e.g., 1-9, 1-8, 1-7, 1-6, 1-5, 1-4, 1-3, 1-2, 1) $R^{38}$, and -carbocyclyl optionally substituted with 1-12 (e.g., 1-11, 1-10, 1-9, 1-8, 1-7, 1-6, 1-5, 1-4, 1-3, 1-2, 1) $R^{39}$; wherein —$(C_{1-4}$ alkylene) is optionally substituted with one or more substituents as defined anywhere herein.

In some embodiments, $R^{21}$ is selected from the group consisting of a single bond, H, unsubstituted —$(C_{1-9}$ alkyl), unsubstituted —$(C_{2-9}$ alkenyl), unsubstituted —$(C_{2-9}$ alkynyl), unsubstituted —$(C_{1-9}$ haloalkyl), —$(C_{1-4}$ alkylene)N$(R^{48})_2$, —$(C_{1-4}$ alkylene)OR$^{49}$, —C(=O)N$(R^{48})_2$, —$(C_{1-4}$ alkylene)$_p$heterocyclyl optionally substituted with 1-10 $R^{38}$, and -carbocyclyl optionally substituted with 1-12 $R^{39}$; wherein —$(C_{1-4}$ alkylene) is optionally substituted with one or more substituents as defined anywhere herein.

In some embodiments, $R^{22}$ and $R^{23}$ are independently selected from the group consisting of a single bond, H, halide, unsubstituted —$(C_{1-9}$ alkyl), unsubstituted —$(C_{2-9}$ alkenyl), unsubstituted —$(C_{2-9}$ alkynyl), unsubstituted —$(C_{1-9}$ haloalkyl), —$(C_{1-4}$ alkylene)$_p$heterocyclyl optionally substituted with 1-10 (e.g., 1-9, 1-8, 1-7, 1-6, 1-5, 1-4, 1-3, 1-2, 1) $R^{38}$, and -carbocyclyl optionally substituted with 1-12 (e.g., 1-11, 1-10, 1-9, 1-8, 1-7, 1-6, 1-5, 1-4, 1-3, 1-2, 1) $R^{39}$; wherein each —$(C_{1-4}$ alkylene) is, independently, optionally substituted with one or more substituents as defined anywhere herein.

In some embodiments, $R^{22}$ and $R^{23}$ are independently selected from the group consisting of a single bond, H, halide, unsubstituted —$(C_{1-9}$ alkyl), unsubstituted —$(C_{2-9}$ alkenyl), unsubstituted —($C_{2-9}$ alkynyl), unsubstituted —($C_{1-9}$ haloalkyl), —($C_{1-4}$ alkylene)$_p$N($R^{48}$)$_2$, —($C_{1-4}$ alkylene)$_p$OR$^{49}$, —C(=O)N($R^{48}$)$_2$, —($C_{1-4}$ alkylene)$_p$heterocyclyl optionally substituted with 1-10 $R^{38}$, and -carbocyclyl optionally substituted with 1-12 $R^{39}$; wherein each —($C_{1-4}$ alkylene) is, independently, optionally substituted with one or more substituents as defined anywhere herein.

In some embodiments, $R^{22}$ and $R^{23}$ are taken together to form a ring which is selected from the group consisting of -heterocyclyl optionally substituted with 1-10 (e.g., 1-9, 1-8, 1-7, 1-6, 1-5, 1-4, 1-3, 1-2, 1) $R^{40}$ and -carbocyclyl optionally substituted with 1-12 (e.g., 1-11, 1-10, 1-9, 1-8, 1-7, 1-6, 1-5, 1-4, 1-3, 1-2, 1) $R^{41}$.

In some embodiments, $R^{24}$, $R^{25}$, and $R^{26}$ are independently selected from the group consisting of a single bond, H, halide, unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), —($C_{1-4}$ alkylene)$_p$heterocyclyl optionally substituted with 1-10 (e.g., 1-9, 1-8, 1-7, 1-6, 1-5, 1-4, 1-3, 1-2, 1) $R^{38}$, and -carbocyclyl optionally substituted with 1-12 (e.g., 1-11, 1-10, 1-9, 1-8, 1-7, 1-6, 1-5, 1-4, 1-3, 1-2, 1) $R^{39}$; wherein each —($C_{1-4}$ alkylene) is, independently, optionally substituted with one or more substituents as defined anywhere herein.

In some embodiments, $R^{24}$, $R^{25}$, and $R^{26}$ are independently selected from the group consisting of a single bond, H, halide, unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), —($C_{1-4}$ alkylene)$_p$N($R^{48}$)$_2$, —($C_{1-4}$ alkylene)$_p$OR$^{49}$, —C(=O)N($R^{48}$)$_2$, —($C_{1-4}$ alkylene)$_p$heterocyclyl optionally substituted with 1-10 $R^{38}$, and -carbocyclyl optionally substituted with 1-12 $R^{39}$; wherein each —($C_{1-4}$ alkylene) is, independently, optionally substituted with one or more substituents as defined anywhere herein.

In some embodiments, one of $R^{24}$ and $R^{25}$ or $R^{25}$ and $R^{26}$ are taken together to form a ring which is selected from the group consisting of -heterocyclyl optionally substituted with 1-10 (e.g., 1-9, 1-8, 1-7, 1-6, 1-5, 1-4, 1-3, 1-2, 1) $R^{40}$ and -carbocyclyl optionally substituted with 1-12 (e.g., 1-11, 1-10, 1-9, 1-8, 1-7, 1-6, 1-5, 1-4, 1-3, 1-2, 1) $R^{41}$.

In some embodiments, $R^{27}$, $R^{28}$, and $R^{29}$ are independently selected from the group consisting of a single bond, H, halide, unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), —($C_{1-4}$ alkylene)$_p$heterocyclyl optionally substituted with 1-10 (e.g., 1-9, 1-8, 1-7, 1-6, 1-5, 1-4, 1-3, 1-2, 1) $R^{38}$, and -carbocyclyl optionally substituted with 1-12 (e.g., 1-11, 1-10, 1-9, 1-8, 1-7, 1-6, 1-5, 1-4, 1-3, 1-2, 1) $R^{39}$; wherein each —($C_{1-4}$ alkylene) is, independently, optionally substituted with one or more substituents as defined anywhere herein.

In some embodiments, $R^{27}$, $R^{28}$, and $R^{29}$ are independently selected from the group consisting of a single bond, H, halide, unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), —($C_{1-4}$ alkylene)$_p$N($R^{48}$)$_2$, —($C_{1-4}$ alkylene)$_p$OR$^{49}$, —C(=O)N($R^{48}$)$_2$, —($C_{1-4}$ alkylene)$_p$heterocyclyl optionally substituted with 1-10 $R^{38}$, and -carbocyclyl optionally substituted with 1-12 $R^{39}$; wherein each —($C_{1-4}$ alkylene) is, independently, optionally substituted with one or more substituents as defined anywhere herein.

In some embodiments, $R^{27}$ and $R^{28}$ are taken together to form a ring which is selected from the group consisting of -heterocyclyl optionally substituted with 1-10 (e.g., 1-9, 1-8, 1-7, 1-6, 1-5, 1-4, 1-3, 1-2, 1) $R^{40}$ and -carbocyclyl optionally substituted with 1-12 (e.g., 1-11, 1-10, 1-9, 1-8, 1-7, 1-6, 1-5, 1-4, 1-3, 1-2, 1) $R^{41}$.

In some embodiments, $R^{30}$ and $R^{31}$ are independently selected from the group consisting of a single bond, H, halide, unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), —($C_{1-4}$ alkylene)$_p$heterocyclyl optionally substituted with 1-10 (e.g., 1-9, 1-8, 1-7, 1-6, 1-5, 1-4, 1-3, 1-2, 1) $R^{38}$, and -carbocyclyl optionally substituted with 1-12 (e.g., 1-11, 1-10, 1-9, 1-8, 1-7, 1-6, 1-5, 1-4, 1-3, 1-2, 1) $R^{39}$; wherein each —($C_{1-4}$ alkylene) is, independently, optionally substituted with one or more substituents as defined anywhere herein.

In some embodiments, $R^{30}$ and $R^{31}$ are independently selected from the group consisting of a single bond, H, halide, unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), —($C_{1-4}$ alkylene)$_p$N($R^{48}$)$_2$, —($C_{1-4}$ alkylene)$_p$OR$^{49}$, —C(=O)N($R^{48}$)$_2$, —($C_{1-4}$ alkylene)$_p$heterocyclyl optionally substituted with 1-10 $R^{38}$, and -carbocyclyl optionally substituted with 1-12 $R^{39}$; wherein each —($C_{1-4}$ alkylene) is, independently, optionally substituted with one or more substituents as defined anywhere herein.

In some embodiments, $R^{30}$ and $R^{31}$ are taken together to form a ring which is selected from the group consisting of -heterocyclyl optionally substituted with 1-10 (e.g., 1-9, 1-8, 1-7, 1-6, 1-5, 1-4, 1-3, 1-2, 1) $R^{40}$ and -carbocyclyl optionally substituted with 1-12 (e.g., 1-11, 1-10, 1-9, 1-8, 1-7, 1-6, 1-5, 1-4, 1-3, 1-2, 1) $R^{41}$.

In some embodiments, $R^{32}$ and $R^{33}$ are independently selected from the group consisting of a single bond, H, halide, unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), —($C_{1-4}$ alkylene)$_p$heterocyclyl optionally substituted with 1-10 (e.g., 1-9, 1-8, 1-7, 1-6, 1-5, 1-4, 1-3, 1-2, 1) $R^{38}$, and -carbocyclyl optionally substituted with 1-12 (e.g., 1-11, 1-10, 1-9, 1-8, 1-7, 1-6, 1-5, 1-4, 1-3, 1-2, 1) $R^{39}$; wherein each —($C_{1-4}$ alkylene) is, independently, optionally substituted with one or more substituents as defined anywhere herein.

In some embodiments, $R^{32}$ and $R^{33}$ are independently selected from the group consisting of a single bond, H, halide, unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), —($C_{1-4}$ alkylene)$_p$N($R^{48}$)$_2$, —($C_{1-4}$ alkylene)$_p$OR$^{49}$, —C(=O)N($R^{48}$)$_2$, —($C_{1-4}$ alkylene)$_p$heterocyclyl optionally substituted with 1-10 $R^{38}$, and -carbocyclyl optionally substituted with 1-12 $R^{39}$; wherein each —($C_{1-4}$ alkylene) is, independently, optionally substituted with one or more substituents as defined anywhere herein.

In some embodiments, $R^{34}$ and $R^{35}$ are independently selected from the group consisting of a single bond, H, halide, unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), —($C_{1-4}$ alkylene)$_p$heterocyclyl optionally substituted with 1-10 (e.g., 1-9, 1-8, 1-7, 1-6, 1-5, 1-4, 1-3, 1-2, 1) $R^{38}$, and -carbocyclyl optionally substituted with 1-12 (e.g., 1-11, 1-10, 1-9, 1-8, 1-7, 1-6, 1-5, 1-4, 1-3, 1-2, 1) $R^{39}$; wherein each —($C_{1-4}$ alkylene) is, independently, optionally substituted with one or more substituents as defined anywhere herein.

In some embodiments, $R^{34}$ and $R^{35}$ are independently selected from the group consisting of a single bond, H, halide, unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), —($C_{1-4}$ alkylene)$_p$N($R^{48}$)$_2$, —($C_{1-4}$ alkylene)$_p$OR$^{49}$, —C(=O)N($R^{48}$)$_2$, —($C_{1-4}$ alkylene)$_p$heterocyclyl optionally substituted with 1-10 $R^{38}$, and -carbocyclyl optionally substituted with 1-12 $R^{39}$; wherein each —($C_{1-4}$ alkylene) is, independently, optionally substituted with one or more substituents as defined anywhere herein.

In some embodiments, $R^{34}$ and $R^{35}$ are taken together to form a ring which is selected from the group consisting of -heterocyclyl optionally substituted with 1-10 (e.g., 1-9, 1-8, 1-7, 1-6, 1-5, 1-4, 1-3, 1-2, 1) $R^{40}$ and -carbocyclyl optionally substituted with 1-12 (e.g., 1-11, 1-10, 1-9, 1-8, 1-7, 1-6, 1-5, 1-4, 1-3, 1-2, 1) $R^{41}$.

In some embodiments, each $R^{36}$ is independently selected from the group consisting of halide, unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), —$XR^{42}$, —C(O)N($R^{47}$)$_2$, —($C_{1-4}$ alkylene)$_p$heterocyclyl optionally substituted with 1-10 (e.g., 1-9, 1-8, 1-7, 1-6, 1-5, 1-4, 1-3, 1-2, 1) $R^{43}$, and —($C_{1-4}$ alkylene)$_p$carbocyclyl optionally substituted with 1-12 (e.g., 1-11, 1-10, 1-9, 1-8, 1-7, 1-6, 1-5, 1-4, 1-3, 1-2, 1) $R^{44}$; wherein each —($C_{1-4}$ alkylene) is, independently, optionally substituted with one or more substituents as defined anywhere herein.

In some embodiments, each $R^{36}$ is independently selected from the group consisting of halide, unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), —$XR^{42}$, —C(=O)N($R^{47}$)$_2$, —($C_{1-4}$ alkylene)$_p$N($R^{50}$)$_2$, —($C_{1-4}$ alkylene)$_p$heterocyclyl optionally substituted with 1-10 $R^{43}$, and —($C_{1-4}$ alkylene)$_p$carbocyclyl optionally substituted with 1-12 $R^{44}$; wherein each —($C_{1-4}$ alkylene) is, independently, optionally substituted with one or more substituents as defined anywhere herein.

In some embodiments, each $R^{37}$ is independently selected from the group consisting of halide, unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), —$XR^{42}$, —C(O)N($R^{47}$)$_2$, —($C_{1-4}$ alkylene)$_p$heterocyclyl optionally substituted with 1-10 (e.g., 1-9, 1-8, 1-7, 1-6, 1-5, 1-4, 1-3, 1-2, 1) $R^{43}$, and —($C_{1-4}$ alkylene)$_p$carbocyclyl optionally substituted with 1-12 (e.g., 1-11, 1-10, 1-9, 1-8, 1-7, 1-6, 1-5, 1-4, 1-3, 1-2, 1) $R^{44}$; wherein each —($C_{1-4}$ alkylene) is, independently, optionally substituted with one or more substituents as defined anywhere herein.

In some embodiments, each $R^{37}$ is independently selected from the group consisting of halide, unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), —$XR^{42}$, —C(=O)N($R^{47}$)$_2$, —($C_{1-4}$ alkylene)$_p$N($R^{50}$)$_2$, —($C_{1-4}$ alkylene)$_p$heterocyclyl optionally substituted with 1-10 $R^{43}$, and —($C_{1-4}$ alkylene)$_p$carbocyclyl optionally substituted with 1-12 $R^{44}$; wherein each —($C_{1-4}$ alkylene) is, independently, optionally substituted with one or more substituents as defined anywhere herein.

In some embodiments, each $R^{38}$ is selected from the group consisting of halide, unsubstituted —($C_{1-5}$ alkyl), unsubstituted —($C_{2-5}$ alkenyl), unsubstituted —($C_{2-5}$ alkynyl), unsubstituted —($C_{1-5}$ haloalkyl), —CN, and —($C_{1-4}$ alkylene)$_p$carbocyclyl optionally substituted with 1-12 (e.g., 1-11, 1-10, 1-9, 1-8, 1-7, 1-6, 1-5, 1-4, 1-3, 1-2, 1) $R^{44}$; wherein each —($C_{1-4}$ alkylene) is, independently, optionally substituted with one or more substituents as defined anywhere herein.

In some embodiments, each $R^{39}$ is selected from the group consisting of halide, unsubstituted —($C_{1-5}$ alkyl), unsubstituted —($C_{2-5}$ alkenyl), unsubstituted —($C_{2-5}$ alkynyl), unsubstituted —($C_{1-5}$ haloalkyl), —CN, and —($C_{1-4}$ alkylene)$_p$carbocyclyl optionally substituted with 1-12 (e.g., 1-11, 1-10, 1-9, 1-8, 1-7, 1-6, 1-5, 1-4, 1-3, 1-2, 1) $R^{44}$; wherein each —($C_{1-4}$ alkylene) is, independently, optionally substituted with one or more substituents as defined anywhere herein.

In some embodiments, each $R^{40}$ is selected from the group consisting of halide, unsubstituted —($C_{1-5}$ alkyl), unsubstituted —($C_{2-5}$ alkenyl), unsubstituted —($C_{2-5}$ alkynyl), unsubstituted —($C_{1-5}$ haloalkyl), —CN, and —($C_{1-4}$ alkylene)$_p$carbocyclyl optionally substituted with 1-12 (e.g., 1-11, 1-10, 1-9, 1-8, 1-7, 1-6, 1-5, 1-4, 1-3, 1-2, 1) $R^{44}$; wherein each —($C_{1-4}$ alkylene) is, independently, optionally substituted with one or more substituents as defined anywhere herein.

In some embodiments, each $R^{41}$ is selected from the group consisting of halide, unsubstituted —($C_{1-5}$ alkyl), unsubstituted —($C_{2-5}$ alkenyl), unsubstituted —($C_{2-5}$ alkynyl), unsubstituted —($C_{1-5}$ haloalkyl), and —CN.

In some embodiments, each $R^{42}$ is selected from the group consisting of unsubstituted —($C_{1-5}$ alkyl), unsubstituted —($C_{2-5}$ alkenyl), unsubstituted —($C_{2-5}$ alkynyl), unsubstituted —($C_{1-5}$ haloalkyl), —($C_{1-4}$ alkylene)$_p$aryl optionally substituted with 1-10 (e.g., 1-9, 1-8, 1-7, 1-6, 1-5, 1-4, 1-3, 1-2, 1) $R^{46}$, —($C_{1-4}$ alkylene)$_p$heterocyclyl optionally substituted with 1-12 (e.g., 1-11, 1-10, 1-9, 1-8, 1-7, 1-6, 1-5, 1-4, 1-3, 1-2, 1) $R^{43}$, and —($C_{1-4}$ alkylene)$_p$carbocyclyl optionally substituted with 1-12 (e.g., 1-11, 1-10, 1-9, 1-8, 1-7, 1-6, 1-5, 1-4, 1-3, 1-2, 1) $R^{44}$; wherein each —($C_{1-4}$ alkylene) is, independently, optionally substituted with one or more substituents as defined anywhere herein.

In some embodiments, each $R^{42}$ is independently selected from the group consisting of H, unsubstituted —($C_{1-5}$ alkyl), unsubstituted —($C_{2-5}$ alkenyl), unsubstituted —($C_{2-5}$ alkynyl), unsubstituted —($C_{1-5}$ haloalkyl), —($C_{1-4}$ alkylene)N($R^{48}$)$_2$, —($C_{1-4}$ alkylene)$_p$aryl optionally substituted with 1-10 $R^{46}$, —($C_{1-4}$ alkylene)$_p$heterocyclyl optionally substituted with 1-12 $R^{43}$, and —($C_{1-4}$ alkylene)$_p$carbocyclyl optionally substituted with 1-12 $R^{44}$; wherein each —($C_{1-4}$ alkylene) is, independently, optionally substituted with one or more substituents as defined anywhere herein.

In some embodiments, each $R^{43}$ is selected from the group consisting of halide, unsubstituted —($C_{1-5}$ alkyl), unsubstituted —($C_{2-5}$ alkenyl), unsubstituted —($C_{2-5}$ alkynyl), unsubstituted —($C_{1-5}$ haloalkyl), —CN, and —($C_{1-4}$ alkylene)$_p$carbocyclyl optionally substituted with 1-12 (e.g., 1-11, 1-10, 1-9, 1-8, 1-7, 1-6, 1-5, 1-4, 1-3, 1-2, 1) $R^{44}$; wherein each —($C_{1-4}$ alkylene) is, independently, optionally substituted with one or more substituents as defined anywhere herein.

In some embodiments, each $R^{43}$ is independently selected from the group consisting of halide, unsubstituted —($C_{1-5}$ alkyl), unsubstituted —($C_{2-5}$ alkenyl), unsubstituted —($C_{2-5}$ alkynyl), unsubstituted —($C_{1-5}$ haloalkyl), —CN, —OH, —C(=O)$R^{51}$, —N($R^{50}$)$_2$, and —($C_{1-4}$ alkylene)$_p$carbocyclyl optionally substituted with 1-12 $R^{44}$; wherein each —($C_{1-4}$ alkylene) is, independently, optionally substituted with one or more substituents as defined anywhere herein.

In some embodiments, each $R^{44}$ is selected from the group consisting of halide, unsubstituted —($C_{1-5}$ alkyl), unsubstituted —($C_{2-5}$ alkenyl), unsubstituted —($C_{2-5}$ alkynyl), unsubstituted —($C_{1-5}$ haloalkyl), and —CN.

In some embodiments, each $R^{45}$ is independently selected from the group consisting of H, unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), —($C_{1-4}$ alkylene)$_p$heterocyclyl optionally substituted with 1-10 (e.g., 1-9, 1-8, 1-7, 1-6, 1-5, 1-4, 1-3, 1-2, 1) $R^{38}$, and -carbocyclyl optionally substituted with 1-12 (e.g., 1-11, 1-10, 1-9, 1-8, 1-7, 1-6, 1-5, 1-4, 1-3, 1-2, 1) $R^{39}$; wherein each —($C_{1-4}$ alkylene) is, independently, optionally substituted with one or more substituents as defined anywhere herein.

In some embodiments, each $R^{45}$ is independently selected from the group consisting of halide, unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), —($C_{1-4}$ alkylene)$_p$N($R^{48}$)$_2$, —($C_{1-4}$ alkylene)$_p$O$R^{49}$, —C(=O)N($R^{48}$)$_2$, —($C_{1-4}$ alkylene)$_p$heterocyclyl optionally substituted with 1-10 $R^{38}$, and -carbocyclyl optionally substituted with 1-12 $R^{39}$; wherein each —($C_{1-4}$ alkylene) is, independently, optionally substituted with one or more substituents as defined anywhere herein.

In some embodiments, two adjacent $R^{45}$ groups are taken together to form a ring which is selected from the group consisting of -heterocyclyl optionally substituted with 1-10 (e.g., 1-9, 1-8, 1-7, 1-6, 1-5, 1-4, 1-3, 1-2, 1) $R^{40}$ and -carbocyclyl optionally substituted with 1-12 (e.g., 1-11, 1-10, 1-9, 1-8, 1-7, 1-6, 1-5, 1-4, 1-3, 1-2, 1) $R^{41}$.

In some embodiments, each $R^{46}$ is independently selected from the group consisting of halide, unsubstituted —($C_{1-5}$ alkyl), unsubstituted —($C_{2-5}$ alkenyl), unsubstituted —($C_{2-5}$ alkynyl), unsubstituted —($C_{1-5}$ haloalkyl), and —CN.

In some embodiments, each $R^{47}$ is independently selected from the group consisting of unsubstituted —($C_{1-5}$ alkyl), unsubstituted —($C_{2-5}$ alkenyl), unsubstituted —($C_{2-5}$ alkynyl), and unsubstituted —($C_{1-5}$ haloalkyl).

In some embodiments, each $R^{47}$ is independently selected from the group consisting of H, unsubstituted —($C_{1-5}$ alkyl), unsubstituted —($C_{2-5}$ alkenyl), unsubstituted —($C_{2-5}$ alkynyl), and unsubstituted —($C_{1-5}$ haloalkyl).

In some embodiments, each $R^{48}$ is independently selected from the group consisting of H, unsubstituted —($C_{1-5}$ alkyl), unsubstituted —($C_{2-5}$ alkenyl), unsubstituted —($C_{2-5}$ alkynyl), and unsubstituted —($C_{1-5}$ haloalkyl).

In some embodiments, each $R^{49}$ is independently selected from the group consisting of H, unsubstituted —($C_{1-5}$ alkyl), unsubstituted —($C_{2-5}$ alkenyl), unsubstituted —($C_{2-5}$ alkynyl), and unsubstituted —($C_{1-5}$ haloalkyl).

In some embodiments, each $R^{50}$ is independently selected from the group consisting of H, unsubstituted —($C_{1-5}$ alkyl), unsubstituted —($C_{2-5}$ alkenyl), unsubstituted —($C_{2-5}$ alkynyl), unsubstituted —($C_{1-5}$ haloalkyl), and —($C_{1-4}$ alkylene)N($R^{48}$)$_2$; wherein —($C_{1-4}$ alkylene) is optionally substituted with one or more substituents as defined anywhere herein.

In some embodiments, each $R^{51}$ is a heteroaryl optionally substituted with 1-6 $R^{52}$.

In some embodiments, each $R^{52}$ is a -heterocyclyl optionally substituted with 1-10 $R^{46}$.

In some embodiments, the heterocyclyl of —($C_{1-4}$ alkylene)$_p$heterocyclyl is optionally substituted with 1-10 $R^{38}$.

In some embodiments, the —($C_{1-4}$ alkylene) of —($C_{1-4}$ alkylene)$_p$heterocyclyl is optionally substituted with 1-10 $R^{38}$.

In some embodiments, the heterocyclyl of —($C_{1-4}$ alkylene)$_p$heterocyclyl is optionally substituted with 1-10 $R^{43}$.

In some embodiments, the —($C_{1-4}$ alkylene) of —($C_{1-4}$ alkylene)$_p$heterocyclyl is optionally substituted with 1-10 $R^{43}$.

In some embodiments, the carbocyclyl of —($C_{1-4}$ alkylene)$_p$carbocyclyl is optionally substituted with 1-12 $R^{44}$.

In some embodiments, the —($C_{1-4}$ alkylene) of —($C_{1-4}$ alkylene)$_p$carbocyclyl optionally substituted with 1-12 $R^{44}$.

In some embodiments, the aryl of —($C_{1-4}$ alkylene)$_p$aryl is optionally substituted with 1-10 $R^{46}$.

In some embodiments, the —($C_{1-4}$ alkylene) of —($C_{1-4}$ alkylene)$_p$aryl is optionally substituted with 1-10 $R^{46}$.

In some embodiments, —($C_{1-4}$ alkylene) is optionally substituted with 1-5 halide or 1-5 unsubstituted —($C_{1-3}$ alkyl).

In some embodiments, —($C_{1-4}$ alkylene) is substituted with 1-2 fluorines.

In some embodiments, —($C_{1-4}$ alkylene) is substituted with 1-2 methyls.

In some embodiments, each X is selected from the group consisting of O, S, and NH.

In some embodiments, each X is selected from the group consisting of O, S, and N$R^{48}$.

In some embodiments, each X is selected from the group consisting of O and S.

In some embodiments, each X is selected from the group consisting of O and NH.

In some embodiments, X is O.

In some embodiments, X is S.

In some embodiments, X is NH.

In some embodiments, X is N$R^{48}$.

In some embodiments, X is NMe.

In some embodiments, each Y is selected from the group consisting of O and S.

In some embodiments, Y is O.

In some embodiments, Y is S.

In some embodiments, each m is independently 1 to 4 (e.g., 1-3, 1-2, 1).

In some embodiments, each n is independently 0 to 3 (e.g., 0-2, 0-1, 0).

In some embodiments, each p is independently 0 or 1.

In some embodiments, each q is independently 0 to 12 (e.g., 0-11, 0-10, 0-9, 0-8, 0-7, 0-6, 0-5, 0-4, 0-3, 0-2, 0-1, 0).

In some embodiments, $R^3$ is

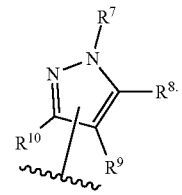

In certain embodiments, $R^9$ is a single bond connecting $R^3$ to the isoquinoline ring, i.e., $R^3$ has the following formula:

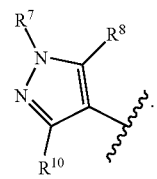

In some embodiments, $R^3$ is

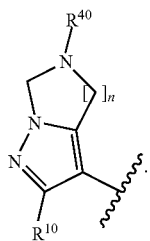

and n is 1 to 3.

In some embodiments, $R^7$ is selected from the group consisting of H, unsubstituted —($C_{1-3}$ alkyl), unsubstituted —($C_{1-2}$ haloalkyl), and —($C_{3-4}$ carbocyclyl) optionally substituted with 1-2 $R^{39}$.

In some embodiments, $R^7$ is selected from the group consisting of H, methyl, —$CF_3$, and cyclopropyl optionally substituted with 1-2 $R^{39}$.

In some embodiments, $R^7$ is selected from the group consisting of H and methyl.

In some embodiments, $R^7$ is methyl.

In some embodiments, $R^7$ is —$CD_3$.

In some embodiments, $R^8$ is selected from the group consisting of H, halide, unsubstituted —($C_{1-2}$ alkyl), unsubstituted —($C_{1-2}$ haloalkyl), and —($C_{1-2}$ alkylene)$OR^{42}$.

In some embodiments, $R^8$ is selected from the group consisting of H, F, methyl, —$CF_3$, —$(CH_2)OH$, and —$(CH_2)OMe$.

In some embodiments, $R^8$ is selected from the group consisting of H, F, methyl, and —$CF_3$.

In some embodiments, $R^8$ is selected from the group consisting of H, F, and methyl.

In some embodiments, $R^8$ is H.

In some embodiments, $R^{10}$ is selected from the group consisting of H and halide.

In some embodiments, $R^{10}$ is selected from the group consisting of H and F.

In some embodiments, $R^{10}$ is H.

In some embodiments, $R^3$ is

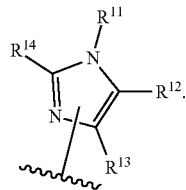

In certain embodiments, $R^{12}$ is a single bond connecting $R^3$ to the isoquinoline ring, i.e., $R^3$ has the following formula:

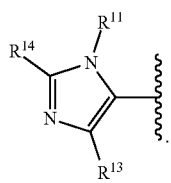

In some embodiments, $R^3$ is

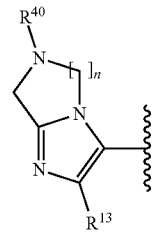

and n is 1 to 3.

In some embodiments, $R^{11}$ is selected from the group consisting of H, unsubstituted —($C_{1-3}$ alkyl), unsubstituted —($C_{1-2}$ haloalkyl), and —($C_{3-4}$ carbocyclyl) optionally substituted with 1-2 $R^{39}$.

In some embodiments, $R^{11}$ is selected from the group consisting of H, methyl, —$CF_3$, and cyclopropyl optionally substituted with 1-2 $R^{39}$.

In some embodiments, $R^{11}$ is selected from the group consisting of H and methyl.

In some embodiments, $R^{11}$ is methyl.

In some embodiments, $R^{11}$ is —$CD_3$.

In some embodiments, $R^{13}$ is selected from the group consisting of H and halide.

In some embodiments, $R^{13}$ is selected from the group consisting of H and F.

In some embodiments, $R^{14}$ is selected from the group consisting of H, halide, unsubstituted —($C_{1-2}$ alkyl), and unsubstituted —($C_{1-2}$ haloalkyl).

In some embodiments, $R^{14}$ is selected from the group consisting of H, F, methyl, and —$CF_3$.

In some embodiments, $R^{14}$ is selected from the group consisting of H and methyl.

In some embodiments, $R^{11}$ and $R^{14}$ are both methyl.

In some embodiments, $R^3$

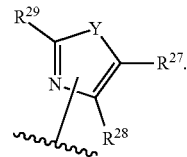

In some embodiments, $R^3$ is

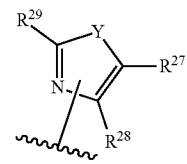

and Y is S.

In some embodiments, $R^3$ is

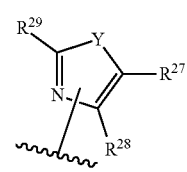

and Y is O.

In certain embodiments, $R^{27}$ is a single bond connecting $R^3$ to the isoquinoline ring, i.e., $R^3$ has the following formula:

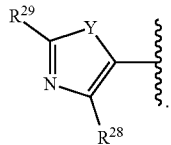

In some embodiments, $R^3$ is

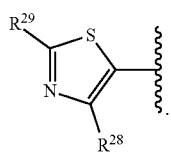

In some embodiments, $R^3$ is

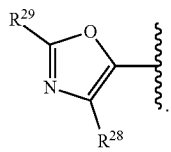

In some embodiments, $R^{28}$ is selected from the group consisting of H and halide.

In some embodiments, $R^{28}$ is selected from the group consisting of H and F.

In some embodiments, $R^{29}$ is selected from the group consisting of H, halide, unsubstituted —($C_{1-2}$ alkyl), and unsubstituted —($C_{1-2}$haloalkyl).

In some embodiments, $R^{29}$ is selected from the group consisting of H, F, methyl, and —$CF_3$.

In some embodiments, $R^3$ is

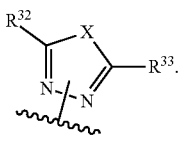

In some embodiments, $R^3$ is

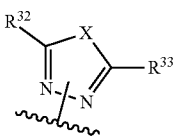

and X is S.

In some embodiments, $R^3$ is

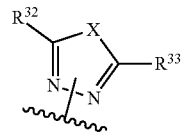

and X is O.

In certain embodiments, $R^{33}$ is a single bond connecting $R^3$ to the isoquinoline ring, i.e., $R^3$ has the following formula:

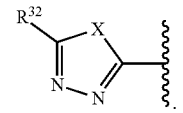

In some embodiments, $R^3$ is

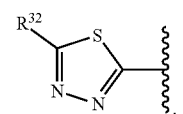

In some embodiments, $R^3$ is

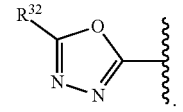

In some embodiments, $R^{32}$ is selected from the group consisting of H, halide, unsubstituted —($C_{1-2}$ alkyl), unsubstituted —($C_{1-2}$haloalkyl), and —$N(R^{53})_2$.

In some embodiments, $R^{32}$ is selected from the group consisting of H, F, methyl, —$CF_3$, —NHMe, and —$NMe_2$.

In some embodiments, $R^{32}$ is selected from the group consisting of H and methyl.

In some embodiments, $R^{32}$ is methyl.

In some embodiments, $R^3$ is

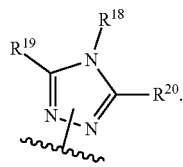

In certain embodiments, $R^{20}$ is a single bond connecting $R^3$ to the isoquinoline ring, i.e., $R^3$ has the following formula:

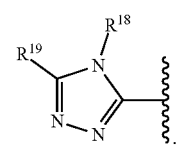

In some embodiments, $R^3$ is

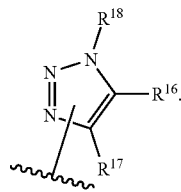

In certain embodiments, $R^{16}$ is a single bond connecting $R^3$ to the isoquinoline ring, i.e., $R^3$ has the following formula:

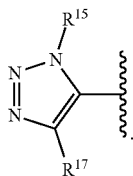

In certain embodiments, $R^{17}$ is a single bond connecting $R^3$ to the isoquinoline ring, i.e., $R^3$ has the following formula:

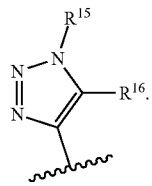

In some embodiments, $R^{15}$ is selected from the group consisting of H and unsubstituted —$(C_{1-2}$ alkyl).

In some embodiments, $R^{15}$ is selected from the group consisting of H and methyl.

In some embodiments, $R^{15}$ is methyl.

In some embodiments, $R^{15}$ is —$CD_3$.

In some embodiments, $R^3$ is

and n is 1 to 3.

In some embodiments, $R^{18}$ is selected from the group consisting of H, unsubstituted —$(C_{1-3}$ alkyl), unsubstituted —$(C_{1-2}$ haloalkyl), and —$(C_{3-4}$ carbocyclyl) optionally substituted with 1-2 $R^{39}$.

In some embodiments, $R^{18}$ is selected from the group consisting of H, methyl, —$CF_3$, and cyclopropyl optionally substituted with 1-2 $R^{39}$.

In some embodiments, $R^{19}$ is selected from the group consisting of H, halide, unsubstituted —$(C_{1-2}$ alkyl), and unsubstituted —$(C_{1-2}$haloalkyl).

In some embodiments, $R^{19}$ is selected from the group consisting of H, F, methyl, and —$CF_3$.

In some embodiments, $R^{39}$ is selected from the group consisting of halide, unsubstituted —$(C_{1-3}$ alkyl), and unsubstituted —$(C_{1-2}$haloalkyl).

In some embodiments, $R^{39}$ is selected from the group consisting of F, methyl, and —$CF_3$.

In some embodiments, $R^{40}$ is selected from the group consisting of H and unsubstituted —$(C_{1-2}$ alkyl).

In some embodiments, $R^{40}$ is selected from the group consisting of H and methyl.

In some embodiments, $R^6$ is selected from the group consisting of -aryl substituted with 1-5 $R^{36}$ and a 6-membered heteroaryl optionally substituted with 1-6 $R^{37}$.

In some embodiments, $R^6$ is selected from the group consisting of -phenyl substituted with 1-5 $R^{36}$, and -pyridinyl optionally substituted with 1-4 $R^{37}$.

In some embodiments, $R^6$ is a -phenyl substituted with one $R^{36}$.

In some embodiments, $R^6$ is a -pyridinyl substituted with one $R^{37}$.

In some embodiments, $R^6$ is a -pyridin-2-yl substituted with one $R^{37}$.

In some embodiments, $R^6$ is a -pyridin-3-yl substituted with one $R^{37}$.

In some embodiments, $R^6$ is a -pyridin-4-yl substituted with one $R^{37}$.

In some embodiments, $R^{36}$ is selected from the group consisting of halide, unsubstituted —$(C_{1-3}$ alkyl), unsubstituted —$(C_{1-3}$ haloalkyl), —$OR^{42}$, —$NHR^{42}$, —$C(O)N(C_{1-3}$ alkyl)$_2$, —$C(O)NH(C_{1-3}$ alkyl), -heterocyclyl optionally substituted with 1-2 $R^{43}$, —$(CH_2)$heterocyclyl optionally substituted with 1-2 $R^{43}$, —$(C_{3-4}$ carbocyclyl) optionally substituted with 1-2 $R^{44}$, and —$(CH_2)(C_{3-4}$ carbocyclyl) optionally substituted with 1-2 $R^{44}$.

In some embodiments, $R^{37}$ is selected from the group consisting of halide, unsubstituted —$(C_{1-3}$ alkyl), unsubstituted —$(C_{1-3}$ haloalkyl), —$OR^{42}$, —$NHR^{42}$, —$C(O)N(C_{1-3}$ alkyl)$_2$, —$C(O)NH(C_{1-3}$ alkyl), -heterocyclyl optionally substituted with 1-2 $R^{43}$, —$(CH_2)$heterocyclyl optionally substituted with 1-2 $R^{43}$, —$(C_{3-4}$ carbocyclyl) optionally substituted with 1-2 $R^{44}$, and —$(CH_2)(C_{3-4}$ carbocyclyl) optionally substituted with 1-2 $R^{44}$.

In some embodiments, the heterocyclyl is selected from the group consisting of azetidinyl, oxetanyl, pyrrolidinyl, tetrahydrofuranyl, piperidinyl, piperazinyl, morpholinyl, and tetrahydropyranyl.

In some embodiments, $R^{42}$ is selected from the group consisting of unsubstituted —$(C_{1-3}$ alkyl), and unsubstituted —$(C_{1-3}$ haloalkyl), —$CH_2$ phenyl optionally substituted with 1-2 halides, -heterocyclyl optionally substituted with one —$(C_{1-3}$ alkyl), —$CH_2$heterocyclyl optionally substituted with one —$(C_{1-3}$alkyl), an unsubstituted -carbocyclyl, and an unsubstituted —$CH_2$carbocyclyl.

In some embodiments, $R^{42}$ is selected from the group consisting of methyl, ethyl, propyl, isopropyl, —$CHF_2$, —$CF_3$, and -heterocyclyl optionally substituted with one Me.

In some embodiments, $R^{42}$ is selected from the group consisting of methyl, ethyl, propyl, isopropyl, —$CHF_2$, —$CF_3$,

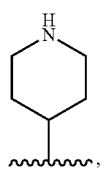

and

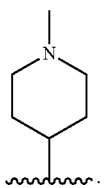

In some embodiments, $R^{43}$ is selected from the group consisting of halide, unsubstituted —($C_{1-2}$ alkyl), unsubstituted —($C_{1-2}$ haloalkyl), and -carbocyclyl optionally substituted with 1-2 halides.

In some embodiments, $R^{43}$ is selected from the group consisting of F, methyl, ethyl, —$CF_3$, and a cyclopropyl.

In some embodiments, $R^{44}$ is selected from the group consisting of halide, unsubstituted —($C_{1-2}$ alkyl), and unsubstituted —($C_{1-2}$ haloalkyl).

In some embodiments, $R^{44}$ is selected from the group consisting of F, methyl, ethyl, —$CF_3$.

In some embodiments, $R^{36}$ is selected from the group consisting of F, methyl, ethyl, n-propyl, isopropyl, —O($C_{1-3}$ alkyl), —O($C_{1-3}$ haloalkyl),

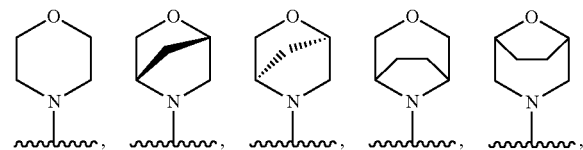

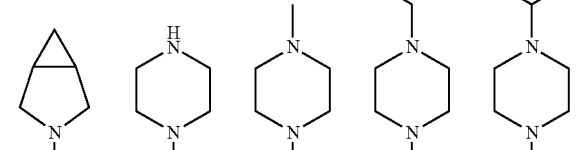

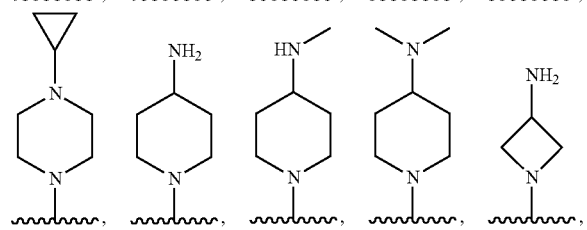

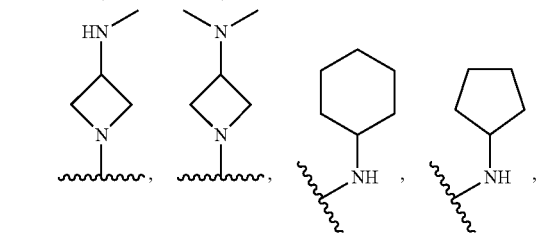

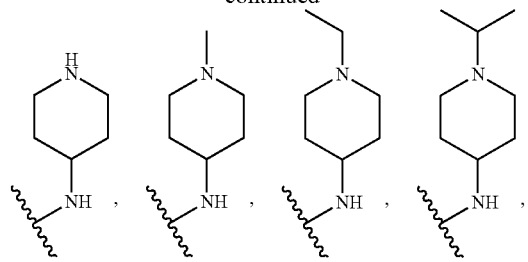

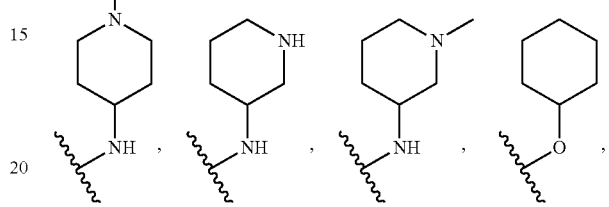

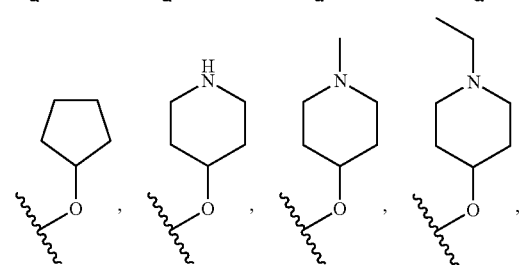

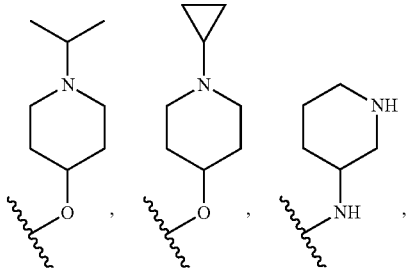

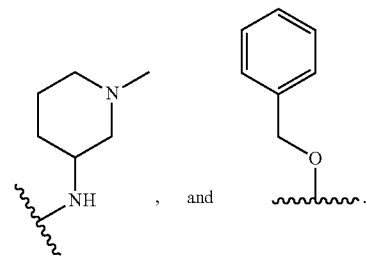

In some embodiments, $R^{37}$ is selected from the group consisting of F, methyl, ethyl, n-propyl, isopropyl, —O($C_{1-3}$ alkyl), —O($C_{1-3}$ haloalkyl),

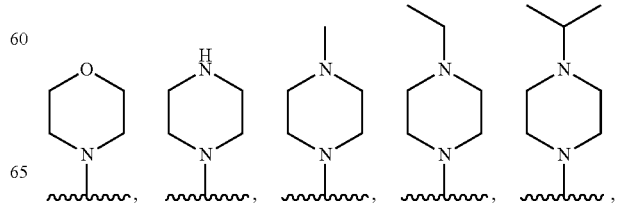

-continued
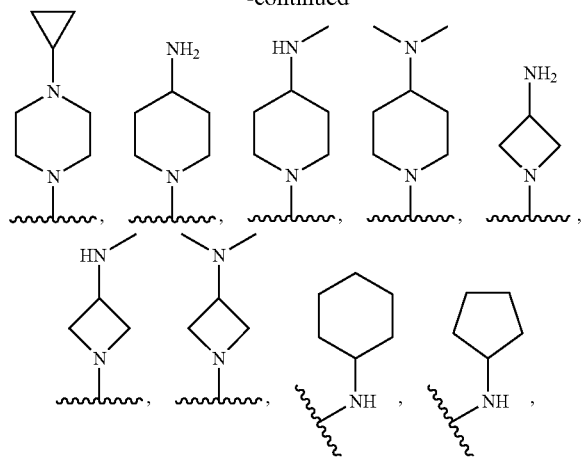
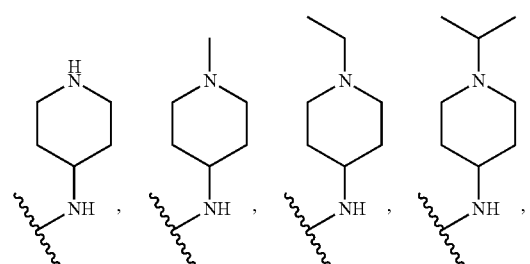
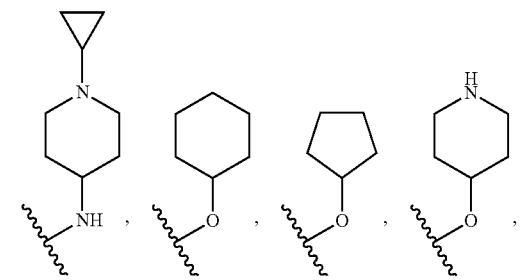
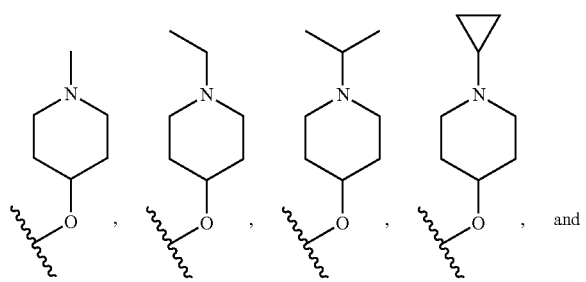
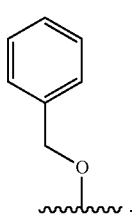
In some embodiments, $R^3$ is selected from the group consisting of:
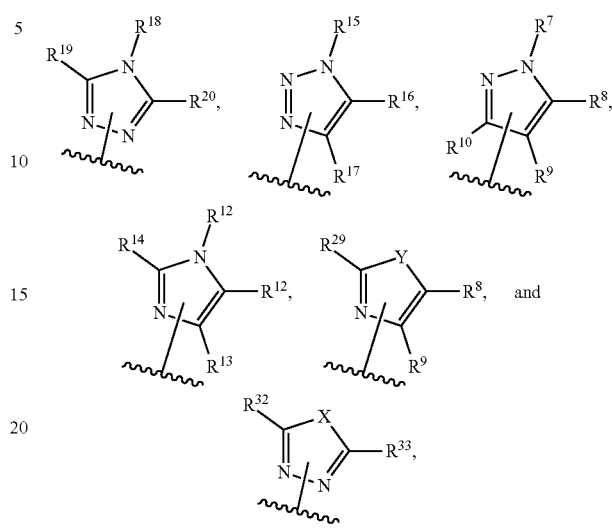
wherein Y is S or O and $R^6$ is a -aryl substituted with 1-5 $R^{36}$.
In some embodiments, $R^3$ is selected from the group consisting of:
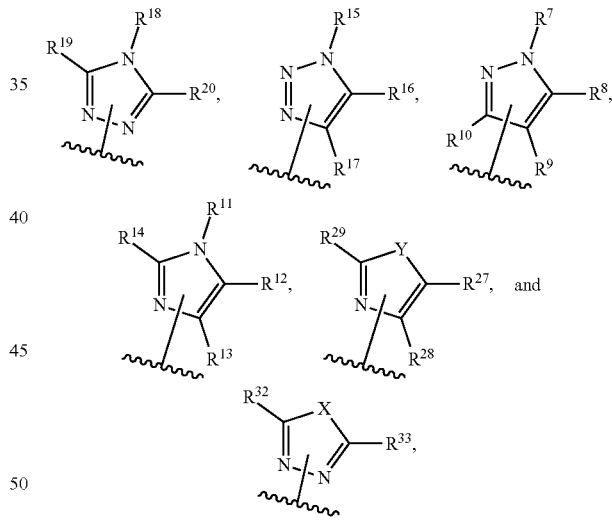
wherein Y is S or O and $R^6$ is a 6-membered heteroaryl optionally substituted with 1-6 $R^{37}$.
In some embodiments, $R^3$ is selected from the group consisting of:
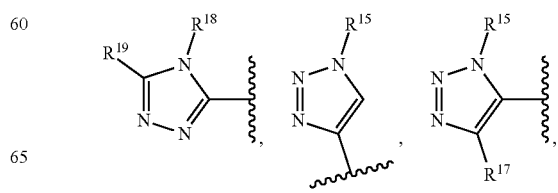

-continued

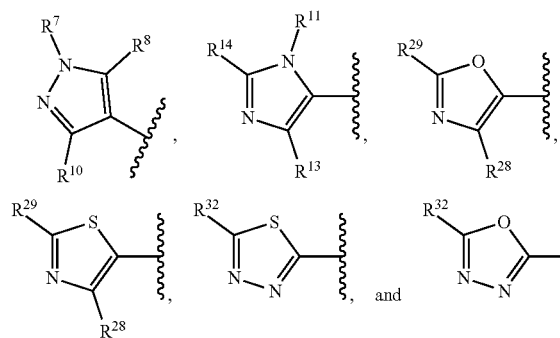

and $R^6$ is a -phenyl substituted with 1-5 $R^{36}$.

In some embodiments, R is selected from the group consisting of:

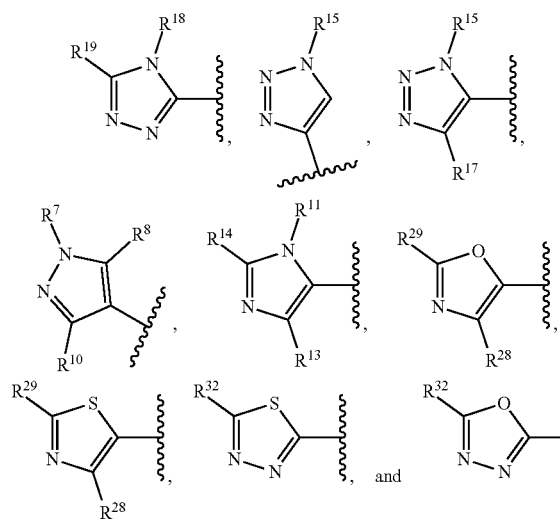

and $R^6$ is a -pyridinyl optionally substituted with 1-4 $R^{37}$.

In some embodiments, $R^3$ is selected from the group consisting of:

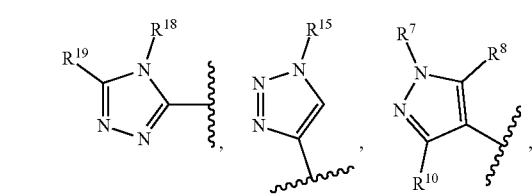

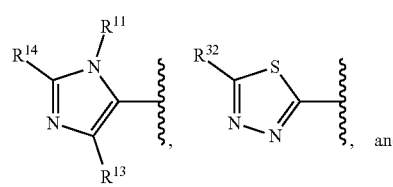

and $R^6$ is a -phenyl substituted with one $R^{36}$.

In some embodiments, $R^3$ is selected from the group consisting of:

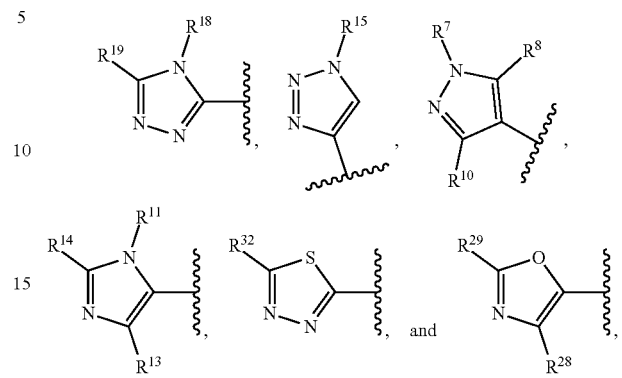

$R^6$ is a -pyridin-2-yl substituted with one $R^{37}$.

In some embodiments, $R^3$ is selected from the group consisting of:

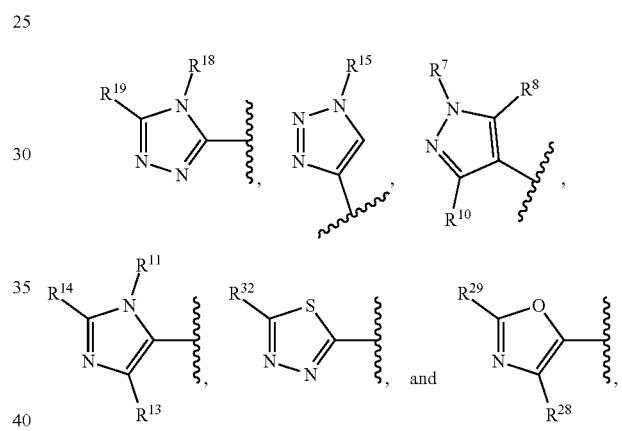

and $R^6$ is a -pyridin-3-yl substituted with one $R^{37}$.

In some embodiments, $R^3$ is selected from the group consisting of:

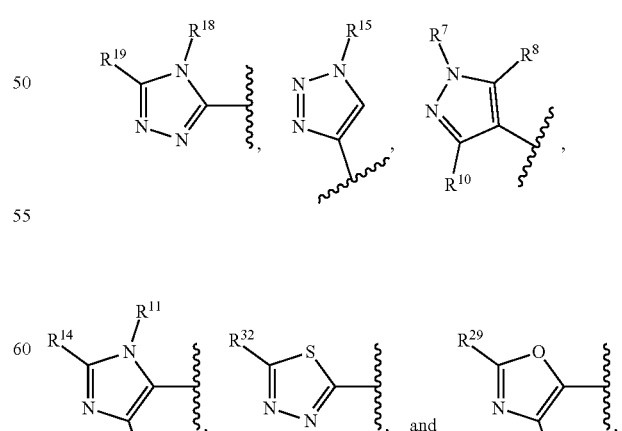

and $R^6$ is a -pyridin-4-yl substituted with one $R^{37}$.

In some embodiments, R³ is selected from the group consisting of:

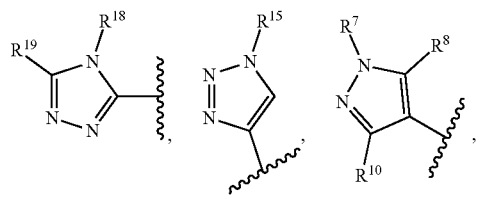

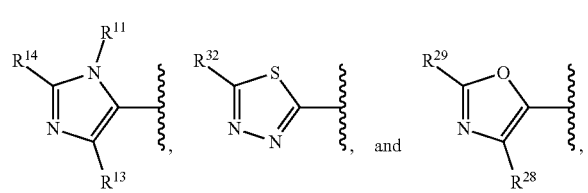

and R⁶ is a -phenyl substituted with one R³⁶; and R³⁶ is selected from the group consisting of F, methyl, ethyl, n-propyl, isopropyl, —O(C$_{1-3}$ alkyl), —O(C$_{1-3}$ haloalkyl),

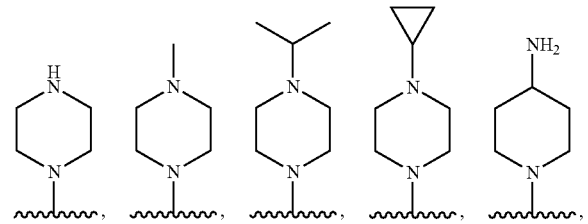

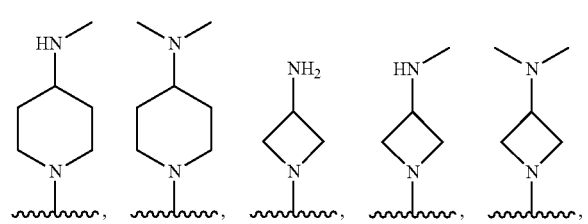

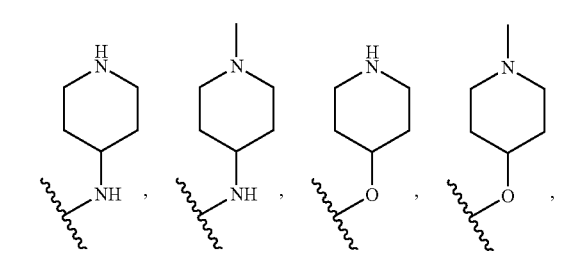

In some embodiments, R³ is selected from the group consisting of:

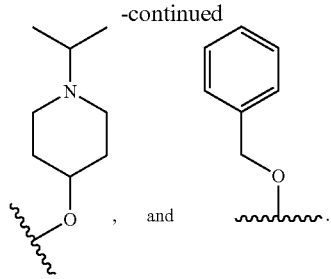

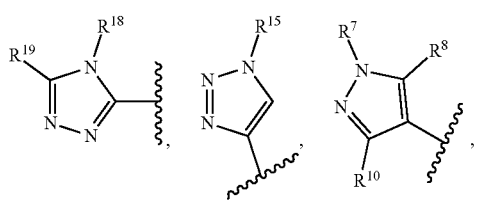

and R⁶ is a -pyridin-2-yl substituted with one R³⁷; and R³⁷ is selected from the group consisting of F, methyl, ethyl, n-propyl, isopropyl, —O(C$_{1-3}$ alkyl), —O(C$_{1-3}$ haloalkyl),

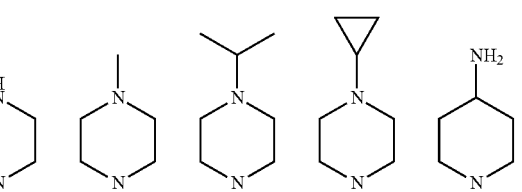

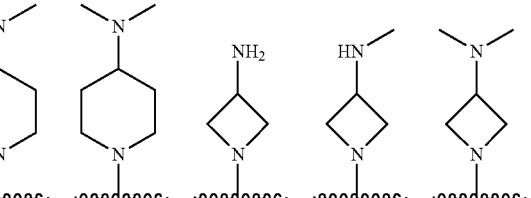

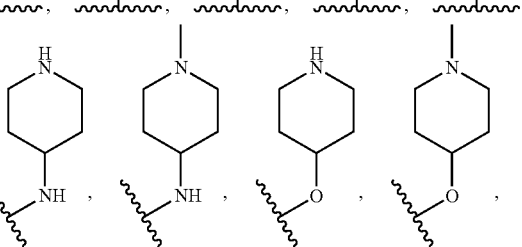

-continued

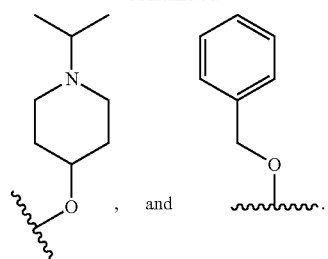
, and
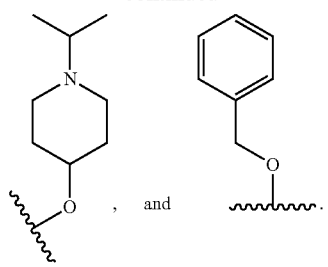
, and

In some embodiments, $R^3$ is selected from the group consisting of:

In some embodiments, $R^3$ is selected from the group consisting of:

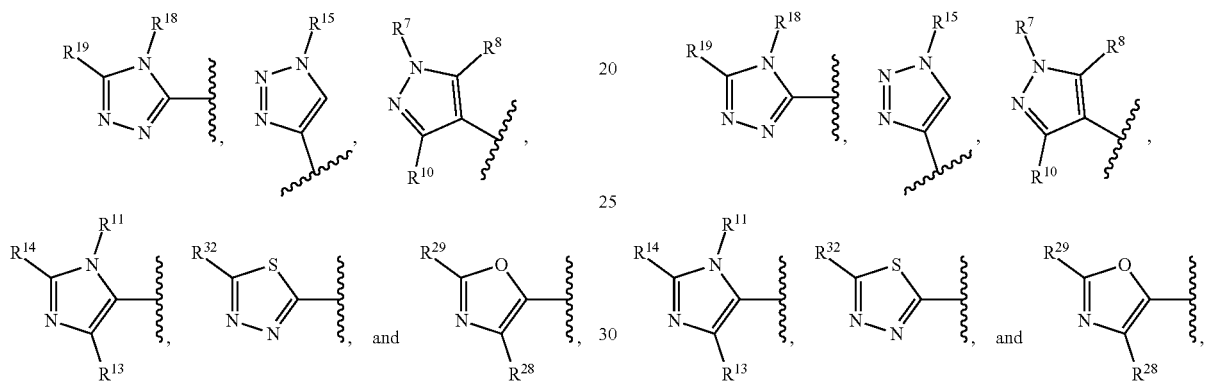

and $R^6$ is a -pyridin-3-yl substituted with one $R^{37}$; and $R^{37}$ is selected from the group consisting of F, methyl, ethyl, n-propyl, isopropyl, —O($C_{1-3}$ alkyl), —O($C_{1-3}$ haloalkyl), and $R^6$ is a -pyridin-4-yl substituted with one $R^{37}$; and $R^{37}$ is selected from the group consisting of F, methyl, ethyl, n-propyl, isopropyl, —O($C_{1-3}$ alkyl), —O($C_{1-3}$ haloalkyl),

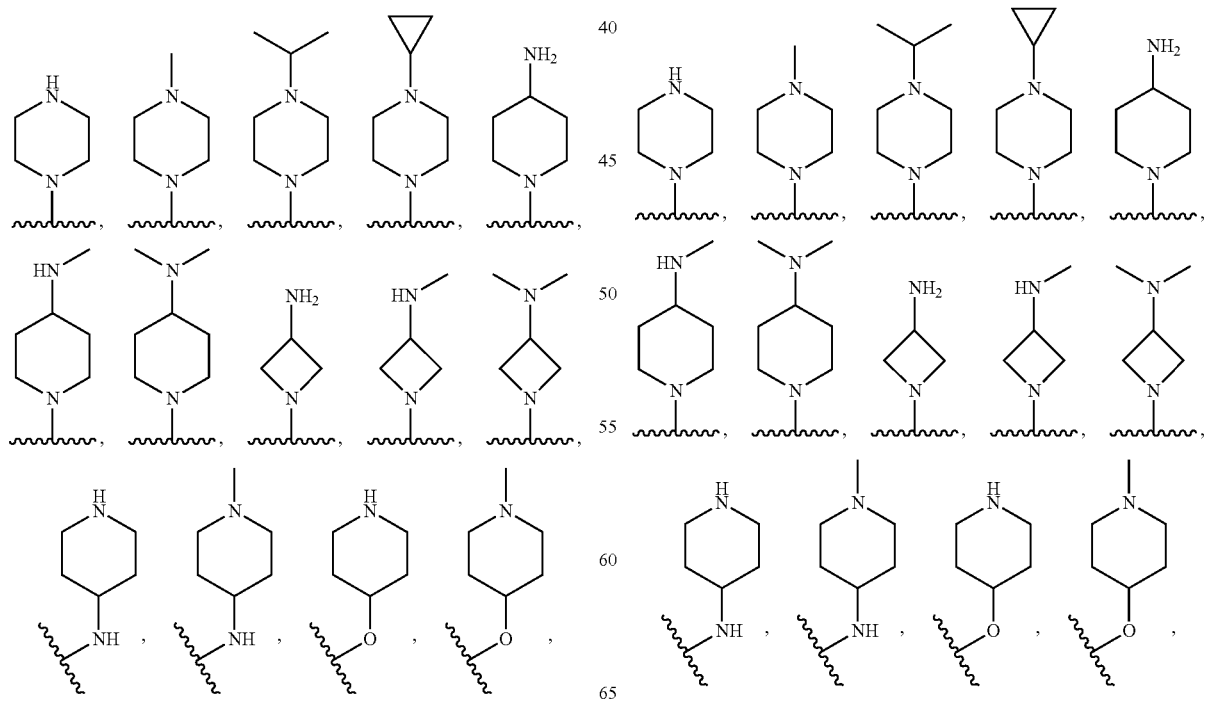

In some embodiments, $R^3$ is selected from the group consisting of:
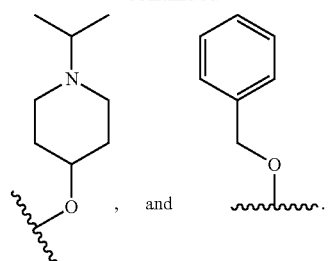
$R^6$ is a -phenyl substituted with one $R^{36}$; and $R^{36}$ is selected from the group consisting of F methyl, —O($C_{1-3}$ alkyl), —O($C_{1-3}$haloalkyl),
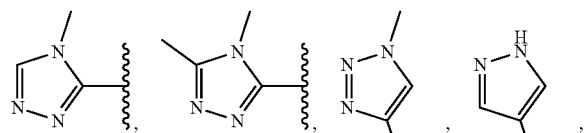
In some embodiments, $R^3$ is selected from the group consisting of:
$R^6$ is a -pyridin-2-yl substituted with one $R^{37}$; and $R^{37}$ is selected from the group consisting of
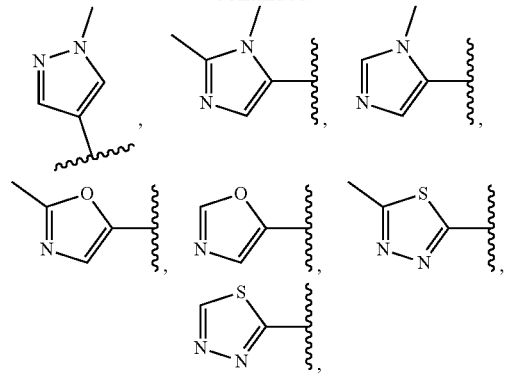

In some embodiments, $R^3$ is selected from the group consisting of:
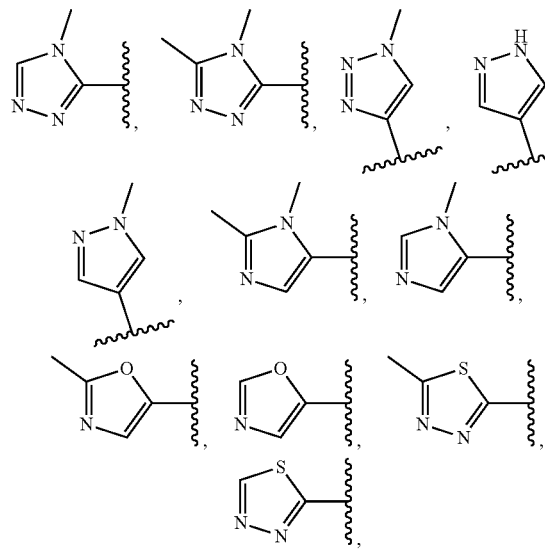
$R^6$ is a -pyridin-3-yl substituted with one $R^{37}$; and $R^{37}$ is selected from the group consisting of
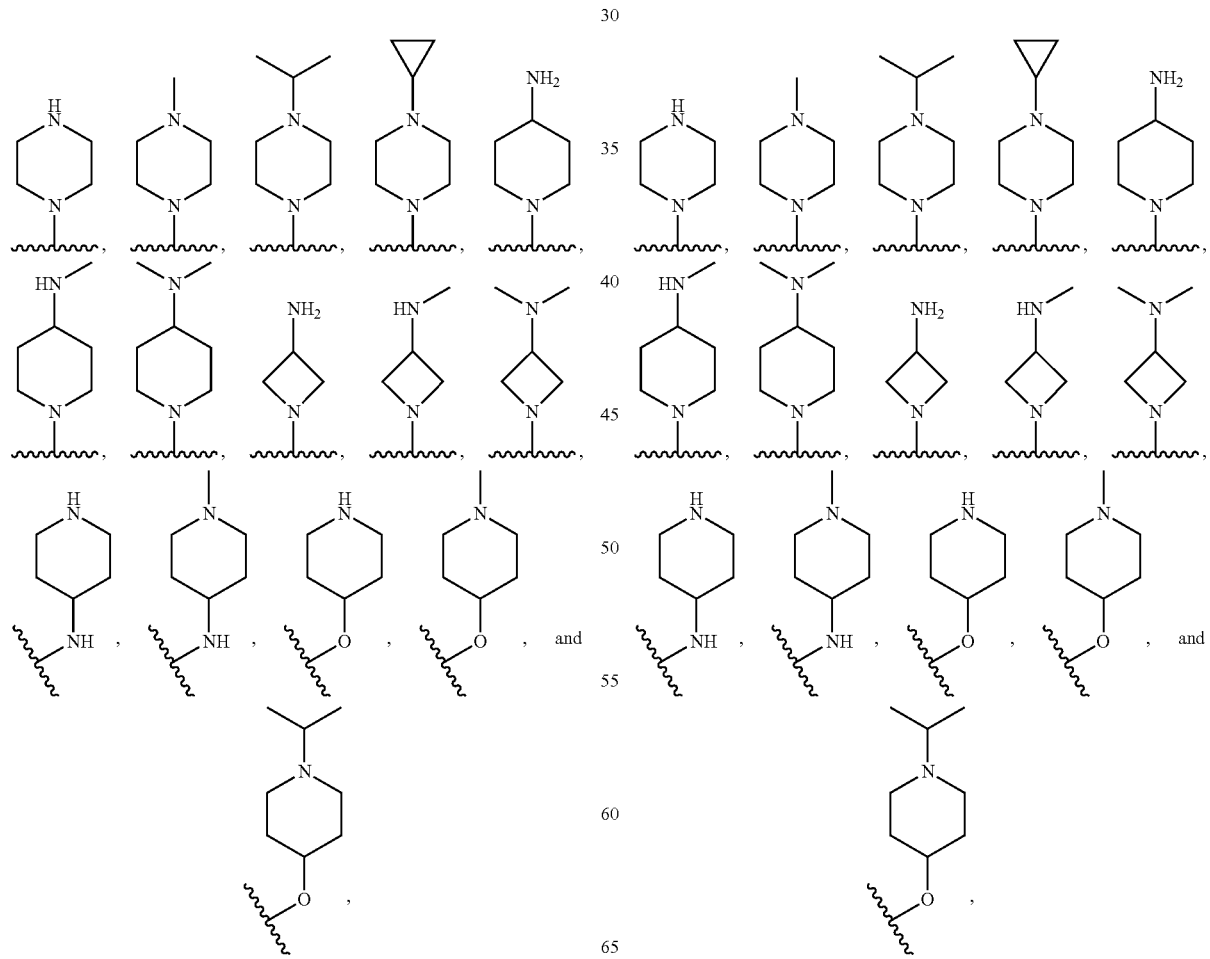
In some embodiments, $R^3$ is selected from the group consisting of:
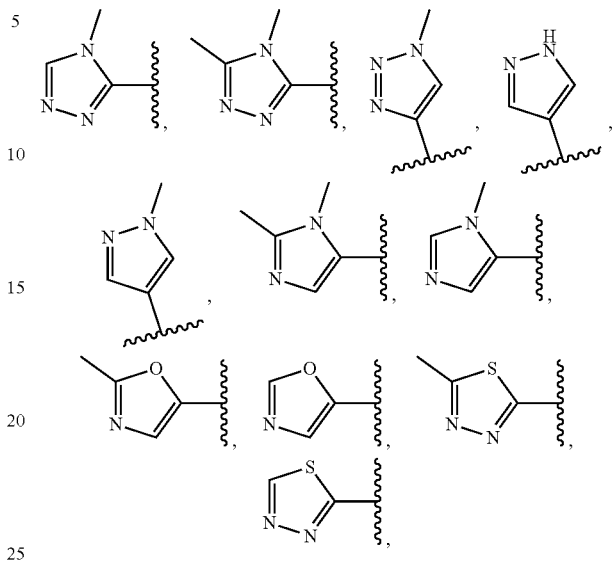
$R^6$ is a -pyridin-4-yl substituted with one $R^{37}$; and $R^{37}$ is selected from the group consisting of In some embodiments, R³ is selected from the group consisting of:
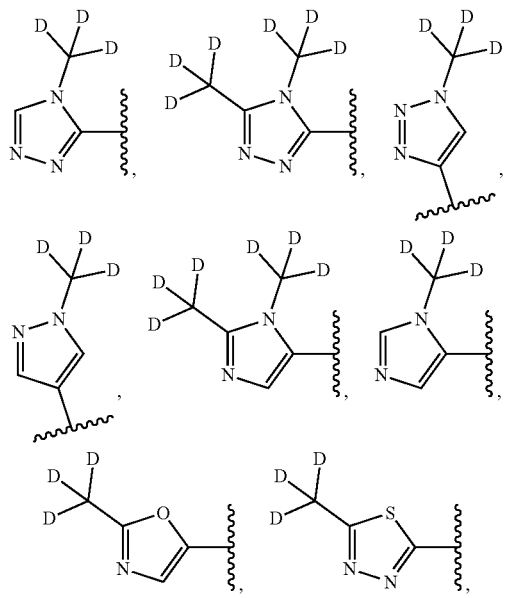
R⁶ is a -pyridin-3-yl substituted with one R³⁷; and R³⁷ is selected from the group consisting of
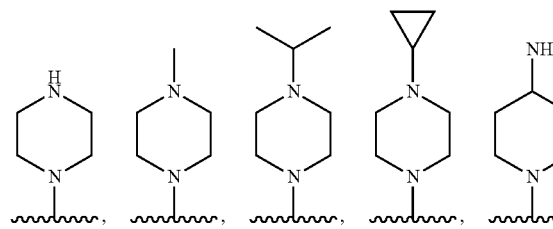
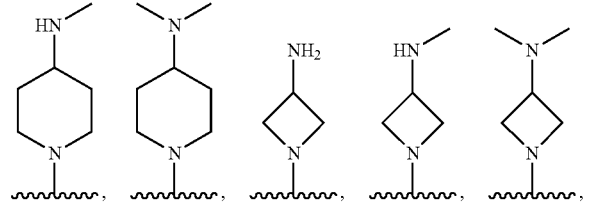
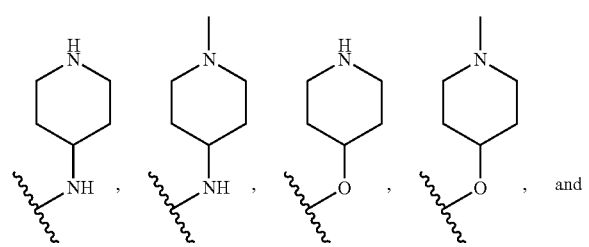
and
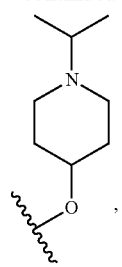
In some embodiments, R³ is selected from the group consisting of:
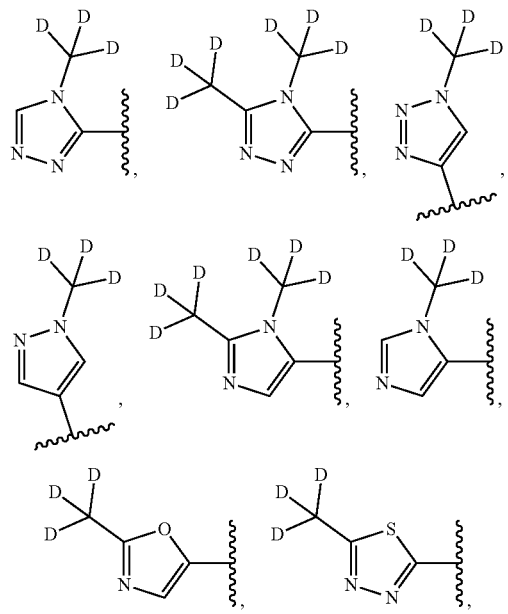
R⁶ is a -pyridin-4-yl substituted with one R³⁷; and R³⁷ is selected from the group consisting of -continued

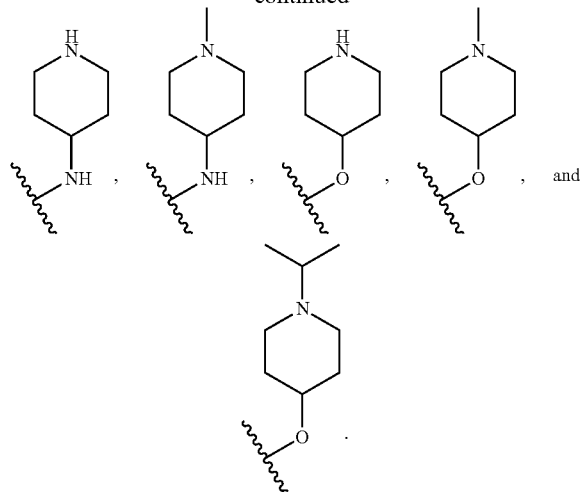

In some embodiments, R³ is selected from the group consisting of:

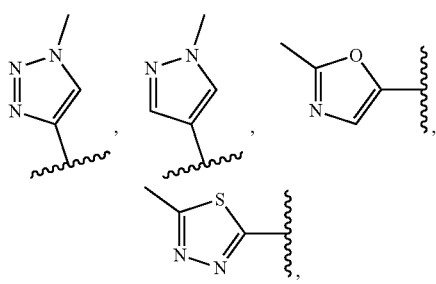

R⁶ is selected from the group consisting of -phenyl optionally substituted with 1-2 R³⁶ and —(C$_{1-2}$ alkylene)$_p$pyridinyl optionally substituted with 1-2 R³⁷.

In some embodiments, R³ is selected from the group consisting of:

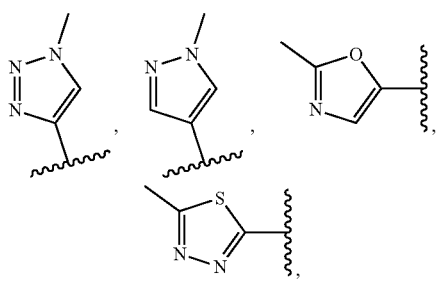

R⁶ is selected from the group consisting of -phenyl substituted with 1-2 R³⁶ and -pyridinyl substituted with 1-2 R³⁷, and R³⁶ is selected from the group consisting of —XR⁴², —(C$_{1-4}$ alkylene)$_p$heterocyclyl optionally substituted with 1-2 R⁴³, and —(C$_{1-4}$ alkylene)$_p$carbocyclyl optionally substituted with 1-2 R⁴⁴, and R³⁷ is selected from the group consisting of —XR⁴², —(C$_{1-4}$ alkylene)$_p$heterocyclyl optionally substituted with 1-2 R⁴³, and —(C$_{1-4}$ alkylene)$_p$carbocyclyl optionally substituted with 1-2 R⁴⁴.

In some embodiments, R³ is selected from the group consisting of:

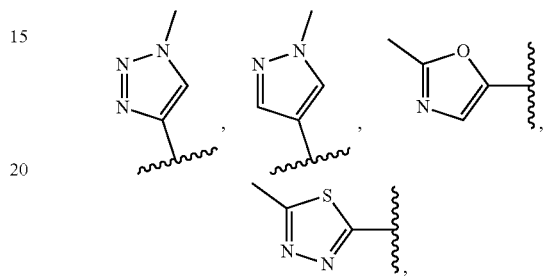

R⁶ is selected from the group consisting of -phenyl substituted with 1 R³⁶ and -pyridinyl substituted with 1 R³⁷, and R³⁶ is selected from the group consisting of —Xheterocyclyl optionally substituted with 1-2 R⁴³, -heterocyclyl optionally substituted with 1-2 R⁴³, and R³⁷ is selected from the group consisting of —Xheterocyclyl optionally substituted with 1-2 R⁴³, -heterocyclyl optionally substituted with 1-2 R⁴³.

In some embodiments, R³ is selected from the group consisting of:

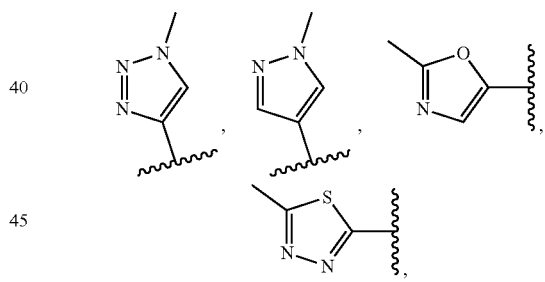

R⁶ is -pyridinyl substituted with 1 R³⁷, and R³⁷ is selected from the group consisting of —Xheterocyclyl optionally substituted with 1-2 R⁴³, -heterocyclyl optionally substituted with 1-2 R⁴³, and X is selected from the group consisting of O, S, —NH.

Illustrative compounds of Formula (I) are shown in Table 1.

TABLE 1

| 1 | 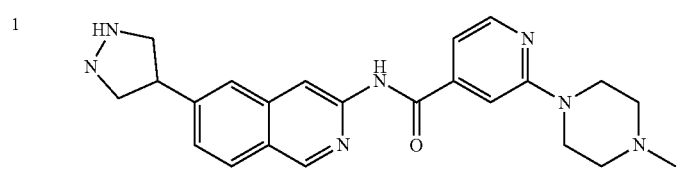 |

TABLE 1-continued
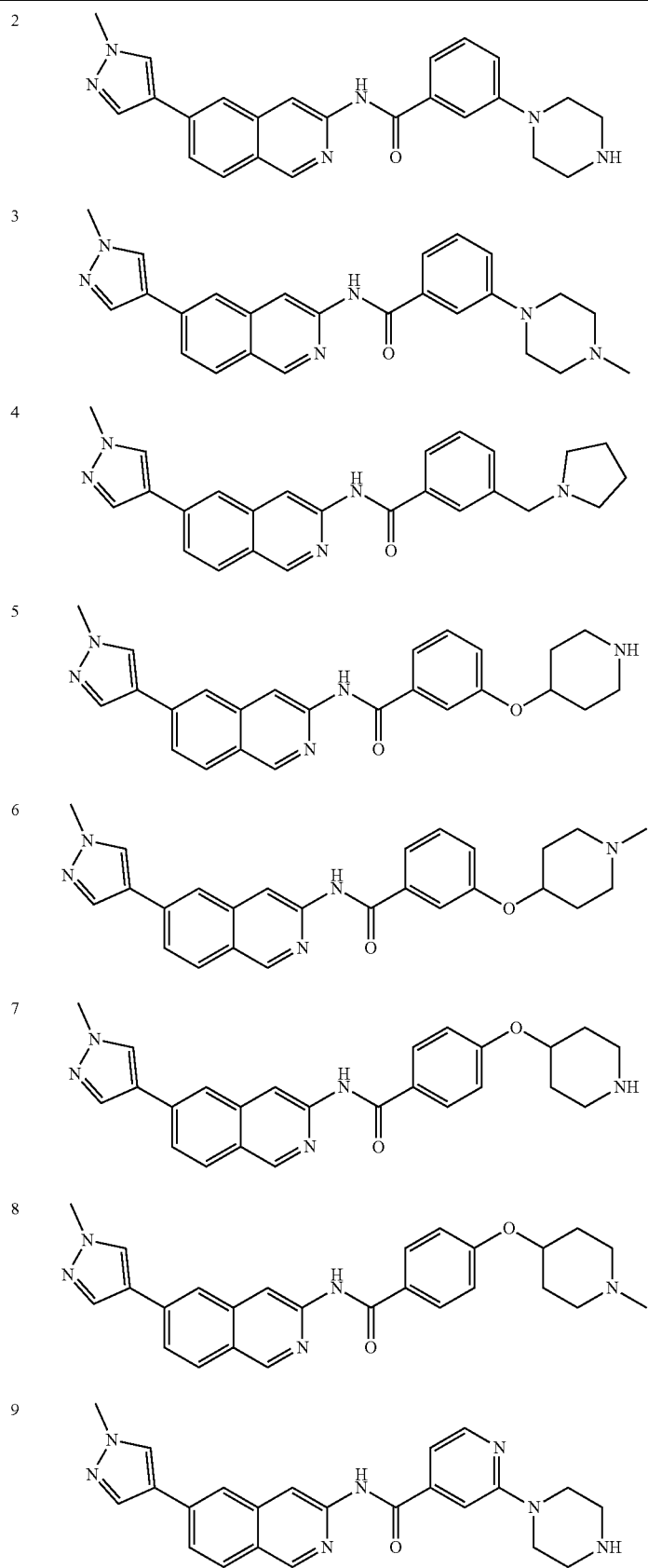

TABLE 1-continued
10 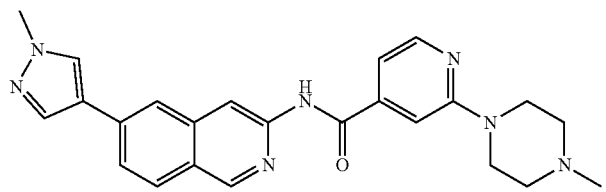
11 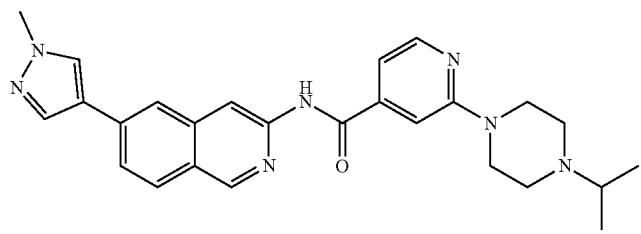 [SMILES: CC(C)N1CCN(c2cc(C(=O)Nc3cc4cc(-c5cnn(C)c5)ccc4cn3)ccn2)CC1]
12 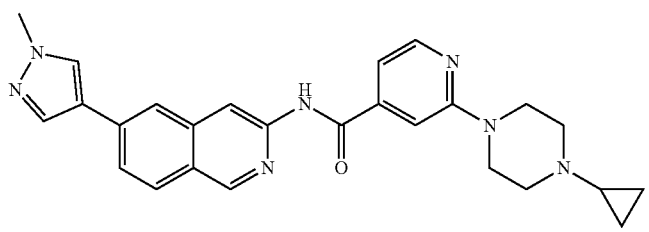 [SMILES: Cn1cc(-c2ccc3cnc(NC(=O)c4ccnc(N5CCN(C6CC6)CC5)c4)cc3c2)cn1]
13 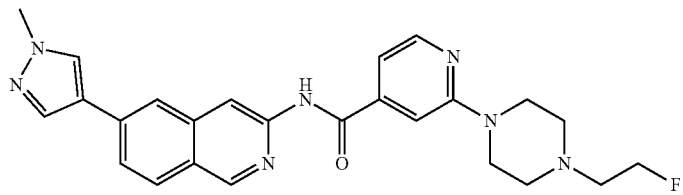 [SMILES: Cn1cc(-c2ccc3cnc(NC(=O)c4ccnc(N5CCN(CCF)CC5)c4)cc3c2)cn1]
14 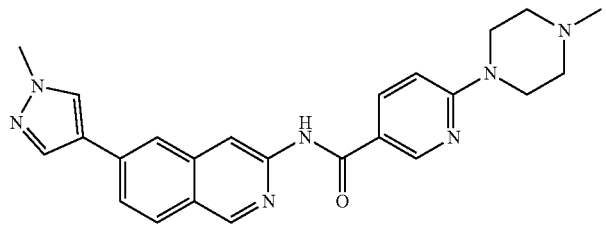
15 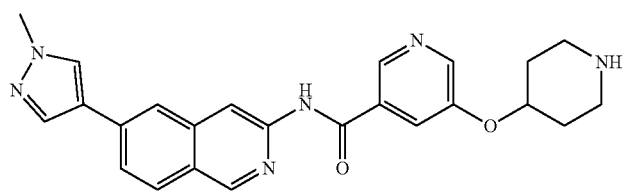 [SMILES: Cn1cc(-c2ccc3cnc(NC(=O)c4cncc(OC5CCNCC5)c4)cc3c2)cn1]
16 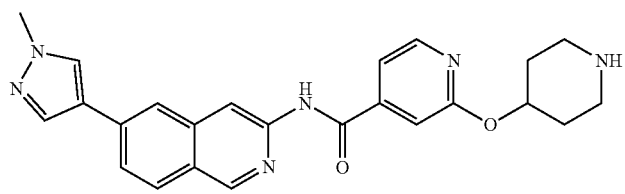 [SMILES: Cn1cc(-c2ccc3cnc(NC(=O)c4ccnc(OC5CCNCC5)c4)cc3c2)cn1]

TABLE 1-continued
17 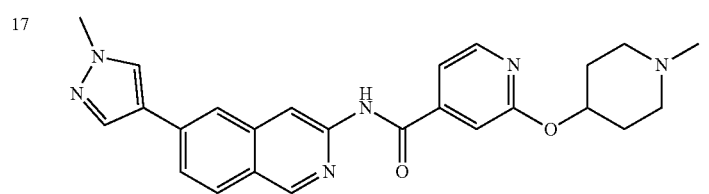
18 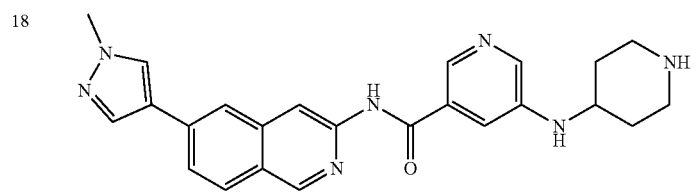
19 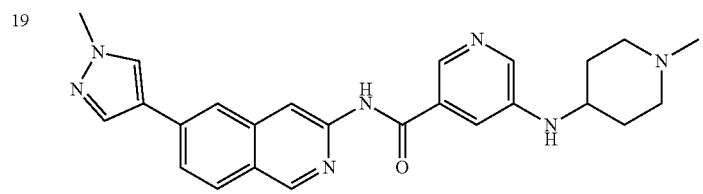
20 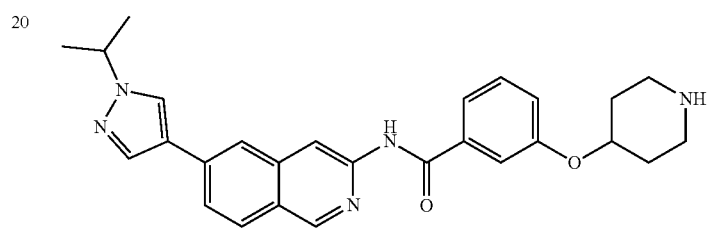
21 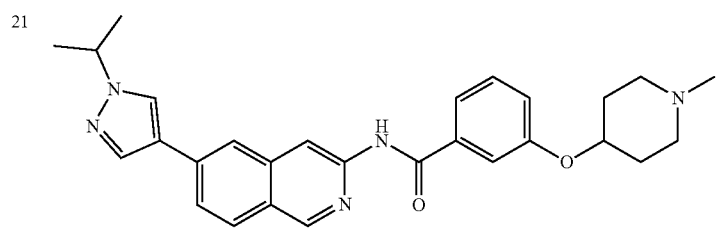
22 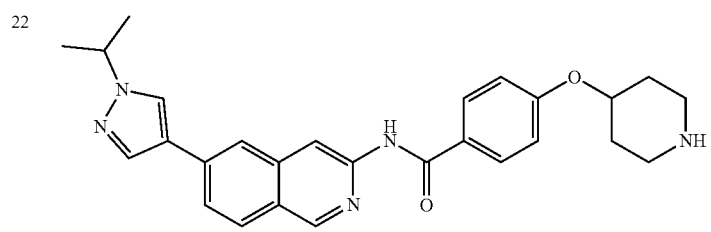
23 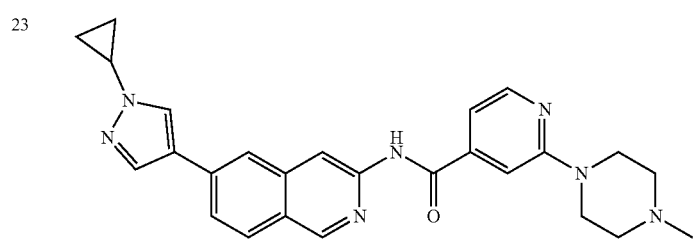

TABLE 1-continued
| 24 | 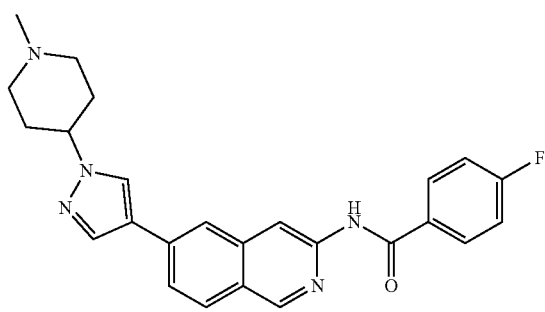 [SMILES: CN1CCC(n2cc(-c3ccc4cnc(NC(=O)c5ccc(F)cc5)cc4c3)cn2)CC1] |
| --- | --- |
| 25 | 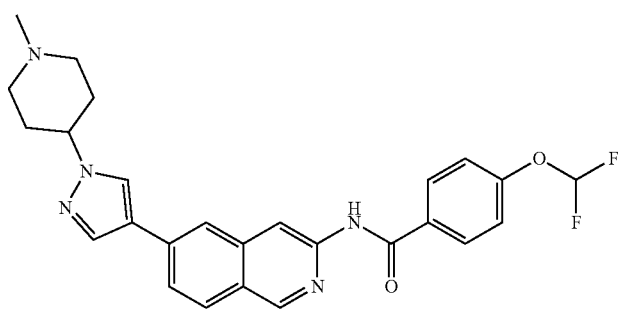 [SMILES: CN1CCC(n2cc(-c3ccc4cnc(NC(=O)c5ccc(OC(F)F)cc5)cc4c3)cn2)CC1] |
| 26 | 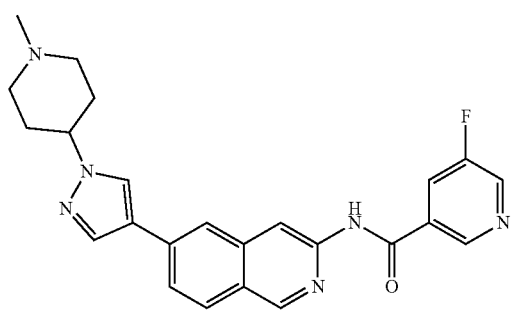 [SMILES: CN1CCC(n2cc(-c3ccc4cnc(NC(=O)c5cncc(F)c5)cc4c3)cn2)CC1] |
| 27 | 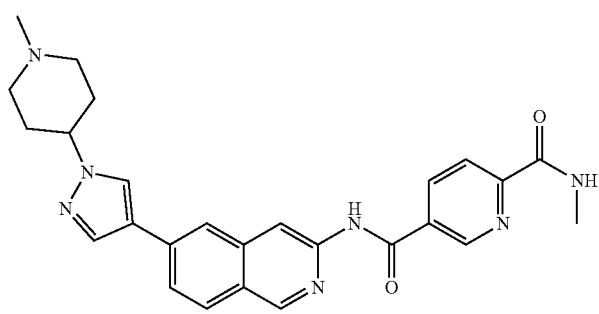 [SMILES: CNC(=O)c1ccc(C(=O)Nc2cc3cc(-c4cnn(C5CCN(C)CC5)c4)ccc3cn2)cn1] |
| 28 | 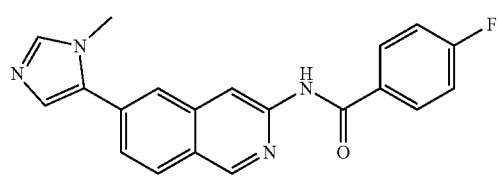 [SMILES: Cn1cncc1-c1ccc2cnc(NC(=O)c3ccc(F)cc3)cc2c1] |
| 29 | 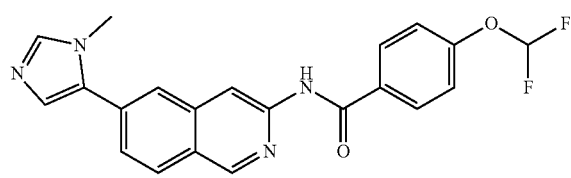 [SMILES: Cn1cncc1-c1ccc2cnc(NC(=O)c3ccc(OC(F)F)cc3)cc2c1] |

TABLE 1-continued
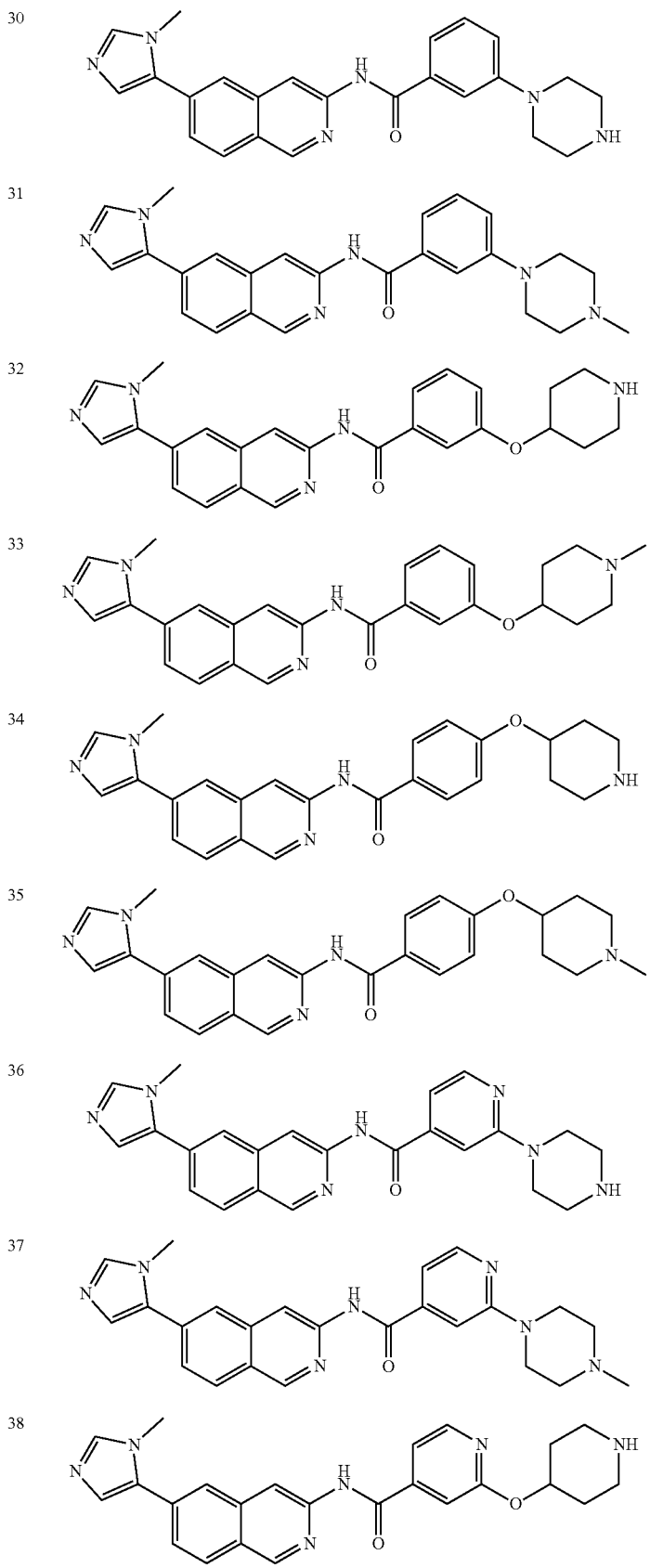

TABLE 1-continued
| 39 | 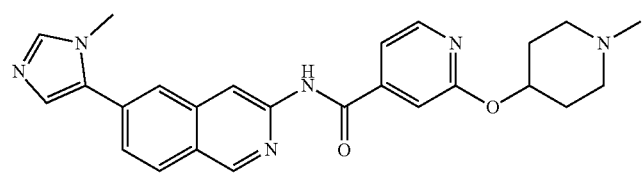 |
| 40 | 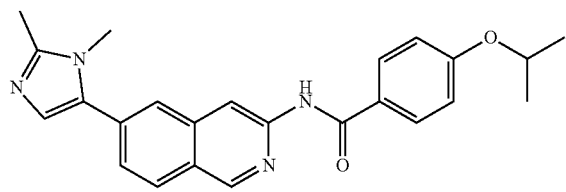 [SMILES: Cc1ncc(-c2ccc3cnc(NC(=O)c4ccc(OC(C)C)cc4)cc3c2)n1C] |
| 41 | 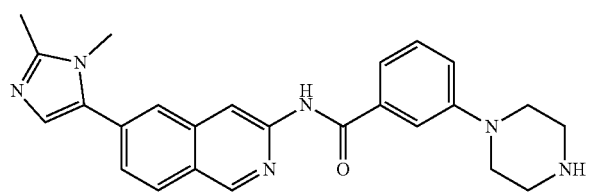 |
| 42 | 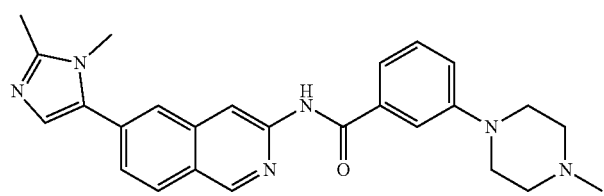 |
| 43 | 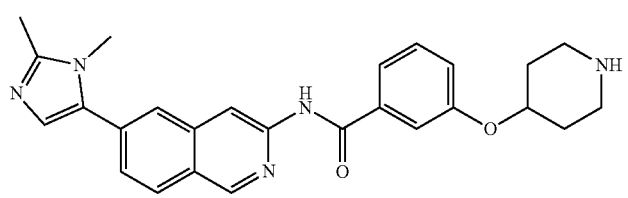 [SMILES: Cc1ncc(-c2ccc3cnc(NC(=O)c4cccc(OC5CCNCC5)c4)cc3c2)n1C] |
| 44 | 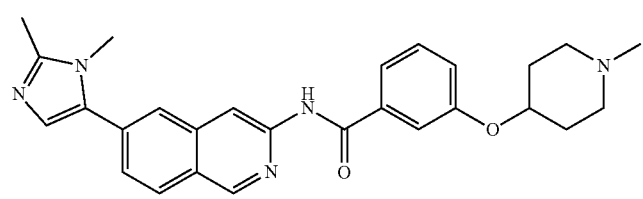 [SMILES: Cc1ncc(-c2ccc3cnc(NC(=O)c4cccc(OC5CCN(C)CC5)c4)cc3c2)n1C] |
| 45 | 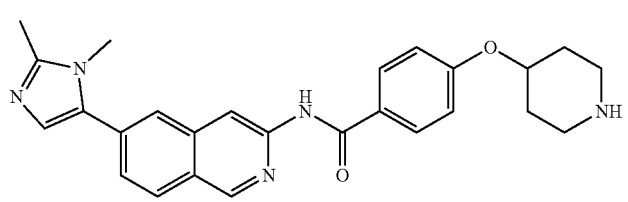 [SMILES: Cc1ncc(-c2ccc3cnc(NC(=O)c4ccc(OC5CCNCC5)cc4)cc3c2)n1C] |
| 46 | 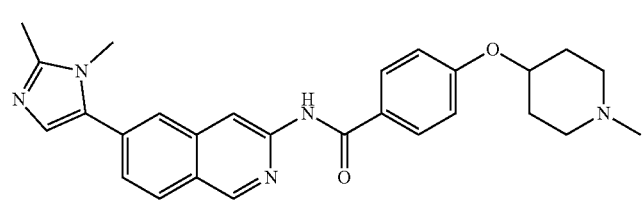 [SMILES: Cc1ncc(-c2ccc3cnc(NC(=O)c4ccc(OC5CCN(C)CC5)cc4)cc3c2)n1C] |

TABLE 1-continued
47
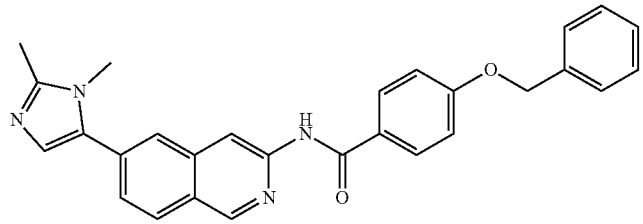 [SMILES: Cc1ncc(-c2ccc3cnc(NC(=O)c4ccc(OCc5ccccc5)cc4)cc3c2)n1C]
48
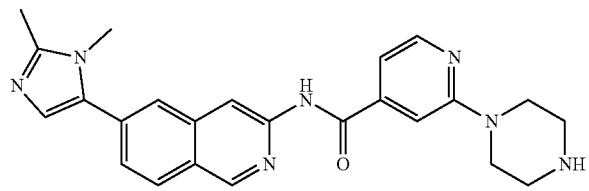
49
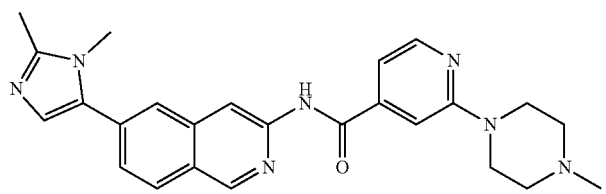 [SMILES: Cc1ncc(-c2ccc3cnc(NC(=O)c4ccnc(N5CCN(C)CC5)c4)cc3c2)n1C]
50
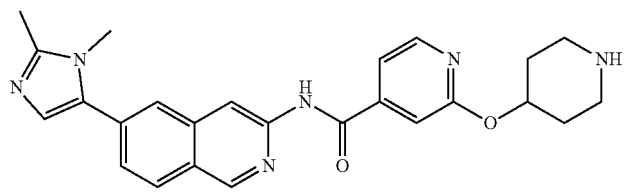
51
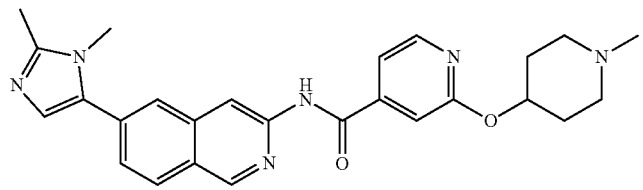 [SMILES: Cc1ncc(-c2ccc3cnc(NC(=O)c4ccnc(OC5CCN(C)CC5)c4)cc3c2)n1C]
52
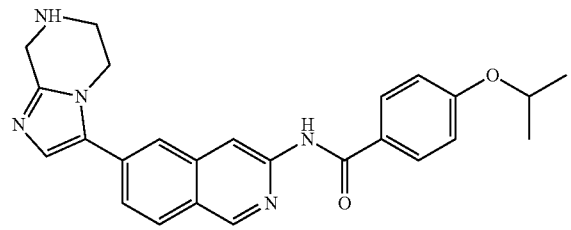 [SMILES: CC(C)Oc1ccc(C(=O)Nc2cc3cc(-c4cnc5n4CCNC5)ccc3cn2)cc1]
53
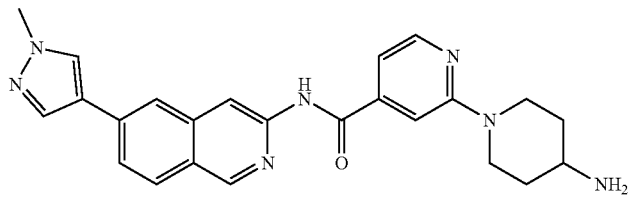 [SMILES: Cn1cc(-c2ccc3cnc(NC(=O)c4ccnc(N5CCC(N)CC5)c4)cc3c2)cn1]

TABLE 1-continued
54
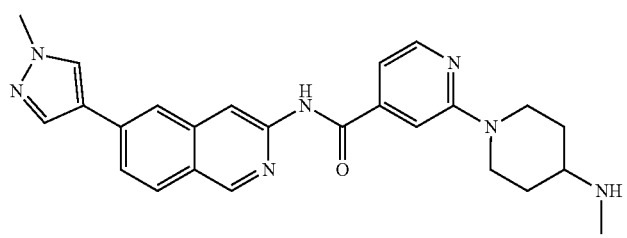 [SMILES: CNC1CCN(c2cc(C(=O)Nc3cc4cc(-c5cnn(C)c5)ccc4cn3)ccn2)CC1]
55
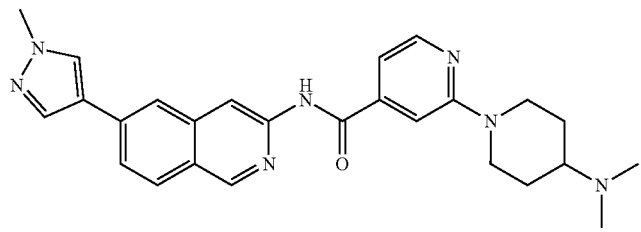 [SMILES: CN(C)C1CCN(c2cc(C(=O)Nc3cc4cc(-c5cnn(C)c5)ccc4cn3)ccn2)CC1]
56
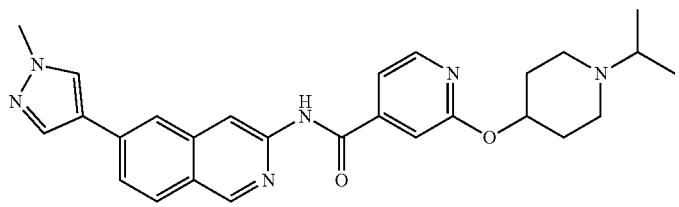
57
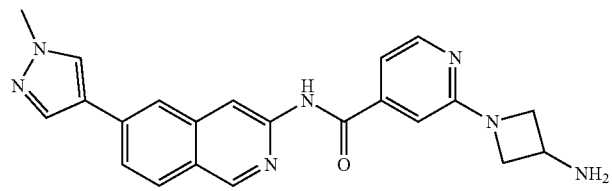 [SMILES: Cn1cc(-c2ccc3cnc(NC(=O)c4ccnc(N5CC(N)C5)c4)cc3c2)cn1]
58
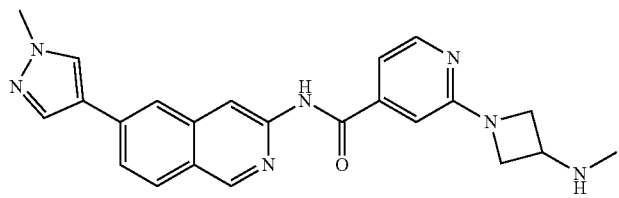 [SMILES: CNC1CN(c2cc(C(=O)Nc3cc4cc(-c5cnn(C)c5)ccc4cn3)ccn2)C1]
59
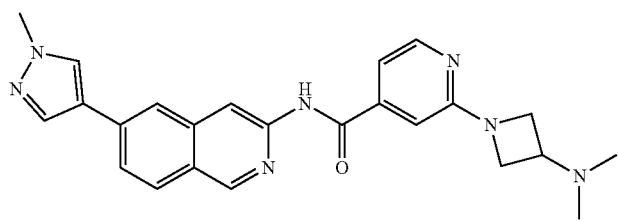 [SMILES: CN(C)C1CN(c2cc(C(=O)Nc3cc4cc(-c5cnn(C)c5)ccc4cn3)ccn2)C1]
60
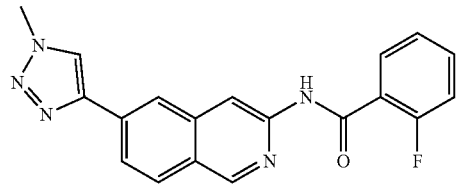 [SMILES: Cn1cc(-c2ccc3cnc(NC(=O)c4ccccc4F)cc3c2)nn1]

TABLE 1-continued
61 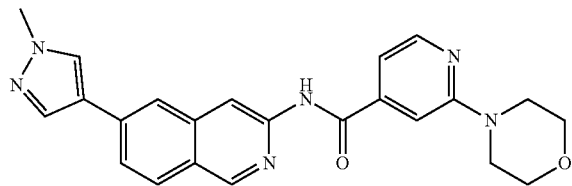 [SMILES: Cn1cc(-c2ccc3cnc(NC(=O)c4ccnc(N5CCOCC5)c4)cc3c2)cn1]
62 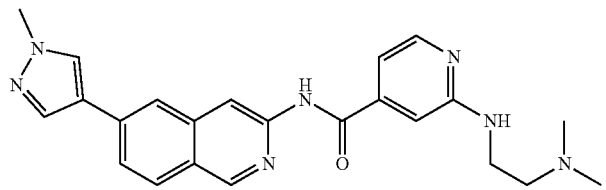
63 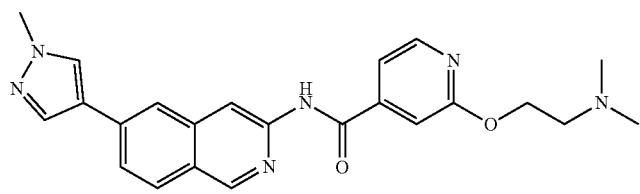 [SMILES: CN(C)CCOc1cc(C(=O)Nc2cc3cc(-c4cnn(C)c4)ccc3cn2)ccn1]
64 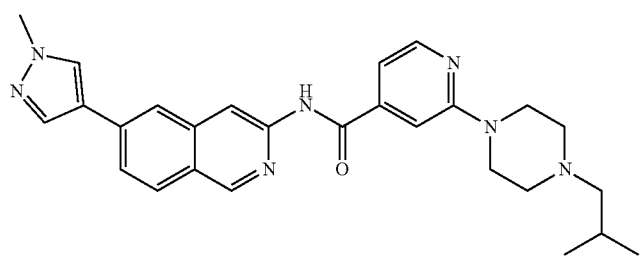 [SMILES: CC(C)CN1CCN(c2cc(C(=O)Nc3cc4cc(-c5cnn(C)c5)ccc4cn3)ccn2)CC1]
65 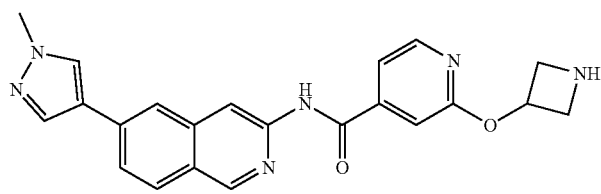
66 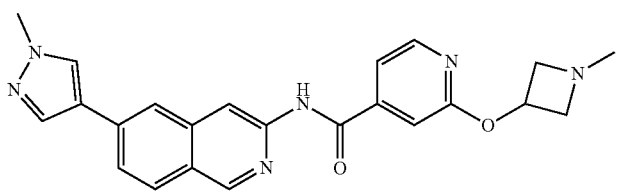 [SMILES: CN1CC(Oc2cc(C(=O)Nc3cc4cc(-c5cnn(C)c5)ccc4cn3)ccn2)C1]
67 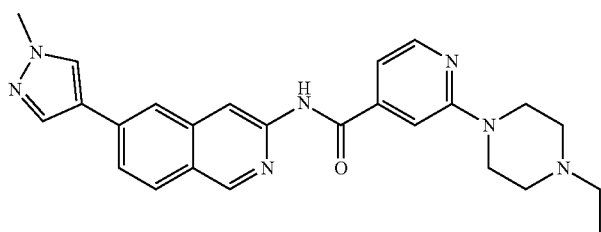 [SMILES: CCN1CCN(c2cc(C(=O)Nc3cc4cc(-c5cnn(C)c5)ccc4cn3)ccn2)CC1]

TABLE 1-continued
| 68 | 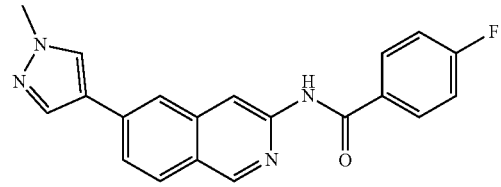 [SMILES: Cn1cc(-c2ccc3cnc(NC(=O)c4ccc(F)cc4)cc3c2)cn1] |
| 69 | 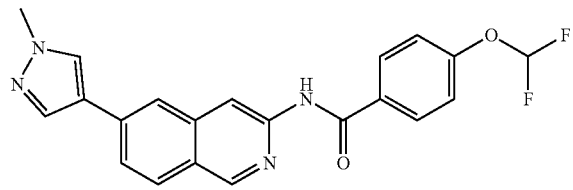 [SMILES: Cn1cc(-c2ccc3cnc(NC(=O)c4ccc(OC(F)F)cc4)cc3c2)cn1] |
| 70 | 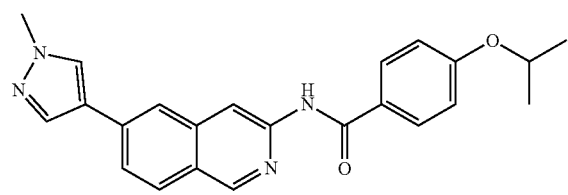 [SMILES: CC(C)Oc1ccc(C(=O)Nc2cc3cc(-c4cnn(C)c4)ccc3cn2)cc1] |
| 71 | 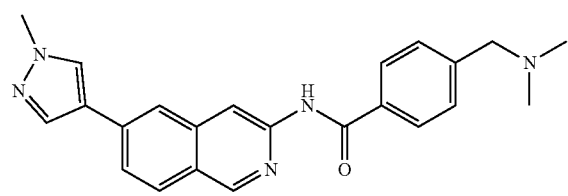 [SMILES: CN(C)Cc1ccc(C(=O)Nc2cc3cc(-c4cnn(C)c4)ccc3cn2)cc1] |
| 72 | 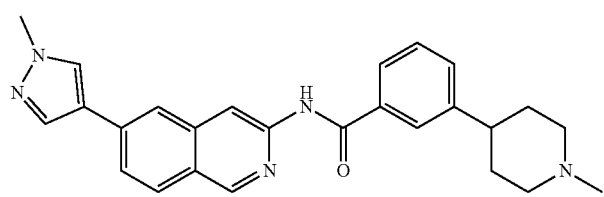 |
| 73 | 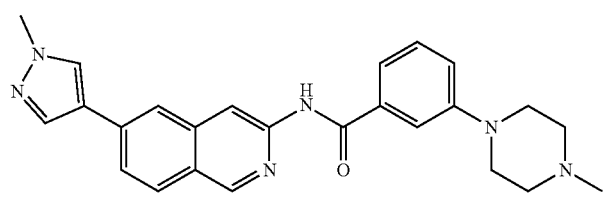 |
| 74 | 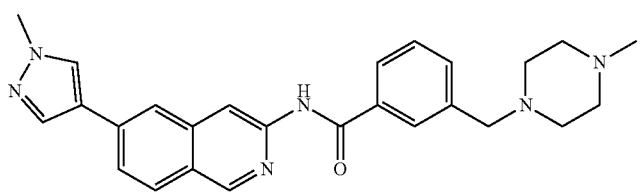 [SMILES: CN1CCN(Cc2cccc(C(=O)Nc3cc4cc(-c5cnn(C)c5)ccc4cn3)c2)CC1] |
| 75 | 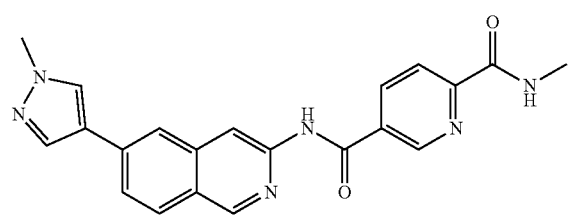 |

TABLE 1-continued
76 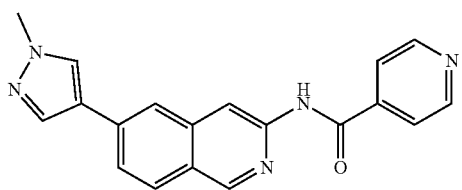 [SMILES: Cn1cc(-c2ccc3cnc(NC(=O)c4ccncc4)cc3c2)cn1]
77 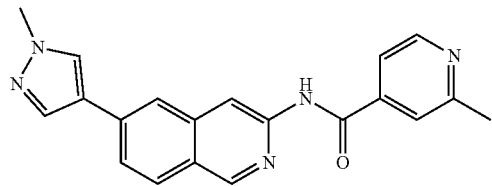 [SMILES: Cc1cc(C(=O)Nc2cc3cc(-c4cnn(C)c4)ccc3cn2)ccn1]
78 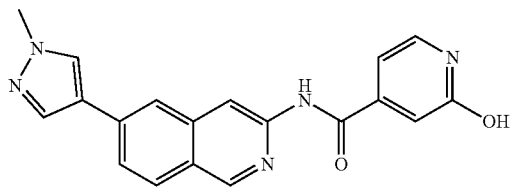 [SMILES: Cn1cc(-c2ccc3cnc(NC(=O)c4ccnc(O)c4)cc3c2)cn1]
79 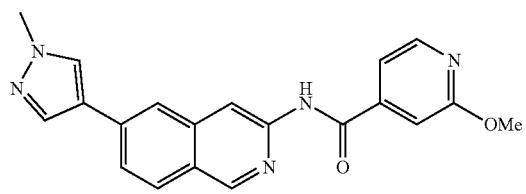 [SMILES: COc1cc(C(=O)Nc2cc3cc(-c4cnn(C)c4)ccc3cn2)ccn1]
80 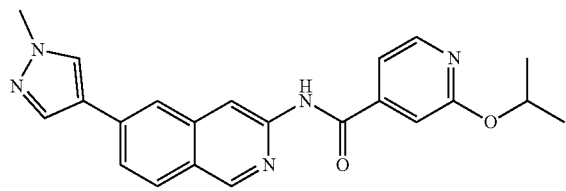 [SMILES: CC(C)Oc1cc(C(=O)Nc2cc3cc(-c4cnn(C)c4)ccc3cn2)ccn1]
81 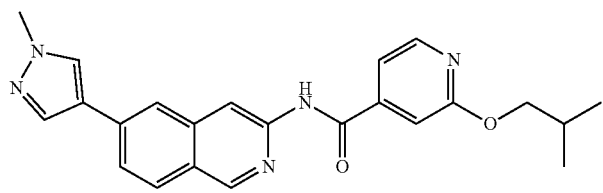 [SMILES: CC(C)COc1cc(C(=O)Nc2cc3cc(-c4cnn(C)c4)ccc3cn2)ccn1]
82 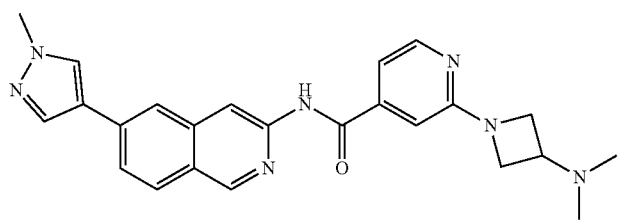 [SMILES: CN(C)C1CN(c2cc(C(=O)Nc3cc4cc(-c5cnn(C)c5)ccc4cn3)ccn2)C1]
83 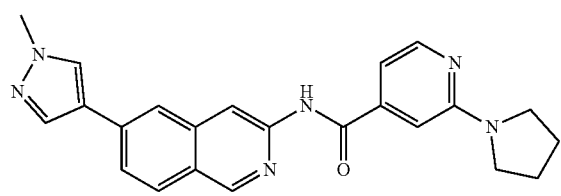 [SMILES: Cn1cc(-c2ccc3cnc(NC(=O)c4ccnc(N5CCCC5)c4)cc3c2)cn1]

TABLE 1-continued
84
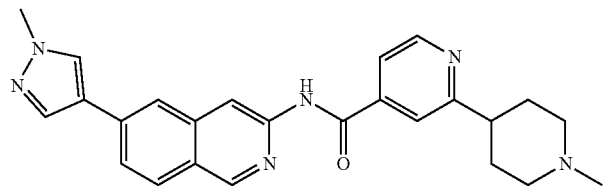 [SMILES: CN1CCC(c2cc(C(=O)Nc3cc4cc(-c5cnn(C)c5)ccc4cn3)ccn2)CC1]
85
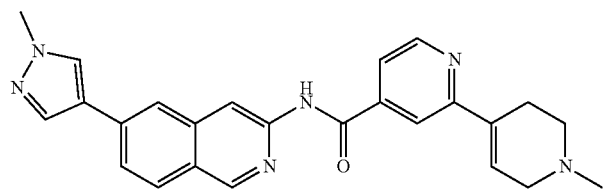 [SMILES: CN1CC=C(c2cc(C(=O)Nc3cc4cc(-c5cnn(C)c5)ccc4cn3)ccn2)CC1]
86
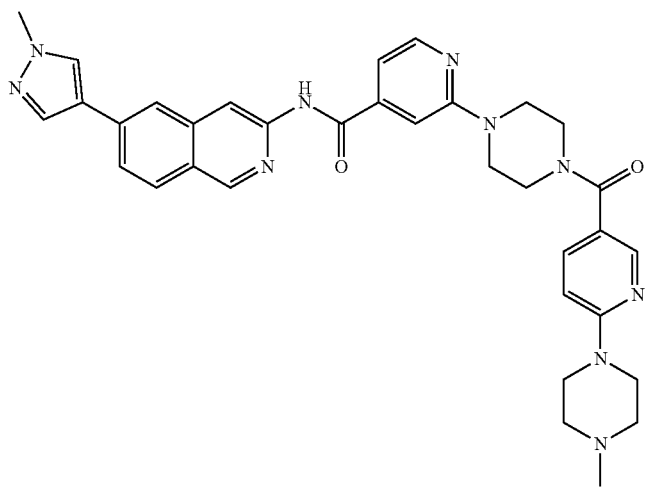 [SMILES: CN1CCN(c2ccc(C(=O)N3CCN(c4cc(C(=O)Nc5cc6cc(-c7cnn(C)c7)ccc6cn5)ccn4)CC3)cn2)CC1]
87
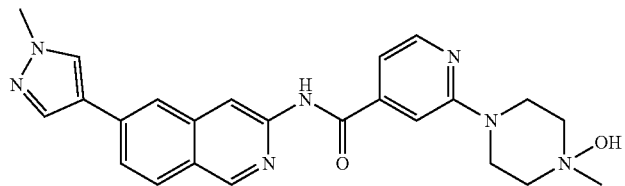
88
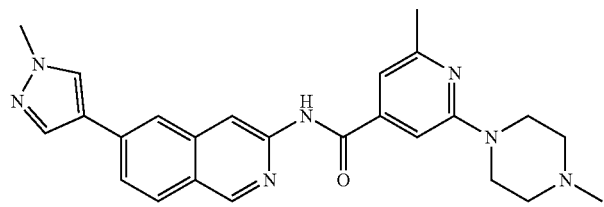 [SMILES: Cc1cc(C(=O)Nc2cc3cc(-c4cnn(C)c4)ccc3cn2)cc(N2CCN(C)CC2)n1]
89
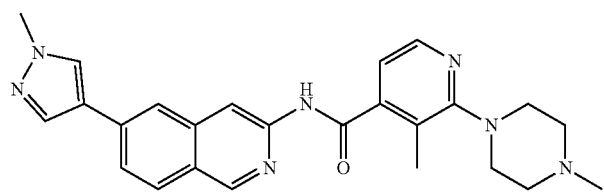 [SMILES: CN1CCN(c2nccc(C(=O)Nc3cc4cc(-c5cnn(C)c5)ccc4cn3)n2)CC1]

TABLE 1-continued
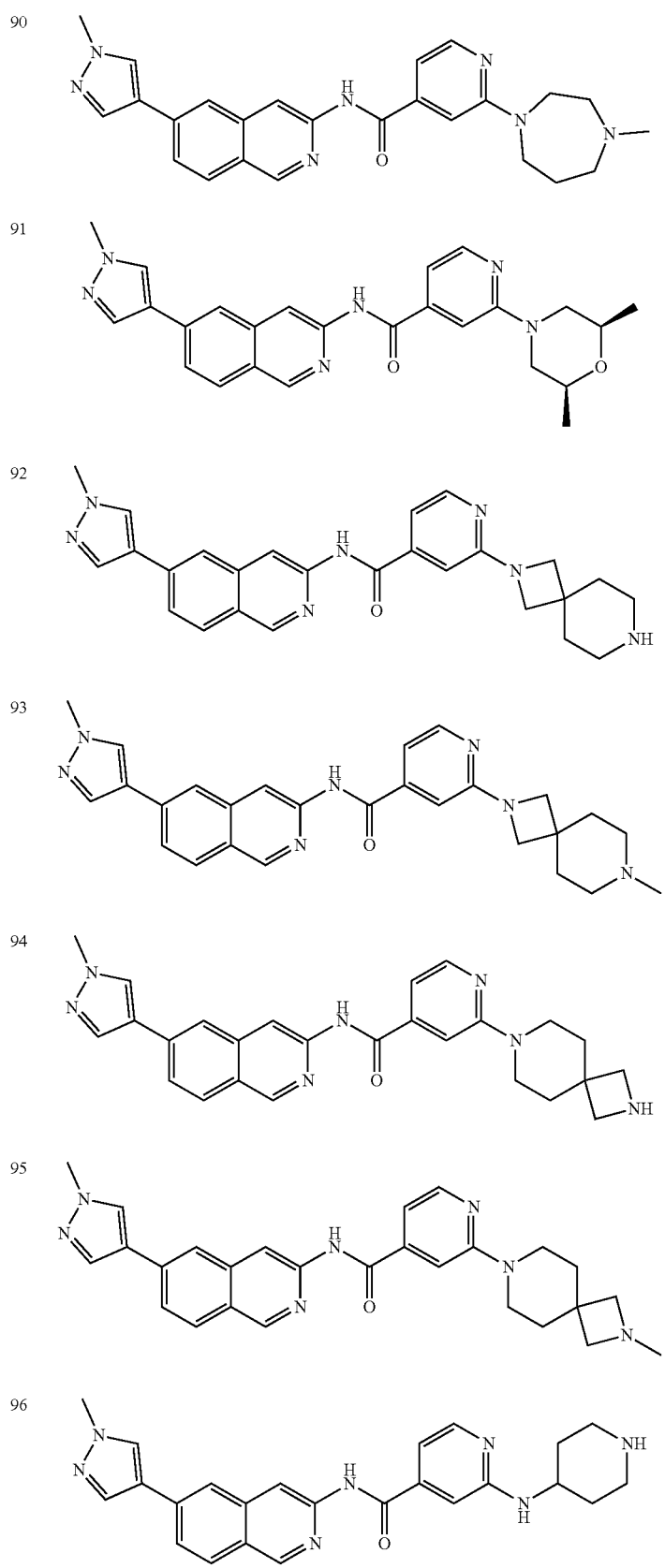

TABLE 1-continued
| 97 | 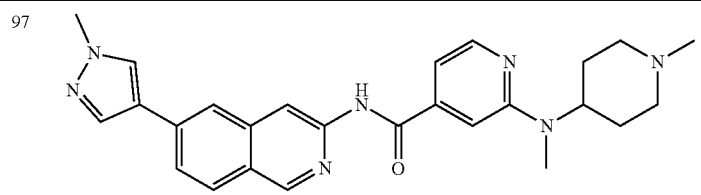 |
| 98 | 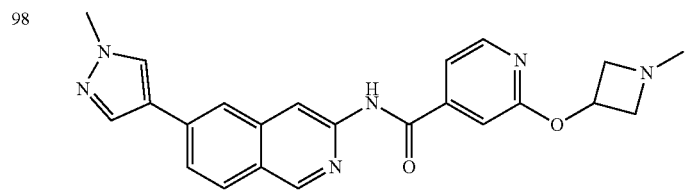 |
| 99 | 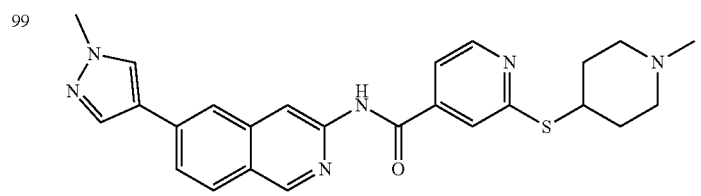 |
| 100 | 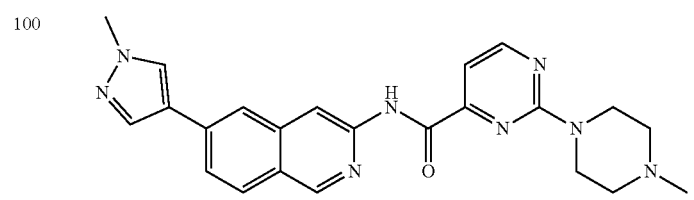 |
| 101 | 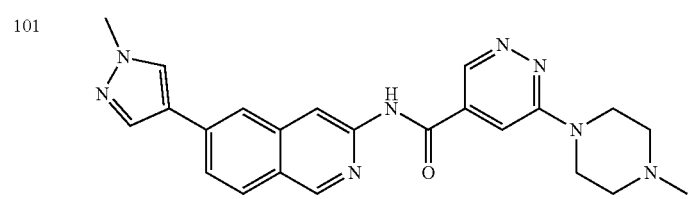 |
| 102 | 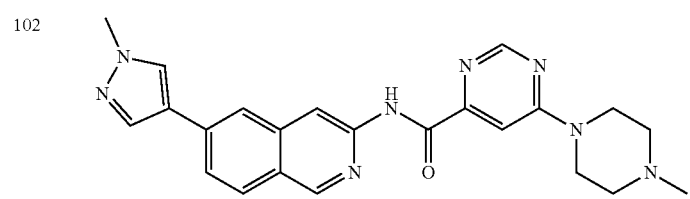 |
| 103 | 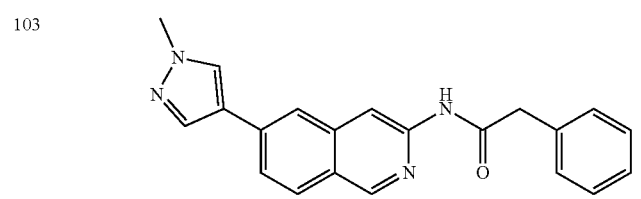 |
| 104 | 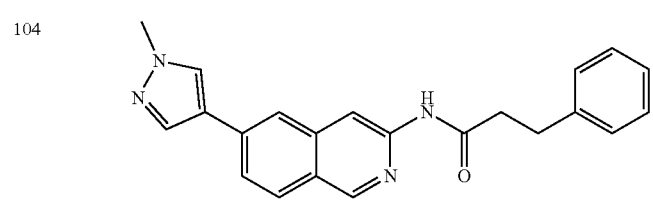 |

TABLE 1-continued

| 105 | (structure) |
| 106 | (structure) |
| 107 | (structure) |
| 108 | (structure) |
| 109 | (structure) |
| 110 | (structure) |
| 111 | (structure) |
| 112 | (structure) |

TABLE 1-continued
| | |
|---|---|
| 113 | 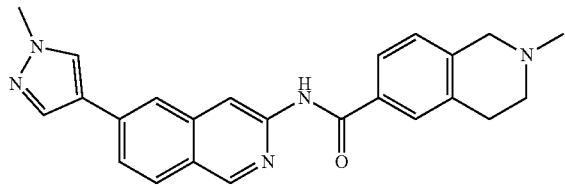 [SMILES: CN1CCc2cc(C(=O)Nc3cc4cc(-c5cnn(C)c5)ccc4cn3)ccc2C1] |
| 114 | 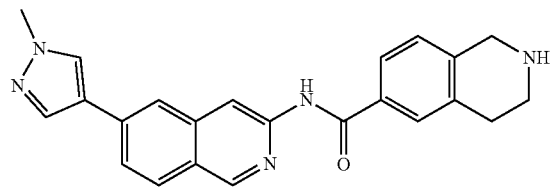 [SMILES: Cn1cc(-c2ccc3cnc(NC(=O)c4ccc5c(c4)CCNC5)cc3c2)cn1] |
| 115 | 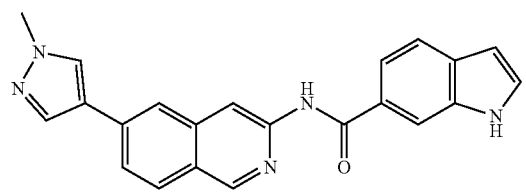 |
| 116 | 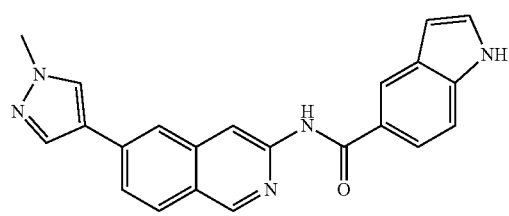 [SMILES: Cn1cc(-c2ccc3cnc(NC(=O)c4ccc5[nH]ccc5c4)cc3c2)cn1] |
| 117 | 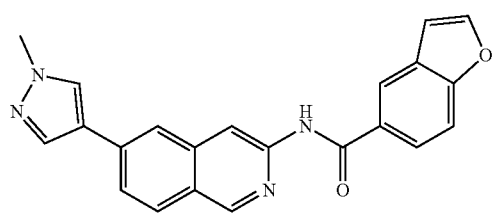 [SMILES: Cn1cc(-c2ccc3cnc(NC(=O)c4ccc5occc5c4)cc3c2)cn1] |
| 118 | 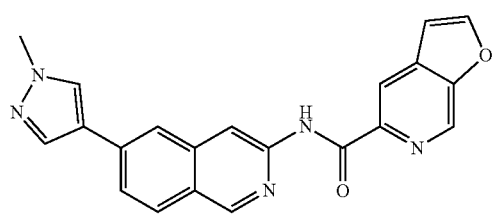 [SMILES: Cn1cc(-c2ccc3cnc(NC(=O)c4cc5ccoc5cn4)cc3c2)cn1] |
| 119 | 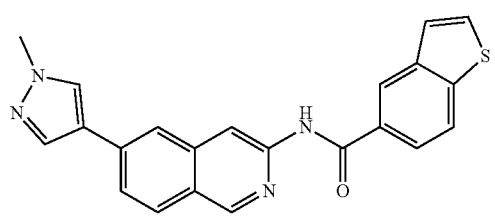 [SMILES: Cn1cc(-c2ccc3cnc(NC(=O)c4ccc5sccc5c4)cc3c2)cn1] |

TABLE 1-continued
| 120 | 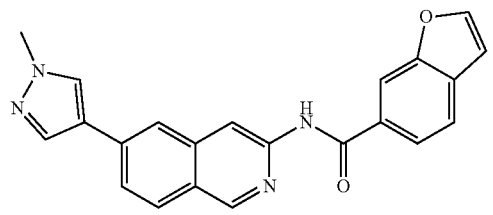 |
| 121 | 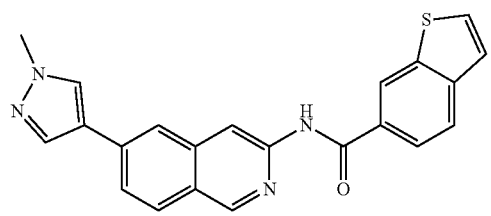 [SMILES: Cn1cc(-c2ccc3cnc(NC(=O)c4ccc5ccsc5c4)cc3c2)cn1] |
| 122 | 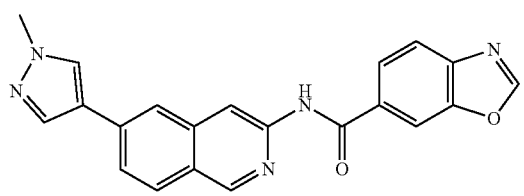 [SMILES: Cn1cc(-c2ccc3cnc(NC(=O)c4ccc5ncoc5c4)cc3c2)cn1] |
| 123 | 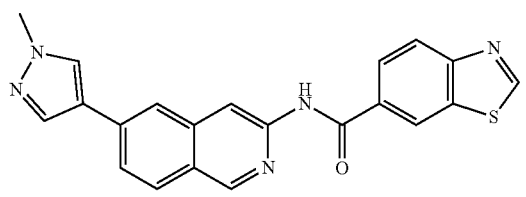 [SMILES: Cn1cc(-c2ccc3cnc(NC(=O)c4ccc5ncsc5c4)cc3c2)cn1] |
| 124 | 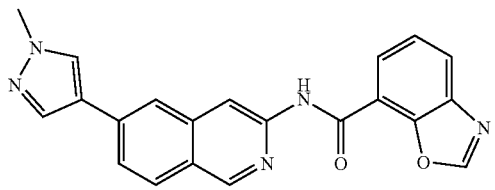 [SMILES: Cn1cc(-c2ccc3cnc(NC(=O)c4cccc5ncoc45)cc3c2)cn1] |
| 125 | 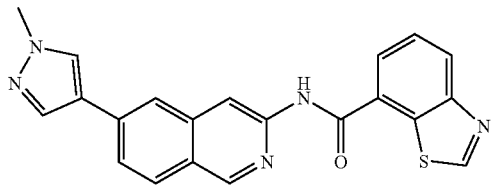 |
| 126 | 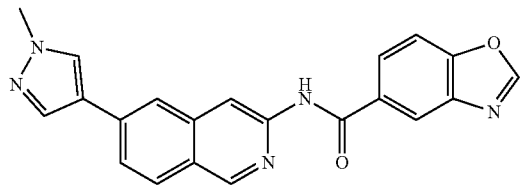 [SMILES: Cn1cc(-c2ccc3cnc(NC(=O)c4ccc5ocnc5c4)cc3c2)cn1] |
| 127 | 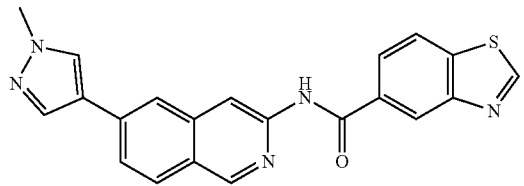 |

TABLE 1-continued
128 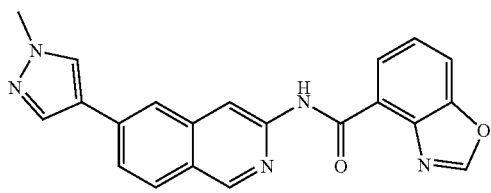 [SMILES: Cn1cc(-c2ccc3cnc(NC(=O)c4cccc5ocnc45)cc3c2)cn1]
129 
130 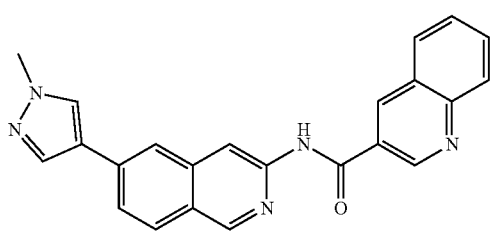 [SMILES: Cn1cc(-c2ccc3cnc(NC(=O)c4cnc5ccccc5c4)cc3c2)cn1]
131 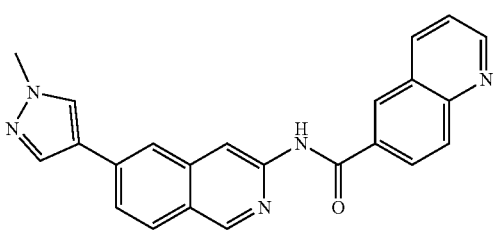 [SMILES: Cn1cc(-c2ccc3cnc(NC(=O)c4ccc5ncccc5c4)cc3c2)cn1]
132 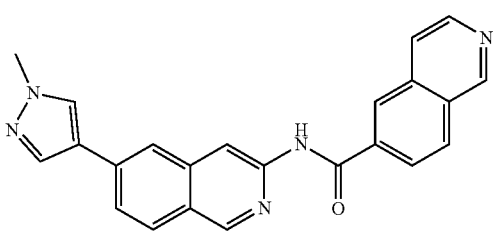 [SMILES: Cn1cc(-c2ccc3cnc(NC(=O)c4ccc5cnccc5c4)cc3c2)cn1]
133 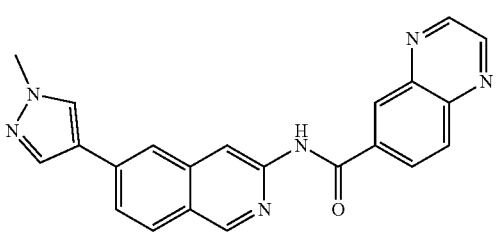 [SMILES: Cn1cc(-c2ccc3cnc(NC(=O)c4ccc5nccnc5c4)cc3c2)cn1]
134 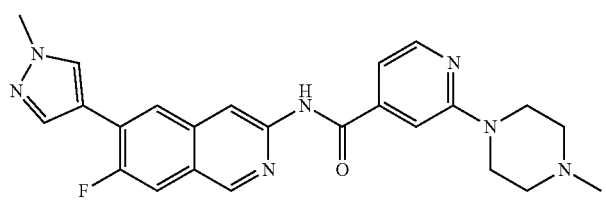

TABLE 1-continued
| 135 | 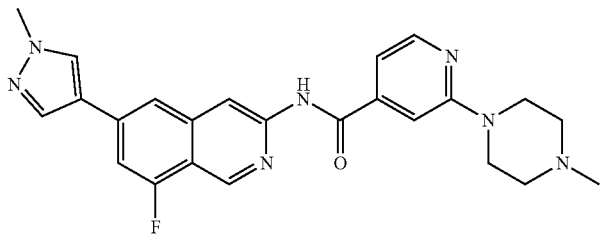 [SMILES: CN1CCN(c2cc(C(=O)Nc3cc4cc(-c5cnn(C)c5)cc(F)c4cn3)ccn2)CC1] |
| --- | --- |
| 136 | 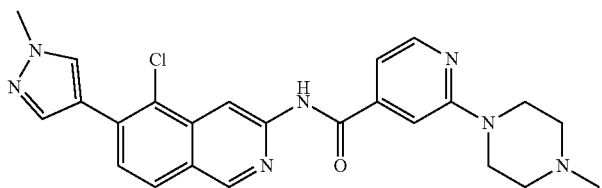 [SMILES: CN1CCN(c2cc(C(=O)Nc3cc4c(Cl)c(-c5cnn(C)c5)ccc4cn3)ccn2)CC1] |
| 137 | 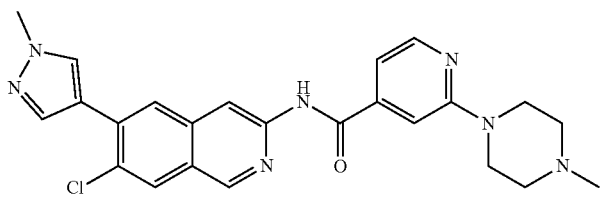 [SMILES: CN1CCN(c2cc(C(=O)Nc3cc4cc(-c5cnn(C)c5)c(Cl)cc4cn3)ccn2)CC1] |
| 138 | 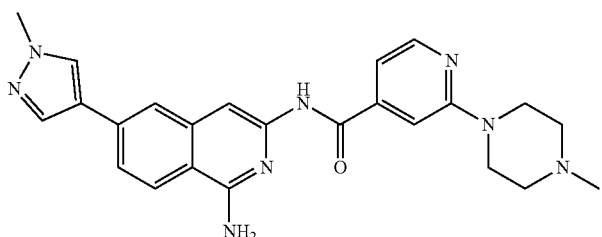 |
| 139 | 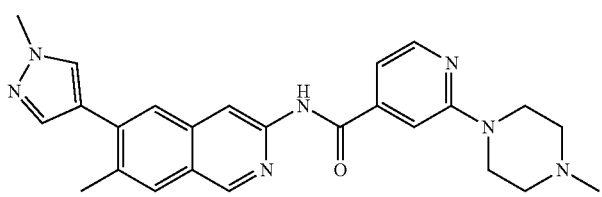 [SMILES: Cc1cc2cnc(NC(=O)c3ccnc(N4CCN(C)CC4)c3)cc2cc1-c1cnn(C)c1] |
| 140 | 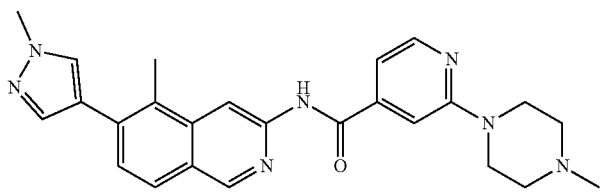 |
| 141 | 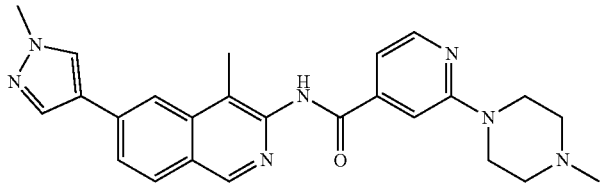 [SMILES: Cc1c(NC(=O)c2ccnc(N3CCN(C)CC3)c2)ncc2ccc(-c3cnn(C)c3)cc12] |

TABLE 1-continued
142
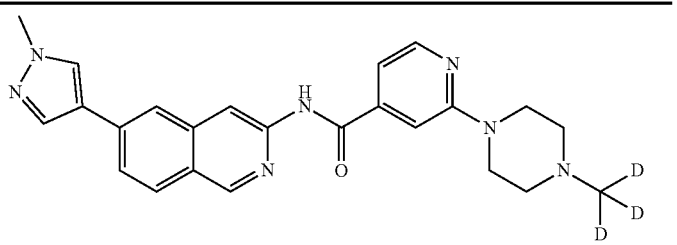
143
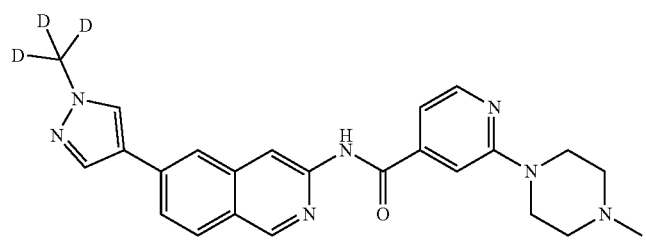 [SMILES: [2H]C([2H])([2H])n1cc(-c2ccc3cnc(NC(=O)c4ccnc(N5CCN(C)CC5)c4)cc3c2)cn1]
144
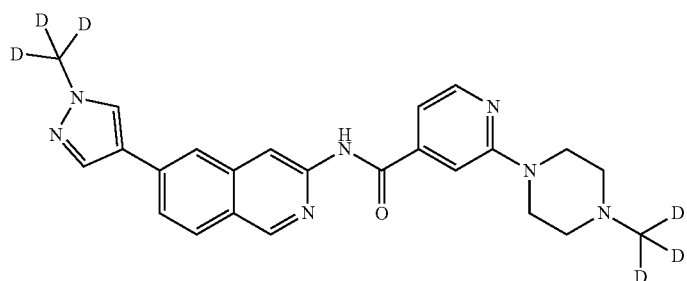 [SMILES: [2H]C([2H])([2H])N1CCN(c2cc(C(=O)Nc3cc4cc(-c5cnn(C([2H])([2H])[2H])c5)ccc4cn3)ccn2)CC1]
145
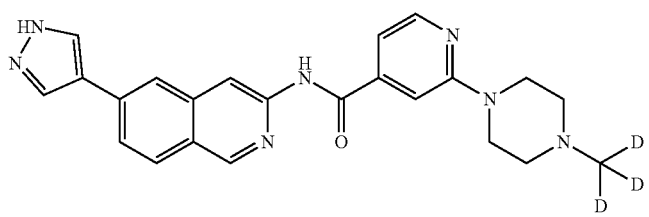 [SMILES: [2H]C([2H])([2H])N1CCN(c2cc(C(=O)Nc3cc4cc(-c5cn[nH]c5)ccc4cn3)ccn2)CC1]
146
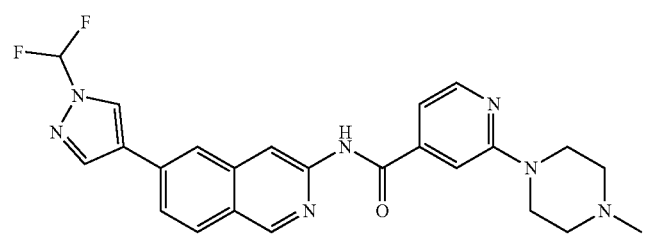 [SMILES: CN1CCN(c2cc(C(=O)Nc3cc4cc(-c5cnn(C(F)F)c5)ccc4cn3)ccn2)CC1]
147
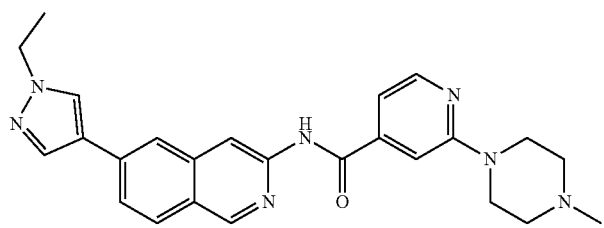 [SMILES: CCn1cc(-c2ccc3cnc(NC(=O)c4ccnc(N5CCN(C)CC5)c4)cc3c2)cn1]
148
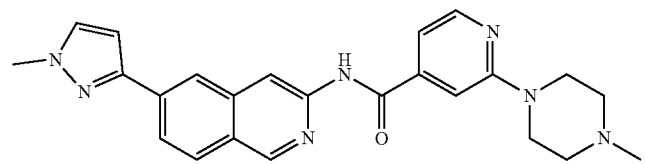

TABLE 1-continued
149 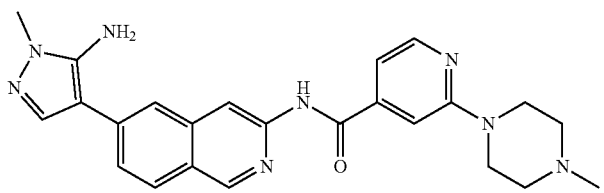 [SMILES: CN1CCN(c2cc(C(=O)Nc3cc4cc(-c5cnn(C)c5N)ccc4cn3)ccn2)CC1]
150 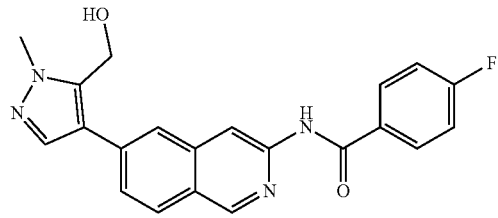 [SMILES: Cn1ncc(-c2ccc3cnc(NC(=O)c4ccc(F)cc4)cc3c2)c1CO]
151 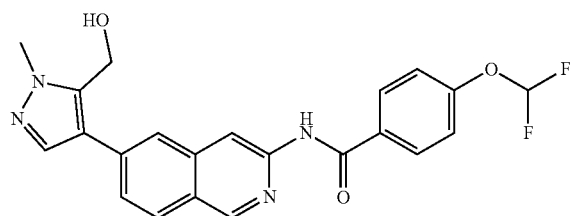
152 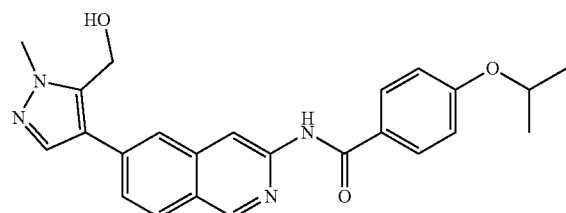
153 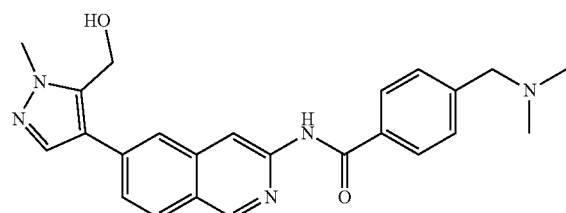
154 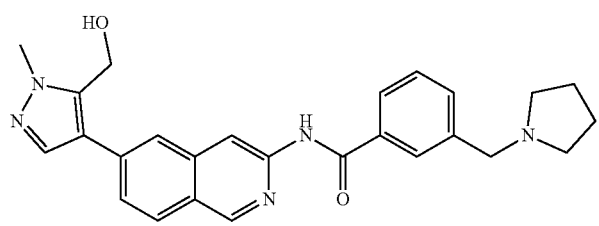 [SMILES: Cn1ncc(-c2ccc3cnc(NC(=O)c4cccc(CN5CCCC5)c4)cc3c2)c1CO]
155 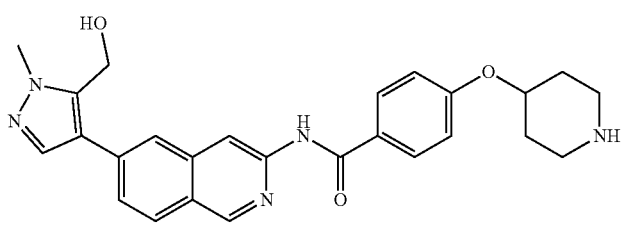 [SMILES: Cn1ncc(-c2ccc3cnc(NC(=O)c4ccc(OC5CCNCC5)cc4)cc3c2)c1CO]

TABLE 1-continued
| 156 | 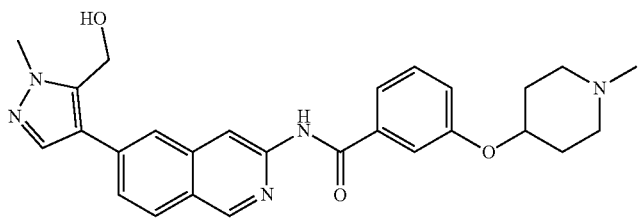 [SMILES: CN1CCC(Oc2cccc(C(=O)Nc3cc4cc(-c5cnn(C)c5CO)ccc4cn3)c2)CC1] |
| 157 | 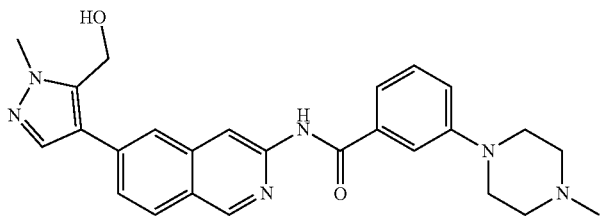 [SMILES: CN1CCN(c2cccc(C(=O)Nc3cc4cc(-c5cnn(C)c5CO)ccc4cn3)c2)CC1] |
| 158 | 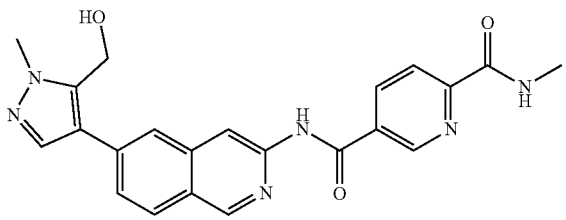 [SMILES: CNC(=O)c1ccc(C(=O)Nc2cc3cc(-c4cnn(C)c4CO)ccc3cn2)cn1] |
| 159 | 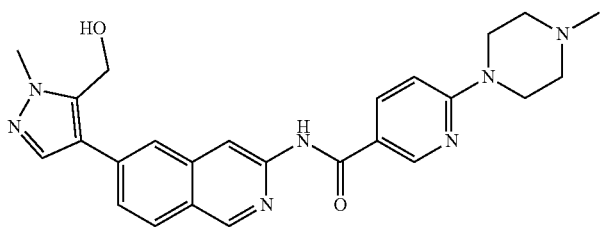 [SMILES: CN1CCN(c2ccc(C(=O)Nc3cc4cc(-c5cnn(C)c5CO)ccc4cn3)cn2)CC1] |
| 160 | 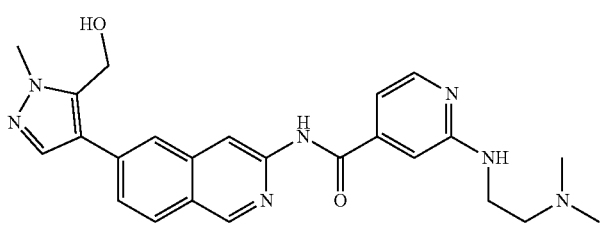 [SMILES: CN(C)CCNc1cc(C(=O)Nc2cc3cc(-c4cnn(C)c4CO)ccc3cn2)ccn1] |
| 161 | 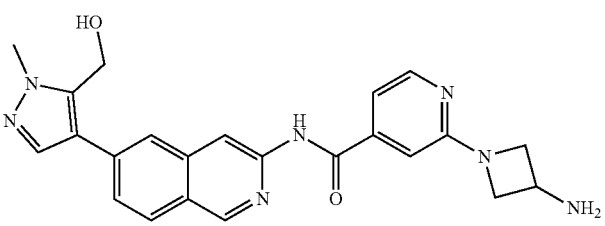 [SMILES: Cn1ncc(-c2ccc3cnc(NC(=O)c4ccnc(N5CC(N)C5)c4)cc3c2)c1CO] |
| 162 | 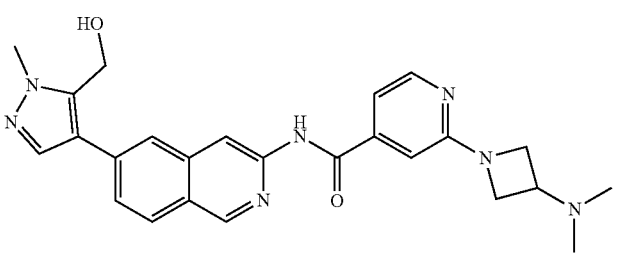 [SMILES: CN(C)C1CN(c2cc(C(=O)Nc3cc4cc(-c5cnn(C)c5CO)ccc4cn3)ccn2)C1] |

TABLE 1-continued
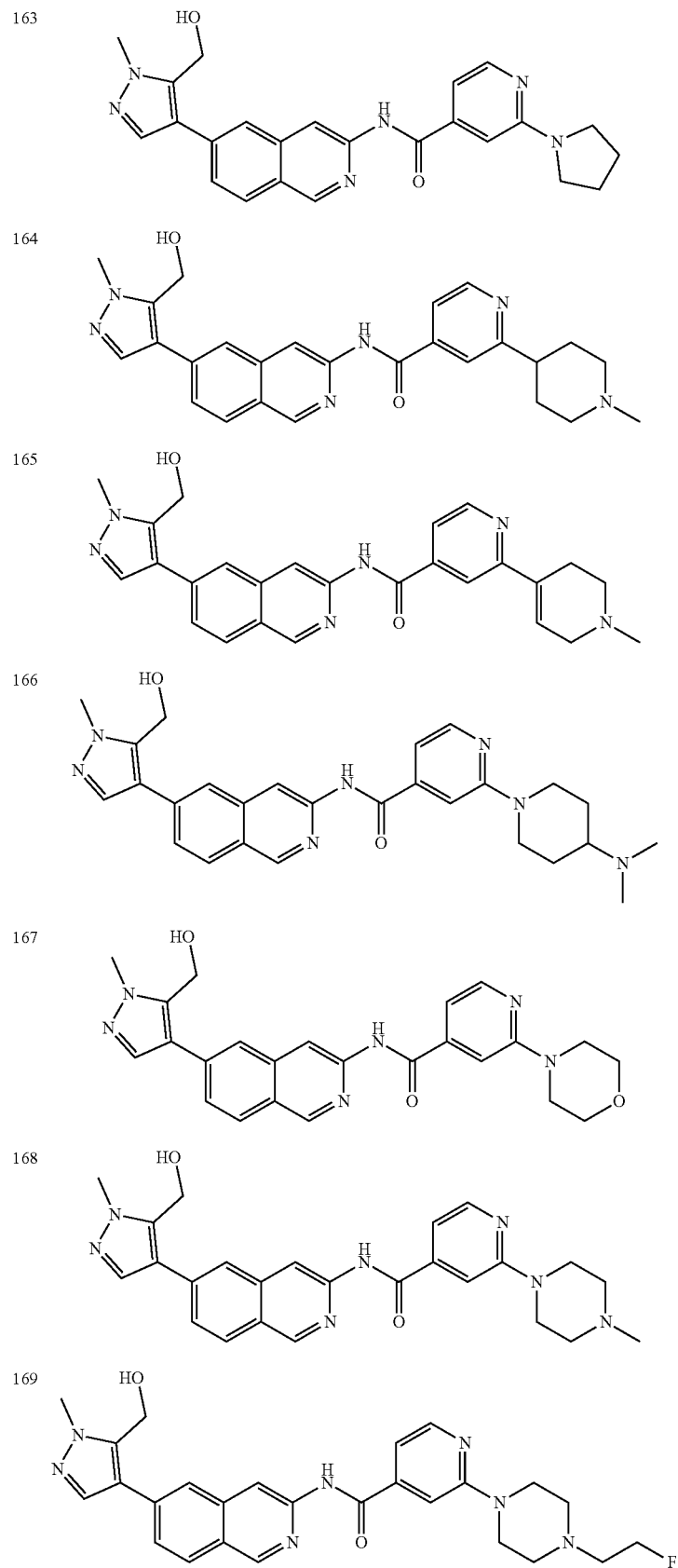

TABLE 1-continued
170 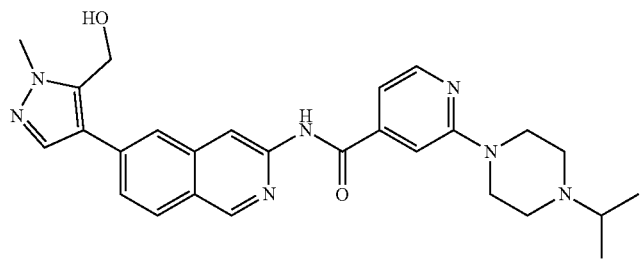 [SMILES: CC(C)N1CCN(c2cc(C(=O)Nc3cc4cc(-c5cnn(C)c5CO)ccc4cn3)ccn2)CC1]
171 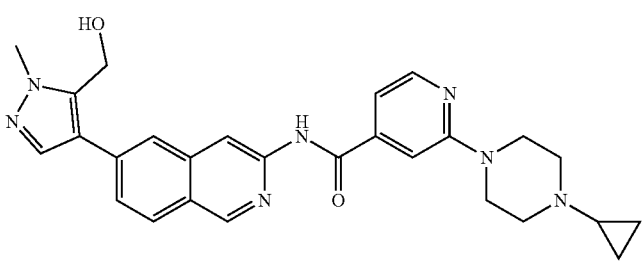 [SMILES: Cn1ncc(-c2ccc3cnc(NC(=O)c4ccnc(N5CCN(C6CC6)CC5)c4)cc3c2)c1CO]
172 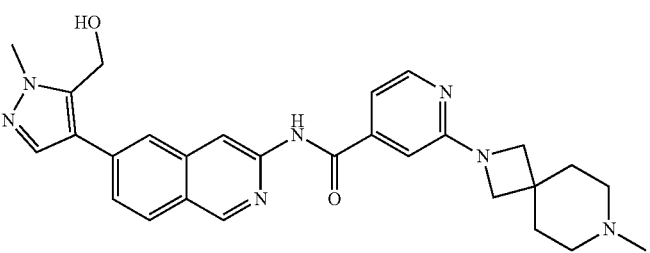 [SMILES: CN1CCC2(CC1)CN(c1cc(C(=O)Nc3cc4cc(-c5cnn(C)c5CO)ccc4cn3)ccn1)C2]
173 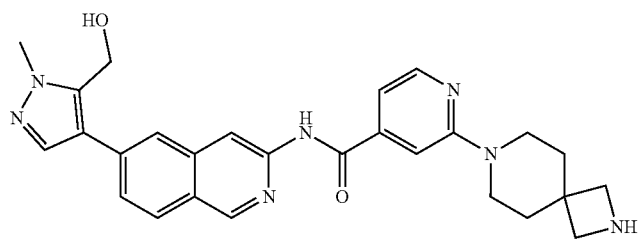 [SMILES: Cn1ncc(-c2ccc3cnc(NC(=O)c4ccnc(N5CCC6(CC5)CNC6)c4)cc3c2)c1CO]
174 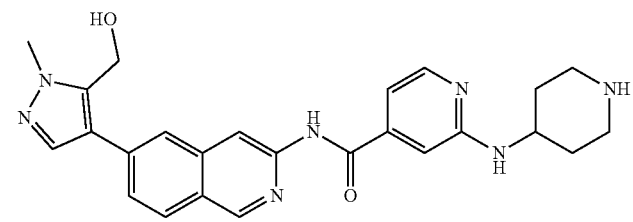 [SMILES: Cn1ncc(-c2ccc3cnc(NC(=O)c4ccnc(NC5CCNCC5)c4)cc3c2)c1CO]
175 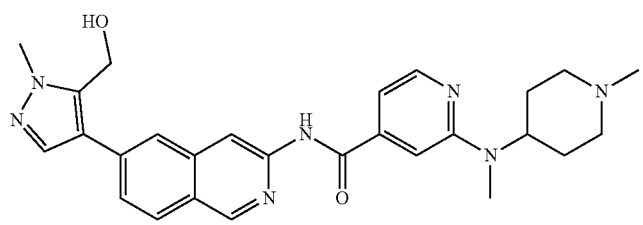

TABLE 1-continued
176 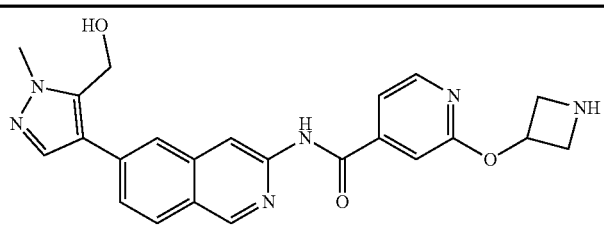
177 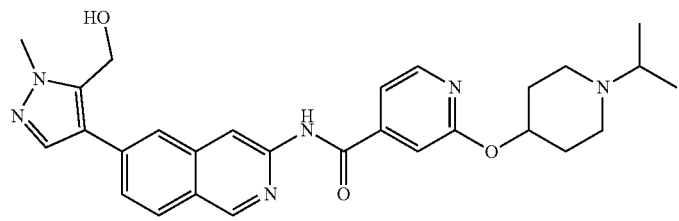 [SMILES: CC(C)N1CCC(Oc2cc(C(=O)Nc3cc4cc(-c5cnn(C)c5CO)ccc4cn3)ccn2)CC1]
178 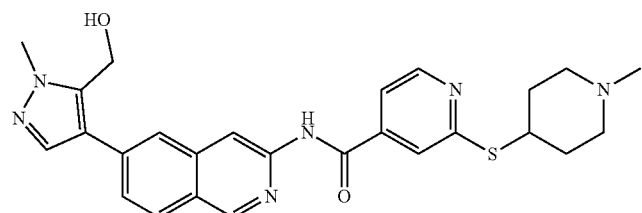
179 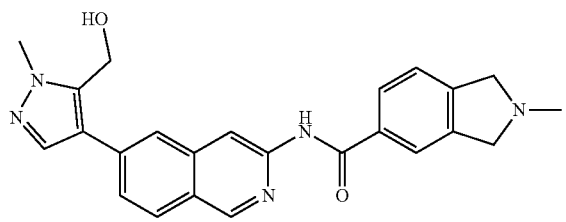 [SMILES: CN1Cc2ccc(C(=O)Nc3cc4cc(-c5cnn(C)c5CO)ccc4cn3)cc2C1]
180 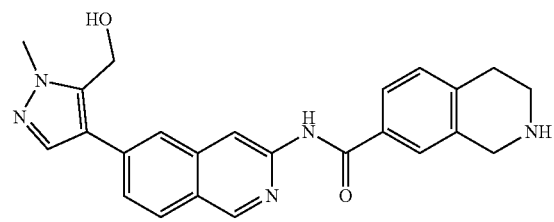 [SMILES: Cn1ncc(-c2ccc3cnc(NC(=O)c4ccc5c(c4)CNCC5)cc3c2)c1CO]
181 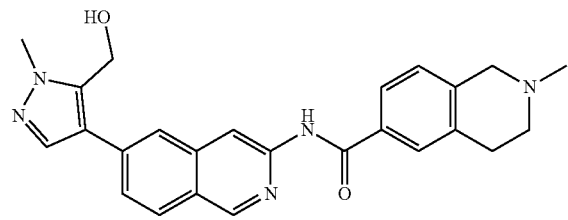 [SMILES: CN1CCc2cc(C(=O)Nc3cc4cc(-c5cnn(C)c5CO)ccc4cn3)ccc2C1]
182 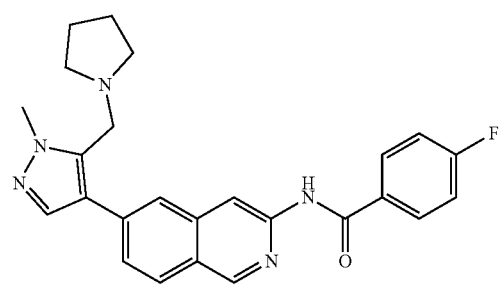 [SMILES: Cn1ncc(-c2ccc3cnc(NC(=O)c4ccc(F)cc4)cc3c2)c1CN1CCCC1]

TABLE 1-continued
183
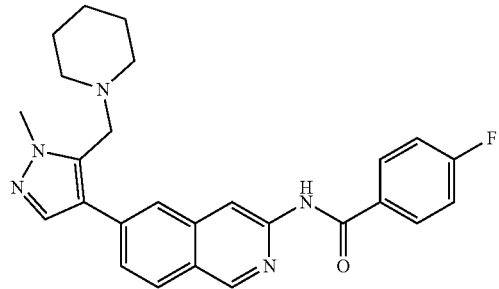 [SMILES: Cn1ncc(-c2ccc3cnc(NC(=O)c4ccc(F)cc4)cc3c2)c1CN1CCCCC1]
184
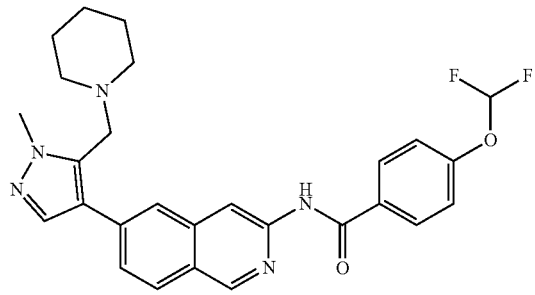 [SMILES: Cn1ncc(-c2ccc3cnc(NC(=O)c4ccc(OC(F)F)cc4)cc3c2)c1CN1CCCCC1]
185
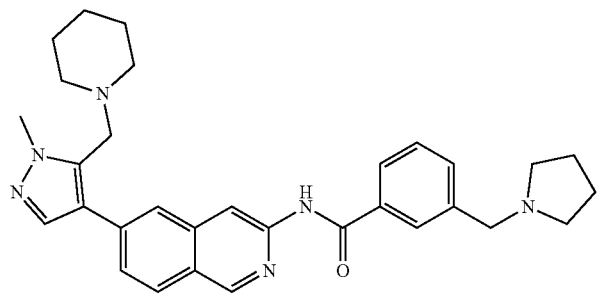 [SMILES: Cn1ncc(-c2ccc3cnc(NC(=O)c4cccc(CN5CCCC5)c4)cc3c2)c1CN1CCCCC1]
186
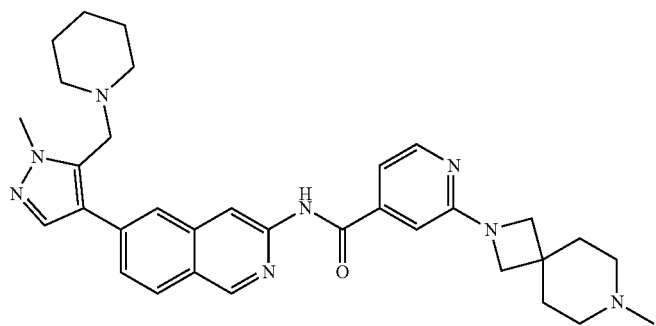 [SMILES: CN1CCC2(CC1)CN(c1cc(C(=O)Nc3cc4cc(-c5cnn(C)c5CN5CCCCC5)ccc4cn3)ccn1)C2]
187
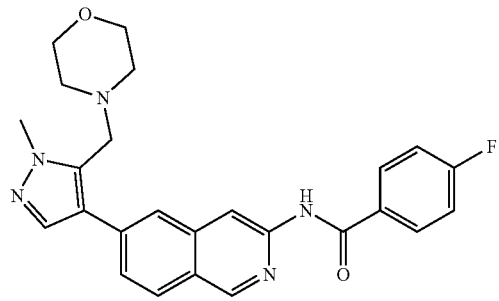 [SMILES: Cn1ncc(-c2ccc3cnc(NC(=O)c4ccc(F)cc4)cc3c2)c1CN1CCOCC1]

TABLE 1-continued
188 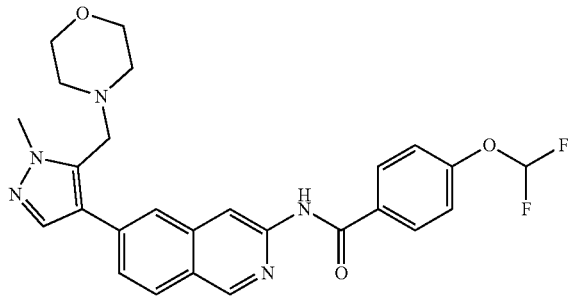 [SMILES: Cn1ncc(-c2ccc3cnc(NC(=O)c4ccc(OC(F)F)cc4)cc3c2)c1CN1CCOCC1]
189 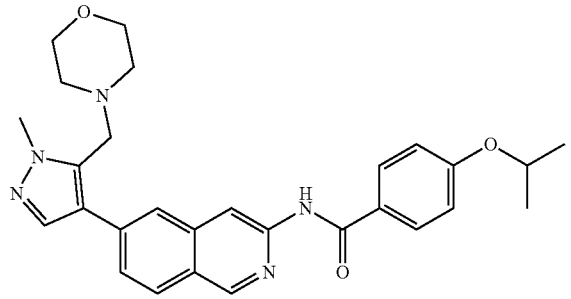 [SMILES: CC(C)Oc1ccc(C(=O)Nc2cc3cc(-c4cnn(C)c4CN4CCOCC4)ccc3cn2)cc1]
190 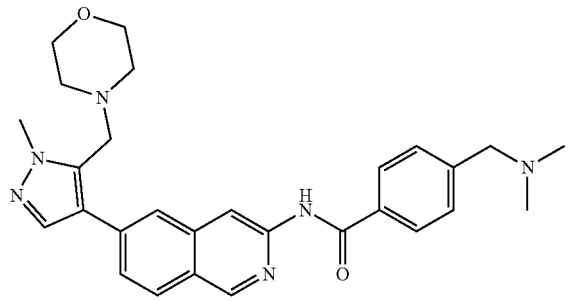 [SMILES: CN(C)Cc1ccc(C(=O)Nc2cc3cc(-c4cnn(C)c4CN4CCOCC4)ccc3cn2)cc1]
191 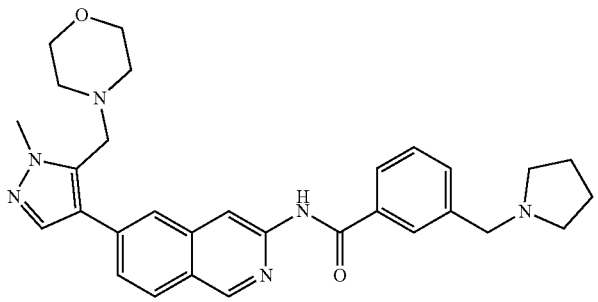 [SMILES: Cn1ncc(-c2ccc3cnc(NC(=O)c4cccc(CN5CCCC5)c4)cc3c2)c1CN1CCOCC1]
192 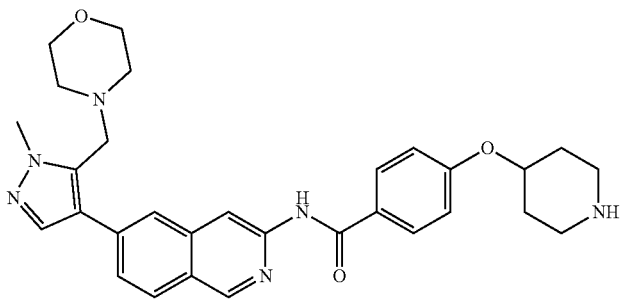 [SMILES: Cn1ncc(-c2ccc3cnc(NC(=O)c4ccc(OC5CCNCC5)cc4)cc3c2)c1CN1CCOCC1]

TABLE 1-continued
193 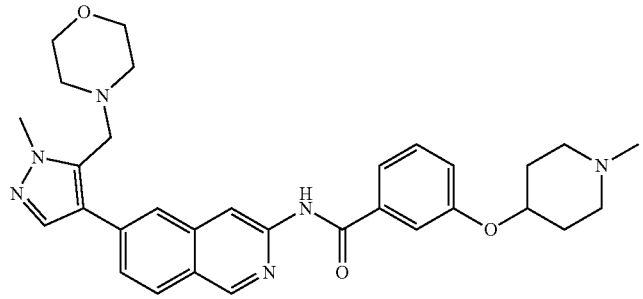 [SMILES: CN1CCC(Oc2cccc(C(=O)Nc3cc4cc(-c5cnn(C)c5CN5CCOCC5)ccc4cn3)c2)CC1]
194 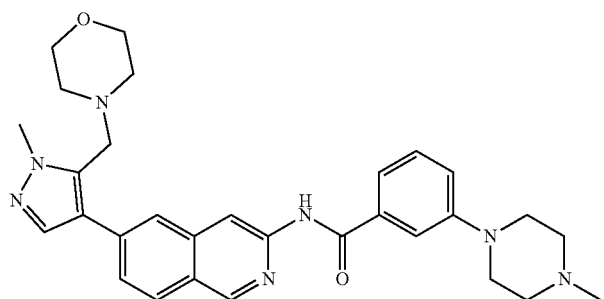
195 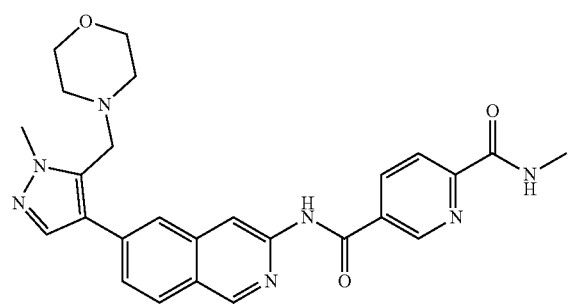 [SMILES: CNC(=O)c1ccc(C(=O)Nc2cc3cc(-c4cnn(C)c4CN4CCOCC4)ccc3cn2)cn1]
196 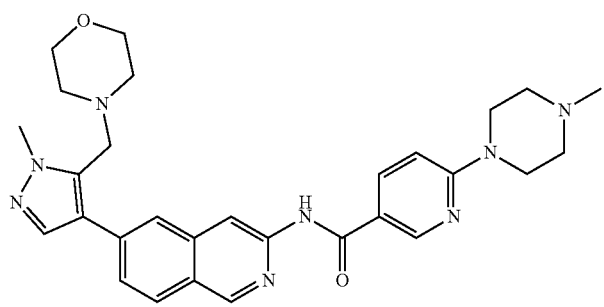
197 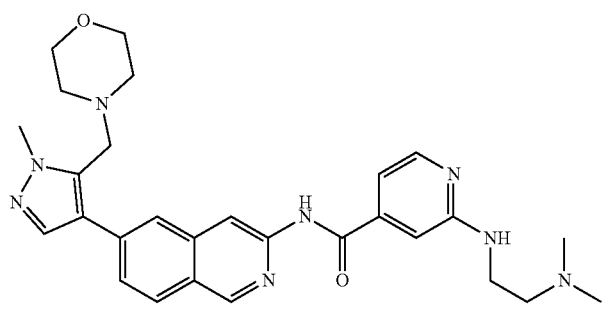

TABLE 1-continued
198 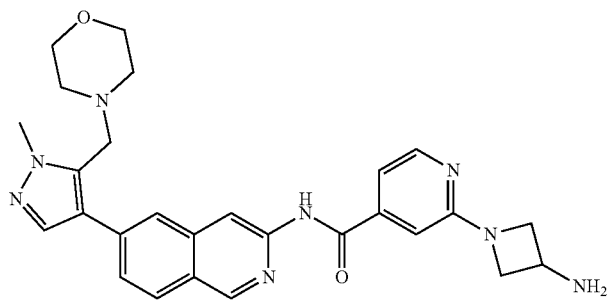 [SMILES: Cn1ncc(-c2ccc3cnc(NC(=O)c4ccnc(N5CC(N)C5)c4)cc3c2)c1CN1CCOCC1]
199 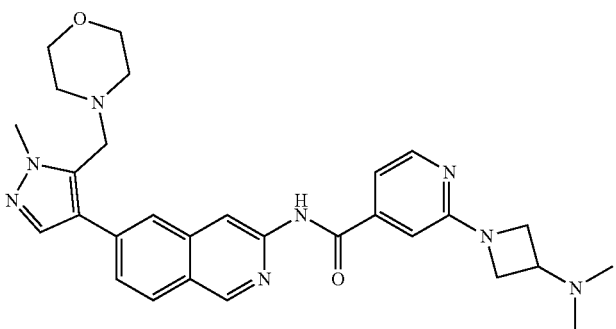 [SMILES: CN(C)C1CN(c2cc(C(=O)Nc3cc4cc(-c5cnn(C)c5CN5CCOCC5)ccc4cn3)ccn2)C1]
200 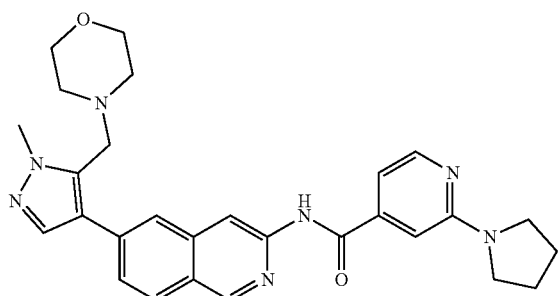
201 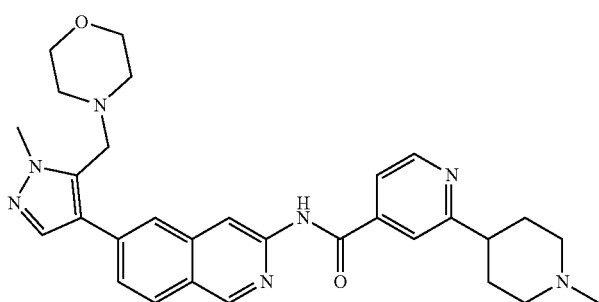
202 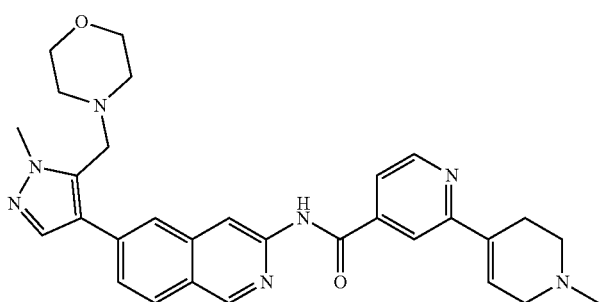

TABLE 1-continued
203 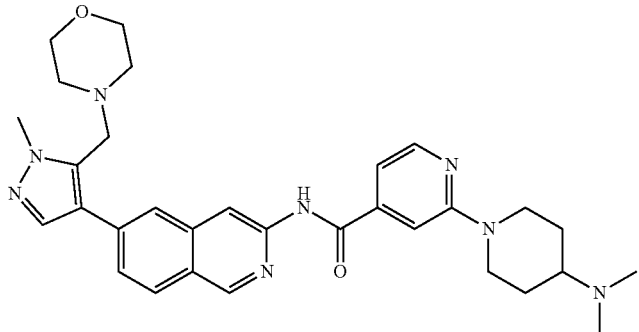
204 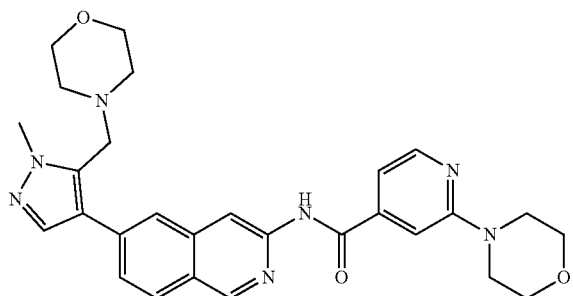
205 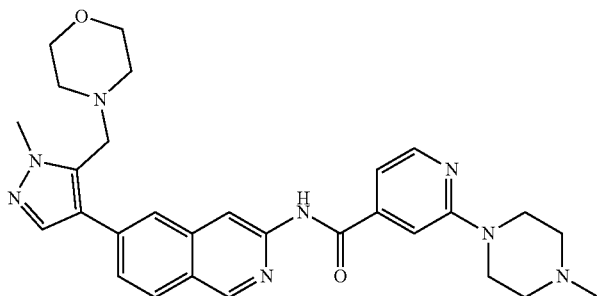
206 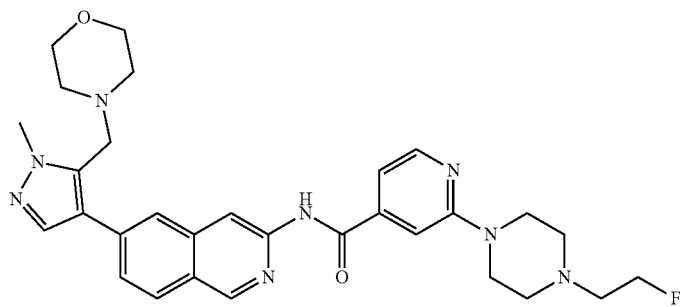 [SMILES: Cn1ncc(-c2ccc3cnc(NC(=O)c4ccnc(N5CCN(CCF)CC5)c4)cc3c2)c1CN1CCOCC1]
207 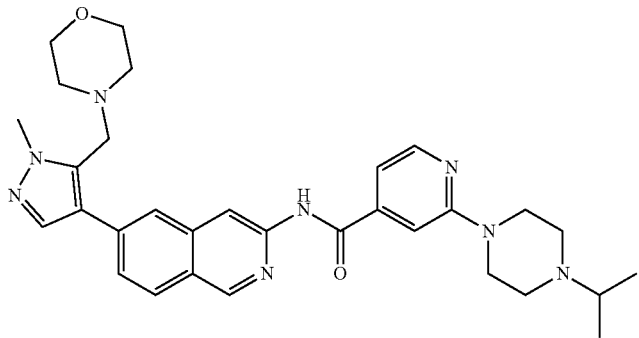 [SMILES: CC(C)N1CCN(c2cc(C(=O)Nc3cc4cc(-c5cnn(C)c5CN5CCOCC5)ccc4cn3)ccn2)CC1]

TABLE 1-continued
208 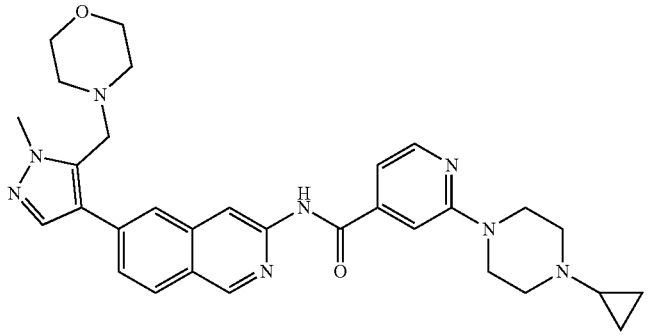 [SMILES: Cn1ncc(-c2ccc3cnc(NC(=O)c4ccnc(N5CCN(C6CC6)CC5)c4)cc3c2)c1CN1CCOCC1]
209 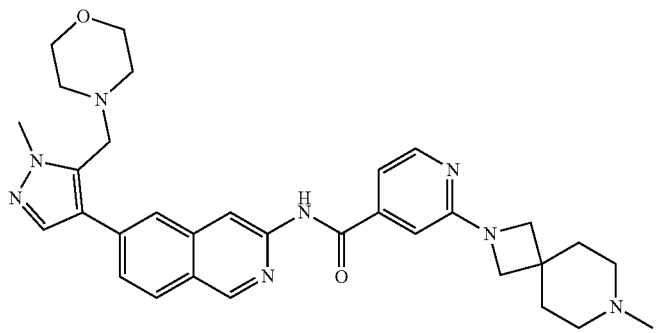 [SMILES: CN1CCC2(CC1)CN(c1cc(C(=O)Nc3cc4cc(-c5cnn(C)c5CN5CCOCC5)ccc4cn3)ccn1)C2]
210 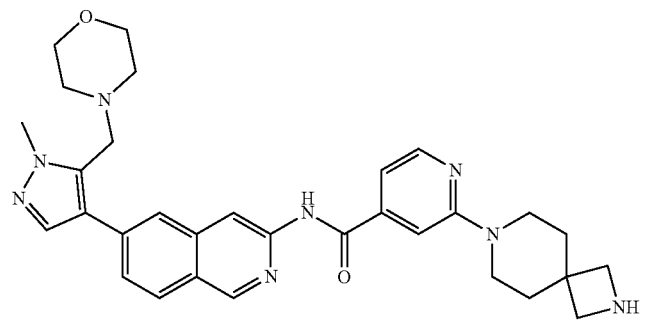 [SMILES: Cn1ncc(-c2ccc3cnc(NC(=O)c4ccnc(N5CCC6(CC5)CNC6)c4)cc3c2)c1CN1CCOCC1]
211 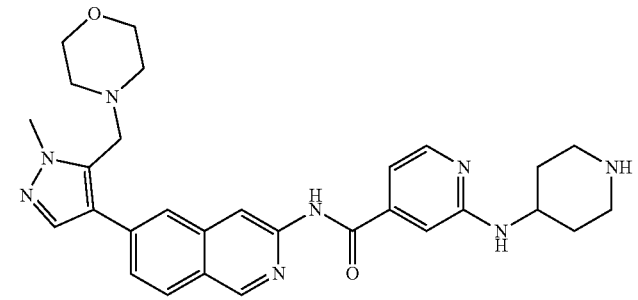 [SMILES: Cn1ncc(-c2ccc3cnc(NC(=O)c4ccnc(NC5CCNCC5)c4)cc3c2)c1CN1CCOCC1]
212 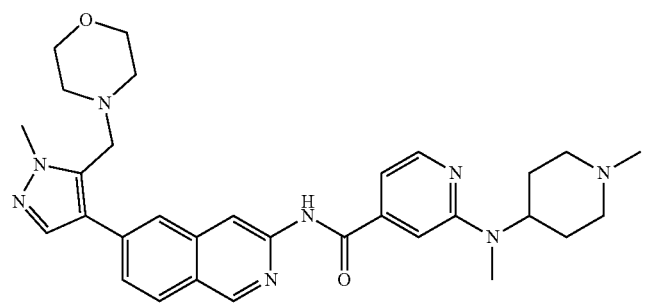 [SMILES: CN1CCC(N(C)c2cc(C(=O)Nc3cc4cc(-c5cnn(C)c5CN5CCOCC5)ccc4cn3)ccn2)CC1]

TABLE 1-continued
213
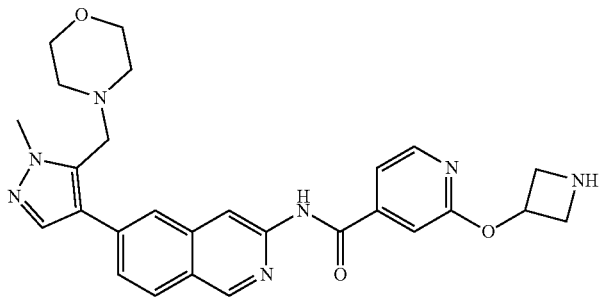 [SMILES: Cn1ncc(-c2ccc3cnc(NC(=O)c4ccnc(OC5CNC5)c4)cc3c2)c1CN1CCOCC1]
214
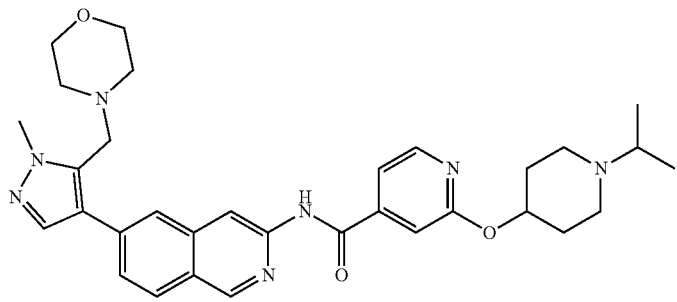 [SMILES: CC(C)N1CCC(Oc2cc(C(=O)Nc3cc4cc(-c5cnn(C)c5CN5CCOCC5)ccc4cn3)ccn2)CC1]
215
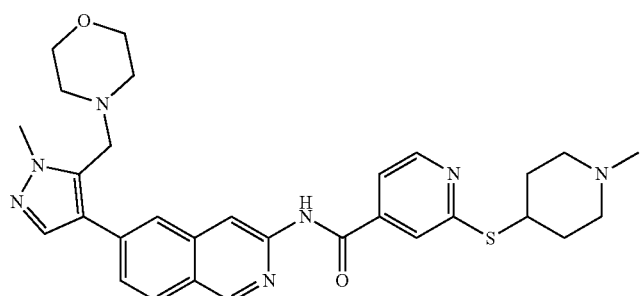
216
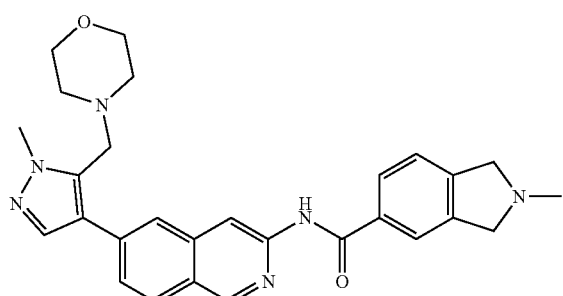
217
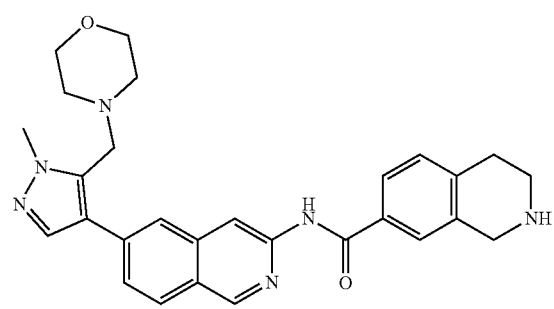 [SMILES: Cn1ncc(-c2ccc3cnc(NC(=O)c4ccc5c(c4)CNCC5)cc3c2)c1CN1CCOCC1]

TABLE 1-continued
218 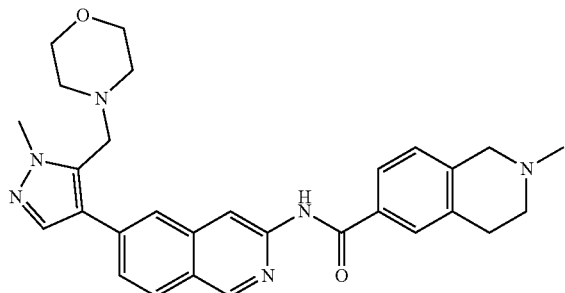
219 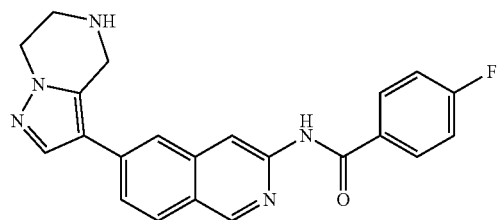
220 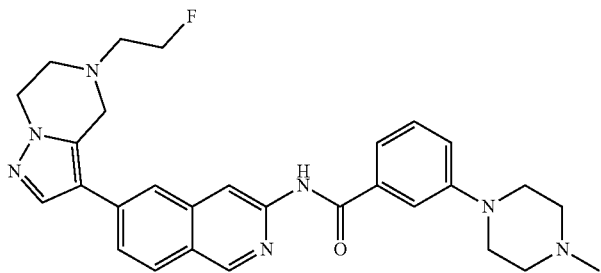
221 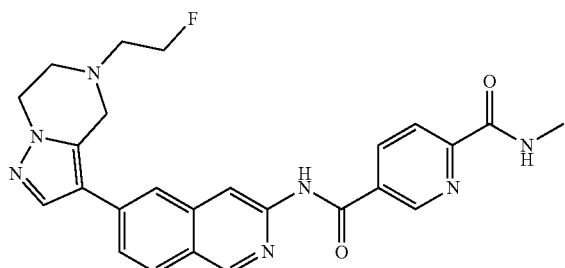
222 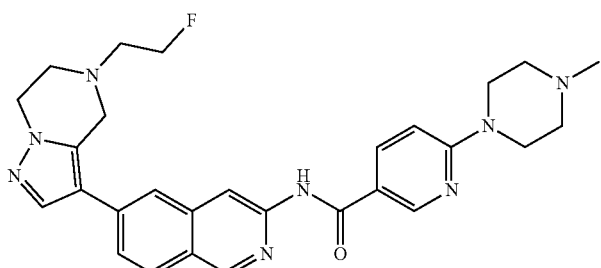
223 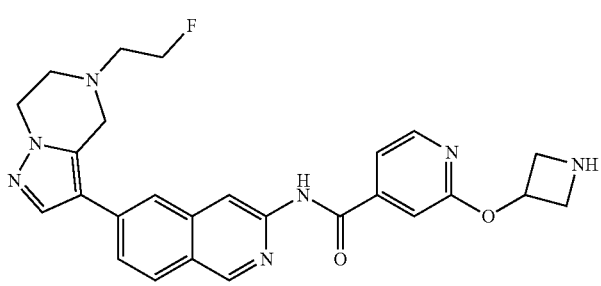 [SMILES: O=C(Nc1cc2cc(-c3cnn4c3CN(CCF)CC4)ccc2cn1)c1ccnc(OC2CNC2)c1]

TABLE 1-continued
224 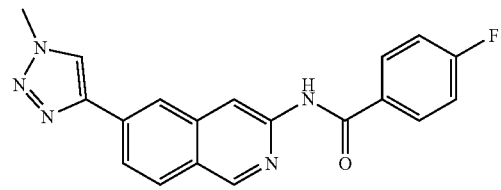
225 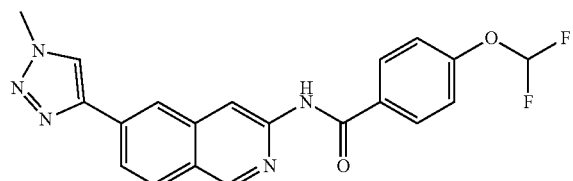
226 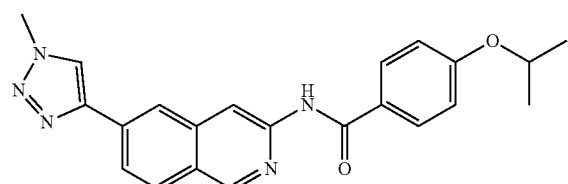
227 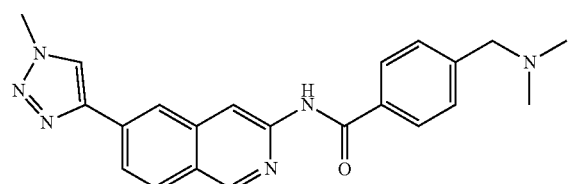
228 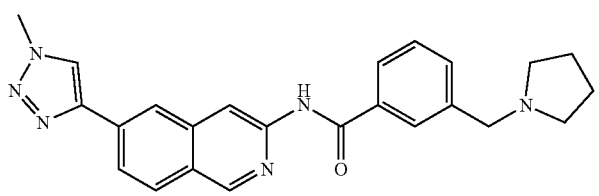 [SMILES: Cn1cc(-c2ccc3cnc(NC(=O)c4cccc(CN5CCCC5)c4)cc3c2)nn1]
229 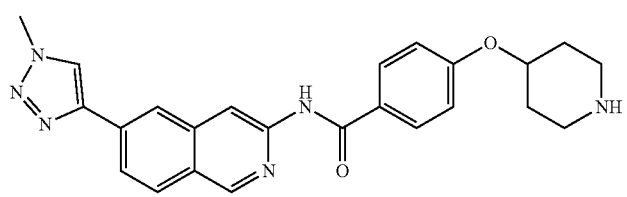 [SMILES: Cn1cc(-c2ccc3cnc(NC(=O)c4ccc(OC5CCNCC5)cc4)cc3c2)nn1]
230 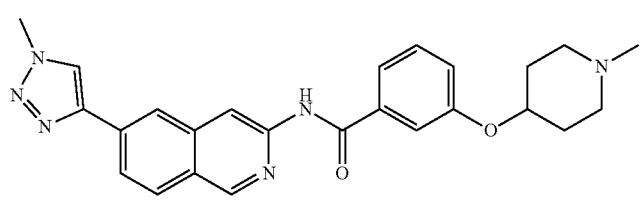 [SMILES: CN1CCC(Oc2cccc(C(=O)Nc3cc4cc(-c5cn(C)nn5)ccc4cn3)c2)CC1]
231 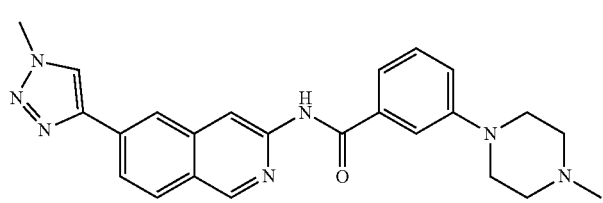

TABLE 1-continued
232 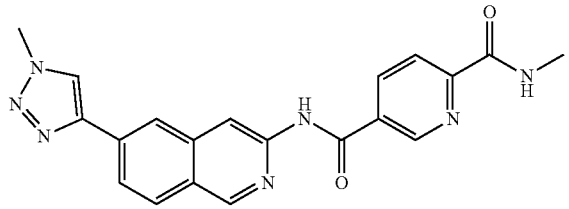 [SMILES: CNC(=O)c1ccc(C(=O)Nc2cc3cc(-c4cn(C)nn4)ccc3cn2)cn1]
233 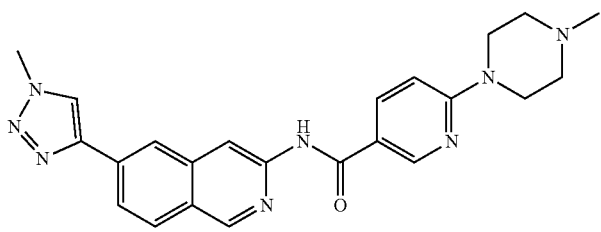 [SMILES: CN1CCN(c2ccc(C(=O)Nc3cc4cc(-c5cn(C)nn5)ccc4cn3)cn2)CC1]
234 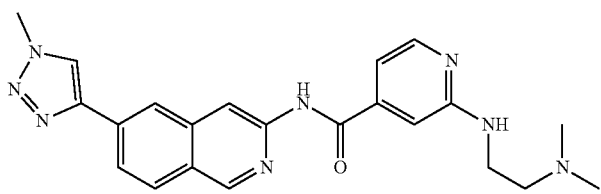 [SMILES: CN(C)CCNc1cc(C(=O)Nc2cc3cc(-c4cn(C)nn4)ccc3cn2)ccn1]
235 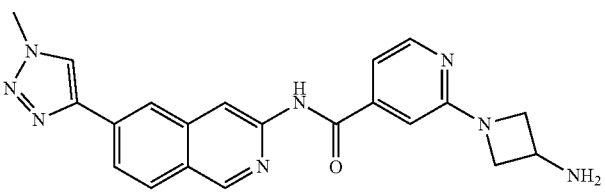 [SMILES: Cn1cc(-c2ccc3cnc(NC(=O)c4ccnc(N5CC(N)C5)c4)cc3c2)nn1]
236 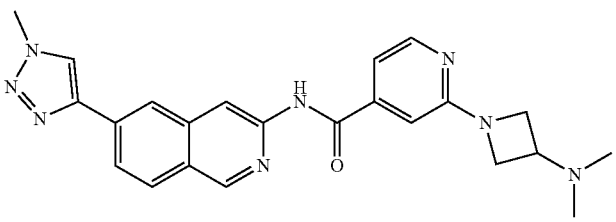 [SMILES: CN(C)C1CN(c2cc(C(=O)Nc3cc4cc(-c5cn(C)nn5)ccc4cn3)ccn2)C1]
237 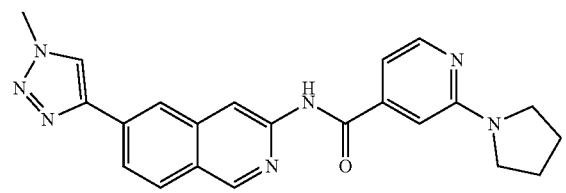
238 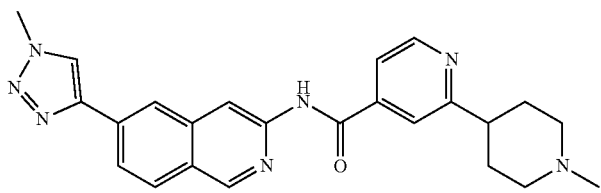

TABLE 1-continued
239 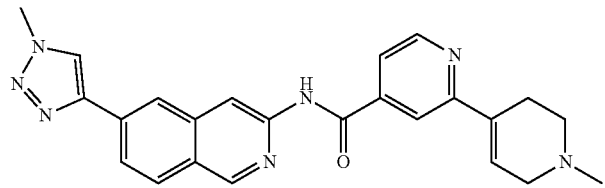
240 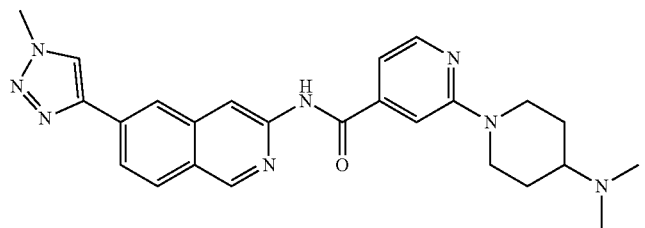
241 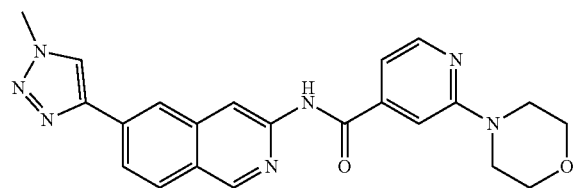 [SMILES: Cn1cc(-c2ccc3cnc(NC(=O)c4ccnc(N5CCOCC5)c4)cc3c2)nn1]
242 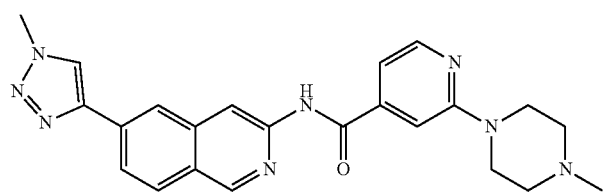
243 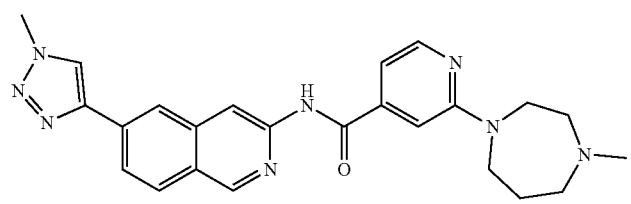 [SMILES: CN1CCCN(c2cc(C(=O)Nc3cc4cc(-c5cn(C)nn5)ccc4cn3)ccn2)CC1]
244 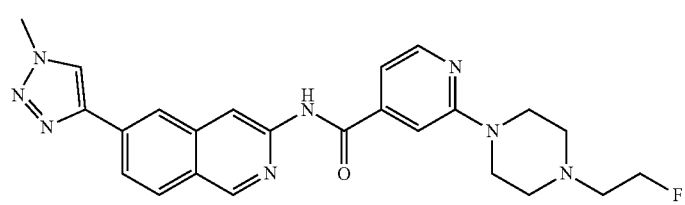 [SMILES: Cn1cc(-c2ccc3cnc(NC(=O)c4ccnc(N5CCN(CCF)CC5)c4)cc3c2)nn1]
245 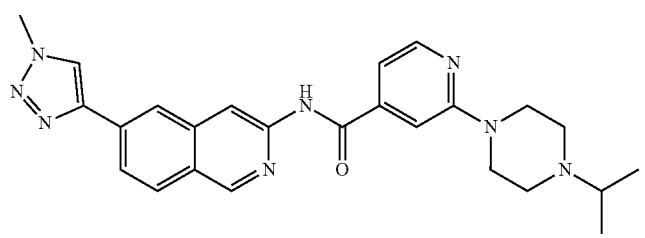

TABLE 1-continued
246 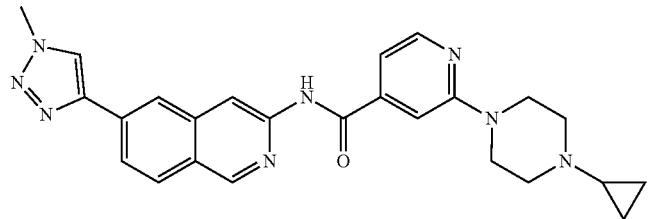
247 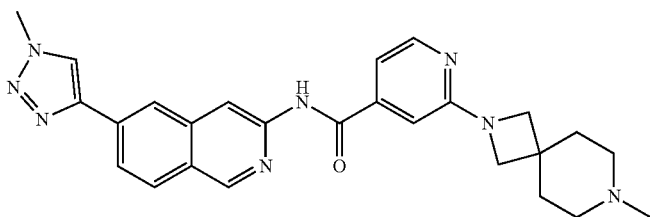
248 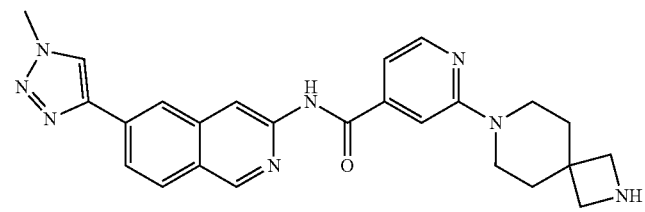 [SMILES: Cn1cc(-c2ccc3cnc(NC(=O)c4ccnc(N5CCC6(CC5)CNC6)c4)cc3c2)nn1]
249 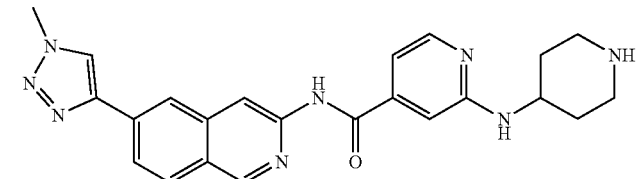
250 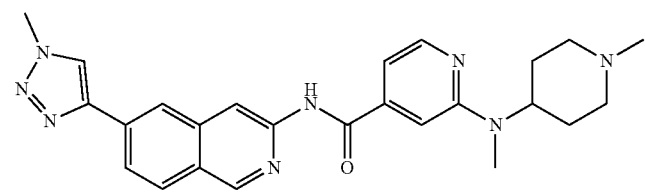
251 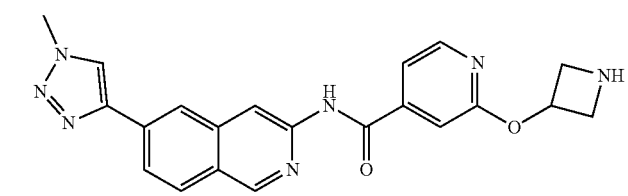 [SMILES: Cn1cc(-c2ccc3cnc(NC(=O)c4ccnc(OC5CNC5)c4)cc3c2)nn1]
252 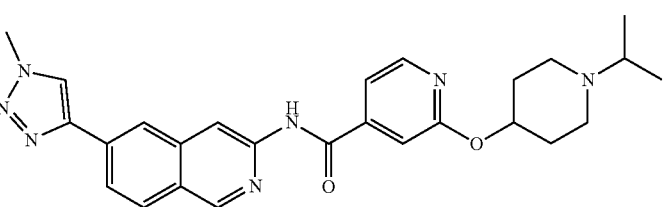

TABLE 1-continued
253 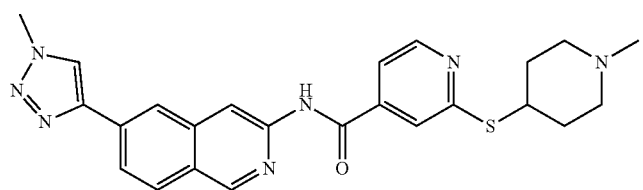 [SMILES: CN1CCC(Sc2cc(C(=O)Nc3cc4cc(-c5cn(C)nn5)ccc4cn3)ccn2)CC1]
254 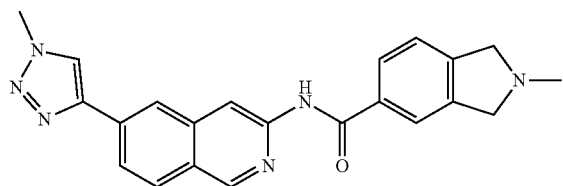
255 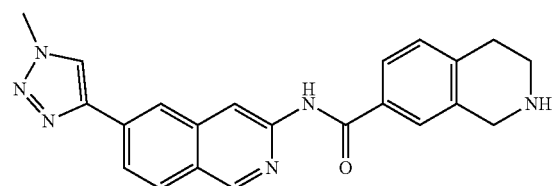
256 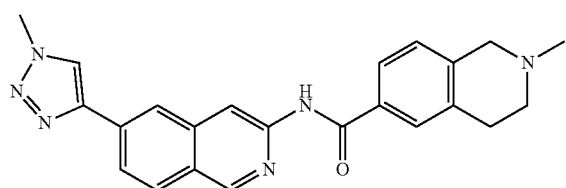
257 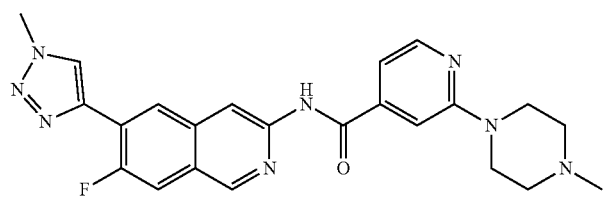 [SMILES: CN1CCN(c2cc(C(=O)Nc3cc4cc(-c5cn(C)nn5)c(F)cc4cn3)ccn2)CC1]
258 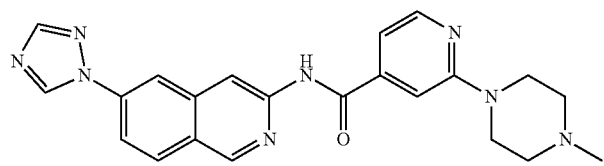 [SMILES: CN1CCN(c2cc(C(=O)Nc3cc4cc(-n5cncn5)ccc4cn3)ccn2)CC1]
259 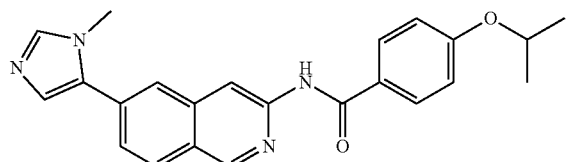
260 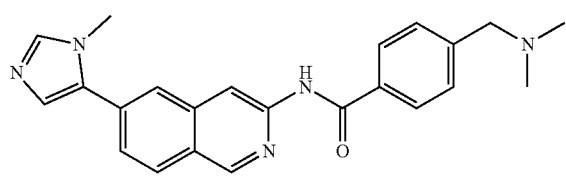 [SMILES: CN(C)Cc1ccc(C(=O)Nc2cc3cc(-c4cncn4C)ccc3cn2)cc1]

TABLE 1-continued
261 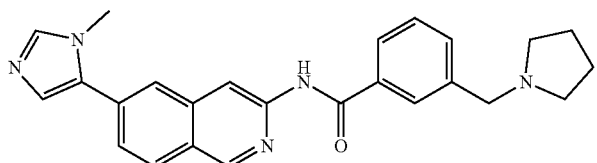
262 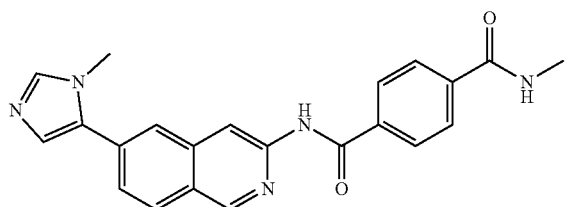
263 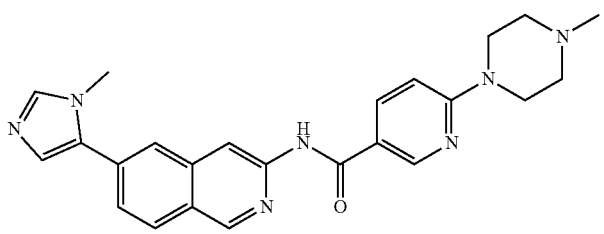 [SMILES: CN1CCN(c2ccc(C(=O)Nc3cc4cc(-c5cncn5C)ccc4cn3)cn2)CC1]
264 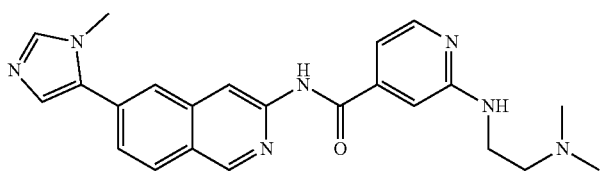 [SMILES: CN(C)CCNc1cc(C(=O)Nc2cc3cc(-c4cncn4C)ccc3cn2)ccn1]
265 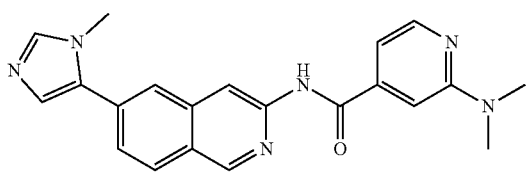 [SMILES: CN(C)c1cc(C(=O)Nc2cc3cc(-c4cncn4C)ccc3cn2)ccn1]
266 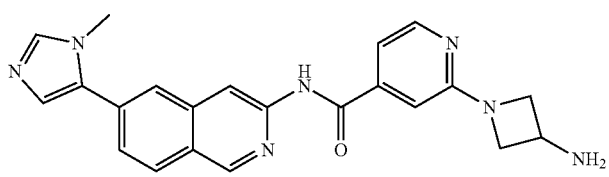 [SMILES: Cn1cncc1-c1ccc2cnc(NC(=O)c3ccnc(N4CC(N)C4)c3)cc2c1]
267 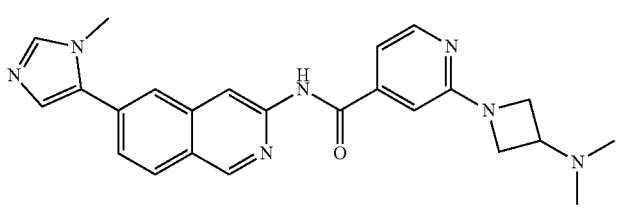 [SMILES: CN(C)C1CN(c2cc(C(=O)Nc3cc4cc(-c5cncn5C)ccc4cn3)ccn2)C1]
268 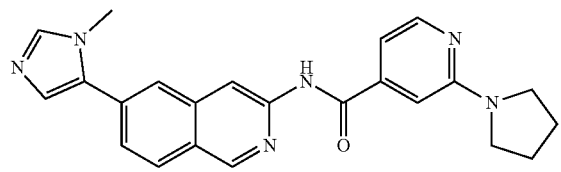 [SMILES: Cn1cncc1-c1ccc2cnc(NC(=O)c3ccnc(N4CCCC4)c3)cc2c1]

TABLE 1-continued
269 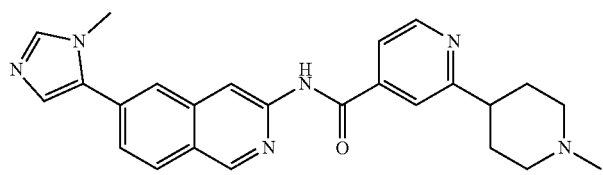 [SMILES: CN1CCC(c2cc(C(=O)Nc3cc4cc(-c5cncn5C)ccc4cn3)ccn2)CC1]
270 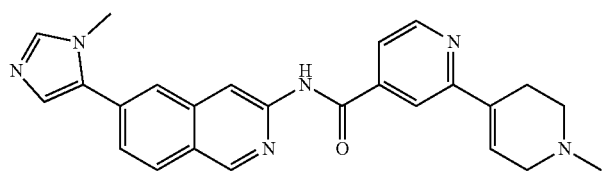 [SMILES: CN1CC=C(c2cc(C(=O)Nc3cc4cc(-c5cncn5C)ccc4cn3)ccn2)CC1]
271 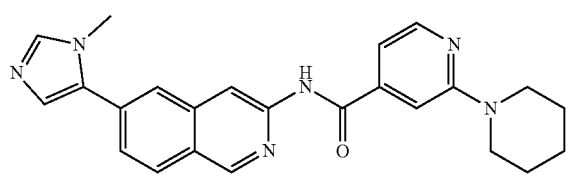 [SMILES: Cn1cncc1-c1ccc2cnc(NC(=O)c3ccnc(N4CCCCC4)c3)cc2c1]
272 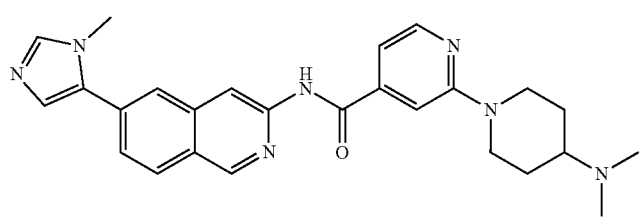 [SMILES: CN(C)C1CCN(c2cc(C(=O)Nc3cc4cc(-c5cncn5C)ccc4cn3)ccn2)CC1]
273 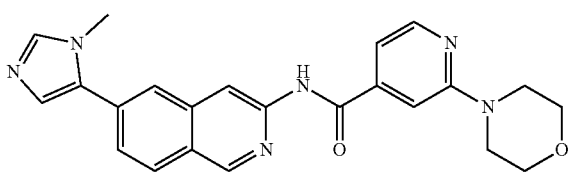 [SMILES: Cn1cncc1-c1ccc2cnc(NC(=O)c3ccnc(N4CCOCC4)c3)cc2c1]
274 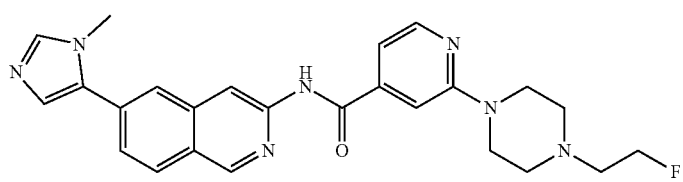 [SMILES: Cn1cncc1-c1ccc2cnc(NC(=O)c3ccnc(N4CCN(CCF)CC4)c3)cc2c1]
275 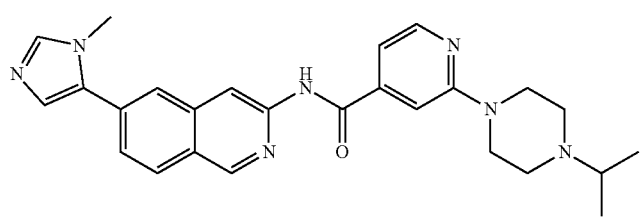 [SMILES: CC(C)N1CCN(c2cc(C(=O)Nc3cc4cc(-c5cncn5C)ccc4cn3)ccn2)CC1]
276 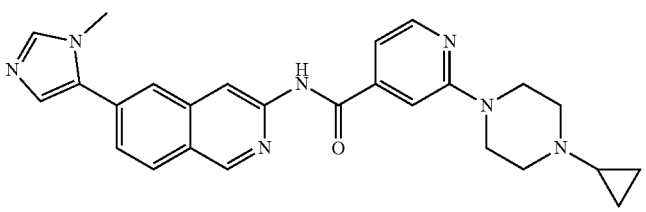 [SMILES: Cn1cncc1-c1ccc2cnc(NC(=O)c3ccnc(N4CCN(C5CC5)CC4)c3)cc2c1]

TABLE 1-continued
277 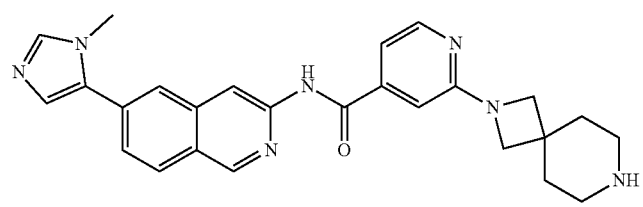 [SMILES: Cn1cncc1-c1ccc2cnc(NC(=O)c3ccnc(N4CC5(CCNCC5)C4)c3)cc2c1]
278 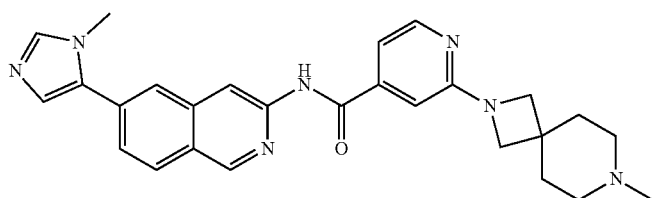 [SMILES: CN1CCC2(CC1)CN(c1cc(C(=O)Nc3cc4cc(-c5cncn5C)ccc4cn3)ccn1)C2]
279 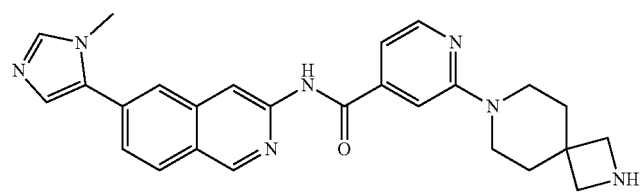 [SMILES: Cn1cncc1-c1ccc2cnc(NC(=O)c3ccnc(N4CCC5(CC4)CNC5)c3)cc2c1]
280 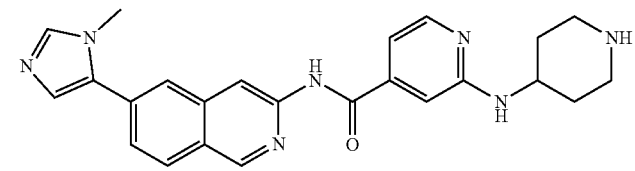
281 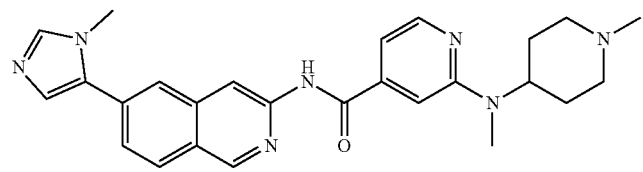 [SMILES: CN1CCC(N(C)c2cc(C(=O)Nc3cc4cc(-c5cncn5C)ccc4cn3)ccn2)CC1]
282 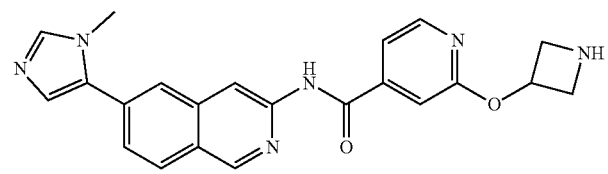 [SMILES: Cn1cncc1-c1ccc2cnc(NC(=O)c3ccnc(OC4CNC4)c3)cc2c1]
283 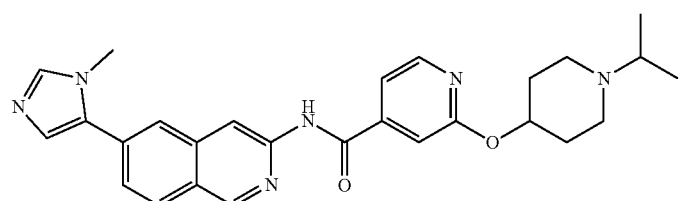
284 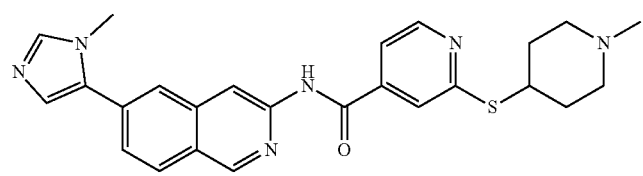 [SMILES: CN1CCC(Sc2cc(C(=O)Nc3cc4cc(-c5cncn5C)ccc4cn3)ccn2)CC1]

TABLE 1-continued
| | |
|---|---|
| 285 | 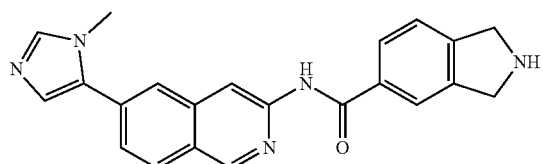 |
| 286 | 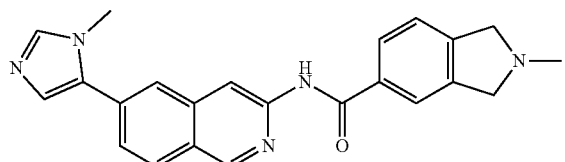 |
| 287 | 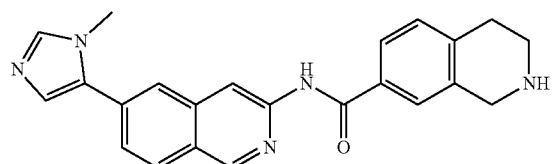 |
| 288 | 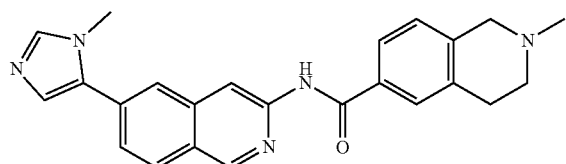 |
| 289 | 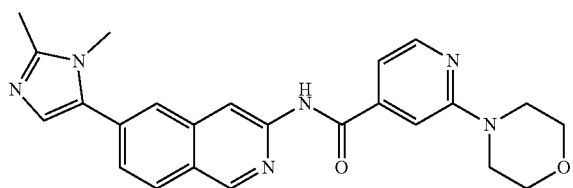 [SMILES: Cc1ncc(-c2ccc3cnc(NC(=O)c4ccnc(N5CCOCC5)c4)cc3c2)n1C] |
| 290 | 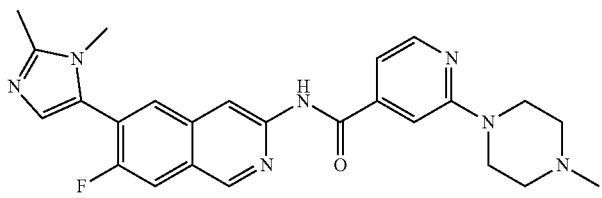 [SMILES: Cc1ncc(-c2cc3cc(NC(=O)c4ccnc(N5CCN(C)CC5)c4)ncc3cc2F)n1C] |
| 291 | 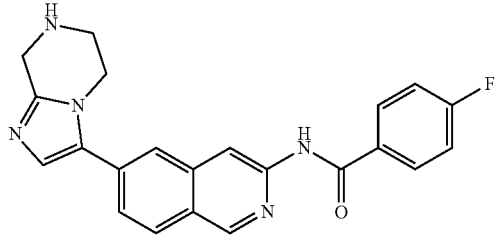 [SMILES: O=C(Nc1cc2cc(-c3cnc4n3CCNC4)ccc2cn1)c1ccc(F)cc1] |
| 292 | 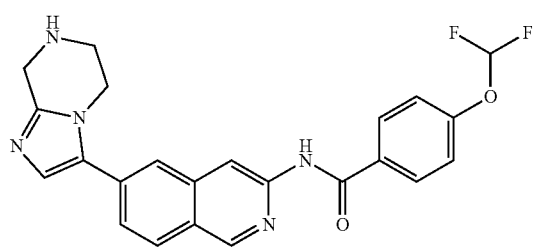 [SMILES: O=C(Nc1cc2cc(-c3cnc4n3CCNC4)ccc2cn1)c1ccc(OC(F)F)cc1] |

TABLE 1-continued
293 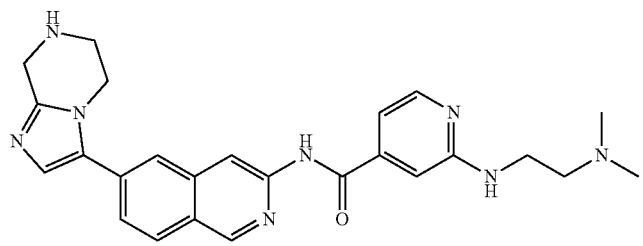 [SMILES: CN(C)CCNc1cc(C(=O)Nc2cc3cc(-c4cnc5n4CCNC5)ccc3cn2)ccn1]
294 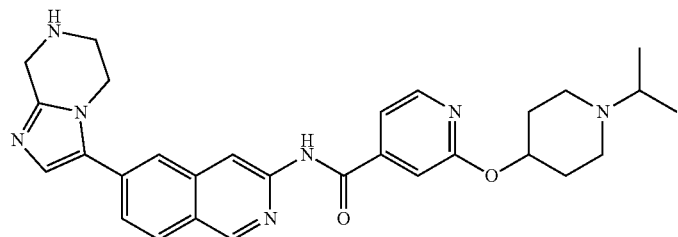
295 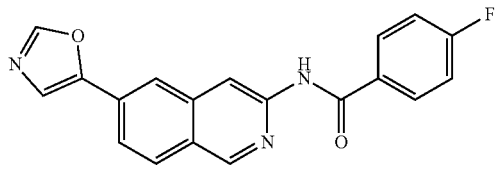 [SMILES: O=C(Nc1cc2cc(-c3cnco3)ccc2cn1)c1ccc(F)cc1]
296 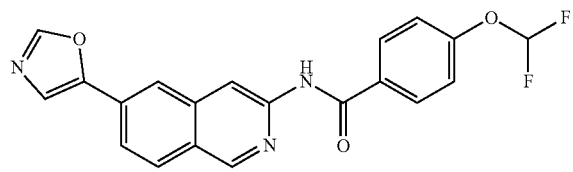
297 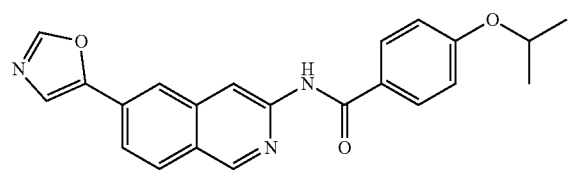 [SMILES: CC(C)Oc1ccc(C(=O)Nc2cc3cc(-c4cnco4)ccc3cn2)cc1]
298 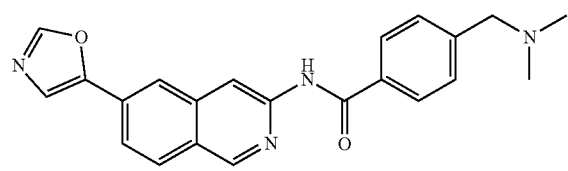 [SMILES: CN(C)Cc1ccc(C(=O)Nc2cc3cc(-c4cnco4)ccc3cn2)cc1]
299 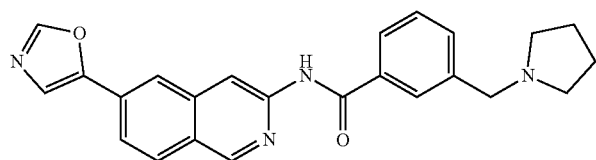 [SMILES: O=C(Nc1cc2cc(-c3cnco3)ccc2cn1)c1cccc(CN2CCCC2)c1]
300 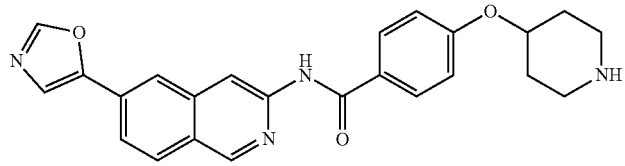 [SMILES: O=C(Nc1cc2cc(-c3cnco3)ccc2cn1)c1ccc(OC2CCNCC2)cc1]

TABLE 1-continued
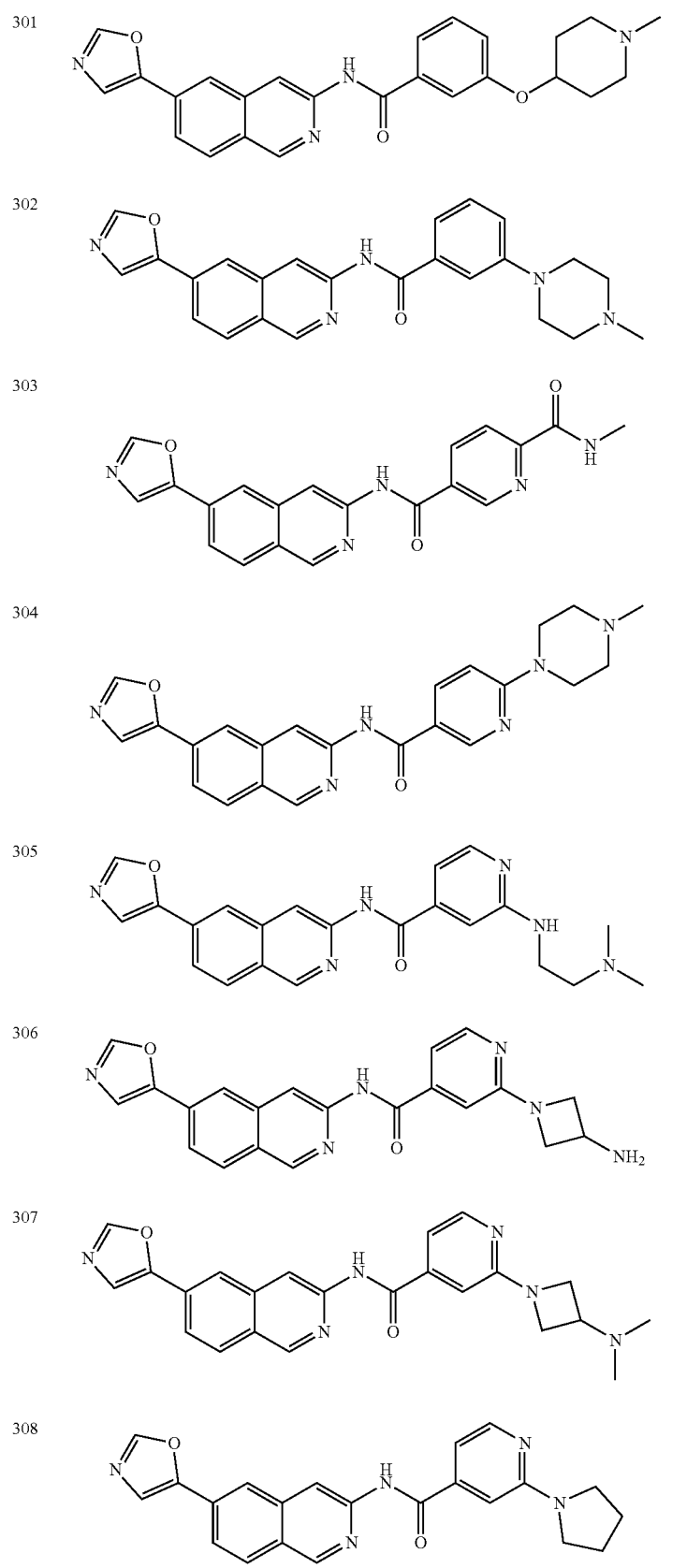

TABLE 1-continued
309 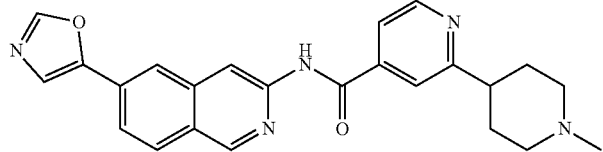 [SMILES: CN1CCC(c2cc(C(=O)Nc3cc4cc(-c5cnco5)ccc4cn3)ccn2)CC1]
310 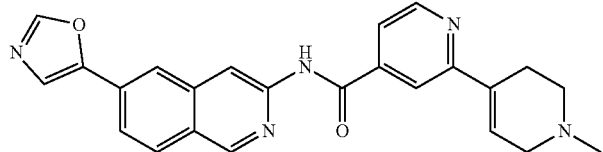
311 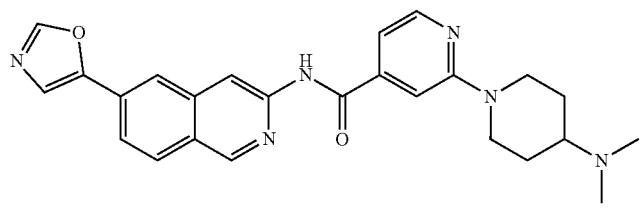 [SMILES: CN(C)C1CCN(c2cc(C(=O)Nc3cc4cc(-c5cnco5)ccc4cn3)ccn2)CC1]
312 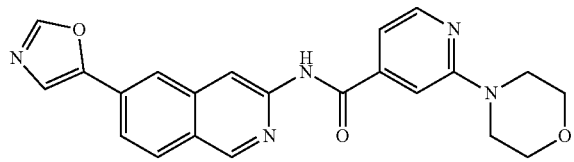 [SMILES: O=C(Nc1cc2cc(-c3cnco3)ccc2cn1)c1ccnc(N2CCOCC2)c1]
313 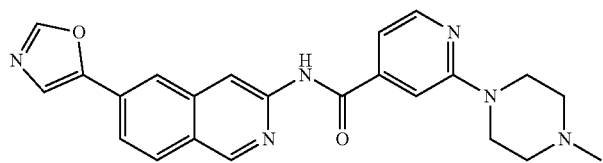
314 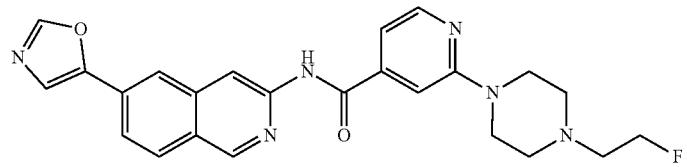 [SMILES: O=C(Nc1cc2cc(-c3cnco3)ccc2cn1)c1ccnc(N2CCN(CCF)CC2)c1]
315 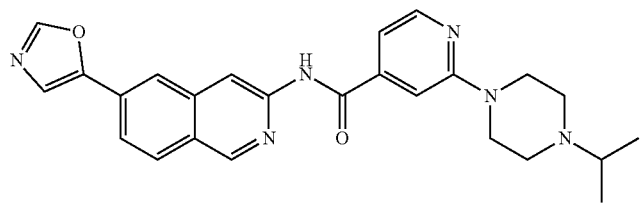 [SMILES: CC(C)N1CCN(c2cc(C(=O)Nc3cc4cc(-c5cnco5)ccc4cn3)ccn2)CC1]
316 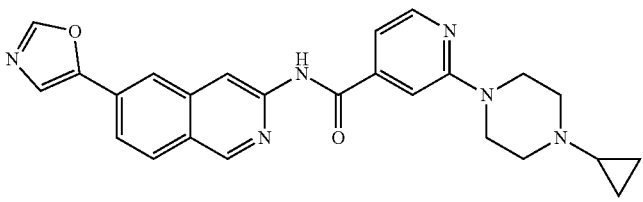 [SMILES: O=C(Nc1cc2cc(-c3cnco3)ccc2cn1)c1ccnc(N2CCN(C3CC3)CC2)c1]

TABLE 1-continued
317 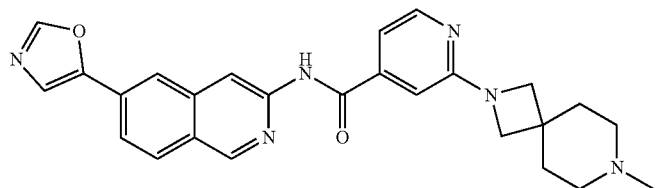
318 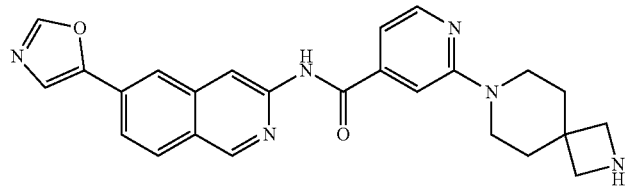 [SMILES: O=C(Nc1cc2cc(-c3cnco3)ccc2cn1)c1ccnc(N2CCC3(CC2)CNC3)c1]
319 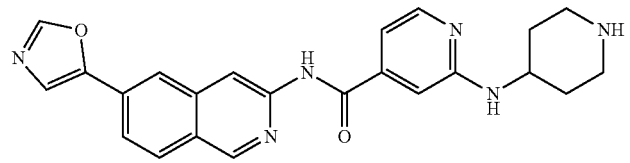 [SMILES: O=C(Nc1cc2cc(-c3cnco3)ccc2cn1)c1ccnc(NC2CCNCC2)c1]
320 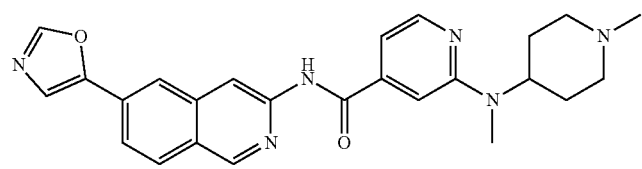 [SMILES: CN1CCC(N(C)c2cc(C(=O)Nc3cc4cc(-c5cnco5)ccc4cn3)ccn2)CC1]
321 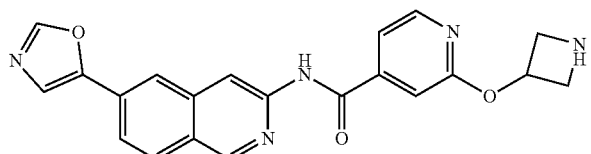
322 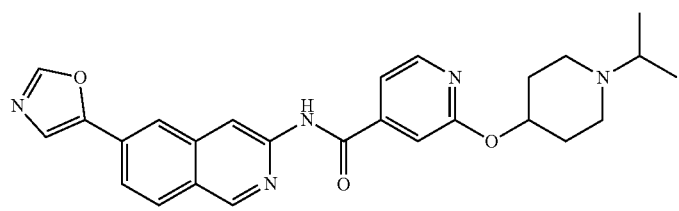 [SMILES: CC(C)N1CCC(Oc2cc(C(=O)Nc3cc4cc(-c5cnco5)ccc4cn3)ccn2)CC1]
323 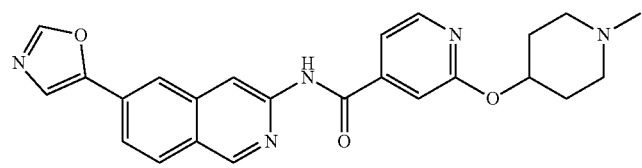 [SMILES: CN1CCC(Oc2cc(C(=O)Nc3cc4cc(-c5cnco5)ccc4cn3)ccn2)CC1]
324 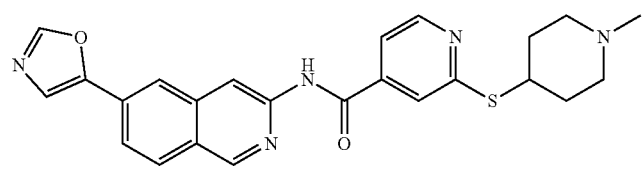
325 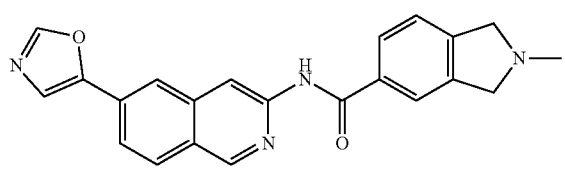 [SMILES: CN1Cc2ccc(C(=O)Nc3cc4cc(-c5cnco5)ccc4cn3)cc2C1]

TABLE 1-continued
326 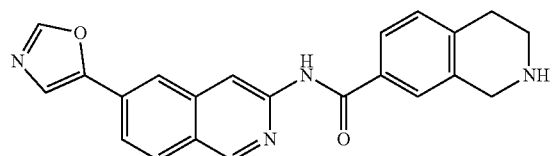
327 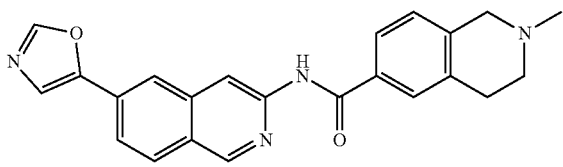 [SMILES: CN1CCc2cc(C(=O)Nc3cc4cc(-c5cnco5)ccc4cn3)ccc2C1]
328 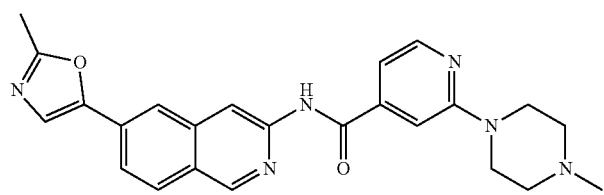
329 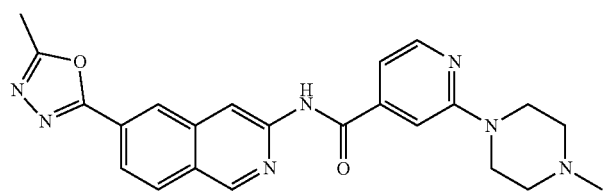
330 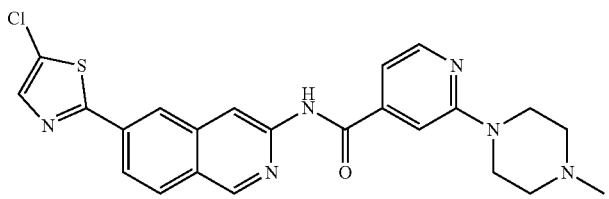 [SMILES: CN1CCN(c2cc(C(=O)Nc3cc4cc(-c5ncc(Cl)s5)ccc4cn3)ccn2)CC1]
331 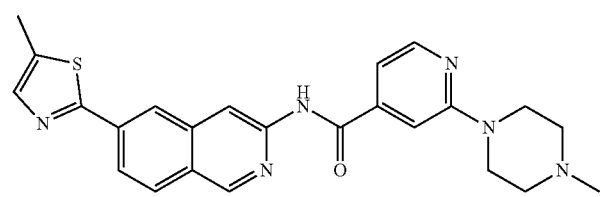 [SMILES: Cc1cnc(-c2ccc3cnc(NC(=O)c4ccnc(N5CCN(C)CC5)c4)cc3c2)s1]
332 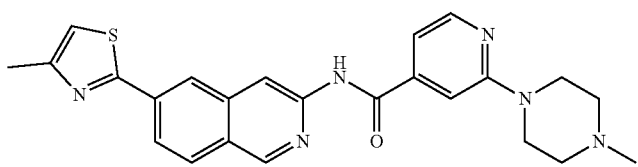
333 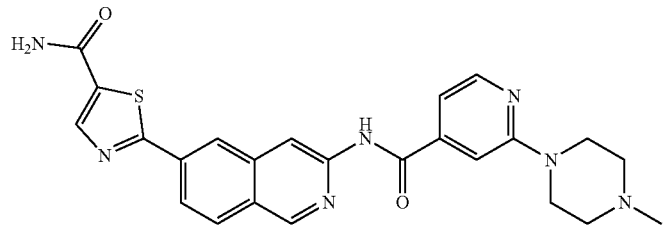 [SMILES: CN1CCN(c2cc(C(=O)Nc3cc4cc(-c5ncc(C(N)=O)s5)ccc4cn3)ccn2)CC1]

TABLE 1-continued
334 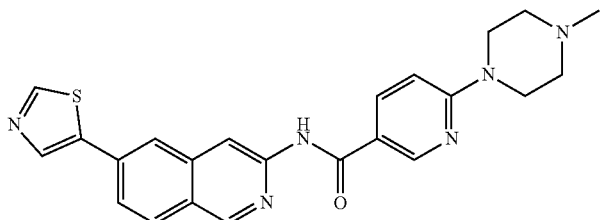
335 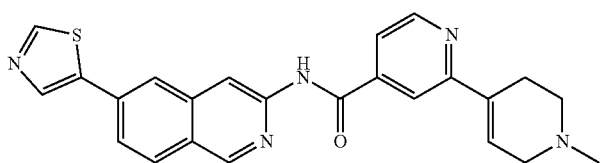
336 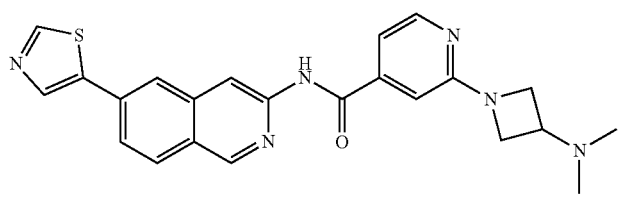
337 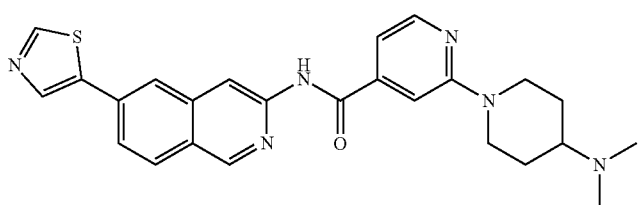
338 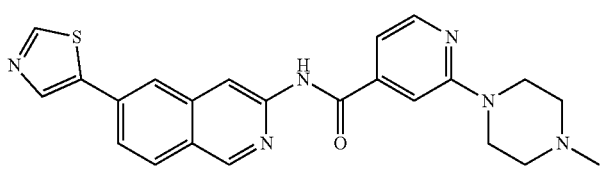 [SMILES: CN1CCN(c2cc(C(=O)Nc3cc4cc(-c5cncs5)ccc4cn3)ccn2)CC1]
339 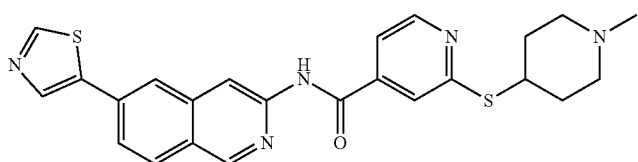
340 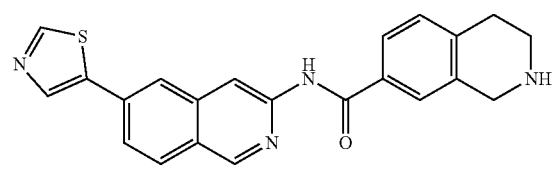
341 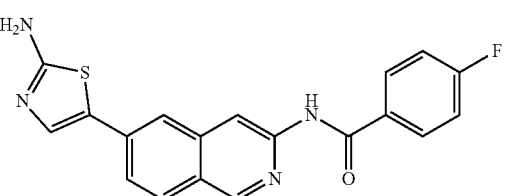

TABLE 1-continued
342 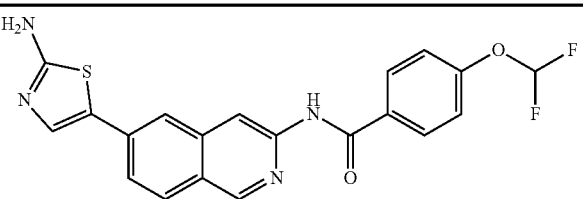
343 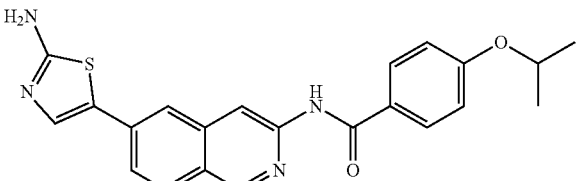
344 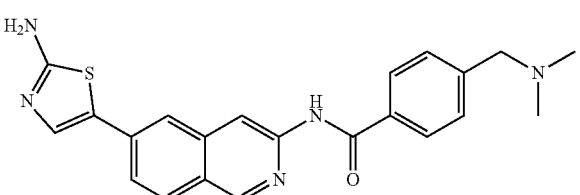
345 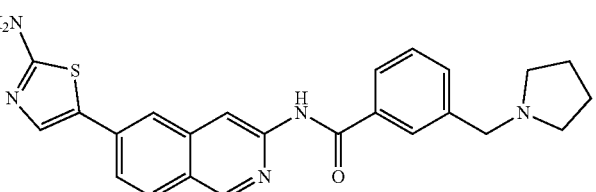
346 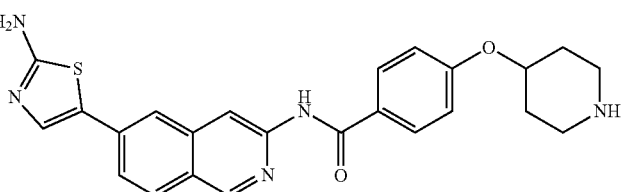
347 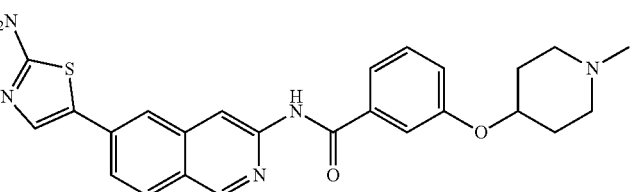
348 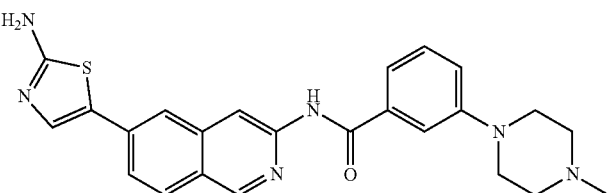
349 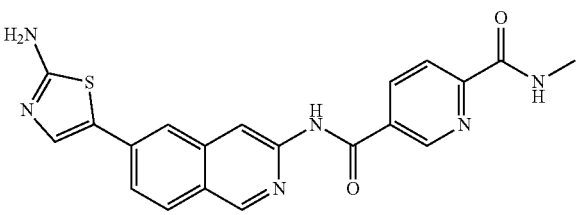 [SMILES: CNC(=O)c1ccc(C(=O)Nc2cc3cc(-c4cnc(N)s4)ccc3cn2)cn1]

TABLE 1-continued
350 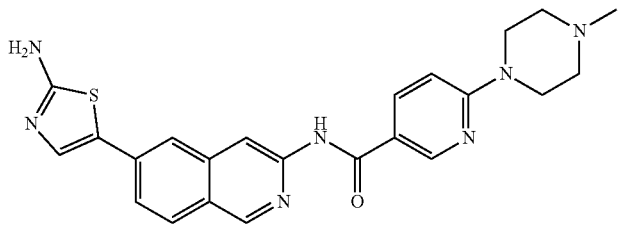 [SMILES: CN1CCN(c2ccc(C(=O)Nc3cc4cc(-c5cnc(N)s5)ccc4cn3)cn2)CC1]
351 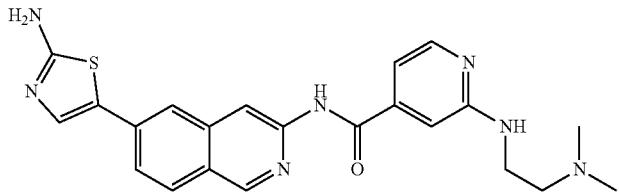 [SMILES: CN(C)CCNc1cc(C(=O)Nc2cc3cc(-c4cnc(N)s4)ccc3cn2)ccn1]
352 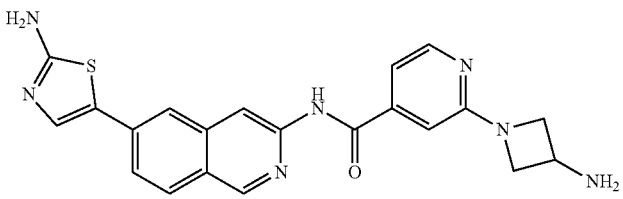 [SMILES: Nc1ncc(-c2ccc3cnc(NC(=O)c4ccnc(N5CC(N)C5)c4)cc3c2)s1]
353 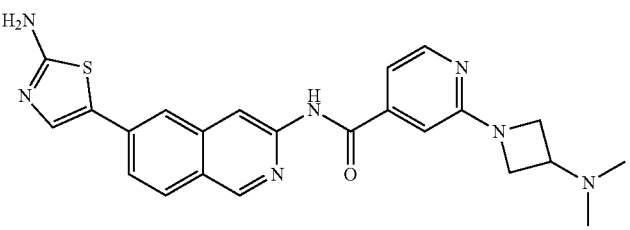 [SMILES: CN(C)C1CN(c2cc(C(=O)Nc3cc4cc(-c5cnc(N)s5)ccc4cn3)ccn2)C1]
354 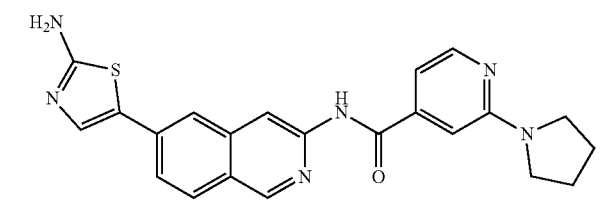 [SMILES: Nc1ncc(-c2ccc3cnc(NC(=O)c4ccnc(N5CCCC5)c4)cc3c2)s1]
355 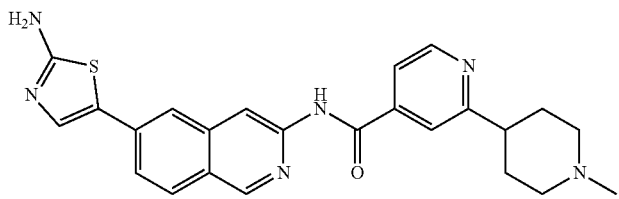 [SMILES: CN1CCC(c2cc(C(=O)Nc3cc4cc(-c5cnc(N)s5)ccc4cn3)ccn2)CC1]
356 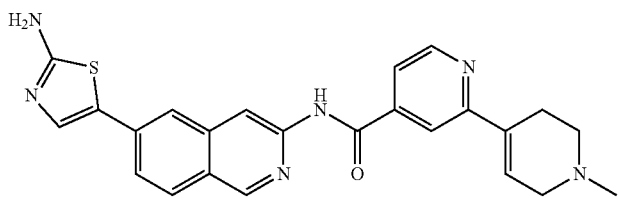 [SMILES: CN1CC=C(c2cc(C(=O)Nc3cc4cc(-c5cnc(N)s5)ccc4cn3)ccn2)CC1]

TABLE 1-continued
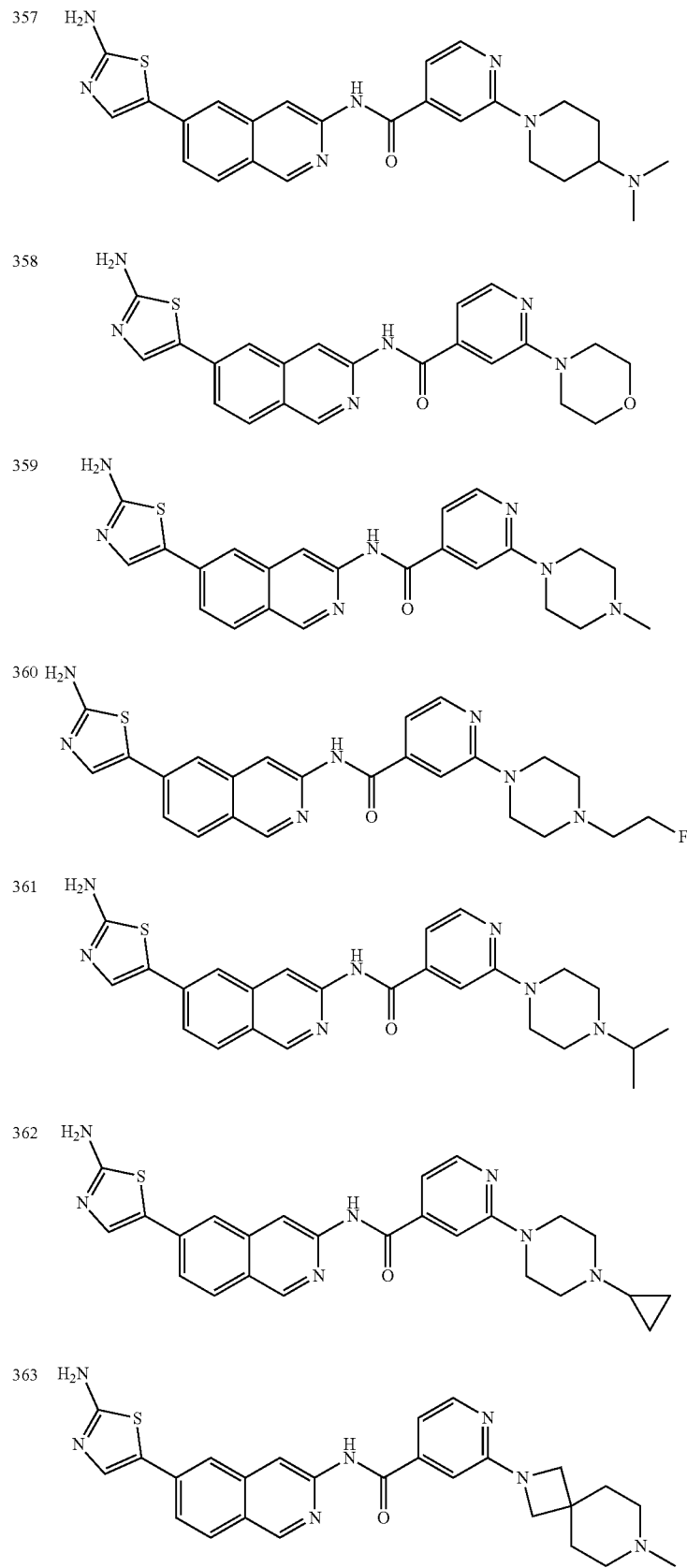

TABLE 1-continued

| 364 | (structure) |
| 365 | (structure) |
| 366 | (structure) |
| 367 | (structure) |
| 368 | (structure) |
| 369 | (structure) |
| 370 | (structure) |
| 371 | (structure) |

TABLE 1-continued
372 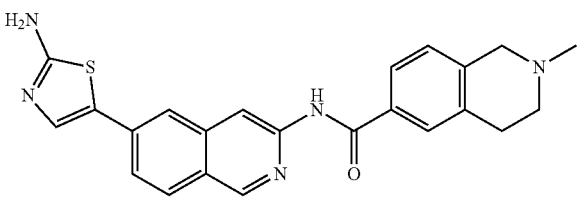 [SMILES: CN1CCc2cc(C(=O)Nc3cc4cc(-c5cnc(N)s5)ccc4cn3)ccc2C1]
373 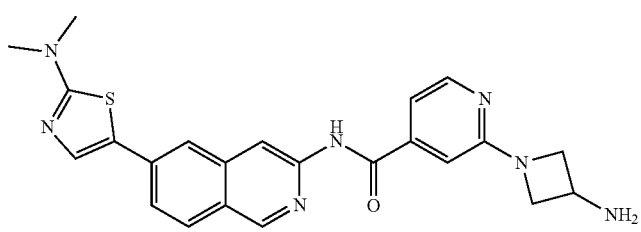 [SMILES: CN(C)c1ncc(-c2ccc3cnc(NC(=O)c4ccnc(N5CC(N)C5)c4)cc3c2)s1]
374 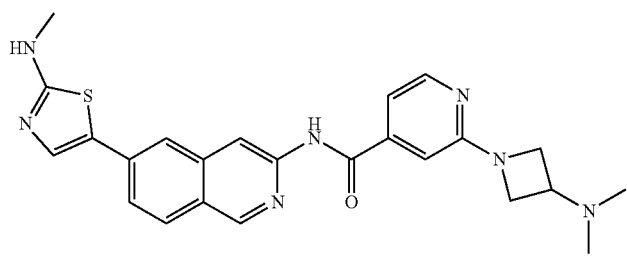 [SMILES: CNc1ncc(-c2ccc3cnc(NC(=O)c4ccnc(N5CC(N(C)C)C5)c4)cc3c2)s1]
375 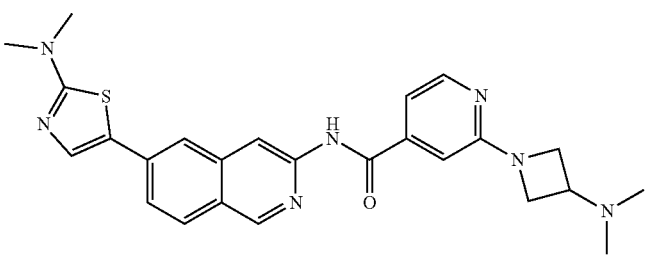
376 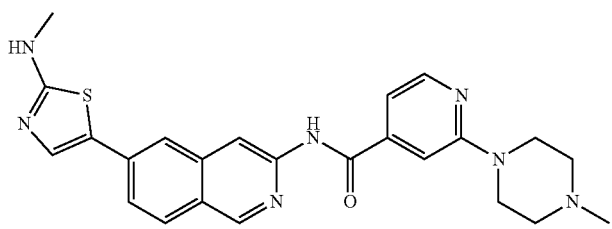 [SMILES: CNc1ncc(-c2ccc3cnc(NC(=O)c4ccnc(N5CCN(C)CC5)c4)cc3c2)s1]
377 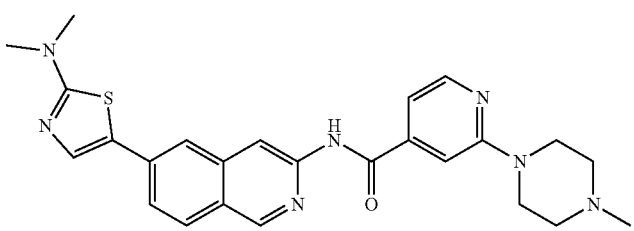

TABLE 1-continued
378 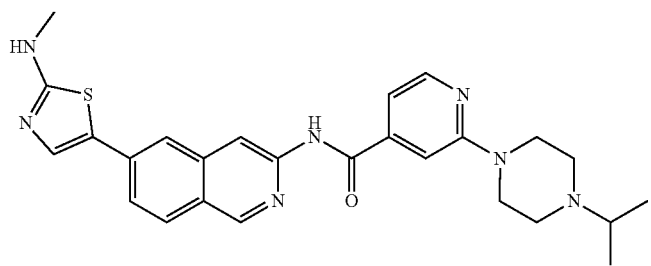 [SMILES: CNc1ncc(-c2ccc3cnc(NC(=O)c4ccnc(N5CCN(C(C)C)CC5)c4)cc3c2)s1]
379 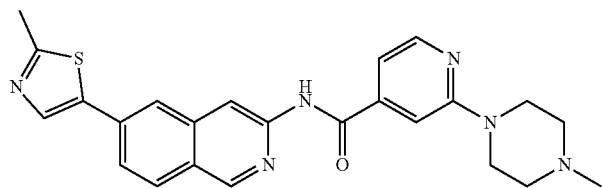 [SMILES: Cc1ncc(-c2ccc3cnc(NC(=O)c4ccnc(N5CCN(C)CC5)c4)cc3c2)s1]
380 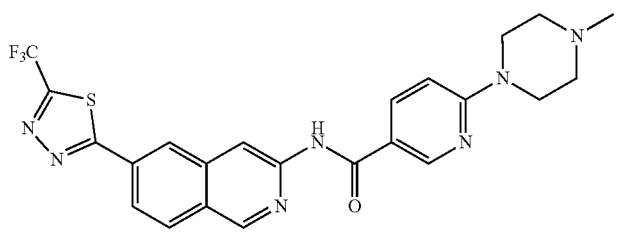 [SMILES: CN1CCN(c2ccc(C(=O)Nc3cc4cc(-c5nnc(C(F)(F)F)s5)ccc4cn3)cn2)CC1]
381 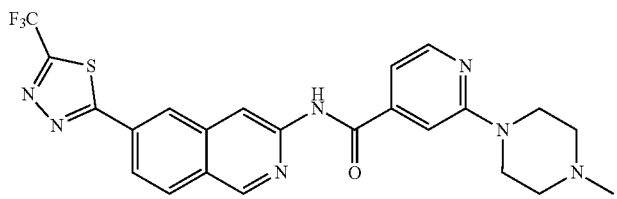 [SMILES: CN1CCN(c2cc(C(=O)Nc3cc4cc(-c5nnc(C(F)(F)F)s5)ccc4cn3)ccn2)CC1]
382 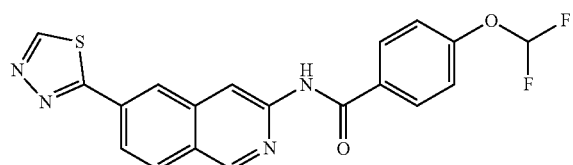
383 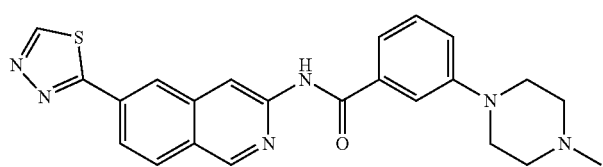 [SMILES: CN1CCN(c2cccc(C(=O)Nc3cc4cc(-c5nncs5)ccc4cn3)c2)CC1]
384 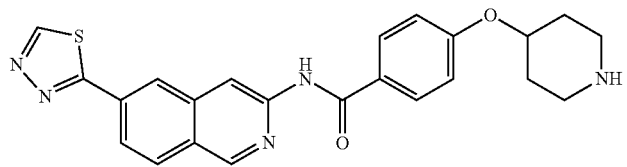 [SMILES: O=C(Nc1cc2cc(-c3nncs3)ccc2cn1)c1ccc(OC2CCNCC2)cc1]
385 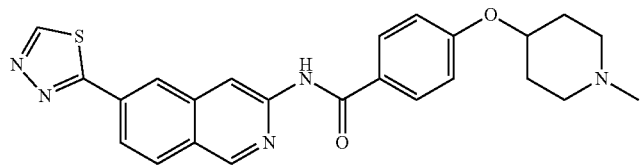 [SMILES: CN1CCC(Oc2ccc(C(=O)Nc3cc4cc(-c5nncs5)ccc4cn3)cc2)CC1]

TABLE 1-continued
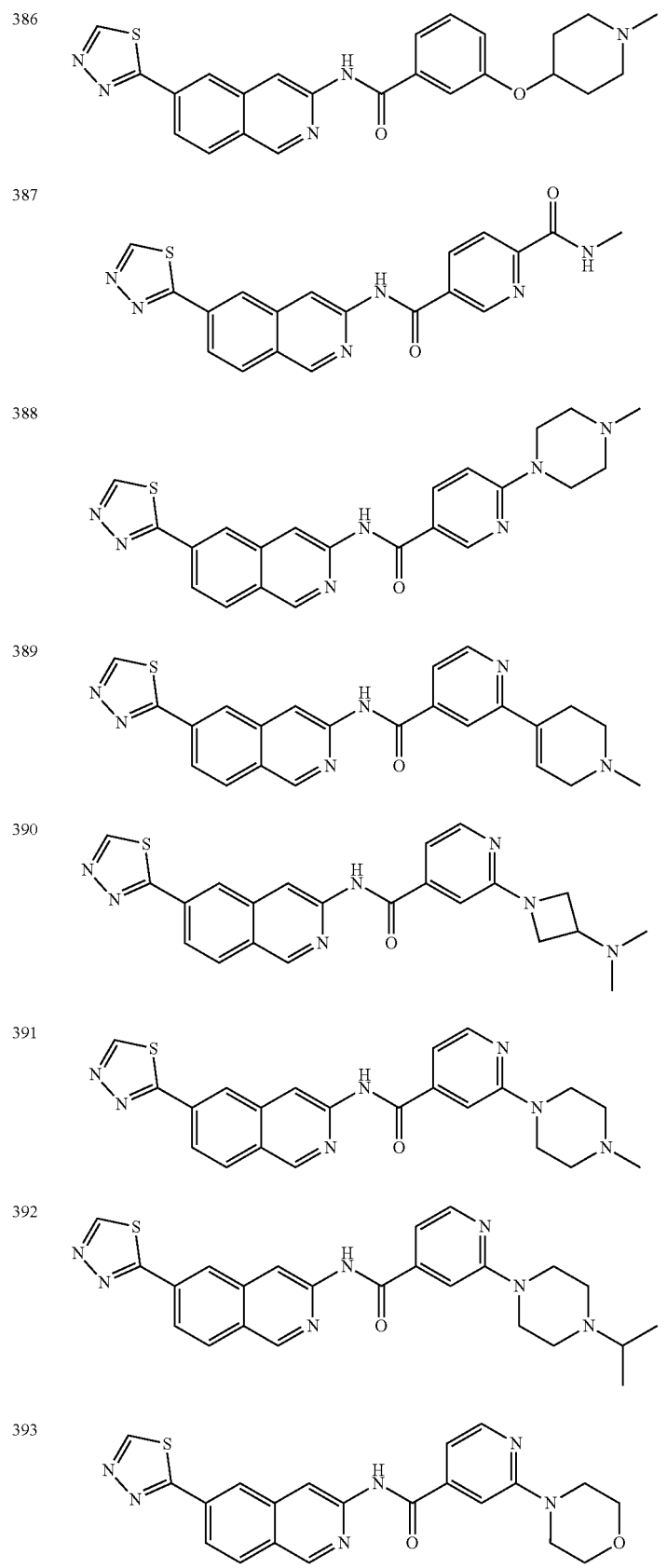

TABLE 1-continued
| | |
|---|---|
| 394 | 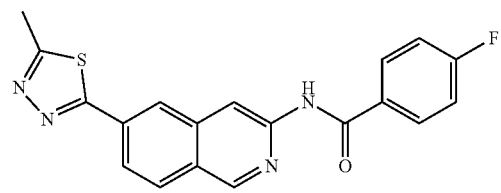 [SMILES: Cc1nnc(-c2ccc3cnc(NC(=O)c4ccc(F)cc4)cc3c2)s1] |
| 395 | 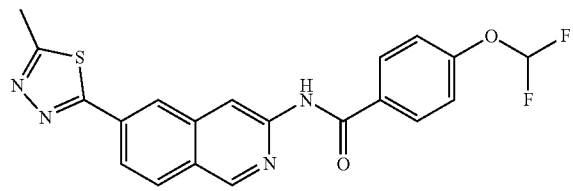 [SMILES: Cc1nnc(-c2ccc3cnc(NC(=O)c4ccc(OC(F)F)cc4)cc3c2)s1] |
| 396 | 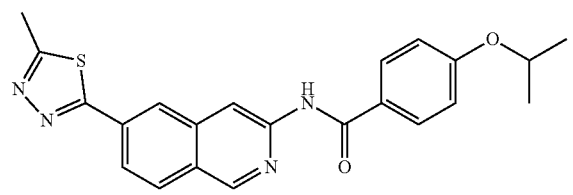 [SMILES: Cc1nnc(-c2ccc3cnc(NC(=O)c4ccc(OC(C)C)cc4)cc3c2)s1] |
| 397 | 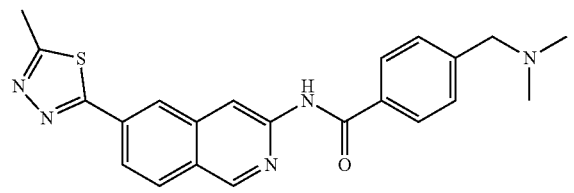 [SMILES: Cc1nnc(-c2ccc3cnc(NC(=O)c4ccc(CN(C)C)cc4)cc3c2)s1] |
| 398 | 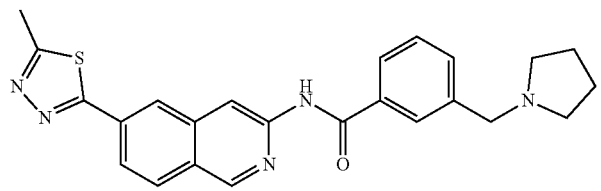 [SMILES: Cc1nnc(-c2ccc3cnc(NC(=O)c4cccc(CN5CCCC5)c4)cc3c2)s1] |
| 399 | 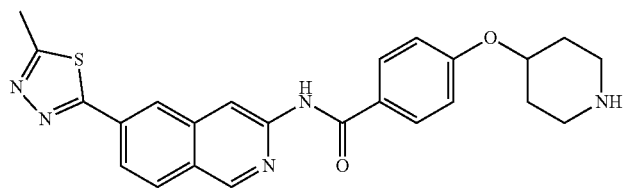 [SMILES: Cc1nnc(-c2ccc3cnc(NC(=O)c4ccc(OC5CCNCC5)cc4)cc3c2)s1] |
| 400 | 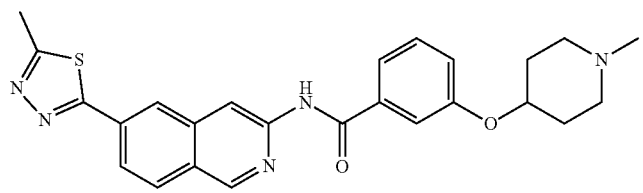 [SMILES: Cc1nnc(-c2ccc3cnc(NC(=O)c4cccc(OC5CCN(C)CC5)c4)cc3c2)s1] |
| 401 | 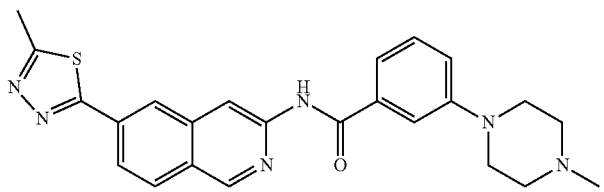 |

TABLE 1-continued
402 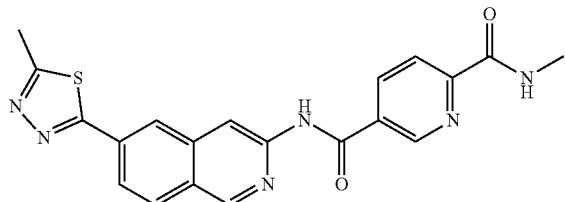
403 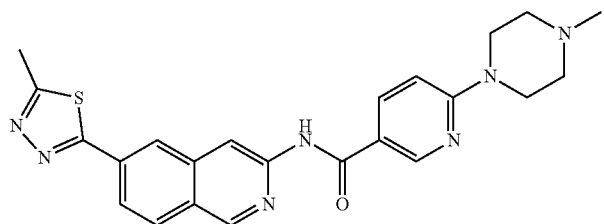
404 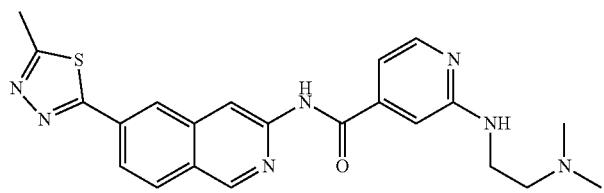 [SMILES: Cc1nnc(-c2ccc3cnc(NC(=O)c4ccnc(NCCN(C)C)c4)cc3c2)s1]
405 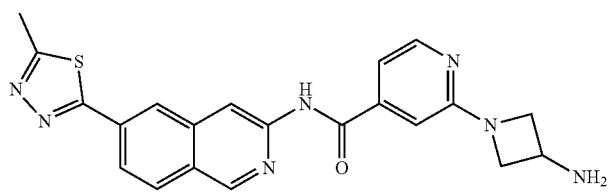 [SMILES: Cc1nnc(-c2ccc3cnc(NC(=O)c4ccnc(N5CC(N)C5)c4)cc3c2)s1]
406 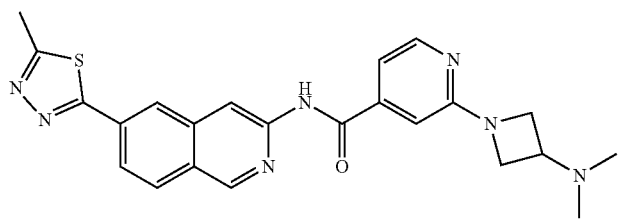 [SMILES: Cc1nnc(-c2ccc3cnc(NC(=O)c4ccnc(N5CC(N(C)C)C5)c4)cc3c2)s1]
407 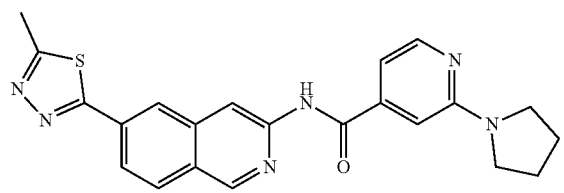 [SMILES: Cc1nnc(-c2ccc3cnc(NC(=O)c4ccnc(N5CCCC5)c4)cc3c2)s1]
408 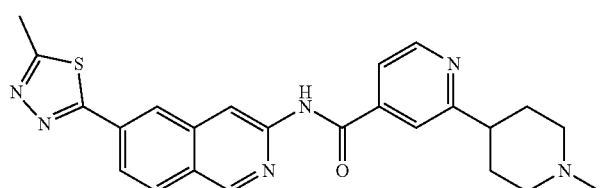

TABLE 1-continued
409 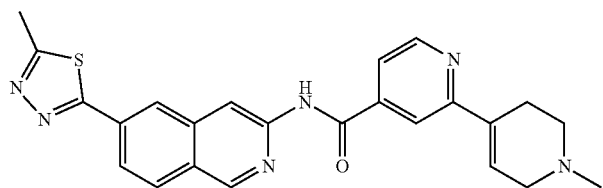 [SMILES: Cc1nnc(-c2ccc3cnc(NC(=O)c4ccnc(C5CCN(C)CC5)c4)cc3c2)s1]
410 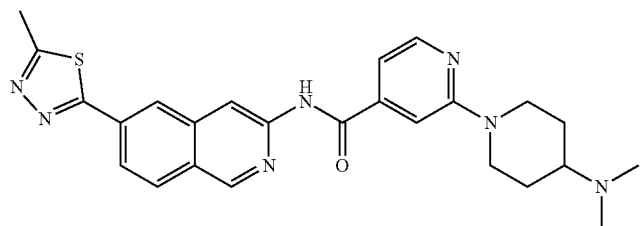
411 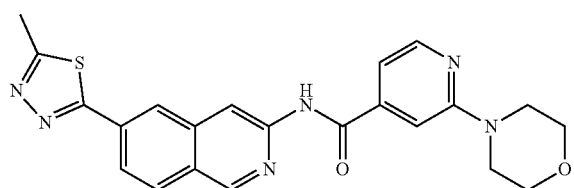
412 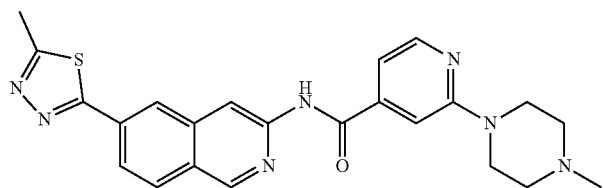
413 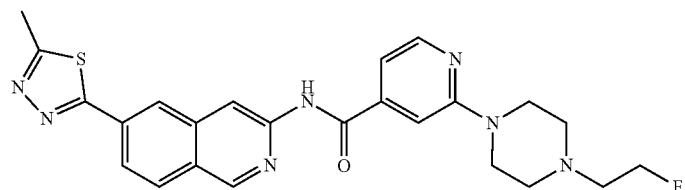
414 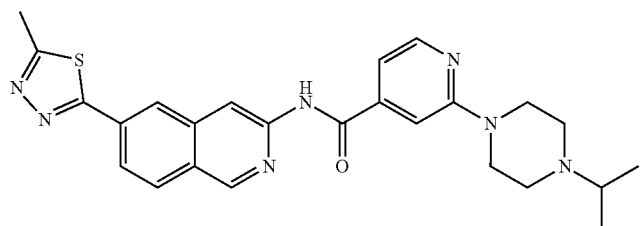
415 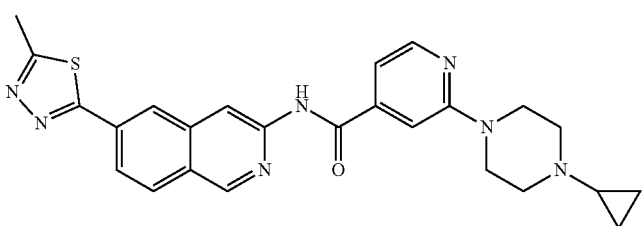

TABLE 1-continued
416
417
418
419
420
421
422
423
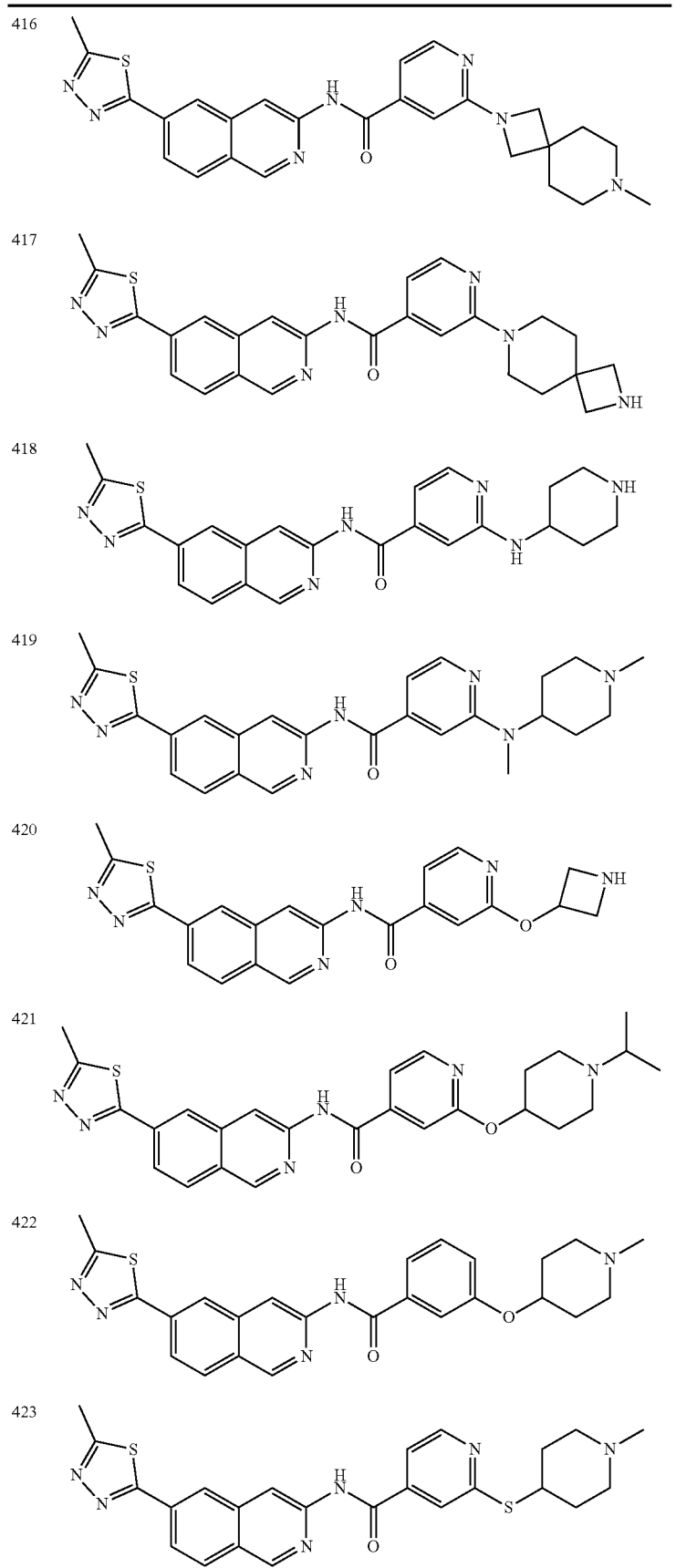

TABLE 1-continued
424 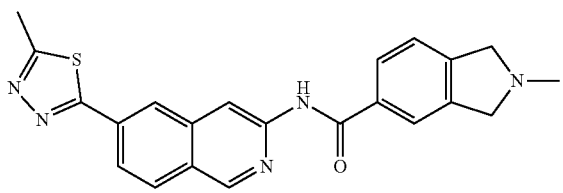 [SMILES: Cc1nnc(-c2ccc3cnc(NC(=O)c4ccc5c(c4)CN(C)C5)cc3c2)s1]
425 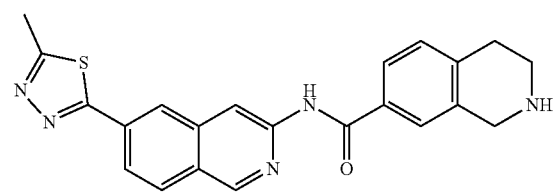 [SMILES: Cc1nnc(-c2ccc3cnc(NC(=O)c4ccc5c(c4)CNCC5)cc3c2)s1]
426 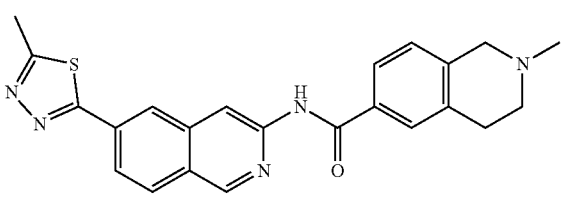 [SMILES: Cc1nnc(-c2ccc3cnc(NC(=O)c4ccc5c(c4)CCN(C)C5)cc3c2)s1]
427 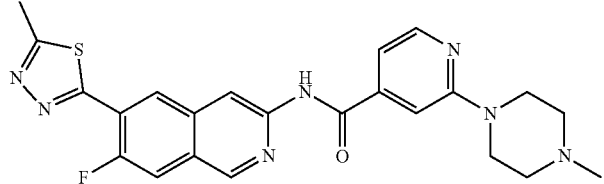 [SMILES: Cc1nnc(-c2cc3cc(NC(=O)c4ccnc(N5CCN(C)CC5)c4)ncc3cc2F)s1]
528 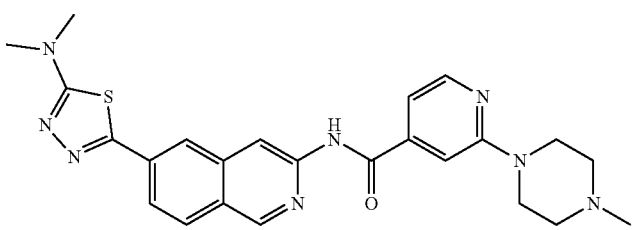
429 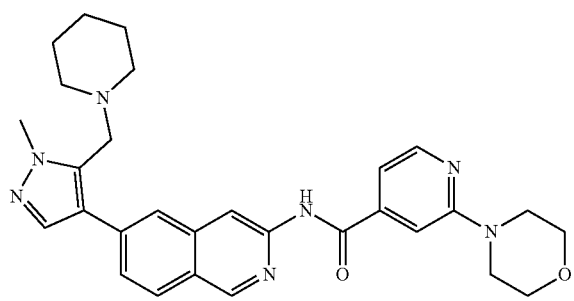 [SMILES: Cn1ncc(-c2ccc3cnc(NC(=O)c4ccnc(N5CCOCC5)c4)cc3c2)c1CN1CCCCC1]
430 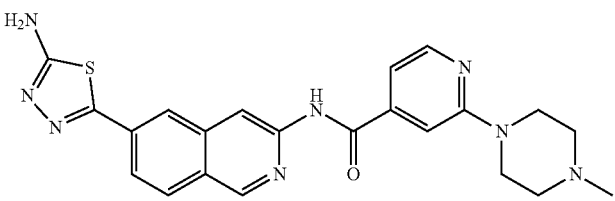 [SMILES: CN1CCN(c2cc(C(=O)Nc3cc4cc(-c5nnc(N)s5)ccc4cn3)ccn2)CC1]

TABLE 1-continued
431 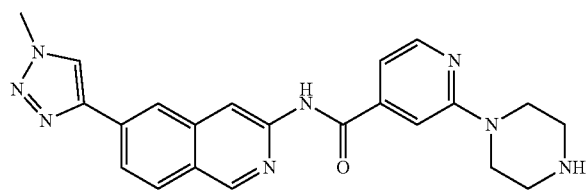 [SMILES: Cn1cc(-c2ccc3cnc(NC(=O)c4ccnc(N5CCNCC5)c4)cc3c2)nn1]
432 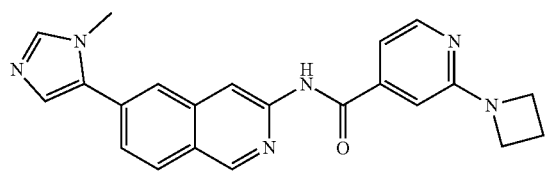 [SMILES: Cn1cncc1-c1ccc2cnc(NC(=O)c3ccnc(N4CCC4)c3)cc2c1]
433 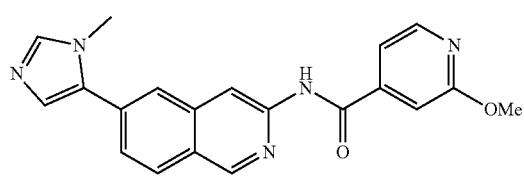 [SMILES: COc1cc(C(=O)Nc2cc3cc(-c4cncn4C)ccc3cn2)ccn1]
434 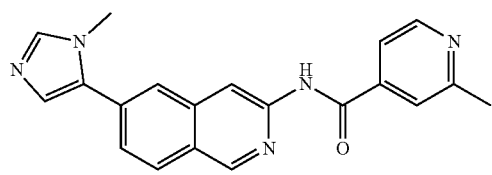 [SMILES: Cc1cc(C(=O)Nc2cc3cc(-c4cncn4C)ccc3cn2)ccn1]
435 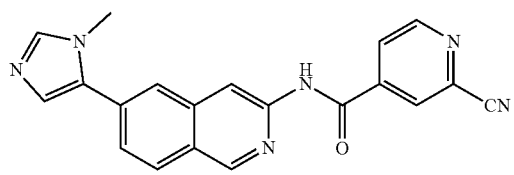 [SMILES: Cn1cncc1-c1ccc2cnc(NC(=O)c3ccnc(C#N)c3)cc2c1]
436 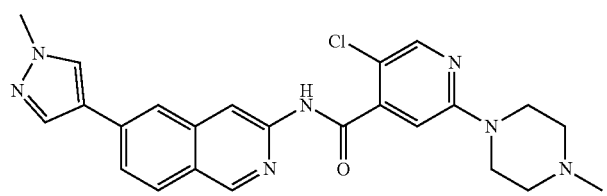 [SMILES: CN1CCN(c2cc(C(=O)Nc3cc4cc(-c5cnn(C)c5)ccc4cn3)c(Cl)cn2)CC1]
437 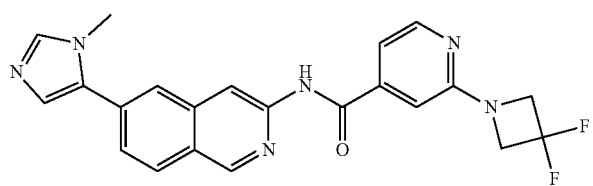 [SMILES: Cn1cncc1-c1ccc2cnc(NC(=O)c3ccnc(N4CC(F)(F)C4)c3)cc2c1]
438 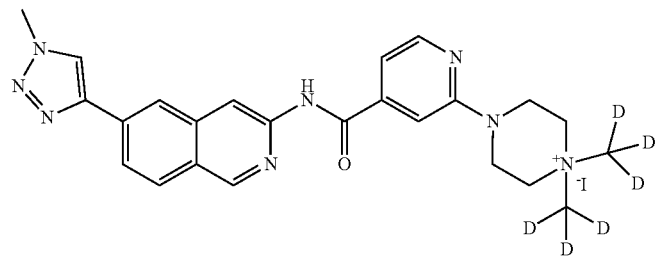

TABLE 1-continued
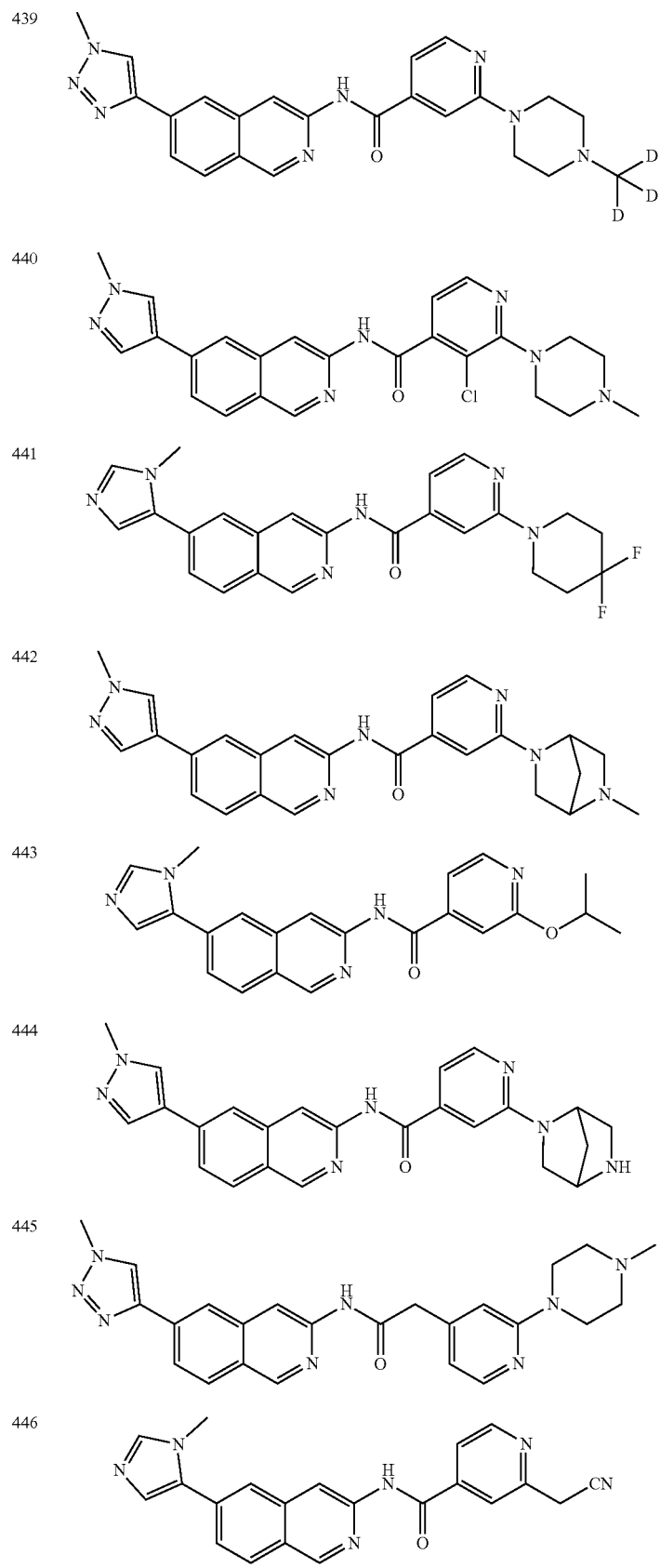

TABLE 1-continued
447 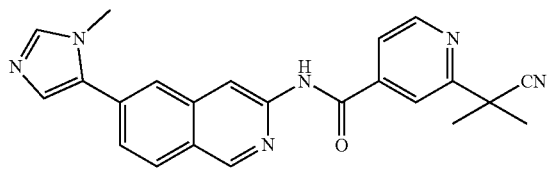 [SMILES: Cn1cncc1-c1ccc2cnc(NC(=O)c3ccnc(C(C)(C)C#N)c3)cc2c1]
448 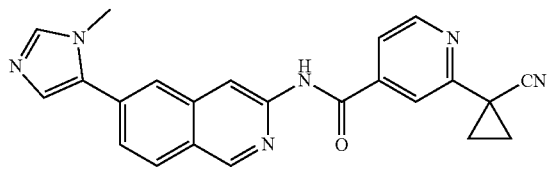 [SMILES: Cn1cncc1-c1ccc2cnc(NC(=O)c3ccnc(C4(C#N)CC4)c3)cc2c1]
449 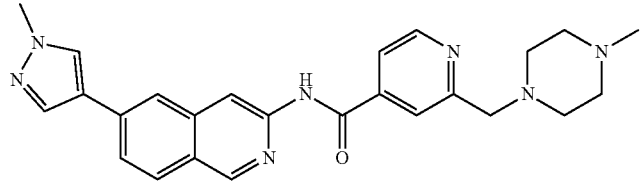 [SMILES: CN1CCN(Cc2cc(C(=O)Nc3cc4cc(-c5cnn(C)c5)ccc4cn3)ccn2)CC1]
450 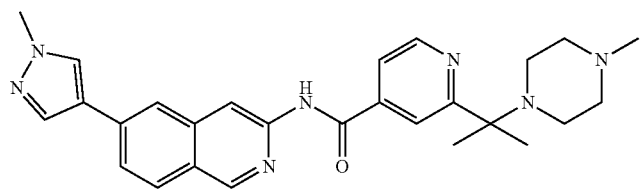 [SMILES: CN1CCN(C(C)(C)c2cc(C(=O)Nc3cc4cc(-c5cnn(C)c5)ccc4cn3)ccn2)CC1]
451 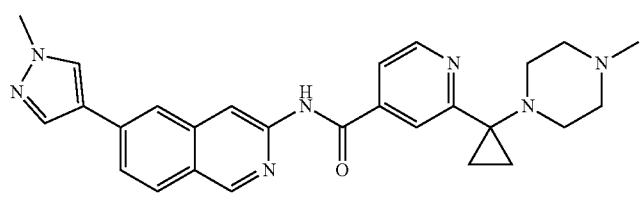 [SMILES: CN1CCN(C2(c3cc(C(=O)Nc4cc5cc(-c6cnn(C)c6)ccc5cn4)ccn3)CC2)CC1]
452 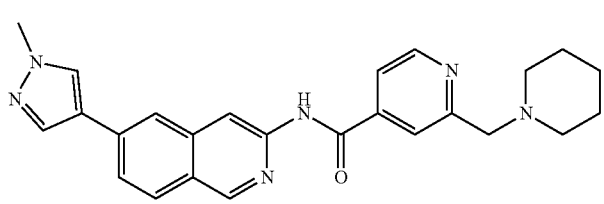 [SMILES: Cn1cc(-c2ccc3cnc(NC(=O)c4ccnc(CN5CCCCC5)c4)cc3c2)cn1]
453 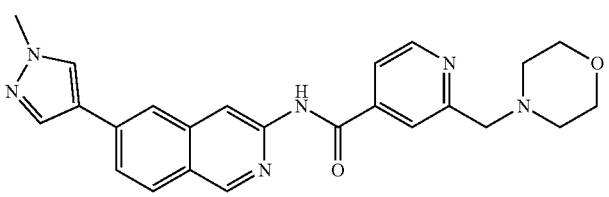 [SMILES: Cn1cc(-c2ccc3cnc(NC(=O)c4ccnc(CN5CCOCC5)c4)cc3c2)cn1]
454 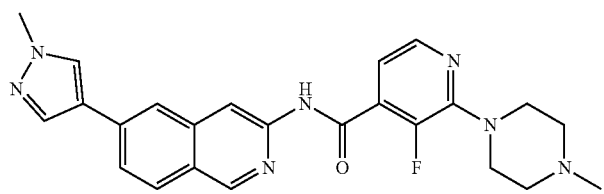 [SMILES: CN1CCN(c2nccc(C(=O)Nc3cc4cc(-c5cnn(C)c5)ccc4cn3)c2F)CC1]

TABLE 1-continued
| | |
|---|---|
| 455 | 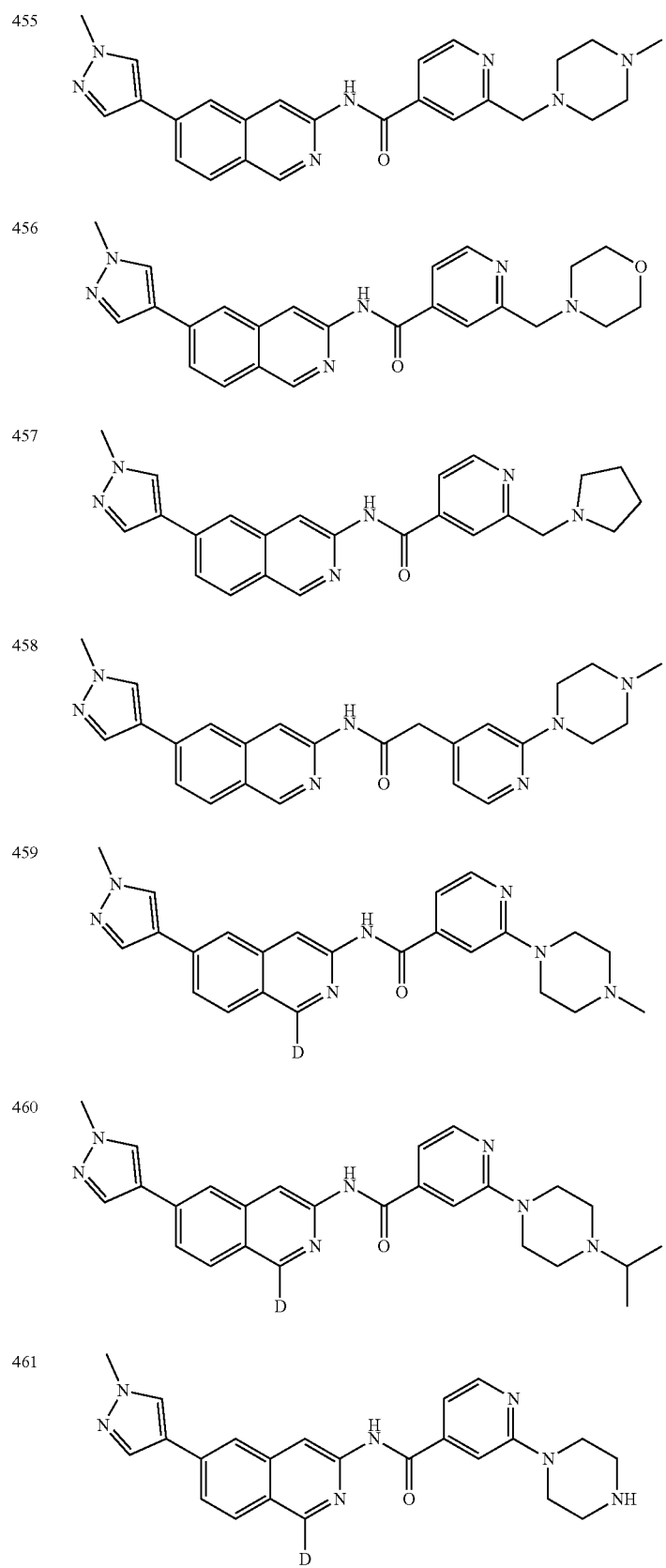 |
| 456 | |
| 457 | |
| 458 | |
| 459 | |
| 460 | |
| 461 | |

TABLE 1-continued

462

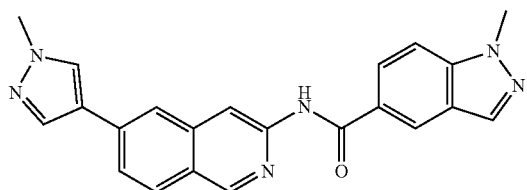

463

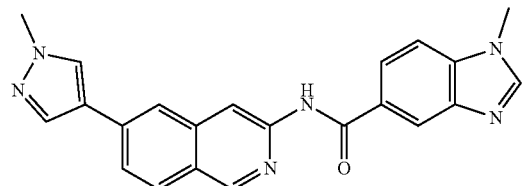

464

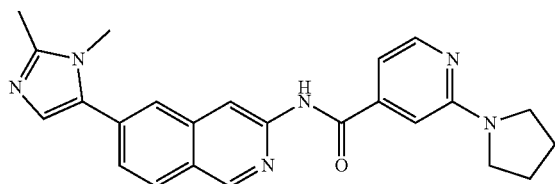

465

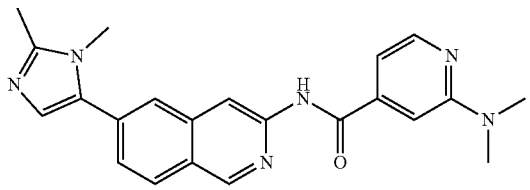

Administration and Pharmaceutical Compositions

Some embodiments include pharmaceutical compositions comprising: (a) a therapeutically effective amount of a compound provided herein, or its corresponding enantiomer, diastereoisomer or tautomer, or pharmaceutically acceptable salt; and (b) a pharmaceutically acceptable carrier.

The compounds provided herein may also be useful in combination (administered together or sequentially) with other known agents.

Non-limiting examples of diseases which can be treated with a combination of a compound of Formula (I) and other known agents are colorectal cancer, ovarian cancer, retinitis pigmentosa, macular degeneration, diabetic retinopathy, idiopathic pulmonary fibrosis/pulmonary fibrosis, and osteoarthritis.

In some embodiments, colorectal cancer can be treated with a combination of a compound of Formula (I) and one or more of the following drugs: 5-Fluorouracil (5-FU), which can be administered with the vitamin-like drug leucovorin (also called folinic acid); capecitabine (XELODA®), irinotecan (CAMPOSTAR®), oxaliplatin (ELOXATIN®). Examples of combinations of these drugs which could be further combined with a compound of Formula (I) are FOLFOX (5-FU, leucovorin, and oxaliplatin), FOLFIRI (5-FU, leucovorin, and irinotecan), FOLFOXIRI (leucovorin, 5-FU, oxaliplatin, and irinotecan) and CapeOx (Capecitabine and oxaliplatin). For rectal cancer, chemo with 5-FU or capecitabine combined with radiation may be given before surgery (neoadjuvant treatment).

In some embodiments, ovarian cancer can be treated with a combination of a compound of Formula (I) and one or more of the following drugs: Topotecan, Liposomal doxorubicin (DOXIL®), Gemcitabine (GEMZAR®), Cyclophosphamide (CYTOXAN®), Vinorelbine (NAVELBINE®), Ifosfamide (IFEX®), Etoposide (VP-16), Altretamine (HEXALEN®), Capecitabine (XELODA®), Irinotecan (CPT-11, CAMPTOSAR®), Melphalan, Pemetrexed (ALIMTA®) and Albumin bound paclitaxel (nab-paclitaxel, ABRAXANE®). Examples of combinations of these drugs which could be further combined with a compound of Formula (I) are TIP (paclitaxel [Taxol], ifosfamide, and cisplatin), VeIP (vinblastine, ifosfamide, and cisplatin) and VIP (etoposide [VP-16], ifosfamide, and cisplatin).

In some embodiments, a compound of Formula (I) can be used to treat cancer in combination with any of the following methods: (a) Hormone therapy such as aromatase inhibitors, LHRH [luteinizing hormone-releasing hormone] analogs and inhibitors, and others; (b) Ablation or embolization procedures such as radiofrequency ablation (RFA), ethanol (alcohol) ablation, microwave thermotherapy and cryosurgery (cryotherapy); (c) Chemotherapy using alkylating agents such as cisplatin and carboplatin, oxaliplatin, mechlorethamine, cyclophosphamide, chlorambucil and ifosfamide; (d) Chemotherapy using anti-metabolites such as azathioprine and mercaptopurine; (e) Chemotherapy using plant alkaloids and terpenoids such as *vinca* alkaloids (i.e. Vincristine, Vinblastine, Vinorelbine and Vindesine) and taxanes; (f) Chemotherapy using podophyllotoxin, etoposide, teniposide and docetaxel; (g) Chemotherapy using topoisomerase inhibitors such as irinotecan, topotecan, amsacrine, etoposide, etoposide phosphate, and teniposide; (h) Chemotherapy using cytotoxic antibiotics such as actinomycin, anthracyclines, doxorubicin, daunorubicin, valrubicin, idarubicin, epirubicin, bleomycin, plicamycin and mitomycin; (i) Chemotherapy using tyrosine-kinase inhibitors such as Imatinib mesylate (GLEEVEC®, also known as STI-571), Gefitinib (Iressa, also known as ZD1839), Erlotinib (marketed as TARCEVA®), Bortezomib (VELCADE®), tamoxifen, tofacitinib, crizotinib, Bcl-2 inhibitors (e.g. obatoclax in clinical trials, ABT-263, and Gossypol), PARP inhibitors (e.g. Iniparib, Olaparib in clinical trials), PI3K inhibitors (e.g. perifosine in a phase III trial), VEGF Receptor 2 inhibitors (e.g. Apatinib), AN-152, (AEZS-108), Braf inhibitors (e.g. vemurafenib, dabrafenib and LGX818), MEK inhibitors (e.g. trametinib and MEK162), CDK inhibitors, (e.g. PD-0332991), salinomycin and Sorafenib; (j) Chemotherapy using monoclonal antibodies such as Rituximab (marketed as MABTHERA® or RITUXAN®), Trastuzumab (Herceptin also known as ErbB2), Cetuximab (marketed as ERBITUX®), and Bevacizumab (marketed as AVASTIN®); and (k) radiation therapy.

In some embodiments, diabetic retinopathy can be treated with a combination of a compound of Formula (I) and one or more of the following natural supplements: Bilberry, Butcher's broom, Ginkgo, Grape seed extract, and Pycnogenol (Pine bark).

In some embodiments, idiopathic pulmonary fibrosis/pulmonary fibrosis can be treated with a combination of a compound of Formula (I) and one or more of the following drugs: pirfenidone (pirfenidone was approved for use in 2011 in Europe under the brand name Esbriet®), prednisone, azathioprine, N-acetylcysteine, interferon-γ 1b, bosentan (bosentan is currently being studied in patients with IPF, [*The American Journal of Respiratory and Critical Care Medicine* (2011), 184(1), 92-9]), Nintedanib (BIBF 1120 and Vargatef), QAX576 [*British Journal of Pharmacology* (2011), 163(1), 141-172], and anti-inflammatory agents such as corticosteroids.

In some embodiments, a compound of Formula (I) can be used to treat idiopathic pulmonary fibrosis/pulmonary fibrosis in combination with any of the following methods: oxygen therapy, pulmonary rehabilitation and surgery.

In some embodiments, a compound of Formula (I) can be used to treat osteoarthritis in combination with any of the following methods: (a) Nonsteroidal anti-inflammatory drugs (NSAIDs) such as ibuprofen, naproxen, aspirin and acetaminophen; (b) physical therapy; (c) injections of corticosteroid medications; (d) injections of hyaluronic acid derivatives (e.g. Hyalgan, Synvisc); (e) narcotics, like codeine; (f) in combination with braces and/or shoe inserts or any device that can immobilize or support your joint to help you keep pressure off it (e.g., splints, braces, shoe inserts or other medical devices); (g) realigning bones (osteotomy); (h) joint replacement (arthroplasty); and (i) in combination with a chronic pain class.

In some embodiments, macular degeneration can be treated with a combination of a compound of Formula (I) and one or more of the following drugs: Bevacizumab (Avastin®), Ranibizumab (Lucentis®), Pegaptanib (Macugen), Aflibercept (Eylea®), verteporfin (Visudyne®) in combination with photodynamic therapy (PDT) or with any of the following methods: (a) in combination with laser to destroy abnormal blood vessels (photocoagulation); and (b) in combination with increased vitamin intake of antioxidant vitamins and zinc.

In some embodiments, retinitis pigmentosa can be treated with a combination of a compound of Formula (I) and one or more of the following drugs: UF-021 (Ocuseva™) vitamin A palmitate and pikachurin or with any of the following methods: (a) with the Argus® II retinal implant; and (b) with stem cell and/or gene therapy.

Administration of the compounds disclosed herein or the pharmaceutically acceptable salts thereof can be via any of the accepted modes of administration, including, but not limited to, orally, subcutaneously, intravenously, intranasally, topically, transdermally, intraperitoneally, intramuscularly, intrapulmonarilly, vaginally, rectally, ontologically, neuro-otologically, intraocularly, subconjuctivally, via anterior eye chamber injection, intravitreally, intraperitoneally, intrathecally, intracystically, intrapleurally, via wound irrigation, intrabuccally, intra-abdominally, intra-articularly, intra-aurally, intrabronchially, intracapsularly, intrameningeally, via inhalation, via endotracheal or endobronchial instillation, via direct instillation into pulmonary cavities, intraspinally, intrasynovially, intrathoracically, via thoracostomy irrigation, epidurally, intratympanically, intracisternally, intravascularly, intraventricularly, intraosseously, via irrigation of infected bone, or via application as part of any admixture with a prosthetic devices. In some embodiments, the administration method includes oral or parenteral administration.

Compounds provided herein intended for pharmaceutical use may be administered as crystalline or amorphous products. Pharmaceutically acceptable compositions may include solid, semi-solid, liquid, solutions, colloidal, liposomes, emulsions, suspensions, complexes, coacervates and aerosols. Dosage forms, such as, e.g., tablets, capsules, powders, liquids, suspensions, suppositories, aerosols, implants, controlled release or the like. They may be obtained, for example, as solid plugs, powders, or films by methods such as precipitation, crystallization, milling, grinding, supercritical fluid processing, coacervation, complex coacervation, encapsulation, emulsification, complexation, freeze drying, spray drying, or evaporative drying. Microwave or radio frequency drying may be used for this purpose. The compounds can also be administered in sustained or controlled release dosage forms, including depot injections, osmotic pumps, pills (tablets and or capsules), transdermal (including electrotransport) patches, implants and the like, for prolonged and/or timed, pulsed administration at a predetermined rate.

The compounds can be administered either alone or in combination with a conventional pharmaceutical carrier, excipient or the like. Pharmaceutically acceptable excipients include, but are not limited to, ion exchangers, alumina, aluminum stearate, lecithin, self-emulsifying drug delivery systems (SEDDS) such as d-α-tocopherol polyethylene glycol 1000 succinate, surfactants used in pharmaceutical dosage forms such as Tweens, poloxamers or other similar polymeric delivery matrices, serum proteins, such as human serum albumin, buffer substances such as phosphates, tris, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium-chloride, zinc salts, colloidal silica, magnesium trisilicate, polyvinyl pyrrolidone, cellulose-based substances, polyethylene glycol, sodium carboxymethyl cellulose, polyacrylates, waxes, polyethylene-polyoxypropylene-block polymers, and wool fat. Cyclodextrins such as α-, β, and γ-cyclodextrin, or chemically modified derivatives such as hydroxyalkylcyclodextrins, including 2- and 3-hydroxypropyl-β-cyclodextrins, or other solubilized derivatives can also be used to enhance delivery of compounds described herein. Dosage forms or compositions containing a compound as described herein in the range of 0.005% to 100% with the balance made up from non-toxic carrier may be prepared. The contemplated compositions may contain 0.001%-100% of a compound provided herein, in one embodiment 0.1-95%, in another embodiment 75-85%, in a further embodiment 20-80%. Actual methods of preparing such dosage forms are known, or will be apparent, to those skilled in this art; for example, see Remington: The Science and Practice of Pharmacy, 22$^{nd}$ Edition (Pharmaceutical Press, London, U K. 2012).

In one embodiment, the compositions will take the form of a unit dosage form such as a pill or tablet and thus the composition may contain, along with a compound provided herein, a diluent such as lactose, sucrose, dicalcium phosphate, or the like; a lubricant such as magnesium stearate or the like; and a binder such as starch, gum acacia, polyvinylpyrrolidine, gelatin, cellulose, cellulose derivatives or the like. In another solid dosage form, a powder, marume, solution or suspension (e.g., in propylene carbonate, vegetable oils, PEG's, poloxamer 124 or triglycerides) is encapsulated in a capsule (gelatin or cellulose base capsule). Unit dosage forms in which one or more compounds provided herein or additional active agents are physically separated are also contemplated; e.g., capsules with granules (or tablets in a capsule) of each drug; two-layer tablets; two-compartment gel caps, etc. Enteric coated or delayed release oral dosage forms are also contemplated.

Liquid pharmaceutically administrable compositions can, for example, be prepared by dissolving, dispersing, etc. a compound provided herein and optional pharmaceutical adjuvants in a carrier (e.g., water, saline, aqueous dextrose, glycerol, glycols, ethanol or the like) to form a solution, colloid, liposome, emulsion, complexes, coacervate or suspension. If desired, the pharmaceutical composition can also contain minor amounts of nontoxic auxiliary substances such as wetting agents, emulsifying agents, co-solvents, solubilizing agents, pH buffering agents and the like (e.g., sodium acetate, sodium citrate, cyclodextrin derivatives, sorbitan monolaurate, triethanolamine acetate, triethanolamine oleate, and the like).

In some embodiments, the unit dosage of compounds of Formula (I) is about 0.25 mg/Kg to about 50 mg/Kg in humans.

In some embodiments, the unit dosage of compounds of Formula (I) is about 0.25 mg/Kg to about 20 mg/Kg in humans.

In some embodiments, the unit dosage of compounds of Formula (I) is about 0.50 mg/Kg to about 19 mg/Kg in humans.

In some embodiments, the unit dosage of compounds of Formula (I) is about 0.75 mg/Kg to about 18 mg/Kg in humans.

In some embodiments, the unit dosage of compounds of Formula (I) is about 1.0 mg/Kg to about 17 mg/Kg in humans.

In some embodiments, the unit dosage of compounds of Formula (I) is about 1.25 mg/Kg to about 16 mg/Kg in humans.

In some embodiments, the unit dosage of compounds of Formula (I) is about 1.50 mg/Kg to about 15 mg/Kg in humans.

In some embodiments, the unit dosage of compounds of Formula (I) is about 1.75 mg/Kg to about 14 mg/Kg in humans.

In some embodiments, the unit dosage of compounds of Formula (I) is about 2.0 mg/Kg to about 13 mg/Kg in humans.

In some embodiments, the unit dosage of compounds of Formula (I) is about 3.0 mg/Kg to about 12 mg/Kg in humans.

In some embodiments, the unit dosage of compounds of Formula (I) is about 4.0 mg/Kg to about 11 mg/Kg in humans.

In some embodiments, the unit dosage of compounds of Formula (I) is about 5.0 mg/Kg to about 10 mg/Kg in humans.

In some embodiments, the compositions are provided in unit dosage forms suitable for single administration.

In some embodiments, the compositions are provided in unit dosage forms suitable for twice a day administration.

In some embodiments, the compositions are provided in unit dosage forms suitable for three times a day administration.

Injectables can be prepared in conventional forms, either as liquid solutions, colloid, liposomes, complexes, coacervate or suspensions, as emulsions, or in solid forms suitable for reconstitution in liquid prior to injection. The percentage of a compound provided herein contained in such parenteral compositions is highly dependent on the specific nature thereof, as well as the activity of the compound and the needs of the patient. However, percentages of active ingredient of 0.01% to 10% in solution are employable, and could be higher if the composition is a solid or suspension, which could be subsequently diluted to the above percentages.

In some embodiments, the composition will comprise about 0.1-10% of the active agent in solution.

In some embodiments, the composition will comprise about 0.1-5% of the active agent in solution.

In some embodiments, the composition will comprise about 0.1-4% of the active agent in solution.

In some embodiments, the composition will comprise about 0.15-3% of the active agent in solution.

In some embodiments, the composition will comprise about 0.2-2% of the active agent in solution.

In some embodiments, the compositions are provided in dosage forms suitable for continuous dosage by intravenous infusion over a period of about 1-96 hours.

In some embodiments, the compositions are provided in dosage forms suitable for continuous dosage by intravenous infusion over a period of about 1-72 hours.

In some embodiments, the compositions are provided in dosage forms suitable for continuous dosage by intravenous infusion over a period of about 1-48 hours.

In some embodiments, the compositions are provided in dosage forms suitable for continuous dosage by intravenous infusion over a period of about 1-24 hours.

In some embodiments, the compositions are provided in dosage forms suitable for continuous dosage by intravenous infusion over a period of about 1-12 hours.

In some embodiments, the compositions are provided in dosage forms suitable for continuous dosage by intravenous infusion over a period of about 1-6 hours.

In some embodiments, these compositions can be administered by intravenous infusion to humans at doses of about 5 mg/m$^2$ to about 300 mg/m$^2$.

In some embodiments, these compositions can be administered by intravenous infusion to humans at doses of about 5 mg/m$^2$ to about 200 mg/m$^2$.

In some embodiments, these compositions can be administered by intravenous infusion to humans at doses of about 5 mg/m$^2$ to about 100 mg/m$^2$.

In some embodiments, these compositions can be administered by intravenous infusion to humans at doses of about 10 mg/m$^2$ to about 50 mg/m$^2$.

In some embodiments, these compositions can be administered by intravenous infusion to humans at doses of about 50 mg/m$^2$ to about 200 mg/m$^2$.

In some embodiments, these compositions can be administered by intravenous infusion to humans at doses of about 75 mg/m² to about 175 mg/m².

In some embodiments, these compositions can be administered by intravenous infusion to humans at doses of about 100 mg/m² to about 150 mg/m².

It is to be noted that concentrations and dosage values may also vary depending on the specific compound and the severity of the condition to be alleviated. It is to be further understood that for any particular patient, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions.

In one embodiment, the compositions can be administered to the respiratory tract (including nasal and pulmonary) e.g., through a nebulizer, metered-dose inhalers, atomizer, mister, aerosol, dry powder inhaler, insufflator, liquid instillation or other suitable device or technique.

In some embodiments, aerosols intended for delivery to the nasal mucosa are provided for inhalation through the nose. For optimal delivery to the nasal cavities, inhaled particle sizes of about 5 to about 100 microns are useful, with particle sizes of about 10 to about 60 microns being preferred. For nasal delivery, a larger inhaled particle size may be desired to maximize impaction on the nasal mucosa and to minimize or prevent pulmonary deposition of the administered formulation. In some embodiments, aerosols intended for delivery to the lung are provided for inhalation through the nose or the mouth. For delivery to the lung, inhaled aerodynamic particle sizes of about less than 10 µm are useful (e.g., about 1 to about 10 microns). Inhaled particles may be defined as liquid droplets containing dissolved drug, liquid droplets containing suspended drug particles (in cases where the drug is insoluble in the suspending medium), dry particles of pure drug substance, drug substance incorporated with excipients, liposomes, emulsions, colloidal systems, coacervates, aggregates of drug nanoparticles, or dry particles of a diluent which contain embedded drug nanoparticles.

In some embodiments, compounds of Formula (I) disclosed herein intended for respiratory delivery (either systemic or local) can be administered as aqueous formulations, as non-aqueous solutions or suspensions, as suspensions or solutions in halogenated hydrocarbon propellants with or without alcohol, as a colloidal system, as emulsions, coacervates, or as dry powders. Aqueous formulations may be aerosolized by liquid nebulizers employing either hydraulic or ultrasonic atomization or by modified micropump systems (like the soft mist inhalers, the Aerodose® or the AERx® systems). Propellant-based systems may use suitable pressurized metered-dose inhalers (pMDIs). Dry powders may use dry powder inhaler devices (DPIs), which are capable of dispersing the drug substance effectively. A desired particle size and distribution may be obtained by choosing an appropriate device.

In some embodiments, the compositions of Formula (I) disclosed herein can be administered to the ear by various methods. For example, a round window catheter (e.g., U.S. Pat. Nos. 6,440,102 and 6,648,873) can be used. Alternatively, formulations can be incorporated into a wick for use between the outer and middle ear (e.g., U.S. Pat. No. 6,120,484) or absorbed to collagen sponge or other solid support (e.g., U.S. Pat. No. 4,164,559).

If desired, formulations of the invention can be incorporated into a gel formulation (e.g., U.S. Pat. Nos. 4,474,752 and 6,911,211).

In some embodiments, compounds of Formula (I) disclosed herein intended for delivery to the ear can be administered via an implanted pump and delivery system through a needle directly into the middle or inner ear (cochlea) or through a cochlear implant stylet electrode channel or alternative prepared drug delivery channel such as but not limited to a needle through temporal bone into the cochlea.

Other options include delivery via a pump through a thin film coated onto a multichannel electrode or electrode with a specially imbedded drug delivery channel (pathways) carved into the thin film for this purpose. In other embodiments the acidic or basic solid compound of Formula (I) can be delivered from the reservoir of an external or internal implanted pumping system.

Formulations of the invention also can be administered to the ear by intratympanic injection into the middle ear, inner ear, or cochlea (e.g., U.S. Pat. No. 6,377,849 and Ser. No. 11/337,815).

Intratympanic injection of therapeutic agents is the technique of injecting a therapeutic agent behind the tympanic membrane into the middle and/or inner ear. In one embodiment, the formulations described herein are administered directly onto the round window membrane via transtympanic injection. In another embodiment, the ion channel modulating agent auris-acceptable formulations described herein are administered onto the round window membrane via a non-transtympanic approach to the inner ear. In additional embodiments, the formulation described herein is administered onto the round window membrane via a surgical approach to the round window membrane comprising modification of the crista fenestrae cochleae.

In some embodiments, the compounds of Formula (I) are formulated in rectal compositions such as enemas, rectal gels, rectal foams, rectal aerosols, suppositories, jelly suppositories, or retention enemas, containing conventional suppository bases such as cocoa butter or other glycerides, as well as synthetic polymers such as polyvinylpyrrolidone, PEG (like PEG ointments), and the like.

Suppositories for rectal administration of the drug (either as a solution, colloid, suspension or a complex) can be prepared by mixing a compound provided herein with a suitable non-irritating excipient that is solid at ordinary temperatures but liquid at the rectal temperature and will therefore melt or erode/dissolve in the rectum and release the compound. Such materials include cocoa butter, glycerinated gelatin, hydrogenated vegetable oils, poloxamers, mixtures of polyethylene glycols of various molecular weights and fatty acid esters of polyethylene glycol. In suppository forms of the compositions, a low-melting wax such as, but not limited to, a mixture of fatty acid glycerides, optionally in combination with cocoa butter, is first melted.

Solid compositions can be provided in various different types of dosage forms, depending on the physicochemical properties of the compound provided herein, the desired dissolution rate, cost considerations, and other criteria. In one of the embodiments, the solid composition is a single unit. This implies that one unit dose of the compound is comprised in a single, physically shaped solid form or article. In other words, the solid composition is coherent, which is in contrast to a multiple unit dosage form, in which the units are incoherent.

Examples of single units which may be used as dosage forms for the solid composition include tablets, such as compressed tablets, film-like units, foil-like units, wafers, lyophilized matrix units, and the like. In one embodiment, the solid composition is a highly porous lyophilized form. Such lyophilizates, sometimes also called wafers or lyophilized tablets, are particularly useful for their rapid disintegration, which also enables the rapid dissolution of the compound.

On the other hand, for some applications the solid composition may also be formed as a multiple unit dosage form as defined above. Examples of multiple units are powders, granules, microparticles, pellets, mini-tablets, beads, lyophilized powders, and the like. In one embodiment, the solid composition is a lyophilized powder. Such a dispersed lyophilized system comprises a multitude of powder particles, and due to the lyophilization process used in the formation of the powder, each particle has an irregular, porous microstructure through which the powder is capable of absorbing water very rapidly, resulting in quick dissolution. Effervescent compositions are also contemplated to aid the quick dispersion and absorption of the compound.

Another type of multiparticulate system which is also capable of achieving rapid drug dissolution is that of powders, granules, or pellets from water-soluble excipients which are coated with a compound provided herein so that the compound is located at the outer surface of the individual particles. In this type of system, the water-soluble low molecular weight excipient may be useful for preparing the cores of such coated particles, which can be subsequently coated with a coating composition comprising the compound and, for example, one or more additional excipients, such as a binder, a pore former, a saccharide, a sugar alcohol, a film-forming polymer, a plasticizer, or other excipients used in pharmaceutical coating compositions.

Also provided herein are kits. Typically, a kit includes one or more compounds or compositions as described herein. In certain embodiments, a kit can include one or more delivery systems, e.g., for delivering or administering a compound as provided herein, and directions for use of the kit (e.g., instructions for treating a patient). In another embodiment, the kit can include a compound or composition as described herein and a label that indicates that the contents are to be administered to a patient with cancer. In another embodiment, the kit can include a compound or composition as described herein and a label that indicates that the contents are to be administered to a patient with one or more of hepatocellular carcinoma, colon cancer, leukemia, lymphoma, sarcoma, ovarian cancer, diabetic retinopathy, pulmonary fibrosis, rheumatoid arthritis, sepsis, ankylosing spondylitis, psoriasis, scleroderma, mycotic and viral infections, bone and cartilage diseases, Alzheimer's disease, lung disease, bone/osteoporotic (wrist, spine, shoulder and hip) fractures, articular cartilage (chondral) defects, degenerative disc disease (or intervertebral disc degeneration), polyposis coli, bone density and vascular defects in the eye (Osteoporosis-pseudoglioma Syndrome, OPPG), familial exudative vitreoretinopathy, retinal angiogenesis, early coronary disease, tetra-amelia, Müllerian-duct regression and virilization, SERKAL syndrome, type II diabetes, Fuhrmann syndrome, Al-Awadi/Raas-Rothschild/Schinzel phocomelia syndrome, odonto-onycho-dermal dysplasia, obesity, split-hand/foot malformation, caudal duplication, tooth agenesis, Wilms tumor, skeletal dysplasia, focal dermal hypoplasia, autosomal recessive anonychia, neural tube defects, alpha-thalassemia (ATRX) syndrome, fragile X syndrome, ICF syndrome, Angelman syndrome, Prader-Willi syndrome, Beckwith-Wiedemann Syndrome, Norrie disease, and Rett syndrome.

Methods of Treatment

The compounds and compositions provided herein can be used as inhibitors and/or modulators of one or more components of the Wnt pathway, which may include one or more Wnt proteins, and thus can be used to treat a variety of disorders and diseases in which aberrant Wnt signaling is implicated, such as cancer and other diseases associated with abnormal angiogenesis, cellular proliferation, and cell cycling. Accordingly, the compounds and compositions provided herein can be used to treat cancer, to reduce or inhibit angiogenesis, to reduce or inhibit cellular proliferation, to correct a genetic disorder, and/or to treat a neurological condition/disorder/disease due to mutations or dysregulation of the Wnt pathway and/or of one or more of Wnt signaling components. Non-limiting examples of diseases which can be treated with the compounds and compositions provided herein include a variety of cancers, diabetic retinopathy, pulmonary fibrosis, rheumatoid arthritis, scleroderma, mycotic and viral infections, bone and cartilage diseases, neurological conditions/diseases such as Alzheimer's disease, amyotrophic lateral sclerosis (ALS), motor neuron disease, multiple sclerosis or autism, lung disease, bone/osteoporotic (wrist, spine, shoulder and hip) fractures, polyposis coli, bone density and vascular defects in the eye (Osteoporosis-pseudoglioma Syndrome, OPPG), familial exudative vitreoretinopathy, retinal angiogenesis, early coronary disease, tetra-amelia, Müllerian-duct regression and virilization, SERKAL syndrome, type II diabetes, Fuhrmann syndrome, Al-Awadi/Raas-Rothschild/Schinzel phocomelia syndrome, odonto-onycho-dermal dysplasia, obesity, split-hand/foot malformation, caudal duplication, tooth agenesis, Wilms tumor, skeletal dysplasia, focal dermal hypoplasia, autosomal recessive anonychia, neural tube defects, alpha-thalassemia (ATRX) syndrome, fragile X syndrome, ICF syndrome, Angelman syndrome, Prader-Willi syndrome, Beckwith-Wiedemann Syndrome, Norrie disease and Rett syndrome.

With respect to cancer, the Wnt pathway is known to be constitutively activated in a variety of cancers including, for example, colon cancer, hepatocellular carcinoma, lung cancer, ovarian cancer, prostate cancer, pancreatic cancer and leukemias such as CML, CLL and T-ALL. Accordingly, the compounds and compositions described herein may be used to treat these cancers in which the Wnt pathway is constitutively activated. In certain embodiments, the cancer is chosen from hepatocellular carcinoma, colon cancer, leukemia, lymphoma, sarcoma and ovarian cancer.

Other cancers can also be treated with the compounds and compositions described herein.

More particularly, cancers that may be treated by the compounds, compositions and methods described herein include, but are not limited to, the following:

1) Breast cancers, including, for example $ER^+$ breast cancer, $ER^-$ breast cancer, $her2^-$ breast cancer, $her2^+$ breast cancer, stromal tumors such as fibroadenomas, phyllodes tumors, and sarcomas, and epithelial tumors such as large duct papillomas; carcinomas of the breast including in situ (noninvasive) carcinoma that includes ductal carcinoma in situ (including Paget's disease) and lobular carcinoma in situ, and invasive (infiltrating) carcinoma including, but not limited to, invasive ductal carcinoma, invasive lobular carcinoma, medullary carcinoma, colloid (mucinous) carcinoma, tubular carcinoma, and invasive papillary carcinoma; and miscellaneous malignant neoplasms. Further examples of breast cancers can include luminal A, luminal B, basal A, basal B, and triple negative breast cancer, which is estrogen receptor negative ($ER^-$), progesterone receptor negative, and her2 negative (her2⁻). In some embodiments, the breast cancer may have a high risk Oncotype score.

2) Cardiac cancers, including, for example sarcoma, e.g., angiosarcoma, fibrosarcoma, rhabdomyosarcoma, and liposarcoma; myxoma; rhabdomyoma; fibroma; lipoma and teratoma.

3) Lung cancers, including, for example, bronchogenic carcinoma, e.g., squamous cell, undifferentiated small cell, undifferentiated large cell, and adenocarcinoma; alveolar and bronchiolar carcinoma; bronchial adenoma; sarcoma; lymphoma; chondromatous hamartoma; and mesothelioma.

4) Gastrointestinal cancer, including, for example, cancers of the esophagus, e.g., squamous cell carcinoma, adenocarcinoma, leiomyosarcoma, and lymphoma; cancers of the stomach, e.g., carcinoma, lymphoma, and leiomyosarcoma; cancers of the pancreas, e.g., ductal adenocarcinoma, insulinoma, glucagonoma, gastrinoma, carcinoid tumors, and vipoma; cancers of the small bowel, e.g., adenocarcinoma, lymphoma, carcinoid tumors, Kaposi's sarcoma, leiomyoma, hemangioma, lipoma, neurofibroma, and fibroma; cancers of the large bowel, e.g., adenocarcinoma, tubular adenoma, villous adenoma, hamartoma, and leiomyoma.

5) Genitourinary tract cancers, including, for example, cancers of the kidney, e.g., adenocarcinoma, Wilm's tumor (nephroblastoma), lymphoma, and leukemia; cancers of the bladder and urethra, e.g., squamous cell carcinoma, transitional cell carcinoma, and adenocarcinoma; cancers of the prostate, e.g., adenocarcinoma, and sarcoma; cancer of the testis, e.g., seminoma, teratoma, embryonal carcinoma, teratocarcinoma, choriocarcinoma, sarcoma, interstitial cell carcinoma, fibroma, fibroadenoma, adenomatoid tumors, and lipoma.

6) Liver cancers, including, for example, hepatoma, e.g., hepatocellular carcinoma; cholangiocarcinoma; hepatoblastoma; angiosarcoma; hepatocellular adenoma; and hemangioma.

7) Bone cancers, including, for example, osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochrondroma (osteocartilaginous exostoses), benign chondroma, chondroblastoma, chondromyxofibroma, osteoid osteoma and giant cell tumors.

8) Nervous system cancers, including, for example, cancers of the skull, e.g., osteoma, hemangioma, granuloma, xanthoma, and osteitis deformans; cancers of the meninges, e.g., meningioma, meningiosarcoma, and gliomatosis; cancers of the brain, e.g., astrocytoma, medulloblastoma, glioma, ependymoma, germinoma (pinealoma), glioblastoma multiform, oligodendroglioma, schwannoma, retinoblastoma, and congenital tumors; and cancers of the spinal cord, e.g., neurofibroma, meningioma, glioma, and sarcoma.

9) Gynecological cancers, including, for example, cancers of the uterus, e.g., endometrial carcinoma; cancers of the cervix, e.g., cervical carcinoma, and pre tumor cervical dysplasia; cancers of the ovaries, e.g., ovarian carcinoma, including serous cystadenocarcinoma, mucinous cystadenocarcinoma, unclassified carcinoma, granulosa theca cell tumors, Sertoli Leydig cell tumors, dysgerminoma, and malignant teratoma; cancers of the vulva, e.g., squamous cell carcinoma, intraepithelial carcinoma, adenocarcinoma, fibrosarcoma, and melanoma; cancers of the vagina, e.g., clear cell carcinoma, squamous cell carcinoma, botryoid sarcoma, and embryonal rhabdomyosarcoma; and cancers of the fallopian tubes, e.g., carcinoma.

10) Hematologic cancers, including, for example, cancers of the blood, e.g., acute myeloid leukemia, chronic myeloid leukemia, acute lymphoblastic leukemia, chronic lymphocytic leukemia, myeloproliferative diseases, multiple myeloma, and myelodysplastic syndrome, Hodgkin's lymphoma, non-Hodgkin's lymphoma (malignant lymphoma) and Waldenström's macroglobulinemia.

11) Skin cancers and skin disorders, including, for example, malignant melanoma and metastatic melanoma, basal cell carcinoma, squamous cell carcinoma, Kaposi's sarcoma, moles dysplastic nevi, lipoma, angioma, dermatofibroma, keloids, and scleroderma.

12) Adrenal gland cancers, including, for example, neuroblastoma.

Cancers may be solid tumors that may or may not be metastatic. Cancers may also occur, as in leukemia, as a diffuse tissue. Thus, the term "tumor cell," as provided herein, includes a cell afflicted by any one of the above identified disorders.

A method of treating cancer using a compound or composition as described herein may be combined with existing methods of treating cancers, for example by chemotherapy, irradiation, or surgery (e.g., oophorectomy). In some embodiments, a compound or composition can be administered before, during, or after another anticancer agent or treatment.

The compounds and compositions described herein can be used as anti-angiogenesis agents and as agents for modulating and/or inhibiting the activity of protein kinases, thus providing treatments for cancer and other diseases associated with cellular proliferation mediated by protein kinases. For example, the compounds described herein can inhibit the activity of one or more kinases. Accordingly, provided herein is a method of treating cancer or preventing or reducing angiogenesis through kinase inhibition.

In addition, and including treatment of cancer, the compounds and compositions described herein can function as cell-cycle control agents for treating proliferative disorders in a patient. Disorders associated with excessive proliferation include, for example, cancers, scleroderma, immunological disorders involving undesired proliferation of leukocytes, and restenosis and other smooth muscle disorders. Furthermore, such compounds may be used to prevent de-differentiation of post-mitotic tissue and/or cells.

Diseases or disorders associated with uncontrolled or abnormal cellular proliferation include, but are not limited to, the following:

a variety of cancers, including, but not limited to, carcinoma, hematopoietic tumors of lymphoid lineage, hematopoietic tumors of myeloid lineage, tumors of mesenchymal origin, tumors of the central and peripheral nervous system and other tumors including melanoma, seminoma and Kaposi's sarcoma.

a disease process which features abnormal cellular proliferation, e.g., benign prostatic hyperplasia, familial adenomatosis polyposis, neurofibromatosis, atherosclerosis, arthritis, glomerulonephritis, restenosis following angioplasty or vascular surgery, inflammatory bowel disease, transplantation rejection, endotoxic shock, and fungal infections. Fibrotic disorders such as skin fibrosis; scleroderma; progressive systemic fibrosis; lung fibrosis; muscle fibrosis; kidney fibrosis; glomerulosclerosis; glomerulonephritis; hypertrophic scar formation; uterine fibrosis; renal fibrosis; cirrhosis of the liver, liver fibrosis; fatty liver disease (FLD); adhesions, such as those occurring in the abdomen, pelvis, spine or tendons; chronic obstructive pulmonary disease; fibrosis following myocardial infarction; pulmonary fibrosis; fibrosis and scarring associated with diffuse/interstitial lung disease; central nervous system fibrosis, such as fibrosis following stroke; fibrosis associated with neuro-degenerative disorders such as Alzheimer's Disease or multiple sclerosis; fibrosis associated with proliferative vitreoretinopathy (PVR); restenosis; endometriosis; ischemic disease and radiation fibrosis.

defective apoptosis-associated conditions, such as cancers (including but not limited to those types mentioned herein), viral infections (including but not limited to herpesvirus, poxvirus, Epstein-Barr virus, Sindbis virus and adenovirus), prevention of AIDS development in HIV-infected individuals, autoimmune diseases (including but not limited to systemic lupus erythematosus, rheumatoid arthritis, sepsis, ankylosing spondylitis, psoriasis, scleroderma, autoimmune mediated glomerulonephritis, inflammatory bowel disease and autoimmune diabetes mellitus), neuro-degenerative disorders (including but not limited to Alzheimer's disease, lung disease, amyotrophic lateral sclerosis, retinitis pigmentosa, Parkinson's disease, AIDS-related dementia, spinal muscular atrophy and cerebellar degeneration), myelodysplastic syndromes, aplastic anemia, ischemic injury associated with myocardial infarctions, stroke and reperfusion injury, arrhythmia, atherosclerosis, toxin-induced or alcohol related liver diseases, hematological diseases (including but not limited to chronic anemia and aplastic anemia), degenerative diseases of the musculoskeletal system (including but not limited to osteoporosis and arthritis), tendinopathies such as tendinitis and tendinosis, aspirin-sensitive rhinosinusitis, cystic fibrosis, multiple sclerosis, kidney diseases and cancer pain.

genetic diseases due to mutations in Wnt signaling components, such as polyposis coli, bone density and vascular defects in the eye (Osteoporosis-pseudoglioma Syndrome, OPPG), familial exudative vitreoretinopathy, retinal angiogenesis, early coronary disease, tetra-amelia, Müllerian-duct regression and virilization, SERKAL syndrome, type II diabetes, Fuhrmann syndrome, Al-Awadi/Raas-Rothschild/Schinzel phocomelia syndrome, odonto-onycho-dermal dysplasia, obesity, split-hand/foot malformation, caudal duplication, tooth agenesis, Wilms tumor, skeletal dysplasia, focal dermal hypoplasia, autosomal recessive anonychia, neural tube defects, alpha-thalassemia (ATRX) syndrome, fragile X syndrome, ICF syndrome, Angelman syndrome, Prader-Willi syndrome, Beckwith-Wiedemann Syndrome, Norrie disease and Rett syndrome.

The compounds and compositions described herein can be used to treat neurological conditions, disorders and/or diseases caused by dysfunction in the Wnt signaling pathway. Non-limiting examples of neurological conditions/disorders/diseases which can be treated with the compounds and compositions provided herein include Alzheimer's disease, aphasia, apraxia, arachnoiditis, ataxia telangiectasia, attention deficit hyperactivity disorder, auditory processing disorder, autism, alcoholism, Bell's palsy, bipolar disorder, brachial plexus injury, Canavan disease, carpal tunnel syndrome, causalgia, central pain syndrome, central pontine myelinolysis, centronuclear myopathy, cephalic disorder, cerebral aneurysm, cerebral arteriosclerosis, cerebral atrophy, cerebral gigantism, cerebral palsy, cerebral vasculitis, cervical spinal stenosis, Charcot-Marie-Tooth disease, Chiari malformation, chronic fatigue syndrome, chronic inflammatory demyelinating polyneuropathy (CIDP), chronic pain, Coffin-Lowry syndrome, complex regional pain syndrome, compression neuropathy, congenital facial diplegia, corticobasal degeneration, cranial arteritis, craniosynostosis, Creutzfeldt-Jakob disease, cumulative trauma disorder, Cushing's syndrome, cytomegalic inclusion body disease (CIBD), Dandy-Walker syndrome, Dawson disease, de Morsier's syndrome, Dejerine-Klumpke palsy, Dejerine-Sottas disease, delayed sleep phase syndrome, dementia, dermatomyositis, developmental dyspraxia, diabetic neuropathy, diffuse sclerosis, Dravet syndrome, dysautonomia, dyscalculia, dysgraphia, dyslexia, dystonia, empty sella syndrome, encephalitis, encephalocele, encephalotrigeminal angiomatosis, encopresis, epilepsy, Erb's palsy, erythromelalgia, essential tremor, Fabry's disease, Fahr's syndrome, familial spastic paralysis, febrile seizure, Fisher syndrome, Friedreich's ataxia, fibromyalgia, Foville's syndrome, Gaucher's disease, Gerstmann's syndrome, giant cell arteritis, giant cell inclusion disease, globoid cell leukodystrophy, gray matter heterotopia, Guillain-Barré syndrome, HTLV-1 associated myelopathy, Hallervorden-Spatz disease, hemifacial spasm, hereditary spastic paraplegia, heredopathia atactica polyneuritiformis, herpes zoster oticus, herpes zoster, Hirayama syndrome, holoprosencephaly, Huntington's disease, hydranencephaly, hydrocephalus, hypercortisolism, hypoxia, immune-mediated encephalomyelitis, inclusion body myositis, incontinentia pigmenti, infantile phytanic acid storage disease, infantile Refsum disease, infantile spasms, inflammatory myopathy, intracranial cyst, intracranial hypertension, Joubert syndrome, Karak syndrome, Kearns-Sayre syndrome, Kennedy disease, Kinsbourne syndrome, Klippel Feil syndrome, Krabbe disease, Kugelberg-Welander disease, kuru, Lafora disease, Lambert-Eaton myasthenic syndrome, Landau-Kleffner syndrome, lateral medullary (Wallenberg) syndrome, Leigh's disease, Lennox-Gastaut syndrome, Lesch-Nyhan syndrome, leukodystrophy, Lewy body dementia, lissencephaly, locked-in syndrome, Lou Gehrig's disease, lumbar disc disease, lumbar spinal stenosis, Lyme disease, Machado-Joseph disease (Spinocerebellar ataxia type 3), macrencephaly, macropsia, megalencephaly, Melkersson-Rosenthal syndrome, Meniere's disease, meningitis, Menkes disease, metachromatic leukodystrophy, microcephaly, micropsia, Miller Fisher syndrome, misophonia, mitochondrial myopathy, Mobius syndrome, monomelic amyotrophy, motor neuron disease, motor skills disorder, Moyamoya disease, mucopolysaccharidoses, multi-infarct dementia, multifocal motor neuropathy, multiple sclerosis, multiple system atrophy, muscular dystrophy, myalgic encephalomyelitis, myasthenia gravis, myelinoclastic diffuse sclerosis, myoclonic Encephalopathy of infants, myoclonus, myopathy, myotubular myopathy, myotonia congenital, narcolepsy, neurofibromatosis, neuroleptic malignant syndrome, lupus erythematosus, neuromyotonia, neuronal ceroid lipofuscinosis, Niemann-Pick disease, O'Sullivan-McLeod syndrome, occipital Neuralgia, occult Spinal Dysraphism Sequence, Ohtahara syndrome, olivopontocerebellar atrophy, opsoclonus myoclonus syndrome, optic neuritis, orthostatic hypotension, palinopsia, paresthesia, Parkinson's disease, paramyotonia congenita, paraneoplastic diseases, paroxysmal attacks, Parry-Romberg syndrome, Pelizaeus-Merzbacher disease, periodic paralyses, peripheral neuropathy, photic sneeze reflex, phytanic acid storage disease, Pick's disease, polymicrogyria (PMG), polymyositis, porencephaly, post-polio syndrome, postherpetic neuralgia (PHN), postural hypotension, Prader-Willi syndrome, primary lateral sclerosis, prion diseases, progressive hemifacial atrophy, progressive multifocal leukoencephalopathy, progressive supranuclear palsy, pseudotumor cerebri, Ramsay Hunt syndrome type I, Ramsay Hunt syndrome type II, Ramsay Hunt syndrome type III, Rasmussen's encephalitis, reflex neurovascular dystrophy, Refsum disease, restless legs syndrome, retrovirus-associated myelopathy, Rett syndrome, Reye's syndrome, rhythmic movement disorder, Romberg syndrome, Saint Vitus dance, Sandhoff disease, schizophrenia, Schilder's disease, schizencephaly, sensory integration dysfunction, septo-optic dysplasia, Shy-Drager syndrome, Sjögren's syndrome, snatiation, Sotos syndrome, spasticity, spina bifida, spinal cord tumors, spinal muscular atrophy, spinocerebellar ataxia, Steele-Richardson-Olszewski syndrome, Stiff-person syndrome, stroke, Sturge-Weber syndrome, subacute sclerosing panencephalitis, subcortical arteriosclerotic encephalopathy, superficial siderosis, Sydenham's chorea, syncope, synesthesia, syringomyelia, tarsal tunnel syndrome, tardive dyskinesia, tardive dysphrenia, Tarlov cyst, Tay-Sachs disease, temporal arteritis, tetanus, tethered spinal cord syndrome, Thomsen disease, thoracic outlet syndrome, tic douloureux, Todd's paralysis, Tourette syndrome, toxic encephalopathy, transient ischemic attack, transmissible spongiform encephalopathies, transverse myelitis, tremor, trigeminal neuralgia, tropical spastic paraparesis, trypanosomiasis, tuberous sclerosis, ubisiosis, Von Hippel-Lindau disease (VHL), Viliuisk Encephalomyelitis (VE), Wallenberg's syndrome, Werdnig, Hoffman disease, west syndrome, Williams syndrome, Wilson's disease and Zellweger syndrome.

The compounds and compositions may also be useful in the inhibition of the development of invasive cancer, tumor angiogenesis and metastasis.

In some embodiments, the disclosure provides a method for treating a disease or disorder associated with aberrant cellular proliferation by administering to a patient in need of such treatment an effective amount of one or more of the compounds of Formula (I), in combination (simultaneously or sequentially) with at least one other agent.

In some embodiments, the disclosure provides a method of treating or ameliorating in a patient a disorder or disease selected from the group consisting of: cancer, pulmonary fibrosis, idiopathic pulmonary fibrosis (IPF), degenerative disc disease, bone/osteoporotic fractures, bone or cartilage disease, and osteoarthritis, the method comprising administering to the patient a therapeutically effective amount of a compound according to claim 1, or a pharmaceutically acceptable salt thereof.

In some embodiments, the pharmaceutical composition comprises a therapeutically effective amount of a compound of Formula (I), or a pharmaceutically acceptable salt thereof, and a pharmaceutically acceptable excipient.

In some embodiments, the method of treats a disorder or disease in which aberrant Wnt signaling is implicated in a patient, the method comprises administering to the patient a therapeutically effective amount of a compound of Formula (I), or a pharmaceutically acceptable salt thereof.

In some embodiments, the disorder or disease is cancer.

In some embodiments, the disorder or disease is systemic inflammation.

In some embodiments, the disorder or disease is metastatic melanoma.

In some embodiments, the disorder or disease is fatty liver disease.

In some embodiments, the disorder or disease is liver fibrosis.

In some embodiments, the disorder or disease is tendon regeneration.

In some embodiments, the disorder or disease is diabetes.

In some embodiments, the disorder or disease is degenerative disc disease.

In some embodiments, the disorder or disease is osteoarthritis.

In some embodiments, the disorder or disease is diabetic retinopathy.

In some embodiments, the disorder or disease is pulmonary fibrosis.

In some embodiments, the disorder or disease is idiopathic pulmonary fibrosis (IPF).

In some embodiments, the disorder or disease is degenerative disc disease.

In some embodiments, the disorder or disease is rheumatoid arthritis.

In some embodiments, the disorder or disease is scleroderma.

In some embodiments, the disorder or disease is a mycotic or viral infection.

In some embodiments, the disorder or disease is a bone or cartilage disease.

In some embodiments, the disorder or disease is Alzheimer's disease.

In some embodiments, the disorder or disease is osteoarthritis.

In some embodiments, the disorder or disease is lung disease

In some embodiments, the disorder or disease is a genetic disease caused by mutations in Wnt signaling components, wherein the genetic disease is selected from: polyposis coli, osteoporosis-pseudoglioma syndrome, familial exudative vitreoretinopathy, retinal angiogenesis, early coronary disease, tetra-amelia syndrome, Müllerian-duct regression and virilization, SERKAL syndrome, diabetes mellitus type 2, Fuhrmann syndrome, Al-Awadi/Raas-Rothschild/Schinzel phocomelia syndrome, odonto-onycho-dermal dysplasia, obesity, split-hand/foot malformation, caudal duplication syndrome, tooth agenesis, Wilms tumor, skeletal dysplasia, focal dermal hypoplasia, autosomal recessive anonychia, neural tube defects, alpha-thalassemia (ATRX) syndrome, fragile X syndrome, ICF syndrome, Angelman syndrome, Prader-Willi syndrome, Beckwith-Wiedemann Syndrome, Norrie disease and Rett syndrome.

In some embodiments, the patient is a human.

In some embodiments, the cancer is chosen from: hepatocellular carcinoma, colon cancer, breast cancer, pancreatic cancer, chronic myeloid leukemia (CML), chronic myelomonocytic leukemia, chronic lymphocytic leukemia (CLL), acute myeloid leukemia, acute lymphocytic leukemia, Hodgkin lymphoma, lymphoma, sarcoma and ovarian cancer.

In some embodiments, the cancer is chosen from: lung cancer—non-small cell, lung cancer—small cell, multiple myeloma, nasopharyngeal cancer, neuroblastoma, osteosarcoma, penile cancer, pituitary tumors, prostate cancer, retinoblastoma, rhabdomyosarcoma, salivary gland cancer, skin cancer—basal and squamous cell, skin cancer—melanoma, small intestine cancer, stomach (gastric) cancers, testicular cancer, thymus cancer, thyroid cancer, uterine sarcoma, vaginal cancer, vulvar cancer, laryngeal or hypopharyngeal cancer, kidney cancer, Kaposi sarcoma, gestational trophoblastic disease, gastrointestinal stromal tumor, gastrointestinal carcinoid tumor, gallbladder cancer, eye cancer (melanoma and lymphoma), Ewing tumor, esophagus cancer, endometrial cancer, colorectal cancer, cervical cancer, brain or spinal cord tumor, bone metastasis, bone cancer, bladder cancer, bile duct cancer, anal cancer and adrenal cortical cancer.

In some embodiments, the cancer is hepatocellular carcinoma.

In some embodiments, the cancer is colon cancer.

In some embodiments, the cancer is colorectal cancer.

In some embodiments, the cancer is breast cancer.

In some embodiments, the cancer is pancreatic cancer.

In some embodiments, the cancer is chronic myeloid leukemia (CML).

In some embodiments, the cancer is chronic myelomonocytic leukemia.

In some embodiments, the cancer is chronic lymphocytic leukemia (CLL).

In some embodiments, the cancer is acute myeloid leukemia.

In some embodiments, the cancer is acute lymphocytic leukemia.

In some embodiments, the cancer is Hodgkin lymphoma.

In some embodiments, the cancer is lymphoma.

In some embodiments, the cancer is sarcoma.

In some embodiments, the cancer is ovarian cancer.

In some embodiments, the cancer is lung cancer—non-small cell.

In some embodiments, the cancer is lung cancer—small cell.

In some embodiments, the cancer is multiple myeloma.

In some embodiments, the cancer is nasopharyngeal cancer.

In some embodiments, the cancer is neuroblastoma.

In some embodiments, the cancer is osteosarcoma.

In some embodiments, the cancer is penile cancer.

In some embodiments, the cancer is pituitary tumors.

In some embodiments, the cancer is prostate cancer.

In some embodiments, the cancer is retinoblastoma.

In some embodiments, the cancer is rhabdomyosarcoma.

In some embodiments, the cancer is salivary gland cancer.

In some embodiments, the cancer is skin cancer—basal and squamous cell.

In some embodiments, the cancer is skin cancer—melanoma.

In some embodiments, the cancer is small intestine cancer.

In some embodiments, the cancer is stomach (gastric) cancers.

In some embodiments, the cancer is testicular cancer.

In some embodiments, the cancer is thymus cancer.

In some embodiments, the cancer is thyroid cancer.

In some embodiments, the cancer is uterine sarcoma.

In some embodiments, the cancer is vaginal cancer.

In some embodiments, the cancer is vulvar cancer.

In some embodiments, the cancer is Wilms tumor.

In some embodiments, the cancer is laryngeal or hypopharyngeal cancer.

In some embodiments, the cancer is kidney cancer.

In some embodiments, the cancer is Kaposi sarcoma.

In some embodiments, the cancer is gestational trophoblastic disease.

In some embodiments, the cancer is gastrointestinal stromal tumor.

In some embodiments, the cancer is gastrointestinal carcinoid tumor.

In some embodiments, the cancer is gallbladder cancer.

In some embodiments, the cancer is eye cancer (melanoma and lymphoma).

In some embodiments, the cancer is Ewing tumor.

In some embodiments, the cancer is esophagus cancer.

In some embodiments, the cancer is endometrial cancer.

In some embodiments, the cancer is colorectal cancer.

In some embodiments, the cancer is cervical cancer.

In some embodiments, the cancer is brain or spinal cord tumor.

In some embodiments, the cancer is bone metastasis.

In some embodiments, the cancer is bone cancer.

In some embodiments, the cancer is bladder cancer.

In some embodiments, the cancer is bile duct cancer.

In some embodiments, the cancer is anal cancer.

In some embodiments, the cancer is adrenal cortical cancer.

In some embodiments, the disorder or disease is a neurological condition, disorder or disease, wherein the neurological condition/disorder/disease is selected from: Alzheimer's disease, frontotemporal dementias, dementia with lewy bodies, prion diseases, Parkinson's disease, Huntington's disease, progressive supranuclear palsy, corticobasal degeneration, multiple system atrophy, amyotrophic lateral sclerosis (ALS), inclusion body myositis, autism, degenerative myopathies, diabetic neuropathy, other metabolic neuropathies, endocrine neuropathies, orthostatic hypotension, multiple sclerosis and Charcot-Marie-Tooth disease.

In some embodiments, the compound of Formula (I) inhibits one or more proteins in the Wnt pathway.

In some embodiments, the compound of Formula (I) inhibits signaling induced by one or more Wnt proteins.

In some embodiments, the Wnt proteins are chosen from: WNT1, WNT2, WNT2B, WNT3, WNT3A, WNT4. WNT5A, WNT5B, WNT6, WNT7A, WNT7B, WNT8A, WNT8B, WNT9A, WNT9B, WNT10A, WNT10B, WNT11, and WNT16.

In some embodiments, the compound of Formula (I) inhibits a kinase activity.

In some embodiments, the method treats a disease or disorder mediated by the Wnt pathway in a patient, the method comprises administering to the patient a therapeutically effective amount of a compound (or compounds) of Formula (I), or a pharmaceutically acceptable salt thereof.

In some embodiments, the compound of Formula (I) inhibits one or more Wnt proteins.

In some embodiments, the method treats a disease or disorder mediated by kinase activity in a patient, the method comprises administering to the patient a therapeutically effective amount of a compound (or compounds) of Formula (I), or a pharmaceutically acceptable salt thereof.

In some embodiments, the disease or disorder comprises tumor growth, cell proliferation, or angiogenesis.

In some embodiments, the method inhibits the activity of a protein kinase receptor, the method comprises contacting the receptor with an effective amount of a compound (or compounds) of Formula (I), or a pharmaceutically acceptable salt thereof.

In some embodiments, the method treats a disease or disorder associated with aberrant cellular proliferation in a patient; the method comprises administering to the patient a therapeutically effective amount of a compound (or compounds) of Formula (I), or a pharmaceutically acceptable salt thereof.

In some embodiments, the method prevents or reduces angiogenesis in a patient; the method comprises administering to the patient a therapeutically effective amount of a compound (or compounds) of Formula (I), or a pharmaceutically acceptable salt thereof.

In some embodiments, the method prevents or reduces abnormal cellular proliferation in a patient; the method comprises administering to the patient a therapeutically effective amount of a compound (or compounds) of Formula (I), or a pharmaceutically acceptable salt thereof.

In some embodiments, the method treats a disease or disorder associated with aberrant cellular proliferation in a patient, the method comprises administering to the patient a pharmaceutical composition comprising one or more of the compounds of claim 1 in combination with a pharmaceutically acceptable carrier and one or more other agents.

Moreover, the compounds and compositions, for example, as inhibitors of the cyclin-dependent kinases (CDKs), can modulate the level of cellular RNA and DNA synthesis and therefore are expected to be useful in the treatment of viral infections such as HIV, human papilloma virus, herpes virus, Epstein-Barr virus, adenovirus, Sindbis virus, pox virus and the like.

Compounds and compositions described herein can inhibit the kinase activity of, for example, CDK/cyclin complexes, such as those active in the $G_0$ or $G_{-1}$ stage of the cell cycle, e.g., CDK2, CDK4, and/or CDK6 complexes.

Evaluation of Biological Activity

The biological activity of the compounds described herein can be tested using any suitable assay known to those of skill in the art, see, e.g., WO 2001/053268 and WO 2005/009997. For example, the activity of a compound may be tested using one or more of the test methods outlined below.

In one example, tumor cells may be screened for Wnt independent growth. In such a method, tumor cells of interest are contacted with a compound (i.e. inhibitor) of interest, and the proliferation of the cells, e.g. by uptake of tritiated thymidine, is monitored. In some embodiments, tumor cells may be isolated from a candidate patient who has been screened for the presence of a cancer that is associated with a mutation in the Wnt signaling pathway. Candidate cancers include, without limitation, those listed above.

In another example, one may utilize in vitro assays for Wnt biological activity, e.g. stabilization of β-catenin and promoting growth of stem cells. Assays for biological activity of Wnt include stabilization of β-catenin, which can be measured, for example, by serial dilutions of a candidate inhibitor composition. An exemplary assay for Wnt biological activity contacts a candidate inhibitor with cells containing constitutively active Wnt/β-catenin signaling. The cells are cultured for a period of time sufficient to stabilize β-catenin, usually at least about 1 hour, and lysed. The cell lysate is resolved by SDS PAGE, then transferred to nitrocellulose and probed with antibodies specific for β-catenin.

In a further example, the activity of a candidate compound can be measured in a Xenopus secondary axis bioassay (Leyns, L. et al. *Cell* (1997), 88(6), 747-756).

To further illustrate this invention, the following examples are included. The examples should not, of course, be construed as specifically limiting the invention. Variations of these examples within the scope of the claims are within the purview of one skilled in the art and are considered to fall within the scope of the invention as described, and claimed herein. The reader will recognize that the skilled artisan, armed with the present disclosure, and skill in the art is able to prepare and use the invention without exhaustive examples.

EXAMPLES

Compound Preparation

The starting materials used in preparing the compounds of the invention are known, made by known methods, or are commercially available. It will be apparent to the skilled artisan that methods for preparing precursors and functionality related to the compounds claimed herein are generally described in the literature. The skilled artisan given the literature and this disclosure is well equipped to prepare any of the compounds.

It is recognized that the skilled artisan in the art of organic chemistry can readily carry out manipulations without further direction, that is, it is well within the scope and practice of the skilled artisan to carry out these manipulations. These include reduction of carbonyl compounds to their corresponding alcohols, oxidations, acylations, aromatic substitutions, both electrophilic and nucleophilic, etherifications, esterification and saponification and the like. These manipulations are discussed in standard texts such as *March's Advanced Organic Chemistry: Reactions, Mechanisms, and Structure* $7^{th}$ Ed., John Wiley & Sons (2013), Carey and Sundberg, *Advanced Organic Chemistry* $5^{th}$ Ed., Springer (2007), *Comprehensive Organic Transformations: A Guide to Functional Group Transformations*, $2^{nd}$ Ed., John Wiley & Sons (1999) (incorporated herein by reference in its entirety) and the like.

The skilled artisan will readily appreciate that certain reactions are best carried out when other functionality is masked or protected in the molecule, thus avoiding any undesirable side reactions and/or increasing the yield of the reaction. Often the skilled artisan utilizes protecting groups to accomplish such increased yields or to avoid the undesired reactions. These reactions are found in the literature and are also well within the scope of the skilled artisan. Examples of many of these manipulations can be found for example in T. Greene and P. Wuts *Protective Groups in Organic Synthesis*, 4th Ed., John Wiley & Sons (2007), incorporated herein by reference in its entirety.

Trademarks used herein are examples only and reflect illustrative materials used at the time of the invention. The skilled artisan will recognize that variations in lot, manufacturing processes, and the like, are expected. Hence the examples, and the trademarks used in them are non-limiting, and they are not intended to be limiting, but are merely an illustration of how a skilled artisan may choose to perform one or more of the embodiments of the invention.

($^1$H) nuclear magnetic resonance spectra (NMR) were measured in the indicated solvents on a Bruker NMR spectrometer (Avance TM DRX300, 300 MHz for $^1$H or Avance TM DRX500, 500 MHz for $^1$H) or Varian NMR spectrometer (Mercury 400BB, 400 MHz for $^1$H). Peak positions are expressed in parts per million (ppm) downfield from tetramethylsilane. The peak multiplicities are denoted as follows, s, singlet; d, doublet; t, triplet; q, quartet; ABq, AB quartet; quin, quintet; sex, sextet; sep, septet; non, nonet; dd, doublet of doublets; ddd, doublet of doublets of doublets; d/ABq, doublet of AB quartet; dt, doublet of triplets; td, triplet of doublets; dq, doublet of quartets; m, multiplet.

The following abbreviations have the indicated meanings:
Boc=tert-butyloxycarbonyl
brine=saturated aqueous sodium chloride
$CDCl_3$=deuterated chloroform
CuI=copper (I) iodide or cuprous iodide
DCE=dichloroethane
DCM=dichloromethane
DIPEA=N,N-diisopropylethylamine DMAP=4-dimethylaminopyridine
DMF=N,N-dimethylformamide
DMSO=dimethylsulfoxide
DMSO-$d_6$=deuterated dimethylsulfoxide
ESIMS=electron spray mass spectrometry
EtOAc=ethyl acetate
HATU=1-[Bis(dimethylamino)methylene]-1H-1,2,3-triazolo[4,5-b]pyridinium 3-oxid hexafluorophosphate
HCl=hydrochloric acid
HOAc=acetic acid
LC/MS=Liquid chromatography-mass spectrometry
MeCN=acetonitrile
MeOH=methanol
$MgSO_4$=magnesium sulfate
$NaBH(OAc)_3$=sodium triacetoxyborohydride
NMR=nuclear magnetic resonance
ON=overnight
$Pd(dppf)Cl_2$=1,1'-bis(diphenylphosphino)ferrocene-palladium(II)dichloride
$Pd(PPh_3)_4$=tetrakis(triphenylphosphine)palladium(0)
r.t.=room temperature
THF=tetrahydrofuran
TLC=thin layer chromatography
pTsO—=p-toluenesulfonate ester The following example schemes are provided for the guidance of the reader, and collectively represent an example method for making the compounds provided herein. Furthermore, other methods for preparing compounds of the invention will be readily apparent to the person of ordinary skill in the art in light of the following reaction schemes and examples. The skilled artisan is thoroughly equipped to prepare these compounds by those methods given the literature and this disclosure. The compound numberings used in the synthetic schemes depicted below are meant for those specific schemes only, and should not be construed as or confused with same numberings in other sections of the application. Unless otherwise indicated, all variables are as defined above.

General Procedure

Compounds of Formula I of the present disclosure can be prepared as depicted in Scheme 1.

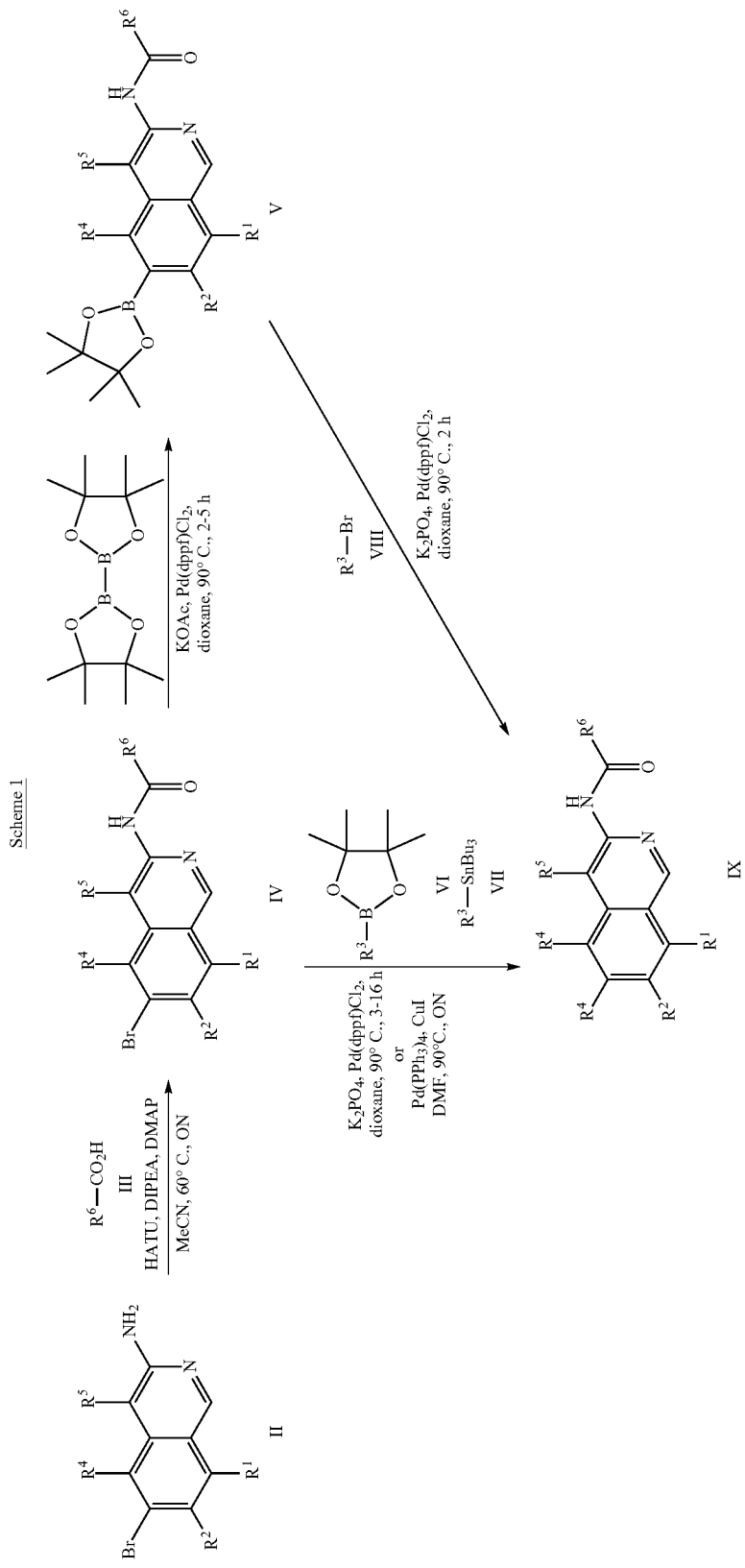

Scheme 1 describes a method for preparation of isoquinoline-3-carboxamide derivatives (IX) by first coupling the amine with a variety of acids (III) to produce amide IV. The bromo derivative IV is then reacted with bis(pinacolato)diboron to give the pinacol ester (V). Suzuki coupling with a variety of 5-membered heteroaryl bromides (VIII) yields the desired R³ substituted isoquinoline IX. Alternatively, the bromo derivative IV is Suzuki coupled with a variety of 5-membered heteroaryl pinacol esters (VI) or coupled to a variety of 5-membered heteroaryl stannanes (VII) to produce the final R³ substituted isoquinoline IX.

In some embodiments, compounds of Formula I of the present disclosure can be prepared as depicted in Scheme 2.

Scheme 2

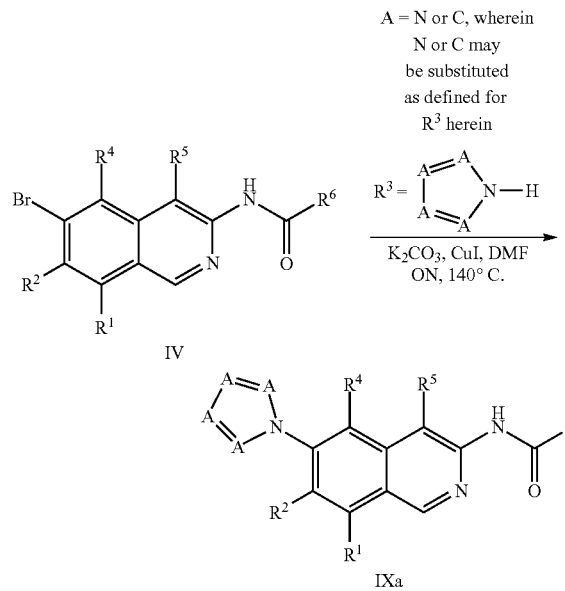

IXa

Scheme 2 describes a method for preparation of isoquinoline-3-carboxamide derivatives (IXa) starting with bromo intermediate IV and couple with the nitrogen of a variety of R³ NH heteroaryls to produce the final R³ substituted isoquinoline IXa.

ILLUSTRATIVE COMPOUND EXAMPLES

Preparation of Intermediate 2-((1-(tert-butoxycarbonyl)piperidin-4-yl)oxy) isonicotinic acid (XII) is depicted below in Scheme 4

Scheme 4

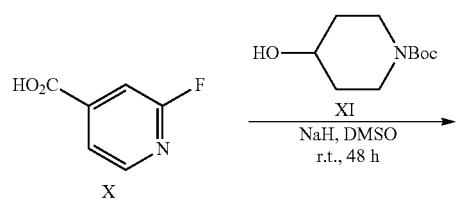

-continued

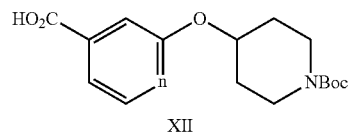

XII

Step 1

To a solution of 2-fluoropyridine-4-carboxylic acid (X) (6.65 g, 47.13 mmol) in DMSO (180 mL) was added tert-butyl 4-hydroxypiperidine-1-carboxylate (XI) (14.23 g, 70.69 mmol) and 2-fluoropyridine-4-carboxylic acid (6.65 g, 47.13 mmol). To this mixture was added NaH (8.48 g, 212.08 mmol) in 3 portions. this mixture was stirred at room temperature for 48 h. The reaction was poured into 1 N NaOH, the water layer was washed with EtOAc, the water layer was then acidified with concentrated HCl (20 mL), extracted with EtOAc and dried over Na₂SO₄. The solvent was removed and the residue was purified by C18 Silica Gel column chromatography (0-40% MeCN/0.1% formic acid in water) to produce 2-((1-(tert-butoxycarbonyl)piperidin-4-yl)oxy)isonicotinic acid (XII) (12.85 g, 39.9 mmol, 84.6% yield) as a white solid. ¹H NMR (499 MHz, DMSO-d₆) δ ppm 1.41 (s, 9H), 1.52-1.62 (m, 2H), 1.90-1.98 (m, 2H), 3.12-3.23 (m, 2H), 3.64-3.72 (m, 2H), 5.21 (tt, J=8.13, 3.95 Hz, 1H), 7.15 (s, 1H), 7.36 (dd, J=5.21, 1.37 Hz, 1H), 8.31 (d, J=5.21 Hz, 1H), 13.62 (br s, 1H); ESIMS found for $C_{16}H_{22}N_2O_5$ m/z 323.1 (M+H).

Preparation of Intermediate 4-((1-(tert-butoxycarbonyl)piperidin-4-yl)oxy)benzoic acid (XV) is depicted below in Scheme 5

Scheme 5

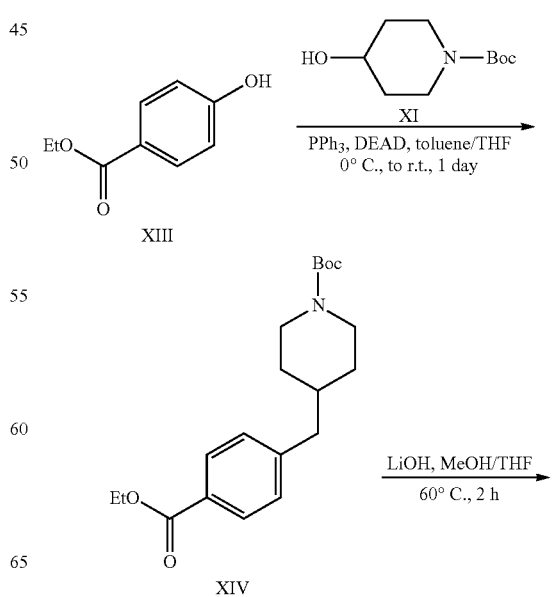

215

-continued

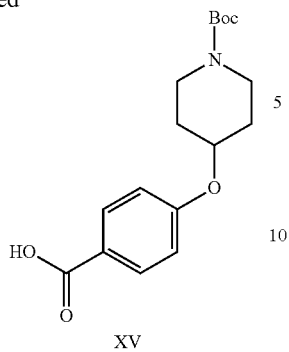

XV

Step 1

To a solution of DEAD (12.3 mL, 27.08 mmol) (40% in toluene) was added to a mixture of ethyl 4-hydroxybenzoate (XIII) (3.0 g, 18.05 mmol), tert-butyl 4-hydroxypiperidine-1-carboxylate (XI) (4.72 g, 23.47 mmol) and triphenylphosphane (6.16 g, 23.47 mmol) in THF (40 mL) at 0° C. The mixture was stirred from 0° C. to room temperature over 1 day before concentrating in vacuo. The residue was diluted with EtOAc, washed with 1 N NaOH and brine, and then evaporated under vacuum. The crude product was purified by chromatography (0→30% EtOAc/hexanes) to give tert-butyl 4-(4-ethoxycarbonylphenoxy)piperidine-1-carboxylate (XIV) (5.4 g, 15.45 mmol, 85.6% yield) as a colorless oil. ESIMS found for $C_{19}H_{27}NO_5$ m/z 372.1 (M+Na).

Step 2

To a solution of tert-butyl 4-(4-ethoxycarbonylphenoxy)piperidine-1-carboxylate (XIV) (5.4 g, 15.45 mmol) in MeOH (10 mL) and THF (10 mL) was added LiOH (15.5 mL, 61.82 mmol) and the mixture stirred at 60° C. for 2 h. The mixture was concentrated and the residue triturated with water. The resulting solution was acidified with 2 N HCl until a solid precipitated. The solid was filtered and washed with water to afford 4-[(1-tert-butoxycarbonyl-4-piperidyl)oxy]benzoic acid (XV) (4.7 g, 14.63 mmol, 94.6% yield) as a white solid. $^1$H NMR (499 MHz, DMSO-$d_6$) δ ppm 1.40 (9H, s), 1.47-1.57 (2H, m), 1.89-1.97 (2H, m), 3.12-3.23 (2H, m), 3.63-3.70 (2H, m), 4.63-4.71 (1H, m), 7.04 (2H, d, J=9.06 Hz), 7.87 (2H, d, J=9.06 Hz); ESIMS found for $C_{17}H_{23}NO_5$ m/z 344.1 (M+Na).

Preparation of Intermediate 1-(methyl-$d_3$)-4-(4,4,5,5-tetramethyl-1,3,2-dioxaborolan-2-yl)-1H-pyrazole (XVII) is depicted below in Scheme 6

Scheme 6

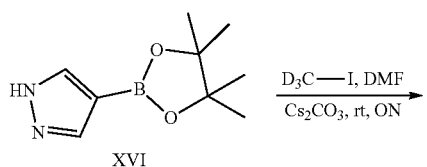

216

-continued

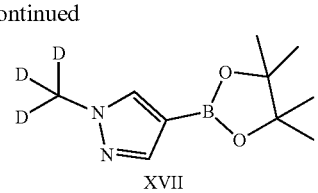

XVII

Step 1

To a stirred suspension of 4-(4,4,5,5-tetramethyl-1,3,2-dioxaborolan-2-yl)-1H-pyrazole (XVI) (1.435 g, 7.4 mmol) and $Cs_2CO_3$ (2.89 g, 8.87 mmol) in DMF (15 mL) was added trideuterio(iodo)methane (0.51 mL, 8.13 mmol) and the mixture was stirred at room temperature overnight. The reaction mixture was filtered and the filtrates were concentrated and dried under high vacuo to obtain 4-(4,4,5,5-tetramethyl-1,3,2-dioxaborolan-2-yl)-1-(trideuteriomethyl)pyrazole (XVII) (3.9 g, 18.48 mmol, 249.8% yield) as a white solid which was used for next step without purification. ESIMS found for $C_{10}H_{14}[^2H_3]BN_2O_2$ m/z 212. (M+1).

Preparation of Intermediate
6-bromoisoquinolin-1-d-3-amine (XIX) is depicted
below in Scheme 8

Scheme 8

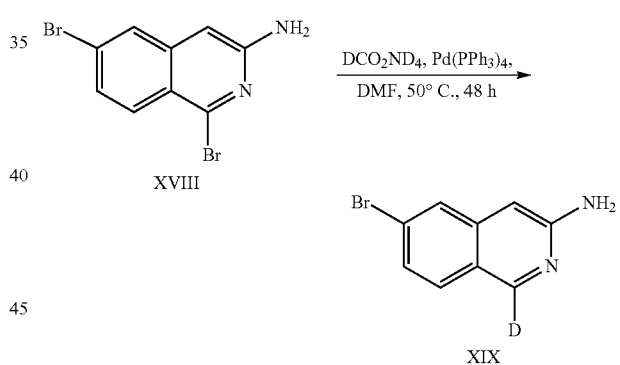

Step 1

To a mixture of 1,6-dibromoisoquinolin-3-amine (XVIII) (0.5 g, 1.66 mmol), ammonium formate-$d_5$ (0.56 g, 8.28 mmol) and Pd(PPh$_3$)$_4$ (191.3 mg, 0.170 mmol) in DMF (5 mL) was heated to 50° C. for 48 h. The solvents were concentrated and the residue was suspended in chloroform. The solid was collected by filtration and washed with water and EtOAc. The solid were dried under high vacuo to obtain 6-bromo-1-deuterio-isoquinolin-3-amine (XIX) (115 mg, 0.513 mmol, 31.0% yield) as a pale yellow solid. $^1$H NMR (500 MHz, DMSO-$d_6$) δ ppm 6.11 (2H, s), 6.55 (1H, s), 7.22 (1H, dd, J=8.78, 1.92 Hz), 7.73 (1H, d, J=8.51 Hz), 7.79 (1H, d, J=1.92 Hz); ESIMS found for $C_9H_6$DBrN$_2$ m/z 224.0 ($^{79}$BrM+H).

Preparation of Intermediate
6-bromo-4-chloroisoquinolin-3-amine (XXII) is
depicted below in Scheme 9

Scheme 9

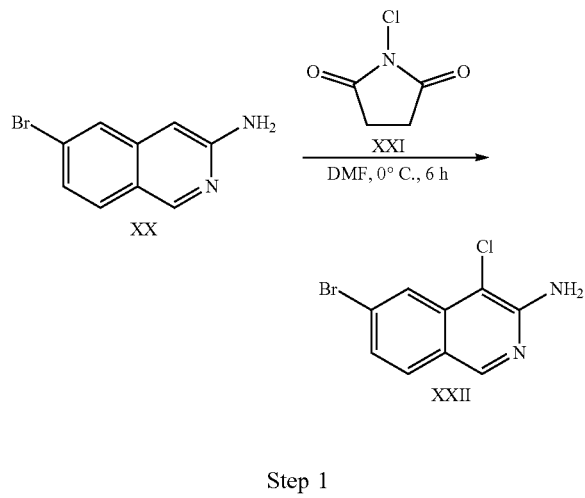

Step 1

To a stirred suspension of 6-bromoisoquinolin-3-amine (XX) (1.0 g, 4.48 mmol) in DMF (15 mL) at 0° C. was added 1-chloropyrrolidine-2,5-dione (XXI) (598.6 mg, 4.48 mmol) portionwise. The mixture was stirred at 0° C. for 6 h. The reaction mixture was added to water (150 mL), stirred for 1 h and the resulting solids were collected by filtration and air dried overnight to obtain 6-bromo-4-chloro-isoquinolin-3-amine (XXII) (922 mg, 3.58 mmol, 79.9% yield) as a beige solid which was used for next step without purification. $^1$H NMR (499 MHz, DMSO-d$_6$) δ ppm 6.55 (2H, s), 7.40 (1H, dd, J=8.64, 1.78 Hz), 7.88 (1H, d, J=8.51 Hz), 7.90 (1H, d, J=1.10 Hz), 8.86 (1H, s); ESIMS found for C$_9$H$_6$BrClN$_2$ m/z 256.9 ($^{79}$BrM+H).

Preparation of Intermediate
6-bromo-4-methylisoquinolin-3-amine (XXV) is
depicted below in Scheme 10

Scheme 10

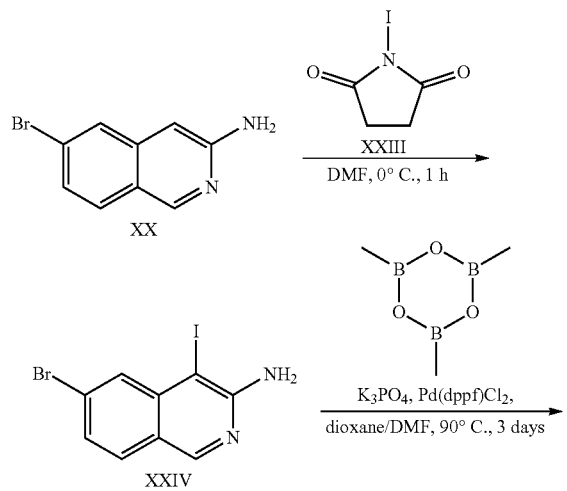

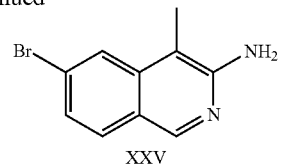

Step 1

To a stirred suspension of 6-bromoisoquinolin-3-amine (XX) (2.g, 8.97 mmol) in DMF (25.1 mL) at 0° C. was added 1-iodopyrrolidine-2,5-dione (XXIII) (2.02 g, 8.97 mmol) portionwise. The mixture was stirred at 0° C. for 1 hr. LC-MS of the mixture showed completion of the reaction and the desired product. The solvent was removed under vacuum, the residue was purified by C18 Silica gel (240 g) [0→100% H$_2$O/MeCN (0.1% Formic acid)] to produce 6-bromo-4-iodo-isoquinolin-3-amine (XXIV) (1.95 g, 5.58 mmol, 62.2% yield) as a brown solid. $^1$H NMR (499 MHz, DMSO-d$_6$) δ ppm 6.41 (2H, br s), 7.40 (1H, dd, J=8.64, 1.78 Hz), 7.76-7.81 (1H, m), 7.82 (1H, d, J=8.51 Hz), 8.81 (1H, s); ESIMS found for C$_9$H$_6$BrIN$_2$ m/z 348.9 ($^{79}$BrM+H).

Step 2

A stirred solution of 6-bromo-4-iodo-isoquinolin-3-amine (XXIV) (1.0 g, 2.87 mmol), 2,4,6-trimethyl-1,3,5,2,4,6-trioxatriborinane (0.72 g, 2.87 mmol), Pd(dppf)Cl$_2$ (0.23 g, 0.29 mmol), and K$_3$PO$_4$ (5.73 mL, 5.73 mmol) in 1,4-dioxane (10 mL) was heated to 90° C. for 3 days. The solvent was removed under high vacuum and the residue was purified by C18 silica gel (240 g) [0→20% H$_2$O/MeCN (0.1% Formic acid)] to produce 6-bromo-4-methyl-isoquinolin-3-amine (XXV) (74 mg, 0.312 mmol, 10.9% yield) as an off-white solid. $^1$H NMR (499 MHz, DMSO-d$_6$) δ ppm 2.23 (3H, br s), 5.91 (2H, br s), 7.27 (1H, br d, J=2.20 Hz), 7.71-7.82 (1H, m), 7.92 (1H, br s), 8.72 (1H, br s); ESIMS found for C$_{10}$H$_9$BrN$_2$ m/z 239.0 ($^{81}$BrM+H).

Preparation of Intermediate
6-bromo-7-fluoroisoquinolin-3-amine (XXVIII) is
depicted below in Scheme 11

Scheme 11

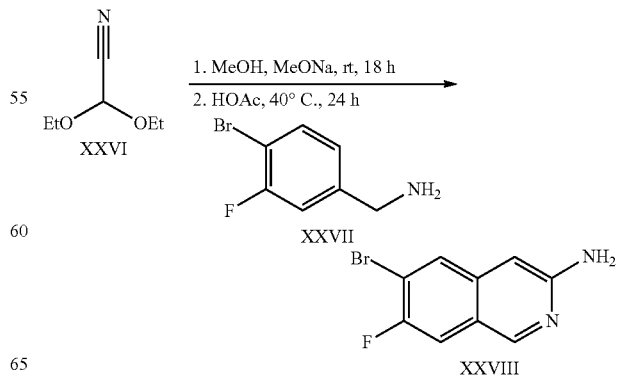

Step 1

To a vial was added 2,2-diethoxyacetonitrile (XXVI) (1.0 g, 7.74 mmol) dissolved MeOH (7.74 mL) followed by addition of MeONa/MeOH (0.18 mL, 0.77 mmol) dropwise. The reaction was stirred at room temperature for 20 h. HOAc (44.3 µL, 0.77 mmol) was added until pH=7-8 (using pH strips). (4-Bromo-3-fluoro-phenyl)methanamine hydrochloride (XXVII) (1.86 g, 7.74 mmol) was added and stirred at 40° C. for 4 h. The solvent was removed under vacuum. Sulfuric acid (12.6 mL, 232.3 mmol) was added and stirred at 40° C. for 16 h. NH$_4$OH (30.8 mL, 240.0 mmol) was added dropwise at 0° C. The solvent was removed under vacuum and the residue was purified by C18 silica gel (240 g) [0→50% H$_2$O/MeCN (0.1% Formic acid)] to produce 6-bromo-7-fluoro-isoquinolin-3-amine (XXVIII) (1.33 g, 5.50 mmol, 71.1% yield) as an off-white solid. $^1$H NMR (499 MHz, DMSO-d$_6$) δ ppm 6.07 (2H, s), 6.61 (1H, s), 7.76 (1H, d, J=9.33 Hz), 8.01 (1H, d, J=6.86 Hz), 8.80 (1H, s); ESIMS found for C$_9$H$_6$BrFN$_2$ m/z 242.9 ($^{81}$BrM+H).

Preparation of Intermediates 6-bromo-7-chloroisoquinolin-3-amine (XXX) and 6-bromo-5-chloroisoquinolin-3-amine (XXXI) is depicted below in Scheme 12

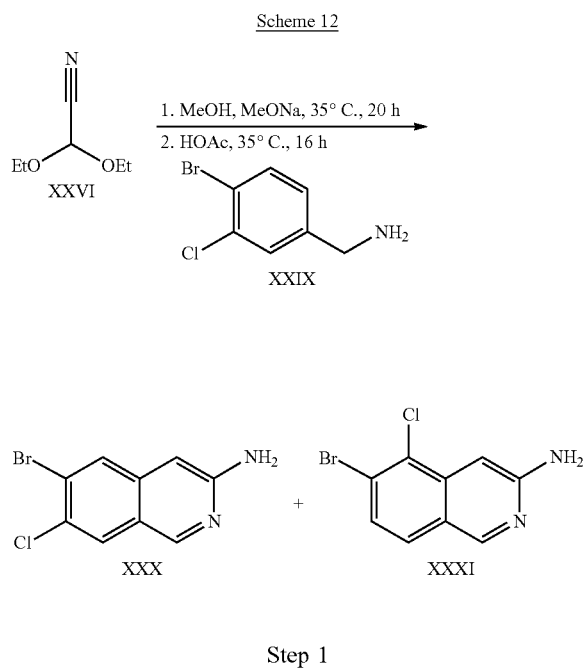

Step 1

To a stirred solution of 2,2-diethoxyacetonitrile (XXVI) (0.59 g, 4.57 mmol) in a vial containing MeOH (4.57 mL) was added MeONa (0.1 mL, 0.46 mmol) dropwise. The reaction was stirred at 35° C. for 20 h. HOAc was added (26.1 µL, 0.46 mmol) (checked that the pH is 7-8 using pH strips) followed by (4-bromo-3-chloro-phenyl)methanamine (XXIX) (1.01 g, 4.57 mmol). The mixture was stirred at 35° C. for 40 h. The solvent was removed under vacuum. Sulfuric Acid (7.43 mL, 137.0 mmol) was then added and stirred at 35° C. for 16 h. NH$_4$OH (60.6 mL, 141.6 mmol) was added at 0° C. The reaction was filtered through Celite and purified by C18 silica gel (240 g) [0→30% H$_2$O/MeCN (0.1% Formic acid)] to produce a 1:1 mixture (by nmr) of 6-bromo-7-chloro-isoquinolin-3-amine (XXX) and 6-bromo-5-chloroisoquinolin-3-amine (XXXI) (633.7 mg, 2.46 mmol, 53.9% yield). $^1$H NMR (499 MHz, DMSO-d$_6$) δ ppm 6.23 (2H, s), 6.46 (2H, s), 6.57 (1H, s), 6.83 (1H, s), 7.40 (1H, d, J=8.51 Hz), 7.74 (1H, d, J=8.51 Hz), 8.05 (1H, s), 8.09 (1H, s), 8.81 (1H, s), 8.88 (1H, s); ESIMS found for C$_9$H$_6$BrClN$_2$ m/z 256.9 ($^{79}$BrM+H).

Preparation of Intermediates 6-bromo-7-methylisoquinolin-3-amine (XXXIII) and 6-bromo-5-methylisoquinolin-3-amine (XXXIV) is depicted below in Scheme 13

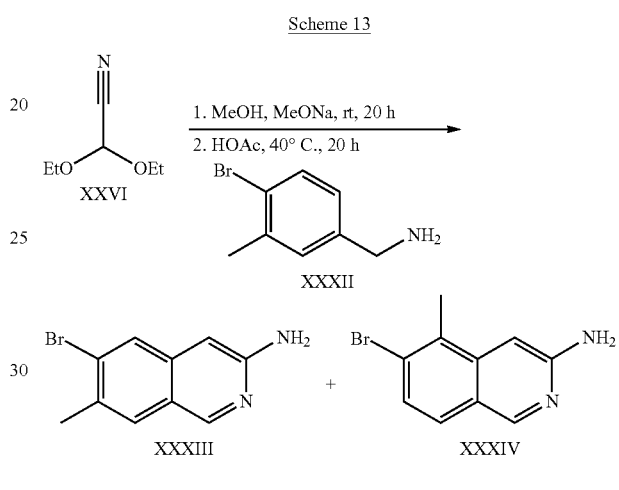

Step 1

To a stirred solution of 2,2-diethoxyacetonitrile (XXVI) (0.33 g, 2.52 mmol) in a vial containing MeOH (2.52 mL) was added MeONa (0.23 mL, 0.25 mmol) dropwise. The reaction was stirred at 22° C. for 20 h. HOAc was added (14.4 µL, 0.25 mmol) (checked that the pH is 7-8 using pH strips) followed by (4-bromo-3-methyl-phenyl)methanamine (XXXII) (0.5 g, 2.52 mmol). The mixture was stirred at 40° C. for 40 h. The solvent was removed under vacuum. Sulfuric Acid (4.09 mL, 75.49 mmol) was then added and stirred at 40° C. for 16 h. NH$_4$OH (33.4 mL, 78 mmol) was added at 0° C. The reaction was filtered through Celite and purified by C18 silica gel (240 g) [0→30% H$_2$O/MeCN (0.1% Formic acid)] to produce a 1:1 mixture (by nmr) of 6-bromo-7-methylisoquinolin-3-amine (XXXIII) and 6-bromo-5-methylisoquinolin-3-amine (XXXIV) (378 mg, 1.59 mmol, 63.4% yield). $^1$H NMR (499 MHz, DMSO-d$_6$) δ ppm 2.40 (3H, s), 2.52 (3H, s), 5.96 (2H, s), 6.12 (1H, s), 6.54 (1H, s), 6.71 (1H, s), 7.27 (1H, d, J=8.78 Hz), 7.58 (1H, d, J=8.78 Hz), 7.73 (1H, s), 7.86 (1H, s), 8.74 (1H, s), 8.79 (1H, s); ESIMS found for C$_{10}$H$_9$BrN$_2$ m/z 237.0 ($^{79}$BrM+H).

Example 1

Preparation of 4-(difluoromethoxy)-N-(6-(1-methyl-1H-imidazol-5-yl) isoquinolin-3-yl)benzamide (29) is depicted below in Scheme 14.

Scheme 14

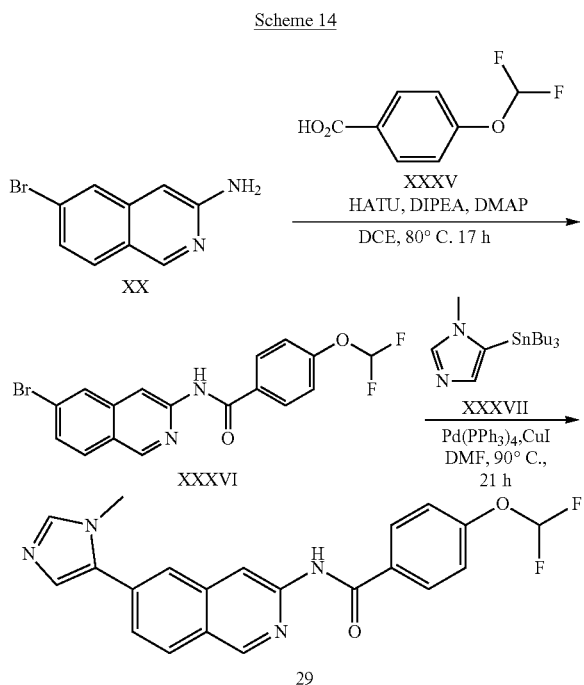

Step 1

A mixture of 4-(difluoromethoxy)benzoic acid (XXXV) (337 mg, 1.79 mmol), HATU (682 mg, 1.79 mmol) and DIPEA (0.47 mL, 2.69 mmol) in DCE (8 mL) was stirred at room temperature for 10 min. To the above mixture was added 6-bromoisoquinolin-3-amine (XX) (200 mg, 0.900 mmol) and DMAP (110 mg, 0.900 mmol) and the resulting mixture was stirred at 80° C. for 17 h. The reaction was poured into 1 N HCl and extracted with DCM (2 X). The combined organic layers were dried, filtered and concentrated. The crude product was purified by silica gel chromatography with EtOAc/Hexanes (0-25%) as the eluent to afford N-(6-bromoisoquinolin-3-yl)-4-(difluoromethoxy)benzamide (XXXVI) as a white solid (300 mg, 0.763 mmol, 85.1% yield). ESIMS found for $C_{17}H_{11}BrF_2N_2O_2$ m/z 395.0 ($M^{Br81}$+H).

Step 2

A mixture of N-(6-bromoisoquinolin-3-yl)-4-(difluoromethoxy)benzamide (XXXVI) (100 mg, 0.250 mmol) tributyl-(3-methylimidazol-4-yl)stannane (XXXVII) (104 mg, 0.280 mmol) Pd(PPh$_3$)$_4$ (23 mg, 0.030 mmol) and CuI (5 mg, 0.030 mmol) was taken in DMF (2 mL). N$_2$ gas was bubbled into the mixture for 10 min and then heated at 90° C. for 21 h. The reaction mixture was cooled to room temperature, concentrated, absorbed on silica gel and purified by flash column chromatography using 7 N NH$_3$—MeOH/CHCl$_3$ (0 to 10%) as eluents. The pure fractions were concentrated, the residue suspended in diethyl ether, sonicated and the resulting solids were collected by filtration, and dried to obtain 4-(difluoromethoxy)-N-(6-(1-methyl-1H-imidazol-5-yl)isoquinolin-3-yl)benzamide (29) as a white solid (16 mg, 0.040 mmol, 15.6% yield). $^1$H NMR (499 MHz, DMSO-d$_6$) δ ppm 3.85 (s, 3H), 7.40 (t, J=73.65 Hz, 1H), 7.32 (d, J=8.78 Hz, 2H), 7.33 (br s, 1H), 7.73 (dd, J=8.37, 1.51 Hz, 1H), 7.81 (s, 1H), 8.09 (s, 1H), 8.15 (d, J=8.51 Hz, 1H), 8.17 (d, J=8.78 Hz, 2H), 8.69 (s, 1H), 9.22 (s, 1H), 10.96 (s, 1H); ESIMS found for $C_{21}H_{16}F_2N_4O_2$ m/z 395.1 (M+1).

Example 2

Preparation of 2-(4-aminopiperidin-1-yl)-N-(6-(1-methyl-1H-pyrazol-4-yl) isoquinolin-3-yl)isonicotinamide (53) and 2-(4-(dimethylamino)piperidin-1-yl)-N-(6-(1-methyl-1H-pyrazol-4-yl)isoquinolin-3-yl)isonicotinamide (55) are depicted below in Scheme 15.

Scheme 15
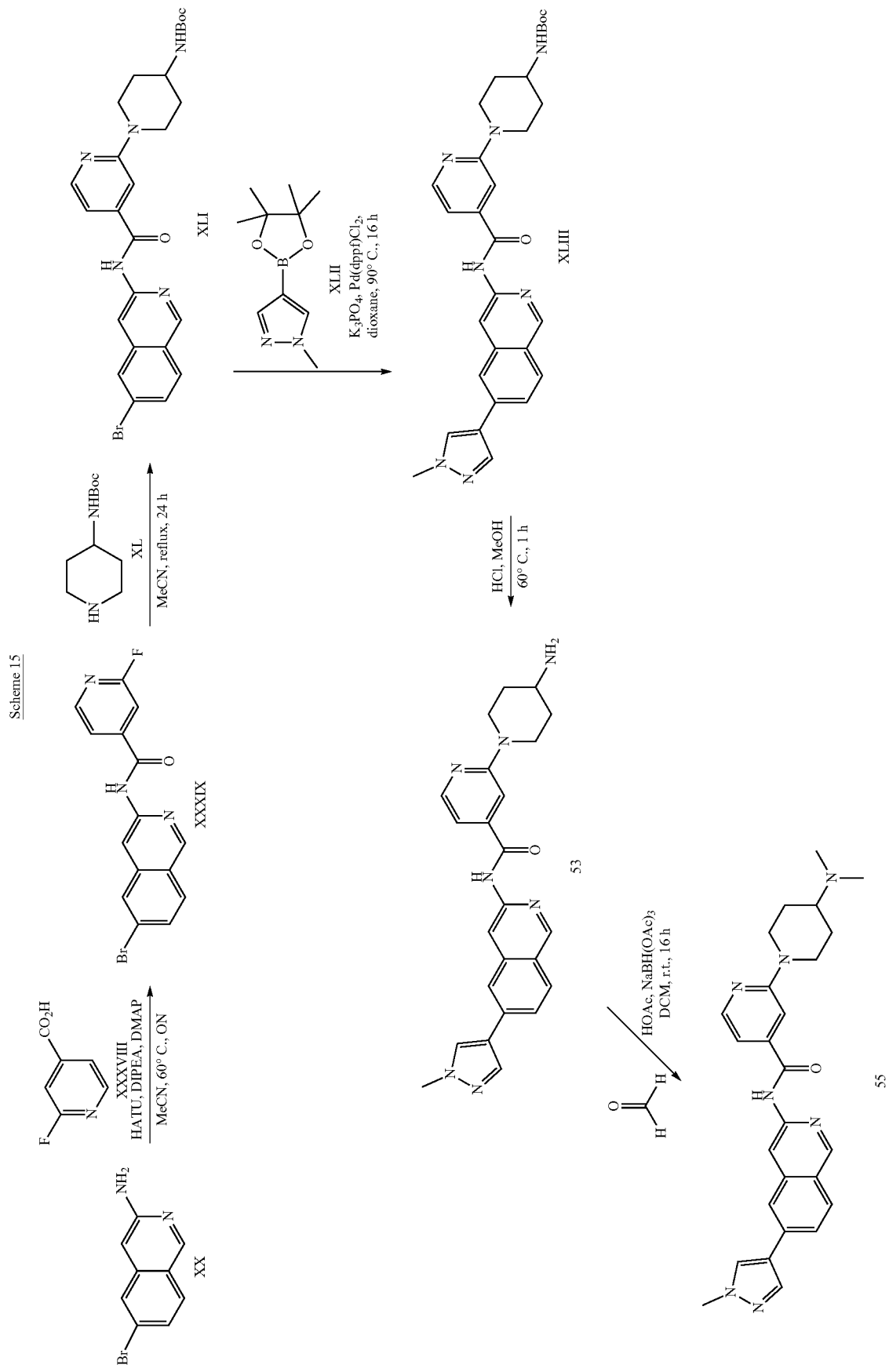

Step 1

To a solution Added 2-fluoropyridine-4-carboxylic acid (XXXVIII) (1.27 g, 8.97 mmol), HATU (1.7 g, 4.48 mmol), DMAP (0.55 g, 4.48 mmol) and 6-bromoisoquinolin-3-amine (XX) (1.0 g, 4.48 mmol) to MeCN (22.4 mL) followed by DIPEA (3.12 mL, 17.93 mmol) at room temperature then stirred at stirred at 60° C. for 90 min. One additional eq of HATU (1.7 g, 4.48 mmol) was added and the reaction was stirred overnight. Another 0.05 eq HATU was added and stirred for another 1 h. The reaction was poured into 300 mL of water, the solid was filtered and washed with MeOH, to produce N-(6-bromoisoquinolin-3-yl)-2-fluoroisonicotinamide (XXXIX) as an off-white solid (1.38 g, 3.99 mmol, 89.0% yield). ESIMS found for $C_{15}H_9BrFN_3O$ m/z 346.2 (M+H).

Step 2

To a suspension of N-(6-bromoisoquinolin-3-yl)-2-fluoroisonicotinamide (XXXIX) (300 mg, 0.870 mmol) in MeCN (4.3 mL) was added tert-butyl N-(4-piperidyl)carbamate (XL) (868 mg, 4.33 mmol). The mixture was heated at reflux for 1 day and then cooled to room temperature. The reaction was concentrated in vacuo and purified by silica gel (24 g) 0 to 100% EtOAc/hexanes to produce tert-butyl (1-(4-((6-bromoisoquinolin-3-yl)carbamoyl)pyridin-2-yl)piperidin-4-yl) carbamate (XLI) as an off-white solid (0.319 g, 0.606 mmol, 69.9% yield). $^1$H NMR (499 MHz, DMSO-$d_6$) δ ppm 1.31-1.45 (m, 2H), 1.39 (s, 9H), 1.80 (br d, J=10.43 Hz, 2H), 2.97 (br t, J=11.53 Hz, 2H), 3.49-3.60 (m, 1H), 4.35 (br d, J=13.17 Hz, 2H), 6.85 (br d, J=7.41 Hz, 1H), 7.10 (dd, J=5.08, 1.23 Hz, 1H), 7.46 (s, 1H), 7.70 (dd, J=8.78, 1.92 Hz, 1H), 8.07 (d, J=8.78 Hz, 1H), 8.24 (d, J=4.94 Hz, 1H), 8.29 (d, J=1.37 Hz, 1H), 8.61 (s, 1H), 9.25 (s, 1H), 11.16 (s, 1H); ESIMS found for $C_{25}H_{28}BrN_5O_3$ m/z 528.1 ($M^{Br81}$+H).

Step 3

To a solution of tert-butyl (1-(4-(((6-bromoisoquinolin-3-yl)carbamoyl)pyridin-2-yl)piperidin-4-yl)carbamate (XLI) (95.0 mg, 0.220 mmol) in 1,4-dioxane (6.0 mL) was added 1-methyl-4-(4,4,5,5-tetramethyl-1,3,2-dioxaborolan-2-yl)-1H-pyrazole (XLII) (55.6 mg, 0.270 mmol), $K_3PO_4$ (210 mg, 0.990 mmol), and Pd(dppf)$Cl_2$ (0.05 g, 0.060 mmol). The mixture was degassed with Argon and heated to 90° C. for 16 h. The solvent was removed under vacuum and the residue was purified by silica gel (220 g) using 0 to 10% 1.7 N $NH_3$ in $CHCl_3$. The solid was tritrated with diethyl ether and placed under vacuum overnight, then tritrated with hot ethanol and dried in a vacuum oven at 50° C. to produce tert-butyl (1-(4-((6-(1-methyl-1H-pyrazol-4-yl)isoquinolin-3-yl)carbamoyl)pyridin-2-yl)piperidin-4-yl)carbamate (XLIII) as an off-white solid (294.4 mg, 0.558 mmol, 93.0% yield). ESIMS found for $C_{29}H_{33}N_7O_3$ m/z 528.3 (M+H).

Step 4

To a solution of tert-butyl (1-(4-((6-(1-methyl-1H-pyrazol-4-yl)isoquinolin-3-yl)carbamoyl)pyridin-2-yl)piperidin-4-yl)carbamate (XLIII) (294.0 mg, 0.560 mmol) in MeOH (5.6 mL) was added HCl (1.39 mL, 5.57 mmol). The reaction was stirred at 60° C. for 1 h. The solvent was removed under vacuum and the residue was purified by silica gel (24 g) using 0 to 10% 1.7 N $NH_3$ in MeOH to produce 2-(4-aminopiperidin-1-yl)-N-(6-(1-methyl-1H-pyrazol-4-yl)isoquinolin-3-yl)isonicotinamide (53) as an off-white solid (195 mg, 0.456 mmol, 81.9% yield). $^1$H NMR (499 MHz, DMSO-$d_6$) δ ppm 1.20-1.29 (m, 2H), 1.76-1.83 (m, 2H), 2.82-2.90 (m, 1H), 2.93-3.02 (m, 2H), 3.91 (s, 3H), 4.32 (br d, J=13.17 Hz, 2H), 7.10 (dd, J=5.21, 1.10 Hz, 1H), 7.45 (s, 1H), 7.81 (dd, J=8.51, 1.65 Hz, 1H), 8.07 (d, J=8.78 Hz, 1H), 8.11 (s, 1H), 8.13 (s, 1H), 8.23 (d, J=4.94 Hz, 1H), 8.38 (s, 1H), 8.59 (s, 1H), 9.12 (s, 1H), 11.03 (br s, 1H); ESIMS found for $C_{24}H_{25}N_7O$ m/z 428.2 (M+1).

Step 5

To a solution of 2-(4-aminopiperidin-1-yl)-N-(6-(1-methyl-1H-pyrazol-4-yl)isoquinolin-3-yl)isonicotinamide (53) (90.0 mg, 0.210 mmol) in DCM (2.1 mL) was added formaldehyde (170.9 mg, 2.11 mmol), HOAc (2.5 mg, 0.042 mmol) and NaBH(OAc)$_3$ (178.5 mg, 0.840 mmol). The reaction was stirred at room temperature for 16 h. The solvent was removed under vacuum and the residue was purified by silica gel (12 g) using 0 to 30% 1.7N $NH_3$ in MeOH/$CHCl_3$ to produce 2-[4-(dimethylamino)-1-piperidyl]-N-[6-(1-methylpyrazol-4-yl)-3-isoquinolyl]pyridine-4-carboxamide (55) as an off-white solid (30.0 mg, 0.066 mmol, 31.3% yield). $^1$H NMR (499 MHz, DMSO-$d_6$) δ ppm 1.37 (qd, J=11.94, 3.70 Hz, 2H), 1.83 (br d, J=11.25 Hz, 2H), 2.19 (s, 6H), 2.30-2.40 (m, 1H), 2.84-2.93 (m, 2H), 3.91 (s, 3H), 4.44 (br d, J=13.17 Hz, 2H), 7.11 (dd, J=5.21, 1.10 Hz, 1H), 7.45 (s, 1H), 7.81 (dd, J=8.51, 1.65 Hz, 1H), 8.07 (d, J=8.51 Hz, 1H), 8.11 (s, 1H), 8.13 (s, 1H), 8.24 (d, J=5.21 Hz, 1H), 8.38 (s, 1H), 8.59 (s, 1H), 9.12 (s, 1H), 11.03 (s, 1H); ESIMS found for $C_{26}H_{29}N_7O$ m/z 456.2 (M+1).

Example 3

Preparation of N-(6-(1-methyl-1H-pyrazol-4-yl)isoquinolin-3-yl)-2-(piperidin-4-yloxy)isonicotinamide (16) and N-(6-(1-methyl-1H-pyrazol-4-yl)isoquinolin-3-yl)-2-((1-methylpiperidin-4-yl)oxy)isonicotinamide (17) are depicted below in Scheme 16

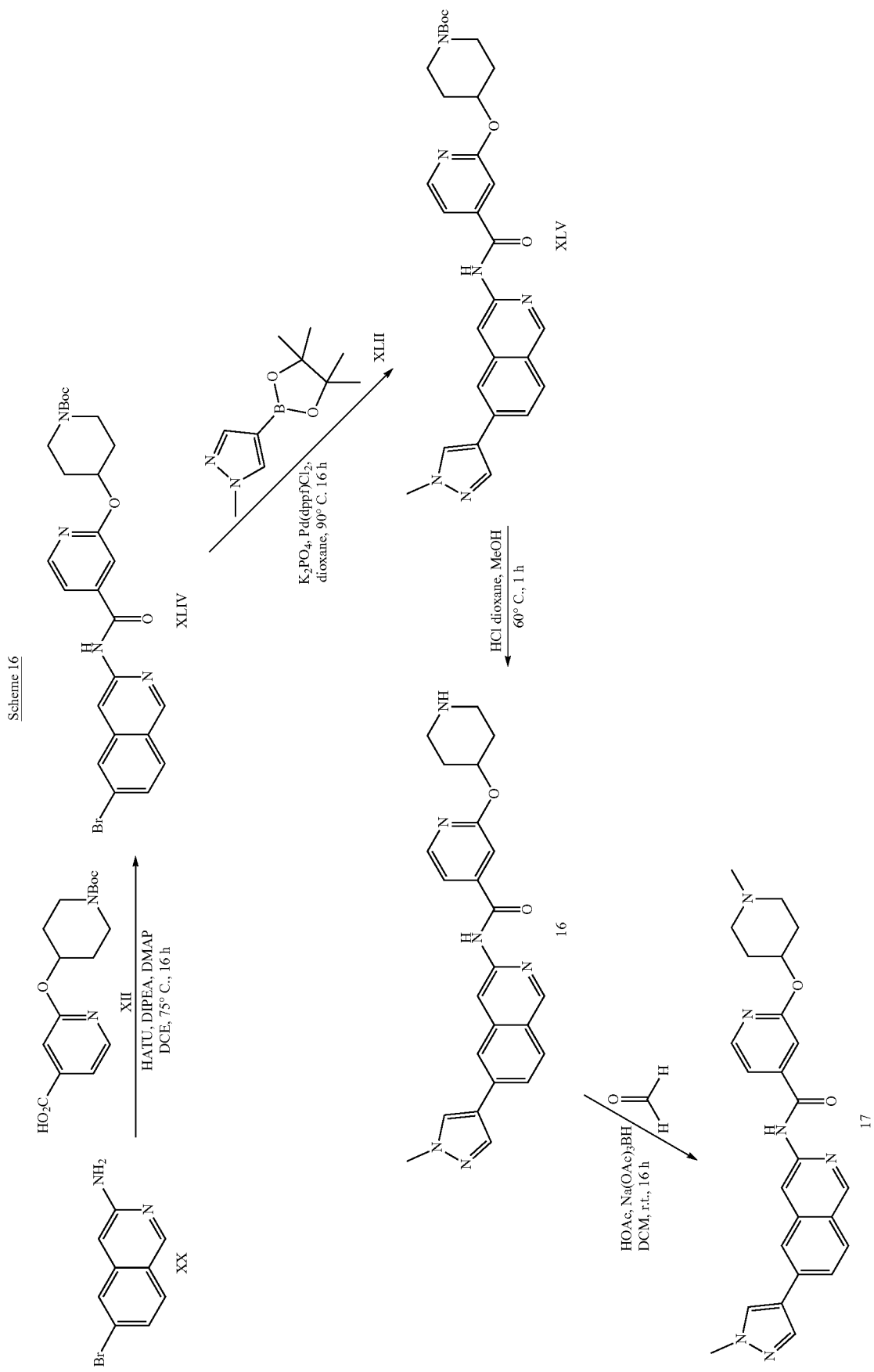

Step 1

To a solution of 6-bromoisoquinolin-3-amine (XX) (3.0 g, 13.45 mmol) and 2-((1-(tert-butoxycarbonyl)piperidin-4-yl)oxy)isonicotinic acid (XII) (10.62 g, 32.94 mmol) in DCE was added DMAP (1.64 g, 13.45 mmol), DIPEA (7.03 mL, 40.35 mmol), HATU (12.32 g, 32.4 mmol) to DCE (67.2 mL) stirred at 75° C. for 16 hours. The solvent was removed under vacuum and purified by silica gel (40 g) using 0 to 50% EtOAc/hexanes to produce tert-butyl 4-((4-((6-bromoisoquinolin-3-yl)carbamoyl)pyridin-2-yl)oxy)piperidine-1-carboxylate (XLIV) as an off-white solid (4.37 g, 8.29 mmol, 61.6% yield). ESIMS found for $C_{25}H_{27}BrN_4O_4$ m/z 426.1 (M-Boc).

Step 2

To a solution of 1-methyl-4-(4,4,5,5-tetramethyl-1,3,2-dioxaborolan-2-yl)-1H-pyrazole (XLII) (2.59 g, 12.43 mmol) in 1,4-dioxane (82.8 mL) was added tert-butyl 4-((4-((6-bromoisoquinolin-3-yl)carbamoyl)pyridin-2-yl)oxy)piperidine-1-carboxylate (XLIV) (4.37 g, 8.29 mmol), $K_3PO_4$ (4.4 g, 20.7 mmol) and Pd(dppf)Cl$_2$ (338.3 mg, 0.410 mmol). The mixture was degassed with Ar and heated to 90° C. for 16 h. The solvent was removed under vacuum and the residue was purified by silica ge (120 g) using 0 to 100% EtOAc/hexanes to produce tert-butyl 4-((4-((6-(1-methyl-1H-pyrazol-4-yl)isoquinolin-3-yl)carbamoyl)pyridin-2-yl)oxy)piperidine-1-carboxylate (XLV) as a white solid (3.56 g, 6.73 mmol, 81.3% yield). ESIMS found for $C_{29}H_{32}N_6O_4$ m/z 529.3 (M+H).

Step 3

To a solution of tert-butyl 4-((4-((6-(1-methyl-1H-pyrazol-4-yl)isoquinolin-3-yl)carbamoyl)pyridin-2-yl)oxy)piperidine-1-carboxylate (XLV) (5.56 g, 6.73 mmol) in MeOH (67.4 mL) was added HCl in dioxane (16.8 mL, 67.35 mmol). The reaction was stirred at 60° C. for 4 h. The solvent was neutralized by 7 N NH$_3$ in MeOH and then removed under vacuum and the residue was purified by silica gel (120 g) using 0 to 10% 1.0 N NH$_3$ in MeOH/CHCl$_3$ to produce N-(6-(1-methyl-1H-pyrazol-4-yl)isoquinolin-3-yl)-2-(piperidin-4-yloxy)isonicotinamide (16) as a white solid (2.51 g, 5.56 mmol, 82.6% yield). $^1$H NMR (499 MHz, DMSO-d$_6$) δ ppm 1.48-1.58 (m, 2H), 1.92-2.00 (m, 2H), 2.56-2.65 (m, 2H), 2.98 (dt, J=12.49, 3.91 Hz, 2H), 3.91 (s, 3H), 5.06-5.15 (m, 1H), 7.34 (s, 1H), 7.50 (dd, J=5.21, 1.37 Hz, 1H), 7.82 (dd, J=8.51, 1.37 Hz, 1H), 8.06 (d, J=8.51 Hz, 1H), 8.11 (s, 1H), 8.15 (s, 1H), 8.31 (d, J=5.21 Hz, 1H), 8.38 (s, 1H), 8.58 (s, 1H), 9.12 (s, 1H), 11.06 (br s, 1H); ESIMS found for $C_{24}H_{24}N_6O_2$ m/z 429.2 (M+1).

Step 4

To a solution of N-(6-(1-methyl-1H-pyrazol-4-yl)isoquinolin-3-yl)-2-(piperidin-4-yloxy)isonicotinamide (16) (1.1 g, 2.57 mmol) in MeOH (25.7 mL) was added formaldehyde (275.2 mg, 3.35 mmol), HOAc (464 mg, 7.72 mmol) and NaBH(OAc)$_3$ (818 mg, 3.86 mmol). The reaction was stirred at room temperature for 16 h. The solvent was removed under vacuum and the residue was purified by silica gel (40 g) using 0 to 30% 1.0 N NH$_3$ in MeOH/CHCl$_3$ to produce N-(6-(1-methyl-1H-pyrazol-4-yl)isoquinolin-3-yl)-2-((1-methylpiperidin-4-yl)oxy) isonicotinamide (17) as an off-white solid (1.02 g, 2.20 mmol, 85.4% yield). $^1$H NMR (499 MHz, DMSO-d$_6$) δ ppm 1.66-1.76 (m, 2H), 1.99 (br dd, J=9.47, 3.70 Hz, 2H), 2.17 (br s, 2H), 2.19 (s, 3H), 2.61-2.70 (m, 2H), 3.91 (s, 3H), 5.01-5.09 (m, 1H), 7.35 (s, 1H), 7.51 (dd, J=5.21, 1.37 Hz, 1H), 7.82 (dd, J=8.64, 1.51 Hz, 1H), 8.06 (d, J=8.78 Hz, 1H), 8.11 (s, 1H), 8.15 (s, 1H), 8.31 (d, J=5.21 Hz, 1H), 8.38 (s, 1H), 8.57 (s, 1H), 9.12 (s, 1H), 11.06 (s, 1H); ESIMS found for $C_{25}H_{26}N_6O_2$ m/z 443.2 (M+1).

Example 4

Preparation of N-(6-(1-methyl-1H-pyrazol-4-yl)isoquinolin-3-yl)-2-(1-methylpiperidin-4-yl)isonicotinamide (84) and 1'-methyl-N-(6-(1-methyl-1H-pyrazol-4-yl) isoquinolin-3-yl)-1',2',3',6'-tetrahydro-[2,4'-bipyridine]-4-carboxamide (85) are depicted below in Scheme 17

Scheme 17

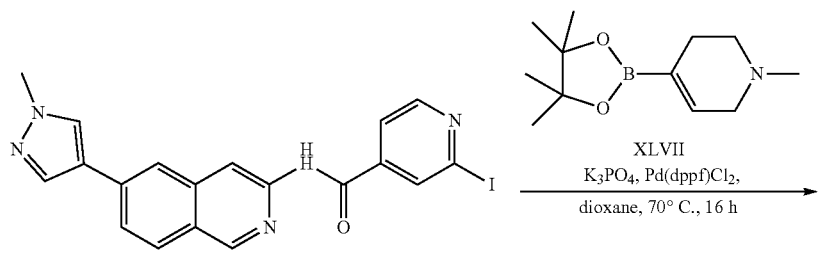

XLVI

XLVII
K$_3$PO$_4$, Pd(dppf)Cl$_2$,
dioxane, 70° C., 16 h

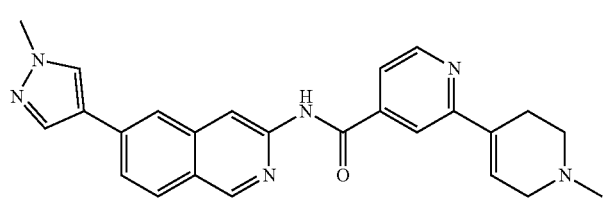

85

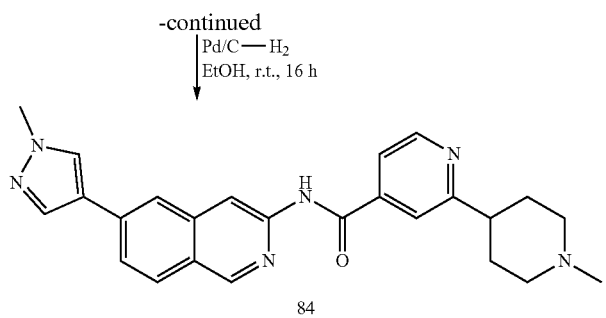

Step 1

In a sealed tube containing 1-methyl-4-(4,4,5,5-tetramethyl-1,3,2-dioxaborolan-2-yl)-3,6-dihydro-2H-pyridine (XLVII) (0.29 g, 1.32 mmol), $K_3PO_4$ (2.2 mL, 2.2 mmol) Pd(dppf)Cl$_2$—CH$_2$Cl$_2$ adduct (180 mg, 0.220 mmol) in 1,4-Dioxane (8 mL) was added 2-iodo-N-[6-(1-methylpyrazol-4-yl)-3-isoquinolyl]pyridine-4-carboxamide (XLVI) (0.4 g, 0.880 mmol). This mixture was degassed with Ar sealed and heated to 70° C. for 16 h. The solvent was removed and the residue was purified by silica gel, (0→10% 1.5 N $NH_3$ in MeOH/CHCl$_3$) to produce 2-(1-methyl-3,6-dihydro-2H-pyridin-4-yl)-N-[6-(1-methylpyrazol-4-yl)-3-isoquinolyl]pyridine-4-carboxamide (85) (247 mg, 0.582 mmol, 66.2% yield) as an off-white solid. ESIMS found for $C_{25}H_{27}BrN_4O_4$ m/z 426.1 (M+H). $^1$H NMR (499 MHz, DMSO-d$_6$) δ ppm 2.31 (3H, s), 2.57-2.63 (2H, m), 2.63-2.70 (2H, m), 3.11 (2H, br d, J=3.02 Hz), 3.91 (3H, s), 6.89 (1H, t, J=3.43 Hz), 7.78 (1H, dd, J=4.94, 1.37 Hz), 7.82 (1H, dd, J=8.51, 1.65 Hz), 8.08 (1H, d, J=8.51 Hz), 8.11 (1H, s), 8.16 (2H, d, J=6.04 Hz), 8.38 (1H, s), 8.61 (1H, s), 8.71 (1H, d, J=4.94 Hz), 9.14 (1H, s), 11.23 (1H, s); ESIMS found for $C_{25}H_{24}N_6O$ m/z 425.0 (M+1).

Step 2

To a solution of 2-(1-methyl-3,6-dihydro-2H-pyridin-4-yl)-N-[6-(1-methylpyrazol-4-yl)-3-isoquinolyl]pyridine-4-carboxamide (85) (200 mg, 0.470 mmol) to EtOH (15 mL), degassed solvent with $N_2$, added palladium on carbon (100.3 mg, 0.050 mmol) and stirred the reaction over $H_2$ for 16 h. The reaction was filtered through Celite, the solvent was removed under vacuum and the residue was purified by silca Gel (24 g) (0→10% 1.5 N $NH_3$ in CHCl$_3$) to produce 2-(1-methyl-4-piperidyl)-N-[6-(1-methylpyrazol-4-yl)-3-isoquinolyl]pyridine-4-carboxamide (84) (100 mg, 0.235 mmol, 49.8% yield) as an off-white solid. $^1$H NMR (500 MHz, DMSO-d$_6$) δ ppm 1.77-1.92 (4H, m), 2.00 (2H, td, J=11.60, 2.61 Hz), 2.21 (3H, s), 2.72 (1H, tt, J=11.49, 4.15 Hz), 2.85-2.93 (2H, m), 3.91 (3H, s), 7.76 (1H, dd, J=5.21, 1.65 Hz), 7.82 (1H, dd, J=8.51, 1.65 Hz), 7.91 (1H, s), 8.07 (1H, d, J=8.51 Hz), 8.12 (1H, d, J=0.82 Hz), 8.15 (1H, d, J=0.82 Hz), 8.39 (1H, s), 8.60 (1H, s), 8.66-8.71 (1H, m), 9.13 (1H, s), 11.17 (1H, s); ESIMS found for $C_{25}H_{26}N_6O$ m/z 427.0 (M+1).

Example 5

Preparation of N-(6-(1-methyl-5-(morpholinomethyl)-1H-pyrazol-4-yl) isoquinolin-3-yl)-2-morpholinoisonicotinamide (204) and N-(6-(1-methyl-5-(piperidin-1-ylmethyl)-1H-pyrazol-4-yl) isoquinolin-3-yl)-2-morpholinoisonicotinamide (429) are depicted below in Scheme 18

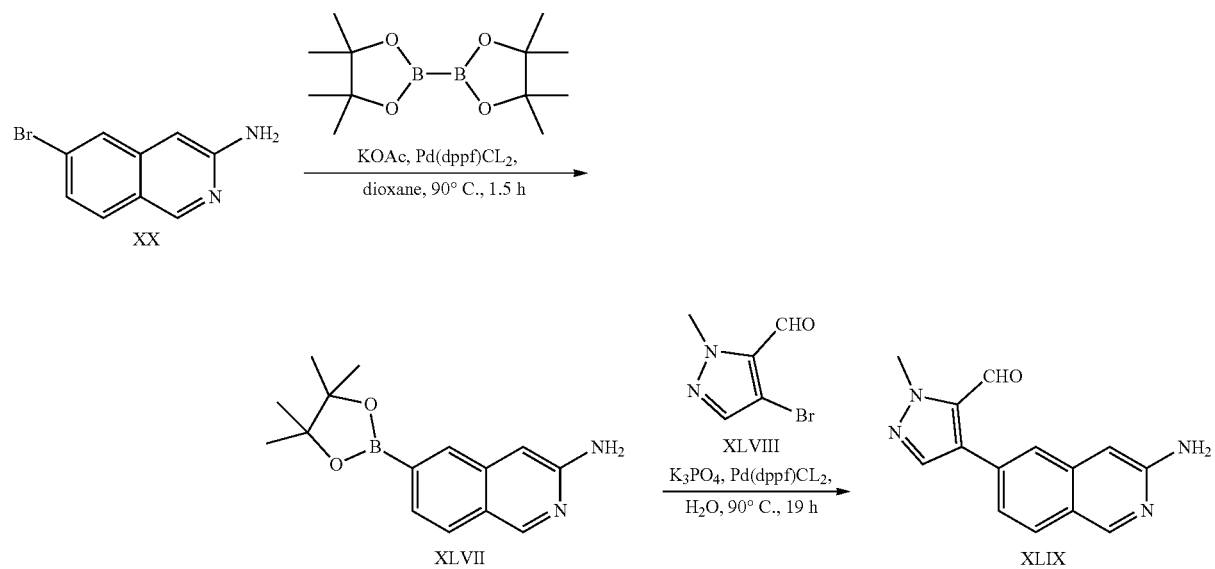

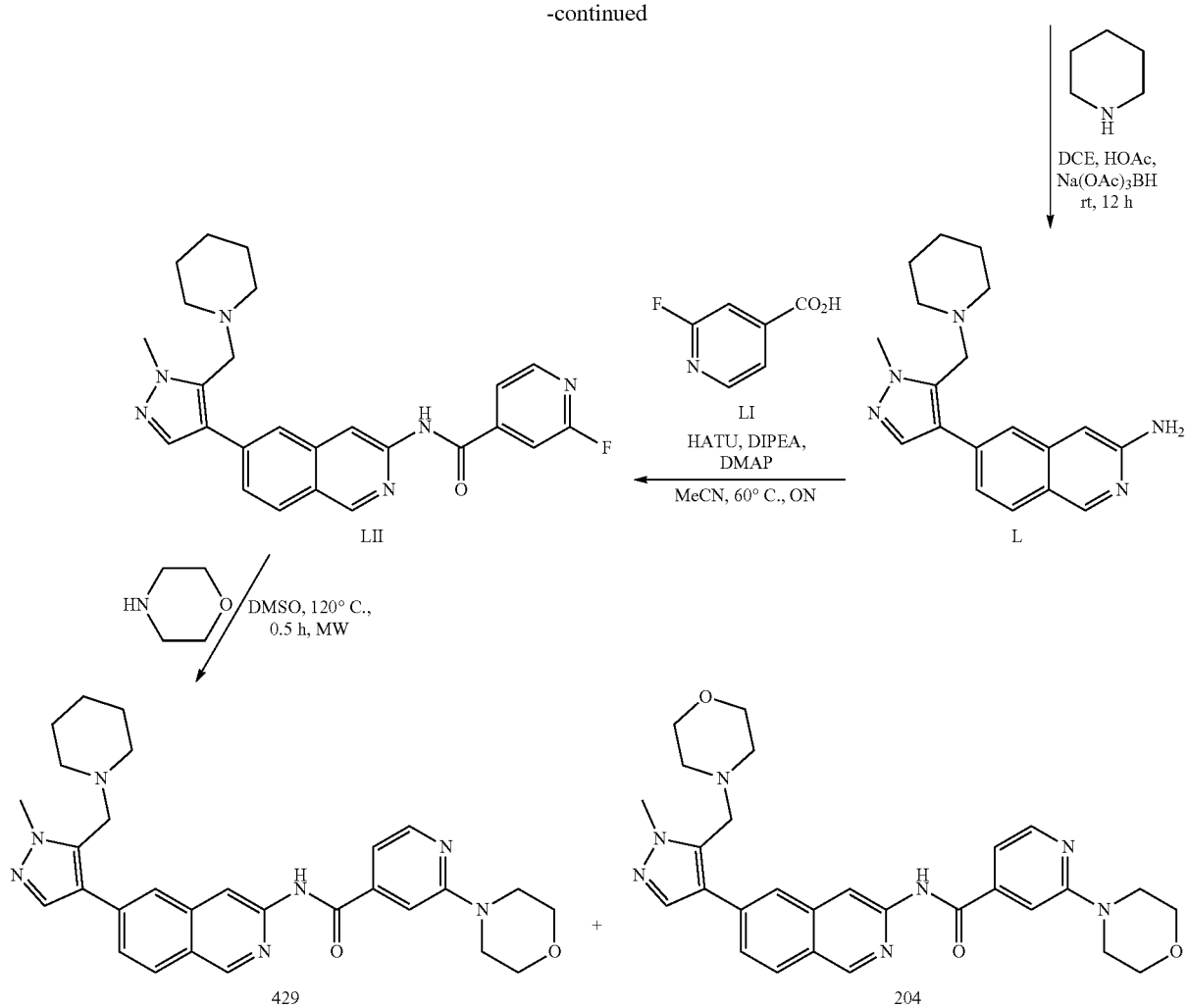

Steps 1-2

To a mixture of 6-bromoisoquinolin-3-amine (XX) (4.0 g, 17.93 mmol), Pd(dppf)Cl$_2$—CH$_2$Cl$_2$ adduct (1.03 g, 1.26 mmol), KOAc (4.39 g, 44.83 mmol) and 4,4,5,5-tetramethyl-2-(4,4,5,5-tetramethyl-1,3,2-dioxaborolan-2-yl)-1,3,2-dioxaborolane (5.01 g, 19.72 mmol) in 1,4-dioxane (50 mL) was bubbled with N$_2$ for 2 min. The reaction mixture was sealed and heated at 90° C. for 1.5 h. The reaction was cooled to room temperature, filtered and washed with EtOAc. The filtrate was concentrated and the residue taken in dioxane (50 mL). To the suspension was added 4-bromo-2-methyl-pyrazole-3-carbaldehyde (XLVIII) (3.39 g, 17.93 mmol) followed by K$_3$PO$_4$ (9.52 g, 44.83 mmol), Pd(dppf)Cl$_2$—CH$_2$Cl$_2$ adduct (1.03 g, 1.26 mmol) and water (15 mL). The mixture was purged with N$_2$ for a min, sealed and heated again at 90° C. for 19 h. The mixture was cooled to room temperature and concentrated to about 20 mL. The concentrate was diluted with EtOAc and filtered through a pad of Celite. The filtrate was diluted with water and the organic layer separated. The organic layer was washed with brine; dried, filtered and concentrated. The residue was triturated in ether and the resulting solid filtered to afford 4-(3-amino-6-isoquinolyl)-2-methyl-pyrazole-3-carbaldehyde (XLIX) (4.1 g, 16.2 mmol, 90.6% yield) as a brown solid. $^1$H NMR (499 MHz, DMSO-d$_6$) δ ppm 0.01 (6H, s), 0.86 (9H, s), 0.88-1.00 (2H, m), 1.23-1.35 (2H, m), 1.35-1.46 (1H, m), 1.69-1.79 (2H, m), 1.85-1.95 (2H, m), 2.21 (1H, tt, J=12.21, 3.57 Hz), 3.38 (2H, d, J=6.31 Hz), 3.57 (3H, s) ESIMS found for C$_{1-4}$H$_{12}$N$_4$O m/z 252.95 (M+1).

Step 3

To a mixture of 4-(3-amino-6-isoquinolyl)-2-methyl-pyrazole-3-carbaldehyde (XLIX) (1.07 g, 4.25 mmol), piperidine (0.84 mL, 8.51 mmol) and catalytic HOAc in DCE (10 mL) was stirred for 30 min. Na(OAc)$_3$BH (1.8 g, 8.51 mmol) was added and stirring was continued for 12 h at room temperature. The reaction mixture was quenched with minimum amount of aq. saturated ammonium chloride solution, and concentrated under vacuum. The residue was adsorbed on silica gel and purified by chromatography (0→20% 7N NH$_3$-MeOH/CHCl$_3$) to obtain 6-[1-methyl-5-(1-piperidylmethyl)pyrazol-4-yl]isoquinolin-3-amine (L) (800 mg, 2.49 mmol, 58.5% yield) as a white solid. ESIMS found for C$_{19}$H$_{23}$N$_5$ m/z 322.2 (M+1).

Step 4

To a suspension of 6-[1-methyl-5-(1-piperidylmethyl)pyrazol-4-yl]isoquinolin-3-amine (L) (0.14 g, 0.440 mmol), 2-fluoropyridine-4-carboxylic acid (LI) (0.07 g, 0.520 mmol), DMAP (0.03 g, 0.220 mmol) and HATU (0.2 g, 0.520 mmol) in DMF (4 mL) was added DIPEA (0.23 mL, 1.31 mmol). The resulting mixture was stirred at 80° C. for 1.5 h. Another 1.2 equiv. of HATU was added to the mixture and stirred at 80° C. for additional 16 h. The reaction mixture was diluted with water and the resulting solid filtered. The crude product was purified by silica gel chromatography (0→10% 7 N NH$_3$—MeOH/CHCl$_3$) to produce 2-fluoro-N-[6-[1-methyl-5-(1-piperidylmethyl)pyrazol-4-yl]-3-isoquinolyl]pyridine-4-carboxamide (LII) (85.0 mg, 0.191 mmol, 43.9% yield) as a brown solid. ESIMS found for $C_{25}H_{25}FN_6O$ m/z 444.9 (M+H).

Step 5

To a solution of 2-fluoro-N-[6-[1-methyl-5-(1-piperidylmethyl)pyrazol-4-yl]-3-isoquinolyl]pyridine-4-carboxamide (LII) (80 mg, 0.180 mmol) in DMSO (1 mL) was added morpholine (0.05 mL, 0.540 mmol). The mixture was sealed in a tube and irradiated with MW at 120° C. for 30 min. The reaction was heated at 90° C. for additional 16 h and the mixture cooled to room temperature, poured into water and the resulting solid filtered. The crude product was purified by silica gel chromatography (0→5% MeOH/CHCl$_3$) as the eluent, followed by HPLC purification (0→65% MeCN/water). Two clean products were separated. The fractions for each product were combined and concentrated. The residue for each product was redissolved in minimum amount of CHCl$_3$/MeOH and filtered through the carbonate resin (loading: 0.23 mmol/500 mg). The filtrate was concentrated and the residue triturated in ether. The resulting solid was filtered to afford N-[6-[1-methyl-5-(1-piperidylmethyl)pyrazol-4-yl]-3-isoquinolyl]-2-morpholino-pyridine-4-carboxamide (429) (23 mg, 0.045 mmol, 25.0% yield) as a white solid; $^1$H NMR (499 MHz, DMSO-d$_6$) δ ppm 1.32-1.44 (2H, m), 1.45-1.55 (4H, m), 2.38 (4H, br s), 3.53-3.62 (4H, m), 3.67 (2H, s), 3.71-3.77 (4H, m), 3.92 (3H, s), 7.21 (1H, dd, J=5.21, 1.10 Hz), 7.47 (1H, s), 7.76 (1H, dd, J=8.51, 1.65 Hz), 7.82 (1H, s), 8.09 (1H, d, J=8.51 Hz), 8.14 (1H, s), 8.29 (1H, d, J=5.21 Hz), 8.61 (1H, s), 9.17 (1H, s), 11.01 (1H, s); ESIMS found for $C_{29}H_{33}N_7O_2$ m/z 512.0 (M+1) and N-[6-[1-methyl-5-(morpholinomethyl)pyrazol-4-yl]-3-isoquinolyl]-2-morpholino-pyridine-4-carboxamide (204) (10 mg, 0.020 mmol, 10.8% yield) as an off white solid. $^1$H NMR (499 MHz, DMSO-d$_6$) δ ppm 2.42 (4H, br d, J=3.84 Hz), 3.53-3.61 (8H, m), 3.70-3.78 (6H, m), 3.94 (3H, s), 7.21 (1H, dd, J=5.21, 1.37 Hz), 7.47 (1H, s), 7.76 (1H, dd, J=8.51, 1.65 Hz), 7.83 (1H, s), 8.11 (2H, d, J=11.25 Hz), 8.29 (1H, d, J=4.94 Hz), 8.62 (1H, s), 9.18 (1H, s), 11.02 (1H, s); ESIMS found for $C_{28}H_{31}N_7O_3$ m/z 514.0 (M+1).

Example 6

Preparation of N-(6-(5-(dimethylamino)-1,3,4-thiadiazol-2-yl)isoquinolin-3-yl)-2-(4-methylpiperazin-1-yl)isonicotinamide (428) and N-(6-(5-amino-1,3,4-thiadiazol-2-yl) isoquinolin-3-yl)-2-(4-methylpiperazin-1-yl)isonicotinamide (430) are depicted below in Scheme 19

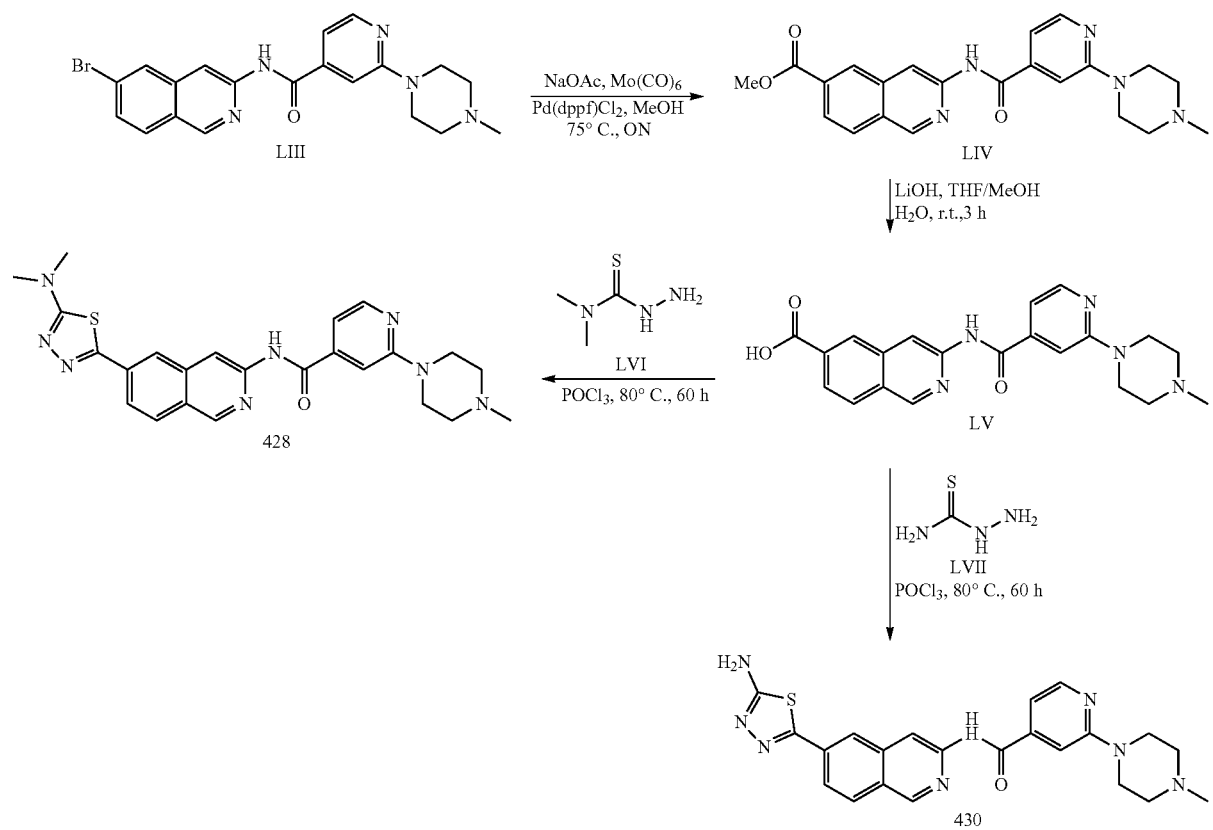

Step 1

To a solution of N-(6-bromo-3-isoquinolyl)-2-(4-methylpiperazin-1-yl)pyridine-4-carboxamide (LIII) (328 mg, 0.770 mmol) in MeOH (4 mL) was added molybdenum hexacorbonyl (557 mg, 2.02 mmol), Pd(dppf)Cl$_2$—CH$_2$Cl$_2$ adduct (125.7 mg, 0.150 mmol) sonicated for a while and stirred at 75° C. for overnight. The reaction was diluted with water, extracted into EtOAc, and purified on a silica gel column (0→100% (20% NH$_3$ in MeOH—CHCl$_3$/CHCl$_3$)) to yield methyl 3-[[2-(4-methylpiperazin-1-yl)pyridine-4-carbonyl]amino]isoquinoline-6-carboxylate (LIV) (232 mg, 0.572 mmol, 74.4% yield). ESIMS found for C$_{22}$H$_{23}$N$_5$O$_3$ m/z 406.2 (M+H).

Step 2

To a solution of methyl 3-[[2-(4-methylpiperazin-1-yl)pyridine-4-carbonyl]amino]isoquinoline-6-carboxylate (LIV) (232 mg, 0.570 mmol) in THF (4 mL) was added MeOH (4 mL) and LiOH (137 mg, 5.72 mmol) in water (3 mL). The reaction was stirred for 3 h at room temperature. The solvent was removed and the residue was suspended in water. Aqueous HCl was added until pH=6 and the solid was collected by filtration to produce 3-[[2-(4-methylpiperazin-1-yl)pyridine-4-carbonyl]amino]isoquinoline-6-carboxylic acid (LV) (162 mg, 0.414 mmol, 72.3% yield) as a yellow solid. ESIMS found for C$_{21}$H$_{21}$N$_5$O$_3$ m/z 392.0 (M+H).

Step 3

A solution of 3-[[2-(4-methylpiperazin-1-yl)pyridine-4-carbonyl]amino]isoquinoline-6-carboxylic acid (LV) (45 mg, 0.110 mmol), 3-amino-1,1-dimethyl-thiourea (LVI) (20.6 mg, 0.170 mmol) in POCl$_3$ (2.25 mL, 24.14 mmol) was heated at 80° C. for 60 h. The reaction was concentrated and quenched with ice and had the pH adjusted to >12 using 1N NaOH. The solid was collected by filtration to obtain N-[6-[5-(dimethylamino)-1,3,4-thiadiazol-2-yl]-3-isoquinolyl]-2-(4-methylpiperazin-1-yl)pyridine-4-carboxamide (428) (14.6 mg, 0.031 mmol, 26.8% yield) as a yellow solid. $^1$H NMR (499 MHz, DMSO-d$_6$) δ ppm 2.32 (3H, br s), 2.52-2.67 (4H, m), 3.19 (6H, s), 3.64 (4H, br s), 7.14-7.21 (1H, m), 7.48 (1H, s), 8.07 (1H, dd, J=8.51, 1.65 Hz), 8.17 (1H, s), 8.24-8.29 (2H, m), 8.70 (1H, s), 9.24 (1H, s), 11.14 (1H, s); ESIMS found for C$_{24}$H$_{26}$N$_8$OS m/z 475.2 (M+1).

Step 4

A solution of 3-[[2-(4-methylpiperazin-1-yl)pyridine-4-carbonyl]amino]isoquinoline-6-carboxylic acid (LV) (60 mg, 0.150 mmol), aminothiourea (LVII) (21.0 mg, 0.230 mmol) in POCl$_3$ (3 mL, 32.19 mmol) was heated at 80° C. for 60 h. The reaction was concentrated and quenched with ice and had the pH adjusted to >12 using 1N NaOH. The solid was collected by filtration and purified by column chromatography (0→100% (10% NH$_3$ MeOH in EtOAc/Hexanes)) to yield N-[6-(5-amino-1,3,4-thiadiazol-2-yl)-3-isoquinolyl]-2-(4-methylpiperazin-1-yl)pyridine-4-carboxamide (430) (3.7 mg, 0.008 mmol, 5.4% yield) as a yellow solid. $^1$H NMR (499 MHz, DMSO-d$_6$) δ ppm 2.27 (3H, br s), 3.62 (4H, br s), 7.12-7.20 (1H, m), 7.48 (1H, s), 7.60 (2H, s), 8.07 (1H, dd, J=8.51, 1.65 Hz), 8.16 (1H, d, J=8.78 Hz), 8.25 (1H, s), 8.27 (1H, d, J=4.94 Hz), 8.71 (1H, s), 9.24 (1H, s), 11.13 (1H, s); ESIMS found for C$_{22}$H$_{22}$N$_8$OS m/z 447.2 (M+1).

Example 7

Preparation of 1-methyl-4-(4-((6-(1-methyl-1H-pyrazol-4-yl)isoquinolin-3-yl)carbamoyl)pyridin-2-yl)piperazine 1-oxide (87) is depicted below in Scheme 20.

Scheme 20

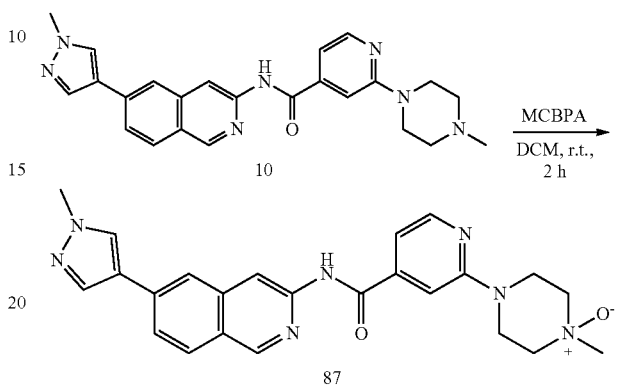

Step 1

To a suspension 2-(4-methylpiperazin-1-yl)-N-[6-(1-methylpyrazol-4-yl)-3-isoquinolyl]pyridine-4-carboxamide (10) (109 mg, 0.250 mmol) in DCM (5 mL) was added 3-chlorobenzenecarboperoxoic acid (66 mg, 0.380 mmol). The mixture was stirred at room temperature for 2 h and concentrated. The crude product was purified by silica gel chromatography (0→10% 7 N NH$_3$-MeOH/CHCl$_3$). The fractions containing the product were concentrated and the residue triturated in ether. The resulting solid was filtered and dried to afford 2-(4-methyl-4-oxido-piperazin-4-ium-1-yl)-N-[6-(1-methylpyrazol-4-yl)-3-isoquinolyl]pyridine-4-carboxamide (87) (65 mg, 0.147 mmol, 57.5% yield) as a white solid. $^1$H NMR (499 MHz, DMSO-d$_6$) δ ppm 2.99 (2H, br d, J=10.70 Hz), 3.11 (3H, s), 3.41 (2H, td, J=11.53, 3.29 Hz), 3.61-3.72 (2H, m), 3.91 (3H, s), 4.25 (2H, br d, J=13.17 Hz), 7.20 (1H, dd, J=5.08, 1.23 Hz), 7.55 (1H, s), 7.82 (1H, dd, J=8.51, 1.65 Hz), 8.07 (1H, d, J=8.51 Hz), 8.11 (1H, s), 8.14 (1H, s), 8.29 (1H, d, J=5.21 Hz), 8.38 (1H, s), 8.60 (1H, s), 9.13 (1H, s), 11.10 (1H, s); ESIMS found for C$_{24}$H$_{25}$N$_7$O$_2$ m/z 444.2 (M+1).

The following compounds were prepared in accordance with the procedure described in the above Examples 1-7.

1

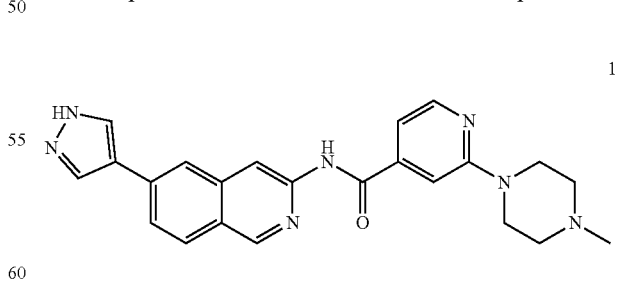

N-(6-(1H-Pyrazol-4-yl)isoquinolin-3-yl)-2-(4-methylpiperazin-1-yl) isonicotinamide 1

Off-white solid (38.0 mg, 0.091 mmol, 39.2% yield). $^1$H NMR (499 MHz, DMSO-d$_6$) δ ppm 2.24 (s, 3H), 2.43 (br t, J=4.80 Hz, 4H), 3.57-3.65 (m, 4H), 7.16 (dd, J=5.21, 0.82

Hz, 1H), 7.46 (s, 1H), 7.88 (dd, J=8.64, 1.51 Hz, 1H), 8.07 (d, J=8.51 Hz, 1H), 8.14-8.31 (m, 1H), 8.19 (s, 1H), 8.26 (d, J=5.21 Hz, 1H), 8.38-8.51 (m, 1H), 8.60 (s, 1H), 9.13 (s, 1H), 11.04 (s, 1H), 13.12 (br s, 1H); ESIMS found for $C_{23}H_{23}N_7O$ m/z 414.2 (M+1).

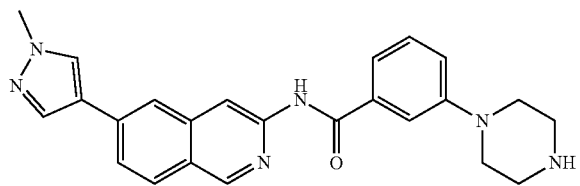

N-(6-(1-Methyl-1H-pyrazol-4-yl)isoquinolin-3-yl)-3-(piperazin-1-yl)benzamide 2

Off-white solid (58.3 mg, 0.141 mmol, 49.1% yield). $^1$H NMR (499 MHz, DMSO-$d_6$) δ ppm 2.94 (br d, J=3.29 Hz, 4H), 3.22 (br d, J=3.84 Hz, 4H), 3.91 (s, 3H), 7.15 (dd, J=8.23, 1.92 Hz, 1H), 7.35 (t, J=7.96 Hz, 1H), 7.48 (d, J=7.41 Hz, 1H), 7.63 (s, 1H), 7.79 (dd, J=8.51, 1.65 Hz, 1H), 8.06 (d, J=8.78 Hz, 1H), 8.10-8.14 (m, 2H), 8.38 (s, 1H), 8.59 (s, 1H), 9.11 (s, 1H), 10.80 (s, 1H); ESIMS found for $C_{24}H_{24}N_6O$ m/z 413.2 (M+1).

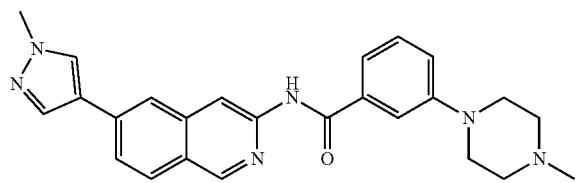

N-(6-(1-Methyl-1H-pyrazol-4-yl)isoquinolin-3-yl)-3-(4-methylpiperazin-1-yl)benzamide 3

White solid (860 mg, 1.92 mmol, 69.3% yield). $^1$H NMR (499 MHz, DMSO-$d_6$) δ ppm 2.24 (s, 3H), 2.48 (br d, J=4.94 Hz, 4H), 3.22-3.28 (m, 4H), 3.91 (s, 3H), 7.15 (dd, J=8.23, 2.20 Hz, 1H), 7.35 (t, J=7.82 Hz, 1H), 7.46 (d, J=7.68 Hz, 1H), 7.64 (s, 1H), 7.79 (dd, J=8.51, 1.65 Hz, 1H), 8.05 (d, J=8.51 Hz, 1H), 8.09-8.14 (m, 2H), 8.38 (s, 1H), 8.59 (s, 1H), 9.11 (s, 1H), 10.80 (s, 1H); ESIMS found for $C_{25}H_{26}N_6O$ m/z 427. (M+1).

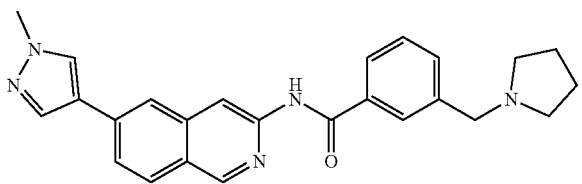 [SMILES: Cn1cc(-c2ccc3cnc(NC(=O)c4ccnc(CN5CCCC5)c4)cc3c2)cn1]

N-(6-(1-Methyl-1H-pyrazol-4-yl)isoquinolin-3-yl)-3-(pyrrolidin-1-ylmethyl)benzamide 4

Light yellow solid (75.5 mg, 0.183 mmol, 41.1% yield). $^1$H NMR (499 MHz, DMSO-$d_6$) δ ppm 1.70-1.76 (m, 4H), 2.49 (br s, 4H), 3.68 (s, 2H), 3.91 (s, 3H), 7.43-7.50 (m, 1H), 7.52-7.57 (m, 1H), 7.80 (dd, J=8.51, 1.65 Hz, 1H), 7.95 (d, J=7.68 Hz, 1H), 8.00 (s, 1H), 8.06 (d, J=8.51 Hz, 1H), 8.11 (s, 1H), 8.13 (s, 1H), 8.38 (s, 1H), 8.59 (s, 1H), 9.11 (s, 1H), 10.80 (s, 1H); ESIMS found for $C_{25}H_{25}N_5O$ m/z 412.2 (M+1).

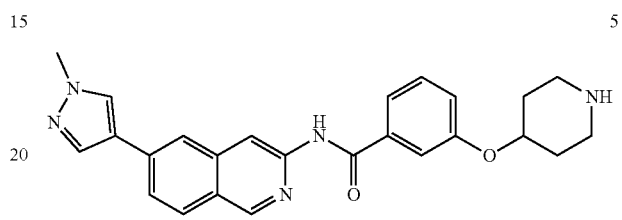

N-(6-(1-Methyl-1H-pyrazol-4-yl)isoquinolin-3-yl)-3-(piperidin-4-yloxy)benzamide 5

Off-white solid (540.6 mg, 1.20 mmol, 81.3% yield). $^1$H NMR (499 MHz, DMSO-$d_6$) δ ppm 1.42-1.54 (m, 2H), 1.92-1.99 (m, 2H), 2.56-2.64 (m, 2H), 2.97 (dt, J=12.62, 4.25 Hz, 2H), 3.91 (s, 3H), 4.49-4.61 (m, 1H), 7.16 (dd, J=8.10, 1.51 Hz, 1H), 7.41 (t, J=8.23 Hz, 1H), 7.59-7.68 (m, 2H), 7.80 (dd, J=8.51, 1.65 Hz, 1H), 8.06 (d, J=8.78 Hz, 1H), 8.10-8.16 (m, 2H), 8.38 (s, 1H), 8.59 (s, 1H), 9.11 (s, 1H), 10.82 (s, 1H); ESIMS found for $C_{25}H_{25}N_5O_2$ m/z 428.2 (M+1).

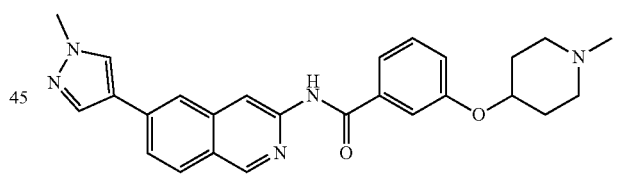

N-(6-(1-Methyl-1H-pyrazol-4-yl)isoquinolin-3-yl)-3-((1-methylpiperidin-4-yl)oxy)benzamide 6

Off-white solid (115.9 mg, 0.249 mmol, 71.1% yield). $^1$H NMR (499 MHz, DMSO-$d_6$) δ ppm 1.61-1.74 (m, 2H), 1.92-2.02 (m, 2H), 2.15-2.26 (m, 2H), 2.19 (s, 3H), 2.58-2.68 (m, 2H), 3.91 (s, 3H), 4.48-4.58 (m, 1H), 7.16 (dd, J=7.96, 1.65 Hz, 1H), 7.42 (t, J=8.23 Hz, 1H), 7.60-7.68 (m, 2H), 7.80 (dd, J=8.51, 1.37 Hz, 1H), 8.06 (d, J=8.51 Hz, 1H), 8.08-8.16 (m, 2H), 8.38 (s, 1H), 8.59 (s, 1H), 9.11 (s, 1H), 10.83 (s, 1H); ESIMS found for $C_{26}H_{27}N_5O_2$ m/z 442.2 (M+1).

Hz, 1H), 8.38 (s, 1H), 8.59 (s, 1H), 9.12 (s, 1H), 11.03 (s, 1H); ESIMS found for $C_{23}H_{23}N_7O$ m/z 414.2 (M+1).

7

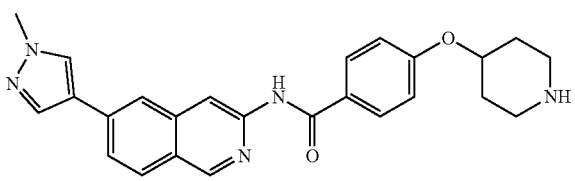

N-(6-(1-Methyl-1H-pyrazol-4-yl)isoquinolin-3-yl)-
4-(piperidin-4-yloxy)benzamide 7

White solid (554 mg, 1.23 mmol, 91.5% yield). $^1$H NMR (499 MHz, DMSO-$d_6$) δ ppm 1.42-1.51 (m, 2H), 1.90-1.98 (m, 2H), 2.55-2.63 (m, 2H), 2.95 (dt, J=12.69, 3.95 Hz, 2H), 3.91 (s, 3H), 4.51-4.58 (m, 1H), 7.05 (d, J=8.78 Hz, 2H), 7.78 (dd, J=8.51, 1.37 Hz, 1H), 8.02-8.08 (m, 3H), 8.11 (s, 1H), 8.11 (br s, 1H), 8.37 (s, 1H), 8.58 (s, 1H), 9.10 (s, 1H), 10.63 (s, 1H); ESIMS found for $C_{25}H_{25}N_5O_2$ m/z 428.2 (M+1).

10

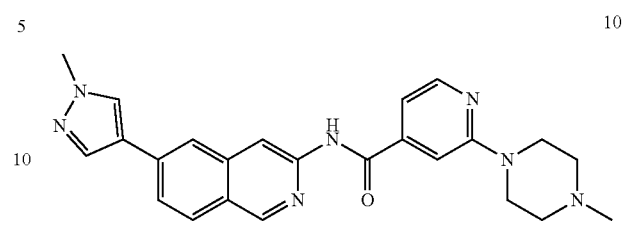

N-(6-(1-Methyl-1H-pyrazol-4-yl)isoquinolin-3-yl)-
2-(4-methylpiperazin-1-yl)isonicotinamide 10

Tan solid (71.6 mg, 0.168 mmol, 66.7% yield). $^1$H NMR (499 MHz, DMSO-$d_6$) δ ppm 2.24 (s, 3H), 2.43 (br t, J=4.80 Hz, 4H), 3.56-3.65 (m, 4H), 3.91 (s, 3H), 7.16 (dd, J=5.08, 0.96 Hz, 1H), 7.46 (s, 1H), 7.81 (dd, J=8.37, 1.51 Hz, 1H), 8.07 (d, J=8.51 Hz, 1H), 8.10-8.16 (m, 2H), 8.26 (d, J=5.21 Hz, 1H), 8.38 (s, 1H), 8.59 (s, 1H), 9.12 (s, 1H), 11.05 (s, 1H); ESIMS found for $C_{24}H_{25}N_7O$ m/z 428.2 (M+1).

8

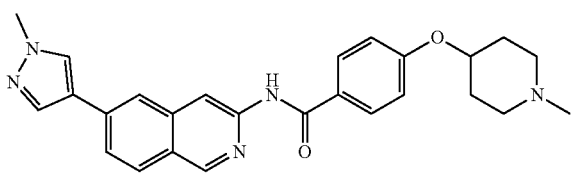

N-(6-(1-Methyl-1H-pyrazol-4-yl)isoquinolin-3-yl)-
4-((1-methylpiperidin-4-yl)oxy)benzamide 8

White solid (82.0 mg, 0.186 mmol, 89.4% yield). $^1$H NMR (499 MHz, DMSO-$d_6$) δ ppm 1.61-1.72 (m, 2H), 1.91-2.02 (m, 2H), 2.14-2.26 (m, 2H), 2.18 (s, 3H), 2.58-2.68 (m, 2H), 3.91 (s, 3H), 4.51 (tt, J=8.16, 3.91 Hz, 1H), 7.06 (d, J=8.78 Hz, 2H), 7.78 (dd, J=8.64, 1.51 Hz, 1H), 8.01-8.07 (m, 3H), 8.09-8.13 (m, 2H), 8.37 (s, 1H), 8.58 (s, 1H), 9.10 (s, 1H), 10.64 (s, 1H); ESIMS found for $C_{26}H_{27}N_5O_2$ m/z 442.2 (M+1).

11

2-(4-Isopropylpiperazin-1-yl)-N-(6-(1-methyl-1H-
pyrazol-4-yl)isoquinolin-3-yl)isonicotinamide 11

White solid (58.7 mg, 0.129 mmol, 88.8% yield). $^1$H NMR (499 MHz, DMSO-$d_6$) δ ppm 1.01 (d, J=6.59 Hz, 6H), 2.53-2.59 (m, 4H), 2.65-2.76 (m, 1H), 3.56-3.62 (m, 4H), 3.91 (s, 3H), 7.15 (d, J=5.21 Hz, 1H), 7.44 (s, 1H), 7.81 (dd, J=8.51, 1.65 Hz, 1H), 8.07 (d, J=8.51 Hz, 1H), 8.11 (s, 1H), 8.14 (s, 1H), 8.25 (d, J=5.21 Hz, 1H), 8.38 (s, 1H), 8.59 (s, 1H), 9.12 (s, 1H), 11.04 (s, 1H); ESIMS found for $C_{26}H_{29}N_7O$ m/z 456.2 (M+1).

9

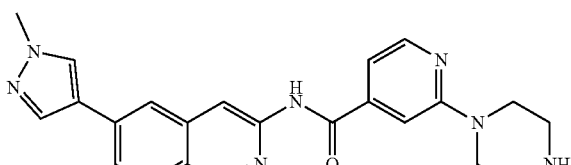

N-(6-(1-Methyl-1H-pyrazol-4-yl)isoquinolin-3-yl)-
2-(piperazin-1-yl) isonicotinamide 9

Off-white solid (57.3 mg, 0.139 mmol, 91.4% yield). $^1$H NMR (499 MHz, DMSO-$d_6$) δ ppm 2.78-2.85 (m, 4H), 3.50-3.56 (m, 4H), 3.91 (s, 3H), 7.14 (dd, J=5.08, 1.24 Hz, 1H), 7.42 (s, 1H), 7.81 (dd, J=8.51, 1.65 Hz, 1H), 8.07 (d, J=8.51 Hz, 1H), 8.11 (s, 1H), 8.14 (s, 1H), 8.25 (d, J=4.94

12

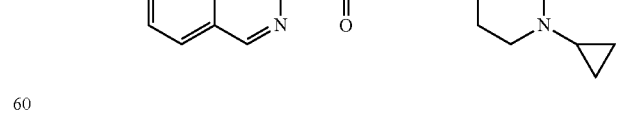

2-(4-Cyclopropylpiperazin-1-yl)-N-(6-(1-methyl-
1H-pyrazol-4-yl) isoquinolin-3-yl)isonicotinamide
12

Off-white solid (124.0 mg, 0.273 mmol, 68.7% yield). $^1$H NMR (499 MHz, DMSO-$d_6$) δ ppm 0.38 (br d, J=2.74 Hz, 2H), 0.46 (br d, J=4.67 Hz, 2H), 1.66 (dt, J=6.24, 3.05 Hz, 1H), 2.61-2.67 (m, 4H), 3.57 (br s, 4H), 3.91 (s, 3H), 7.15 (d, J=4.94 Hz, 1H), 7.46 (s, 1H), 7.81 (d, J=8.23 Hz, 1H), 8.07 (d, J=8.51 Hz, 1H), 8.11 (s, 1H), 8.14 (s, 1H), 8.25 (d, J=4.94 Hz, 1H), 8.38 (s, 1H), 8.59 (s, 1H), 9.12 (s, 1H), 11.04 (s, 1H); ESIMS found for $C_{26}H_{27}N_7O$ m/z 454.2 (M+1).

13

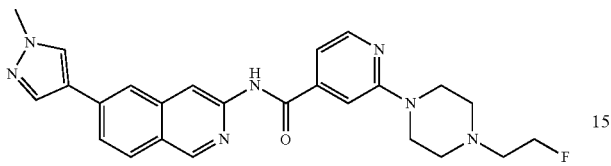

2-(4-(2-Fluoroethyl)piperazin-1-yl)-N-(6-(1-methyl-1H-pyrazol-4-yl) isoquinolin-3-yl)isonicotinamide 13

White solid (13.2 mg, 0.029 mmol, 17.5% yield). $^1$H NMR (499 MHz, DMSO-$d_6$) δ ppm 2.55-2.61 (m, 4H), 2.69 (dt, J=28.85, 4.95 Hz, 2H), 3.59-3.64 (m, 4H), 4.59 (dt, J=47.85, 4.95 Hz, 2H), 7.16 (dd, J=5.08, 0.96 Hz, 1H), 7.47 (s, 1H), 7.81 (dd, J=8.51, 1.37 Hz, 1H), 8.07 (d, J=8.51 Hz, 1H), 8.11 (s, 1H), 8.14 (s, 1H), 8.26 (d, J=4.94 Hz, 1H), 8.38 (s, 1H), 8.59 (s, 1H), 9.13 (s, 1H), 11.04 (s, 1H); ESIMS found for $C_{25}H_{26}FN_7O$ m/z 460.2 (M+1).

14

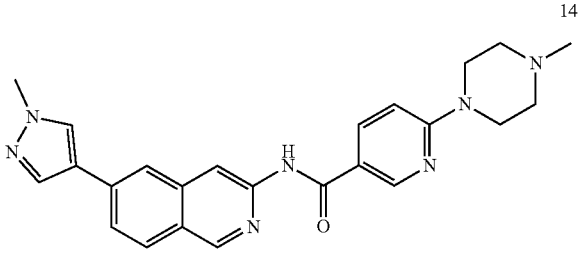 [SMILES: CN1CCN(c2ccc(C(=O)Nc3cc4cc(-c5cnn(C)c5)ccc4cn3)cn2)CC1]

N-(6-(1-Methyl-1H-pyrazol-4-yl)isoquinolin-3-yl)-6-(4-methylpiperazin-1-yl)nicotinamide 14

Beige solid (28.0 mg, 0.062 mmol, 66.3% yield). $^1$H NMR (499 MHz, DMSO-$d_6$) δ ppm 2.22 (s, 3H), 2.40 (t, J=5.08 Hz, 4H), 3.60-3.67 (m, 4H), 3.91 (s, 3H), 6.90 (d, J=9.06 Hz, 1H), 7.78 (dd, J=8.51, 1.65 Hz, 1H), 8.04 (d, J=8.78 Hz, 1H), 8.08-8.12 (m, 2H), 8.19 (dd, J=9.06, 2.47 Hz, 1H), 8.37 (s, 1H), 8.57 (s, 1H), 8.84 (d, J=2.20 Hz, 1H), 9.09 (s, 1H), 10.63 (s, 1H); ESIMS found for $C_{24}H_{25}N_7O$ m/z 428.2 (M+1).

15

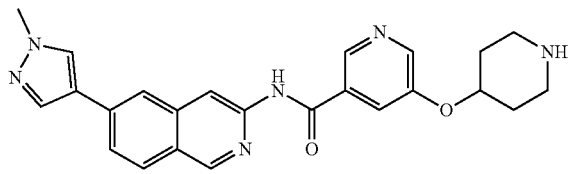

N-(6-(1-Methyl-1H-pyrazol-4-yl)isoquinolin-3-yl)-5-(piperidin-4-yloxy) nicotinamide 15

White solid (29.0 mg, 0.064 mmol, 75.5% yield). $^1$H NMR (499 MHz, DMSO-$d_6$) δ ppm 1.45-1.55 (m, 2H), 1.95-2.01 (m, 2H), 2.57-2.65 (m, 2H), 2.98 (dt, J=12.83, 4.15 Hz, 2H), 3.91 (s, 3H), 4.60-4.69 (m, 1H), 7.82 (dd, J=8.51, 1.37 Hz, 1H), 7.98-8.02 (m, 1H), 8.07 (d, J=8.51 Hz, 1H), 8.11 (s, 1H), 8.14 (s, 1H), 8.38 (s, 1H), 8.45 (d, J=2.74 Hz, 1H), 8.60 (s, 1H), 8.75 (d, J=1.65 Hz, 1H), 9.13 (s, 1H), 11.11 (br s, 1H); ESIMS found for $C_{24}H_{24}N_6O_2$ m/z 429.2 (M+1).

16

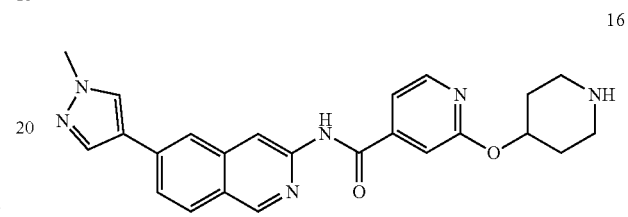

N-(6-(1-Methyl-1H-pyrazol-4-yl)isoquinolin-3-yl)-2-(piperidin-4-yloxy) isonicotinamide 16

Off-white solid (113.3 mg, 0.264 mmol, 58.8% yield). $^1$H NMR (499 MHz, DMSO-$d_6$) δ ppm 1.47-1.61 (2H, m), 1.92-2.01 (2H, m), 2.57-2.67 (2H, m), 2.98 (2H, dt, J=12.49, 3.91 Hz), 3.91 (3H, s), 5.06-5.15 (1H, m), 7.34 (1H, s), 7.50 (1H, dd, J=5.21, 1.37 Hz), 7.82 (1H, dd, J=8.51, 1.37 Hz), 8.06 (1H, d, J=8.51 Hz), 8.11 (1H, s), 8.15 (1H, s), 8.31 (1H, d, J=5.21 Hz), 8.38 (1H, s), 8.58 (1H, s), 9.12 (1H, s), 11.06 (1H, br s); ESIMS found for $C_{24}H_{24}N_6O_2$ m/z 429.2 (M+1).

17

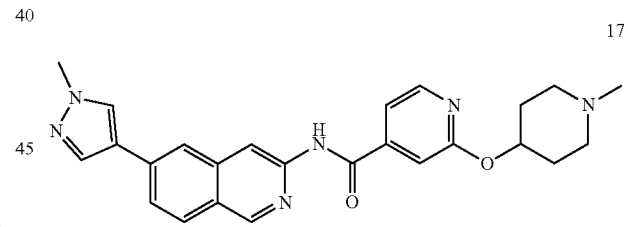

N-(6-(1-Methyl-1H-pyrazol-4-yl)isoquinolin-3-yl)-2-((1-methylpiperidin-4-yl)oxy)isonicotinamide 17

Off-white solid (1.02 g, 2.20 mmol, 85.4% yield). $^1$H NMR (499 MHz, DMSO-$d_6$) δ ppm 1.64-1.77 (2H, m), 1.99 (2H, br dd, J=8.92, 3.98 Hz), 2.17 (2H, br s), 2.19 (3H, s), 2.60-2.70 (2H, m), 3.91 (3H, s), 5.04 (1H, tt, J=8.40, 3.95 Hz), 7.35 (1H, s), 7.51 (1H, dd, J=5.21, 1.37 Hz), 7.82 (1H, dd, J=8.51, 1.65 Hz), 8.06 (1H, d, J=8.78 Hz), 8.11 (1H, s), 8.15 (1H, s), 8.31 (1H, d, J=5.21 Hz), 8.38 (1H, s), 8.57 (1H, s), 9.12 (1H, s), 11.06 (1H, s); ESIMS found for $C_{25}H_{26}N_6O_2$ m/z 443.2 (M+1).

18

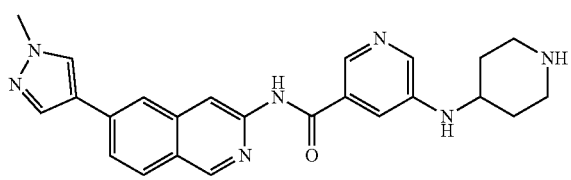

N-(6-(1-Methyl-1H-pyrazol-4-yl)isoquinolin-3-yl)-5-(piperidin-4-ylamino) nicotinamide 18

Off-white solid (274.3 mg, 0.610 mmol, 65.6% yield). $^1$H NMR (499 MHz, DMSO-$d_6$) δ ppm 1.22-1.36 (m, 3H), 1.86 (br d, J=9.88 Hz, 2H), 2.52-2.60 (m, 2H), 2.92-3.01 (m, 2H), 3.73-3.84 (m, 1H), 3.91 (s, 3H), 6.70 (d, J=7.68 Hz, 1H), 6.98 (s, 1H), 6.99-7.04 (m, 1H), 7.81 (dd, J=8.51, 1.37 Hz, 1H), 8.06 (d, J=8.51 Hz, 1H), 8.09 (d, J=5.21 Hz, 1H), 8.11 (s, 1H), 8.14 (s, 1H), 8.38 (s, 1H), 8.55 (s, 1H), 9.11 (s, 1H), 10.78 (br s, 1H); ESIMS found for $C_{24}H_{25}N_7O$ m/z 428.2 (M+1).

19

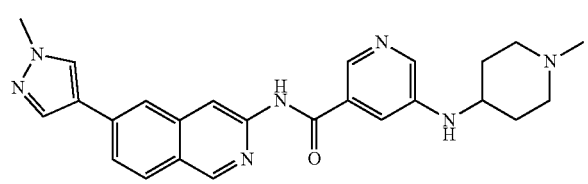

N-(6-(1-Methyl-1H-pyrazol-4-yl)isoquinolin-3-yl)-5-((1-methylpiperidin-4-yl)amino)nicotinamide 19

Off-white solid (42.3 mg, 0.091 mmol, 51.9% yield). $^1$H NMR (499 MHz, DMSO-$d_6$) δ ppm 1.41-1.53 (m, 2H), 1.84-1.93 (m, 2H), 2.00 (br t, J=10.84 Hz, 2H), 2.17 (s, 3H), 2.73 (br d, J=11.80 Hz, 2H), 3.65-3.76 (m, 1H), 3.91 (s, 3H), 6.69 (d, J=7.41 Hz, 1H), 6.99 (s, 1H), 7.01 (dd, J=5.35, 1.51 Hz, 1H), 7.81 (dd, J=8.51, 1.65 Hz, 1H), 8.06 (d, J=8.51 Hz, 1H), 8.09 (d, J=5.21 Hz, 1H), 8.11 (s, 1H), 8.14 (s, 1H), 8.38 (s, 1H), 8.55 (s, 1H), 9.11 (s, 1H), 10.79 (s, 1H); ESIMS found for $C_{25}H_{27}N_7O$ m/z 442.2 (M+1).

20

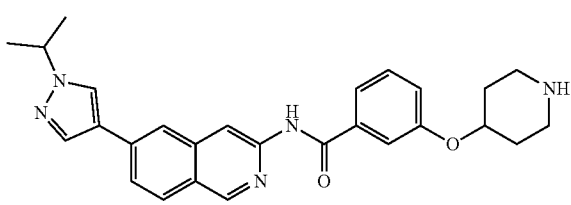

N-(6-(1-Isopropyl-1H-pyrazol-4-yl)isoquinolin-3-yl)-3-(piperidin-4-yloxy)benzamide 20

White solid (77.3 mg, 0.170 mmol, 77.3% yield). $^1$H NMR (500 MHz, DMSO-$d_6$) δ ppm 1.44-1.54 (m, 2H), 1.49 (d, J=6.59 Hz, 6H), 1.92-2.01 (m, 2H), 2.61 (ddd, J=12.49, 10.02, 2.74 Hz, 2H), 2.98 (dt, J=12.69, 4.22 Hz, 2H), 4.50-4.60 (m, 2H), 7.13-7.19 (m, 1H), 7.41 (t, J=8.10 Hz, 1H), 7.61-7.65 (m, 2H), 7.83 (dd, J=8.51, 1.65 Hz, 1H), 8.05 (d, J=8.51 Hz, 1H), 8.11 (s, 1H), 8.15 (s, 1H), 8.48 (s, 1H), 8.59 (s, 1H), 9.11 (s, 1H), 10.80 (s, 1H); ESIMS found for $C_{27}H_{29}N_5O_2$ m/z 456.2 (M+1).

21

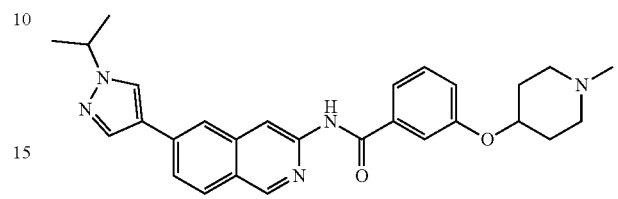

N-(6-(1-Isopropyl-1H-pyrazol-4-yl)isoquinolin-3-yl)-3-((1-methylpiperidin-4-yl)oxy)benzamide 21

Off-white solid (54.6 mg, 0.116 mmol, 92.8% yield). $^1$H NMR (500 MHz, DMSO-$d_6$) δ ppm 1.49 (d, J=6.59 Hz, 6H), 1.63-1.74 (m, 2H), 1.93-2.02 (m, 2H), 2.16-2.26 (m, 2H), 2.19 (s, 3H), 2.58-2.68 (m, 2H), 4.50-4.59 (m, 2H), 7.13-7.21 (m, 1H), 7.42 (t, J=8.23 Hz, 1H), 7.61-7.67 (m, 2H), 7.83 (dd, J=8.51, 1.65 Hz, 1H), 8.06 (d, J=8.51 Hz, 1H), 8.11 (s, 1H), 8.16 (s, 1H), 8.49 (s, 1H), 8.59 (s, 1H), 9.11 (s, 1H), 10.81 (s, 1H); ESIMS found for $C_{28}H_{31}N_5O_2$ m/z 470.3 (M+1).

22

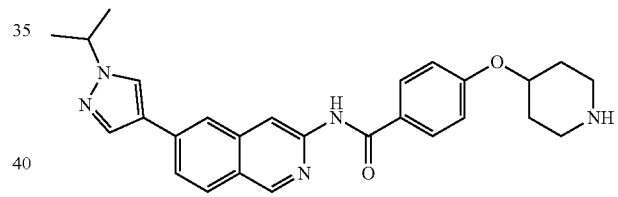

N-(6-(1-Isopropyl-1H-pyrazol-4-yl)isoquinolin-3-yl)-4-(piperidin-4-yloxy)benzamide 22

White solid (52.0 mg, 0.108 mmol, 75.3% yield). $^1$H NMR (499 MHz, DMSO-$d_6$) δ ppm 1.42-1.54 (m, 2H), 1.48 (d, J=6.59 Hz, 6H), 1.91-1.99 (m, 2H), 2.55-2.64 (m, 2H), 2.95 (dt, J=12.83, 4.15 Hz, 2H), 4.50-4.59 (m, 2H), 7.05 (d, J=8.78 Hz, 2H), 7.82 (dd, J=8.51, 1.37 Hz, 1H), 8.02-8.08 (m, 3H), 8.11 (s, 1H), 8.14 (s, 1H), 8.48 (s, 1H), 8.58 (s, 1H), 9.09 (s, 1H), 10.62 (s, 1H); ESIMS found for $C_{27}H_{29}N_5O_2$ m/z 456.2 (M+1).

23

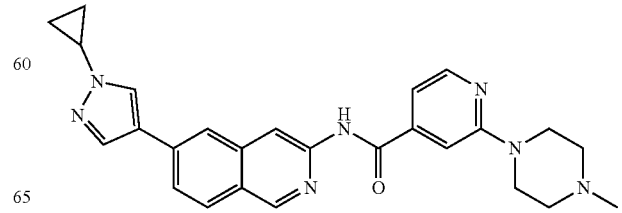

N-(6-(1-Cyclopropyl-1H-pyrazol-4-yl)isoquinolin-3-yl)-2-(4-methylpiperazin-1-yl)isonicotinamide 23

Off-white solid (83.0 mg, 0.183 mmol, 78.0% yield). $^1$H NMR (499 MHz, DMSO-$d_6$) δ ppm 0.99-1.04 (m, 2H), 1.09-1.14 (m, 2H), 2.24 (s, 3H), 2.43 (br t, J=4.94 Hz, 4H), 3.58-3.65 (m, 4H), 3.79 (tt, J=7.38, 3.88 Hz, 1H), 7.12-7.19 (m, 1H), 7.46 (s, 1H), 7.84 (dd, J=8.64, 1.51 Hz, 1H), 8.06 (d, J=8.51 Hz, 1H), 8.11 (s, 1H), 8.16 (s, 1H), 8.26 (d, J=4.94 Hz, 1H), 8.49 (s, 1H), 8.59 (s, 1H), 9.12 (s, 1H), 11.04 (s, 1H); ESIMS found for $C_{26}H_{27}N_7O$ m/z 454.2 (M+1).

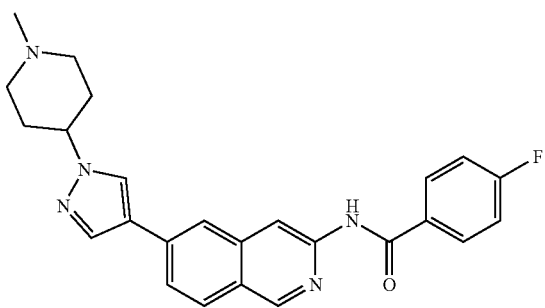

4-Fluoro-N-(6-(1-(1-methylpiperidin-4-yl)-1H-pyrazol-4-yl)isoquinolin-3-yl)benzamide 24

Beige solid (49.0 mg, 0.108 mmol, 53.4% yield). $^1$H NMR (499 MHz, DMSO-$d_6$) δ ppm 1.94-2.13 (m, 6H), 2.22 (s, 3H), 2.88 (br d, J=11.25 Hz, 2H), 4.11-4.21 (m, 1H), 7.36 (t, J=8.92 Hz, 2H), 7.83 (dd, J=8.51, 1.37 Hz, 1H), 8.06 (d, J=8.51 Hz, 1H), 8.12-8.20 (m, 4H), 8.51 (s, 1H), 8.59 (s, 1H), 9.11 (s, 1H), 10.89 (s, 1H); ESIMS found for $C_{25}H_{24}FN_5O$ m/z 430.2 (M+1).

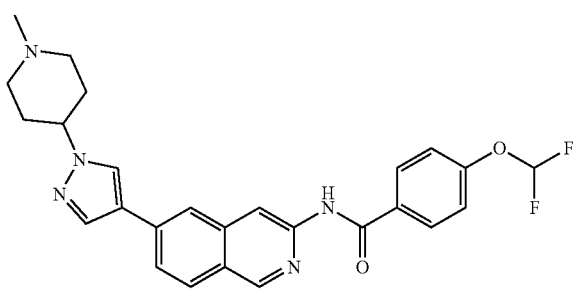

4-(Difluoromethoxy)-N-(6-(1-(1-methylpiperidin-4-yl)-1H-pyrazol-4-yl) isoquinolin-3-yl)benzamide 25

Beige solid (67.0 mg, 0.133 mmol, 52.4% yield). $^1$H NMR (499 MHz, DMSO-$d_6$) δ ppm 1.95-2.11 (m, 6H), 2.22 (s, 3H), 2.88 (br d, J=10.98 Hz, 2H), 4.11-4.20 (m, 1H), 7.40 (t, J=73.95 Hz, 1H), 7.31 (d, J=8.78 Hz, 2H), 7.83 (dd, J=8.51, 1.37 Hz, 1H), 8.06 (d, J=8.51 Hz, 1H), 8.13 (s, 1H), 8.15-8.18 (m, 3H), 8.51 (s, 1H), 8.59 (s, 1H), 9.11 (s, 1H), 10.88 (s, 1H); ESIMS found for $C_{26}H_{25}F_2N_5O_2$ m/z 478.2 (M+1).

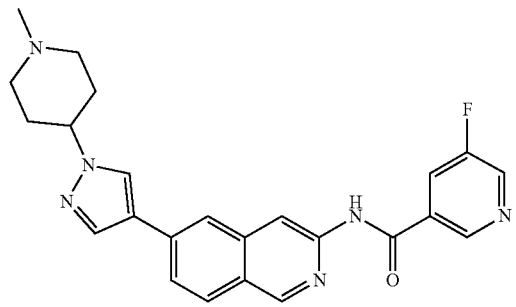

5-Fluoro-N-(6-(1-(1-methylpiperidin-4-yl)-1H-pyrazol-4-yl)isoquinolin-3-yl) nicotinamide 26

White solid (38.0 mg, 0.088 mmol, 75.9% yield). $^1$H NMR (499 MHz, DMSO-$d_6$) δ ppm 1.95-2.11 (m, 6H), 2.22 (s, 3H), 2.88 (br d, J=11.25 Hz, 2H), 4.11-4.20 (m, 1H), 7.86 (dd, J=8.78, 1.37 Hz, 1H), 8.07 (d, J=8.51 Hz, 1H), 8.14 (s, 1H), 8.19 (s, 1H), 8.33 (dt, J=9.47, 2.26 Hz, 1H), 8.52 (s, 1H), 8.60 (s, 1H), 8.80 (d, J=2.74 Hz, 1H), 9.07 (s, 1H), 9.13 (s, 1H), 11.24 (s, 1H); ESIMS found for $C_{24}H_{23}FN_6O$ m/z 431.2 (M+1).

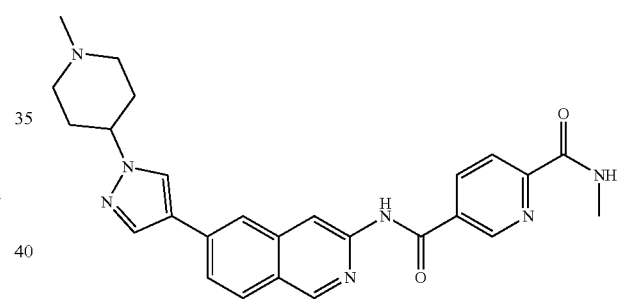

$N^2$-Methyl-$N^5$-(6-(1-(1-methylpiperidin-4-yl)-1H-pyrazol-4-yl)isoquinolin-3-yl)pyridine-2,5-dicarboxamide 27

Beige solid (23.0 mg, 0.049 mmol, 31.4% yield). $^1$H NMR (499 MHz, DMSO-$d_6$) δ ppm 1.96-2.12 (m, 6H), 2.22 (s, 3H), 2.89 (br s, 2H), 2.85 (d, J=4.67 Hz, 3H), 4.12-4.20 (m, 1H), 7.86 (dd, J=8.51, 1.65 Hz, 1H), 8.07 (d, J=8.51 Hz, 1H), 8.13-8.17 (m, 2H), 8.19 (s, 1H), 8.52 (s, 1H), 8.55 (dd, J=7.96, 2.20 Hz, 1H), 8.62 (s, 1H), 8.94 (q, J=4.85 Hz, 1H), 9.13 (s, 1H), 9.21 (d, J=1.92 Hz, 1H), 11.30 (s, 1H); ESIMS found for $C_{26}H_{27}N_7O_2$ m/z 470.2 (M+1).

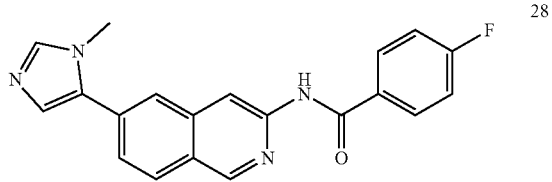 [SMILES: Cn1cncc1-c1ccc2cnc(NC(=O)c3ccc(F)cc3)cc2c1]

4-Fluoro-N-(6-(1-methyl-1H-imidazol-5-yl)isoquinolin-3-yl)benzamide 28

Beige solid (43.0 mg, 0.122 mmol, 46.7% yield). $^1$H NMR (499 MHz, METHANOL-$d_4$) δ ppm 3.86 (s, 3H), 7.28 (t, J=8.78 Hz, 2H), 7.45 (br s, 1H), 7.68 (d, J=8.51 Hz, 1H), 7.94 (br s, 1H), 8.00 (s, 1H), 8.06-8.15 (m, 3H), 8.66 (s, 1H), 9.13 (br s, 1H); ESIMS found for $C_{20}H_{15}FN_4O$ m/z 347.1 (M+1).

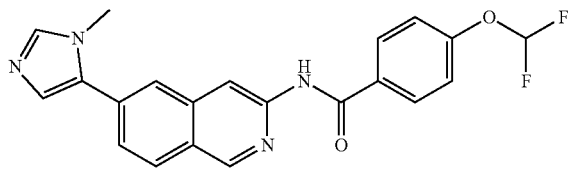

4-(Difluoromethoxy)-N-(6-(1-methyl-1H-imidazol-5-yl)isoquinolin-3-yl)benzamide 29

White solid (16.0 mg, 0.040 mmol, 15.6% yield). $^1$H NMR (499 MHz, DMSO-$d_6$) δ ppm 3.85 (3H, s), 7.41 (1H, t, J=73.70 Hz), 7.31 (1H, s), 7.32 (1H, s), 7.33 (1H, br s), 7.73 (1H, dd, J=8.37, 1.51 Hz), 7.81 (1H, s), 8.09 (1H, s), 8.15 (1H, d, J=8.51 Hz), 8.16-8.17 (1H, m), 8.17-8.21 (1H, m), 8.69 (1H, s), 9.22 (1H, s), 10.96 (1H, s); ESIMS found for $C_{21}H_{16}F_2N_4O_2$ m/z 395.1 (M+1).

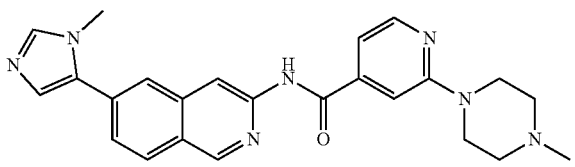

N-(6-(1-Methyl-1H-imidazol-5-yl)isoquinolin-3-yl)-2-(4-methylpiperazin-1-yl)isonicotinamide 37

White solid (102.0 mg, 0.239 mmol, 82.9% yield). $^1$H NMR (500 MHz, DMSO-$d_6$) δ ppm 2.23 (3H, s), 2.38-2.46 (4H, m), 3.55-3.64 (4H, m), 3.85 (3H, s), 7.16 (1H, dd, J=5.08, 1.23 Hz), 7.33 (1H, d, J=1.10 Hz), 7.48 (1H, s), 7.74 (1H, dd, J=8.51, 1.65 Hz), 7.81 (1H, s), 8.10 (1H, d, J=0.82 Hz), 8.15 (1H, d, J=8.51 Hz), 8.24-8.28 (1H, m), 8.70 (1H, s), 9.23 (1H, s), 11.11 (1H, s); ESIMS found for $C_{24}H_{25}N_7O$ m/z 428.2 (M+1).

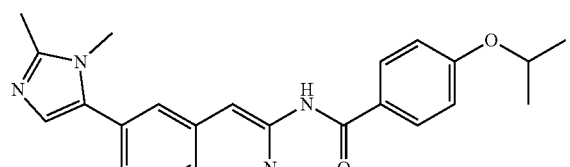

N-(6-(1,2-Dimethyl-1H-imidazol-5-yl)isoquinolin-3-yl)-4-isopropoxybenzamide 40

Light green solid (33.0 mg, 0.082 mmol, 31.7% yield). $^1$H NMR (500 MHz, DMSO-$d_6$) δ ppm 1.31 (d, J=6.04 Hz, 6H), 2.47 (br s, 3H), 3.71 (br s, 3H), 4.75 (dquin, J=12.06, 5.97, 5.97, 5.97, 5.97 Hz, 1H), 7.03 (d, J=9.06 Hz, 2H), 7.32 (br s, 1H), 7.65 (br d, J=8.23 Hz, 1H), 8.02 (br s, 1H), 8.05-8.09 (m, 2H), 8.15 (br d, J=8.51 Hz, 1H), 8.68 (br s, 1H), 9.22 (br s, 1H), 10.71 (br s, 1H); ESIMS found for $C_{24}H_{24}N_4O_2$ m/z 401.2 (M+1).

N-(6-(1,2-Dimethyl-1H-imidazol-5-yl)isoquinolin-3-yl)-4-(piperidin-4-yloxy)benzamide 45

White solid (30.0 mg, 0.065 mmol, 41.1% yield). $^1$H NMR (499 MHz, DMSO-$d_6$) δ ppm 1.42-1.53 (m, 2H), 1.91-1.98 (m, 2H), 2.40 (s, 3H), 2.55-2.63 (m, 2H), 2.95 (dt, J=12.62, 4.12 Hz, 2H), 3.68 (s, 3H), 4.49-4.58 (m, 1H), 7.06 (d, J=8.78 Hz, 2H), 7.13 (s, 1H), 7.64 (dd, J=8.51, 1.65 Hz, 1H), 7.97 (s, 1H), 8.06 (d, J=8.78 Hz, 2H), 8.12 (d, J=8.51 Hz, 1H), 8.66 (s, 1H), 9.19 (s, 1H), 10.69 (s, 1H); ESIMS found for $C_{26}H_{27}N_5O_2$ m/z 442.1 (M+1).

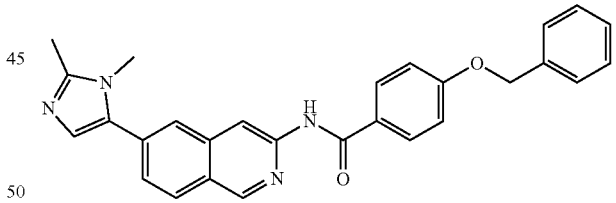

4-(Benzyloxy)-N-(6-(1,2-dimethyl-1H-imidazol-5-yl)isoquinolin-3-yl)benzamide 47

Beige solid (114.0 mg, 0.254 mmol, 64.8% yield). $^{11}$H NMR (499 MHz, DMSO-$d_6$) δ ppm 2.41 (s, 3H), 3.69 (s, 3H), 5.22 (s, 2H), 7.12-7.19 (m, 3H), 7.31-7.38 (m, 1H), 7.42 (t, J=7.41 Hz, 2H), 7.48 (d, J=7.14 Hz, 2H), 7.64 (dd, J=8.64, 1.51 Hz, 1H), 7.99 (s, 1H), 8.10 (d, J=8.78 Hz, 2H), 8.13 (d, J=8.51 Hz, 1H), 8.67 (s, 1H), 9.20 (s, 1H), 10.73 (s, 1H); ESIMS found for $C_{28}H_{24}N_4O_2$ m/z 449.2 (M+1).

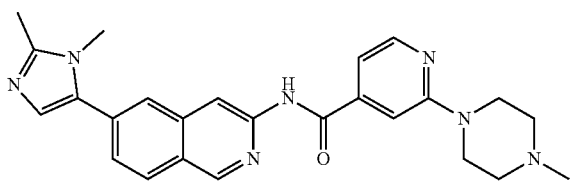

N-(6-(1,2-Dimethyl-1H-imidazol-5-yl)isoquinolin-3-yl)-2-(4-methylpiperazin-1-yl)isonicotinamide 49

Beige solid (12.0 mg, 0.027 mmol, 11.4% yield). $^1$H NMR (499 MHz, DMSO-d$_6$) δ ppm 2.24 (3H, s), 2.40 (3H, s), 2.41-2.44 (4H, m), 3.53-3.64 (4H, m), 3.68 (3H, s), 7.14 (1H, s), 7.16 (1H, dd, J=5.21, 1.10 Hz), 7.47 (1H, s), 7.67 (1H, dd, J=8.51, 1.65 Hz), 8.00 (1H, s), 8.14 (1H, d, J=8.51 Hz), 8.26 (1H, d, J=4.94 Hz), 8.67 (1H, s), 9.22 (1H, s), 11.09 (1H, s); ESIMS found for C$_{25}$H$_{27}$N$_7$O m/z 442.0 (M+1).

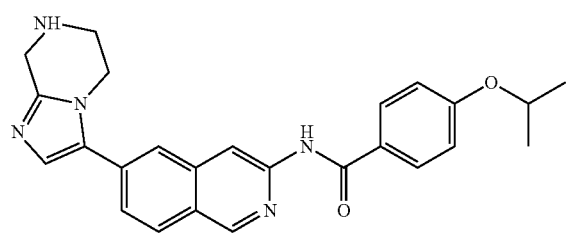

4-Isopropoxy-N-(6-(5,6,7,8-tetrahydroimidazo[1,2-a]pyrazin-3-yl) isoquinolin-3-yl) benzamide 52

Beige solid (20.0 mg, 0.044 mmol, 27.0% yield). $^1$H NMR (499 MHz, DMSO-d$_6$) δ ppm 1.31 (d, J=6.04 Hz, 6H), 2.79 (br s, 1H), 3.08 (br t, J=5.21 Hz, 2H), 3.96 (s, 2H), 4.13 (t, J=5.21 Hz, 2H), 4.75 (spt, J=6.04 Hz, 1H), 7.03 (d, J=8.78 Hz, 2H), 7.31 (s, 1H), 7.69 (dd, J=8.64, 1.51 Hz, 1H), 8.01 (s, 1H), 8.07 (d, J=8.78 Hz, 2H), 8.10 (d, J=8.78 Hz, 1H), 8.66 (s, 1H), 9.17 (s, 1H), 10.67 (s, 1H); ESIMS found for C$_{25}$H$_{25}$N$_5$O$_2$ m/z 428.2 (M+1).

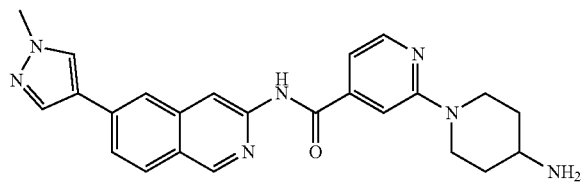

4-(4-Aminopiperidin-1-yl)-N-(6-(1-methyl-1H-pyrazol-4-yl)isoquinolin-3-yl)isonicotinamide 53

Off-white solid (195.0 mg, 0.456 mmol, 81.9% yield). $^1$H NMR (499 MHz, DMSO-d$_6$) δ ppm 1.19-1.29 (2H, m), 1.76-1.85 (2H, m), 2.80-2.90 (1H, m), 2.93-3.04 (2H, m), 3.91 (3H, s), 4.32 (2H, br d, J=13.17 Hz), 7.10 (1H, dd, J=5.21, 1.10 Hz), 7.45 (1H, s), 7.81 (1H, dd, J=8.51, 1.65 Hz), 8.07 (1H, d, J=8.78 Hz), 8.11 (1H, s), 8.13 (1H, s), 8.23 (1H, d, J=4.94 Hz), 8.38 (1H, s), 8.59 (1H, s), 9.12 (1H, s), 11.03 (1H, br s); ESIMS found for C$_{24}$H$_{25}$N$_7$O m/z 428.2 (M+1).

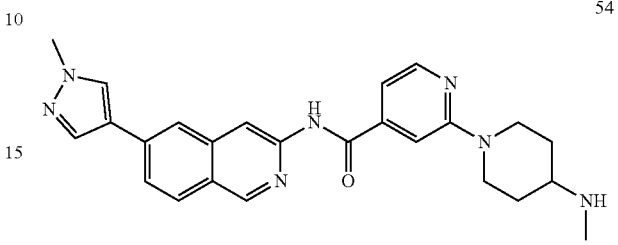

N-(6-(1-Methyl-1H-pyrazol-4-yl)isoquinolin-3-yl)-2-(4-(methylamino) piperidin-1-yl)isonicotinamide 54

White solid (69.0 mg, 0.156 mmol, 41.0% yield). $^1$H NMR (499 MHz, DMSO-d$_6$) δ ppm 1.17-1.31 (m, 2H), 1.88 (br d, J=10.43 Hz, 2H), 2.31 (s, 3H), 2.52-2.60 (m, 1H), 3.01 (br t, J=11.11 Hz, 2H), 3.91 (s, 3H), 4.29 (br d, J=13.17 Hz, 2H), 7.10 (d, J=5.21 Hz, 1H), 7.44 (s, 1H), 7.81 (d, J=8.51 Hz, 1H), 8.07 (d, J=8.51 Hz, 1H), 8.11 (s, 1H), 8.13 (s, 1H), 8.23 (d, J=4.94 Hz, 1H), 8.38 (s, 1H), 8.59 (s, 1H), 9.12 (s, 1H), 11.03 (br s, 1H); ESIMS found for C$_{25}$H$_{27}$N$_7$O m/z 442.2 (M+1).

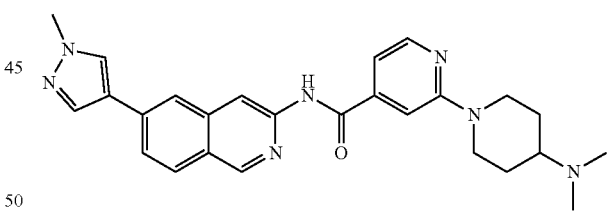

2-(4-(Dimethylamino)piperidin-1-yl)-N-(6-(1-methyl-1H-pyrazol-4-yl) isoquinolin-3-yl)isonicotinamide 55

Off-white solid (30.0 mg, 0.066 mmol, 31.3% yield). $^1$H NMR (499 MHz, DMSO-d$_6$) δ ppm 1.37 (2H, qd, J=11.94, 3.70 Hz), 1.83 (2H, br d, J=11.25 Hz), 2.19 (6H, s), 2.30-2.40 (1H, m), 2.83-2.94 (2H, m), 3.91 (3H, s), 4.44 (2H, br d, J=13.17 Hz), 7.11 (1H, dd, J=5.21, 1.10 Hz), 7.45 (1H, s), 7.81 (1H, dd, J=8.51, 1.65 Hz), 8.07 (1H, d, J=8.51 Hz), 8.11 (1H, s), 8.13 (1H, s), 8.24 (1H, d, J=5.21 Hz), 8.38 (1H, s), 8.59 (1H, s), 9.12 (1H, s), 11.03 (1H, s); ESIMS found for C$_{26}$H$_{29}$N$_7$O m/z 456.2 (M+1).

56

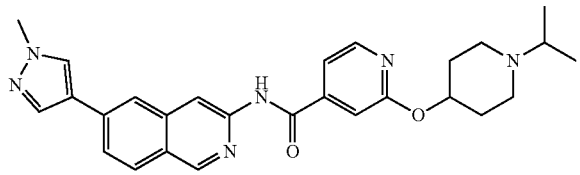

2-((1-Isopropylpiperidin-4-yl)oxy)-N-(6-(1-methyl-1H-pyrazol-4-yl) isoquinolin-3-yl)isonicotinamide 56

White solid (20.0 mg, 0.043 mmol, 12.1% yield). $^1$H NMR (499 MHz, DMSO-$d_6$) δ ppm 0.99 (d, J=6.31 Hz, 6H), 1.61-1.71 (m, 2H), 1.96-2.05 (m, 2H), 2.28-2.39 (m, 2H), 2.68-2.79 (m, 3H), 3.91 (s, 3H), 4.98-5.07 (m, 1H), 7.35 (s, 1H), 7.50 (dd, J=5.35, 1.51 Hz, 1 H), 7.82 (dd, J=8.64, 1.51 Hz, 1H), 8.06 (d, J=8.51 Hz, 1H), 8.11 (d, J=0.82 Hz, 1H), 8.15 (s, 1H), 8.31 (d, J=5.76 Hz, 1H), 8.38 (s, 1H), 8.57 (s, 1H), 9.12 (s, 1H), 11.06 (s, 1H); ESIMS found for $C_{27}H_{30}N_6O_2$ m/z 471.2 (M+1).

57

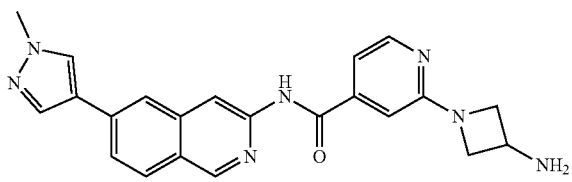

2-(3-Aminoazetidin-1-yl)-N-(6-(1-methyl-1H-pyrazol-4-yl)isoquinolin-3-yl) isonicotinamide 57

Off-white solid (200.4 mg, 0.502 mmol, 65.7% yield). $^1$H NMR (499 MHz, DMSO-$d_6$) δ ppm 2.17 (br s, 2H), 3.62 (dd, J=8.10, 5.90 Hz, 2H), 3.80-3.89 (m, 1H), 4.19 (t, J=7.68 Hz, 2H), 7.01 (s, 1H), 7.14 (dd, J=5.21, 1.37 Hz, 1H), 7.81 (dd, J=8.64, 1.51 Hz, 1H), 8.07 (d, J=8.51 Hz, 1H), 8.11 (s, 1H), 8.13 (s, 1H), 8.19 (d, J=5.21 Hz, 1H), 8.38 (s, 1H), 8.58 (s, 1H), 9.12 (s, 1H), 10.97 (s, 1H); ESIMS found for $C_{22}H_{21}N_7O$ m/z 400.2 (M+1).

59

2-(3-(Dimethylamino)azetidin-1-yl)-N-(6-(1-methyl-1H-pyrazol-4-yl) isoquinolin-3-yl)isonicotinamide 59

Off-white solid (286.7 mg, 0.671 mmol, 77.6% yield). $^1$H NMR (499 MHz, DMSO-$d_6$) δ ppm 2.14 (6H, s), 3.19-3.26 (1H, m), 3.81 (2H, dd, J=8.51, 5.21 Hz), 3.91 (3H, s), 4.04-4.12 (2H, m), 7.03 (1H, s), 7.15 (1H, dd, J=5.21, 1.65 Hz), 7.81 (1H, dd, J=8.51, 1.65 Hz), 8.06 (1H, d, J=8.78 Hz), 8.10 (1H, d, J=0.82 Hz), 8.13 (1H, s), 8.21 (1H, d, J=5.21 Hz), 8.37 (1H, s), 8.57 (1H, s), 9.12 (1H, s), 10.92 (1H, s); ESIMS found for $C_{24}H_{25}N_7O$ m/z 428.0 (M+1).

60

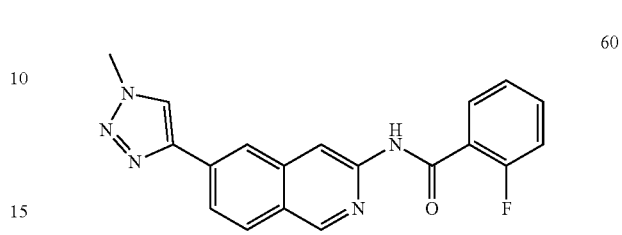

1-Fluoro-N-(6-(1-methyl-1H-1,2,3-triazol-4-yl)iso-quinolin-3-yl)benzamide 60

Off-white solid (18.0 mg, 0.052 mmol, 13.0% yield). $^1$H NMR (499 MHz, DMSO-$d_6$) δ ppm 4.15 (s, 3H), 7.32-7.39 (m, 2H), 7.55-7.65 (m, 1H), 7.76 (td, J=7.55, 1.65 Hz, 1H), 8.08 (dd, J=8.51, 1.65 Hz, 1H), 8.16 (d, J=8.78 Hz, 1H), 8.39 (s, 1H), 8.64 (s, 1H), 8.75 (s, 1H), 9.17 (s, 1H), 10.88 (s, 1H); ESIMS found for $C_{19}H_{14}FN_5O$ m/z 348.2 (M+1).

61

N-(6-(1-Methyl-1H-pyrazol-4-yl)isoquinolin-3-yl)-2-morpholinoisonicotinamide 61

Tan solid (72.9 mg, 0.176 mmol, 60.9% yield). $^1$H NMR (499 MHz, DMSO-$d_6$) δ ppm 3.54-3.61 (m, 4H), 3.71-3.77 (m, 4H), 3.91 (s, 3H), 7.21 (dd, J=5.08, 1.23 Hz, 1H), 7.47 (s, 1H), 7.81 (dd, J=8.51, 1.65 Hz, 1H), 8.07 (d, J=8.78 Hz, 1H), 8.11 (s, 1H), 8.14 (s, 1H), 8.29 (d, J=5.21 Hz, 1H), 8.38 (s, 1H), 8.60 (s, 1H), 9.13 (s, 1H), 11.05 (s, 1H); ESIMS found for $C_{23}H_{22}N_6O_2$ m/z 415.2 (M+1).

62

2-((2-(Dimethylamino)ethyl)amino)-N-(6-(1-methyl-1H-pyrazol-4-yl) isoquinolin-3-yl)isonicotinamide 62

Tan solid (79.2 mg, 0.191 mmol, 66.0% yield). $^1$H NMR (499 MHz, DMSO-$d_6$) δ ppm 2.19 (s, 6H), 2.43 (t, J=6.72

Hz, 2H), 3.35-3.43 (m, 2H), 3.91 (s, 3H), 6.61 (t, J=5.49 Hz, 1H), 7.02 (dd, J=5.21, 1.37 Hz, 1H), 7.04 (s, 1H), 7.81 (dd, J=8.51, 1.65 Hz, 1H), 8.06 (d, J=8.78 Hz, 1H), 8.08-8.12 (m, 2H), 8.14 (s, 1H), 8.38 (s, 1H), 8.56 (s, 1H), 9.11 (s, 1H), 10.80 (s, 1H); ESIMS found for $C_{23}H_{25}N_7O$ m/z 416.2 (M+1).

63

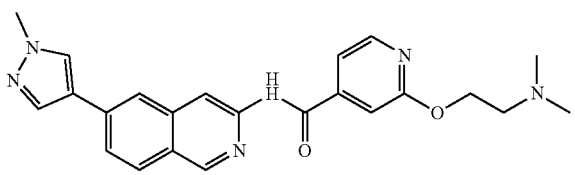

2-(2-(Dimethylamino)ethoxy)-N-(6-(1-methyl-1H-pyrazol-4-yl)isoquinolin-3-yl)isonicotinamide 63

Tan solid (84.1 mg, 0.202 mmol, 70.1% yield). $^1$H NMR (499 MHz, DMSO-$d_6$) δ ppm 2.23 (s, 6H), 2.65 (t, J=5.76 Hz, 2H), 3.91 (s, 3H), 4.41 (t, J=5.90 Hz, 2H), 7.39 (d, J=0.82 Hz, 1H), 7.53 (dd, J=5.21, 1.37 Hz, 1H), 7.82 (dd, J=8.51, 1.65 Hz, 1H), 8.07 (d, J=8.51 Hz, 1H), 8.11 (s, 1H), 8.15 (s, 1H), 8.33 (d, J=5.21 Hz, 1H), 8.38 (s, 1H), 8.58 (s, 1H), 9.12 (s, 1H), 11.08 (s, 1H); ESIMS found for $C_{23}H_{24}N_6O_2$ m/z 417.2 (M+1).

64

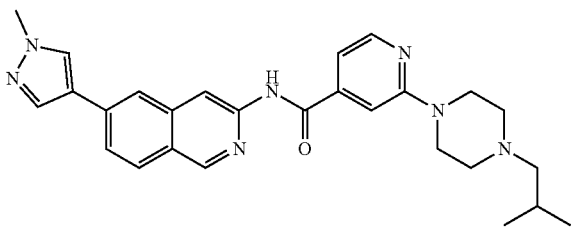

2-(4-Isobutylpiperazin-1-yl)-N-(6-(1-methyl-1H-pyrazol-4-yl)isoquinolin-3-yl)isonicotinamide 64

Off-white solid (61.3 mg, 0.131 mmol, 45.2% yield). $^1$H NMR (499 MHz, DMSO-$d_6$) δ ppm 0.90 (d, J=6.59 Hz, 6H), 1.83 (dquin, J=13.48, 6.85, 6.85, 6.85, 6.85 Hz, 1H), 2.09 (d, J=7.41 Hz, 2H), 2.45 (br t, J=4.94 Hz, 4H), 3.57-3.64 (m, 4H), 3.91 (s, 3H), 7.12-7.18 (m, 1H), 7.45 (s, 1H), 7.81 (dd, J=8.51, 1.37 Hz, 1H), 8.07 (d, J=8.51 Hz, 1H), 8.11 (s, 1H), 8.14 (s, 1H), 8.25 (d, J=5.21 Hz, 1H), 8.38 (s, 1H), 8.59 (s, 1H), 9.12 (s, 1H), 11.04 (s, 1H); ESIMS found for $C_{27}H_{31}N_7O$ m/z 470.2 (M+1).

65

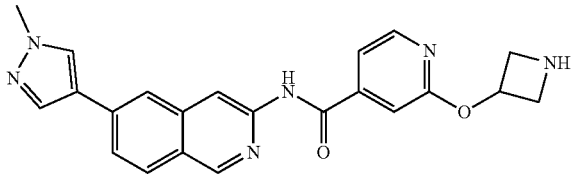

2-(Azetidin-3-yloxy)-N-(6-(1-methyl-1H-pyrazol-4-yl)isoquinolin-3-yl) isonicotinamide 65

Off-white solid (64.9 mg, 0.162 mmol, 23.1% yield). $^1$H NMR (499 MHz, DMSO-$d_6$) δ ppm 3.51-3.58 (m, 2H), 3.77 (br t, J=7.68 Hz, 2H), 3.91 (s, 3H), 5.39 (quin, J=6.24 Hz, 1H), 7.40 (s, 1H), 7.54 (dd, J=5.21, 1.37 Hz, 1H), 7.82 (dd, J=8.51, 1.37 Hz, 1H), 8.07 (d, J=8.51 Hz, 1H), 8.11 (s, 1H), 8.15 (s, 1H), 8.30 (d, J=5.21 Hz, 1H), 8.38 (s, 1H), 8.58 (s, 1H), 9.13 (s, 1H), 11.09 (br s, 1H); ESIMS found for $C_{22}H_{20}N_6O_2$ m/z 401.2 (M+1).

66

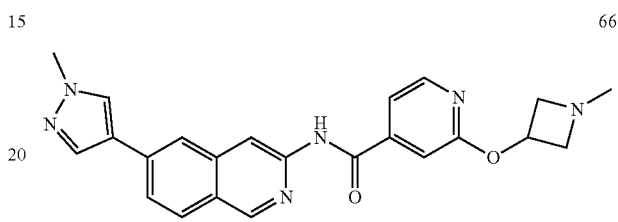

N-(6-(1-Methyl-1H-pyrazol-4-yl)isoquinolin-3-yl)-2-((1-methylazetidin-3-yl)oxy)isonicotinamide 66

Off-white solid (144.0 mg, 0.347 mmol, 48.1% yield). $^1$H NMR (499 MHz, DMSO-$d_6$) δ ppm 2.30 (3H, s), 2.99-3.05 (2H, m), 3.69-3.77 (2H, m), 3.91 (3H, s), 5.16 (1H, quin, J=5.76 Hz), 7.40 (1H, d, J=1.37 Hz), 7.55 (1H, dd, J=5.21, 1.37 Hz), 7.82 (1H, dd, J=8.51, 1.65 Hz), 8.07 (1H, d, J=8.78 Hz), 8.11 (1H, s), 8.15 (1H, s), 8.30 (1H, d, J=5.49 Hz), 8.38 (1H, s), 8.58 (1H, s), 9.12 (1H, s), 11.09 (1H, s); ESIMS found for $C_{23}H_{22}N_6O_2$ m/z 415.0 (M+1).

67

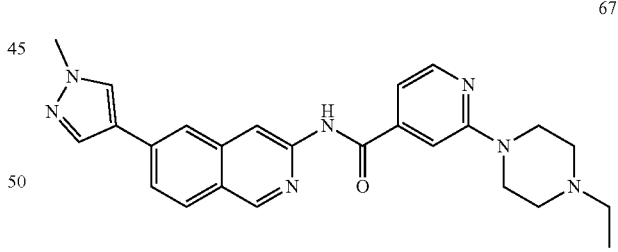

2-(4-Ethylpiperazin-1-yl)-N-(6-(1-methyl-1H-pyrazol-4-yl)isoquinolin-3-yl) isonicotinamide 67

Tan solid (98.3 mg, 0.223 mmol, 77.1% yield). $^1$H NMR (499 MHz, DMSO-$d_6$) δ ppm 1.05 (3H, t, J=7.27 Hz), 2.38 (2H, q, J=7.14 Hz), 2.46-2.49 (4H, m), 3.57-3.64 (4H, m), 3.91 (3H, s), 7.16 (1H, dd, J=4.94, 1.10 Hz), 7.46 (1H, s), 7.81 (1H, dd, J=8.51, 1.65 Hz), 8.07 (1H, d, J=8.51 Hz), 8.11 (1H, s), 8.14 (1H, s), 8.26 (1H, d, J=5.21 Hz), 8.38 (1H, s), 8.59 (1H, s), 9.12 (1H, s), 11.04 (1H, s) ESIMS found for $C_{25}H_{27}N_7O$ m/z 442.2 (M+1).

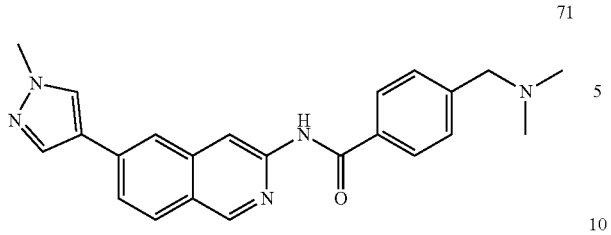

71

4-((Dimethylamino)methyl)-N-(6-(1-methyl-1H-pyrazol-4-yl)isoquinolin-3-yl)benzamide 71

Off-white solid (15.2 mg, 0.039 mmol, 14.1% yield). $^1$H NMR (499 MHz, DMSO-$d_6$) δ ppm 2.19 (6H, s), 3.49 (2H, s), 3.91 (3H, s), 7.44 (2H, d, J=8.23 Hz), 7.79 (1H, dd, J=8.51, 1.65 Hz), 8.05 (3H, d, J=8.23 Hz), 8.10 (1H, s), 8.12 (1H, s), 8.36 (1H, s), 8.59 (1H, s), 9.11 (1H, s), 10.70 (1H, s); ESIMS found for $C_{23}H_{23}N_5O$ m/z 386.0 (M+1).

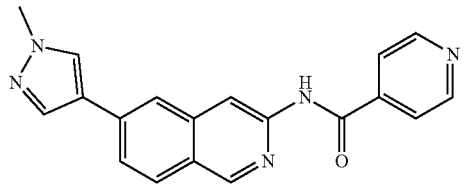

76

N-(6-(1-Methyl-1H-pyrazol-4-yl)isoquinolin-3-yl) isonicotinamide 76

Brown solid (80 mg, 0.243 mmol, 41.9% yield). $^1$H NMR (499 MHz, DMSO-$d_6$) δ ppm 3.91 (3H, s), 7.84 (1H, dd, J=8.51, 1.65 Hz), 8.09 (1H, d, J=8.51 Hz), 8.12 (1H, s), 8.16-8.21 (3H, m), 8.39 (1H, s), 8.60 (1H, s), 8.92 (2H, d, J=6.31 Hz), 9.16 (1H, s), 11.38 (1H, s); ESIMS found for $C_{19}H_{15}N_5O$ m/z 330.1 (M+1).

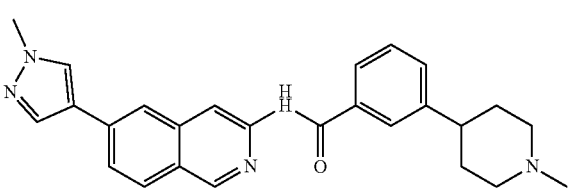

72

N-(6-(1-Methyl-1H-pyrazol-4-yl)isoquinolin-3-yl)-3-(1-methylpiperidin-4-yl)benzamide 72

Off-white solid (78.0 mg, 0.174 mmol, 75.6% yield). $^1$H NMR (499 MHz, DMSO-$d_6$) δ ppm 1.72-1.84 (4H, m), 2.00 (2H, td, J=10.91, 3.16 Hz), 2.22 (3H, s), 2.52-2.60 (1H, m), 2.90 (2H, br d, J=11.25 Hz), 3.91 (3H, s), 7.40-7.51 (2H, m), 7.79 (1H, dd, J=8.51, 1.37 Hz), 7.89 (1H, br d, J=7.41 Hz), 8.01 (1H, s), 8.05 (1H, d, J=8.51 Hz), 8.10 (1H, s), 8.12 (1H, s), 8.37 (1H, s), 8.59 (1H, s), 9.11 (1H, s), 10.80 (1H, s); ESIMS found for $C_{26}H_{27}N_5O$ m/z 426.05 (M+1).

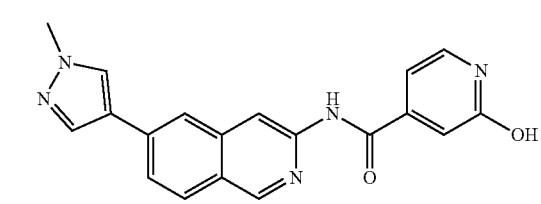

78

2-Hydroxy-N-(6-(1-methyl-1H-pyrazol-4-yl)isoquinolin-3-yl) isonicotinamide 78

Off-white solid (89.0 mg, 0.258 mmol, 21.0% yield). $^1$H NMR (499 MHz, DMSO-$d_6$) δ ppm 3.91 (3H, s), 6.62 (1H, dd, J=6.72, 1.51 Hz), 6.92 (1H, d, J=1.10 Hz), 7.50 (1H, d, J=6.59 Hz), 7.81 (1H, dd, J=8.51, 1.37 Hz), 8.06 (1H, d, J=8.51 Hz), 8.10 (1H, s), 8.14 (1H, s), 8.37 (1H, s), 8.53 (1H, s), 9.11 (1H, s), 10.97 (1H, s), 11.81 (1H, br s); ESIMS found for $C_{19}H_{15}N_5O_2$ m/z 345.9 (M+1).

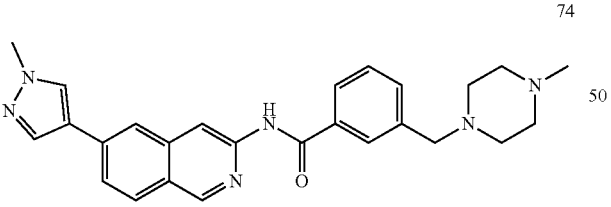

74

N-(6-(1-Methyl-1H-pyrazol-4-yl)isoquinolin-3-yl)-3-((4-methylpiperazin-1-yl)methyl)benzamide 74

Off-white solid (65.0 mg, 0.196 mmol, 33.1% yield). $^1$H NMR (499 MHz, DMSO-$d_6$) δ ppm 2.16 (3H, s), 2.27-2.38 (4H, m), 2.38-2.45 (4H, m), 3.54 (2H, s), 3.92 (3H, s), 7.44-7.50 (1H, m), 7.50-7.55 (1H, m), 7.79 (1H, dd, J=8.64, 1.51 Hz), 7.96 (1H, br d, J=7.68 Hz), 7.98 (1H, s), 8.06 (1H, d, J=8.51 Hz), 8.10 (1H, s), 8.12 (1H, s), 8.37 (1H, s), 8.58 (1H, s), 9.11 (1H, s), 10.74 (1H, s); ESIMS found for $C_{26}H_{28}N_6O$ m/z 441.0 (M+1).

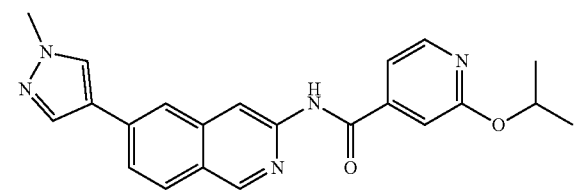

80

2-Isopropoxy-N-(6-(1-methyl-1H-pyrazol-4-yl)isoquinolin-3-yl) isonicotinamide 80

Off-white solid (49.2 mg, 0.127 mmol, 38.0% yield). $^1$H NMR (499 MHz, DMSO-$d_6$) δ ppm 1.33 (6H, d, J=6.31 Hz), 3.91 (3H, s), 5.30 (1H, spt, J=6.17 Hz), 7.30 (1H, s), 7.50 (1H, dd, J=5.35, 1.51 Hz), 7.82 (1H, dd, J=8.51, 1.65 Hz), 8.06 (1H, d, J=8.51 Hz), 8.11 (1H, s), 8.15 (1H, s), 8.32 (1H, d, J=5.21 Hz), 8.38 (1H, s), 8.58 (1H, s), 9.12 (1H, s), 11.05 (1H, s); ESIMS found for $C_{22}H_{21}N_5O_2$ m/z 388.2 (M+1).

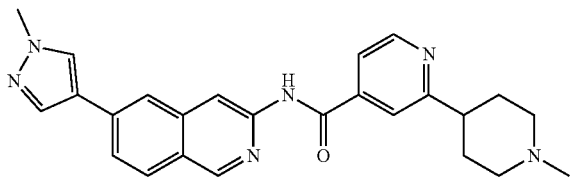

N-(6-(1-Methyl-1H-pyrazol-4-yl)isoquinolin-3-yl)-2-(1-methylpiperidin-4-yl)isonicotinamide 84

Off-white solid (100.0 mg, 0.235 mmol, 49.8% yield). $^1$H NMR (500 MHz, DMSO-d$_6$) δ ppm 1.77-1.92 (4H, m), 2.00 (2H, td, J=11.60, 2.61 Hz), 2.21 (3H, s), 2.72 (1H, tt, J=11.49, 4.15 Hz), 2.85-2.93 (2H, m), 3.91 (3H, s), 7.76 (1H, dd, J=5.21, 1.65 Hz), 7.82 (1H, dd, J=8.51, 1.65 Hz), 7.91 (1H, s), 8.07 (1H, d, J=8.51 Hz), 8.12 (1H, d, J=0.82 Hz), 8.15 (1H, d, J=0.82 Hz), 8.39 (1H, s), 8.60 (1H, s), 8.66-8.71 (1H, m), 9.13 (1H, s), 11.17 (1H, s); ESIMS found for C$_{25}$H$_{26}$N$_6$O m/z 427.0 (M+1).

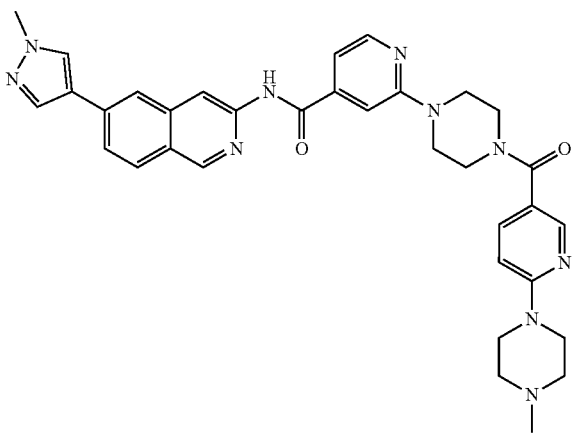

N-(6-(1-Methyl-1H-pyrazol-4-yl)isoquinolin-3-yl)-2-(4-(6-(4-methylpiperazin-1-yl)nicotinoyl)piperazin-1-yl)isonicotinamide 86

Off-white solid (30.0 mg, 0.049 mmol, 89.4% yield). $^1$H NMR (499 MHz, Solvent) δ ppm 2.21 (3H, s), 2.36-2.41 (4H, m), 3.42 (2H, br s), 3.49-3.56 (4H, m), 3.64 (2H, br s), 3.75 (4H, br s), 3.91 (3H, s), 6.64 (1H, dd, J=5.08, 0.96 Hz), 6.82 (1H, s), 7.20 (1H, dd, J=5.21, 1.10 Hz), 7.49 (1H, s), 7.81 (1H, dd, J=8.64, 1.51 Hz), 8.07 (1H, d, J=8.51 Hz), 8.11 (1H, d, J=0.82 Hz), 8.14 (1H, s), 8.18 (1H, d, J=4.94 Hz), 8.29 (1H, d, J=5.21 Hz), 8.38 (1H, s), 8.60 (1H, s), 9.13 (1H, s), 11.06 (1H, s); ESIMS found for C$_{34}$H$_{36}$N$_{10}$O$_2$ m/z 617.3 (M+1).

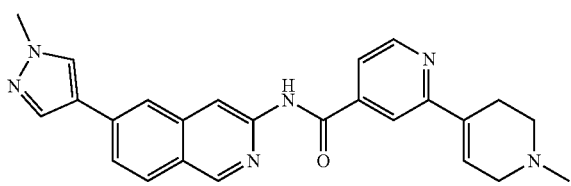

1'-Methyl-N-(6-(1-methyl-1H-pyrazol-4-yl)isoquinolin-3-yl)-1',2',3',6'-tetrahydro-[2,4'-bipyridine]-4-carboxamide 85

Off-white solid (89.0 mg, 0.210 mmol, 17.1% yield). $^1$H NMR (499 MHz, DMSO-d$_6$) δ ppm 2.31 (3H, s), 2.57-2.63 (2H, m), 2.63-2.70 (2H, m), 3.11 (2H, br d, J=3.02 Hz), 3.91 (3H, s), 6.89 (1H, t, J=3.43 Hz), 7.78 (1H, dd, J=4.94, 1.37 Hz), 7.82 (1H, dd, J=8.51, 1.65 Hz), 8.08 (1H, d, J=8.51 Hz), 8.11 (1H, s), 8.16 (2H, d, J=6.04 Hz), 8.38 (1H, s), 8.61 (1H, s), 8.71 (1H, d, J=4.94 Hz), 9.14 (1H, s), 11.23 (1H, s); ESIMS found for C$_{25}$H$_{24}$N$_6$O m/z 425.0 (M+1).

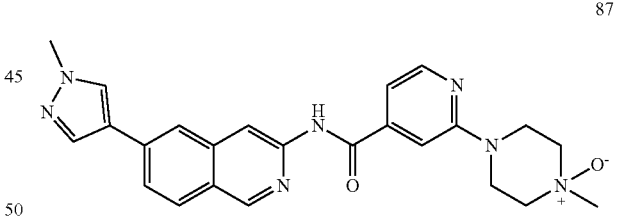

1-Methyl-4-(4-((6-(1-methyl-1H-pyrazol-4-yl)isoquinolin-3-yl)carbamoyl)pyridin-2-yl)piperazine 1-oxide 87

White solid (65.0 mg, 0.147 mmol, 57.5% yield). $^1$H NMR (499 MHz, DMSO-d$_6$) δ ppm 2.99 (2H, br d, J=10.70 Hz), 3.11 (3H, s), 3.41 (2H, td, J=11.53, 3.29 Hz), 3.61-3.72 (2H, m), 3.91 (3H, s), 4.25 (2H, br d, J=13.17 Hz), 7.20 (1H, dd, J=5.08, 1.23 Hz), 7.55 (1H, s), 7.82 (1H, dd, J=8.51, 1.65 Hz), 8.07 (1H, d, J=8.51 Hz), 8.11 (1H, s), 8.14 (1H, s), 8.29 (1H, d, J=5.21 Hz), 8.38 (1H, s), 8.60 (1H, s), 9.13 (1H, s), 11.10 (1H, s); ESIMS found for C$_{24}$H$_{25}$N$_7$O$_2$ m/z 444.2 (M+1).

88

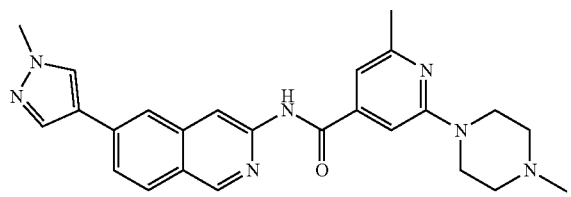

2-Methyl-N-(6-(1-methyl-1H-pyrazol-4-yl)isoquinolin-3-yl)-6-(4-methylpiperazin-1-yl)isonicotinamide 88

Brown solid (33.2 mg, 0.075 mmol, 26.8% yield). $^1$H NMR (499 MHz, DMSO-d$_6$) δ ppm 2.23 (3H, s), 2.39 (3H, s), 2.40-2.44 (4H, m), 3.54-3.62 (4H, m), 3.91 (3H, s), 7.04 (1H, s), 7.26 (1H, s), 7.81 (1H, dd, J=8.51, 1.65 Hz), 8.06 (1H, d, J=8.51 Hz), 8.11 (1H, s), 8.14 (1H, d, J=0.82 Hz), 8.38 (1H, s), 8.58 (1H, s), 9.12 (1H, s), 10.94 (1H, s); ESIMS found for C$_{25}$H$_{27}$N$_7$O m/z 442.2 (M+1).

89

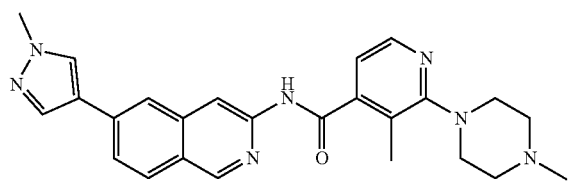

3-Methyl-N-(6-(1-methyl-1H-pyrazol-4-yl)isoquinolin-3-yl)-2-(4-methylpiperazin-1-yl)isonicotinamide 89

Brown solid (18.8 mg, 0.043 mmol, 11.2% yield). $^1$H NMR (499 MHz, DMSO-d$_6$) δ ppm 2.24 (3H, s), 2.29 (3H, s), 2.45-2.54 (4H, m), 3.09 (4H, br s), 3.91 (3H, s), 7.08 (1H, d, J=4.94 Hz), 7.80 (1H, dd, J=8.51, 1.65 Hz), 8.04 (1H, d, J=8.78 Hz), 8.11 (1H, s), 8.16 (1H, s), 8.21 (1H, d, J=4.94 Hz), 8.38 (1H, s), 8.58 (1H, s), 9.07 (1H, s), 11.00 (1H, s); ESIMS found for C$_{25}$H$_{27}$N$_7$O m/z 442.2 (M+1).

90

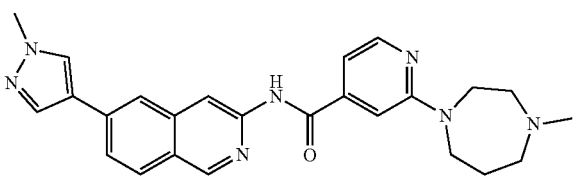

2-(4-Methyl-1,4-diazepan-1-yl)-N-(6-(1-methyl-1H-pyrazol-4-yl) isoquinolin-3-yl)isonicotinamide 90

Off-white solid (82.0 mg, 0.186 mmol, 32.3% yield). $^1$H NMR (499 MHz, DMSO-d$_6$) δ ppm 1.93 (2H, quin, J=5.76 Hz), 2.27 (3H, s), 2.48 (2H, br s), 2.59-2.67 (2H, m), 3.69 (2H, t, J=6.17 Hz), 3.78-3.85 (2H, m), 3.91 (3H, s), 7.05 (1H, dd, J=5.08, 0.96 Hz), 7.21 (1H, s), 7.81 (1H, dd, J=8.51, 1.65 Hz), 8.07 (1H, d, J=8.78 Hz), 8.11 (1H, s), 8.13 (1H, s), 8.20 (1H, d, J=4.94 Hz), 8.38 (1H, s), 8.59 (1H, s), 9.12 (1H, s), 11.02 (1H, s); ESIMS found for C$_{25}$H$_{27}$N$_7$O m/z 442.2 (M+1).

91

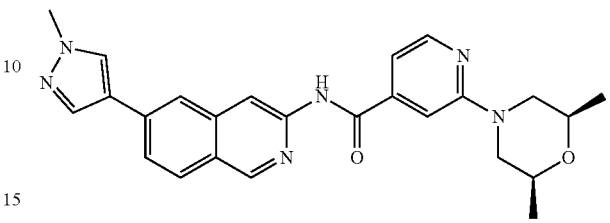

2-((2S,6R)-2,6-Dimethylmorpholino)-N-(6-(1-methyl-1H-pyrazol-4-yl) isoquinolin-3-yl)isonicotinamide 91

Tan solid (32.0 mg, 0.072 mmol, 31.9% yield). $^1$H NMR (499 MHz, DMSO-d$_6$) δ ppm 1.20 (6H, d, J=6.04 Hz), 2.44-2.49 (2H, m), 3.60-3.70 (2H, m), 3.91 (3H, s), 4.28 (2H, br dd, J=12.76, 1.51 Hz), 7.18 (1H, dd, J=5.21, 1.37 Hz), 7.44 (1H, s), 7.81 (1H, dd, J=8.51, 1.65 Hz), 8.07 (1H, d, J=8.78 Hz), 8.10 (1H, d, J=0.82 Hz), 8.13 (1H, s), 8.27 (1H, d, J=5.49 Hz), 8.37 (1H, s), 8.58 (1H, s), 9.12 (1H, s), 10.94 (1H, s); ESIMS found for C$_{25}$H$_{26}$N$_6$O$_2$ m/z 443.0 (M+1).

92

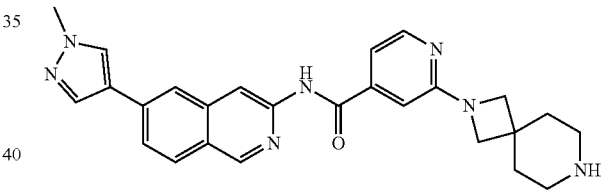

N-(6-(1-Methyl-1H-pyrazol-4-yl)isoquinolin-3-yl)-2-(2,7-diazaspiro[3.5]nonan-2-yl)isonicotinamide 92

Off-white solid (120.0 mg, 0.265 mmol, 47.1% yield). $^1$H NMR (499 MHz, DMSO-d$_6$) δ ppm 1.66 (4H, br t, J=4.94 Hz), 2.66 (4H, br s), 3.73 (4H, s), 3.91 (3H, s), 7.02 (1H, s), 7.12 (1H, dd, J=5.21, 1.37 Hz), 7.81 (1H, dd, J=8.64, 1.51 Hz), 8.07 (1H, d, J=8.51 Hz), 8.11 (1H, s), 8.13 (1H, s), 8.19 (1H, d, J=4.94 Hz), 8.38 (1H, s), 8.58 (1H, s), 9.12 (1H, s), 10.96 (1H, br s); ESIMS found for C$_{26}$H$_{27}$N$_7$O m/z 454.2 (M+1).

93

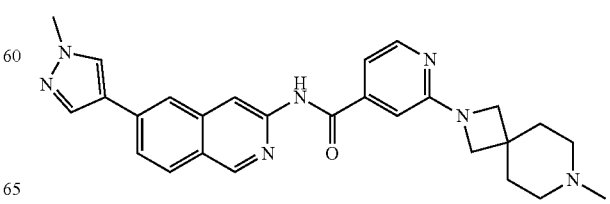

N-(6-(1-Methyl-1H-pyrazol-4-yl)isoquinolin-3-yl)-2-(7-methyl-2,7-diazaspiro[3.5]nonan-2-yl)isonicotinamide 93

White solid (63.9 mg, 0.137 mmol, 77.5% yield). $^1$H NMR (499 MHz, DMSO-d$_6$) δ ppm 1.76 (4H, br t, J=5.21 Hz), 2.15 (3H, s), 2.27 (4H, br s), 3.74 (4H, s), 3.91 (3H, s), 7.03 (1H, s), 7.13 (1H, dd, J=5.21, 1.37 Hz), 7.81 (1H, dd, J=8.51, 1.65 Hz), 8.07 (1H, d, J=8.51 Hz), 8.11 (1H, s), 8.13 (1H, s), 8.20 (1H, d, J=5.76 Hz), 8.38 (1H, s), 8.58 (1H, s), 9.12 (1H, s), 10.96 (1H, s); ESIMS found for C$_{27}$H$_{29}$N$_7$O m/z 468.1 (M+1).

94

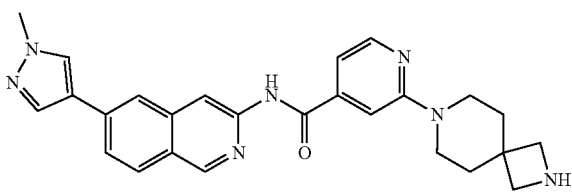

N-(6-(1-Methyl-1H-pyrazol-4-yl)isoquinolin-3-yl)-2-(2,7-diazaspiro[3.5]nonan-7-yl)isonicotinamide 94

Off-white solid (190.0 mg, 0.419 mmol, 76.0% yield). $^1$H NMR (499 MHz, DMSO-d$_6$) δ ppm 1.72-1.79 (4H, m), 3.32-3.43 (4H, m), 3.54-3.60 (4H, m), 3.91 (3H, s), 7.11 (1H, dd, J=5.21, 1.10 Hz), 7.46 (1H, s), 7.81 (1H, dd, J=8.64, 1.51 Hz), 8.07 (1H, d, J=8.51 Hz), 8.11 (1H, s), 8.13 (1H, s), 8.23 (1H, d, J=5.21 Hz), 8.38 (1H, s), 8.59 (1H, s), 9.12 (1H, s), 11.02 (1H, br s); ESIMS found for C$_{26}$H$_{27}$N$_7$O m/z 454.1 (M+1).

95

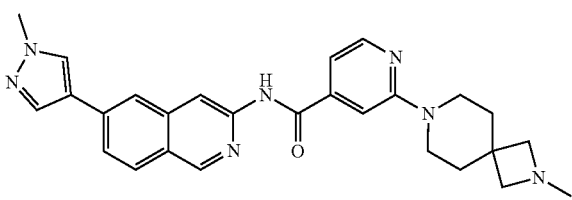

N-(6-(1-Methyl-1H-pyrazol-4-yl)isoquinolin-3-yl)-2-(2-methyl-2,7-diazaspiro[3.5]nonan-7-yl)isonicotinamide 95

White solid (136.0 mg, 0.291 mmol, 79.5% yield). $^1$H NMR (499 MHz, DMSO-d$_6$) δ ppm 1.66-1.76 (4H, m), 2.24 (3H, s), 2.97 (4H, s), 3.53-3.62 (4H, m), 3.91 (3H, s), 7.10 (1H, dd, J=5.08, 1.23 Hz), 7.45 (1H, s), 7.81 (1H, dd, J=8.51, 1.65 Hz), 8.07 (1H, d, J=8.51 Hz), 8.11 (1H, s), 8.13 (1H, s), 8.23 (1H, d, J=4.94 Hz), 8.38 (1H, s), 8.59 (1H, s), 9.12 (1H, s), 11.02 (1H, s); ESIMS found for C$_{27}$H$_{29}$N$_7$O m/z 468.0 (M+1).

97

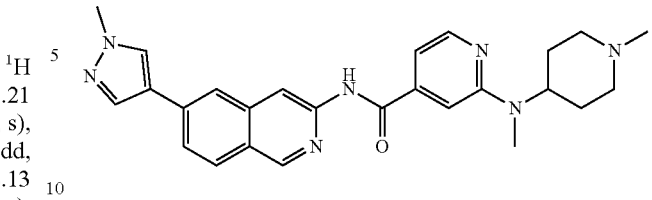

2-(Methyl(1-methylpiperidin-4-yl)amino)-N-(6-(1-methyl-1H-pyrazol-4-yl) isoquinolin-3-yl)isonicotinamide 97

Tan solid (72.9 mg, 0.160 mmol, 55.4% yield). $^1$H NMR (499 MHz, DMSO-d$_6$) δ ppm 1.50-1.62 (2H, m), 1.80 (2H, qd, J=12.08, 3.84 Hz), 1.97-2.08 (2H, m), 2.19 (3H, s), 2.86 (2H, br d, J=11.25 Hz), 2.93 (3H, s), 3.91 (3H, s), 4.49 (1H, ddt, J=11.63, 7.79, 4.01, 4.01 Hz), 7.07 (1H, dd, J=5.08, 1.23 Hz), 7.18 (1H, s), 7.81 (1H, dd, J=8.51, 1.65 Hz), 8.07 (1H, d, J=8.51 Hz), 8.11 (1H, s), 8.13 (1H, s), 8.22 (1H, d, J=5.21 Hz), 8.38 (1H, s), 8.58 (1H, s), 9.12 (1H, s), 10.99 (1H, s); ESIMS found for C$_{26}$H$_{29}$N$_7$O m/z 456.2 (M+1).

99

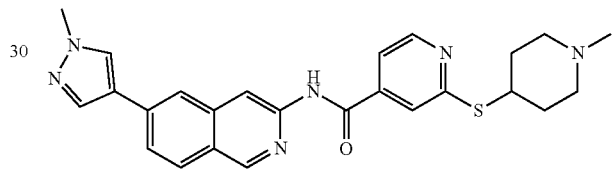

N-(6-(1-Methyl-1H-pyrazol-4-yl)isoquinolin-3-yl)-2-((1-methylpiperidin-4-yl)thio)isonicotinamide 99

Off-white solid (50.0 mg, 0.109 mmol, 15.1% yield). $^1$H NMR (499 MHz, DMSO-d$_6$) δ ppm 1.60-1.72 (2H, m), 1.99-2.08 (2H, m), 2.12 (2H, br t, J=10.84 Hz), 2.17 (3H, s), 2.65-2.73 (2H, m), 3.78-3.88 (1H, m), 3.91 (3H, s), 7.64 (1H, dd, J=5.08, 1.51 Hz), 7.79-7.85 (2H, m), 8.07 (1H, d, J=8.51 Hz), 8.11 (1H, s), 8.15 (1H, s), 8.38 (1H, s), 8.57 (1H, s), 8.59-8.64 (1H, m), 9.12 (1H, s), 11.14 (1H, s); ESIMS found for C$_{25}$H$_{26}$N$_6$OS m/z 458.9 (M+1).

100

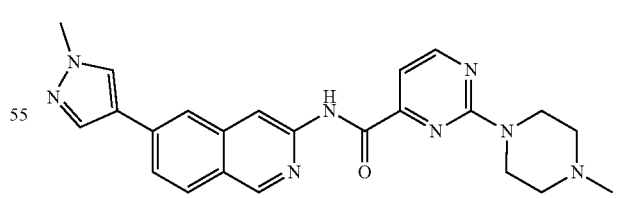

N-(6-(1-Methyl-1H-pyrazol-4-yl)isoquinolin-3-yl)-2-(4-methylpiperazin-1-yl)pyrimidine-4-carboxamide 100

Tan solid (78.0 mg, 0.182 mmol, 63.0% yield). $^1$H NMR (499 MHz, DMSO-d$_6$) δ ppm 2.25 (3H, s), 2.44 (4H, br t, J=4.94 Hz), 3.82-3.89 (4H, m), 3.91 (3H, s), 7.30 (1H, d, J=4.67 Hz), 7.83 (1H, dd, J=8.64, 1.51 Hz), 8.08 (1H, d, J=8.78 Hz), 8.12 (1H, s), 8.17 (1H, s), 8.39 (1H, s), 8.58 (1H, s), 8.69 (1H, d, J=4.67 Hz), 9.12 (1H, s), 10.36 (1H, s); ESIMS found for C$_{23}$H$_{24}$N$_8$O m/z 429.2 (M+1).

s), 7.20-7.27 (1H, m), 7.33 (2H, t, J=7.68 Hz), 7.37-7.44 (2H, m), 7.75 (1H, dd, J=8.51, 1.65 Hz), 8.00 (1H, d, J=8.51 Hz), 8.03 (1H, s), 8.07 (1H, s), 8.34 (1H, s), 8.40 (1H, s), 9.04 (1H, s), 10.75 (1H, s); ESIMS found for C$_{21}$H$_{18}$N$_4$O m/z 343.1 (M+1).

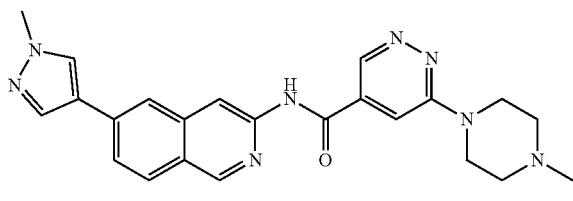

N-(6-(1-Methyl-1H-pyrazol-4-yl)isoquinolin-3-yl)-6-(4-methylpiperazin-1-yl)pyridazine-4-carboxamide 101

Off-white solid (6.2 mg, 0.015 mmol, 3.4% yield). $^1$H NMR (499 MHz, DMSO-d$_6$) δ ppm 2.16 (3H, br s), 2.40 (4H, br s), 3.43 (4H, br d, J=3.57 Hz), 3.91 (3H, s), 7.72 (1H, s), 7.80 (1H, dd, J=8.51, 1.65 Hz), 8.04 (1H, d, J=8.78 Hz), 8.10 (1H, d, J=0.82 Hz), 8.14 (1H, s), 8.36 (1H, s), 8.54 (1H, br s), 9.08 (1H, s), 11.04 (1H, s), 12.68 (1H, s); ESIMS found for C$_{23}$H$_{24}$N$_8$O m/z 429.0 (M+1).

N-(6-(1-Methyl-1H-pyrazol-4-yl)isoquinolin-3-yl)-3-phenylpropanamide 104

Beige solid (67.0 mg, 0.188 mmol, 42.2% yield). $^1$H NMR (499 MHz, DMSO-d$_6$) δ ppm 2.72-2.80 (2H, m), 2.92-2.96 (2H, m), 3.90 (3H, s), 7.15-7.22 (1H, m), 7.26-7.32 (4H, m), 7.74 (1H, dd, J=8.51, 1.37 Hz), 7.99 (1H, d, J=8.51 Hz), 8.06 (1H, s), 8.09 (1H, s), 8.36 (1H, s), 8.44 (1H, s), 9.02 (1H, s), 10.54 (1H, s); ESIMS found for C$_{22}$H$_{20}$N$_4$O m/z 357.2 (M+1).

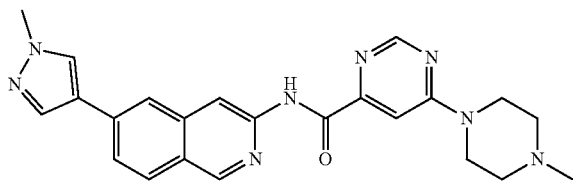

N-(6-(1-Methyl-1H-pyrazol-4-yl)isoquinolin-3-yl)-6-(4-methylpiperazin-1-yl)pyrimidine-4-carboxamide 102

White solid (72.1 mg, 0.168 mmol, 39.1% yield). $^1$H NMR (499 MHz, DMSO-d$_6$) δ ppm 2.25 (3H, s), 2.44 (3H, br s), 3.76 (4H, br s), 3.91 (3H, s), 7.48 (1H, d, J=0.82 Hz), 7.82 (1H, dd, J=8.51, 1.65 Hz), 8.07 (1H, d, J=8.51 Hz), 8.11 (1H, s), 8.16 (1H, s), 8.38 (1H, s), 8.58 (1H, s), 8.67 (1H, d, J=1.10 Hz), 9.11 (1H, s), 10.41 (1H, s); ESIMS found for C$_{23}$H$_{24}$N$_8$O m/z 429.0 (M+1).

N-(6-(1-Methyl-1H-pyrazol-4-yl)isoquinolin-3-yl)-2-(pyridin-3-yl)acetamide 105

Brownish orange solid (21.0 mg, 0.061 mmol, 13.7% yield). $^1$H NMR (499 MHz, DMSO-d$_6$) δ ppm 3.83 (2H, s), 3.89 (3H, s), 7.37 (1H, dd, J=7.82, 4.80 Hz), 7.76 (1H, dd, J=8.51, 1.65 Hz), 7.79 (1H, dt, J=7.82, 1.85 Hz), 8.01 (1H, d, J=8.51 Hz), 8.03 (1H, s), 8.07 (1 H, s), 8.34 (1H, s), 8.39 (1H, s), 8.47 (1H, dd, J=4.67, 1.65 Hz), 8.57 (1H, d, J=1.65 Hz), 9.05 (1H, s), 10.86 (1H, s); ESIMS found for C$_{20}$H$_{17}$N$_5$O m/z 344.1 (M+1).

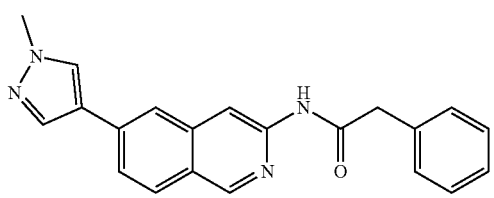

N-(6-(1-Methyl-1H-pyrazol-4-yl)isoquinolin-3-yl)-2-phenylacetamide 103

Beige solid (57.0 mg, 0.167 mmol, 37.3% yield). $^1$H NMR (499 MHz, DMSO-d$_6$) δ ppm 3.77 (2H, s), 3.89 (3H,

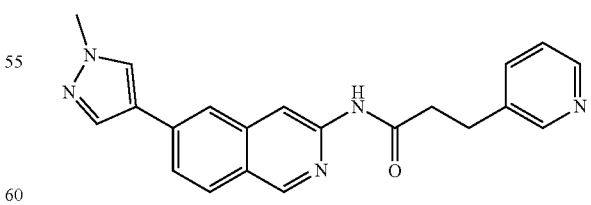

N-(6-(1-Methyl-1H-pyrazol-4-yl)isoquinolin-3-yl)-3-(pyridin-3-yl) propanamide 106

Brown solid (65.0 mg, 0.182 mmol, 40.8% yield). $^1$H NMR (499 MHz, DMSO-d$_6$) δ ppm 2.76-2.83 (2H, m), 2.93-3.00 (2H, m), 3.90 (3H, s), 7.31 (1H, dd, J=7.82, 4.80 Hz), 7.69 (1H, dt, J=7.82, 1.85 Hz), 7.75 (1H, dd, J=8.51, 1.65 Hz), 7.99 (1H, d, J=8.51 Hz), 8.06 (1H, s), 8.09 (1H, d, J=0.82 Hz), 8.36 (1H, s), 8.40 (1H, dd, J=4.80, 1.51 Hz), 8.43 (1H, s), 8.51 (1H, d, J=1.92 Hz), 9.01 (1H, s), 10.56 (1H, s); ESIMS found for C$_{21}$H$_{19}$N$_5$O m/z 358.1 (M+1).

s), 7.39 (1H, d, J=7.68 Hz), 7.79 (1H, dd, J=8.51, 1.65 Hz), 7.92 (1H, dd, J=7.96, 1.37 Hz), 7.97 (1H, s), 8.05 (1H, d, J=8.51 Hz), 8.11 (1H, s), 8.13 (1H, s), 8.37 (1H, s), 8.59 (1H, s), 9.10 (1H, s), 10.70 (1H, s); ESIMS found for C$_{22}$H$_{19}$N$_5$O m/z 369.95 (M+1).

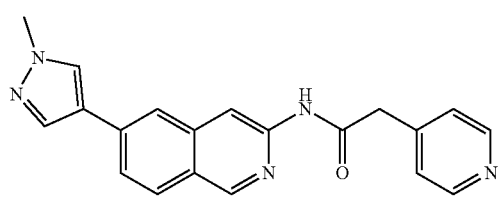

N-(6-(1-Methyl-1H-pyrazol-4-yl)isoquinolin-3-yl)-2-(pyridin-4-yl)acetamide 107

Beige solid (30.0 mg, 0.087 mmol, 19.6% yield). $^1$H NMR (499 MHz, DMSO-d$_6$) δ ppm 3.84 (2H, s), 3.89 (3H, s), 7.39 (2H, d, J=6.04 Hz), 7.76 (1H, dd, J=8.64, 1.51 Hz), 8.01 (1H, d, J=8.51 Hz), 8.04 (1H, s), 8.07 (1H, s), 8.35 (1H, s), 8.40 (1H, s), 8.49-8.55 (2H, m), 9.05 (1H, s), 10.88 (1H, s); ESIMS found for C$_{20}$H$_{17}$N$_5$O m/z 344.1 (M+1).

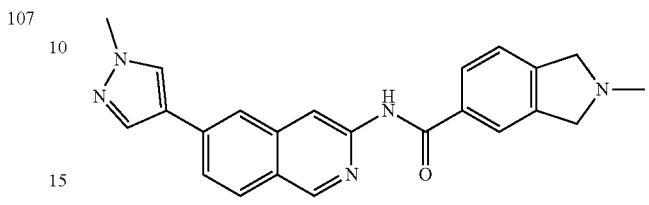

2-Methyl-N-(6-(1-methyl-1H-pyrazol-4-yl)isoquinolin-3-yl)isoindoline-5-carboxamide 110

Off-white solid. $^1$H NMR (499 MHz, DMSO-d$_6$) δ ppm 2.52 (3H, s), 3.88 (4H, s), 3.91 (3H, s), 7.37 (1H, d, J=7.68 Hz), 7.79 (1H, dd, J=8.51, 1.65 Hz), 7.90-7.97 (2H, m), 8.05 (1H, d, J=8.78 Hz), 8.10 (1H, d, J=0.82 Hz), 8.12 (1H, s), 8.37 (1H, s), 8.58 (1H, s), 9.10 (1H, s), 10.70 (1H, s); ESIMS found for C$_{23}$H$_{21}$N$_5$O m/z 383.95 (M+1).

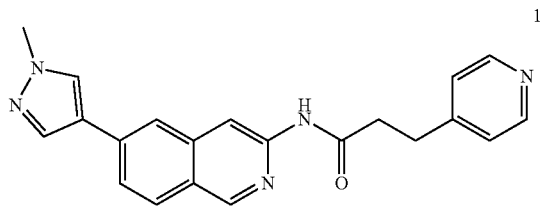

N-(6-(1-Methyl-1H-pyrazol-4-yl)isoquinolin-3-yl)-3-(pyridin-4-yl) propanamide 108

Beige solid (45.0 mg, 0.126 mmol, 28.2% yield). $^1$H NMR (499 MHz, DMSO-d$_6$) δ ppm 2.77-2.85 (2H, m), 2.92-3.00 (2H, m), 3.90 (3H, s), 7.27-7.33 (2H, m), 7.75 (1H, dd, J=8.51, 1.37 Hz), 8.00 (1H, d, J=8.78 Hz), 8.06 (1H, s), 8.09 (1H, d, J=0.82 Hz), 8.35 (1H, s), 8.43 (1H, s), 8.44-8.50 (2H, m), 9.02 (1H, s), 10.58 (1H, s); ESIMS found for C$_{21}$H$_{19}$N$_5$O m/z 358.2 (M+1).

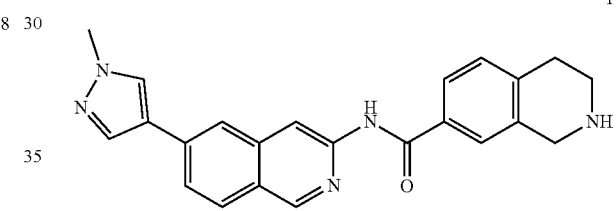

N-(6-(1-Methyl-1H-pyrazol-4-yl)isoquinolin-3-yl)-1,2,3,4-tetrahydroisoquinoline-7-carboxamide 111

Off-white solid (120.0 mg, 0.313 mmol, 32.5% yield). $^1$H NMR (499 MHz, DMSO-d$_6$) δ ppm 2.73-2.78 (2H, m), 2.97 (2H, t, J=5.90 Hz), 3.90-3.93 (2H, m), 3.91 (3H, s), 7.20 (1H, d, J=7.96 Hz), 7.75-7.85 (3H, m), 8.05 (1H, d, J=8.51 Hz), 8.11 (1H, s), 8.12 (1H, s), 8.37 (1H, s), 8.58 (1H, s), 9.10 (1H, s), 10.63 (1H, s); ESIMS found for C$_{23}$H$_{21}$N$_5$O m/z 384.0 (M+1).

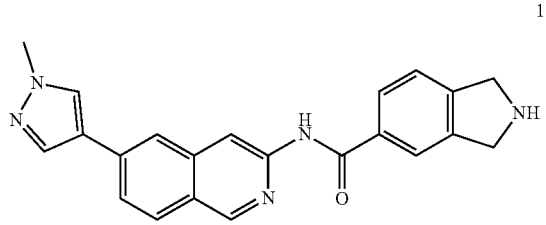

N-(6-(1-Methyl-1H-pyrazol-4-yl)isoquinolin-3-yl) isoindoline-5-carboxamide 109

Off-white solid (120.0 mg, 0.325 mmol, 33.7% yield). $^1$H NMR (499 MHz, DMSO-d$_6$) δ ppm 3.91 (3H, s), 4.14 (4H,

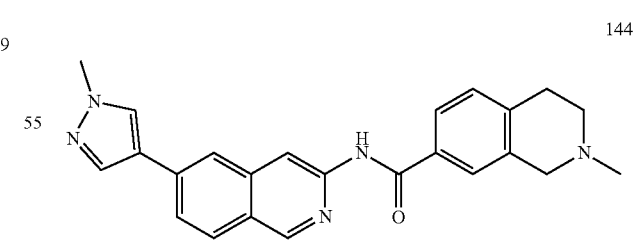

2-Methyl-N-(6-(1-methyl-1H-pyrazol-4-yl)isoquinolin-3-yl)-1,2,3,4-tetrahydroisoquinoline-7-carboxamide 112

Off-white solid (115.9 mg, 0.277 mmol, 93.2% yield). $^1$H NMR (499 MHz, DMSO-d$_6$) δ ppm 2.37 (3H, s), 2.63 (2H, br t, J=5.90 Hz), 2.89 (2H, br t, J=5.76 Hz), 3.52-3.59 (2H, m), 3.91 (3H, s), 7.25 (1H, d, J=7.96 Hz), 7.76-7.89 (3H, m), 8.05 (1H, d, J=8.51 Hz), 8.10 (1H, s), 8.12 (1H, s), 8.37 (1H, s), 8.58 (1H, s), 9.10 (1H, s), 10.65 (1H, s); ESIMS found for C$_{24}$H$_{23}$N$_5$O m/z 398.0 (M+1).

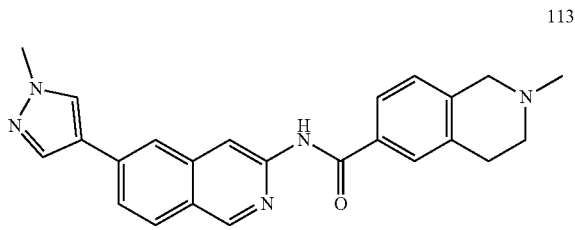 [SMILES: CN1CCc2cc(C(=O)Nc3cc4cc(-c5cnn(C)c5)ccc4cn3)ccc2C1]

113

2-Methyl-N-(6-(1-methyl-1H-pyrazol-4-yl)isoquinolin-3-yl)-1,2,3,4-tetrahydroisoquinoline-6-carboxamide 113

Off-white solid (115.9 mg, 0.277 mmol, 65.2% yield). $^1$H NMR (499 MHz, DMSO-d$_6$) δ ppm 2.36 (3H, s), 2.64 (2H, t, J=5.90 Hz), 2.91 (2H, br t, J=5.63 Hz), 3.55 (2H, s), 3.91 (3H, s), 7.19 (1H, d, J=7.96 Hz), 7.81 (2H, ddd, J=17.36, 8.30, 1.51 Hz), 7.86 (1H, s), 8.05 (1H, d, J=8.51 Hz), 8.10 (1H, s), 8.12 (1H, s), 8.37 (1H, s), 8.58 (1H, s), 9.10 (1H, s), 10.66 (1H, s); ESIMS found for C$_{24}$H$_{23}$N$_5$O m/z 398.0 (M+1).

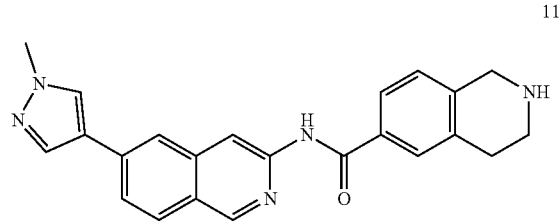

114

N-(6-(1-Methyl-1H-pyrazol-4-yl)isoquinolin-3-yl)-1,2,3,4-tetrahydroisoquinoline-6-carboxamide 114

Off-white solid (170.0 mg, 0.443 mmol, 31.3% yield). $^1$H NMR (499 MHz, DMSO-d$_6$) δ ppm 2.78 (2H, br t, J=5.76 Hz), 2.98 (2H, t, J=5.90 Hz), 3.86-3.97 (5H, m), 7.15 (1H, d, J=7.68 Hz), 7.76-7.82 (2H, m), 7.83 (1H, s), 8.05 (1H, d, J=8.78 Hz), 8.11 (1H, s), 8.12 (1H, s), 8.37 (1H, s), 8.58 (1H, s), 9.10 (1H, s), 10.64 (1H, s); ESIMS found for C$_{23}$H$_{21}$N$_5$O m/z 384.0 (M+1).

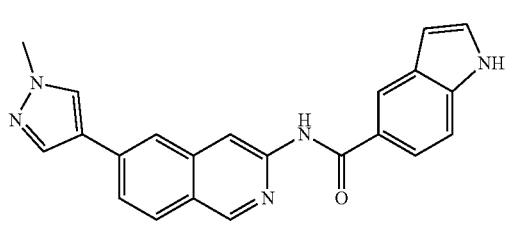

116

N-(6-(1-Methyl-1H-pyrazol-4-yl)isoquinolin-3-yl)-1H-indole-5-carboxamide 116

White solid (18.0 mg, 0.049 mmol, 10.9% yield). $^1$H NMR (499 MHz, DMSO-d$_6$) δ ppm 3.91 (3H, s), 6.59 (1H, ddd, J=2.95, 1.99, 0.82 Hz), 7.44-7.48 (1H, m), 7.49 (1H, d, J=8.51 Hz), 7.78 (1H, dd, J=8.51, 1.65 Hz), 7.86 (1H, dd, J=8.64, 1.78 Hz), 8.05 (1H, d, J=8.78 Hz), 8.11 (1H, s), 8.12 (1H, d, J=0.82 Hz), 8.38 (1H, s), 8.42 (1H, d, J=1.65 Hz), 8.62 (1H, s), 9.11 (1H, s), 10.53 (1H, s), 11.39 (1H, br s); ESIMS found for C$_{22}$H$_{17}$N$_5$O m/z 368.1 (M+1).

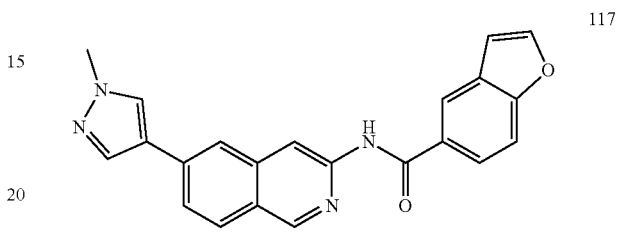

117

N-(6-(1-Methyl-1H-pyrazol-4-yl)isoquinolin-3-yl)benzofuran-5-carboxamide 117

Light yellow solid (8.7 mg, 0.024 mmol, 7.2% yield). $^1$H NMR (499 MHz, DMSO-d$_6$) δ ppm 3.91 (3H, s), 7.11 (1H, d, J=1.37 Hz), 7.73 (1H, d, J=8.51 Hz), 7.80 (1H, dd, J=8.51, 1.65 Hz), 8.06 (2H, d, J=8.51 Hz), 8.11 (1H, s), 8.12 (1H, d, J=2.20 Hz), 8.14 (1H, s), 8.38 (1H, s), 8.45 (1H, d, J=1.92 Hz), 8.62 (1H, s), 9.12 (1H, s), 10.83 (1H, s); ESIMS found for C$_{22}$H$_{16}$N$_4$O$_2$ m/z 369.1 (M+1).

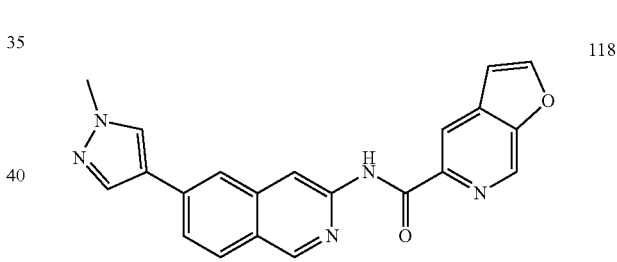

118

N-(6-(1-Methyl-1H-pyrazol-4-yl)isoquinolin-3-yl)furo[2,3-c]pyridine-5-carboxamide 118

Light yellow solid (10.8 mg, 0.029 mmol, 9.4% yield). $^1$H NMR (499 MHz, DMSO-d$_6$) δ ppm 3.92 (3H, s), 7.30 (1H, d, J=1.92 Hz), 7.82 (1H, dd, J=8.51, 1.37 Hz), 8.07 (1H, d, J=8.51 Hz), 8.13 (1H, s), 8.18 (1H, s), 8.39 (1H, s), 8.43 (1H, d, J=1.92 Hz), 8.64 (1H, s), 8.65 (1H, s), 9.12 (1H, s), 9.15 (1H, s), 10.59 (1H, s); ESIMS found for C$_{21}$H$_{15}$N$_5$O$_2$ m/z 370.1 (M+1).

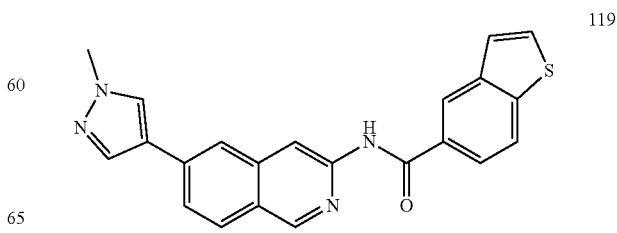

119

N-(6-(1-Methyl-1H-pyrazol-4-yl)isoquinolin-3-yl)benzo[b]thiophene-5-carboxamide 119

Yellow solid (20.0 mg, 0.052 mmol, 14.8% yield). $^1$H NMR (499 MHz, DMSO-$d_6$) δ ppm 3.92 (3H, s), 7.61 (1H, d, J=5.49 Hz), 7.80 (1H, dd, J=8.51, 1.65 Hz), 7.90 (1H, d, J=5.49 Hz), 8.02-8.09 (2H, m), 8.12 (1H, s), 8.13-8.19 (2H, m), 8.39 (1H, s), 8.63 (1H, s), 8.66 (1H, d, J=1.10 Hz), 9.13 (1H, s), 10.89 (1H, s); ESIMS found for $C_{22}H_{16}N_4OS$ m/z 385.1 (M+1).

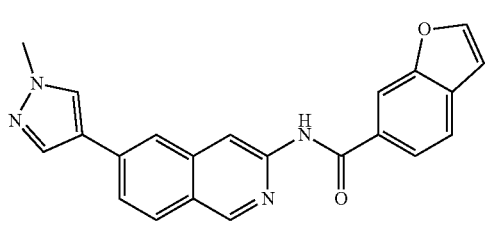

N-(6-(1-Methyl-1H-pyrazol-4-yl)isoquinolin-3-yl)benzofuran-6-carboxamide 120

Light yellow solid (6.9 mg, 0.019 mmol, 6.0% yield). $^1$H NMR (499 MHz, DMSO-$d_6$) δ ppm 3.92 (3H, s), 7.08 (1H, dd, J=2.20, 0.82 Hz), 7.80 (1H, d, J=8.23 Hz), 7.80 (1H, dd, J=8.51, 1.65 Hz), 8.01 (1H, dd, J=8.10, 1.51 Hz), 8.06 (1H, d, J=8.78 Hz), 8.12 (1H, s), 8.14 (1H, s), 8.19 (1H, d, J=2.20 Hz), 8.39 (1H, s), 8.39 (1H, s), 8.62 (1H, s), 9.13 (1H, s), 10.88 (1H, s); ESIMS found for $C_{22}H_{16}N_4O_2$ m/z 369.1 (M+1).

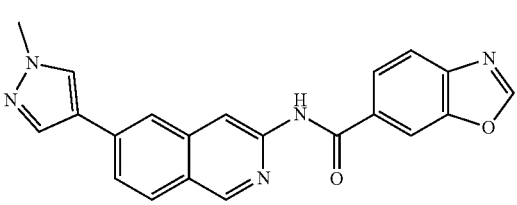

N-(6-(1-Methyl-1H-pyrazol-4-yl)isoquinolin-3-yl)benzo[d]oxazole-6-carboxamide 122

Yellow solid (33.4 mg, 0.090 mmol, 20.3% yield). $^1$H NMR (499 MHz, DMSO-$d_6$) δ ppm 3.91 (3H, s), 7.81 (1H, dd, J=8.51, 1.65 Hz), 7.94 (1H, d, J=8.51 Hz), 8.07 (1H, d, J=8.51 Hz), 8.12 (1H, s), 8.13-8.17 (2H, m), 8.38 (1H, s), 8.54 (1H, d, J=1.10 Hz), 8.63 (1H, s), 8.93 (1H, s), 9.13 (1H, s), 11.00 (1H, s); ESIMS found for $C_{21}H_{15}N_5O_2$ m/z 370.1 (M+1).

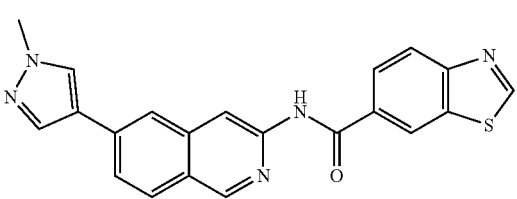

N-(6-(1-Methyl-1H-pyrazol-4-yl)isoquinolin-3-yl)benzo[d]thiazole-6-carboxamide 123

Yellow solid (35.0 mg, 0.091 mmol, 20.4% yield). $^1$H NMR (499 MHz, DMSO-$d_6$) δ ppm 3.92 (3H, s), 7.81 (1H, dd, J=8.51, 1.65 Hz), 8.07 (1H, d, J=8.51 Hz), 8.12 (1H, s), 8.16 (1H, s), 8.18-8.25 (2H, m), 8.38 (1H, s), 8.64 (1H, s), 8.91-8.96 (1H, m), 9.13 (1H, s), 9.58 (1H, s), 10.98 (1H, s); ESIMS found for $C_{21}H_{15}N_5OS$ m/z 386.1 (M+1).

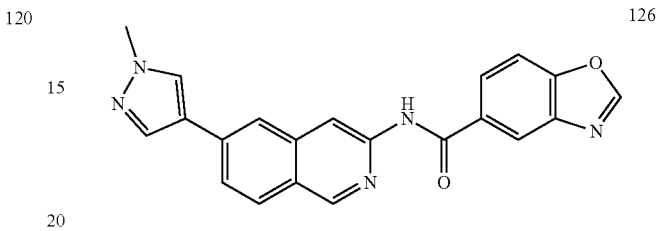

N-(6-(1-Methyl-1H-pyrazol-4-yl)isoquinolin-3-yl)benzo[d]oxazole-5-carboxamide 126

Yellow solid (52.7 mg, 0.143 mmol, 32.0% yield). $^1$H NMR (499 MHz, DMSO-$d_6$) δ ppm 3.92 (3H, s), 7.81 (1H, dd, J=8.51, 1.37 Hz), 7.92 (1H, d, J=8.51 Hz), 8.07 (1H, d, J=8.78 Hz), 8.12 (1H, s), 8.15 (1H, s), 8.18 (1H, dd, J=8.51, 1.65 Hz), 8.38 (1H, s), 8.57 (1H, d, J=1.65 Hz), 8.62 (1H, s), 8.88 (1H, s), 9.13 (1H, s), 10.99 (1H, s); ESIMS found for $C_{21}H_{15}N_5O_2$ m/z 370.1 (M+1).

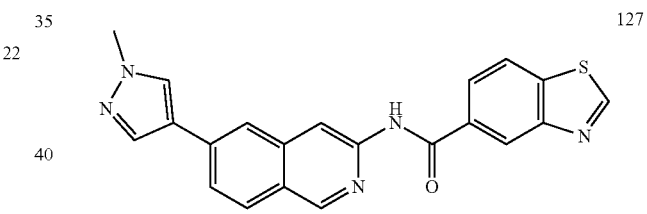

N-(6-(1-Methyl-1H-pyrazol-4-yl)isoquinolin-3-yl)benzo[d]thiazole-5-carboxamide 127

Yellow solid (41.7 mg, 0.108 mmol, 24.3% yield). $^1$H NMR (499 MHz, DMSO-$d_6$) δ ppm 3.92 (3H, s), 7.81 (1H, dd, J=8.51, 1.65 Hz), 8.07 (1H, d, J=8.51 Hz), 8.12 (1H, d, J=0.82 Hz), 8.14-8.16 (1H, m), 8.18 (1H, dd, J=8.51, 1.65 Hz), 8.33 (1H, d, J=8.51 Hz), 8.39 (1H, s), 8.64 (1H, s), 8.82 (1H, d, J=1.37 Hz), 9.14 (1H, s), 9.52 (1H, s), 11.06 (1H, s); ESIMS found for $C_{21}H_{15}N_5OS$ m/z 386.1 (M+1).

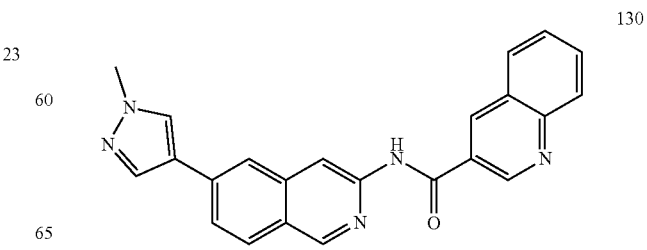

N-(6-(1-Methyl-1H-pyrazol-4-yl)isoquinolin-3-yl)quinoline-3-carboxamide 130

Beige solid (55.0 mg, 0.145 mmol, 32.5% yield). $^1$H NMR (499 MHz, DMSO-d$_6$) δ ppm 3.92 (3H, s), 7.70-7.78 (1H, m), 7.82 (1H, dd, J=8.51, 1.65 Hz), 7.91 (1H, ddd, J=8.30, 6.93, 1.23 Hz), 8.08 (1H, d, J=8.51 Hz), 8.10-8.14 (2H, m), 8.15 (1H, d, J=7.96 Hz), 8.17 (1H, s), 8.40 (1H, s), 8.66 (1H, s), 9.11 (1H, d, J=2.20 Hz), 9.15 (1H, s), 9.43 (1H, d, J=2.20 Hz), 11.26 (1H, s); ESIMS found for C$_{23}$H$_{17}$N$_5$O m/z 380.2 (M+1).

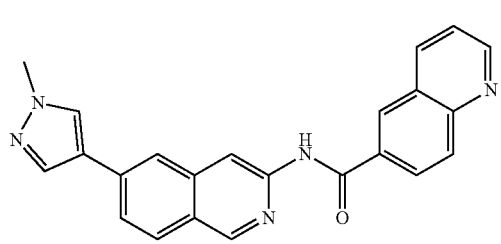

N-(6-(1-Methyl-1H-pyrazol-4-yl)isoquinolin-3-yl)quinoline-6-carboxamide 131

Beige solid (57.0 mg, 0.150 mmol, 33.7% yield). $^1$H NMR (499 MHz, DMSO-d$_6$) δ ppm 3.92 (3H, s), 7.65 (1H, dd, J=8.23, 4.12 Hz), 7.82 (1H, dd, J=8.51, 1.65 Hz), 8.08 (1H, d, J=8.51 Hz), 8.10-8.16 (2H, m), 8.17 (1H, s), 8.35 (1H, dd, J=8.78, 2.20 Hz), 8.39 (1H, s), 8.52-8.57 (1H, m), 8.66 (1H, s), 8.81 (1H, d, J=2.20 Hz), 9.03 (1H, dd, J=4.25, 1.78 Hz), 9.15 (1H, s), 11.08 (1H, s); ESIMS found for C$_{23}$H$_{17}$N$_5$O m/z 380.1 (M+1).

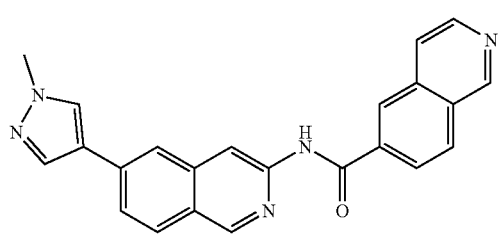

N-(6-(1-Methyl-1H-pyrazol-4-yl)isoquinolin-3-yl)isoquinoline-6-carboxamide 132

Beige solid (10.0 mg, 0.026 mmol, 5.9% yield). $^1$H NMR (499 MHz, DMSO-d$_6$) δ ppm 3.92 (3H, s), 7.82 (1H, dd, J=8.51, 1.65 Hz), 7.99 (1H, d, J=5.76 Hz), 8.08 (1H, d, J=8.51 Hz), 8.13 (1H, s), 8.17 (1H, s), 8.21-8.30 (2H, m), 8.39 (1H, s), 8.62 (1H, d, J=5.76 Hz), 8.65 (1H, s), 8.74 (1H, s), 9.15 (1H, s), 9.44 (1H, s), 11.15 (1H, s); ESIMS found for C$_{23}$H$_{17}$N$_5$O m/z 380.1 (M+1).

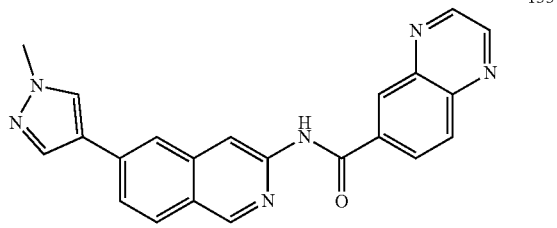

N-(6-(1-Methyl-1H-pyrazol-4-yl)isoquinolin-3-yl)quinoxaline-6-carboxamide 133

Beige solid (29.0 mg, 0.076 mmol, 17.1% yield). $^1$H NMR (499 MHz, DMSO-d$_6$) δ ppm 3.92 (3H, s), 7.83 (1H, dd, J=8.51, 1.65 Hz), 8.08 (1H, d, J=8.51 Hz), 8.13 (1H, s), 8.17 (1H, s), 8.23 (1H, d, J=8.78 Hz), 8.39 (1H, s), 8.44 (1H, dd, J=8.78, 1.92 Hz), 8.66 (1H, s), 8.84 (1H, d, J=1.92 Hz), 9.06 (1H, d, J=1.65 Hz), 9.08 (1H, d, J=1.65 Hz), 9.15 (1H, s), 11.31 (1H, s); ESIMS found for C$_{22}$H$_{16}$N$_6$O m/z 381.1 (M+1).

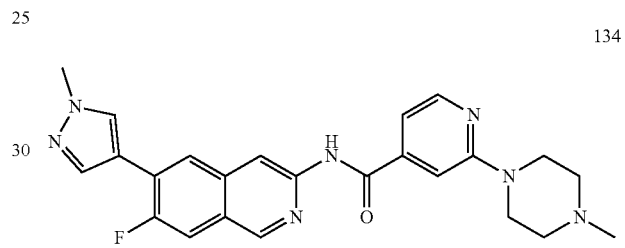

N-(7-Fluoro-6-(1-methyl-1H-pyrazol-4-yl)isoquinolin-3-yl)-2-(4-methylpiperazin-1-yl)isonicotinamide 134

Off-white solid (36.0 mg, 0.081 mmol, 26.0% yield). $^1$H NMR (499 MHz, DMSO-d$_6$) δ ppm 2.23 (3H, s), 2.42 (4H, t, J=4.94 Hz), 3.55-3.65 (4H, m), 3.94 (3H, s), 7.15 (1H, dd, J=5.08, 1.23 Hz), 7.46 (1H, s), 7.97 (1H, d, J=11.80 Hz), 8.14 (1H, s), 8.26 (1H, d, J=4.94 Hz), 8.33 (1H, d, J=2.74 Hz), 8.37 (1H, d, J=7.41 Hz), 8.65 (1H, s), 9.14 (1H, s), 11.08 (1H, s); ESIMS found for C$_{24}$H$_{24}$FN$_7$O m/z 446.2 (M+1).

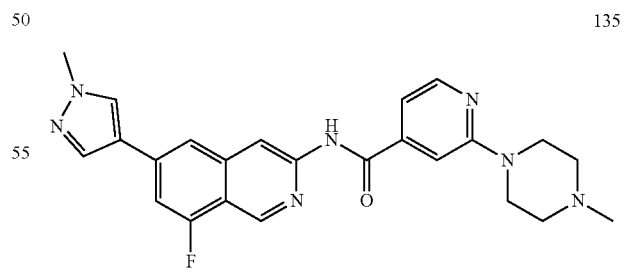

N-(8-Fluoro-6-(1-methyl-1H-pyrazol-4-yl)isoquinolin-3-yl)-2-(4-methylpiperazin-1-yl)isonicotinamide 135

Off-white solid (65.0 mg, 0.146 mmol, 64.8% yield). $^1$H NMR (499 MHz, DMSO-d$_6$) δ ppm 2.23 (3H, s), 2.42 (4H, br t, J=4.80 Hz), 3.56-3.64 (4H, m), 3.91 (3H, s), 7.09-7.20 (1H, m), 7.46 (1H, s), 7.66 (1H, d, J=12.08 Hz), 8.02 (1H, s), 8.15 (1H, s), 8.26 (1H, d, J=5.21 Hz), 8.42 (1H, s), 8.65 (1H, s), 9.24 (1H, s), 11.19 (1H, s); ESIMS found for $C_{24}H_{24}FN_7O$ m/z 446.2 (M+1).

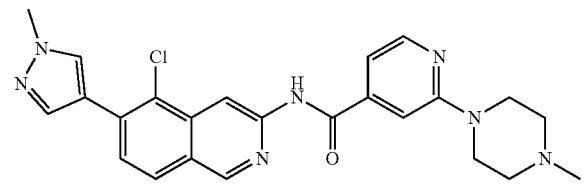

N-(5-Chloro-6-(1-methyl-1H-pyrazol-4-yl)isoquinolin-3-yl)-2-(4-methylpiperazin-1-yl)isonicotinamide
136

White solid (20.0 mg, 0.043 mmol, 41.3% yield). $^1$H NMR (499 MHz, DMSO-d$_6$) δ ppm 2.26 (3H, s), 2.47 (4H, br s), 3.62 (4H, br s), 3.96 (3H, s), 7.19 (1H, dd, J=5.08, 0.96 Hz), 7.49 (1H, s), 7.84 (1H, d, J=8.51 Hz), 8.08-8.12 (2H, m), 8.27 (1H, d, J=5.21 Hz), 8.48 (1H, s), 9.05 (1H, s), 9.24 (1H, s), 11.24 (1H, s); ESIMS found for $C_{24}H_{24}ClN_7O$ m/z 462.2 (M+1).

137

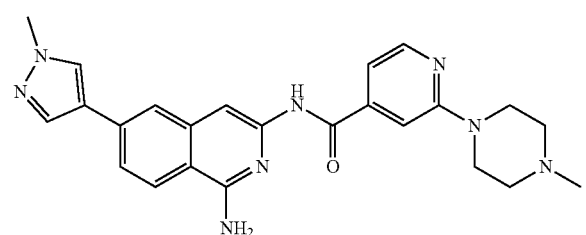

N-(7-Chloro-6-(1-methyl-1H-pyrazol-4-yl)isoquinolin-3-yl)-2-(4-methylpiperazin-1-yl)isonicotinamide
137

White solid (18.0 mg, 0.039 mmol, 37.2% yield). $^1$H NMR (499 MHz, DMSO-d$_6$) δ ppm 2.27 (3H, s), 2.47 (4H, br s), 3.61 (4H, br s), 3.94 (3H, s), 7.15 (1H, dd, J=5.21, 1.10 Hz), 7.46 (1H, s), 8.01 (1H, d, J=0.82 Hz), 8.20 (1H, s), 8.26 (1H, d, J=5.49 Hz), 8.32 (1H, s), 8.34 (1H, s), 8.64 (1H, s), 9.18 (1H, s), 11.13 (1H, s); ESIMS found for $C_{24}H_{24}ClN_7O$ m/z 462.2 (M+1).

138

N-(1-Amino-6-(1-methyl-1H-pyrazol-4-yl)isoquinolin-3-yl)-2-(4-methylpiperazin-1-yl)isonicotinamide
138

Tan solid (4.8 mg, 0.011 mmol, 7.4% yield). $^1$H NMR (499 MHz, DMSO-d$_6$) δ ppm 2.24 (3H, s), 2.39-2.46 (4H, m), 3.53-3.62 (4H, m), 3.89 (3H, s), 6.89 (1H, s), 7.07 (1H, dd, J=5.08, 1.24 Hz), 7.26 (1H, s), 7.60 (1H, dd, J=8.23, 1.65 Hz), 7.81 (1H, d, J=1.65 Hz), 8.03 (1H, s), 8.08 (1H, d, J=8.51 Hz), 8.28-8.33 (2H, m), 10.39 (1H, br s), 11.08 (1H, br s); ESIMS found for $C_{24}H_{26}N_8O$ m/z 444.2 (M+2).

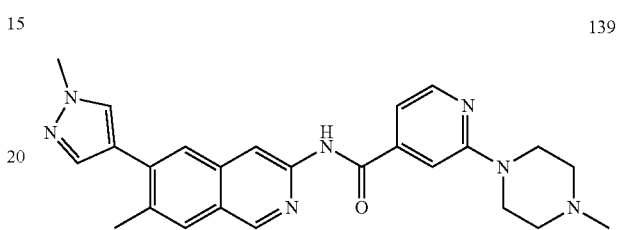

N-(7-Methyl-6-(1-methyl-1H-pyrazol-4-yl)isoquinolin-3-yl)-2-(4-methylpiperazin-1-yl)isonicotinamide
139

Beige solid (28.0 mg, 0.063 mmol, 63.7% yield). $^1$H NMR (499 MHz, DMSO-d$_6$) δ ppm 2.24 (3H, s), 2.43 (4H, br t, J=4.94 Hz), 2.67 (3H, s), 3.57-3.64 (4H, m), 3.94 (3H, s), 7.18 (1H, dd, J=5.08, 1.23 Hz), 7.48 (1H, s), 7.58 (1H, d, J=8.51 Hz), 7.79 (1H, d, J=0.82 Hz), 7.95 (1H, d, J=8.78 Hz), 8.10 (1H, s), 8.26 (1H, d, J=5.76 Hz), 8.85 (1H, s), 9.16 (1H, s), 11.10 (1H, s); ESIMS found for $C_{25}H_{27}N_7O$ m/z 442.2 (M+1).

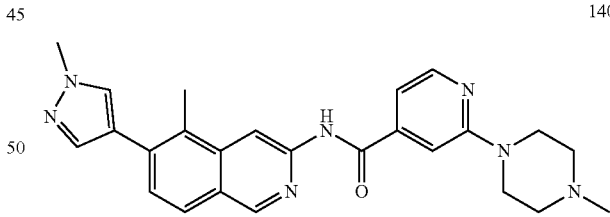

N-(5-Methyl-6-(1-methyl-1H-pyrazol-4-yl)isoquinolin-3-yl)-2-(4-methylpiperazin-1-yl)isonicotinamide
140

White solid (20.0 mg, 0.045 mmol, 54.6% yield). $^1$H NMR (499 MHz, DMSO-d$_6$) δ ppm 2.24 (3H, s), 2.43 (4H, br t, J=4.94 Hz), 2.67 (3H, s), 3.58-3.63 (4H, m), 3.94 (3H, s), 7.18 (1H, dd, J=5.21, 1.10 Hz), 7.48 (1H, s), 7.58 (1H, d, J=8.51 Hz), 7.79 (1H, s), 7.95 (1H, d, J=8.51 Hz), 8.10 (1H, s), 8.26 (1H, d, J=5.21 Hz), 8.85 (1H, s), 9.16 (1H, s), 11.10 (1H, s); ESIMS found for $C_{25}H_{27}N_7O$ m/z 442.2 (M+1).

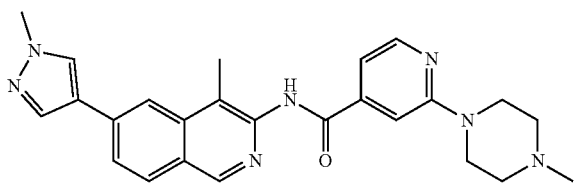

N-(4-Methyl-6-(1-methyl-1H-pyrazol-4-yl)isoquinolin-3-yl)-2-(4-methylpiperazin-1-yl)isonicotinamide 141

Off-white solid (16.5 mg, 0.037 mmol, 12.4% yield). $^1$H NMR (499 MHz, DMSO-$d_6$) δ ppm 2.23 (3H, s), 2.40-2.45 (4H, m), 2.51 (3H, br s), 3.55-3.63 (4H, m), 3.92 (3H, s), 7.16 (1H, dd, J=5.08, 0.96 Hz), 7.40 (1H, s), 7.92 (1H, dd, J=8.51, 1.65 Hz), 8.12 (1H, d, J=8.23 Hz), 8.16 (1H, s), 8.23 (1H, s), 8.28 (1H, d, J=4.94 Hz), 8.46 (1H, s), 9.04 (1H, s), 10.73 (1H, s); ESIMS found for $C_{25}H_{27}N_7O$ m/z 442.2 (M+1).

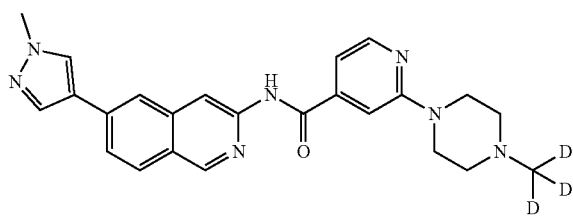

N-(6-(1-Methyl-1H-pyrazol-4-yl)isoquinolin-3-yl)-2-(4-(methyl-$d_3$) piperazin-1-yl)isonicotinamide 142

Beige solid (38.0 mg, 0.088 mmol, 94.7% yield). $^1$H NMR (499 MHz, DMSO-$d_6$) δ ppm 2.45 (4H, br s), 3.61 (4H, br s), 3.91 (3H, s), 7.16 (1H, dd, J=5.21, 1.10 Hz), 7.46 (1H, s), 7.81 (1H, dd, J=8.51, 1.65 Hz), 8.07 (1H, d, J=8.51 Hz), 8.11 (1H, s), 8.14 (1H, s), 8.26 (1H, d, J=5.21 Hz), 8.38 (1H, s), 8.59 (1H, s), 9.12 (1H, s), 11.04 (1H, s); ESIMS found for $C_{24}H_{22}[^2H_3]N_7O$ m/z 431.2 (M+1).

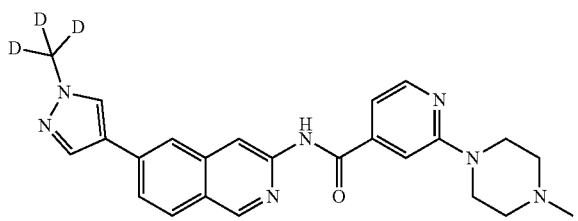

N-(6-(1-(Methyl-$d_3$)-1H-pyrazol-4-yl)isoquinolin-3-yl)-2-(4-methylpiperazin-1-yl)isonicotinamide 143

Beige solid (27.0 mg, 0.063 mmol, 38.2% yield). $^1$H NMR (499 MHz, DMSO-$d_6$) δ ppm 2.23 (3H, s), 2.43 (4H, t, J=4.94 Hz), 3.58-3.63 (4H, m), 7.16 (1H, dd, J=5.21, 1.10 Hz), 7.46 (1H, s), 7.81 (1H, dd, J=8.51, 1.65 Hz), 8.07 (1H, d, J=8.51 Hz), 8.11 (1H, s), 8.14 (1H, s), 8.26 (1H, d, J=5.21 Hz), 8.38 (1H, s), 8.59 (1H, s), 9.12 (1H, s), 11.04 (1H, s); ESIMS found for $C_{24}H_{22}[^2H_3]N_7O$ m/z 431.2 (M+1).

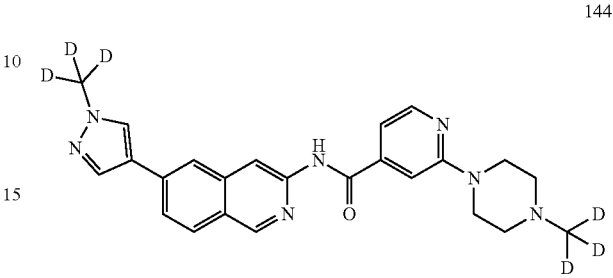

N-(6-(1-(Methyl-d3)-1H-pyrazol-4-yl)isoquinolin-3-yl)-2-(4-(methyl-d3) piperazin-1-yl)isonicotinamide 144

Beige solid (30.0 mg, 0.069 mmol, 70.7% yield). $^1$H NMR (499 MHz, DMSO-$d_6$) δ ppm 2.42 (4H, br t, J=4.80 Hz), 3.56-3.64 (4H, m), 7.15 (1H, dd, J=5.21, 0.82 Hz), 7.46 (1H, s), 7.81 (1H, dd, J=8.51, 1.37 Hz), 8.07 (1H, d, J=8.51 Hz), 8.11 (1H, s), 8.14 (1H, s), 8.26 (1H, d, J=5.21 Hz), 8.38 (1H, s), 8.59 (1H, s), 9.12 (1H, s), 11.04 (1H, s); ESIMS found for $C_{24}H_{19}[^2H_6]N_7O$ m/z 434.2 (M+1).

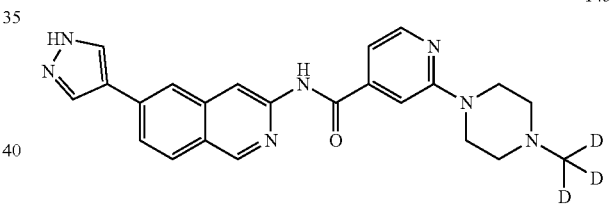

N-(6-(1H-Pyrazol-4-yl)isoquinolin-3-yl)-2-(4-(methyl-$d_3$)piperazin-1-yl) isonicotinamide 145

White solid (80.0 mg, 0.173 mmol, 37.1% yield). $^1$H NMR (499 MHz, DMSO-$d_6$) δ ppm 2.39-2.46 (4H, m), 3.57-3.65 (4H, m), 7.16 (1H, dd, J=5.08, 1.24 Hz), 7.46 (1H, s), 7.88 (1H, dd, J=8.51, 1.65 Hz), 8.07 (1H, d, J=8.51 Hz), 8.19 (2H, br s), 8.26 (1H, d, J=4.94 Hz), 8.46 (1H, br s), 8.60 (1H, s), 9.13 (1H, s), 11.04 (1H, s), 13.12 (1H, br s); ESIMS found for $C_{23}H_{20}[^2H_3]N_7O$ m/z 417.2 (M+1).

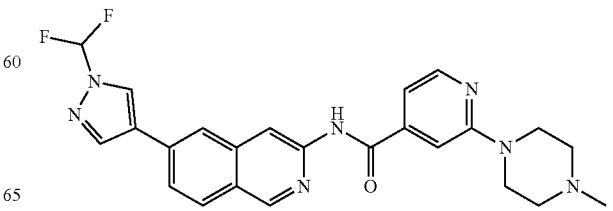

N-(6-(1-(Difluoromethyl)-1H-pyrazol-4-yl)isoquinolin-3-yl)-2-(4-methylpiperazin-1-yl)isonicotinamide 146

Beige solid (60.0 mg, 0.130 mmol, 78.8% yield). $^1$H NMR (499 MHz, DMSO-d$_6$) δ ppm 2.24 (3H, s), 2.43 (4H, t, J=4.94 Hz), 3.58-3.64 (4H, m), 7.16 (1H, dd, J=5.21, 1.10 Hz), 7.47 (1H, s), 7.89 (1H, t, J=59.40 Hz), 7.94 (1H, dd, J=8.51, 1.65 Hz), 8.14 (1H, d, J=8.51 Hz), 8.26 (1H, d, J=5.21 Hz), 8.34 (1H, s), 8.52 (1H, s), 8.65 (1H, s), 8.97 (1H, s), 9.18 (1H, s), 11.09 (1H, s); ESIMS found for C$_{24}$H$_{23}$F$_2$N$_7$O m/z 464.2 (M+1).

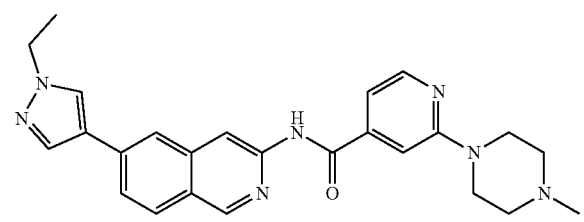

N-(6-(1-Ethyl-1H-pyrazol-4-yl)isoquinolin-3-yl)-2-(4-methylpiperazin-1-yl) isonicotinamide 147

Off-white solid (25.0 mg, 0.057 mmol, 34.5% yield). $^1$H NMR (499 MHz, DMSO-d$_6$) δ ppm 1.44 (3H, t, J=7.27 Hz), 2.23 (3H, s), 2.43 (4H, t, J=5.08 Hz), 3.57-3.64 (4H, m), 4.20 (2H, q, J=7.41 Hz), 7.16 (1H, dd, J=5.21, 1.37 Hz), 7.46 (1H, s), 7.83 (1H, dd, J=8.51, 1.65 Hz), 8.07 (1H, d, J=8.78 Hz), 8.12 (1H, s), 8.15 (1H, s), 8.26 (1H, d, J=5.21 Hz), 8.45 (1H, s), 8.59 (1H, s), 9.12 (1H, s), 11.04 (1H, s); ESIMS found for C$_{25}$H$_{27}$N$_7$O m/z 442.2 (M+1).

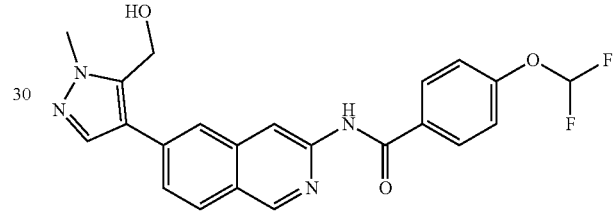

N-(6-(1-Methyl-1H-pyrazol-3-yl)isoquinolin-3-yl)-2-(4-methylpiperazin-1-yl)isonicotinamide 148

Beige solid (53.0 mg, 0.124 mmol, 75.5% yield). $^1$H NMR (499 MHz, DMSO-d$_6$) δ ppm 2.23 (3H, s), 2.43 (4H, t, J=4.94 Hz), 3.58-3.64 (4H, m), 3.94 (3H, s), 6.97 (1H, d, J=2.47 Hz), 7.16 (1H, dd, J=4.94, 1.10 Hz), 7.47 (1H, s), 7.82 (1H, d, J=2.20 Hz), 8.02-8.08 (1H, m), 8.08-8.13 (1H, m), 8.26 (1H, d, J=4.94 Hz), 8.31 (1H, s), 8.64 (1H, s), 9.17 (1H, s), 11.06 (1H, s); ESIMS found for C$_{24}$H$_{25}$N$_7$O m/z 428.2 (M+1).

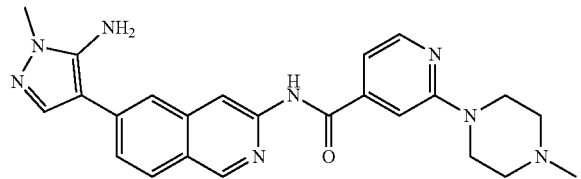

N-(6-(5-Amino-1-methyl-1H-pyrazol-4-yl)isoquinolin-3-yl)-2-(4-methylpiperazin-1-yl)isonicotinamide 149

Off-white solid (15.0 mg, 0.034 mmol, 12.0% yield). $^1$H NMR (499 MHz, DMSO-d$_6$) δ ppm 2.24 (3H, s), 2.40-2.46 (4H, m), 3.57-3.62 (4H, m), 3.64 (3H, s), 5.72 (2H, s), 7.15 (1H, d, J=4.12 Hz), 7.46 (1H, s), 7.67 (1H, s), 7.72 (1H, dd, J=8.64, 1.51 Hz), 7.93 (1H, s), 7.99 (1H, d, J=8.51 Hz), 8.26 (1H, d, J=5.21 Hz), 8.59 (1H, s), 9.06 (1H, s), 10.92 (1H, s); ESIMS found for C$_{24}$H$_{26}$N$_8$O m/z 443.0 (M+1).

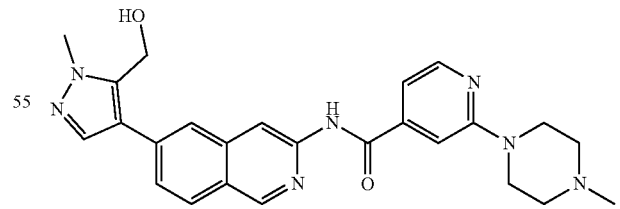

4-(Difluoromethoxy)-N-(6-(5-(hydroxymethyl)-1-methyl-1H-pyrazol-4-yl) isoquinolin-3-yl)benzamide 151

White solid (11.2 mg, 0.026 mmol, 5.1% yield). $^1$H NMR (499 MHz, DMSO-d$_6$) δ ppm 3.94 (3H, s), 4.66 (2H, d, J=5.49 Hz), 5.58 (1H, t, J=5.49 Hz), 7.40 (1H, t, J=74.00 Hz), 7.31 (2H, d, J=8.78 Hz), 7.73 (1H, dd, J=8.37, 1.51 Hz), 7.84 (1H, s), 8.03 (1H, s), 8.11 (1H, d, J=8.51 Hz), 8.14-8.20 (2H, m), 8.63 (1H, s), 9.18 (1H, s), 10.92 (1H, s); ESIMS found for C$_{22}$H$_{18}$F$_2$N$_4$O$_3$ m/z 424.9 (M+1).

N-(6-(5-(Hydroxymethyl)-1-methyl-1H-pyrazol-4-yl)isoquinolin-3-yl)-2-(4-methylpiperazin-1-yl)isonicotinamide 168

White solid (73.0 mg, 0.160 mmol, 45.1% yield). $^1$H NMR (499 MHz, DMSO-d$_6$) δ ppm 2.24 (3H, s), 2.43 (4H, t, J=4.94 Hz), 3.56-3.64 (4H, m), 3.94 (3H, s), 4.66 (2H, d, J=5.21 Hz), 5.58 (1H, t, J=5.35 Hz), 7.16 (1H, dd, J=5.21, 1.10 Hz), 7.47 (1H, s), 7.75 (1H, dd, J=8.51, 1.65 Hz), 7.84 (1H, s), 8.03 (1H, s), 8.12 (1H, d, J=8.51 Hz), 8.26 (1H, d, J=5.21 Hz), 8.64 (1H, s), 9.19 (1H, s), 11.08 (1H, s); ESIMS found for $C_{25}H_{27}N_7O_2$ m/z 458.2 (M+1).

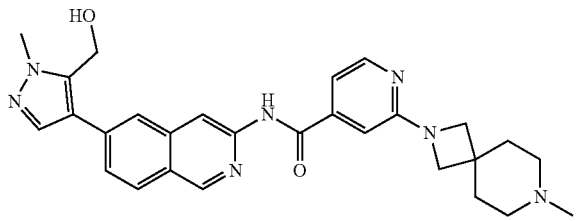

172

N-(6-(5-(Hydroxymethyl)-1-methyl-1H-pyrazol-4-yl)isoquinolin-3-yl)-2-(7-methyl-2,7-diazaspiro[3.5]nonan-2-yl)isonicotinamide 172

Off-white solid (6.0 mg, 0.012 mmol, 24.7% yield). $^1$H NMR (499 MHz, DMSO-$d_6$) δ ppm 1.76 (4H, br t, J=5.08 Hz), 2.15 (3H, s), 2.28 (4H, br s), 3.74 (4H, s), 3.94 (3H, s), 4.66 (2H, br d, J=3.84 Hz), 5.54-5.62 (1H, m), 7.03 (1H, s), 7.13 (1H, dd, J=5.21, 1.37 Hz), 7.74 (1H, dd, J=8.51, 1.65 Hz), 7.84 (1H, s), 8.03 (1H, s), 8.12 (1H, d, J=8.51 Hz), 8.20 (1H, d, J=5.21 Hz), 8.62 (1H, s), 9.18 (1H, s), 11.00 (1H, s); ESIMS found for $C_{28}H_{31}N_7O_2$ m/z 498.3 (M+1).

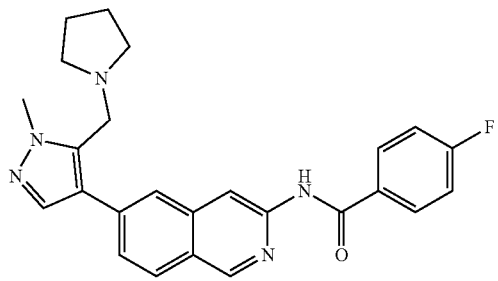

182

4-Fluoro-N-(6-(1-methyl-5-(pyrrolidin-1-ylmethyl)-1H-pyrazol-4-yl) isoquinolin-3-yl)benzamide 182

White solid (15.0 mg, 0.033 mmol, 22.6% yield). $^1$H NMR (500 MHz, DMSO-$d_6$) δ ppm 1.68 (4H, br t, J=3.02 Hz), 2.43-2.48 (4H, m), 3.85 (2H, s), 3.93 (3H, s), 7.36 (2H, t, J=8.78 Hz), 7.74 (1H, dd, J=8.51, 1.65 Hz), 7.81 (1H, s), 8.05 (1H, s), 8.09 (1H, d, J=8.51 Hz), 8.13-8.21 (2H, m), 8.59 (1H, s), 9.16 (1H, s), 10.90 (1H, s); ESIMS found for $C_{25}H_{24}FN_5O$ m/z 430.0 (M+1).

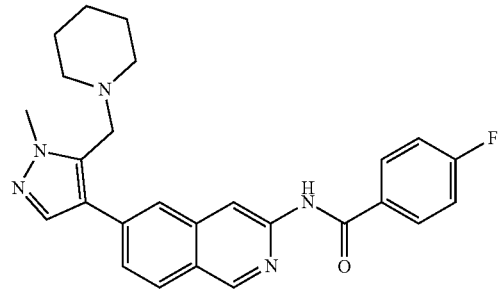

183

4-Fluoro-N-(6-(1-methyl-5-(piperidin-1-ylmethyl)-1H-pyrazol-4-yl) isoquinolin-3-yl)benzamide 183

Beige foam (43.0 mg, 0.092 mmol, 34.5% yield). $^1$H NMR (499 MHz, DMSO-$d_6$) δ ppm 1.33-1.42 (2H, m), 1.46-1.55 (4H, m), 2.37 (4H, br s), 3.67 (2H, s), 3.92 (3H, s), 7.35 (2H, t, J=8.92 Hz), 7.74 (1H, dd, J=8.51, 1.37 Hz), 7.82 (1H, s), 8.08 (1H, d, J=8.51 Hz), 8.13 (1H, s), 8.14-8.21 (2H, m), 8.60 (1H, s), 9.16 (1H, s), 10.85 (1H, s); ESIMS found for $C_{26}H_{26}FN_5O$ m/z 444.0 (M+1).

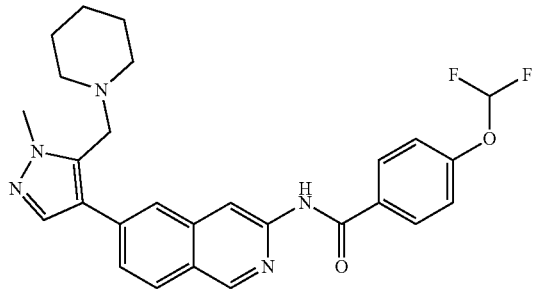

184

4-(Difluoromethoxy)-N-(6-(1-methyl-5-(piperidin-1-ylmethyl)-1H-pyrazol-4-yl)isoquinolin-3-yl)benzamide 184

White solid (13.4 mg, 0.026 mmol, 5.0% yield). $^1$H NMR (499 MHz, DMSO-$d_6$) δ ppm 1.34-1.43 (2H, m), 1.46-1.55 (4H, m), 2.38 (4H, br s), 3.67 (2H, s), 3.92 (3H, s), 7.40 (2H, t, J=73.70 Hz), 7.31 (2H, d, J=8.51 Hz), 7.75 (1H, dd, J=8.51, 1.37 Hz), 7.83 (1H, s), 8.09 (1H, d, J=8.51 Hz), 8.14 (1H, s), 8.15-8.20 (2H, m), 8.61 (1H, s), 9.16 (1H, s), 10.90 (1H, s); ESIMS found for $C_{27}H_{27}F_2N_5O_2$ m/z 491.9 (M+1).

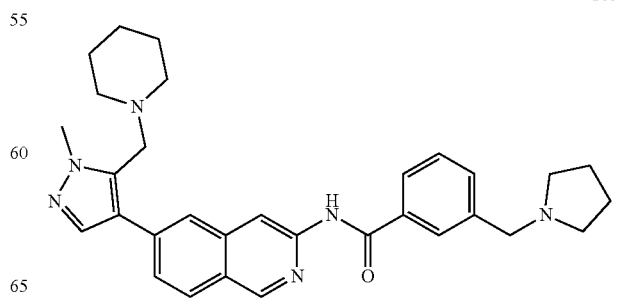

185

N-(6-(1-Methyl-5-(piperidin-1-ylmethyl)-1H-pyrazol-4-yl)isoquinolin-3-yl)-3-(pyrrolidin-1-ylmethyl)benzamide 185

White solid (35.0 mg, 0.065 mmol, 9.6% yield). $^1$H NMR (499 MHz, DMSO-$d_6$) δ ppm 1.34-1.44 (2H, m), 1.47-1.55 (4H, m), 1.71 (4H, dt, J=6.66, 3.12 Hz), 2.38 (4H, br s), 2.44-2.49 (4H, m), 3.66 (2H, s), 3.67 (2H, s), 3.92 (3H, s), 7.41-7.50 (1H, m), 7.50-7.58 (1H, m), 7.75 (1H, dd, J=8.51, 1.65 Hz), 7.83 (1H, s), 7.95 (1H, d, J=7.68 Hz), 8.00 (1H, s), 8.08 (1H, d, J=8.78 Hz), 8.14 (1H, s), 8.60 (1H, s), 9.16 (1H, s), 10.82 (1H, s); ESIMS found for $C_{31}H_{36}N_6O$ m/z 509.3 (M+1).

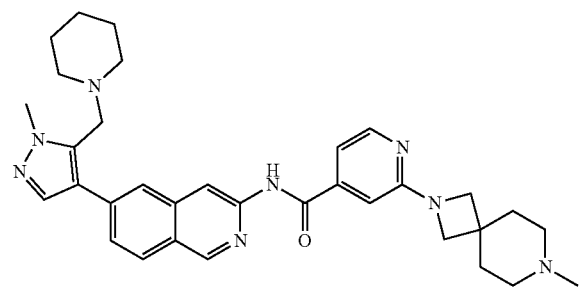

186

N-(6-(1-Methyl-5-(piperidin-1-ylmethyl)-1H-pyrazol-4-yl)isoquinolin-3-yl)-2-(7-methyl-2,7-diazaspiro[3.5]nonan-2-yl)isonicotinamide 186

Off-white solid (8.0 mg, 0.014 mmol, 23.2% yield). $^1$H NMR (499 MHz, DMSO-$d_6$) δ ppm 1.39 (2H, br d, J=4.39 Hz), 1.46-1.53 (4H, m), 1.76 (4H, br t, J=5.08 Hz), 2.15 (3H, s), 2.19-2.33 (4H, m), 2.38 (4H, br s), 3.67 (2H, s), 3.74 (4H, s), 3.92 (3H, s), 7.03 (1H, s), 7.13 (1H, dd, J=5.21, 1.37 Hz), 7.77 (1H, dd, J=8.51, 1.37 Hz), 7.83 (1H, s), 8.09 (1H, d, J=8.51 Hz), 8.15 (1H, s), 8.20 (1H, d, J=5.21 Hz), 8.60 (1H, s), 9.17 (1H, s), 10.98 (1H, s); ESIMS found for $C_{33}H_{40}N_8O$ m/z 565.4 (M+1).

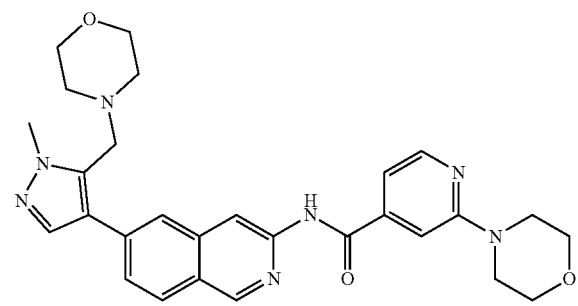

204

N-(6-(1-Methyl-5-(morpholinomethyl)-1H-pyrazol-4-yl)isoquinolin-3-yl)-2-morpholinoisonicotinamide 204

Off-white solid (10.0 mg, 0.020 mmol, 10.8% yield). $^1$H NMR (499 MHz, DMSO-$d_6$) δ ppm 2.42 (4H, br d, J=3.84 Hz), 3.53-3.61 (8H, m), 3.70-3.78 (6H, m), 3.94 (3H, s), 7.21 (1H, dd, J=5.21, 1.37 Hz), 7.47 (1H, s), 7.76 (1H, dd, J=8.51, 1.65 Hz), 7.83 (1H, s), 8.11 (2H, d, J=11.25 Hz), 8.29 (1H, d, J=4.94 Hz), 8.62 (1H, s), 9.18 (1H, s), 11.02 (1H, s); ESIMS found for $C_{28}H_{31}N_7O_3$ m/z 514.0 (M+1).

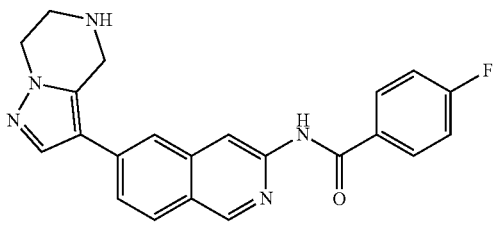

219

4-Fluoro-N-(6-(4,5,6,7-tetrahydropyrazolo[1,5-a]pyrazin-3-yl)isoquinolin-3-yl)benzamide 219

Off-white solid (20.0 mg, 0.052 mmol, 22.3% yield). $^1$H NMR (499 MHz, DMSO-$d_6$) δ ppm 3.18 (2H, br t, J=5.21 Hz), 4.07 (2H, br t, J=5.21 Hz), 4.25 (2H, s), 7.33-7.41 (2H, m), 7.68 (1H, dd, J=8.51, 1.37 Hz), 7.86 (1H, s), 8.00 (1H, s), 8.07 (1H, d, J=8.51 Hz), 8.12-8.21 (2H, m), 8.61 (1H, s), 9.13 (1H, s), 10.86 (1H, s); ESIMS found for $C_{22}H_{18}FN_5O$ m/z 387.9 (M+1).

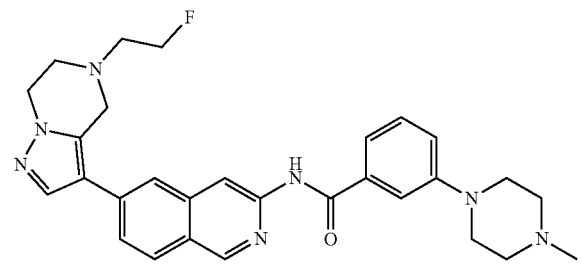

220

N-(6-(5-(2-Fluoroethyl)-4,5,6,7-tetrahydropyrazolo[1,5-a]pyrazin-3-yl) isoquinolin-3-yl)-3-(4-methylpiperazin-1-yl)benzamide 220

Yellow solid (2.0 mg, 0.004 mmol, 2.1% yield). $^1$H NMR (499 MHz, METHANOL-$d_4$) δ ppm 2.37 (3H, s), 2.65-2.69 (4H, m), 3.00-3.05 (1H, m), 3.14 (4H, dt, J=57.10, 5.50 Hz), 3.33-3.36 (4H, m), 3.70-3.77 (1H, m), 4.15 (2H, s), 4.28 (2H, t, J=5.49 Hz), 4.62-4.76 (2H, m), 6.70 (1H, br d, J=6.31 Hz), 7.23 (1H, dd, J=7.96, 2.20 Hz), 7.39-7.46 (1H, m), 7.46-7.52 (1H, m), 7.60 (1H, d, J=1.65 Hz), 7.67 (1H, dd, J=8.51, 1.65 Hz), 7.81 (1H, s), 7.95 (1H, s), 8.59 (1H, s), 9.05 (1H, s); ESIMS found for $C_{29}H_{32}FN_7O$ m/z 514.3 (M+1).

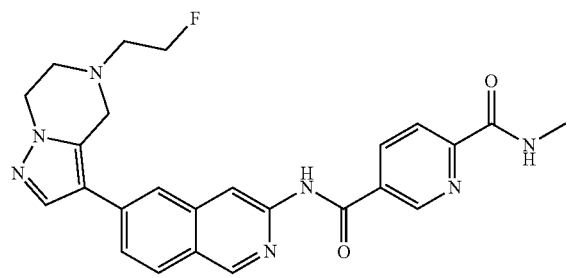

221

N⁵-(6-(5-(2-Fluoroethyl)-4,5,6,7-tetrahydropyrazolo
[1,5-a]pyrazin-3-yl) isoquinolin-3-yl)-N²-methylpyridine-2,5-dicarboxamide 221

White solid (66.0 mg, 0.139 mmol, 62.9% yield). ¹H NMR (499 MHz, DMSO-d₆) δ ppm 2.85 (3H, br d, J=4.39 Hz), 2.94-3.04 (2H, m), 3.08 (2H, br s), 4.10 (2H, s), 4.19 (2H, br s), 4.59-4.75 (2H, m), 7.71 (1H, br d, J=8.51 Hz), 7.87 (1H, s), 8.04 (1H, s), 8.10 (1H, br d, J=8.51 Hz), 8.16 (1H, br d, J=7.96 Hz), 8.56 (1H, br d, J=7.68 Hz), 8.66 (1H, s), 8.94 (1H, br d, J=4.67 Hz), 9.16 (1H, s), 9.22 (1H, s), 11.31 (1H, s); ESIMS found for $C_{25}H_{24}FN_7O_2$ m/z 474.2 (M+1).

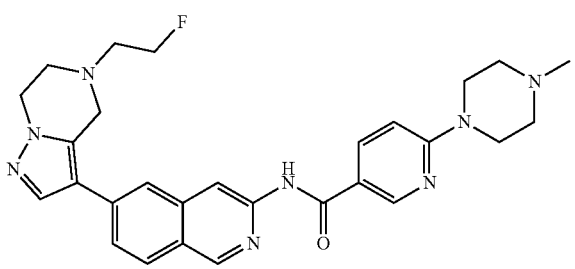

222

N-(6-(5-(2-Fluoroethyl)-4,5,6,7-tetrahydropyrazolo
[1,5-a]pyrazin-3-yl) isoquinolin-3-yl)-6-(4-methylpiperazin-1-yl)nicotinamide 222

Yellow solid (21.0 mg, 0.041 mmol, 11.6% yield). ¹H NMR (499 MHz, DMSO-d₆) δ ppm 2.23 (3H, s), 2.38-2.43 (4H, m), 3.00 (3H, dt, J=28.60, 4.70 Hz), 3.09 (2H, br t, J=5.35 Hz), 3.61-3.70 (4H, m), 4.10 (2H, s), 4.19 (2H, br t, J=5.35 Hz), 4.67 (2H, dt, J=47.80, 5.00 Hz), 6.90 (1H, d, J=9.06 Hz), 7.66 (1H, dd, J=8.64, 1.51 Hz), 7.81 (1H, s), 8.01 (1H, s), 8.07 (1H, d, J=8.51 Hz), 8.20 (1H, dd, J=9.06, 2.47 Hz), 8.60 (1H, s), 8.85 (1H, d, J=2.47 Hz), 9.12 (1H, s), 10.58 (1H, s); ESIMS found for $C_{28}H_{31}FN_8O$ m/z 515.0 (M+1).

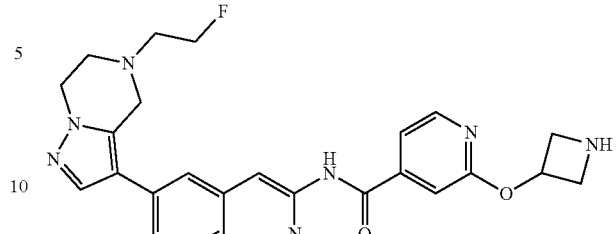

223

2-(Azetidin-3-yloxy)-N-(6-(5-(2-fluoroethyl)-4,5,6,
7-tetrahydropyrazolo[1,5-a]pyrazin-3-yl)isoquinolin-
3-yl)isonicotinamide 223

Beige solid (5.0 mg, 0.010 mmol, 10.0% yield). ¹H NMR (499 MHz, DMSO-d₆) δ ppm 2.99 (2H, dt, J=28.60, 5.00 Hz), 3.08 (2H, br t, J=5.35 Hz), 3.71 (2H, br d, J=4.67 Hz), 3.96 (2H, br s), 4.10 (2H, s), 4.19 (2H, br t, J=5.35 Hz), 4.67 (2H, dt, J=47.80, 4.70 Hz), 5.41 (1H, quin, J=5.90 Hz), 7.43 (1H, s), 7.59 (1H, br d, J=4.67 Hz), 7.71 (1H, dd, J=8.51, 1.65 Hz), 7.87 (1H, s), 8.03 (1H, s), 8.10 (1H, d, J=8.51 Hz), 8.31 (1H, d, J=5.21 Hz), 8.63 (1H, s), 9.16 (1H, s), 11.12 (1H, br s); ESIMS found for $C_{26}H_{26}FN_7O_2$ m/z 488.2 (M+1).

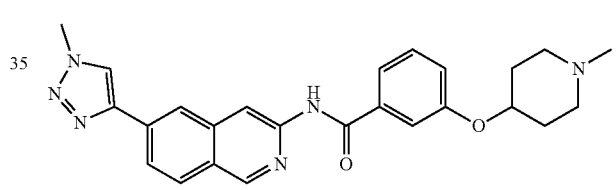

230

N-(6-(1-Methyl-1H-1,2,3-triazol-4-yl)isoquinolin-3-
yl)-3-((1-methylpiperidin-4-yl)oxy)benzamide 230

Off-yellow solid (34.5 mg, 0.074 mmol, 40.7% yield). ¹H NMR (499 MHz, DMSO-d₆) δ ppm 1.62-1.75 (2H, m), 1.93-2.02 (2H, m), 2.15-2.27 (2H, m), 2.20 (3H, s), 2.58-2.67 (2H, m), 4.15 (3H, s), 4.47-4.59 (1H, m), 7.17 (1H, ddd, J=8.30, 2.40, 1.10 Hz), 7.42 (1H, t, J=8.10 Hz), 7.59-7.69 (2H, m), 8.06 (1H, dd, J=8.51, 1.65 Hz), 8.17 (1H, d, J=8.51 Hz), 8.37 (1H, s), 8.65 (1H, s), 8.74 (1H, s), 9.20 (1H, s), 10.83 (1H, s); ESIMS found for $C_{25}H_{26}N_6O_2$ m/z 443.0 (M+1).

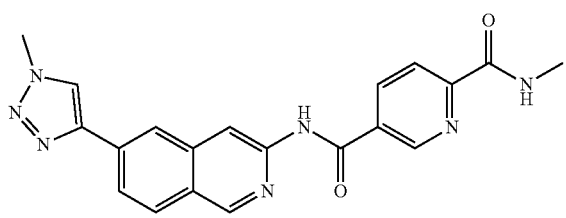

232

N²-methyl-N⁵-(6-(1-methyl-1H-1,2,3-triazol-4-yl)isoquinolin-3-yl)pyridine-2,5-dicarboxamide 232

Yellow solid (12.7 mg, 0.033 mmol, 7.4% yield). $^1$H NMR (499 MHz, DMSO-$d_6$) δ ppm 2.86 (3H, d, J=4.67 Hz), 4.15 (3H, s), 8.09 (1H, dd, J=8.51, 1.65 Hz), 8.17 (2H, dd, J=12.21, 8.37 Hz), 8.40 (1H, s), 8.57 (1H, dd, J=8.10, 2.33 Hz), 8.67 (1H, s), 8.75 (1H, s), 8.89 (1H, q, J=4.48 Hz), 9.22 (2H, s), 11.31 (1H, s); ESIMS found for $C_{20}H_{17}N_7O_2$ m/z 387.9. (M+1).

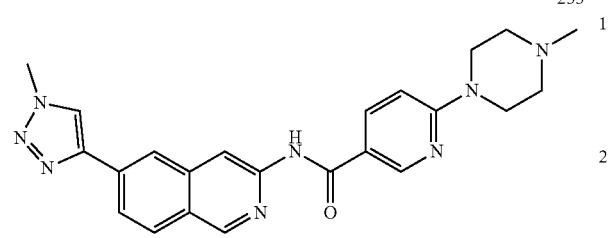

N-(6-(1-Methyl-1H-1,2,3-triazol-4-yl)isoquinolin-3-yl)-6-(4-methylpiperazin-1-yl)nicotinamide 233

Yellow solid (42.7 mg, 0.100 mmol, 28.3% yield). $^1$H NMR (499 MHz, DMSO-$d_6$) δ ppm 2.23 (3H, s), 2.38-2.43 (4H, m), 3.61-3.68 (4H, m), 4.15 (3H, s), 6.89 (1H, d, J=9.06 Hz), 8.04 (1H, dd, J=8.51, 1.65 Hz), 8.14 (1H, d, J=8.51 Hz), 8.20 (1H, dd, J=9.06, 2.47 Hz), 8.34 (1H, s), 8.63 (1H, s), 8.73 (1H, s), 8.85 (1H, d, J=2.47 Hz), 9.17 (1H, s), 10.64 (1H, s); ESIMS found for $C_{23}H_{24}N_5O$ m/z 429.0 (M+1).

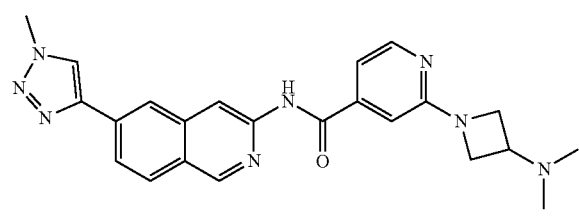

2-(3-(Dimethylamino)azetidin-1-yl)-N-(6-(1-methyl-1H-1,2,3-triazol-4-yl)isoquinolin-3-yl)isonicotinamide 236

Beige solid (30.0 mg, 0.070 mmol, 24.4% yield). $^1$H NMR (499 MHz, DMSO-$d_6$) δ ppm 2.14 (6H, s), 3.19-3.25 (1H, m), 3.81 (2H, dd, J=8.37, 5.35 Hz), 4.07 (2H, t, J=7.68 Hz), 4.15 (3H, s), 7.04 (1H, s), 7.16 (1H, dd, J=5.21, 1.37 Hz), 8.08 (1H, dd, J=8.51, 1.37 Hz), 8.17 (1H, d, J=8.51 Hz), 8.20-8.26 (1H, m), 8.38 (1H, s), 8.64 (1H, s), 8.74 (1H, s), 9.20 (1H, s), 10.99 (1H, s); ESIMS found for $C_{23}H_{24}N_5O$ m/z 429.0 (M+1).

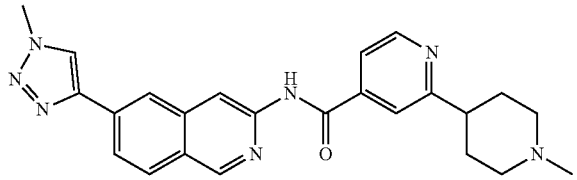

N-(6-(1-Methyl-1H-1,2,3-triazol-4-yl)isoquinolin-3-yl)-2-(1-methylpiperidin-4-yl)isonicotinamide 238

Off-white solid (36.0 mg, 0.084 mmol, 68.6% yield). $^1$H NMR (499 MHz, DMSO-$d_6$) δ ppm 1.77-1.93 (4H, m), 2.00 (2H, td, J=11.53, 2.47 Hz), 2.21 (3H, s), 2.73 (1H, tt, J=11.46, 4.05 Hz), 2.90 (2H, br d, J=11.25 Hz), 4.15 (3H, s), 7.77 (1H, dd, J=4.94, 1.65 Hz), 7.92 (1H, s), 8.09 (1H, dd, J=8.51, 1.65 Hz), 8.18 (1H, d, J=8.78 Hz), 8.40 (1H, s), 8.67 (1H, s), 8.69 (1H, d, J=5.21 Hz), 8.76 (1H, s), 9.22 (1H, s), 11.23 (1H, s); ESIMS found for $C_{24}H_{25}N_7O$ m/z 428.2 (M+1).

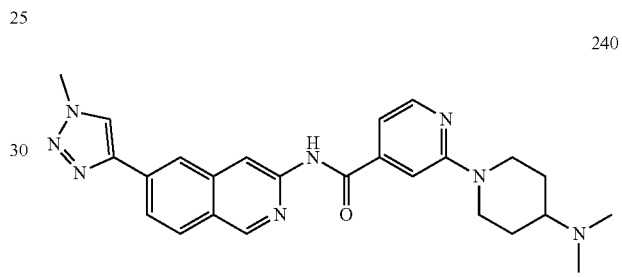

2-(4-(Dimethylamino)piperidin-1-yl)-N-(6-(1-methyl-1H-1,2,3-triazol-4-yl) isoquinolin-3-yl)isonicotinamide 240

White solid (18.0 mg, 0.039 mmol, 28.6% yield). $^1$H NMR (499 MHz, DMSO-$d_6$) δ ppm 1.40 (2H, qd, J=11.98, 3.84 Hz), 1.85 (2H, br d, J=11.80 Hz), 2.24 (6H, s), 2.37-2.46 (1H, m), 2.81-2.92 (2H, m), 4.15 (3H, s), 4.44 (2H, br d, J=13.17 Hz), 7.13 (1H, dd, J=5.08, 0.96 Hz), 7.46 (1H, s), 8.07 (1H, dd, J=8.51, 1.37 Hz), 8.17 (1H, d, J=8.51 Hz), 8.25 (1H, d, J=5.21 Hz), 8.38 (1H, s), 8.65 (1H, s), 8.74 (1H, s), 9.21 (1H, s), 11.04 (1H, s); ESIMS found for $C_{25}H_{28}N_8O$ m/z 457.0 (M+1).

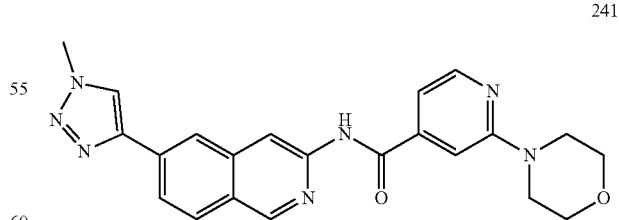

N-(6-(1-Methyl-1H-1,2,3-triazol-4-yl)isoquinolin-3-yl)-2-morpholinoisonicotinamide 241

Off-white solid (70.0 mg, 0.169 mmol, 53.6% yield). $^1$H NMR (499 MHz, DMSO-$d_6$) δ ppm 3.52-3.63 (4H, m), 3.70-3.78 (4H, m), 4.15 (3H, s), 7.22 (1H, dd, J=5.08, 1.23 Hz), 7.47 (1H, s), 8.08 (1H, dd, J=8.51, 1.65 Hz), 8.17 (1H, d, J=8.78 Hz), 8.29 (1H, d, J=4.94 Hz), 8.38 (1H, s), 8.66 (1H, s), 8.74 (1H, s), 9.21 (1H, s), 11.06 (1H, s); ESIMS found for C$_{22}$H$_{21}$N$_7$O$_2$ m/z 415.9 (M+1).

242

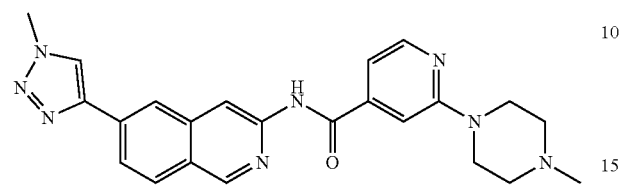

N-(6-(1-Methyl-1H-1,2,3-triazol-4-yl)isoquinolin-3-yl)-2-(4-methylpiperazin-1-yl)isonicotinamide 242

White solid (38.0 mg, 0.089 mmol, 37.8% yield). $^1$H NMR (499 MHz, DMSO-d$_6$) δ ppm 2.23 (3H, s), 2.43 (4H, br t, J=4.67 Hz), 3.56-3.66 (4H, m), 4.15 (3H, s), 7.17 (1H, d, J=4.94 Hz), 7.47 (1H, s), 8.04-8.10 (1H, m), 8.18 (1H, d, J=8.51 Hz), 8.26 (1H, d, J=4.94 Hz), 8.38 (1H, s), 8.66 (1H, s), 8.75 (1H, s), 9.21 (1H, s), 11.10 (1H, s); ESIMS found for C$_{23}$H$_{24}$N$_8$O m/z 429.0 (M+1).

243

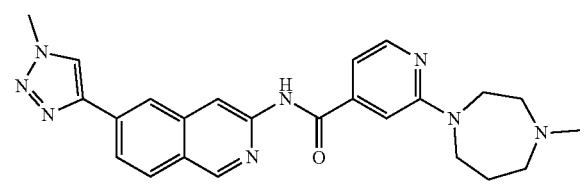

2-(4-Methyl-1,4-diazepan-1-yl)-N-(6-(1-methyl-1H-1,2,3-triazol-4-yl) isoquinolin-3-yl)isonicotinamide 243

Beige solid (47.0 mg, 0.106 mmol, 37.0% yield). $^1$H NMR (499 MHz, DMSO-d$_6$) δ ppm 1.93 (2H, dt, J=11.39, 5.83 Hz), 2.27 (3H, s), 2.48 (2H, br s), 2.63 (2H, dd, J=5.63, 4.25 Hz), 3.69 (2H, t, J=6.17 Hz), 3.78-3.85 (2H, m), 4.15 (3H, s), 7.06 (1H, dd, J=5.21, 1.10 Hz), 7.21 (1H, s), 8.08 (1H, dd, J=8.51, 1.65 Hz), 8.18 (1H, d, J=8.51 Hz), 8.21 (1H, d, J=4.94 Hz), 8.38 (1H, s), 8.65 (1H, s), 8.76 (1H, s), 9.21 (1H, s), 11.08 (1H, s); ESIMS found for C$_{24}$H$_{26}$N$_8$O m/z 443.2 (M+1).

245

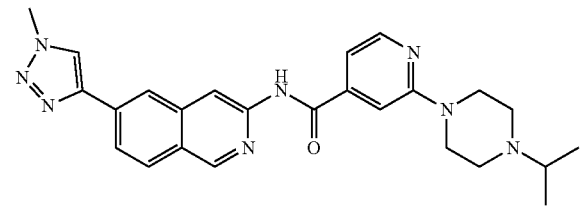

2-(4-Isopropylpiperazin-1-yl)-N-(6-(1-methyl-1H-1,2,3-triazol-4-yl) isoquinolin-3-yl)isonicotinamide 245

Beige solid (198.0 mg, 0.434 mmol, 36.8% yield). $^1$H NMR (500 MHz, DMSO-d$_6$) δ ppm 1.01 (6H, d, J=6.59 Hz), 2.53-2.59 (4H, m), 2.65-2.75 (1H, m), 3.53-3.63 (4H, m), 4.15 (3H, s), 7.16 (1H, dd, J=5.21, 1.37 Hz), 7.45 (1H, s), 8.08 (1H, dd, J=8.51, 1.37 Hz), 8.18 (1H, d, J=8.78 Hz), 8.26 (1H, d, J=5.21 Hz), 8.38 (1H, s), 8.66 (1H, s), 8.76 (1H, s), 9.21 (1H, s), 11.11 (1H, s); ESIMS found for C$_{25}$H$_{28}$N$_8$O m/z 457.2 (M+1).

249

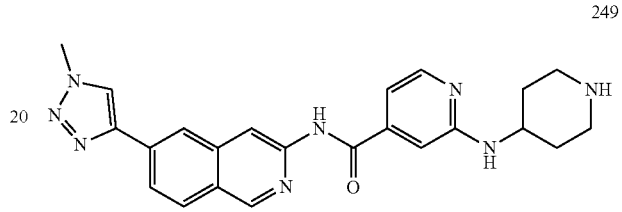

N-(6-(1-Methyl-1H-1,2,3-triazol-4-yl)isoquinolin-3-yl)-2-(piperidin-4-ylamino)isonicotinamide 249

White solid (7.0 mg, 0.016 mmol, 57.6% yield). $^1$H NMR (499 MHz, DMSO-d$_6$) δ ppm 1.33-1.46 (2H, m), 1.93 (2H, br d, J=10.15 Hz), 2.69 (2H, br t, J=10.98 Hz), 3.06 (2H, br d, J=12.62 Hz), 3.81-3.93 (1H, m), 4.15 (3H, s), 6.78 (1H, d, J=7.68 Hz), 7.00 (1H, s), 7.03 (1H, dd, J=5.21, 1.37 Hz), 8.07 (1H, dd, J=8.51, 1.37 Hz), 8.10 (1H, d, J=5.49 Hz), 8.17 (1H, d, J=8.51 Hz), 8.39 (1H, s), 8.62 (1H, s), 8.75 (1H, s), 9.20 (1H, s), 10.88 (1H, br s); ESIMS found for C$_{23}$H$_{24}$N$_8$O m/z 429.0 (M+1).

250

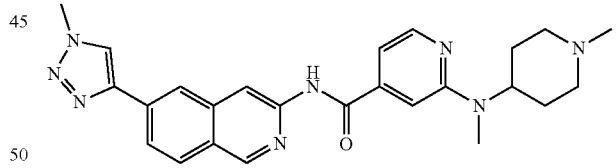

2-(Methyl(1-methylpiperidin-4-yl)amino)-N-(6-(1-methyl-1H-1,2,3-triazol-4-yl)isoquinolin-3-yl)isonicotinamide 250

Brown solid (19.0 mg, 0.042 mmol, 14.5% yield). $^1$H NMR (499 MHz, DMSO-d$_6$) δ ppm 1.49-1.64 (2H, m), 1.75-1.87 (2H, m), 2.05 (2H, br t, J=10.84 Hz), 2.20 (3H, s), 2.82-2.90 (2H, m), 2.94 (3H, s), 4.15 (3H, s), 4.45-4.56 (1H, m), 7.08 (1H, dd, J=5.08, 1.23 Hz), 7.19 (1H, s), 8.07 (1H, dd, J=8.37, 1.51 Hz), 8.17 (1H, d, J=8.51 Hz), 8.23 (1H, d, J=5.21 Hz), 8.37 (1H, s), 8.65 (1H, s), 8.74 (1H, s), 9.21 (1H, s), 11.01 (1H, s); ESIMS found for C$_{25}$H$_{28}$N$_8$O m/z 457.0 (M+1).

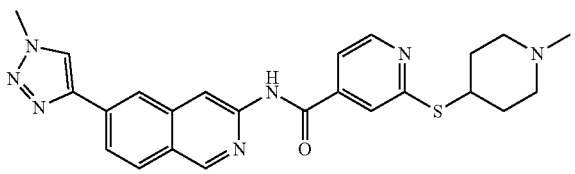

N-(6-(1-Methyl-1H-1,2,3-triazol-4-yl)isoquinolin-3-yl)-2-((1-methylpiperidin-4-yl)thio)isonicotinamide 253

Off-white solid (28.0 mg, 0.061 mmol, 19.4% yield). $^1$H NMR (499 MHz, DMSO-d$_6$) δ ppm 1.58-1.72 (2H, m), 1.99-2.07 (2H, m), 2.12 (2H, br t, J=10.29 Hz), 2.17 (3H, s), 2.69 (2H, br d, J=10.70 Hz), 3.84 (1H, br t, J=9.74 Hz), 4.15 (3H, s), 7.64 (1H, dd, J=5.21, 1.65 Hz), 7.82 (1H, s), 8.09 (1H, dd, J=8.51, 1.65 Hz), 8.18 (1H, d, J=8.51 Hz), 8.39 (1H, s), 8.62 (1H, d, J=5.21 Hz), 8.64 (1H, s), 8.75 (1H, s), 9.21 (1H, s), 11.22 (1H, s); ESIMS found for C$_{24}$H$_{25}$N$_7$OS m/z 460.2 (M+1).

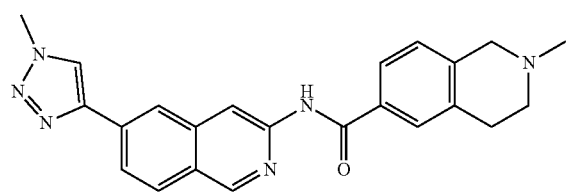

2-Methyl-N-(6-(1-methyl-1H-1,2,3-triazol-4-yl)isoquinolin-3-yl)-1,2,3,4-tetrahydroisoquinoline-6-carboxamide 256

Off-white solid (39.0 mg, 0.093 mmol, 85.9% yield). $^1$H NMR (499 MHz, DMSO-d$_6$) δ ppm 2.37 (3H, s), 2.64 (2H, t, J=5.90 Hz), 2.92 (2H, br t, J=5.76 Hz), 3.56 (2H, s), 4.15 (3H, s), 7.19 (1H, d, J=7.96 Hz), 7.83 (1H, dd, J=7.96, 1.92 Hz), 7.88 (1H, s), 8.06 (1H, dd, J=8.51, 1.65 Hz), 8.16 (1H, d, J=8.78 Hz), 8.36 (1H, d, J=0.82 Hz), 8.64 (1H, s), 8.74 (1H, s), 9.18 (1H, s), 10.69 (1H, s); ESIMS found for C$_{23}$H$_{22}$N$_6$O m/z 399.0 (M+1).

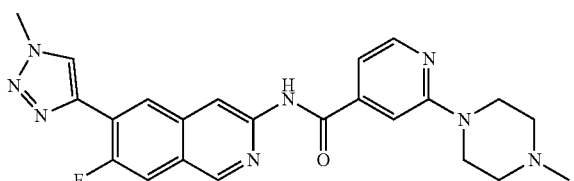

N-(7-Fluoro-6-(1-methyl-1H-1,2,3-triazol-4-yl)isoquinolin-3-yl)-2-(4-methylpiperazin-1-yl)isonicotinamide 257

Light brown solid (14.0 mg, 0.031 mmol, 17.8% yield). $^1$H NMR (499 MHz, DMSO-d$_6$) δ ppm 2.24 (3H, s), 2.43 (4H, br t, J=4.94 Hz), 3.57-3.66 (4H, m), 4.17 (3H, s), 7.17 (1H, dd, J=5.21, 1.10 Hz), 7.47 (1H, s), 8.07 (1H, d, J=11.25 Hz), 8.26 (1H, d, J=5.49 Hz), 8.60 (1H, d, J=4.39 Hz), 8.67 (1H, d, J=6.86 Hz), 8.71 (1H, s), 9.22 (1H, s), 11.11 (1H, s); ESIMS found for C$_{23}$H$_{23}$FN$_8$O m/z 447.2 (M+1).

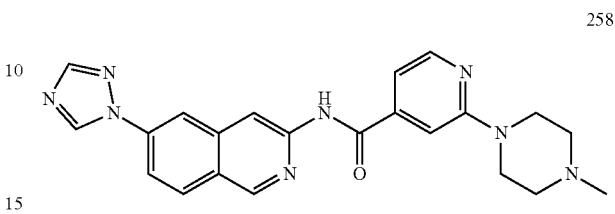

N-(6-(1H-1,2,4-Triazol-1-yl)isoquinolin-3-yl)-2-(4-methylpiperazin-1-yl) isonicotinamide 258

Beige solid (40.0 mg, 0.097 mmol, 41.1% yield). $^1$H NMR (499 MHz, DMSO-d$_6$) δ ppm 2.24 (3H, s), 2.43 (4H, t, J=4.94 Hz), 3.56-3.66 (4H, m), 7.16 (1H, dd, J=5.21, 1.10 Hz), 7.47 (1H, s), 8.11 (1H, dd, J=8.78, 1.92 Hz), 8.26 (1H, d, J=5.21 Hz), 8.32 (1H, d, J=9.06 Hz), 8.35 (1H, s), 8.48 (1H, d, J=1.92 Hz), 8.73 (1H, s), 9.29 (1H, s), 9.53 (1H, s), 11.18 (1H, s); ESIMS found for C$_{22}$H$_{22}$N$_8$O m/z 415.2 (M+1).

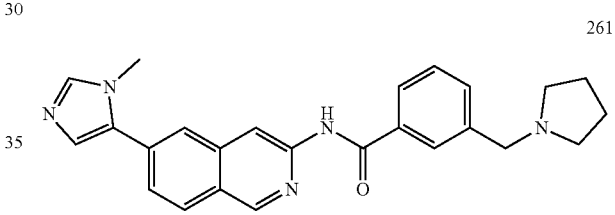

N-(6-(1-Methyl-1H-imidazol-5-yl)isoquinolin-3-yl)-3-(pyrrolidin-1-ylmethyl)benzamide 261

White solid (25.0 mg, 0.061 mmol, 27.2% yield). $^1$H NMR (499 MHz, DMSO-d$_6$) δ ppm 1.72 (4H, dt, J=6.66, 3.12 Hz), 2.48 (4H, br s), 3.67 (2H, s), 3.85 (3H, s), 7.32 (1H, d, J=0.82 Hz), 7.41-7.51 (1H, m), 7.54 (1H, br d, J=7.68 Hz), 7.72 (1H, dd, J=8.51, 1.65 Hz), 7.80 (1H, s), 7.96 (1H, br d, J=7.96 Hz), 8.01 (1H, s), 8.08 (1H, s), 8.14 (1H, d, J=8.51 Hz), 8.68 (1H, s), 9.21 (1H, s), 10.81 (1H, s); ESIMS found for C$_{25}$H$_{25}$N$_5$O m/z 412.0 (M+1).

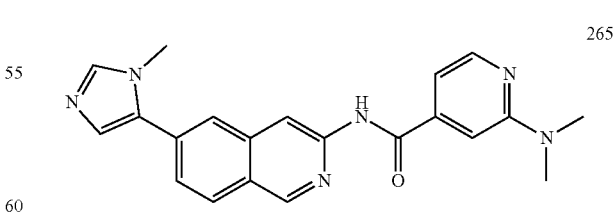

2-(Dimethylamino)-N-(6-(1-methyl-1H-imidazol-5-yl)isoquinolin-3-yl) isonicotinamide 265

White solid (16.0 mg, 0.043 mmol, 14.9% yield). $^1$H NMR (499 MHz, DMSO-d$_6$) δ ppm 3.11 (6H, s), 3.85 (3H, s), 7.09 (1H, dd, J=5.08, 1.23 Hz), 7.25 (1H, s), 7.33 (1H, d, J=1.10 Hz), 7.29-7.29 (1H, m), 7.74 (1H, dd, J=8.51, 1.65 Hz), 7.81 (1H, s), 8.10 (1H, d, J=0.82 Hz), 8.15 (1H, d, J=8.51 Hz), 8.23 (1H, d, J=5.21 Hz), 8.69 (1H, s), 9.22 (1H, s), 11.07 (1H, s); ESIMS found for $C_{21}H_{20}N_6O$ m/z 373.2 (M+1).

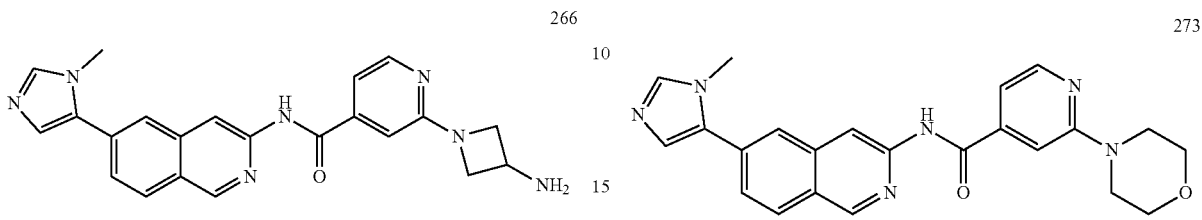

2-(3-Aminoazetidin-1-yl)-N-(6-(1-methyl-1H-imidazol-5-yl)isoquinolin-3-yl)isonicotinamide 266

Yellow solid (25.3 mg, 0.063 mmol, 51.0% yield). $^1$H NMR (499 MHz, DMSO-d$_6$) δ ppm 2.15 (2H, br s), 3.62 (2H, dd, J=8.23, 5.76 Hz), 3.79-3.89 (4H, m), 4.19 (2H, t, J=7.68 Hz), 7.02 (1H, s), 7.14 (1H, dd, J=5.21, 1.37 Hz), 7.33 (1H, d, J=1.10 Hz), 7.74 (1H, dd, J=8.51, 1.65 Hz), 7.81 (1H, s), 8.09 (1H, s), 8.15 (1H, d, J=8.51 Hz), 8.20 (1H, d, J=5.21 Hz), 8.68 (1H, s), 9.22 (1H, s), 11.04 (1H, br s); ESIMS found for $C_{22}H_{21}N_7O$ m/z 400.2 (M+1).

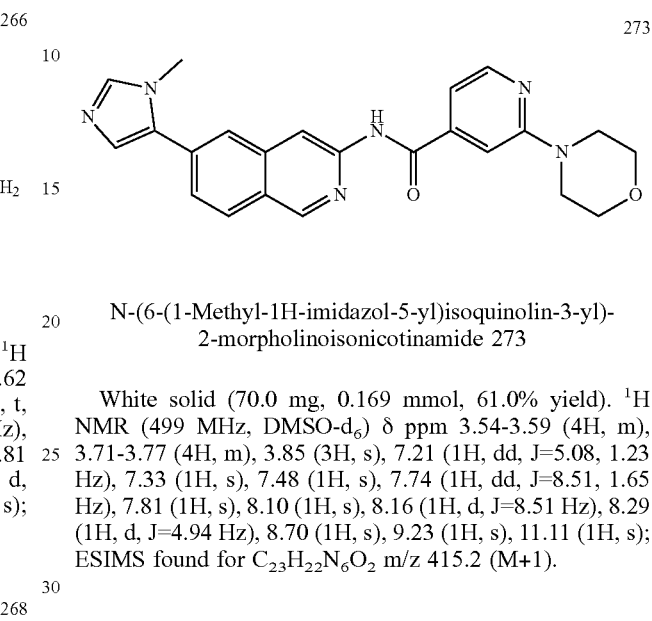

N-(6-(1-Methyl-1H-imidazol-5-yl)isoquinolin-3-yl)-2-(pyrrolidin-1-yl) isonicotinamide 268

White solid (69.0 mg, 0.173 mmol, 62.6% yield). $^1$H NMR (499 MHz, DMSO-d$_6$) δ ppm 1.94-2.03 (4H, m), 3.47 (4H, br t, J=6.59 Hz), 3.85 (3H, s), 7.06 (1H, dd, J=5.21, 1.37 Hz), 7.08 (1H, s), 7.33 (1H, s), 7.74 (1H, dd, J=8.51, 1.65 Hz), 7.81 (1H, s), 8.09 (1H, s), 8.15 (1H, d, J=8.78 Hz), 8.21 (1H, d, J=5.21 Hz), 8.69 (1H, s), 9.22 (1H, s), 11.04 (1H, s); ESIMS found for $C_{23}H_{22}N_6O$ m/z 399.2 (M+1).

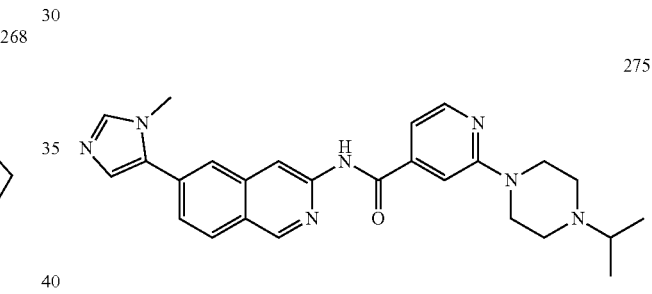

N-(6-(1-Methyl-1H-imidazol-5-yl)isoquinolin-3-yl)-2-(piperidin-1-yl) isonicotinamide 271

White solid (85.0 mg, 0.206 mmol, 74.5% yield). $^1$H NMR (499 MHz, DMSO-d$_6$) δ ppm 1.53-1.62 (4H, m), 1.62-1.69 (2H, m), 3.61-3.66 (4H, m), 3.85 (3H, s), 7.09 (1H, dd, J=5.21, 1.37 Hz), 7.33 (1H, s), 7.44 (1H, s), 7.74 (1H, dd, J=8.51, 1.65 Hz), 7.81 (1H, s), 8.09 (1H, s), 8.15 (1H, d, J=8.51 Hz), 8.23 (1H, d, J=5.21 Hz), 8.69 (1H, s), 9.22 (1H, s), 11.09 (1H, s); ESIMS found for $C_{24}H_{24}N_6O$ m/z 413.2 (M+1).

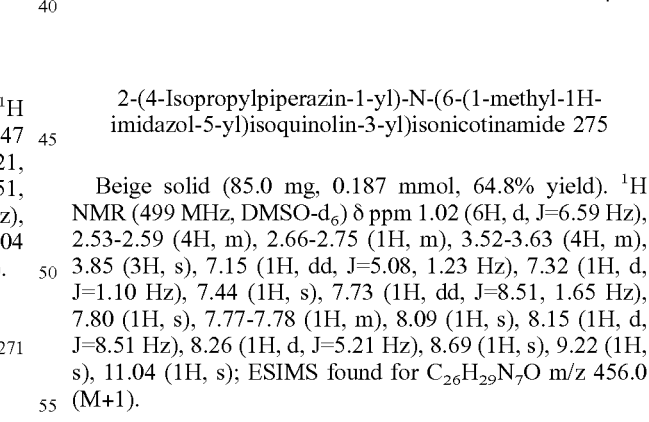

N-(6-(1-Methyl-1H-imidazol-5-yl)isoquinolin-3-yl)-2-morpholinoisonicotinamide 273

White solid (70.0 mg, 0.169 mmol, 61.0% yield). $^1$H NMR (499 MHz, DMSO-d$_6$) δ ppm 3.54-3.59 (4H, m), 3.71-3.77 (4H, m), 3.85 (3H, s), 7.21 (1H, dd, J=5.08, 1.23 Hz), 7.33 (1H, s), 7.48 (1H, s), 7.74 (1H, dd, J=8.51, 1.65 Hz), 7.81 (1H, s), 8.10 (1H, s), 8.16 (1H, d, J=8.51 Hz), 8.29 (1H, d, J=4.94 Hz), 8.70 (1H, s), 9.23 (1H, s), 11.11 (1H, s); ESIMS found for $C_{23}H_{22}N_6O_2$ m/z 415.2 (M+1).

2-(4-Isopropylpiperazin-1-yl)-N-(6-(1-methyl-1H-imidazol-5-yl)isoquinolin-3-yl)isonicotinamide 275

Beige solid (85.0 mg, 0.187 mmol, 64.8% yield). $^1$H NMR (499 MHz, DMSO-d$_6$) δ ppm 1.02 (6H, d, J=6.59 Hz), 2.53-2.59 (4H, m), 2.66-2.75 (1H, m), 3.52-3.63 (4H, m), 3.85 (3H, s), 7.15 (1H, dd, J=5.08, 1.23 Hz), 7.32 (1H, d, J=1.10 Hz), 7.44 (1H, s), 7.73 (1H, dd, J=8.51, 1.65 Hz), 7.80 (1H, s), 7.77-7.78 (1H, m), 8.09 (1H, s), 8.15 (1H, d, J=8.51 Hz), 8.26 (1H, d, J=5.21 Hz), 8.69 (1H, s), 9.22 (1H, s), 11.04 (1H, s); ESIMS found for $C_{26}H_{29}N_7O$ m/z 456.0 (M+1).

2-(4-Cyclopropylpiperazin-1-yl)-N-(6-(1-methyl-1H-imidazol-5-yl) isoquinolin-3-yl)isonicotinamide 276

White solid (46.0 mg, 0.101 mmol, 73.6% yield). $^1$H NMR (500 MHz, DMSO-d$_6$) δ ppm 0.34-0.41 (2H, m), 0.41-0.49 (2H, m), 1.66 (1H, tt, J=6.62, 3.53 Hz), 2.62-2.68 (4H, m), 3.52-3.61 (4H, m), 3.85 (3H, s), 7.15 (1H, dd, J=5.08, 1.23 Hz), 7.33 (1H, d, J=1.10 Hz), 7.47 (1H, s), 7.74 (1H, dd, J=8.51, 1.65 Hz), 7.81 (1H, s), 8.10 (1H, s), 8.15 (1H, d, J=8.78 Hz), 8.26 (1H, d, J=5.21 Hz), 8.69 (1H, s), 9.23 (1H, s), 11.12 (1H, s); ESIMS found for C$_{26}$H$_{27}$N$_7$O m/z 454.0 (M+1).

277

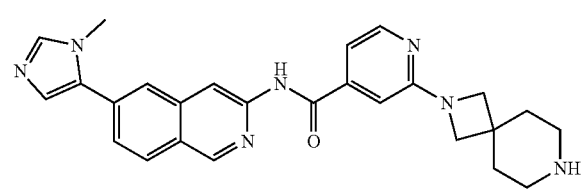

N-(6-(1-Methyl-1H-imidazol-5-yl)isoquinolin-3-yl)-2-(2,7-diazaspiro[3.5]nonan-2-yl)isonicotinamide 277

Off-white solid (131.6 mg, 0.290 mmol, 31.2% yield). $^1$H NMR (499 MHz, DMSO-d$_6$) δ ppm 1.62-1.71 (4H, m), 2.66 (4H, br s), 3.73 (4H, s), 3.85 (3H, s), 7.03 (1H, s), 7.12 (1H, dd, J=5.21, 1.37 Hz), 7.33 (1H, s), 7.74 (1H, dd, J=8.51, 1.65 Hz), 7.81 (1H, s), 8.10 (1H, s), 8.15 (1H, d, J=8.51 Hz), 8.20 (1H, d, J=5.21 Hz), 8.68 (1H, s), 9.22 (1H, s), 11.04 (1H, br s); ESIMS found for C$_{26}$H$_{27}$N$_7$O m/z 454.2 (M+1).

278

N-(6-(1-Methyl-1H-imidazol-5-yl)isoquinolin-3-yl)-2-(7-methyl-2,7-diazaspiro[3.5]nonan-2-yl)isonicotinamide 278

Off-white solid (39.0 mg, 0.079 mmol, 35.9% yield). $^1$H NMR (499 MHz, DMSO-d$_6$) δ ppm 1.76 (4H, br t, J=5.08 Hz), 2.14 (3H, s), 2.27 (4H, br s), 3.73 (4H, s), 3.85 (3H, s), 7.03 (1H, s), 7.13 (1H, dd, J=5.08, 1.51 Hz), 7.33 (1H, s), 7.74 (1H, dd, J=8.51, 1.65 Hz), 7.81 (1H, s), 8.10 (1H, s), 8.15 (1H, d, J=8.51 Hz), 8.20 (1H, d, J=5.21 Hz), 8.68 (1H, s), 9.22 (1H, s), 11.04 (1H, s); ESIMS found for C$_{27}$H$_{29}$N$_7$O m/z 468.2 (M+1).

285

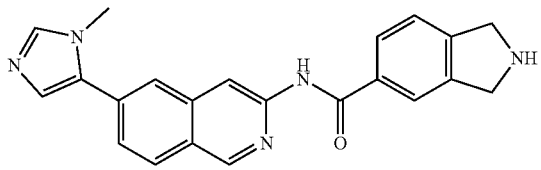

N-(6-(1-Methyl-1H-imidazol-5-yl)isoquinolin-3-yl) isoindoline-5-carboxamide 285

Off-white solid (233.7 mg, 0.633 mmol, 68.1% yield). $^1$H NMR (499 MHz, DMSO-d$_6$) δ ppm 3.85 (4H, s), 4.07 (1H, s), 4.27 (3H, s), 7.33 (1H, s), 7.44 (1H, d, J=7.96 Hz), 7.72 (1H, dd, J=8.51, 1.65 Hz), 7.81 (1H, s), 7.97 (1H, dd, J=7.82, 1.24 Hz), 8.01 (1H, s), 8.09 (1H, s), 8.14 (1H, d, J=8.51 Hz), 8.69 (1H, s), 9.21 (1H, s), 10.84 (1H, s); ESIMS found for C$_{22}$H$_{19}$N$_5$O m/z 370.2 (M+1).

286

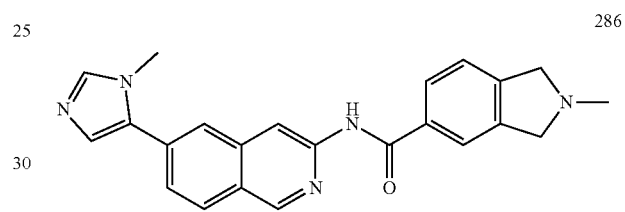

2-Methyl-N-(6-(1-methyl-1H-imidazol-5-yl)isoquinolin-3-yl)isoindoline-5-carboxamide 286

Off-white solid (39.0 mg, 0.097 mmol, 17.8% yield). $^1$H NMR (499 MHz, DMSO-d$_6$) δ ppm 2.51 (4H, br s), 3.85 (3H, s), 3.87 (4H, s), 7.33 (1H, s), 7.37 (1H, d, J=7.96 Hz), 7.72 (1H, dd, J=8.64, 1.51 Hz), 7.81 (1H, s), 7.89-7.98 (2H, m), 8.09 (1H, s), 8.14 (1H, d, J=8.51 Hz), 8.68 (1H, s), 9.20 (1H, s), 10.80 (1H, s); ESIMS found for C$_{23}$H$_{21}$N$_5$O m/z 384.2 (M+1).

289

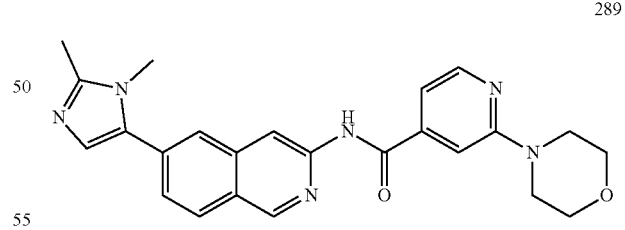

N-(6-(1,2-Dimethyl-1H-imidazol-5-yl)isoquinolin-3-yl)-2-morpholinoisonicotinamide 289

Beige solid (37.0 mg, 0.085 mmol, 35.0% yield). $^1$H NMR (499 MHz, DMSO-d$_6$) δ ppm 2.40 (3H, s), 3.54-3.61 (4H, m), 3.68 (3H, s), 3.70-3.77 (4H, m), 7.14 (1H, s), 7.21 (1H, dd, J=5.08, 1.23 Hz), 7.47 (1H, s), 7.67 (1H, dd, J=8.51, 1.65 Hz), 8.00 (1H, s), 8.14 (1H, d, J=8.78 Hz), 8.29 (1H, d, J=4.94 Hz), 8.67 (1H, s), 9.21 (1H, s), 11.05 (1H, s); ESIMS found for C$_{24}$H$_{24}$N$_6$O$_2$ m/z 429.0 (M+1).

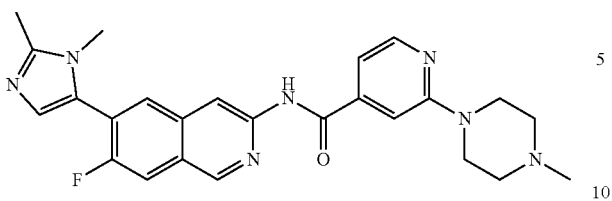

N-(6-(1,2-Dimethyl-1H-imidazol-5-yl)-7-fluoroisoquinolin-3-yl)-2-(4-methylpiperazin-1-yl)isonicotinamide 290

Off-white solid (54.0 mg, 0.118 mmol, 42.4% yield). $^1$H NMR (499 MHz, DMSO-$d_6$) δ ppm 2.23 (3H, s), 2.41 (3H, s), 2.41-2.45 (4H, m), 3.54 (3H, d, J=0.82 Hz), 3.58-3.63 (4H, m), 7.07 (1H, d, J=0.82 Hz), 7.15 (1H, dd, J=5.21, 1.10 Hz), 7.47 (1H, s), 8.05 (1H, d, J=10.43 Hz), 8.08 (1H, d, J=7.14 Hz), 8.26 (1H, d, J=5.21 Hz), 8.71 (1H, s), 9.23 (1H, s), 11.14 (1H, s); ESIMS found for $C_{25}H_{26}FN_7O$ m/z 460.2 (M+1).

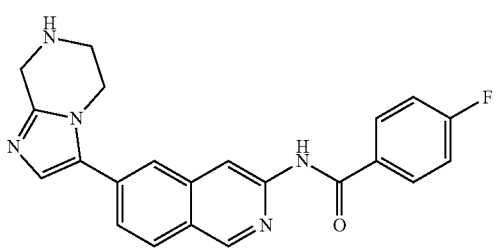

4-Fluoro-N-(6-(5,6,7,8-tetrahydroimidazo[1,2-a]pyrazin-3-yl)isoquinolin-3-yl)benzamide 291

Beige solid (55.0 mg, 0.142 mmol, 83.4% yield). $^1$H NMR (499 MHz, DMSO-$d_6$) δ ppm 2.79 (1H, br s), 3.09 (2H, t, J=5.21 Hz), 3.96 (2H, s), 4.14 (2H, t, J=5.21 Hz), 7.31 (1H, s), 7.36 (2H, t, J=8.78 Hz), 7.71 (1H, dd, J=8.64, 1.51 Hz), 8.03 (1H, s), 8.11 (1H, d, J=8.51 Hz), 8.14-8.21 (2H, m), 8.67 (1H, s), 9.18 (1H, s), 10.92 (1H, s); ESIMS found for $C_{22}H_{18}FN_5O$ m/z 387.9 (M+1).

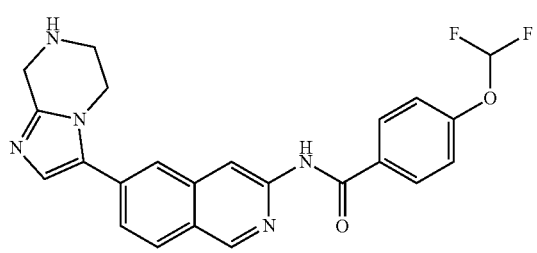

4-(Difluoromethoxy)-N-(6-(5,6,7,8-tetrahydroimidazo[1,2-a]pyrazin-3-yl) isoquinolin-3-yl)benzamide 292

Yellow solid (12.7 mg, 0.029 mmol, 12.4% yield). $^1$H NMR (499 MHz, DMSO-$d_6$) δ ppm 2.78 (1H, br s), 3.09 (2H, br t, J=5.21 Hz), 3.96 (2H, s), 4.14 (2H, t, J=5.35 Hz), 7.40 (1H, t, J=73.70 Hz), 7.31 (3H, t, J=4.25 Hz), 7.71 (1H, dd, J=8.51, 1.65 Hz), 8.03 (1H, s), 8.12 (1H, d, J=8.51 Hz), 8.14-8.20 (2H, m), 8.68 (1H, s), 9.19 (1H, s), 10.93 (1H, s); ESIMS found for $C_{23}H_{19}F_2N_5O_2$ m/z 435.9 (M+1).

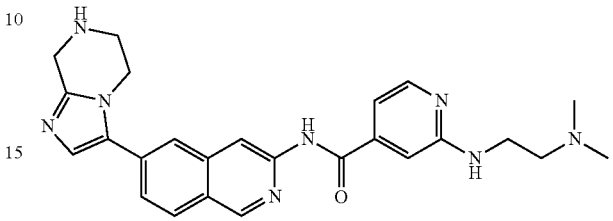

2-((2-(Dimethylamino)ethyl)amino)-N-(6-(5,6,7,8-tetrahydroimidazo[1,2-a]pyrazin-3-yl)isoquinolin-3-yl)isonicotinamide 293

Beige solid (8.0 mg, 0.018 mmol, 11.5% yield). $^1$H NMR (499 MHz, DMSO-$d_6$) δ ppm 2.20 (6H, s), 2.44 (2H, br t, J=6.59 Hz), 3.09 (2H, br t, J=5.35 Hz), 3.39 (2H, q, J=6.31 Hz), 3.96 (2H, s), 4.13 (2H, br t, J=5.35 Hz), 6.57 (1H, br t, J=5.63 Hz), 7.03 (1H, dd, J=5.21, 1.37 Hz), 7.05 (1H, s), 7.31 (1H, s), 7.72 (1H, dd, J=8.64, 1.51 Hz), 8.03 (1H, s), 8.11 (2H, d, J=6.04 Hz), 8.64 (1H, s), 9.17 (1H, s), 10.79 (1H, br s); ESIMS found for $C_{25}H_{28}N_8O$ m/z 457.0 (M+1).

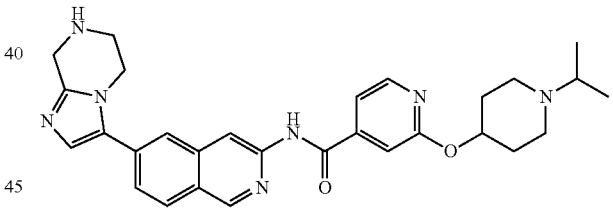

5-((1-Isopropylpiperidin-4-yl)oxy)-N-(6-(5,6,7,8-tetrahydroimidazo[1,2-a]pyrazin-3-yl)isoquinolin-3-yl)isonicotinamide 294

Beige solid (22.0 mg, 0.043 mmol, 21.9% yield). $^1$H NMR (499 MHz, DMSO-$d_6$) δ ppm 0.99 (6H, d, J=6.59 Hz), 1.60-1.72 (2H, m), 1.95-2.04 (2H, m), 2.30-2.39 (2H, m), 2.68-2.84 (4H, m), 3.08 (2H, br t, J=5.21 Hz), 3.96 (2H, s), 4.14 (2H, t, J=5.35 Hz), 5.02 (1H, tt, J=8.54, 4.08 Hz), 7.32 (1H, s), 7.35 (1H, s), 7.50 (1H, dd, J=5.49, 1.37 Hz), 7.73 (1H, dd, J=8.64, 1.51 Hz), 8.05 (1H, s), 8.12 (1H, d, J=8.51 Hz), 8.31 (1H, d, J=5.21 Hz), 8.66 (1H, s), 9.19 (1H, s), 11.10 (1H, s); ESIMS found for $C_{29}H_{33}N_7O_2$ m/z 512.3 (M+1).

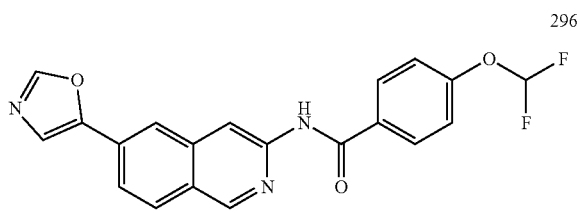 [SMILES: O=C(Nc1cc2cc(-c3cnco3)ccc2cn1)c1ccc(OC(F)F)cc1]

4-(Difluoromethoxy)-N-(6-(oxazol-5-yl)isoquinolin-3-yl)benzamide 296

Brown solid (16.1 mg, 0.042 mmol, 7.4% yield). $^1$H NMR (500 MHz, DMSO-d$_6$) δ ppm 7.41 (1H, t, J=73.60 Hz), 7.29-7.34 (2H, m), 7.92 (1H, dd, J=8.51, 1.65 Hz), 7.98 (1H, s), 8.14-8.22 (3H, m), 8.29 (1H, s), 8.59 (1H, s), 8.69 (1H, s), 9.22 (1H, s), 10.99 (1H, s); ESIMS found for C$_{20}$H$_{13}$F$_2$N$_3$O$_3$ m/z 381.9 (M+1).

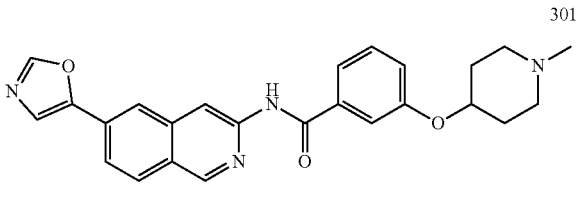 [SMILES: CN1CCC(Oc2cccc(C(=O)Nc3cc4cc(-c5cnco5)ccc4cn3)c2)CC1]

3-((1-Methylpiperidin-4-yl)oxy)-N-(6-(oxazol-5-yl)isoquinolin-3-yl) benzamide 301

Yellow solid (35.1 mg, 0.078 mmol, 58.6% yield). $^1$H NMR (499 MHz, DMSO-d$_6$) δ ppm 1.61-1.75 (2H, m), 1.92-2.02 (2H, m), 2.14-2.25 (2H, m), 2.19 (3H, s), 2.58-2.67 (2H, m), 4.48-4.59 (1H, m), 7.14-7.21 (1H, m), 7.42 (1H, t, J=8.10 Hz), 7.61-7.68 (2H, m), 7.92 (1H, dd, J=8.51, 1.65 Hz), 7.98 (1H, s), 8.19 (1H, d, J=8.51 Hz), 8.29 (1H, s), 8.24-8.25 (1H, m), 8.60 (1H, s), 8.69 (1H, s), 9.22 (1H, s), 10.93 (1H, s); ESIMS found for C$_{25}$H$_{24}$N$_4$O$_3$ m/z 429.1 (M+1).

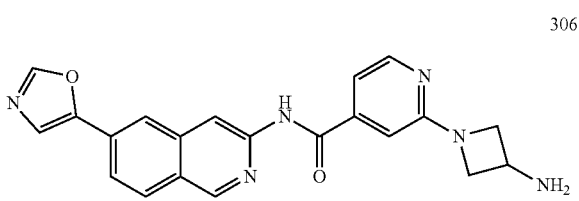 [SMILES: NC1CN(c2cc(C(=O)Nc3cc4cc(-c5cnco5)ccc4cn3)ccn2)C1]

2-(3-Aminoazetidin-1-yl)-N-(6-(oxazol-5-yl)isoquinolin-3-yl) isonicotinamide 306

Yellow solid (5.1 mg, 0.013 mmol, 3.5% yield). $^1$H NMR (499 MHz, DMSO-d$_6$) δ ppm 3.62 (2H, dd, J=8.23, 5.76 Hz), 3.85 (1H, quin, J=6.38 Hz), 4.19 (2H, t, J=7.68 Hz), 7.01 (1H, s), 7.14 (1H, dd, J=5.21, 1.37 Hz), 7.94 (1H, dd, J=8.51, 1.65 Hz), 7.98 (1H, s), 8.19 (1H, d, J=2.47 Hz), 8.21 (1H, s), 8.29 (1H, s), 8.59 (1H, s), 8.68 (1H, s), 9.23 (1H, s), 11.07 (1H, br s); ESIMS found for C$_{21}$H$_{18}$N$_6$O$_2$ m/z 387.2 (M+1).

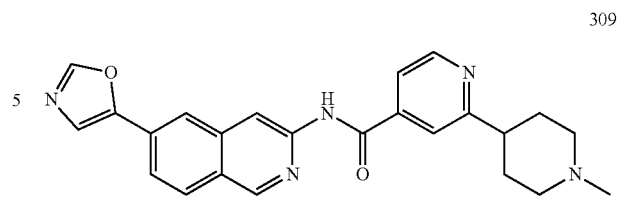

2-(1-Methylpiperidin-4-yl)-N-(6-(oxazol-5-yl)isoquinolin-3-yl) isonicotinamide 309

Off-white solid (15.0 mg, 0.036 mmol, 51.5% yield). $^1$H NMR (499 MHz, DMSO-d$_6$) δ ppm 1.78-1.92 (4H, m), 2.00 (2H, td, J=11.53, 2.47 Hz), 2.21 (3H, s), 2.73 (1H, tt, J=11.49, 4.15 Hz), 2.90 (2H, br d, J=11.25 Hz), 7.77 (1H, dd, J=5.21, 1.65 Hz), 7.92 (1H, s), 7.94 (1H, dd, J=8.51, 1.65 Hz), 7.98 (1H, s), 8.20 (1H, d, J=8.51 Hz), 8.31 (1H, s), 8.60 (1H, s), 8.69 (1H, d, J=4.94 Hz), 8.70 (1H, s), 9.24 (1H, s), 11.26 (1H, s); ESIMS found for C$_{24}$H$_{23}$N$_5$O$_2$ m/z 414.2 (M+1).

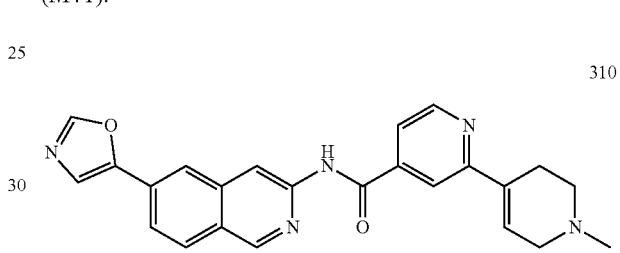

1'-Methyl-N-(6-(oxazol-5-yl)isoquinolin-3-yl)-1',2',3',6'-tetrahydro-[2,4'-bipyridine]-4-carboxamide 310

Tan solid (51.0 mg, 0.124 mmol, 54.8% yield). $^1$H NMR (499 MHz, DMSO-d$_6$) δ ppm 2.31 (3H, s), 2.56-2.63 (2H, m), 2.65 (2H, br d, J=2.74 Hz), 3.11 (2H, br d, J=3.02 Hz), 6.89 (1H, br s), 7.78 (1H, dd, J=4.94, 1.37 Hz), 7.94 (1H, dd, J=8.51, 1.65 Hz), 7.98 (1H, s), 8.17 (1H, s), 8.21 (1H, d, J=8.51 Hz), 8.31 (1H, s), 8.59 (1H, s), 8.65-8.75 (2H, m), 9.24 (1H, s), 11.33 (1H, s); ESIMS found for C$_{24}$H$_{21}$N$_5$O$_2$ m/z 412.2 (M+1).

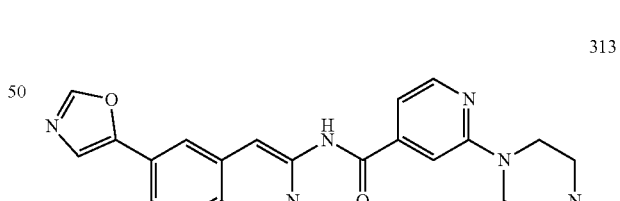

2-(4-Methylpiperazin-1-yl)-N-(6-(oxazol-5-yl)isoquinolin-3-yl) isonicotinamide 313

Brown solid (13.0 mg, 0.031 mmol, 19.1% yield). $^1$H NMR (499 MHz, DMSO-d$_6$) δ ppm 2.23 (3H, s), 2.43 (4H, t, J=4.94 Hz), 3.55-3.64 (4H, m), 7.16 (1H, dd, J=5.21, 1.10 Hz), 7.47 (1H, s), 7.93 (1H, dd, J=8.51, 1.65 Hz), 7.98 (1H, s), 8.20 (1H, d, J=8.51 Hz), 8.26 (1H, d, J=4.94 Hz), 8.30 (1H, s), 8.59 (1H, s), 8.69 (1H, s), 9.23 (1H, s), 11.13 (1H, s); ESIMS found for C$_{23}$H$_{22}$N$_6$O$_2$ m/z 415.2 (M+1).

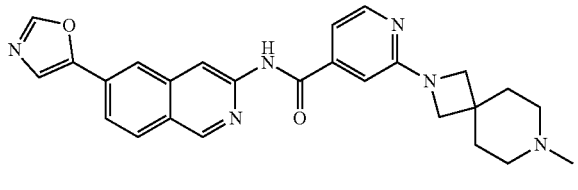

2-(7-Methyl-2,7-diazaspiro[3.5]nonan-2-yl)-N-(6-(oxazol-5-yl)isoquinolin-3-yl)isonicotinamide 317

Off-white solid (24.0 mg, 0.050 mmol, 57.7% yield). $^1$H NMR (499 MHz, DMSO-d$_6$) δ ppm 1.76 (4H, br t, J=5.08 Hz), 2.15 (3H, s), 2.27 (4H, br s), 3.74 (4H, s), 7.03 (1H, s), 7.13 (1H, dd, J=5.35, 1.51 Hz), 7.94 (1H, dd, J=8.51, 1.65 Hz), 7.98 (1H, s), 8.19 (1H, d, J=2.74 Hz), 8.21 (1H, s), 8.30 (1H, s), 8.59 (1H, s), 8.68 (1H, s), 9.23 (1H, s), 11.06 (1H, s); ESIMS found for $C_{26}H_{26}N_6O_2$ m/z 455.2 (M+1).

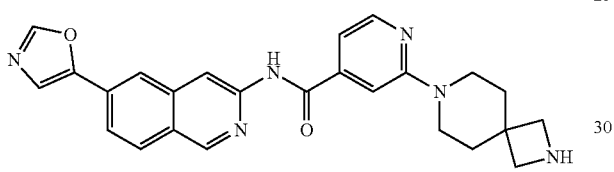

N-(6-(Oxazol-5-yl)isoquinolin-3-yl)-2-(2,7-diazaspiro[3.5]nonan-7-yl) isonicotinamide 318

Beige solid (9.0 mg, 0.020 mmol, 50.2% yield). $^1$H NMR (499 MHz, DMSO-d$_6$) δ ppm 1.74 (4H, br s), 3.27 (4H, br s), 3.58 (4H, br d, J=4.67 Hz), 7.11 (1H, br d, J=4.67 Hz), 7.46 (1H, s), 7.94 (1H, dd, J=8.51, 1.37 Hz), 7.98 (1H, s), 8.20 (1H, d, J=8.51 Hz), 8.24 (1H, d, J=4.94 Hz), 8.30 (1H, s), 8.60 (1H, s), 8.69 (1H, s), 9.24 (1H, s), 11.13 (1H, br s); ESIMS found for $C_{25}H_{24}N_6O_2$ m/z 441.2 (M+1).

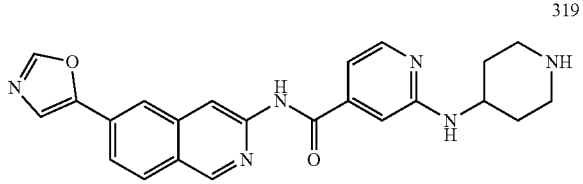 [SMILES: O=C(Nc1cc2cc(-c3cnco3)ccc2cn1)c1ccnc(NC2CCNCC2)c1]

N-(6-(Oxazol-5-yl)isoquinolin-3-yl)-2-(piperidin-4-ylamino)isonicotinamide 319

White solid (18.0 mg, 0.043 mmol, 8.3% yield). $^1$H NMR (499 MHz, DMSO-d$_6$) δ ppm 1.65-1.76 (2H, m), 2.04-2.13 (2H, m), 2.97-3.07 (2H, m), 3.25-3.30 (2H, m), 4.05 (1H, br s), 7.09 (1H, br d, J=4.12 Hz), 7.93 (1H, dd, J=8.51, 1.65 Hz), 7.98 (1H, s), 8.12 (1H, d, J=5.49 Hz), 8.19 (1H, d, J=8.78 Hz), 8.31 (1H, s), 8.59 (1H, s), 8.65 (1H, s), 8.99 (2H, br s), 9.22 (1H, s), 10.94 (1H, s); ESIMS found for $C_{23}H_{22}N_6O_2$ m/z 415.2 (M+1).

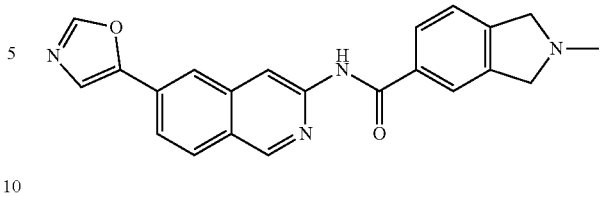

2-Methyl-N-(6-(oxazol-5-yl)isoquinolin-3-yl)isoindoline-5-carboxamide 325

Off-white solid (39.0 mg, 0.100 mmol, 57.1% yield). $^1$H NMR (499 MHz, DMSO-d$_6$) δ ppm 2.51 (3H, br s), 3.88 (4H, s), 7.37 (1H, d, J=7.96 Hz), 7.88-7.96 (3H, m), 7.98 (1H, s), 8.18 (1H, d, J=8.78 Hz), 8.29 (1H, s), 8.59 (1H, s), 8.68 (1H, s), 9.21 (1H, s), 10.83 (1H, s); ESIMS found for $C_{22}H_{18}N_4O_2$ m/z 371.1 (M+1).

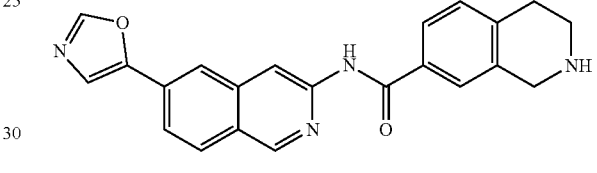

N-(6-(Oxazol-5-yl)isoquinolin-3-yl)-1,2,3,4-tetrahydroisoquinoline-7-carboxamide 326

Off-white solid (17.0 mg, 0.046 mmol, 26.0% yield). $^1$H NMR (499 MHz, DMSO-d$_6$) δ ppm 2.74-2.81 (2H, m), 2.99 (2H, br t, J=5.76 Hz), 3.90-3.96 (2H, m), 7.22 (1H, d, J=7.96 Hz), 7.80 (1H, s), 7.81-7.85 (1H, m), 7.91 (1H, dd, J=8.51, 1.65 Hz), 7.98 (1H, s), 8.18 (1H, d, J=8.78 Hz), 8.28 (1H, s), 8.59 (1H, s), 8.68 (1H, s), 9.21 (1H, s), 10.76 (1H, s); ESIMS found for $C_{22}H_{18}N_4O_2$ m/z 371.2 (M+1).

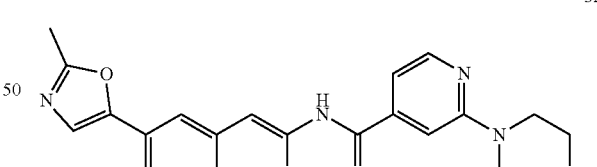

N-(6-(2-Methyloxazol-5-yl)isoquinolin-3-yl)-2-(4-methylpiperazin-1-yl) isonicotinamide 328

Beige solid (149.0 mg, 0.348 mmol, 74.1% yield). $^1$H NMR (499 MHz, DMSO-d$_6$) δ ppm 2.23 (3H, s), 2.43 (4H, t, J=4.94 Hz), 2.55 (3H, s), 3.56-3.66 (4H, m), 7.16 (1H, dd, J=5.21, 1.10 Hz), 7.46 (1H, s), 7.82 (1H, s), 7.88 (1H, dd, J=8.51, 1.65 Hz), 8.16 (1H, d, J=8.78 Hz), 8.20 (1H, s), 8.26 (1H, d, J=5.21 Hz), 8.66 (1H, s), 9.20 (1H, s), 11.11 (1H, s); ESIMS found for $C_{24}H_{24}N_6O_2$ m/z 429.2 (M+1).

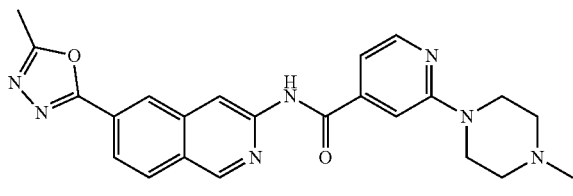

N-(6-(5-Methyl-1,3,4-oxadiazol-2-yl)isoquinolin-3-yl)-2-(4-methylpiperazin-1-yl)isonicotinamide 329

Beige solid (20.0 mg, 0.047 mmol, 19.9% yield). $^1$H NMR (499 MHz, DMSO-$d_6$) δ ppm 2.24 (3H, s), 2.43 (4H, br t, J=4.80 Hz), 2.65 (3H, s), 3.56-3.67 (4H, m), 7.17 (1H, dd, J=5.08, 1.23 Hz), 7.47 (1H, s), 8.11 (1H, dd, J=8.51, 1.65 Hz), 8.27 (1H, d, J=4.94 Hz), 8.30 (1H, d, J=8.51 Hz), 8.58 (1H, s), 8.78 (1H, s), 9.34 (1H, s), 11.20 (1H, s); ESIMS found for $C_{23}H_{23}N_7O_2$ m/z 430.0 (M+1).

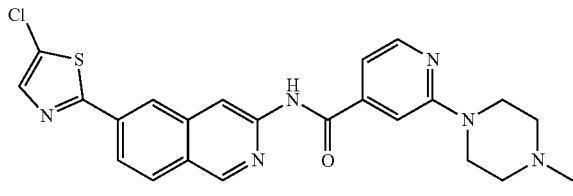

N-(6-(5-Chlorothiazol-2-yl)isoquinolin-3-yl)-2-(4-methylpiperazin-1-yl) isonicotinamide 330

Yellow solid (1.3 mg, 0.003 mmol, 1.1% yield). $^1$H NMR (499 MHz, DMSO-$d_6$) δ ppm 2.24 (3H, s), 2.40-2.46 (4H, m), 3.58-3.64 (4H, m), 7.10-7.20 (1H, m), 7.46 (1H, s), 7.89 (1H, dd, J=8.64, 1.78 Hz), 8.18 (1H, d, J=8.23 Hz), 8.26 (1H, d, J=5.21 Hz), 8.28 (1H, s), 8.38 (1H, s), 8.69 (1H, s), 9.24 (1H, s), 11.09 (1H, s); ESIMS found for $C_{23}H_{21}ClN_6OS$ m/z 464.9 (M+1).

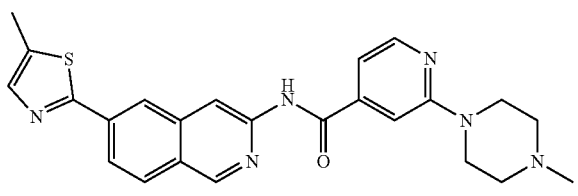

2-(4-Methylpiperazin-1-yl)-N-(6-(5-methylthiazol-2-yl)isoquinolin-3-yl) isonicotinamide 331

Off-yellow solid (11.5 mg, 0.026 mmol, 9.4% yield). $^1$H NMR (499 MHz, DMSO-$d_6$) δ ppm 2.24 (3H, s), 2.38-2.47 (4H, m), 2.56 (3H, d, J=1.10 Hz), 3.56-3.66 (4H, m), 7.17 (1H, dd, J=5.21, 1.10 Hz), 7.47 (1H, s), 7.73 (1H, d, J=1.37 Hz), 8.09 (1H, dd, J=8.51, 1.65 Hz), 8.19 (1H, d, J=8.51 Hz), 8.26 (1H, d, J=5.21 Hz), 8.43 (1H, s), 8.71 (1H, s), 9.25 (1H, s), 11.09 (1H, s); ESIMS found for $C_{24}H_{24}N_6OS$ m/z 444.9 (M+1).

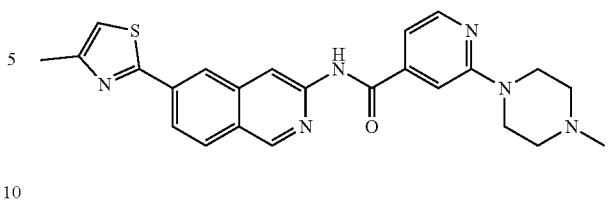

2-(4-Methylpiperazin-1-yl)-N-(6-(4-methylthiazol-2-yl)isoquinolin-3-yl) isonicotinamide 332

Black solid (23.6 mg, 0.053 mmol, 18.4% yield). $^1$H NMR (499 MHz, DMSO-$d_6$) δ ppm 2.24 (3H, s), 2.40-2.46 (4H, m), 2.49 (3H, br s), 3.55-3.65 (4H, m), 7.17 (1H, dd, J=5.08, 1.24 Hz), 7.46 (1H, br s), 7.47 (1H, d, J=0.82 Hz), 8.11 (1H, dd, J=8.51, 1.65 Hz), 8.20 (1H, d, J=8.51 Hz), 8.26 (1H, d, J=4.94 Hz), 8.49 (1H, s), 8.72 (1H, s), 9.26 (1H, s), 11.09 (1H, s); ESIMS found for $C_{24}H_{24}N_6OS$ m/z 444.9 (M+1).

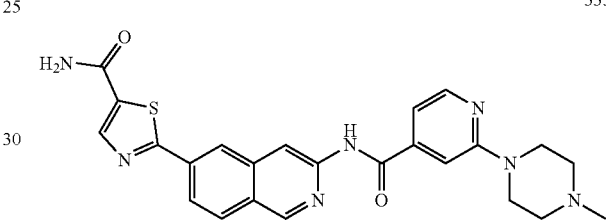

2-(3-(2-(4-Methylpiperazin-1-yl)isonicotinamido)isoquinolin-6-yl)thiazole-5-carboxamide 333

Yellow solid (7.6 mg, 0.016 mmol, 5.8% yield). $^1$H NMR (499 MHz, DMSO-$d_6$) δ ppm 2.24 (3H, s), 2.41-2.45 (4H, m), 3.58-3.64 (4H, m), 7.17 (1H, dd, J=5.08, 1.23 Hz), 7.47 (1H, s), 7.69 (1H, br s), 8.15 (1H, dd, J=8.64, 1.78 Hz), 8.24 (2H, br d, J=8.78 Hz), 8.27 (1H, d, J=4.94 Hz), 8.54 (1H, s), 8.60 (1H, s), 8.75 (1H, s), 9.29 (1H, s), 11.13 (1H, s); ESIMS found for $C_{24}H_{23}N_7O_2S$ m/z 473.9 (M+1).

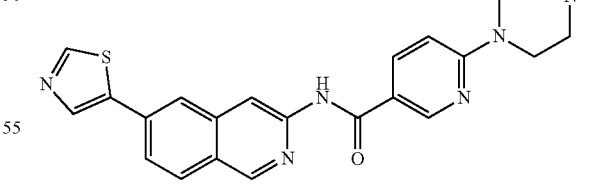

6-(4-Methylpiperazin-1-yl)-N-(6-(thiazol-5-yl)isoquinolin-3-yl)nicotinamide 334

White solid (64.1 mg, 0.149 mmol, 42.3% yield). $^1$H NMR (499 MHz, DMSO-$d_6$) δ ppm 2.23 (3H, s), 2.37-2.45 (4H, m), 3.60-3.68 (4H, m), 6.90 (1H, d, J=9.06 Hz), 7.89 (1H, dd, J=8.51, 1.92 Hz), 8.14 (1H, d, J=8.51 Hz), 8.20 (1H, dd, J=9.06, 2.47 Hz), 8.25 (1H, d, J=0.82 Hz), 8.57

(1H, s), 8.66 (1H, s), 8.85 (1H, d, J=2.47 Hz), 9.19 (2H, d, J=2.47 Hz), 10.66 (1H, s); ESIMS found for C$_{23}$H$_{22}$N$_6$OS m/z 430.9 (M+1).

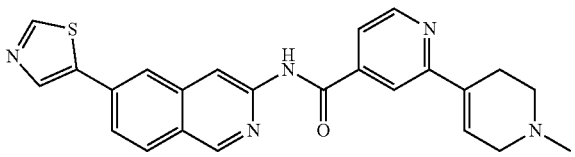

1'-Methyl-N-(6-(thiazol-5-yl)isoquinolin-3-yl)-1',2',3',6'-tetrahydro-[2,4'-bipyridine]-4-carboxamide 335

Off-white solid (7.6 mg, 0.018 mmol, 33.9% yield). $^1$H NMR (499 MHz, DMSO-d$_6$) δ ppm 2.31 (3H, s), 2.56-2.63 (2H, m), 2.63-2.69 (2H, m), 3.11 (2H, br d, J=3.02 Hz), 6.85-6.93 (1H, m), 7.78 (1H, dd, J=4.94, 1.37 Hz), 7.94 (1H, dd, J=8.51, 1.65 Hz), 8.13-8.22 (2H, m), 8.32 (1H, d, J=0.82 Hz), 8.60 (1H, s), 8.71 (2H, dd, J=3.43, 1.51 Hz), 9.21 (1H, s), 9.24 (1H, s), 11.33 (1H, s); ESIMS found for C$_{24}$H$_{21}$N$_5$OS m/z 428.2 (M+1).

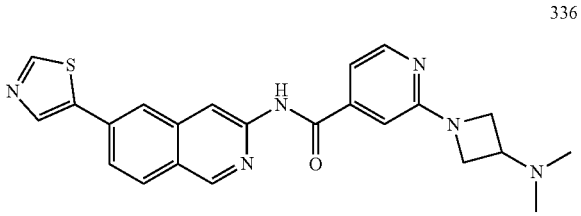

2-(3-(Dimethylamino)azetidin-1-yl)-N-(6-(thiazol-5-yl)isoquinolin-3-yl) isonicotinamide 336

Beige solid (15.0 mg, 0.035 mmol, 12.2% yield). $^1$H NMR (499 MHz, DMSO-d$_6$) δ ppm 2.14 (6H, s), 3.19-3.25 (1H, m), 3.81 (2H, dd, J=8.23, 5.21 Hz), 4.07 (2H, t, J=7.68 Hz), 7.04 (1H, s), 7.15 (1H, dd, J=5.21, 1.37 Hz), 7.93 (1H, dd, J=8.51, 1.65 Hz), 8.17 (1H, d, J=8.78 Hz), 8.21 (1H, d, J=5.21 Hz), 8.30 (1H, s), 8.58 (1H, s), 8.67 (1H, s), 9.20 (1H, s), 9.22 (1H, s), 11.01 (1H, s); ESIMS found for C$_{23}$H$_{22}$N$_6$OS m/z 430.9 (M+1).

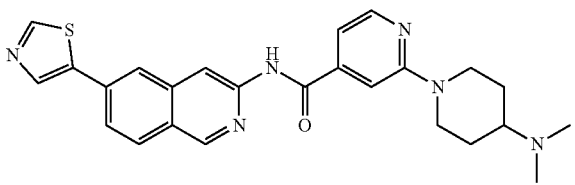

2-(4-(Dimethylamino)piperidin-1-yl)-N-(6-(thiazol-5-yl)isoquinolin-3-yl) isonicotinamide 337

Off-white solid (390.0 mg, 0.851 mmol, 80.6% yield). $^1$H NMR (499 MHz, DMSO-d$_6$) δ ppm 1.31-1.46 (2H, m), 1.84 (2H, br d, J=10.70 Hz), 2.19 (6H, s), 2.34 (1H, ddd, J=10.98, 7.41, 3.29 Hz), 2.88 (2H, br t, J=11.80 Hz), 4.44 (2H, br d, J=12.62 Hz), 7.05-7.15 (1H, m), 7.46 (1H, s), 7.93 (1H, dd, J=8.51, 1.65 Hz), 8.17 (1H, d, J=8.51 Hz), 8.24 (1H, d, J=5.21 Hz), 8.31 (1H, s), 8.59 (1H, s), 8.69 (1H, s), 9.21 (1H, s), 9.23 (1H, s), 11.12 (1H, s); ESIMS found for C$_{25}$H$_{26}$N$_6$OS m/z 459.2 (M+1).

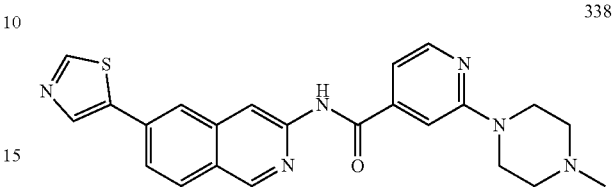

2-(4-Methylpiperazin-1-yl)-N-(6-(thiazol-5-yl)isoquinolin-3-yl) isonicotinamide 338

Off-yellow solid (42.9 mg, 0.100 mmol, 42.5% yield). $^1$H NMR (499 MHz, DMSO-d$_6$) δ ppm 2.24 (3H, s), 2.37-2.46 (4H, m), 3.55-3.66 (4H, m), 7.16 (1H, d, J=4.12 Hz), 7.46 (1H, s), 7.92 (1H, dd, J=8.51, 1.65 Hz), 8.17 (1H, d, J=8.51 Hz), 8.26 (1H, d, J=5.21 Hz), 8.30 (1H, s), 8.58 (1H, s), 8.68 (1H, s), 9.20 (1H, s), 9.22 (1H, s), 11.07 (1H, s); ESIMS found for C$_{23}$H$_{22}$N$_6$OS m/z 430.9 (M+1).

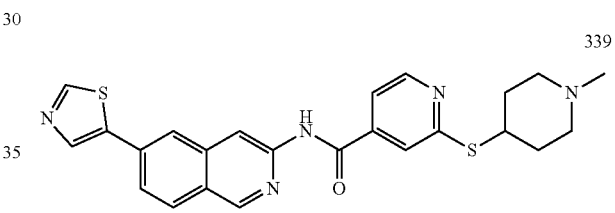

2-((1-Methylpiperidin-4-yl)thio)-N-(6-(thiazol-5-yl)isoquinolin-3-yl) isonicotinamide 339

Off-white solid (54.7 mg, 0.119 mmol, 41.3% yield). $^1$H NMR (499 MHz, DMSO-d$_6$) δ ppm 1.58-1.74 (2H, m), 1.98-2.07 (2H, m), 2.12 (2H, br t, J=10.15 Hz), 2.17 (3H, s), 2.65-2.75 (2H, m), 3.79-3.90 (1H, m), 7.64 (1H, dd, J=5.08, 1.51 Hz), 7.82 (1H, s), 7.94 (1H, dd, J=8.51, 1.65 Hz), 8.17 (1H, d, J=8.51 Hz), 8.32 (1H, s), 8.59 (1H, s), 8.62 (1H, d, J=5.21 Hz), 8.68 (1H, s), 9.21 (1H, s), 9.23 (1H, s), 11.24 (1H, s); ESIMS found for C$_{24}$H$_{23}$N$_5$OS$_2$ m/z 462.1 (M+1).

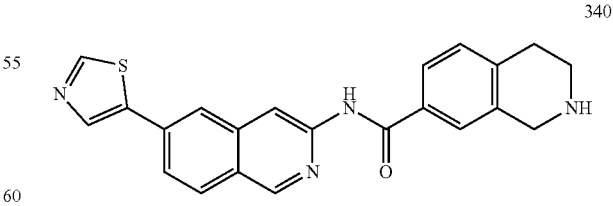

N-(6-(Thiazol-5-yl)isoquinolin-3-yl)-1,2,3,4-tetrahydroisoquinoline-7-carboxamide 340

Off-white solid (57.3 mg, 0.148 mmol, 39.0% yield). $^1$H NMR (499 MHz, DMSO-d$_6$) δ ppm 2.73-2.80 (2H, m), 2.98

(2H, br t, J=5.76 Hz), 3.93 (2H, s), 7.22 (1H, d, J=8.23 Hz), 7.71 (1H, br d, J=5.76 Hz), 7.79 (1H, s), 7.89-7.96 (1H, m), 8.16 (1H, d, J=8.78 Hz), 8.29 (1H, s), 8.59 (1H, s), 8.67 (1H, s), 9.20 (2H, s), 10.75 (1H, s); ESIMS found for $C_{22}H_{18}N_4OS$ m/z 387.1 (M+1).

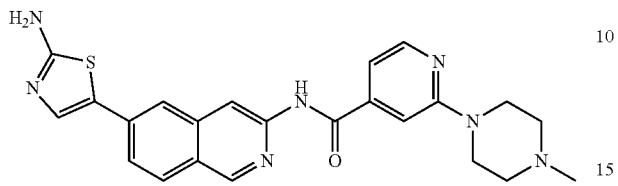

N-(6-(2-Aminothiazol-5-yl)isoquinolin-3-yl)-2-(4-methylpiperazin-1-yl) isonicotinamide 359

Off-yellow solid (3.8 mg, 0.009 mmol, 3.1% yield). $^1$H NMR (499 MHz, DMSO-$d_6$) δ ppm 2.24 (3H, s), 2.40-2.44 (4H, m), 3.57-3.64 (4H, m), 7.15 (1H, dd, J=5.08, 1.24 Hz), 7.33-7.38 (2H, m), 7.45 (1H, s), 7.71 (1H, s), 7.73-7.80 (2H, m), 8.01 (1H, d, J=8.23 Hz), 8.26 (1H, d, J=4.94 Hz), 8.55 (1H, s), 9.09 (1H, s), 10.98 (1H, s); ESIMS found for $C_{23}H_{23}N_7OS$ m/z 445.9 (M+1).

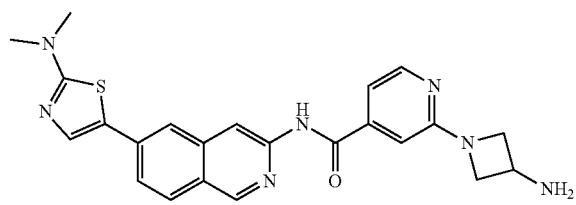

2-(3-Aminoazetidin-1-yl)-N-(6-(2-(dimethylamino)thiazol-5-yl)isoquinolin-3-yl)isonicotinamide 373

Yellow solid (21.5 mg, 0.048 mmol, 39.3% yield). $^1$H NMR (499 MHz, DMSO-$d_6$) δ ppm 3.13 (6H, s), 3.63 (2H, dd, J=8.23, 5.76 Hz), 3.85 (1H, quin, J=6.45 Hz), 4.19 (2H, t, J=7.82 Hz), 7.00 (1H, s), 7.13 (1H, dd, J=5.21, 1.37 Hz), 7.80 (1H, dd, J=8.64, 1.78 Hz), 7.85 (1H, s), 7.91 (1H, s), 8.03 (1H, d, J=8.51 Hz), 8.19 (1H, d, J=5.21 Hz), 8.54 (1H, s), 9.10 (1H, s), 10.97 (1H, s); ESIMS found for $C_{23}H_{23}N_7OS$ m/z 446.1 (M+1).

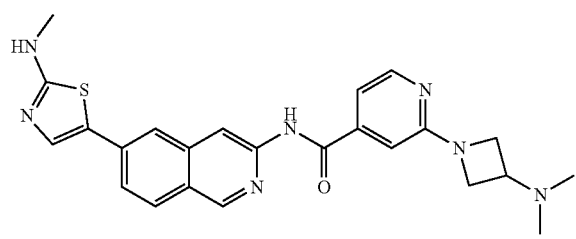

2-(3-(Dimethylamino)azetidin-1-yl)-N-(6-(2-(methylamino)thiazol-5-yl) isoquinolin-3-yl)isonicotinamide 374

Yellow solid (10.3 mg, 0.022 mmol, 5.7% yield). $^1$H NMR (499 MHz, DMSO-$d_6$) δ ppm 2.13 (6H, s), 2.90 (3H, d, J=4.67 Hz), 3.19-3.26 (1H, m), 3.80 (2H, dd, J=8.37, 5.35 Hz), 4.06 (2H, t, J=7.68 Hz), 7.03 (1H, s), 7.14 (1H, dd, J=5.21, 1.37 Hz), 7.77-7.80 (2H, m), 7.81 (1H, s), 7.95 (1H, q, J=4.67 Hz), 8.02 (1H, d, J=8.23 Hz), 8.21 (1H, d, J=5.21 Hz), 8.54 (1H, s), 9.09 (1H, s), 10.97 (1H, s); ESIMS found for $C_{24}H_{25}N_7OS$ m/z 460.2 (M+1).

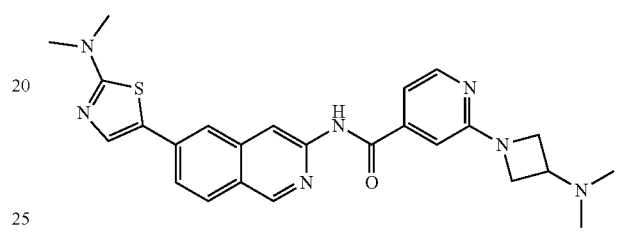

2-(3-(Dimethylamino)azetidin-1-yl)-N-(6-(2-(dimethylamino)thiazol-5-yl) isoquinolin-3-yl)isonicotinamide 375

Yellow solid (34.6 mg, 0.073 mmol, 27.6% yield). $^1$H NMR (499 MHz, DMSO-$d_6$) δ ppm 2.13 (6H, s), 3.13 (6H, s), 3.18-3.26 (1H, m), 3.80 (2H, dd, J=8.51, 5.21 Hz), 4.06 (2H, t, J=7.68 Hz), 7.03 (1H, s), 7.15 (1H, dd, J=5.21, 1.37 Hz), 7.79 (1H, dd, J=8.51, 1.65 Hz), 7.84 (1H, s), 7.90 (1H, s), 8.02 (1H, d, J=8.51 Hz), 8.20 (1H, d, J=5.49 Hz), 8.54 (1H, s), 9.09 (1H, s), 10.98 (1H, br s); ESIMS found for $C_{24}H_{27}N_7OS$ m/z 474.2 (M+1).

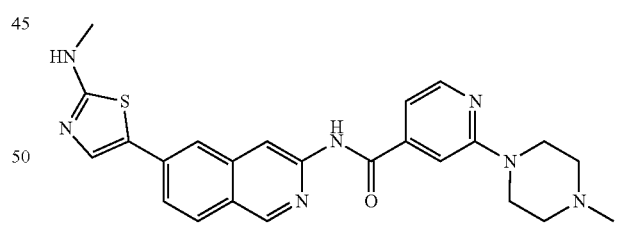

N-(6-(2-(Methylamino)thiazol-5-yl)isoquinolin-3-yl)-2-(4-methylpiperazin-1-yl)isonicotinamide 376

Yellow solid (59.0 mg, 0.128 mmol, 29.2% yield). $^1$H NMR (499 MHz, DMSO-$d_6$) δ ppm 2.23 (3H, s), 2.42 (4H, br t, J=4.94 Hz), 2.90 (3H, d, J=4.67 Hz), 3.56-3.63 (4H, m), 7.15 (1H, dd, J=5.08, 1.23 Hz), 7.46 (1H, s), 7.76-7.80 (2H, m), 7.81 (1H, s), 7.95 (1H, q, J=4.57 Hz), 8.02 (1H, d, J=8.51 Hz), 8.25 (1H, d, J=5.21 Hz), 8.55 (1H, s), 9.10 (1H, s), 11.03 (1H, s); ESIMS found for $C_{24}H_{25}N_7OS$ m/z 460.2 (M+1).

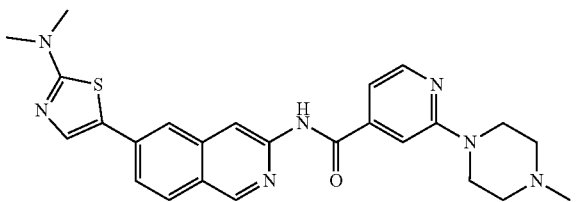

N-(6-(2-(Dimethylamino)thiazol-5-yl)isoquinolin-3-yl)-2-(4-methylpiperazin-1-yl)isonicotinamide 377

Yellow solid (25.6 mg, 0.054 mmol, 11.8% yield). $^1$H NMR (499 MHz, DMSO-d$_6$) δ ppm 2.20-2.27 (3H, m), 2.39-2.47 (4H, m), 3.09-3.20 (6H, m), 3.55-3.66 (4H, m), 7.15 (1H, dd, J=4.94, 1.10 Hz), 7.46 (1H, s), 7.80 (1H, dd, J=8.64, 1.78 Hz), 7.85 (1H, s), 7.91 (1H, s), 8.03 (1H, d, J=8.51 Hz), 8.25 (1H, d, J=5.21 Hz), 8.56 (1H, s), 9.10 (1H, s), 11.03 (1H, s); ESIMS found for C$_{25}$H$_{27}$N$_7$OS m/z 474.2 (M+1).

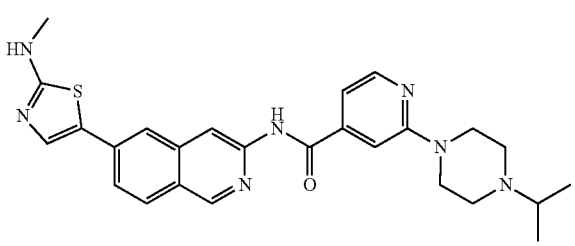

2-(4-Isopropylpiperazin-1-yl)-N-(6-(2-(methylamino)thiazol-5-yl) isoquinolin-3-yl)isonicotinamide 378

Yellow solid (53.8 mg, 0.110 mmol, 35.1% yield). $^1$H NMR (499 MHz, DMSO-d$_6$) δ ppm 1.02 (6H, br d, J=6.04 Hz), 2.56 (4H, br s), 2.70 (1H, br s), 2.90 (3H, d, J=4.67 Hz), 3.58 (4H, br s), 7.14 (1H, d, J=4.67 Hz), 7.44 (1H, s), 7.75-7.81 (2H, m), 7.81 (1H, s), 7.95 (1H, q, J=4.85 Hz), 8.02 (1H, d, J=8.51 Hz), 8.25 (1H, d, J=4.94 Hz), 8.55 (1H, s), 9.10 (1H, s), 11.03 (1H, s); ESIMS found for C$_{26}$H$_{29}$N$_7$OS m/z 488.2 (M+1).

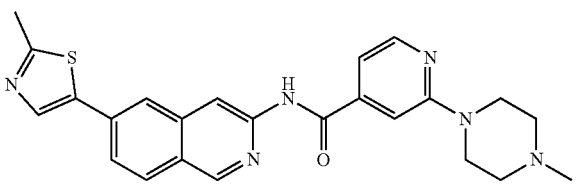

2-(4-Methylpiperazin-1-yl)-N-(6-(2-methylthiazol-5-yl)isoquinolin-3-yl) isonicotinamide 379

Off-yellow solid (44.4 mg, 0.100 mmol, 42.6% yield). $^1$H NMR (499 MHz, DMSO-d$_6$) δ ppm 2.24 (3H, s), 2.38-2.46 (4H, m), 2.73 (3H, s), 3.55-3.66 (4H, m), 7.16 (1H, dd, J=5.08, 0.96 Hz), 7.46 (1H, s), 7.85 (1H, dd, J=8.51, 1.65 Hz), 8.13 (1H, d, J=8.51 Hz), 8.17 (1H, s), 8.26 (1H, d, J=5.21 Hz), 8.29 (1H, s), 8.65 (1H, s), 9.19 (1H, s), 11.05 (1H, s); ESIMS found for C$_{24}$H$_{24}$N$_6$OS m/z 444.9 (M+1).

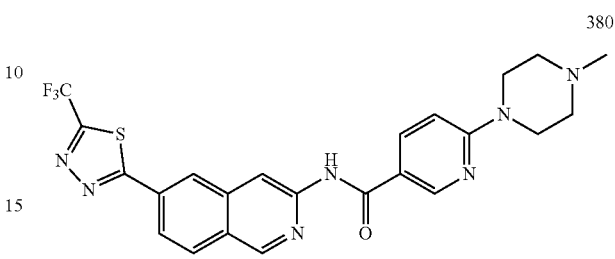

6-(4-Methylpiperazin-1-yl)-N-(6-(5-(trifluoromethyl)-1,3,4-thiadiazol-2-yl) isoquinolin-3-yl)nicotinamide 380

White solid (5.2 mg, 0.010 mmol, 6.9% yield). $^1$H NMR (499 MHz, DMSO-d$_6$) δ ppm 2.23 (3H, s), 2.40 (4H, br t, J=4.80 Hz), 3.60-3.71 (4H, m), 6.91 (1H, d, J=9.06 Hz), 8.21 (2H, dd, J=8.64, 1.78 Hz), 8.30 (1H, d, J=8.51 Hz), 8.76 (1H, s), 8.80 (1H, s), 8.86 (1H, d, J=2.20 Hz), 9.34 (1H, s), 10.84 (1H, s); ESIMS found for C$_{23}$H$_{20}$F$_3$N$_7$OS m/z 500.1 (M+1).

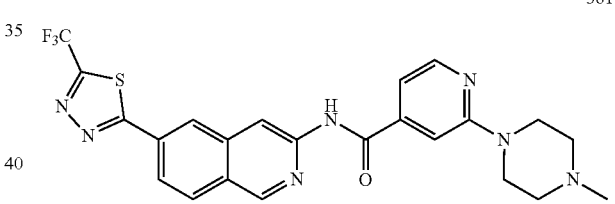

2-(4-Methylpiperazin-1-yl)-N-(6-(5-(trifluoromethyl)-1,3,4-thiadiazol-2-yl) isoquinolin-3-yl)isonicotinamide 381

White solid (4.0 mg, 0.008 mmol, 3.0% yield). $^1$H NMR (499 MHz, DMSO-d$_6$) δ ppm 2.24 (3H, s), 2.43 (4H, br t, J=4.80 Hz), 3.55-3.65 (4H, m), 7.17 (1H, dd, J=5.21, 1.10 Hz), 7.48 (1H, s), 8.21-8.26 (1H, m), 8.27 (1H, d, J=5.21 Hz), 8.30-8.37 (1H, m), 8.82 (2H, d, J=8.51 Hz), 9.37 (1H, s), 11.25 (1H, s); ESIMS found for C$_{23}$H$_{20}$F$_3$N$_7$OS m/z 500.1 (M+1).

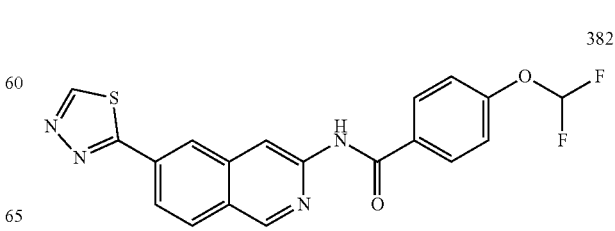

N-(6-(1,3,4-Thiadiazol-2-yl)isoquinolin-3-yl)-4-(difluoromethoxy)benzamide 382

White solid (5.0 mg, 0.013 mmol, 6.2% yield). $^1$H NMR (499 MHz, DMSO-$d_6$) δ ppm 7.41 (2H, t, J=73.70 Hz), 7.32 (2H, d, J=8.78 Hz), 8.16-8.19 (2H, m), 8.20-8.23 (1H, m), 8.26-8.32 (1H, m), 8.66 (1H, s), 8.79 (1H, s), 9.32 (1H, s), 9.75 (1H, s), 11.07 (1H, s); ESIMS found for $C_{19}H_{12}F_2N_4O_2S$ m/z 398.8 (M+1).

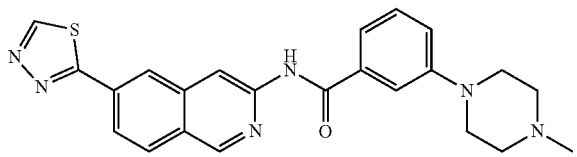

383

N-(6-(1,3,4-Thiadiazol-2-yl)isoquinolin-3-yl)-3-(4-methylpiperazin-1-yl)benzamide 383

Yellow solid (9.4 mg, 0.022 mmol, 4.5% yield). $^1$H NMR (499 MHz, DMSO-$d_6$) δ ppm 2.24 (2H, s), 2.46-2.49 (4H, m), 3.23-3.29 (4H, m), 7.10-7.21 (1H, m), 7.36 (1H, t, J=7.96 Hz), 7.46-7.53 (1H, m), 7.62-7.70 (1H, m), 8.16-8.24 (1H, m), 8.24-8.32 (1H, m), 8.64 (1H, d, J=0.82 Hz), 8.79 (1H, s), 9.31 (1H, s), 9.74 (1H, s), 10.96 (1H, s); ESIMS found for $C_{23}H_{22}N_6OS$ m/z 431.9 (M+1).

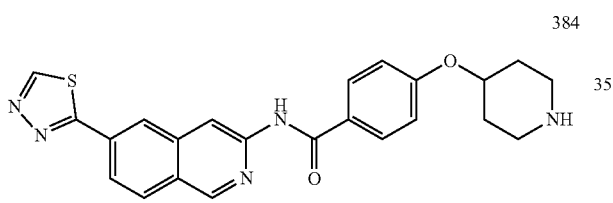

384

N-(6-(1,3,4-Thiadiazol-2-yl)isoquinolin-3-yl)-4-(piperidin-4-yloxy)benzamide 384

White solid (15.7 mg, 0.036 mmol, 69.1% yield). $^1$H NMR (499 MHz, DMSO-$d_6$) δ ppm 1.41-1.54 (2H, m), 1.95 (2H, br dd, J=8.64, 3.16 Hz), 2.56-2.66 (2H, m), 2.96 (2H, dt, J=12.49, 3.91 Hz), 4.49-4.60 (1H, m), 7.01-7.10 (2H, m), 8.01-8.14 (2H, m), 8.14-8.23 (1H, m), 8.23-8.32 (1H, m), 8.63 (1H, s), 8.78 (1H, s), 9.30 (1H, s), 9.74 (1H, s), 10.80 (1H, s); ESIMS found for $C_{23}H_{21}N_5O_2S$ m/z 432.1 (M+1).

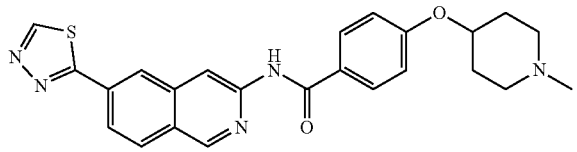

385

N-(6-(1,3,4-Thiadiazol-2-yl)isoquinolin-3-yl)-4-((1-methylpiperidin-4-yl)oxy)benzamide 385

Off-yellow solid (17.7 mg, 0.038 mmol, 40.7% yield). $^1$H NMR (499 MHz, DMSO-$d_6$) δ ppm 1.60-1.73 (2H, m), 1.97 (2H, br dd, J=9.47, 3.98 Hz), 2.16-2.24 (2H, m), 2.18 (3H, s), 2.57-2.69 (2H, m), 4.52 (1H, tt, J=8.13, 3.95 Hz), 7.07 (2H, d, J=9.06 Hz), 8.03-8.14 (2H, m), 8.14-8.23 (1H, m), 8.23-8.30 (1H, m), 8.64 (1H, s), 8.78 (1H, s), 9.30 (1H, s), 9.74 (1H, s), 10.82 (1H, s); ESIMS found for $C_{24}H_{23}N_5O_2S$ m/z 445.9 (M+1).

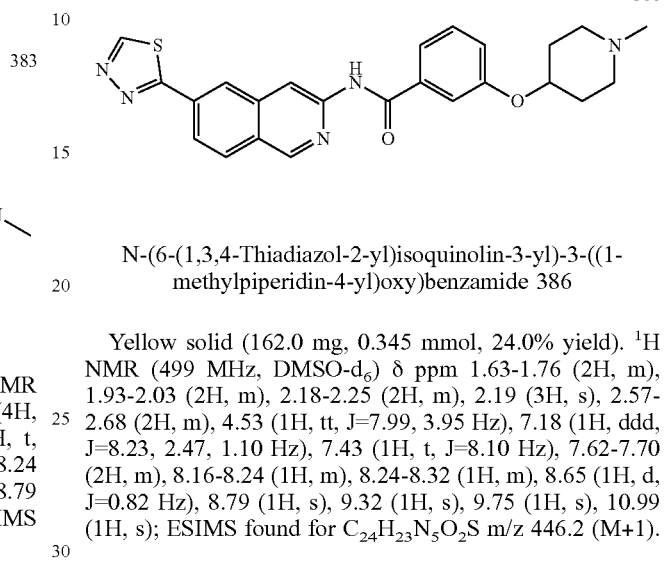

386

N-(6-(1,3,4-Thiadiazol-2-yl)isoquinolin-3-yl)-3-((1-methylpiperidin-4-yl)oxy)benzamide 386

Yellow solid (162.0 mg, 0.345 mmol, 24.0% yield). $^1$H NMR (499 MHz, DMSO-$d_6$) δ ppm 1.63-1.76 (2H, m), 1.93-2.03 (2H, m), 2.18-2.25 (2H, m), 2.19 (3H, s), 2.57-2.68 (2H, m), 4.53 (1H, tt, J=7.99, 3.95 Hz), 7.18 (1H, ddd, J=8.23, 2.47, 1.10 Hz), 7.43 (1H, t, J=8.10 Hz), 7.62-7.70 (2H, m), 8.16-8.24 (1H, m), 8.24-8.32 (1H, m), 8.65 (1H, d, J=0.82 Hz), 8.79 (1H, s), 9.32 (1H, s), 9.75 (1H, s), 10.99 (1H, s); ESIMS found for $C_{24}H_{23}N_5O_2S$ m/z 446.2 (M+1).

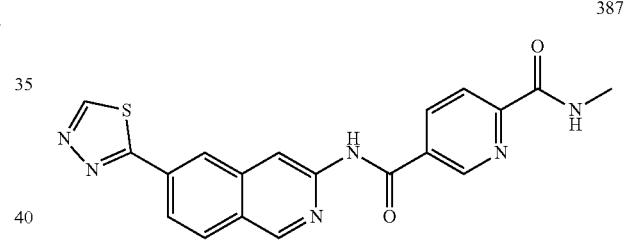

387

$N^5$-(6-(1,3,4-Thiadiazol-2-yl)isoquinolin-3-yl)-$N^2$-methylpyridine-2,5-dicarboxamide 387

White solid (5.2 mg, 0.013 mmol, 6.3% yield). $^1$H NMR (499 MHz, DMSO-$d_6$) δ ppm 2.86 (3H, d, J=4.94 Hz), 8.16 (1H, d, J=7.96 Hz), 8.20-8.27 (1H, m), 8.27-8.32 (1H, m), 8.57 (1H, dd, J=8.23, 2.20 Hz), 8.69 (1H, s), 8.82 (1H, s), 8.95 (1H, q, J=4.57 Hz), 9.23 (1H, d, J=1.37 Hz), 9.34 (1H, s), 9.75 (1H, s), 11.47 (1H, s); ESIMS found for $C_{19}H_{14}N_6O_2S$ m/z 391.1 (M+1).

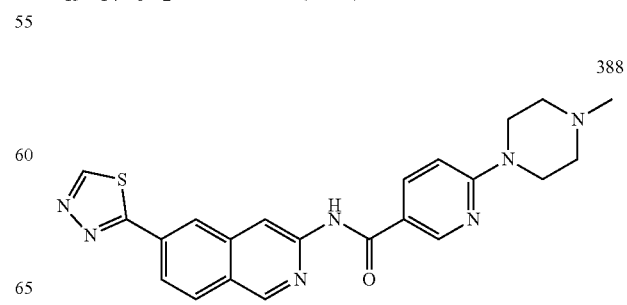

388

313

N-(6-(1,3,4-Thiadiazol-2-yl)isoquinolin-3-yl)-6-(4-methylpiperazin-1-yl) nicotinamide 388

Brown solid (14.1 mg, 0.033 mmol, 10.7% yield). $^1$H NMR (499 MHz, DMSO-d$_6$) δ ppm 2.22 (3H, s), 2.40 (4H, t, J=5.08 Hz), 3.60-3.71 (4H, m), 6.91 (1H, d, J=9.06 Hz), 8.14-8.23 (2H, m), 8.23-8.30 (1H, m), 8.62 (1H, s), 8.76 (1H, s), 8.86 (1H, d, J=2.47 Hz), 9.30 (1H, s), 9.74 (1H, s), 10.80 (1H, s); ESIMS found for C$_{22}$H$_{21}$N$_7$OS m/z 431.9 (M+1).

389

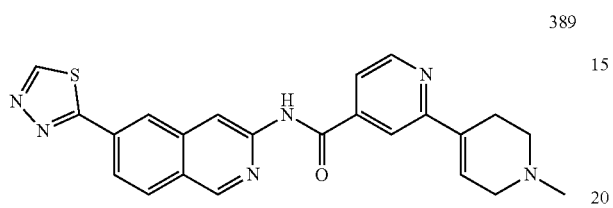

N-(6-(1,3,4-Thiadiazol-2-yl)isoquinolin-3-yl)-1'-methyl-1',2',3',6'-tetrahydro-[2,4'-bipyridine]-4-carboxamide 389

White solid (2.5 mg, 0.006 mmol, 5.7% yield). $^1$H NMR (499 MHz, DMSO-d$_6$) δ ppm 2.31 (3H, s), 2.58-2.63 (2H, m), 2.64-2.69 (2H, m), 3.08-3.15 (2H, m), 6.90 (1H, t, J=3.43 Hz), 7.79 (1H, dd, J=4.94, 1.37 Hz), 8.18 (1H, s), 8.21-8.26 (1H, m), 8.26-8.35 (1H, m), 8.64-8.74 (2H, m), 8.82 (1H, s), 9.35 (1H, s), 9.75 (1H, s), 11.41 (1H, br s); ESIMS found for C$_{23}$H$_{20}$N$_6$OS m/z 429.1 (M+1).

390

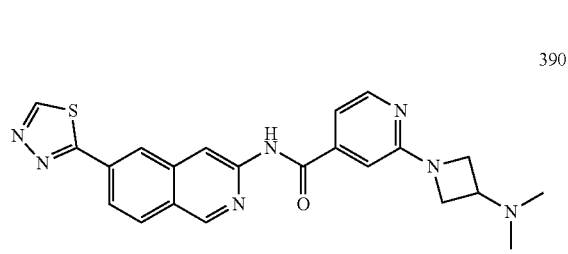 [SMILES: CN(C)C1CN(c2cc(C(=O)Nc3cc4cc(-c5nncs5)ccc4cn3)ccn2)C1]

N-(6-(1,3,4-Thiadiazol-2-yl)isoquinolin-3-yl)-2-(3-(dimethylamino)azetidin-1-yl)isonicotinamide 390

White solid (15.0 mg, 0.035 mmol, 10.1% yield). $^1$H NMR (499 MHz, DMSO-d$_6$) δ ppm 2.14 (6H, s), 3.17-3.26 (1H, m), 3.81 (2H, dd, J=8.37, 5.35 Hz), 4.07 (2H, t, J=7.55 Hz), 7.05 (1H, s), 7.16 (1H, dd, J=5.21, 1.10 Hz), 8.18-8.25 (2H, m), 8.25-8.33 (1H, m), 8.66 (1H, s), 8.78 (1H, s), 9.33 (1H, s), 9.75 (1H, s), 11.15 (1H, s); ESIMS found for C$_{22}$H$_{21}$N$_7$OS m/z 432.1 (M+1).

391

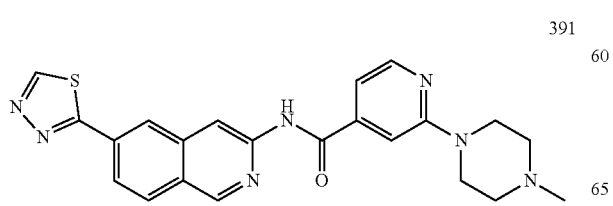

314

N-(6-(1,3,4-Thiadiazol-2-yl)isoquinolin-3-yl)-2-(4-methylpiperazin-1-yl) isonicotinamide 391

White solid (15.2 mg, 0.035 mmol, 9.6% yield). $^1$H NMR (499 MHz, DMSO-d$_6$) δ ppm 2.24 (3H, s), 2.44 (4H, br d, J=4.12 Hz), 3.61 (4H, br s), 7.17 (1H, br d, J=4.94 Hz), 7.47 (1H, s), 8.18-8.25 (1H, m), 8.25-8.33 (2H, m), 8.65 (1H, s), 8.78 (1H, s), 9.32 (1H, s), 9.69-9.78 (1H, m), 11.15 (1H, br s); ESIMS found for C$_{22}$H$_{21}$N$_7$OS m/z 431.9 (M+1).

392

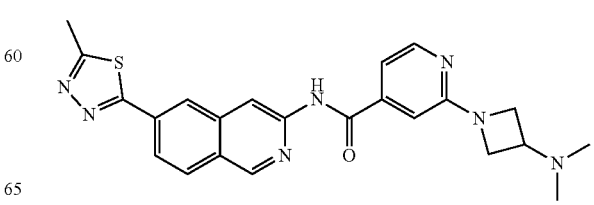

N-(6-(1,3,4-Thiadiazol-2-yl)isoquinolin-3-yl)-2-(4-isopropylpiperazin-1-yl) isonicotinamide 392

Yellow solid (10.1 mg, 0.022 mmol, 16.1% yield). $^1$H NMR (499 MHz, DMSO-d$_6$) δ ppm 1.02 (6H, d, J=6.59 Hz), 2.52-2.60 (4H, m), 2.66-2.76 (1H, m), 3.53-3.64 (4H, m), 7.16 (1H, dd, J=5.21, 1.37 Hz), 7.46 (1H, s), 8.18-8.25 (1H, m), 8.26 (1H, d, J=5.21 Hz), 8.27-8.32 (1H, m), 8.67 (1H, d, J=0.82 Hz), 8.80 (1H, s), 9.33 (1H, s), 9.75 (1H, s), 11.20 (1H, s); ESIMS found for C$_{24}$H$_{25}$N$_7$OS m/z 460.2 (M+1).

393

N-(6-(1,3,4-Thiadiazol-2-yl)isoquinolin-3-yl)-2-morpholinoisonicotinamide 393

Beige solid (10.0 mg, 0.024 mmol, 8.0% yield). $^1$H NMR (499 MHz, DMSO-d$_6$) δ ppm 3.54-3.60 (4H, m), 3.69-3.76 (4H, m), 7.22 (1H, dd, J=5.21, 1.10 Hz), 7.48 (1H, s), 8.18-8.25 (1H, m), 8.25-8.33 (2H, m), 8.67 (1H, s), 8.80 (1H, s), 9.33 (1H, s), 9.75 (1H, s), 11.21 (1H, s); ESIMS found for C$_{21}$H$_{18}$N$_6$O$_2$S m/z 419.1 (M+1).

406

2-(3-(Dimethylamino)azetidin-1-yl)-N-(6-(5-methyl-1,3,4-thiadiazol-2-yl) isoquinolin-3-yl)isonicotinamide 406

Beige solid (20.0 mg, 0.045 mmol, 25.2% yield). $^1$H NMR (499 MHz, DMSO-d$_6$) δ ppm 2.13 (6H, s), 2.84 (3H, s), 3.17-3.26 (1H, m), 3.81 (2H, dd, J=8.51, 5.49 Hz), 4.07 (2H, t, J=7.55 Hz), 7.05 (1H, s), 7.16 (1H, dd, J=5.21, 1.37 Hz), 8.16 (1H, dd, J=8.51, 1.65 Hz), 8.22 (1H, d, J=4.94 Hz), 8.26 (1H, d, J=8.78 Hz), 8.55 (1H, s), 8.76 (1H, s), 9.31 (1H, s), 11.14 (1H, s); ESIMS found for $C_{23}H_{23}N_7OS$ m/z 446.2 (M+1).

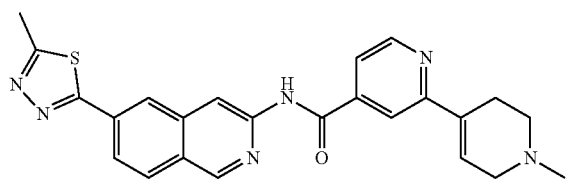

409

1'-Methyl-N-(6-(5-methyl-1,3,4-thiadiazol-2-yl)isoquinolin-3-yl)-1',2',3',6'-tetrahydro-[2,4'-bipyridine]-4-carboxamide 409

Off-white solid (2.6 g, 5.87 mmol, 56.9% yield). $^1$H NMR (499 MHz, DMSO-d$_6$) δ ppm 2.31 (3H, s), 2.56-2.63 (2H, m), 2.63-2.69 (2H, m), 2.84 (3H, s), 3.08-3.16 (2H, m), 6.89 (1H, dt, J=3.29, 1.92 Hz), 7.79 (1H, dd, J=4.94, 1.65 Hz), 8.12-8.22 (2H, m), 8.26 (1H, d, J=8.78 Hz), 8.57 (1H, d, J=0.82 Hz), 8.72 (1H, d, J=4.94 Hz), 8.80 (1H, s), 9.33 (1H, s), 11.39 (1H, s); ESIMS found for $C_{24}H_{22}N_6OS$ m/z 443.2 (M+1).

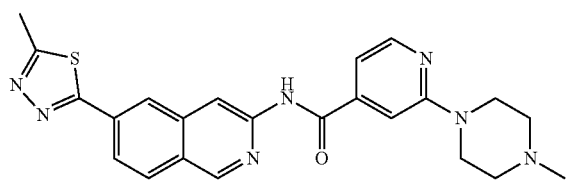

412

N-(6-(5-Methyl-1,3,4-thiadiazol-2-yl)isoquinolin-3-yl)-2-(4-methylpiperazin-1-yl)isonicotinamide 412

Beige solid (35.0 mg, 0.079 mmol, 38.3% yield). $^1$H NMR (500 MHz, DMSO-d$_6$) δ ppm 2.23 (3H, s), 2.41-2.46 (4H, m), 2.84 (3H, s), 3.55-3.66 (4H, m), 7.16 (1H, dd, J=5.21, 1.10 Hz), 7.48 (1H, s), 8.16 (1H, dd, J=8.51, 1.65 Hz), 8.20-8.30 (2H, m), 8.55 (1H, s), 8.78 (1H, s), 9.31 (1H, s), 11.20 (1H, s); ESIMS found for $C_{23}H_{23}N_7OS$ m/z 446.2 (M+1).

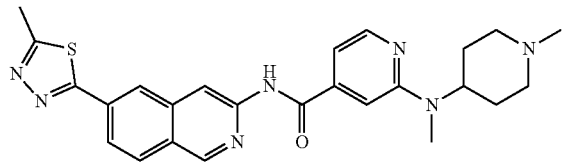

419

2-(Methyl(1-methylpiperidin-4-yl)amino)-N-(6-(5-methyl-1,3,4-thiadiazol-2-yl)isoquinolin-3-yl)isonicotinamide 419

Beige solid (35.0 mg, 0.074 mmol, 36.0% yield). $^1$H NMR (500 MHz, DMSO-d$_6$) δ ppm 1.49-1.61 (2H, m), 1.80 (2H, qd, J=12.12, 3.70 Hz), 1.98-2.08 (2H, m), 2.19 (3H, s), 2.86 (2H, br d, J=11.53 Hz), 2.93 (3H, s), 4.50 (1H, ddt, J=11.66, 7.89, 3.95, 3.95 Hz), 7.08 (1H, dd, J=5.21, 1.37 Hz), 7.19 (1H, s), 8.16 (1H, dd, J=8.51, 1.65 Hz), 8.23 (1H, d, J=5.21 Hz), 8.25 (1H, d, J=8.78 Hz), 8.55 (1H, s), 8.77 (1H, s), 9.31 (1H, s), 11.16 (1H, s); ESIMS found for $C_{25}H_{27}N_7OS$ m/z 474.2 (M+1).

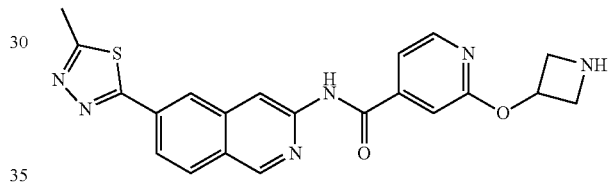

420

2-(Azetidin-3-yloxy)-N-(6-(5-methyl-1,3,4-thiadiazol-2-yl)isoquinolin-3-yl) isonicotinamide 420

Beige solid (4.0 mg, 0.010 mmol, 10.1% yield). $^1$H NMR (500 MHz, DMSO-d$_6$) δ ppm 2.84 (3H, s), 3.50-3.59 (2H, m), 3.72-3.81 (2H, m), 5.35-5.45 (1H, m), 7.41 (1H, s), 7.55 (1H, dd, J=5.49, 1.37 Hz), 8.17 (1H, dd, J=8.51, 1.65 Hz), 8.26 (1H, d, J=8.51 Hz), 8.31 (1H, d, J=5.49 Hz), 8.57 (1H, s), 8.77 (1H, s), 9.32 (1H, s), 11.26 (1H, br s); ESIMS found for $C_{21}H_{18}N_6O_2S$ m/z 419.1 (M+1).

422

N-(6-(5-methyl-1,3,4-thiadiazol-2-yl)isoquinolin-3-yl)-3-((1-methylpiperidin-4-yl)oxy)benzamide 422

Yellow solid (22.8 mg, 0.047 mmol, 10.7% yield). $^1$H NMR (499 MHz, DMSO-d$_6$) δ ppm 1.63-1.74 (2H, m), 1.93-2.00 (2H, m), 2.16-2.24 (2H, m), 2.19 (3H, s), 2.56-2.69 (2H, m), 2.84 (3H, s), 4.53 (1H, tt, J=8.03, 3.91 Hz), 7.18 (1H, ddd, J=8.16, 2.40, 0.96 Hz), 7.43 (1H, t, J=8.10

Hz), 7.59-7.69 (2H, m), 8.15 (1H, dd, J=8.51, 1.65 Hz), 8.25 (1H, d, J=8.78 Hz), 8.54 (1H, d, J=0.82 Hz), 8.77 (1H, s), 9.30 (1H, s), 10.98 (1H, s); ESIMS found for $C_{25}H_{25}N_5O_2S$ m/z 460.2 (M+1).

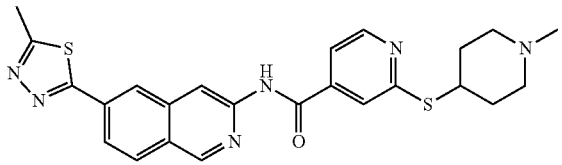

423

N-(6-(5-Methyl-1,3,4-thiadiazol-2-yl)isoquinolin-3-yl)-2-((1-methylpiperidin-4-yl)thio)isonicotinamide 423

Light yellow solid (44.0 mg, 0.092 mmol, 33.7% yield). $^1$H NMR (499 MHz, DMSO-$d_6$) δ ppm 1.60-1.72 (2H, m), 1.98-2.07 (2H, m), 2.12 (2H, br t, J=10.43 Hz), 2.17 (3H, s), 2.69 (2H, br d, J=10.98 Hz), 2.84 (3H, s), 3.84 (1H, br t, J=10.15 Hz), 7.64 (1H, dd, J=5.21, 1.37 Hz), 7.82 (1H, s), 8.17 (1H, dd, J=8.51, 1.65 Hz), 8.26 (1H, d, J=8.51 Hz), 8.56 (1H, s), 8.62 (1H, d, J=5.21 Hz), 8.76 (1H, s), 9.31 (1H, s), 11.30 (1H, s); ESIMS found for $C_{24}H_{24}N_6OS_2$ m/z 477.1 (M+1).

427

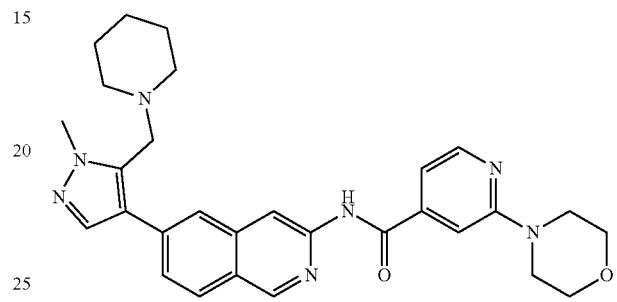

N-(7-Fluoro-6-(5-methyl-1,3,4-thiadiazol-2-yl)isoquinolin-3-yl)-2-(4-methylpiperazin-1-yl)isonicotinamide 427

Off-white solid (15.0 mg, 0.032 mmol, 17.9% yield). $^{11}$H NMR (499 MHz, DMSO-$d_6$) δ ppm 2.24 (3H, s), 2.39-2.45 (4H, m), 2.86 (3H, s), 3.58-3.64 (4H, m), 7.16 (1H, dd, J=5.21, 1.37 Hz), 7.47 (1H, s), 8.20 (1H, d, J=11.25 Hz), 8.26 (1H, d, J=4.94 Hz), 8.23-8.24 (1H, m), 8.79 (1H, s), 8.84 (1H, d, J=7.14 Hz), 9.30 (1H, s), 11.20 (1H, s); ESIMS found for $C_{23}H_{22}FN_7OS$ m/z 464.2 (M+1).

428

N-(6-(5-(Dimethylamino)-1,3,4-thiadiazol-2-yl)isoquinolin-3-yl)-2-(4-methylpiperazin-1-yl)isonicotinamide 428

Yellow solid (14.6 mg, 0.031 mmol, 26.8% yield). $^1$H NMR (499 MHz, DMSO-$d_6$) δ ppm 2.32 (3H, br s), 2.52-2.67 (4H, m), 3.19 (6H, s), 3.64 (4H, br s), 7.14-7.21 (1H, m), 7.48 (1H, s), 8.07 (1H, dd, J=8.51, 1.65 Hz), 8.17 (1H, s), 8.24-8.29 (2H, m), 8.70 (1H, s), 9.24 (1H, s), 11.14 (1H, s); ESIMS found for $C_{24}H_{26}N_8OS$ m/z 475.2 (M+1).

429

N-(6-(1-Methyl-5-(piperidin-1-ylmethyl)-1H-pyrazol-4-yl)isoquinolin-3-yl)-2-morpholinoisonicotinamide 429

White solid (23.0 mg, 0.045 mmol, 25.0% yield). $^1$H NMR (499 MHz, DMSO-$d_6$) δ ppm 1.32-1.44 (2H, m), 1.45-1.55 (4H, m), 2.38 (4H, br s), 3.53-3.62 (4H, m), 3.67 (2H, s), 3.71-3.77 (4H, m), 3.92 (3H, s), 7.21 (1H, dd, J=5.21, 1.10 Hz), 7.47 (1H, s), 7.76 (1H, dd, J=8.51, 1.65 Hz), 7.82 (1H, s), 8.09 (1H, d, J=8.51 Hz), 8.14 (1H, s), 8.29 (1H, d, J=5.21 Hz), 8.61 (1H, s), 9.17 (1H, s), 11.01 (1H, s); ESIMS found for $C_{29}H_{33}N_7O_2$ m/z 512.0 (M+1).

430

N-(6-(5-Amino-1,3,4-thiadiazol-2-yl)isoquinolin-3-yl)-2-(4-methylpiperazin-1-yl)isonicotinamide 430

Yellow solid (3.7 mg, 0.008 mmol, 5.4% yield). $^1$H NMR (499 MHz, DMSO-$d_6$) δ ppm 2.27 (3H, br s), 3.62 (4H, br s), 7.12-7.20 (1H, m), 7.48 (1H, s), 7.60 (2H, s), 8.07 (1H, dd, J=8.51, 1.65 Hz), 8.16 (1H, d, J=8.78 Hz), 8.25 (1H, s), 8.27 (1H, d, J=4.94 Hz), 8.71 (1H, s), 9.24 (1H, s), 11.13 (1H, s); ESIMS found for $C_{22}H_{22}N_8OS$ m/z 447.2 (M+1).

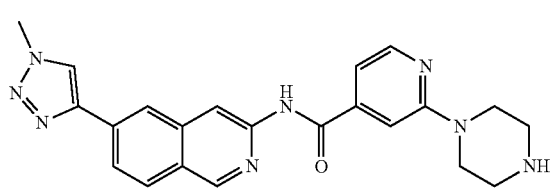

431

N-(6-(1-Methyl-1H-1,2,3-triazol-4-yl)isoquinolin-3-yl)-2-(piperazin-1-yl) isonicotinamide 431

Beige solid (76.0 mg, 0.183 mmol, 42.6% yield). $^1$H NMR (499 MHz, DMSO-$d_6$) δ ppm 2.77-2.85 (4H, m), 3.50-3.58 (4H, m), 4.15 (3H, s), 7.14 (1H, dd, J=5.21, 1.10 Hz), 7.43 (1H, s), 8.08 (1H, dd, J=8.51, 1.37 Hz), 8.18 (1H, d, J=8.51 Hz), 8.25 (1H, d, J=5.21 Hz), 8.38 (1H, s), 8.66 (1H, s), 8.76 (1H, s), 9.21 (1H, s), 11.09 (1H, s); ESIMS found for $C_{22}H_{22}N_8O$ m/z 415.2 (M+1).

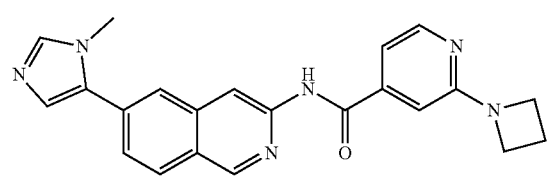

432

2-(Azetidin-1-yl)-N-(6-(1-methyl-1H-imidazol-5-yl)isoquinolin-3-yl) isonicotinamide 432

Off-white solid (73.7 mg, 0.192 mmol, 66.6% yield). $^1$H NMR (499 MHz, DMSO-$d_6$) δ ppm 2.31-2.41 (2H, m), 3.85 (3H, s), 4.03 (4H, t, J=7.41 Hz), 7.01 (1H, d, J=0.82 Hz), 7.15 (1H, dd, J=5.21, 1.65 Hz), 7.33 (1H, d, J=1.10 Hz), 7.74 (1H, dd, J=8.37, 1.78 Hz), 7.81 (1H, s), 8.09 (1H, s), 8.15 (1H, d, J=8.51 Hz), 8.21 (1H, d, J=5.21 Hz), 8.68 (1H, s), 9.22 (1H, s), 11.04 (1H, s); ESIMS found for $C_{22}H_{20}N_6O$ m/z 385.2 (M+1).

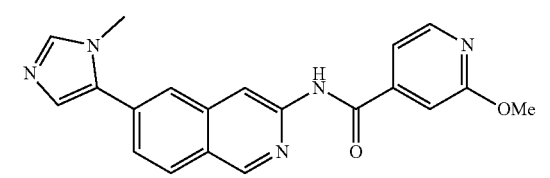

433

2-Methoxy-N-(6-(1-methyl-1H-imidazol-5-yl)isoquinolin-3-yl) isonicotinamide 433

Off-white solid (28.0 mg, 0.078 mmol, 34.9% yield). $^1$H NMR (499 MHz, DMSO-$d_6$) δ ppm 3.85 (3H, s), 3.93 (3H, s), 7.33 (1H, s), 7.42 (1H, d, J=1.37 Hz), 7.55 (1H, dd, J=5.21, 1.37 Hz), 7.75 (1H, dd, J=8.51, 1.65 Hz), 7.81 (1H, s), 8.11 (1H, d, J=0.82 Hz), 8.16 (1H, d, J=8.51 Hz), 8.35 (1H, d, J=5.21 Hz), 8.69 (1H, s), 9.23 (1H, s), 11.16 (1H, s); ESIMS found for $C_{20}H_{17}N_5O_2$ m/z 360.1 (M+1).

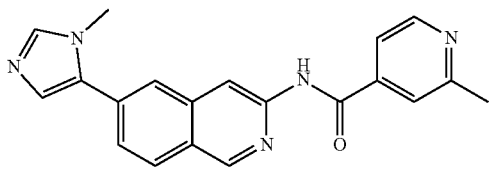

434

2-Methyl-N-(6-(1-methyl-1H-imidazol-5-yl)isoquinolin-3-yl)isonicotinamide 434

Off-white solid (32.1 mg, 0.094 mmol, 41.9% yield). $^1$H NMR (499 MHz, DMSO-$d_6$) δ ppm 2.58 (3H, s), 3.85 (3H, s), 7.33 (1H, d, J=0.82 Hz), 7.71-7.78 (2H, m), 7.81 (1H, s), 7.86 (1H, s), 8.12 (1H, s), 8.16 (1H, d, J=8.51 Hz), 8.64 (1H, d, J=4.94 Hz), 8.69 (1H, s), 9.23 (1H, s), 11.14 (1H, s); ESIMS found for $C_{20}H_{17}N_5O$ m 344.1 (M+1).

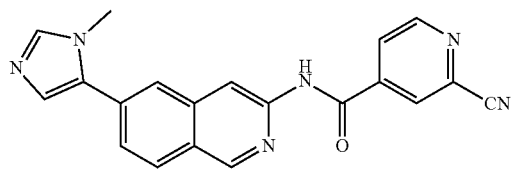

435

2-Cyano-N-(6-(1-methyl-1H-imidazol-5-yl)isoquinolin-3-yl)isonicotinamide 435

Off-white solid (36.0 mg, 0.102 mmol, 45.6% yield). $^1$H NMR (499 MHz, DMSO-$d_6$) δ ppm 3.86 (3H, s), 7.34 (1H, d, J=0.82 Hz), 7.77 (1H, dd, J=8.51, 1.65 Hz), 7.81 (1H, s), 8.14 (1H, s), 8.17 (1H, d, J=8.51 Hz), 8.26 (1H, dd, J=4.94, 1.65 Hz), 8.60 (1H, d, J=0.82 Hz), 8.70 (1H, s), 8.93-8.99 (1H, m), 9.24 (1H, s), 11.44 (1H, s); ESIMS found for $C_{20}H_{14}N_6O$ m/z 355.1 (M+1).

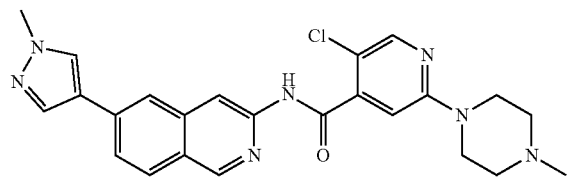

436

5-Chloro-N-(6-(1-methyl-1H-pyrazol-4-yl)isoquinolin-3-yl)-2-(4-methylpiperazin-1-yl)isonicotinamide 436

Off-white solid (18.7 mg, 0.041 mmol, 67.2% yield). $^1$H NMR (499 MHz, DMSO-$d_6$) δ ppm 2.21 (3H, s), 2.39 (4H, br t, J=4.94 Hz), 3.49-3.58 (4H, m), 3.91 (3H, s), 7.08 (1H, s), 7.81 (1H, dd, J=8.51, 1.65 Hz), 8.05 (1H, d, J=8.78 Hz), 8.11 (1H, s), 8.16 (1H, s), 8.19 (1H, s), 8.38 (1H, s), 8.55 (1H, s), 9.08 (1H, s), 11.15 (1H, s); ESIMS found for $C_{24}H_{24}ClN_7O$ m/z 462.2 (M+1).

437

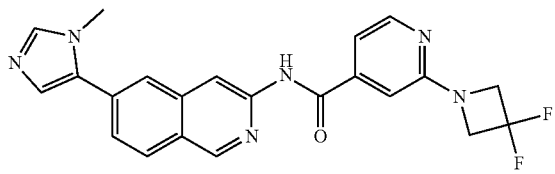

2-(3,3-Difluoroazetidin-1-yl)-N-(6-(1-methyl-1H-imidazol-5-yl)isoquinolin-3-yl)isonicotinamide 437

White solid (11.5 mg, 0.027 mmol, 9.5% yield). $^1$H NMR (499 MHz, DMSO-d$_6$) δ ppm 3.85 (3H, s), 4.49 (4H, t, J=12.49 Hz), 7.24 (1H, s), 7.31 (1H, dd, J=5.21, 1.37 Hz), 7.33 (1H, s), 7.75 (1H, dd, J=8.64, 1.51 Hz), 7.81 (1H, s), 8.10 (1H, s), 8.16 (1H, d, J=8.51 Hz), 8.31 (1H, d, J=5.21 Hz), 8.69 (1H, s), 9.23 (1H, s), 11.11 (1H, s); ESIMS found for $C_{22}H_{18}F_2N_6O$ m/z 421.1 (M+1).

438

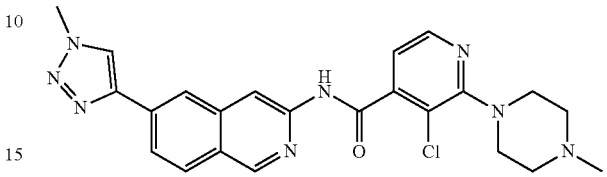

2-(4,4-Bis(methyl-d3)-4λ4-piperazin-1-yl)-N-(6-(1-methyl-1H-1,2,3-triazol-4-yl)isoquinolin-3-yl)isonicotinamide 438

Beige solid (62.0 mg, 0.108 mmol, 74.3% yield). $^1$H NMR (499 MHz, DMSO-d$_6$) δ ppm 3.53 (4H, t, J=5.21 Hz), 3.94-4.04 (4H, m), 4.15 (3H, s), 7.32 (1H, dd, J=5.21, 1.10 Hz), 7.61 (1H, s), 8.08 (1H, dd, J=8.64, 1.51 Hz), 8.19 (1H, d, J=8.78 Hz), 8.35 (1H, d, J=5.21 Hz), 8.40 (1H, s), 8.68 (1H, s), 8.76 (1H, s), 9.23 (1H, s), 11.13 (1H, s); ESIMS found for $C_{24}H_{21}[^2H_6]N_5O$ m/z 449.3 (M+).

439

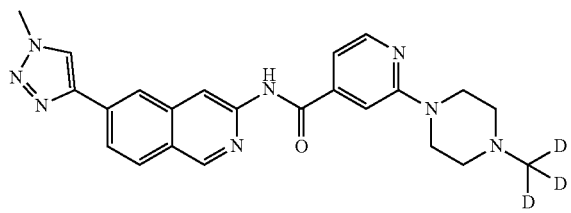

N-(6-(1-Methyl-1H-1,2,3-triazol-4-yl)isoquinolin-3-yl)-2-(4-(methyl-d3) piperazin-1-yl)isonicotinamide 439

Beige solid (44.0 mg, 0.102 mmol, 35.5% yield). $^1$H NMR (499 MHz, DMSO-d$_6$) δ ppm 2.43 (4H, t, J=4.94 Hz), 3.56-3.63 (4H, m), 4.15 (3H, s), 7.17 (1H, dd, J=5.08, 0.96 Hz), 7.47 (1H, s), 8.08 (1H, dd, J=8.37, 1.51 Hz), 8.18 (1H, d, J=8.51 Hz), 8.26 (1H, d, J=5.21 Hz), 8.38 (1H, s), 8.66 (1H, s), 8.76 (1H, s), 9.21 (1H, s), 11.11 (1H, s); ESIMS found for $C_{23}H_{21}[^2H_3]N_5O$ m/z 432. (M+1).

440

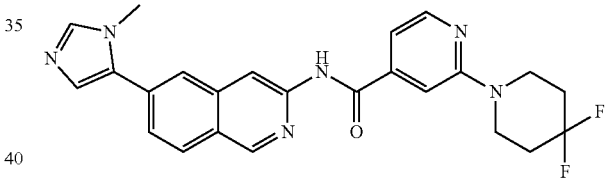

3-Chloro-N-(6-(1-methyl-1H-pyrazol-4-yl)isoquinolin-3-yl)-2-(4-methylpiperazin-1-yl)isonicotinamide 440

Off-white solid (90.7 mg, 0.196 mmol, 29.4% yield). $^1$H NMR (499 MHz, DMSO-d$_6$) δ ppm 2.24 (3H, s), 2.49 (4H, br s), 3.26-3.31 (4H, m), 3.91 (3H, s), 7.17 (1H, d, J=4.67 Hz), 7.81 (1H, dd, J=8.51, 1.65 Hz), 8.05 (1H, d, J=8.51 Hz), 8.11 (1H, s), 8.17 (1H, s), 8.29 (1H, d, J=4.67 Hz), 8.38 (1H, s), 8.55 (1H, s), 9.07 (1H, s), 11.21 (1H, s); ESIMS found for $C_{24}H_{24}ClN_7O$ m/z 462.2 (M+1).

441

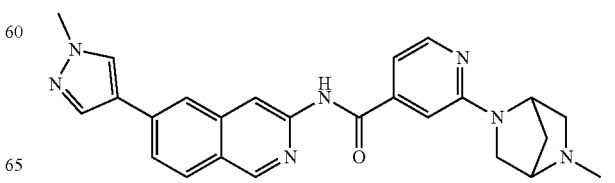

2-(4,4-Difluoropiperidin-1-yl)-N-(6-(1-methyl-1H-imidazol-5-yl)isoquinolin-3-yl)isonicotinamide 441

White solid (18.9 mg, 0.042 mmol, 24.4% yield). $^1$H NMR (499 MHz, DMSO-d$_6$) δ ppm 1.99-2.09 (4H, m), 3.81 (4H, br d, J=5.76 Hz), 3.85 (3H, s), 7.19 (1H, dd, J=5.21, 1.10 Hz), 7.33 (1H, d, J=0.82 Hz), 7.58 (1H, s), 7.74 (1H, dd, J=8.51, 1.65 Hz), 7.81 (1H, s), 8.10 (1H, s), 8.16 (1H, d, J=8.51 Hz), 8.29 (1H, d, J=5.21 Hz), 8.70 (1H, s), 9.23 (1H, s), 11.14 (1H, s); ESIMS found for $C_{24}H_{22}F_2N_6O$ m/z 449.2 (M+1).

442

N-(6-(1-Methyl-1H-pyrazol-4-yl)isoquinolin-3-yl)-2-(5-methyl-2,5-diazabicyclo[2.2.1]heptan-2-yl)isonicotinamide 442

Off-white solid (74.4 mg, 0.161 mmol, 59.5% yield). $^1$H NMR (499 MHz, DMSO-$d_6$) δ ppm 1.77 (1H, br d, J=9.06 Hz), 1.90 (1H, br d, J=8.78 Hz), 2.30 (3H, s), 2.48 (1H, br s), 2.86 (1H, dd, J=9.47, 1.78 Hz), 3.34 (1H, dd, J=9.88, 2.20 Hz), 3.49 (1H, br s), 3.57 (1H, br d, J=9.88 Hz), 3.91 (3H, s), 4.70 (1H, br s), 7.05 (1H, dd, J=5.21, 1.37 Hz), 7.11 (1H, s), 7.81 (1H, dd, J=8.64, 1.51 Hz), 8.07 (1H, d, J=8.51 Hz), 8.09-8.16 (2H, m), 8.19 (1H, d, J=4.94 Hz), 8.38 (1H, s), 8.59 (1H, s), 9.12 (1H, s), 10.98 (1H, s); ESIMS found for $C_{25}H_{25}N_7O$ m/z 440.2 (M+1).

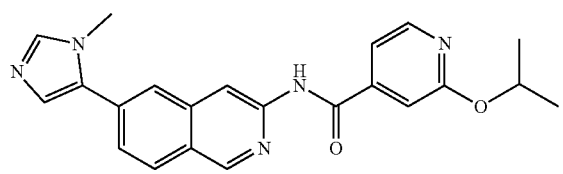

443

2-Isopropoxy-N-(6-(1-methyl-1H-imidazol-5-yl)isoquinolin-3-yl) isonicotinamide 443

Off-white solid (94.6 mg, 0.244 mmol, 54.8% yield). $^1$H NMR (499 MHz, DMSO-$d_6$) δ ppm 1.33 (6H, d, J=6.31 Hz), 3.85 (3H, s), 5.30 (1H, spt, J=6.17 Hz), 7.30 (1H, s), 7.33 (1H, d, J=0.82 Hz), 7.50 (1H, dd, J=5.21, 1.37 Hz), 7.75 (1H, dd, J=8.37, 1.78 Hz), 7.81 (1H, s), 8.11 (1H, s), 8.15 (1H, d, J=8.51 Hz), 8.32 (1H, d, J=5.21 Hz), 8.68 (1H, s), 9.22 (1H, s), 11.11 (1H, s); ESIMS found for $C_{22}H_{21}N_5O_2$ m/z 388.2 (M+1).

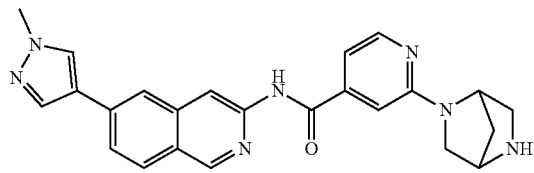

444

2-(2,5-Diazabicyclo[2.2.1]heptan-2-yl)-N-(6-(1-methyl-1H-pyrazol-4-yl) isoquinolin-3-yl)isonicotinamide 444

Off-white solid (145.0 mg, 0.324 mmol, 88.5% yield). $^1$H NMR (499 MHz, DMSO-$d_6$) δ ppm 1.71 (1H, br d, J=9.06 Hz), 1.82 (1H, br d, J=9.33 Hz), 2.86 (1H, br d, J=9.61 Hz), 2.96 (1H, br d, J=8.78 Hz), 3.29 (1H, br s), 3.52 (1H, dd, J=9.33, 1.37 Hz), 3.75 (1H, br s), 3.91 (3H, s), 4.76 (1H, br s), 7.07 (1H, d, J=4.94 Hz), 7.12 (1H, br s), 7.81 (1H, dd, J=8.51, 1.65 Hz), 8.07 (1H, d, J=8.51 Hz), 8.11 (1H, s), 8.13 (1H, s), 8.19 (1H, d, J=4.94 Hz), 8.38 (1H, s), 8.59 (1H, s), 9.12 (1H, s), 10.97 (1H, s); ESIMS found for $C_{24}H_{23}N_7O$ m/z 426.2 (M+1).

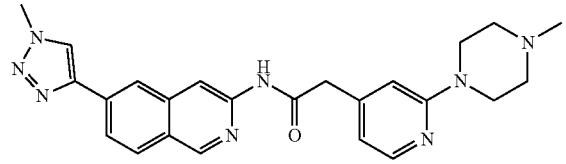

445

N-(6-(1-Methyl-1H-1,2,3-triazol-4-yl)isoquinolin-3-yl)-2-(2-(4-methylpiperazin-1-yl)pyridin-4-yl)acetamide 445

Beige solid (2.0 mg, 0.005 mmol, 3.1% yield). $^1$H NMR (499 MHz, DMSO-$d_6$) δ ppm 2.22 (3H, s), 2.40 (4H, br t, J=4.94 Hz), 3.45-3.51 (4H, m), 3.71 (2H, s), 4.13 (3H, s), 6.66 (1H, d, J=4.67 Hz), 6.83 (1H, s), 8.01-8.06 (2H, m), 8.12 (1H, d, J=8.78 Hz), 8.28 (1H, s), 8.46 (1H, s), 8.72 (1H, s), 9.13 (1H, s), 10.85 (1H, s); ESIMS found for $C_{24}H_{26}N_8O$ m/z 443.2 (M+1).

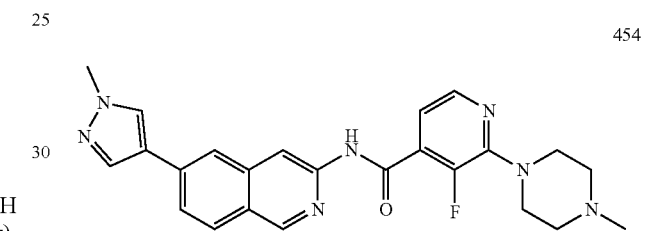

454

3-Fluoro-N-(6-(1-methyl-1H-pyrazol-4-yl)isoquinolin-3-yl)-2-(4-methylpiperazin-1-yl)isonicotinamide 454

Off-white solid (85.9 mg, 0.193 mmol, 24.0% yield). $^1$H NMR (499 MHz, DMSO-$d_6$) δ ppm 2.23 (3H, s), 2.42-2.47 (4H, m), 3.41-3.49 (4H, m), 3.91 (3H, s), 7.05 (1H, t, J=4.39 Hz), 7.82 (1H, dd, J=8.51, 1.65 Hz), 8.06 (1H, d, J=8.51 Hz), 8.08 (1H, d, J=4.94 Hz), 8.11 (1H, s), 8.16 (1H, s), 8.38 (1H, s), 8.55 (1H, s), 9.09 (1H, s), 11.17 (1H, s); ESIMS found for $C_{24}H_{24}FN_7O$ m/z 446.2 (M+1).

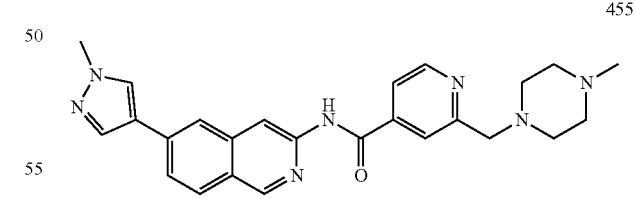

455

N-(6-(1-Methyl-1H-pyrazol-4-yl)isoquinolin-3-yl)-2-((4-methylpiperazin-1-yl)methyl)isonicotinamide 455

Off-white solid (12.5 mg, 0.028 mmol, 15.5% yield). $^1$H NMR (499 MHz, DMSO-$d_6$) δ ppm 2.17 (3H, s), 2.36 (4H, dt, J=3.77, 2.09 Hz), 2.42-2.49 (4H, m), 3.68 (2H, s), 3.91 (3H, s), 7.83 (1H, dd, J=13.45, 1.65 Hz), 7.83 (1H, d, J=1.65 Hz), 7.95 (1H, s), 8.07 (1H, d, J=8.51 Hz), 8.12 (1H, s), 8.15

(1H, s), 8.39 (1H, s), 8.59 (1H, s), 8.68 (1H, d, J=4.94 Hz), 9.13 (1H, s), 11.18 (1H, s); ESIMS found for $C_{25}H_{27}N_7O$ m/z 442.2 (M+1).

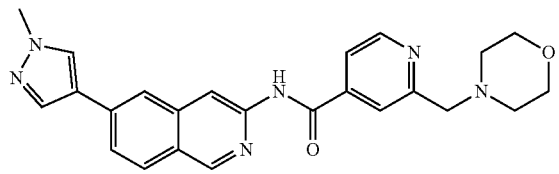

N-(6-(1-Methyl-1H-pyrazol-4-yl)isoquinolin-3-yl)-2-(morpholinomethyl) isonicotinamide 456

Off-white solid (13.6 mg, 0.032 mmol, 80.7% yield). $^1$H NMR (499 MHz, DMSO-$d_6$) δ ppm 2.47 (4H, br s), 3.59-3.65 (4H, m), 3.69 (2H, s), 3.91 (3H, s), 7.83 (1H, br dd, J=16.47, 1.65 Hz), 7.83-7.84 (1H, m), 7.98 (1H, s), 8.08 (1H, d, J=8.51 Hz), 8.12 (1H, s), 8.15 (1H, s), 8.39 (1H, s), 8.59 (1H, s), 8.69 (1H, d, J=4.94 Hz), 9.13 (1H, s), 11.19 (1H, s); ESIMS found for $C_{24}H_{24}N_6O_2$ m/z 429.2 (M+1).

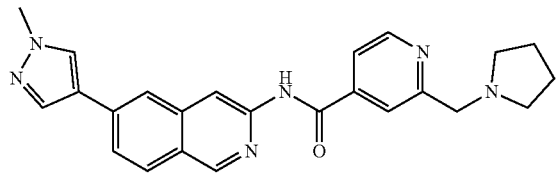

N-(6-(1-Methyl-1H-pyrazol-4-yl)isoquinolin-3-yl)-2-(pyrrolidin-1-ylmethyl) isonicotinamide 457

Off-white solid (12.0 mg, 0.029 mmol, 80.7% yield). $^1$H NMR (499 MHz, DMSO-$d_6$) δ ppm 1.74 (4H, dt, J=6.52, 3.19 Hz), 2.56 (4H, br s), 3.82 (2H, s), 3.91 (3H, s), 7.81-7.84 (2H, m), 7.96 (1H, s), 8.07 (1H, d, J=8.51 Hz), 8.12 (1H, s), 8.15 (1H, s), 8.39 (1H, s), 8.59 (1H, s), 8.67 (1H, d, J=4.94 Hz), 9.13 (1H, s), 11.19 (1H, s); ESIMS found for $C_{24}H_{24}N_6O$ m/z 413.2 (M+1).

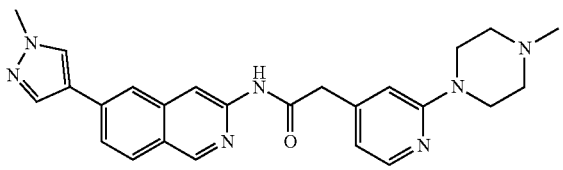

N-(6-(1-Methyl-1H-pyrazol-4-yl)isoquinolin-3-yl)-2-(2-(4-methylpiperazin-1-yl)pyridin-4-yl)acetamide 458

Beige solid (10.0 mg, 0.023 mmol, 5.3% yield). $^1$H NMR (499 MHz, DMSO-$d_6$) δ ppm 2.21 (3H, s), 2.37-2.42 (4H, m), 3.43-3.49 (4H, m), 3.70 (2H, s), 3.89 (3H, s), 6.66 (1H, d, J=4.94 Hz), 6.83 (1H, s), 7.76 (1H, dd, J=8.51, 1.65 Hz), 8.01 (1H, d, J=8.51 Hz), 8.03-8.05 (2H, m), 8.08 (1H, s), 8.35 (1H, s), 8.39 (1H, s), 9.04 (1H, s), 10.77 (1H, s); ESIMS found for $C_{25}H_{27}N_7O$ m/z 442.2 (M+1).

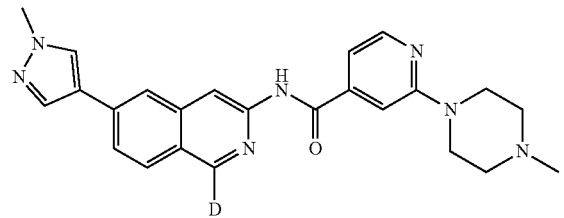

N-(6-(1-Methyl-1H-pyrazol-4-yl)isoquinolin-3-yl-1-d)-2-(4-methylpiperazin-1-yl)isonicotinamide 459

Off-white solid (69.0 mg, 0.179 mmol, 64.5% yield). $^1$H NMR (499 MHz, DMSO-$d_6$) δ ppm 2.23 (3H, s), 2.43 (4H, t, J=4.94 Hz), 3.56-3.64 (4H, m), 3.91 (3H, s), 7.16 (1H, dd, J=5.08, 1.24 Hz), 7.46 (1H, s), 7.81 (1H, dd, J=8.64, 1.51 Hz), 8.07 (1H, d, J=8.51 Hz), 8.11 (1H, s), 8.14 (1H, s), 8.26 (1H, d, J=4.94 Hz), 8.38 (1H, s), 8.59 (1H, s), 11.04 (1H, s); ESIMS found for $C_{24}H_{24}[^2H]N_7O$ m/z 429. (M+1).

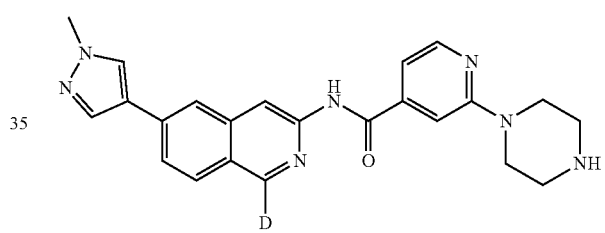

N-(6-(1-Methyl-1H-pyrazol-4-yl)isoquinolin-3-yl-1-d)-2-(piperazin-1-yl) isonicotinamide 461

Off-white solid (69.0 mg, 0.179 mmol, 64.5% yield). $^1$H NMR (499 MHz, DMSO-$d_6$) δ ppm 2.77-2.84 (4H, m), 3.48-3.57 (4H, m), 3.91 (3H, s), 7.13 (1H, dd, J=5.08, 1.24 Hz), 7.42 (1H, s), 7.81 (1H, dd, J=8.51, 1.65 Hz), 8.07 (1H, d, J=8.51 Hz), 8.11 (1H, s), 8.14 (1H, s), 8.25 (1H, d, J=5.21 Hz), 8.38 (1H, s), 8.59 (1H, s), 11.03 (1H, s); ESIMS found for $C_{23}H_{22}[^2H]N_7O$ m/z 415. (M+1).

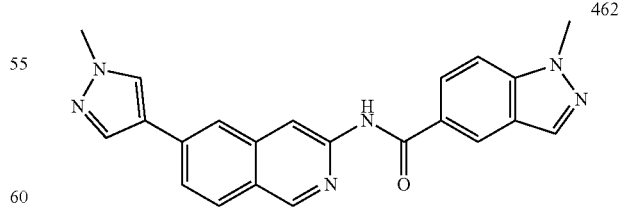

1-Methyl-N-(6-(1-methyl-1H-pyrazol-4-yl)isoquinolin-3-yl)-1H-indazole-5-carboxamide 462

Light yellow solid (32.0 mg, 0.084 mmol, 18.8% yield). $^1$H NMR (499 MHz, DMSO-$d_6$) δ ppm 3.92 (3H, s), 4.11

(3H, s), 7.75 (1H, d, J=9.06 Hz), 7.80 (1H, dd, J=8.51, 1.65 Hz), 8.06 (1H, d, J=8.51 Hz), 8.12 (1H, dd, J=8.92, 1.51 Hz), 8.12 (1H, s), 8.14 (1H, s), 8.24 (1H, s), 8.38 (1H, s), 8.62 (2H, s), 9.12 (1H, s), 10.82 (1H, s); ESIMS found for $C_{22}H_{18}N_6O$ m/z 383.15 (M+1).

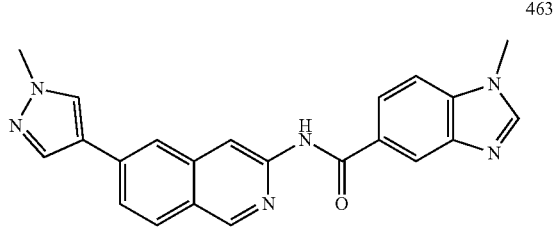 [SMILES: Cn1cc(-c2ccc3cnc(NC(=O)c4ccc5c(c4)ncn5C)cc3c2)cn1]

1-Methyl-N-(6-(1-methyl-1H-pyrazol-4-yl)isoquinolin-3-yl)-1H-benzo[d]imidazole-5-carboxamide 463

Light yellow solid (35.6 mg, 0.093 mmol, 20.8% yield). $^1$H NMR (499 MHz, DMSO-$d_6$) δ ppm 3.90 (3H, s), 3.92 (3H, s), 7.70 (1H, d, J=8.51 Hz), 7.79 (1H, dd, J=8.51, 1.65 Hz), 8.06 (2H, d, J=8.51 Hz), 8.11 (1H, s), 8.13 (1H, s), 8.33 (1H, s), 8.38 (1H, s), 8.47 (1H, d, J=1.65 Hz), 8.62 (1H, s), 9.12 (1H, s), 10.78 (1H, s); ESIMS found for $C_{22}H_{18}N_6O$ m/z 383.2 (M+1).

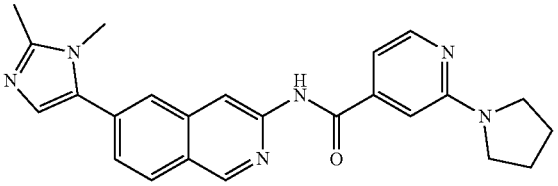

N-(6-(1,2-Dimethyl-1H-imidazol-5-yl)isoquinolin-3-yl)-2-(pyrrolidin-1-yl) isonicotinamide 464

Off-white solid (51.7 mg, 0.125 mmol, 45.3% yield). $^1$H NMR (499 MHz, DMSO-$d_6$) δ ppm 1.95-2.01 (4H, m), 2.40 (3H, s), 3.45-3.51 (4H, m), 3.68 (3H, s), 7.06 (1H, dd, J=5.21, 1.37 Hz), 7.08 (1H, s), 7.14 (1H, s), 7.67 (1H, dd, J=8.51, 1.65 Hz), 8.00 (1H, s), 8.14 (1H, d, J=8.78 Hz), 8.17-8.23 (1H, m), 8.67 (1H, s), 9.22 (1H, s), 11.03 (1H, s); ESIMS found for $C_{24}H_{24}N_6O$ m/z 413.2 (M+1).

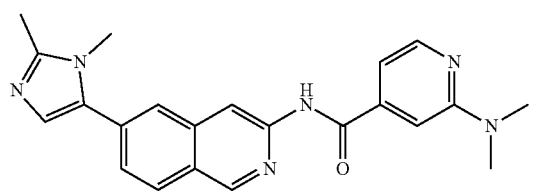

N-(6-(1,2-Dimethyl-1H-imidazol-5-yl)isoquinolin-3-yl)-2-(dimethylamino) isonicotinamide 465

Off-white solid (69.0 mg, 0.179 mmol, 64.5% yield). $^1$H NMR (499 MHz, DMSO-$d_6$) δ ppm 2.40 (3H, s), 3.11 (6H, s), 3.68 (3H, s), 7.09 (1H, dd, J=5.21, 1.10 Hz), 7.14 (1H, s), 7.25 (1H, s), 7.67 (1H, dd, J=8.51, 1.65 Hz), 8.00 (1H, s), 8.14 (1H, d, J=8.51 Hz), 8.23 (1H, d, J=4.94 Hz), 8.68 (1H, s), 9.22 (1H, s), 11.07 (1H, s); ESIMS found for $C_{22}H_{22}N_6O$ m/z 387.2 (M+1).

Example 4

The screening assay for Wnt activity is described as follows. Reporter cell lines can be generated by stably transducing cancer cell lines (e.g., colon cancer) or primary cells (e.g., IEC-6 intestinal cells) with a lentiviral construct that includes a Wnt-responsive promoter driving expression of the firefly luciferase gene.

SW480 colon carcinoma cells were transduced with a lentiviral vector expressing luciferase with a human Sp5 promoter consisting of a sequence of eight TCF/LEF binding sites. SW480 cells stably expressing the Sp5-Luc reporter gene and a hygromycin resistance gene were selected by treatment with 150 μg/mL of hygromycin for 7 days. These stably transduced SW480 cells were expanded in cell culture and used for all further screening activities. Each compound was dissolved in DMSO as a 10 mM stock and used to prepare compound source plates. Serial dilution (1:3, 10-point dose-response curves starting from 10 μM) and compound transfer was performed using the ECHO 550 (Labcyte, Sunnyvale, Calif.) into 384-well white solid bottom assay plates (Greiner Bio-One) with appropriate DMSO backfill for a final DMSO concentration of 0.1%. For Sp5-Luc reporter gene assays, the cells were plated at 4,000 cells/well in 384-well plates with a DMEM medium containing 1% fetal bovine serum, and 1% Penicillin-Streptomycin and incubated for 36 to 48 hours at 37° C. and 5% $CO_2$. Following incubation, 15 μl of BriteLite Plus luminescence reagent (Perkin Elmer) was added to each well of the 384-well assay plates. The plates were placed on an orbital shaker for 2 min and then luminescence was quantified using the Envision (Perkin Elmer) plate reader. Readings were normalized to DMSO only treated cells, and normalized activities were utilized for $EC_{50}$ calculations using the dose-response log (inhibitor) vs. response-variable slope (four parameters) nonlinear regression feature available in GraphPad Prism 5.0 (or Dotmatics). For $EC_{50}$ of >10 μM, the percent inhibition at 10 μM is provided.

Table 2 shows the measured activity for representative compounds of Formula I as described herein.

TABLE 2

| Compound | $EC_{50}$ (μM) |
| --- | --- |
| 1 | 0.067 |
| 2 | 0.091 |
| 3 | 0.116 |
| 4 | 0.370 |
| 5 | 0.089 |
| 6 | 0.070 |
| 7 | 0.113 |
| 8 | 0.170 |
| 9 | 0.039 |
| 10 | 0.046 |
| 11 | 0.116 |
| 12 | 0.487 |
| 13 | 0.171 |
| 14 | 0.153 |
| 15 | >10 (8.0%) |
| 16 | 0.062 |
| 17 | 0.058 |
| 18 | 0.200 |
| 19 | 0.066 |

TABLE 2-continued

| Compound | EC$_{50}$ (μM) |
|---|---|
| 20 | 0.705 |
| 21 | 0.745 |
| 22 | 2.109 |
| 23 | 0.425 |
| 24 | >10 (0%) |
| 25 | >10 (48.8%) |
| 26 | 3.785 |
| 27 | 4.362 |
| 28 | 0.472 |
| 29 | 0.307 |
| 37 | 0.033 |
| 40 | 0.684 |
| 45 | 0.449 |
| 47 | 3.357 |
| 49 | 0.098 |
| 52 | 1.003 |
| 53 | 0.039 |
| 54 | 0.035 |
| 55 | 0.032 |
| 56 | 0.031 |
| 57 | 0.109 |
| 59 | 0.062 |
| 60 | 0.680 |
| 61 | 0.182 |
| 62 | 0.127 |
| 63 | 0.108 |
| 64 | 0.298 |
| 65 | 0.422 |
| 66 | 0.047 |
| 67 | 0.057 |
| 71 | 0.044 |
| 72 | 0.062 |
| 74 | 0.052 |
| 76 | 0.295 |
| 78 | 0.776 |
| 80 | 0.597 |
| 84 | 0.021 |
| 85 | 0.034 |
| 86 | 0.162 |
| 87 | 3.639 |
| 88 | 0.131 |
| 89 | 3.376 |
| 90 | 0.132 |
| 91 | 0.107 |
| 92 | 0.103 |
| 93 | 0.036 |
| 94 | 0.110 |
| 95 | >10 (3.5%) |
| 97 | 0.041 |
| 99 | 0.041 |
| 100 | 8.409 |
| 101 | 1.041 |
| 102 | 0.979 |
| 103 | 2.272 |
| 104 | 0.177 |
| 105 | 0.764 |
| 106 | 0.307 |
| 107 | 0.912 |
| 108 | 0.193 |
| 109 | 0.312 |
| 110 | 0.320 |
| 111 | 0.184 |
| 112 | 0.128 |
| 113 | 0.120 |
| 114 | 0.131 |
| 116 | 0.136 |
| 117 | 0.375 |
| 118 | >10 (0%) |
| 119 | 0.554 |
| 120 | 0.328 |
| 122 | 0.238 |
| 123 | 0.264 |
| 126 | 0.185 |
| 127 | 0.214 |
| 130 | 0.250 |
| 131 | 0.285 |
| 132 | 0.365 |
| 133 | 0.223 |
| 134 | 0.058 |
| 135 | 0.236 |
| 136 | 2.124 |
| 137 | 0.949 |
| 138 | 3.188 |
| 139 | 2.962 |
| 140 | 0.152 |
| 141 | >10 (8.8%) |
| 142 | 0.055 |
| 143 | 0.045 |
| 144 | 0.051 |
| 145 | 0.039 |
| 146 | 0.749 |
| 147 | 0.179 |
| 148 | 3.766 |
| 149 | 0.047 |
| 151 | 0.265 |
| 168 | 0.106 |
| 172 | 0.270 |
| 182 | 0.230 |
| 183 | 0.414 |
| 184 | 0.182 |
| 185 | 0.189 |
| 186 | 0.074 |
| 204 | 0.023 |
| 219 | 0.890 |
| 220 | 0.463 |
| 221 | 0.608 |
| 222 | 0.189 |
| 223 | 0.489 |
| 230 | 0.037 |
| 232 | 0.256 |
| 233 | 0.120 |
| 236 | 0.070 |
| 238 | 0.036 |
| 240 | 0.035 |
| 241 | 0.183 |
| 242 | 0.042 |
| 243 | 0.094 |
| 245 | 0.038 |
| 249 | 1.223 |
| 250 | 0.055 |
| 253 | 0.054 |
| 256 | 0.117 |
| 257 | 3.911 |
| 258 | 1.749 |
| 261 | 0.101 |
| 265 | 0.106 |
| 266 | 0.057 |
| 268 | 0.104 |
| 271 | 0.114 |
| 273 | 0.083 |
| 275 | 0.012 |
| 276 | 0.093 |
| 277 | 0.156 |
| 278 | 0.088 |
| 285 | 0.090 |
| 286 | 0.107 |
| 289 | 0.174 |
| 290 | 0.104 |
| 291 | 0.710 |
| 292 | 0.375 |
| 293 | 2.268 |
| 294 | 0.161 |
| 296 | >10 (14.6%) |
| 301 | 0.101 |
| 306 | 1.019 |
| 309 | 0.103 |
| 310 | 1.692 |
| 313 | 2.139 |
| 317 | 0.279 |
| 318 | 0.396 |
| 319 | 0.844 |
| 325 | 3.564 |
| 326 | 1.722 |
| 328 | 0.113 |
| 329 | 0.162 |
| 330 | >10 (15.0%) |

TABLE 2-continued

| Compound | EC$_{50}$ (μM) |
|---|---|
| 331 | >10 (28.7%) |
| 332 | 3.841 |
| 333 | 1.042 |
| 334 | 0.126 |
| 335 | 0.107 |
| 336 | 0.060 |
| 337 | 0.091 |
| 338 | 0.057 |
| 339 | 0.699 |
| 340 | 0.346 |
| 359 | 0.013 |
| 373 | 6.427 |
| 374 | 0.211 |
| 375 | >10 (44.7%) |
| 376 | 0.113 |
| 377 | 5.568 |
| 378 | 0.268 |
| 379 | 0.100 |
| 380 | >10 (11.2%) |
| 381 | 3.515 |
| 382 | 0.509 |
| 383 | 0.116 |
| 384 | 0.162 |
| 385 | 0.211 |
| 386 | 0.106 |
| 387 | >10 (46.4%) |
| 388 | 0.139 |
| 389 | 0.561 |
| 390 | 0.117 |
| 391 | 0.043 |
| 392 | 0.111 |
| 393 | 0.080 |
| 406 | 0.116 |
| 409 | 0.041 |
| 412 | 0.059 |
| 419 | 0.069 |
| 420 | 0.449 |
| 422 | 0.107 |
| 423 | 0.040 |
| 427 | 3.676 |
| 428 | 0.138 |
| 429 | 0.073 |
| 430 | 0.036 |
| 431 | 0.047 |
| 432 | 0.109 |
| 433 | 0.559 |
| 434 | 0.104 |
| 435 | 0.136 |
| 436 | 3.134 |
| 437 | 0.500 |
| 438 | 2.511 |
| 439 | 0.048 |
| 440 | >10 (48.0%) |
| 441 | 0.228 |
| 442 | 0.116 |
| 443 | 0.501 |
| 444 | 0.133 |
| 445 | 0.144 |
| 454 | 0.324 |
| 455 | 0.113 |
| 456 | 0.497 |
| 457 | 0.475 |
| 458 | 0.214 |
| 459 | 0.055 |
| 461 | 0.043 |
| 462 | 0.193 |
| 463 | 0.159 |
| 464 | 0.480 |
| 465 | 0.231 |

Example 5

Representative compounds were screened using the assay procedure for DYRKIA kinase activity as described below. Each compound was dissolved in DMSO as a 10 mM stock and used to prepare compound source plates. Serial dilution (1:3, 11-point dose-response curves from 10 μM to 0.00016 μM) and compound transfer was performed using the ECHO 550 (Labcyte, Sunnyvale, Calif.) into 1536-well black-walled round bottom plates (Corning).

The DYRKIA kinase assay was run using the Ser/Thr 18 peptide Z-lyte assay kit according to manufacturer's instructions (Life Technologies—a Division of Thermo-Fisher). This is a non-radioactive assay using fluorescence resonance energy transfer (FRET) between coumarin and fluorescein to detect kinase activity which is represented as a ratio of coumarin emission/fluorescein emission.

Briefly, recombinant DYRKIA kinase, ATP and Ser/Thr peptide 18 were prepared in 1× Kinase buffer to final concentrations of 0.19 μg/mL, 30 μM, and 4 μM respectively. The mixture was allowed to incubate with the representative compounds for one hour at room temperature. All reactions were performed in duplicate. Unphosphorylated ("0% Control") and phosphorylated ("100% control") forms of Ser/Thr 18 served as control reactions. Additionally, an 11-point dose-response curve of Staurosporine (1 uM top) was run to serve as a positive compound control.

After incubation, Development Reagent A was diluted in Development Buffer then added to the reaction and allowed to further incubate for one hour at room temperature. The plate was read at Ex 400 Em 455 to detect the coumarin signal and Ex 400 Em 520 to measure the signal (EnVision Multilabel Plate Reader, PerkinElmer).

The Emission ratio (Em) was calculated as a ratio of the coumarin (C) emission signal (at 445 nm)/Fluorescein (F) emission signal (at 520 nm). The percent phosphorylation was then calculated using the following formula: [1−((Em ratio×F100%)−C100%)/((C0%−C100%)+(Em ratio×(F100%−F0%)))]. Dose-response curves were generated and inhibitory concentration (IC$_{50}$) values were calculated using non-linear regression curve fit in the Dotmatics' Studies Software (Bishops Stortford, UK).

Table 3 shows the measured activity for representative compounds of Formula I as described herein.

TABLE 3

| Compound | EC$_{50}$ (μM) |
|---|---|
| 1 | 0.0012 |
| 2 | 0.0013 |
| 3 | 0.0009 |
| 4 | 0.0025 |
| 5 | 0.0012 |
| 6 | 0.0011 |
| 7 | 0.0012 |
| 8 | 0.0009 |
| 9 | 0.0004 |
| 10 | 0.0010 |
| 11 | 0.0013 |
| 12 | 0.0029 |
| 13 | 0.0020 |
| 14 | 0.0009 |
| 15 | 0.3124 |
| 16 | 0.0011 |
| 17 | 0.0018 |
| 18 | 0.0017 |
| 19 | 0.0015 |
| 20 | 0.0552 |
| 21 | 0.0632 |
| 22 | 0.0551 |
| 23 | 0.0100 |
| 24 | 0.0673 |
| 25 | 0.1583 |
| 26 | 0.0412 |
| 27 | 0.0333 |
| 28 | 0.0011 |
| 29 | 0.0012 |

TABLE 3-continued

| Compound | EC$_{50}$ (μM) |
|---|---|
| 37 | 0.0009 |
| 40 | 0.0035 |
| 45 | 0.0018 |
| 47 | 0.0397 |
| 49 | 0.0042 |
| 52 | 0.0031 |
| 53 | 0.0020 |
| 54 | 0.0020 |
| 55 | 0.0011 |
| 56 | 0.0014 |
| 57 | 0.0026 |
| 59 | 0.0013 |
| 60 | 0.0037 |
| 61 | 0.0026 |
| 62 | 0.0023 |
| 63 | 0.0027 |
| 64 | 0.0033 |
| 65 | 0.0030 |
| 66 | 0.0055 |
| 67 | 0.0017 |
| 71 | 0.0019 |
| 72 | 0.0019 |
| 74 | 0.0070 |
| 76 | 0.0028 |
| 78 | 0.0021 |
| 80 | 0.0136 |
| 84 | 0.0029 |
| 85 | 0.0016 |
| 86 | 0.0019 |
| 87 | 0.0039 |
| 88 | 0.0028 |
| 89 | 0.0223 |
| 90 | 0.0023 |
| 91 | 0.0067 |
| 92 | 0.0010 |
| 93 | 0.0007 |
| 94 | 0.0013 |
| 95 | 0.0034 |
| 97 | 0.0013 |
| 99 | 0.0025 |
| 100 | 0.0444 |
| 101 | 0.0257 |
| 102 | 0.0093 |
| 103 | 0.0055 |
| 104 | 0.0077 |
| 105 | 0.0435 |
| 106 | 0.0034 |
| 107 | 0.0021 |
| 108 | 0.0024 |
| 109 | 0.0022 |
| 110 | 0.0024 |
| 111 | 0.0017 |
| 112 | 0.0023 |
| 113 | 0.0019 |
| 114 | 0.0022 |
| 116 | 0.0047 |
| 117 | 0.0056 |
| 118 | 0.0320 |
| 119 | 0.0103 |
| 120 | 0.0127 |
| 122 | 0.0041 |
| 123 | 0.0035 |
| 126 | 0.0038 |
| 127 | 0.0053 |
| 130 | 0.0032 |
| 131 | 4.9972 |
| 132 | 0.0032 |
| 133 | 0.0044 |
| 134 | 0.0016 |
| 135 | 0.0039 |
| 136 | 0.0038 |
| 137 | 0.0062 |
| 138 | 0.0553 |
| 139 | 0.0185 |
| 140 | 0.0042 |
| 141 | 0.3745 |
| 142 | 0.0016 |
| 143 | 0.0015 |
| 144 | 0.0012 |
| 145 | 0.0008 |
| 146 | 0.0374 |
| 147 | 0.0057 |
| 148 | 0.2215 |
| 149 | 0.0020 |
| 151 | 0.0043 |
| 168 | 0.0034 |
| 172 | 0.0015 |
| 182 | 0.0063 |
| 183 | 0.0203 |
| 184 | 0.0311 |
| 185 | 0.0023 |
| 186 | 0.0024 |
| 204 | 0.0021 |
| 219 | 0.0027 |
| 220 | 0.0063 |
| 221 | 0.0026 |
| 222 | 0.0014 |
| 223 | 0.0045 |
| 230 | 0.0019 |
| 232 | 0.0017 |
| 233 | 0.0015 |
| 236 | 0.0012 |
| 238 | 0.0027 |
| 240 | 0.0018 |
| 241 | 0.0025 |
| 242 | 0.0017 |
| 243 | 0.0024 |
| 245 | 0.0016 |
| 249 | 0.0018 |
| 250 | 0.0022 |
| 253 | 0.0014 |
| 256 | 0.0017 |
| 257 | 0.0184 |
| 258 | 0.0189 |
| 261 | 0.0016 |
| 265 | 0.0019 |
| 266 | 0.0013 |
| 268 | 0.0019 |
| 271 | 0.0021 |
| 273 | 0.0011 |
| 275 | 0.0006 |
| 276 | 0.0011 |
| 277 | 0.0008 |
| 278 | 0.0028 |
| 285 | 0.0012 |
| 286 | 0.0008 |
| 289 | 0.0033 |
| 290 | 0.0029 |
| 291 | 0.0116 |
| 292 | 0.0057 |
| 293 | 0.0145 |
| 294 | 0.0105 |
| 296 | 0.0053 |
| 301 | 0.0009 |
| 306 | 0.0023 |
| 309 | 0.0015 |
| 310 | 0.0017 |
| 313 | 0.0021 |
| 317 | 0.0011 |
| 318 | 0.0017 |
| 319 | 0.0014 |
| 325 | 0.0018 |
| 326 | 0.0026 |
| 328 | 0.0036 |
| 329 | 0.0046 |
| 330 | 0.0115 |
| 331 | 0.1220 |
| 332 | 0.3297 |
| 333 | 0.0435 |
| 334 | 0.0010 |
| 335 | 0.0015 |
| 336 | 0.0011 |
| 337 | 0.0017 |
| 338 | 0.0010 |
| 339 | 0.0395 |
| 340 | 0.0012 |

TABLE 3-continued

| Compound | EC$_{50}$ (µM) |
|---|---|
| 359 | 0.0037 |
| 373 | 0.0177 |
| 374 | 0.0038 |
| 375 | 0.0126 |
| 376 | 0.0067 |
| 377 | 0.0093 |
| 378 | 0.0028 |
| 379 | 0.0025 |
| 380 | 0.8647 |
| 381 | >10 (48.9%) |
| 382 | 0.0023 |
| 383 | 0.0021 |
| 384 | 0.0012 |
| 385 | 0.0009 |
| 386 | 0.0015 |
| 387 | 0.0030 |
| 388 | 0.0008 |
| 389 | 0.0053 |
| 390 | 0.0014 |
| 391 | 0.0007 |
| 392 | 0.0011 |
| 393 | 0.0012 |
| 406 | 0.0027 |
| 409 | 0.0025 |
| 412 | 0.0022 |
| 419 | 0.0019 |
| 420 | 0.0071 |
| 422 | 0.0026 |
| 423 | 0.0025 |
| 427 | 0.0137 |
| 428 | 0.0073 |
| 429 | 0.0064 |
| 430 | 0.0023 |
| 431 | 0.0019 |
| 432 | 0.0016 |
| 433 | 0.0068 |
| 434 | 0.0013 |
| 435 | 0.0010 |
| 436 | 0.0212 |
| 437 | 0.0013 |
| 438 | 0.0024 |
| 439 | 0.0024 |
| 440 | 0.0191 |
| 441 | 0.0011 |
| 442 | 0.0017 |
| 443 | 0.0019 |
| 444 | 0.0021 |
| 445 | 0.0023 |
| 454 | 0.0059 |
| 455 | 0.0024 |
| 456 | 0.0030 |
| 457 | 0.0037 |
| 458 | 0.0015 |
| 459 | 0.0014 |
| 461 | 0.0015 |
| 462 | 0.0017 |
| 463 | 0.0014 |
| 464 | 0.0058 |
| 465 | 0.0087 |

Example 6

Representative compounds were screened using the assay procedure for GSKβD kinase activity as described below.

Each compound is dissolved in DMSO as a 10 mM stock and used to prepare compound source plates. Serial dilution (1:3, 11-point dose-response curves from 10 µM to 0.0003 µM) and compound transfer was performed using the ECHO 550 (Labcyte, Sunnyvale, Calif.) into 1536-well black-walled round bottom plates (Corning).

The GSKβD kinase assay is run using the Ser/Thr 09 peptide Z-lyte assay kit according to manufacturer's instructions (Life Technologies—a Division of Thermo-Fisher). This is a non-radioactive assay using fluorescence resonance energy transfer (FRET) between coumarin and fluorescein to detect kinase activity which is represented as ratio of coumarin emission/fluorescein emission.

Briefly, recombinant GSKβD kinase, ATP and Ser/Thr peptide 09 are prepared in 1× Kinase buffer to final concentrations of 0.04 µg/mL, 46 µM, and 4 µM respectively. The mixture is allowed to incubate with the representative compounds for one hour at room temperature. All reactions were performed in duplicate. Unphosphorylated ("0% Control") and phosphorylated ("100% control") forms of Ser/Thr 18 serve as control reactions.

After incubation, diluted Development Buffer is added to the reaction and allowed to further incubate for one hour at room temperature. The plate is read at Ex 400 Em 455 to detect the coumarin signal and Ex 400 Em 520 to measure the signal (EnVision Multilabel Plate Reader, PerkinElmer).

The Emission ratio (Em) is calculated as a ratio of the coumarin (C) emission signal (at 445 nm)/Fluorescein (F) emission signal (at 520 nm). The percent phosphorylation is then calculated using the following formula: [1−((Em ratio× F100%)−C100%)/((C0%−C100%)+(Em ratio×(F100%−F0%)))].

Dose-response curves are generated and inhibitory concentration (IC$_{50}$) values are calculated using non-linear regression curve fit in the Dotmatics' Studies Software (Bishops Stortford, UK).

Table 4 shows the activity of representative compounds of Formula I as provided herein.

TABLE 4

| Compound | EC$_{50}$ (µM) |
|---|---|
| 1 | 3.346 |
| 2 | 3.689 |
| 3 | 3.726 |
| 4 | 2.066 |
| 5 | 3.250 |
| 6 | 2.931 |
| 7 | 0.330 |
| 8 | 0.668 |
| 9 | 3.403 |
| 10 | 1.842 |
| 11 | 3.895 |
| 12 | 4.032 |
| 13 | 4.265 |
| 14 | 0.479 |
| 15 | 9.838 |
| 16 | 1.258 |
| 17 | 1.532 |
| 18 | 3.756 |
| 19 | 6.027 |
| 20 | 9.838 |
| 21 | 9.838 |
| 22 | 9.838 |
| 23 | >10 |
| 24 | >10 |
| 25 | >10 |
| 26 | >10 |
| 27 | >10 |
| 28 | 0.537 |
| 29 | 0.818 |
| 37 | 3.519 |
| 40 | >10 |
| 45 | 1.884 |
| 47 | >10 |
| 49 | >10 |
| 52 | 4.322 |
| 53 | 0.859 |
| 54 | 2.421 |
| 55 | 1.435 |
| 56 | 3.967 |
| 57 | 2.037 |
| 59 | 3.856 |
| 60 | 0.439 |

TABLE 4-continued

| Compound | EC$_{50}$ (μM) |
|---|---|
| 61 | 2.225 |
| 62 | 2.825 |
| 63 | 2.701 |
| 64 | 5.842 |
| 65 | 1.085 |
| 66 | 2.712 |
| 67 | 3.649 |
| 71 | 0.728 |
| 72 | 5.046 |
| 74 | 4.124 |
| 76 | 0.937 |
| 78 | 1.291 |
| 80 | >10 |
| 84 | 1.523 |
| 85 | 0.506 |
| 86 | 3.051 |
| 87 | 3.566 |
| 88 | 8.925 |
| 89 | 7.389 |
| 90 | 3.862 |
| 91 | 9.164 |
| 92 | 5.321 |
| 93 | 6.272 |
| 94 | 4.553 |
| 95 | >10 |
| 97 | 6.640 |
| 99 | 1.566 |
| 100 | >10 |
| 101 | >10 |
| 102 | 9.067 |
| 103 | 0.040 |
| 104 | 0.012 |
| 105 | 0.009 |
| 106 | 0.002 |
| 107 | 0.010 |
| 108 | 0.001 |
| 109 | 0.469 |
| 110 | 1.795 |
| 111 | 2.150 |
| 112 | 3.832 |
| 113 | 1.713 |
| 114 | 2.137 |
| 116 | 1.138 |
| 117 | >10 |
| 118 | >10 |
| 119 | >10 |
| 120 | >10 |
| 122 | 4.616 |
| 123 | 0.492 |
| 126 | 2.097 |
| 127 | 2.891 |
| 130 | 4.464 |
| 131 | >10 (5.2%) |
| 132 | >10 |
| 133 | 3.207 |
| 134 | >10 |
| 135 | 7.398 |
| 136 | >10 |
| 137 | >10 |
| 138 | 0.666 |
| 139 | >10 |
| 140 | >10 |
| 141 | >10 |
| 142 | 6.388 |
| 143 | 3.270 |
| 144 | 1.359 |
| 145 | 3.694 |
| 146 | >10 |
| 147 | 7.824 |
| 148 | >10 |
| 149 | 2.941 |
| 151 | >10 |
| 168 | >10 |
| 172 | >10 |
| 182 | 1.882 |
| 183 | 0.704 |
| 184 | 1.959 |
| 185 | 1.445 |

TABLE 4-continued

| Compound | EC$_{50}$ (μM) |
|---|---|
| 186 | 1.859 |
| 204 | 0.763 |
| 219 | 0.986 |
| 220 | 4.438 |
| 221 | 0.343 |
| 222 | 0.780 |
| 223 | 1.914 |
| 230 | 0.886 |
| 232 | 0.112 |
| 233 | 0.100 |
| 236 | 0.299 |
| 238 | 0.750 |
| 240 | 0.212 |
| 241 | 0.514 |
| 242 | 0.361 |
| 243 | 0.809 |
| 245 | 0.740 |
| 249 | 1.090 |
| 250 | 0.568 |
| 253 | 0.295 |
| 256 | 0.378 |
| 257 | >10 |
| 258 | >10 |
| 261 | 1.884 |
| 265 | 3.429 |
| 266 | 2.498 |
| 268 | 3.128 |
| 271 | 4.550 |
| 273 | 2.901 |
| 275 | 4.177 |
| 276 | 1.853 |
| 277 | 1.520 |
| 278 | >10 |
| 285 | 0.256 |
| 286 | 0.938 |
| 289 | 6.000 |
| 290 | >10 |
| 291 | 2.176 |
| 292 | 1.876 |
| 293 | 3.571 |
| 294 | 6.573 |
| 296 | >10 |
| 301 | 8.288 |
| 306 | >10 |
| 309 | 2.693 |
| 310 | 0.584 |
| 313 | 7.538 |
| 317 | >10 |
| 318 | 2.822 |
| 319 | 7.099 |
| 325 | 5.953 |
| 326 | 6.980 |
| 328 | 1.410 |
| 329 | 0.811 |
| 330 | >10 |
| 331 | >10 |
| 332 | 5.472 |
| 333 | >10 |
| 334 | 0.593 |
| 335 | 0.685 |
| 336 | 1.477 |
| 337 | 3.832 |
| 338 | 2.073 |
| 339 | 8.182 |
| 340 | 2.603 |
| 359 | 1.833 |
| 373 | >10 |
| 374 | 5.461 |
| 375 | >10 |
| 376 | >10 |
| 377 | >10 |
| 378 | 3.696 |
| 379 | 3.192 |
| 380 | >10 |
| 381 | >10 (6.1%) |
| 382 | 0.367 |
| 383 | 0.829 |
| 384 | 0.212 |

TABLE 4-continued

| Compound | EC$_{50}$ (µM) |
|---|---|
| 385 | 0.256 |
| 386 | 0.608 |
| 387 | 0.101 |
| 388 | 0.085 |
| 389 | 0.827 |
| 390 | 0.955 |
| 391 | 0.595 |
| 392 | 1.957 |
| 393 | 0.460 |
| 406 | 0.142 |
| 409 | 0.242 |
| 412 | 0.368 |
| 419 | 1.164 |
| 420 | 0.333 |
| 422 | 1.201 |
| 423 | 0.351 |
| 427 | >10 |
| 428 | 1.412 |
| 429 | 1.658 |
| 430 | 0.610 |
| 431 | 0.563 |
| 432 | 4.216 |
| 433 | 7.370 |
| 434 | 1.860 |
| 435 | 2.368 |
| 436 | >10 |
| 437 | 3.472 |
| 438 | 1.646 |
| 439 | 0.453 |
| 440 | 4.544 |
| 441 | 4.314 |
| 442 | 7.115 |
| 443 | 5.029 |
| 444 | 4.103 |
| 445 | 0.003 |
| 454 | 1.350 |
| 455 | 2.892 |
| 456 | 2.226 |
| 457 | >10 |
| 458 | 0.010 |
| 459 | 3.845 |
| 461 | 3.198 |
| 462 | >10 (41.3%) |
| 463 | 0.261 |
| 464 | 9.708 |
| 465 | >10 (51.0%) |

Example 7

Representative compounds were screened using the assay procedure to assess the effect on cell viability as described below.

SW480 colon carcinoma cells were transduced with a lentiviral vector expressing luciferase with a human Sp5 promoter consisting of a sequence of eight TCF/LEF binding sites. SW480 cells stably expressing the Sp5-Luc reporter gene and a hygromycin resistance gene were selected by treatment with 150 µg/mL of hygromycin for 7 days. These stably transduced SW480 cells were expanded in cell culture and used for all further screening activities. Each compound was dissolved in DMSO as a 10 mM stock and used to prepare compound source plates. Serial dilution (1:3, 8-point dose-response curves from 10 µM to 0.0045 µM) and compound transfer was performed using the ECHO 550 (Labcyte, Sunnyvale, Calif.) into 384-well white solid bottom assay plates (Greiner Bio-One) with appropriate DMSO backfill for a final DMSO concentration of 0.10%.

For the Cell Viability Assays, the cells were plated at 2,000 cells/well in 384-well plates with a DMEM medium containing 1% fetal bovine serum, and 1% Penicillin-Streptomycin and incubated for four days hours at 37° C. and 5% CO$_2$. Eight replicates of DMSO-treated cells served as controls and cells treated with compound were performed in duplicate.

After incubation, 10 µL of CellTiter-Glo (Promega) was added to each well allowed to incubate for approximately 12 minutes. This reagent "results in cell lysis and generation of a luminescent signal proportional to the amount of ATP present. The amount of ATP is directly proportional to the number of cells present in culture, in agreement with previous reports. The CellTiter-Glo® Assay generates a "glow-type" luminescent signal, produced by the luciferase reaction (Promega.com)".

After incubation, the plates were read at Ex 560 nm Em 590 nm (Cytation 3, BioTek). Dose-response curves were generated and EC$_{50}$ concentration values were calculated using non-linear regression curve fit in the GraphPad Prism (San Diego, Calif.) or Dotmatics' Studies Software (Bishops Stortford, UK). For EC$_{50}$ of >10 µM, the percent inhibition at 10 µM is provided.

Table 5 shows the activity of representative compounds of Formula I as provided herein.

TABLE 5

| Compound | EC$_{50}$ (µM) |
|---|---|
| 1 | 0.165 |
| 2 | 0.091 |
| 3 | 0.105 |
| 4 | 0.390 |
| 5 | 0.038 |
| 6 | 0.049 |
| 7 | 0.089 |
| 8 | 0.087 |
| 9 | 0.037 |
| 10 | 0.101 |
| 11 | 0.222 |
| 12 | 0.632 |
| 13 | 0.159 |
| 14 | 0.269 |
| 15 | >10 |
| 16 | 0.048 |
| 17 | 0.075 |
| 18 | 0.137 |
| 19 | 0.080 |
| 20 | 0.478 |
| 21 | 0.677 |
| 22 | 0.745 |
| 23 | 0.733 |
| 24 | 9.391 |
| 25 | >10 |
| 26 | 1.700 |
| 27 | >10 |
| 28 | 0.547 |
| 29 | 0.368 |
| 37 | 0.060 |
| 40 | 0.826 |
| 45 | 0.187 |
| 47 | 2.900 |
| 49 | 0.430 |
| 52 | 1.454 |
| 53 | 0.072 |
| 54 | 0.060 |
| 55 | 0.076 |
| 56 | 0.094 |
| 57 | 0.476 |
| 59 | 0.213 |
| 60 | 0.886 |
| 61 | 0.406 |
| 62 | 0.455 |
| 63 | 0.225 |
| 64 | 0.413 |
| 65 | 0.427 |
| 66 | 0.111 |
| 67 | 0.139 |
| 71 | 0.044 |

TABLE 5-continued

| Compound | EC$_{50}$ (μM) |
|---|---|
| 72 | 0.107 |
| 74 | 0.266 |
| 76 | 0.564 |
| 78 | 3.556 |
| 80 | 0.869 |
| 84 | 0.059 |
| 85 | 0.234 |
| 86 | 0.402 |
| 87 | 5.293 |
| 88 | 0.228 |
| 89 | >10 (41.5%) |
| 90 | 0.165 |
| 91 | 0.415 |
| 92 | 0.323 |
| 93 | 0.126 |
| 94 | 0.470 |
| 95 | 7.608 |
| 97 | 0.182 |
| 99 | 0.089 |
| 100 | >10 (34.8%) |
| 101 | 3.251 |
| 102 | 4.969 |
| 103 | 4.344 |
| 104 | 0.037 |
| 105 | 0.694 |
| 106 | 0.367 |
| 107 | 0.890 |
| 108 | 0.567 |
| 109 | 0.834 |
| 110 | 0.675 |
| 111 | 0.447 |
| 112 | 0.318 |
| 113 | 0.369 |
| 114 | 0.410 |
| 116 | 0.210 |
| 117 | 0.544 |
| 118 | >10 (10.6%) |
| 119 | 0.649 |
| 120 | 0.058 |
| 122 | 0.301 |
| 123 | 0.400 |
| 126 | 0.105 |
| 127 | 0.149 |
| 130 | 0.360 |
| 131 | 0.406 |
| 132 | 0.359 |
| 133 | 0.258 |
| 134 | 0.242 |
| 135 | 2.292 |
| 136 | 2.127 |
| 137 | 1.542 |
| 138 | 4.142 |
| 139 | 4.949 |
| 140 | 0.308 |
| 141 | >10 (12.2%) |
| 142 | 0.099 |
| 143 | 0.114 |
| 144 | 0.100 |
| 145 | 0.080 |
| 146 | 3.190 |
| 147 | 0.318 |
| 148 | 2.174 |
| 149 | 0.073 |
| 151 | 0.343 |
| 168 | 0.121 |
| 172 | 0.486 |
| 182 | 0.464 |
| 183 | 0.586 |
| 184 | 0.325 |
| 185 | 0.236 |
| 186 | 0.115 |
| 204 | 0.058 |
| 219 | 2.255 |
| 220 | 0.645 |
| 221 | 1.413 |
| 222 | 0.371 |
| 223 | 4.893 |
| 230 | 0.084 |
| 232 | 0.418 |
| 233 | 0.310 |
| 236 | 0.193 |
| 238 | 0.065 |
| 240 | 0.066 |
| 241 | 0.446 |
| 242 | 2.437 |
| 243 | 0.214 |
| 245 | 0.123 |
| 249 | 2.519 |
| 250 | 0.159 |
| 253 | 0.238 |
| 256 | 0.277 |
| 257 | 3.581 |
| 258 | 2.221 |
| 261 | 0.286 |
| 265 | 0.174 |
| 266 | 0.174 |
| 268 | 0.168 |
| 271 | 0.460 |
| 273 | 0.106 |
| 275 | 0.012 |
| 276 | 0.503 |
| 277 | 0.569 |
| 278 | 1.583 |
| 285 | 0.690 |
| 286 | 0.297 |
| 289 | 0.405 |
| 290 | 0.234 |
| 291 | 2.771 |
| 292 | 0.491 |
| 293 | 3.024 |
| 294 | 0.469 |
| 296 | >10 (17.3%) |
| 301 | 0.682 |
| 306 | 2.492 |
| 309 | 0.310 |
| 310 | 4.996 |
| 313 | 2.796 |
| 317 | 1.730 |
| 318 | 0.799 |
| 319 | 5.486 |
| 325 | 9.738 |
| 326 | 2.651 |
| 328 | 0.334 |
| 329 | 0.512 |
| 330 | >10 (13.3%) |
| 331 | 6.588 |
| 332 | 5.109 |
| 333 | >10 (45.9%) |
| 334 | 0.275 |
| 335 | 0.266 |
| 336 | 0.246 |
| 337 | 0.400 |
| 338 | 0.328 |
| 339 | 4.763 |
| 340 | 1.050 |
| 359 | 0.045 |
| 373 | 6.837 |
| 374 | 0.383 |
| 375 | >10 (23.5%) |
| 376 | 0.387 |
| 377 | 8.204 |
| 378 | 0.852 |
| 379 | 0.464 |
| 380 | >10 (19.9%) |
| 381 | 9.050 |
| 382 | 7.854 |
| 383 | 0.276 |
| 384 | 0.426 |
| 385 | 4.465 |
| 386 | 0.222 |
| 387 | >10 (32.4%) |
| 388 | 0.334 |
| 389 | 0.595 |
| 390 | 0.388 |
| 391 | 0.132 |
| 392 | 0.260 |

TABLE 5-continued

| Compound | EC$_{50}$ (μM) |
|---|---|
| 393 | 0.475 |
| 406 | 0.336 |
| 409 | 0.124 |
| 412 | 0.218 |
| 419 | 0.273 |
| 420 | 0.542 |
| 422 | 3.151 |
| 423 | 0.113 |
| 427 | 8.055 |
| 428 | 0.403 |
| 429 | 0.464 |
| 430 | 0.058 |
| 431 | 0.089 |
| 432 | 0.273 |
| 433 | 1.091 |
| 434 | 0.245 |
| 435 | 0.429 |
| 436 | 3.641 |
| 437 | 0.782 |
| 438 | 3.528 |
| 439 | 0.108 |
| 440 | 4.307 |
| 441 | 0.535 |
| 442 | 0.283 |
| 443 | 1.052 |
| 444 | 0.272 |
| 445 | 0.470 |
| 454 | 0.578 |
| 455 | 0.112 |
| 456 | 0.765 |
| 457 | 0.449 |
| 458 | 0.208 |
| 462 | 0.443 |
| 463 | 0.381 |
| 464 | 0.481 |
| 465 | 0.413 |

Example 6

Representative compounds were screened using the assay procedure for tau phosphorylation activity described below.

SH-SY5Y cells (human neuroblastoma) were cultured in DMEM/F-12 medium supplemented with 15% FBS, Non-essential Amino Acid and Penicillin/Streptomycin. Two days before treatment, cells were seeded onto 96 well plates at 5×10$^4$ cells/well.

The above synthesized compounds were screened using the cell assay procedure to assess decrease Tau phosphorylation at Ser396 (pSer396) described below.

DMSO-resuspended compounds were dispensed to 8 wells as a serial titration from 10 μM to 4.6 nM final in medium and cells were exposed overnight (16-18 h) in a humidified incubator at 36.6c before harvest. Wells were visually checked for cell death or change in morphology and supernatants were tested for cytotoxicity by measurement of lactate dehydrogenase release (LDH, CytoToxOne kit, Promega) if necessary. As controls, commercially available DYRKIA inhibitors, Harmine and Indy which were shown to have good DYRKIA inhibition in the kinase assay with no CDK1 activity (EC$_{50}$ 18 and 53 nM respectively, 6 μM for CDK1) but weak EC$_{50}$ in the Tau assay >10 μM.

Cells were lysed with RIPA buffer complemented with phosphatase and protease inhibitors then lysates were spun down at 12,000 g for 10 min to remove any cellular debris. Lysates are then either directly tested for pSer396 by ELISA (Life Technology, Kit KHB7031) or loaded on NuPage Bis-Tris gels for western blot analysis. Colorimetric detection of ELISA signal is performed by Cytation3 plate reader (Biotek) and the chemiluminescence signal for HRP-linked antibodies used in western blotting is detected using a Carestream Image Station. The same pSer396 antibody is used for detection of pTau in both assays.

Blot densitometry for pSer396 and β-actin were analyzed using ImageJ (NIH) and pSer396 Tau ELISA signal was used to plot, draw the curve fitting, and determine each compounds EC$_{50}$ in Prism (GraphPad).

Table 6 shows the activity of representative compounds as provided herein.

TABLE 6

| Compound | pSer396 Tau EC$_{50}$ (μM) |
|---|---|
| 5 | 1.390 |
| 6 | >10 |
| 7 | 1.100 |
| 14 | 3.900 |
| 60 | 3.500 |
| 109 | >10 |
| 221 | >10 |
| 232 | 0.095 |
| 233 | 0.174 |
| 236 | >10 |
| 240 | >10 |
| 242 | >10 |
| 253 | 1.800 |
| 256 | 1.200 |
| 285 | 7.600 |
| 382 | >10 |
| 384 | 0.583 |
| 385 | 0.337 |
| 387 | >10 |
| 388 | 1.100 |
| 393 | >10 |
| 406 | >10 |
| 409 | >10 |
| 412 | >10 |
| 420 | >10 |
| 423 | 5.600 |

Example 7

Representative compounds were screened using primary human fibroblasts (derived from IPF patients) treated with TGF-β1 to determine their ability to inhibit the fibrotic process.

Human Fibroblast Cell Culture: Primary human fibroblasts derived from IPF patients (LL29 cells) [[1]Xiaoqiu Liu, et. al., "Fibrotic Lung Fibroblasts Show Blunted Inhibition by cAMP Due to Deficient cAMP Response Element-Binding Protein Phosphorylation", *Journal of Pharmacology and Experimental Therapeutics* (2005), 315(2), 678-687; [2]Watts, K. L., et. al., "RhoA signaling modulates cyclin D1 expression in human lung fibroblasts; implications for idiopathic pulmonary fibrosis", *Respiratory Research* (2006), 7(1), 88] were obtained from American Type Culture Collection (ATCC) and expanded in F12 medium supplemented with 15% Fetal Bovine Serum and 1% Penicillin/Streptomycin.

Compound Screening: Each compound was dissolved in DMSO as a 10 mM stock and used to prepare compound source plates. Serial dilution (1:2, 11-point dose-response curves from 10 μM to 0.94 nM) and compound transfer was performed using the ECHO 550 (Labcyte, Sunnyvale, Calif.) into 384-well clear bottom assay plates (Greiner Bio-One) with appropriate DMSO backfill for a final DMSO concentration of 0.1%. LL29 cells were plated at 1,500 cells/well in 70 μL/well F12 medium supplemented with 1% Fetal Bovine Serum. TGF-β1 (Peprotech; 20 ng/mL) was added to the plates to induce fibrosis (ref 1 and 2 above). Wells treated with TGF-β1 and containing DMSO were used as positive control, and cells with only DMSO were negative control. Cells were incubated at 37° C. and 5% $CO_2$ for 4 days. Following incubation for 4 days, SYTOX green nucleic acid stain (Life Technologies [Thermo Fisher Scientific]) was added to the wells at a final concentration of 1 μM and incubated at room temperature for 30 min. Cells were then fixed using 4% formaldehyde (Electron Microscopy Sciences), washed 3 times with PBS followed by blocking and permeabilization using 3% Bovine Serum Albumin (BSA; Sigma) and 0.3% Triton X-100 (Sigma) in PBS. Cells were then stained with antibody specific to α-smooth muscle actin (αSMA; Abcam) (ref. 1 and 2 above) in 3% Bovine Serum Albumin (BSA; Sigma) and 0.3% Triton X-100 (Sigma) in PBS, and incubated overnight at 4° C. Cells were then washed 3 times with PBS, followed by incubation with Alexa Flor-647 conjugated secondary antibody (Life Technologies [Thermo Fisher Scientific]) and DAPI in 3% Bovine Serum Albumin (BSA; Sigma) and 0.3% Triton X-100 (Sigma) in PBS at room temperature for 1 hour. Cells were then washed 3 times with PBS and plates were sealed for imaging. αSMA staining was imaged by excitation at 630 nm and emission at 665 nm and quantified using the Compartmental Analysis program on the CellInsight CX5 (Thermo Scientific). Dead or apoptotic cells were excluded from analysis based on positive SYTOX green staining. % of total cells positive for αSMA were counted in each well and normalized to the average of 11 wells treated with TGF-β 1 on the same plate using Dotmatics' Studies Software. The normalized averages (fold change over untreated) of 3 replicate wells for each compound concentration were used to create dose-responses curves and $EC_{50}$ values were calculated using non-linear regression curve fit in the Dotmatics' Studies Software. For $EC_{50}$ of >10 μM, the percent inhibition at 10 μM is provided.

Table 7 shows the activity of representative compounds of Formula I as provided herein.

TABLE 7

| Compound | $EC_{50}$ (μM) |
|---|---|
| 1 | 0.079 |
| 2 | 1.162 |
| 3 | 0.158 |
| 4 | 0.239 |
| 5 | 0.179 |
| 6 | 0.195 |
| 7 | 2.563 |
| 8 | 0.196 |
| 9 | 0.083 |
| 10 | 0.085 |
| 11 | 0.071 |
| 12 | 1.058 |
| 13 | 0.194 |
| 14 | 0.061 |
| 15 | >10 (36.3%) |
| 16 | 1.000 |
| 17 | 0.937 |
| 18 | 0.152 |
| 19 | 0.083 |
| 20 | 3.881 |
| 21 | 2.370 |
| 22 | 3.826 |
| 23 | 0.769 |
| 24 | >10 (24.3%) |
| 25 | 1.656 |
| 26 | 1.200 |
| 27 | 1.677 |
| 28 | 0.207 |
| 29 | 0.302 |

TABLE 7-continued

| Compound | $EC_{50}$ (μM) |
|---|---|
| 37 | 0.142 |
| 40 | 2.006 |
| 45 | 0.992 |
| 47 | 1.099 |
| 49 | 1.249 |
| 52 | 3.894 |
| 53 | 0.553 |
| 54 | 0.120 |
| 55 | 0.081 |
| 56 | >10 (30.2%) |
| 57 | 0.133 |
| 59 | 0.013 |
| 60 | >10 (24.6%) |
| 61 | 0.694 |
| 62 | 0.167 |
| 63 | 0.263 |
| 64 | >10 (40.9%) |
| 65 | 1.991 |
| 66 | 0.603 |
| 67 | 0.030 |
| 71 | 1.915 |
| 72 | 0.135 |
| 74 | 6.836 |
| 78 | >10 (0.5%) |
| 84 | 0.094 |
| 85 | 1.244 |
| 86 | 0.433 |
| 87 | >10 (48.7%) |
| 91 | 0.204 |
| 92 | 0.708 |
| 93 | 0.270 |
| 94 | 0.678 |
| 95 | >10 (3.0%) |
| 97 | 0.117 |
| 99 | 0.079 |
| 100 | 0.829 |
| 101 | 5.193 |
| 102 | 0.820 |
| 109 | 0.601 |
| 110 | 0.187 |
| 111 | 0.167 |
| 112 | 0.181 |
| 113 | 0.217 |
| 114 | 0.186 |
| 116 | 0.298 |
| 122 | 1.296 |
| 123 | 0.262 |
| 127 | 0.207 |
| 130 | 0.273 |
| 131 | 0.154 |
| 132 | >10 (37.6%) |
| 133 | 0.151 |
| 134 | 0.244 |
| 135 | 0.653 |
| 136 | 0.312 |
| 137 | 0.333 |
| 138 | 1.525 |
| 139 | 2.120 |
| 140 | 0.317 |
| 143 | 0.094 |
| 145 | 0.092 |
| 146 | 1.847 |
| 147 | 0.128 |
| 148 | 1.251 |
| 149 | 0.149 |
| 151 | 0.859 |
| 168 | 0.466 |
| 172 | 0.463 |
| 182 | 0.509 |
| 183 | 0.644 |
| 184 | 0.194 |
| 185 | 0.300 |
| 186 | 0.585 |
| 204 | 0.143 |
| 219 | >10 (25.1%) |
| 220 | 0.276 |
| 221 | 0.978 |
| 222 | 0.190 |

TABLE 7-continued

| Compound | EC$_{50}$ (μM) |
|---|---|
| 223 | >10 (13.5%) |
| 230 | 0.181 |
| 232 | 0.612 |
| 233 | 0.144 |
| 236 | >10 (39.7%) |
| 238 | 0.145 |
| 240 | 0.120 |
| 241 | 0.499 |
| 242 | 0.197 |
| 245 | 2.152 |
| 249 | 3.022 |
| 250 | 0.127 |
| 253 | 0.360 |
| 256 | 0.752 |
| 257 | 1.202 |
| 258 | 0.329 |
| 261 | 1.246 |
| 265 | 0.293 |
| 266 | 0.353 |
| 268 | 0.324 |
| 271 | 0.133 |
| 273 | 0.253 |
| 275 | 0.292 |
| 276 | 0.147 |
| 277 | 0.869 |
| 278 | 5.494 |
| 285 | 1.391 |
| 286 | 0.665 |
| 289 | 0.329 |
| 290 | 0.562 |
| 291 | 6.396 |
| 292 | 1.264 |
| 293 | 5.338 |
| 294 | 0.544 |
| 296 | 0.198 |
| 301 | 0.501 |
| 306 | 0.820 |
| 309 | 0.392 |
| 310 | 0.920 |
| 313 | 0.306 |
| 317 | 1.139 |
| 318 | 1.480 |
| 319 | 4.728 |
| 325 | 0.863 |
| 326 | 0.611 |
| 328 | 0.159 |
| 329 | 0.339 |
| 330 | >10 (6.0%) |
| 331 | 2.196 |
| 332 | 2.230 |
| 333 | >10 (15.8%) |
| 334 | 0.090 |
| 335 | 0.196 |
| 336 | 0.254 |
| 337 | 1.589 |
| 338 | 0.335 |
| 339 | 3.846 |
| 340 | 0.299 |
| 359 | 0.087 |
| 373 | 1.270 |
| 374 | 1.382 |
| 375 | 2.654 |
| 376 | 1.043 |
| 377 | 2.701 |
| 378 | 1.292 |
| 379 | 0.379 |
| 380 | 4.899 |
| 381 | >10 (38.4%) |
| 382 | 0.624 |
| 383 | 0.438 |
| 384 | 0.406 |
| 385 | 1.948 |
| 386 | 0.437 |
| 387 | >10 (37.7%) |
| 388 | 0.807 |
| 389 | 4.200 |
| 390 | 0.538 |
| 391 | 2.764 |
| 392 | 0.297 |
| 393 | 0.350 |
| 406 | 1.280 |
| 409 | 0.281 |
| 412 | 0.245 |
| 419 | 1.005 |
| 420 | 2.467 |
| 422 | 0.202 |
| 423 | 0.307 |
| 427 | 4.578 |
| 428 | >10 (12.5%) |
| 429 | 0.411 |
| 430 | 0.139 |

Example 8

Representative compounds were screened using the following assay procedure to determine their ability to inhibit IL-6 and therefore demonstrate their anti-inflammatory properties.

Human Peripheral Blood Mononuclear Cells: Fresh Normal PB MNC (Catalog #PB001, AllCells, Alameda, Calif.) were shipped overnight at 4° C. and resuspended in Roswell Park Memorial Institute (RPMI) 1640 Medium, with GlutaMAX Supplement (Catalog #61870127, ThermoFisher Scientific, Waltham, Mass.) supplemented with 1% Penicillin-Streptomycin (Catalog #15140163, ThermoFisher Scientific, Waltham, Mass.) and 1% fetal bovine serum (FBS) (Catalog #16140089, ThermoFisher Scientific, Waltham, Mass.) assay media.

Compound Screening: Fresh normal human peripheral blood mononuclear cells (huPBMCs) were resuspended in 1% FBS-RPMI assay media with 1% Penicillin-Streptomycin 1% to a cell concentration of 1×10e6 cells/mL. Each compound was dissolved in DMSO (Catalog #D8418-100 ml, Sigma-Aldrich, St. Louis, Mo.) as a 10 mM stock and used to prepare compound source plates. Serial dilution (1:3, 10-point dose-response curves starting from 10 μM) and compound transfer was performed using the ECHO 550 (Labcyte, Sunnyvale, Calif.) into 384-well white Proxiplate-Plus assay plates (Catalog #6008289, PerkinElmer, Shelton, Conn.) with appropriate DMSO backfill for a final DMSO concentration of 0.25%. huPBMCs were plated at 5000 cells/well in the 384-well Proxiplate-Plus assay plates and incubated at 37° C.-5% CO$_2$ for 2 hours. 50 ng/mL of Lipopolysaccharides from *Escherichia coli* 0111:B4 (Catalog #L5293-2ML, Sigma-Aldrich, St. Louis, Mo.) was added after 2 hours and cells were incubated for another 22 hours at 37° C.-5% CO$_2$. After 22 hour incubation, a mixture of anti-IL6 XL665 and anti-IL-6 Cryptate diluted in reconstitution buffer (Catalog #62IL6PEC, Cisbio Inc., Bedford, Mass.) was added to each well. Following incubation for 3 hours at room temperature, Homogeneous Time-Resolved Fluorescence (HTRF) was measured using the Envision (Perkin Elmer, Shelton, Conn.) at 665 nm and 620 nM. The ratio of fluorescence at 665 nm to 620 nm was used as a readout for IL-6 quantification. All samples were processed in duplicate. Readings were normalized to DMSO treated cells and normalized activities were utilized for EC$_{50}$ calculations. EC$_{50}$ was determined using software generated by Dotmatics Limited (Windhill Bishops Stortford Herts, UK) using the Levenberg-Marquardt 4 parameter fitting procedure with finite different gradients. For EC$_{50}$ of >10 μM, the percent inhibition at 10 μM is provided.

Table 8 shows the activity of representative compounds of Formula I as provided herein.

TABLE 8

| Compound | $EC_{50}$ (µM) |
|---|---|
| 1 | 0.389 |
| 2 | 0.270 |
| 3 | 0.287 |
| 4 | 1.714 |
| 5 | 0.143 |
| 6 | 0.173 |
| 7 | 0.307 |
| 8 | 1.541 |
| 9 | 0.166 |
| 10 | 0.428 |
| 11 | 0.215 |
| 12 | 2.621 |
| 13 | 0.489 |
| 14 | 0.584 |
| 15 | >10 (2.8%) |
| 16 | 0.805 |
| 17 | 1.028 |
| 18 | 0.376 |
| 19 | 0.194 |
| 20 | 1.178 |
| 21 | 1.323 |
| 22 | 1.209 |
| 23 | 2.474 |
| 24 | >10 (5.5%) |
| 25 | >10 (41.8%) |
| 26 | 4.477 |
| 27 | 4.510 |
| 28 | 0.834 |
| 29 | 0.669 |
| 37 | 0.379 |
| 40 | 3.648 |
| 45 | 1.499 |
| 47 | 1.301 |
| 49 | 0.614 |
| 52 | >10 (31.2%) |
| 53 | 1.156 |
| 54 | 0.208 |
| 55 | 0.308 |
| 56 | 0.172 |
| 57 | 0.364 |
| 59 | 0.339 |
| 60 | >10 (9.6%) |
| 61 | 2.625 |
| 62 | 0.725 |
| 63 | 0.455 |
| 64 | 1.329 |
| 65 | 2.815 |
| 66 | 0.259 |
| 67 | 0.293 |
| 71 | 0.477 |
| 72 | 0.196 |
| 74 | 0.485 |
| 76 | 3.190 |
| 78 | >10 (6.0%) |
| 80 | >10 (31.3%) |
| 84 | 0.187 |
| 85 | 1.049 |
| 86 | >10 (36.2%) |
| 87 | >10 (13.4%) |
| 88 | 1.562 |
| 89 | >10 (4.0%) |
| 90 | 1.081 |
| 91 | 1.858 |
| 92 | 0.671 |
| 93 | 1.811 |
| 94 | 2.007 |
| 95 | 1.653 |
| 97 | 0.823 |
| 99 | 0.791 |
| 100 | >10 (1.3%) |
| 101 | >10 (18.2%) |
| 102 | >10 (12.2%) |
| 103 | 1.081 |
| 104 | 1.125 |

TABLE 8-continued

| Compound | $EC_{50}$ (µM) |
|---|---|
| 105 | 0.362 |
| 106 | 0.369 |
| 107 | 0.426 |
| 108 | 0.361 |
| 109 | 1.699 |
| 110 | 0.942 |
| 111 | 1.048 |
| 112 | 4.463 |
| 113 | 0.791 |
| 114 | 1.386 |
| 116 | 2.346 |
| 117 | 3.252 |
| 118 | >10 (14.3%) |
| 119 | >10 (17.4%) |
| 120 | 1.383 |
| 122 | >10 (41.7%) |
| 123 | 1.187 |
| 126 | >10 (6.0%) |
| 127 | >10 (26.1%) |
| 130 | >10 (18.3%) |
| 131 | >10 (16.4%) |
| 132 | >10 (8.3%) |
| 133 | >10 (35.2%) |
| 134 | >10 (46.7%) |
| 135 | 7.724 |
| 136 | 2.355 |
| 137 | 3.928 |
| 138 | >10 (4.5%) |
| 139 | >10 (1.2%) |
| 140 | 3.093 |
| 141 | >10 (4.6%) |
| 142 | 0.666 |
| 143 | 0.232 |
| 144 | 0.375 |
| 145 | 0.293 |
| 146 | >10 (22.4%) |
| 147 | 0.650 |
| 148 | >10 (5.2%) |
| 149 | 0.307 |
| 151 | 1.042 |
| 168 | 1.161 |
| 172 | 0.890 |
| 182 | 0.613 |
| 183 | 0.733 |
| 184 | 4.005 |
| 185 | 0.865 |
| 186 | 0.216 |
| 204 | 2.637 |
| 219 | 7.679 |
| 220 | 3.292 |
| 221 | 3.773 |
| 222 | 1.486 |
| 223 | >10 (12.7%) |
| 230 | 0.216 |
| 232 | 7.768 |
| 233 | 0.566 |
| 236 | 2.136 |
| 238 | 0.325 |
| 240 | 0.237 |
| 241 | 1.118 |
| 242 | 0.349 |
| 243 | 2.657 |
| 245 | 1.211 |
| 249 | 3.976 |
| 250 | 1.503 |
| 253 | 1.274 |
| 256 | 0.744 |
| 257 | >10 (3.9%) |
| 258 | >10 (12.9%) |
| 261 | 2.599 |
| 265 | 0.936 |
| 266 | 0.371 |
| 268 | 2.838 |
| 271 | 1.610 |
| 273 | 0.829 |
| 275 | 0.292 |
| 276 | 3.078 |
| 277 | 0.819 |

TABLE 8-continued

| Compound | EC$_{50}$ (μM) |
|---|---|
| 278 | 3.352 |
| 285 | 3.009 |
| 286 | 1.123 |
| 289 | 0.828 |
| 290 | 1.410 |
| 291 | >10 (47.1%) |
| 292 | 9.705 |
| 293 | >10 (32.2%) |
| 294 | >10 (48.9%) |
| 296 | >10 (4.4%) |
| 301 | >10 (33.0%) |
| 306 | 3.107 |
| 309 | 5.244 |
| 310 | >10 (17.3%) |
| 313 | 8.611 |
| 317 | >10 (11.4%) |
| 318 | 5.272 |
| 319 | >10 (3.7%) |
| 325 | >10 (9.7%) |
| 326 | 8.423 |
| 328 | 9.285 |
| 329 | 3.206 |
| 330 | >10 (6.8%) |
| 331 | 5.799 |
| 332 | 7.290 |
| 333 | >10 (18.2%) |
| 334 | 3.891 |
| 335 | 3.535 |
| 336 | 1.579 |
| 337 | >10 (4.0%) |
| 338 | 3.821 |
| 339 | >10 (6.3%) |
| 340 | 2.114 |
| 359 | 3.396 |
| 373 | >10 (8.0%) |
| 374 | >10 (12.1%) |
| 375 | >10 (4.3%) |
| 376 | >10 (11.9%) |
| 377 | >10 (4.8%) |
| 378 | >10 (27.0%) |
| 379 | 1.594 |
| 380 | >10 (3.1%) |
| 381 | >10 (26.4%) |
| 382 | >10 (11.8%) |
| 383 | 1.048 |
| 384 | 1.060 |
| 385 | >10 (23.4%) |
| 386 | 5.074 |
| 387 | >10 (6.1%) |
| 388 | 1.140 |
| 389 | >10 (27.6%) |
| 390 | 7.186 |
| 391 | 0.867 |
| 392 | 8.722 |
| 393 | 1.119 |
| 406 | >10 (15.1%) |
| 409 | >10 (32.5%) |
| 412 | 1.180 |
| 419 | >10 (43.6%) |
| 420 | >10 (11.7%) |
| 422 | 0.452 |
| 423 | 4.204 |
| 427 | >10 (15.6%) |
| 428 | >10 (36.4%) |
| 429 | 1.806 |
| 430 | 0.388 |
| 431 | 0.499 |
| 432 | 1.157 |
| 433 | >10 (12.5%) |
| 434 | 3.259 |
| 435 | >10 (7.2%) |
| 436 | >10 (11.3%) |
| 437 | 2.718 |
| 438 | >10 (30.9%) |
| 439 | 0.747 |
| 440 | >10 (4.7%) |
| 441 | 0.819 |
| 442 | 1.286 |

TABLE 8-continued

| Compound | EC$_{50}$ (μM) |
|---|---|
| 443 | >10 (47.2%) |
| 444 | 0.921 |
| 445 | 0.992 |
| 454 | 1.217 |
| 455 | 0.749 |
| 456 | 2.203 |
| 457 | 1.852 |
| 458 | 0.170 |

What is claimed is:

1. A method of treating a disorder or disease in a patient, wherein the disorder or disease is selected from the group consisting of: a bone or cartilage disease, osteoarthritis, and degenerative disc disease, the method comprising administering to the patient a therapeutically effective amount of a compound of Formula I, or a pharmaceutically acceptable salt thereof:

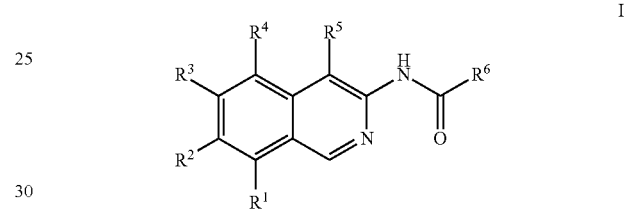

wherein:
$R^1$, $R^2$, $R^4$, and $R^5$ are independently selected from the group consisting of H, halide, amino, unsubstituted —($C_{1-3}$ haloalkyl), and unsubstituted —($C_{1-3}$ alkyl);
$R^3$ is selected from the group consisting of:

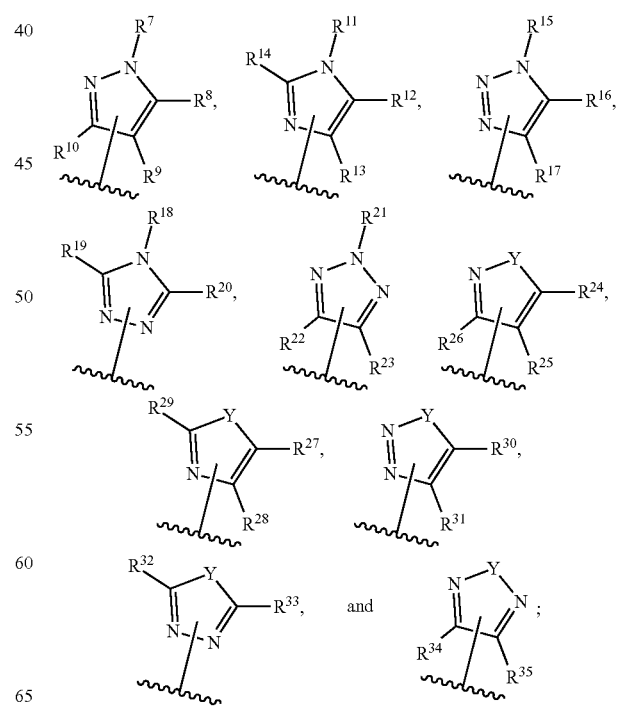

wherein each of $R^7$-$R^{35}$ is, independently, a substituent as defined anywhere herein or a single bond connecting $R^3$ to the isoquinoline ring; wherein only one of $R^7$-$R^{10}$ (when present) is a bond, only one of $R^{11}$-$R^{14}$ (when present) is a bond, only one of $R^{15}$-$R^{17}$ (when present) is a bond, only one of $R^{18}$-$R^{20}$ (when present) is a bond, only one of $R^{21}$-$R^{23}$ (when present) is a bond, only one of $R^{24}$-$R^{26}$ (when present) is a bond, only one of $R^{27}$-$R^{29}$ (when present) is a bond, only one of $R^{30}$-$R^{31}$ (when present) is a bond, only one of $R^{32}$-$R^{33}$ (when present) is a bond, and only one of $R^{34}$-$R^{35}$ (when present) is a bond; wherein any one of the nitrogen atoms attached to $R^7$, $R^{11}$, $R^{15}$, $R^{18}$, or $R^{21}$ can serve as the point of attachment of $R^3$ to the isoquinoline ring; wherein any one of the carbon atoms attached to $R^8$, $R^9$, $R^{10}$, $R^{12}$, $R^{13}$, $R^{14}$, $R^{16}$, $R^{17}$, $R^{19}$, $R^{20}$, $R^{22}$, $R^{23}$, $R^{24}$, $R^{25}$, $R^{26}$, $R^{27}$, $R^{28}$, $R^{29}$, $R^{30}$, $R^{31}$, $R^{32}$, $R^{33}$, $R^{34}$, or $R^{35}$ can serve as the point of attachment of $R^3$ to the isoquinoline ring; as that:

when the nitrogen atom to which $R^7$ is attached serves as the point of attachment of $R^3$ to the isoquinoline ring, then $R^7$ is a single bond connecting $R^3$ to the isoquinoline ring;

when the carbon atom to which $R^8$ is attached serves as the point of attachment of $R^3$ to the isoquinoline ring, then $R^8$ is a single bond connecting $R^3$ to the isoquinoline ring;

when the carbon atom to which $R^9$ is attached serves as the point of attachment of $R^3$ to the isoquinoline ring, then $R^9$ is a single bond connecting $R^3$ to the isoquinoline ring;

when the carbon atom to which $R^{10}$ is attached serves as the point of attachment of $R^3$ to the isoquinoline ring, then $R^{10}$ is a single bond connecting $R^3$ to the isoquinoline ring;

when the nitrogen atom to which $R^{11}$ is attached serves as the point of attachment of $R^3$ to the isoquinoline ring, then $R^{11}$ is a single bond connecting $R^3$ to the isoquinoline ring;

when the carbon atom to which $R^{12}$ is attached serves as the point of attachment of $R^3$ to the isoquinoline ring, then $R^{12}$ is a single bond connecting $R^3$ to the isoquinoline ring;

when the carbon atom to which $R^{13}$ is attached serves as the point of attachment of $R^3$ to the isoquinoline ring, then $R^{13}$ is a single bond connecting $R^3$ to the isoquinoline ring;

when the carbon atom to which $R^{14}$ is attached serves as the point of attachment of $R^3$ to the isoquinoline ring, then $R^{14}$ is a single bond connecting $R^3$ to the isoquinoline ring;

when the nitrogen atom to which $R^{15}$ is attached serves as the point of attachment of $R^3$ to the isoquinoline ring, then $R^{15}$ is a single bond connecting $R^3$ to the isoquinoline ring;

when the carbon atom to which $R^{16}$ is attached serves as the point of attachment of $R^3$ to the isoquinoline ring, then $R^{16}$ is a single bond connecting $R^3$ to the isoquinoline ring;

when the carbon atom to which $R^{17}$ is attached serves as the point of attachment of $R^3$ to the isoquinoline ring, then $R^{17}$ is a single bond connecting $R^3$ to the isoquinoline ring;

when the nitrogen atom to which $R^{18}$ is attached serves as the point of attachment of $R^3$ to the isoquinoline ring, then $R^{18}$ is a single bond connecting $R^3$ to the isoquinoline ring;

when the carbon atom to which $R^{19}$ is attached serves as the point of attachment of $R^3$ to the isoquinoline ring, then $R^{19}$ is a single bond connecting $R^3$ to the isoquinoline ring;

when the carbon atom to which $R^{20}$ is attached serves as the point of attachment of $R^3$ to the isoquinoline ring, then $R^{20}$ is a single bond connecting $R^3$ to the isoquinoline ring;

when the nitrogen atom to which $R^{21}$ is attached serves as the point of attachment of $R^3$ to the isoquinoline ring, then $R^{21}$ is a single bond connecting $R^3$ to the isoquinoline ring;

when the carbon atom to which $R^{22}$ is attached serves as the point of attachment of $R^3$ to the isoquinoline ring, then $R^{22}$ is a single bond connecting $R^3$ to the isoquinoline ring;

when the carbon atom to which $R^{23}$ is attached serves as the point of attachment of $R^3$ to the isoquinoline ring, then $R^{23}$ is a single bond connecting $R^3$ to the isoquinoline ring;

when the carbon atom to which $R^{24}$ is attached serves as the point of attachment of $R^3$ to the isoquinoline ring, then $R^{24}$ is a single bond connecting $R^3$ to the isoquinoline ring;

when the carbon atom to which $R^{25}$ is attached serves as the point of attachment of $R^3$ to the isoquinoline ring, then $R^{25}$ is a single bond connecting $R^3$ to the isoquinoline ring;

when the carbon atom to which $R^{26}$ is attached serves as the point of attachment of $R^3$ to the isoquinoline ring, then $R^{26}$ is a single bond connecting $R^3$ to the isoquinoline ring;

when the carbon atom to which $R^{27}$ is attached serves as the point of attachment of $R^3$ to the isoquinoline ring, then $R^{27}$ is a single bond connecting $R^3$ to the isoquinoline ring;

when the carbon atom to which $R^{28}$ is attached serves as the point of attachment of $R^3$ to the isoquinoline ring, then $R^{28}$ is a single bond connecting $R^3$ to the isoquinoline ring;

when the carbon atom to which $R^{29}$ is attached serves as the point of attachment of $R^3$ to the isoquinoline ring, then $R^{29}$ is a single bond connecting $R^3$ to the isoquinoline ring;

when the carbon atom to which $R^{30}$ is attached serves as the point of attachment of $R^3$ to the isoquinoline ring, then $R^{30}$ is a single bond connecting $R^3$ to the isoquinoline ring;

when the carbon atom to which $R^{31}$ is attached serves as the point of attachment of $R^3$ to the isoquinoline ring, then $R^{31}$ is a single bond connecting $R^3$ to the isoquinoline ring;

when the carbon atom to which $R^{32}$ is attached serves as the point of attachment of $R^3$ to the isoquinoline ring, then $R^{32}$ is a single bond connecting $R^3$ to the isoquinoline ring;

when the carbon atom to which $R^{33}$ is attached serves as the point of attachment of $R^3$ to the isoquinoline ring, then $R^{33}$ is a single bond connecting $R^3$ to the isoquinoline ring;

when the carbon atom to which $R^{34}$ is attached serves as the point of attachment of $R^3$ to the isoquinoline ring, then $R^{34}$ is a single bond connecting $R^3$ to the isoquinoline ring;

when the carbon atom to which $R^{35}$ is attached serves as the point of attachment of $R^3$ to the isoquinoline ring, then $R^{35}$ is a single bond connecting $R^3$ to the isoquinoline ring;

$R^6$ is selected from the group consisting of -phenyl substituted with 1-5 $R^{36}$, —$(C_{1-3}$ alkylene$)_p$pyridinyl optionally substituted with 1-6 $R^{37}$, and a 6-10 membered heteroaryl optionally substituted with 1-6 $R^{37}$; wherein the carbonyl of Formula I is attached to an aromatic ring of the heteroaryl; wherein —$(C_{1-3}$ alkylene) is optionally substituted with one or more substituents as defined anywhere herein;

$R^7$ is selected from the group consisting of a single bond, unsubstituted —$(C_{1-9}$ alkyl), unsubstituted —$(C_{2-9}$ alkenyl), unsubstituted —$(C_{2-9}$ alkynyl), unsubstituted —$(C_{1-9}$ haloalkyl), —$(C_{1-4}$ alkylene)N$(R^{48})_2$, —$(C_{1-4}$ alkylene)OR$^{49}$, —C(=O)N$(R^{48})_2$, —$(C_{1-4}$ alkylene)$_p$heterocyclyl optionally substituted with 1-10 $R^{38}$, and -carbocyclyl optionally substituted with 1-12 $R^{39}$; wherein —$(C_{1-4}$ alkylene) is optionally substituted with one or more substituents as defined anywhere herein;

$R^8$, $R^9$, and $R^{10}$ are independently selected from the group consisting of a single bond, H, halide, unsubstituted —$(C_{1-9}$ alkyl), unsubstituted —$(C_{2-9}$ alkenyl), unsubstituted —$(C_{2-9}$ alkynyl), unsubstituted —$(C_{1-9}$ haloalkyl), —$(C_{1-4}$ alkylene)$_p$N$(R^{48})_2$, —$(C_{1-4}$ alkylene)$_p$OR$^{49}$, —C(=O)N$(R^{48})_2$, —$(C_{1-4}$ alkylene)$_p$heterocyclyl optionally substituted with 1-10 $R^{38}$, and -carbocyclyl optionally substituted with 1-12 $R^{39}$; wherein each —$(C_{1-4}$ alkylene) is, independently, optionally substituted with one or more substituents as defined anywhere herein;

alternatively, one of $R^7$ and $R^8$, $R^8$ and $R^9$, or $R^9$ and $R^{10}$ are taken together to form a ring which is selected from the group consisting of -heterocyclyl optionally substituted with 1-10 $R^{40}$ and -carbocyclyl optionally substituted with 1-12 $R^{41}$;

$R^{11}$ is selected from the group consisting of a single bond, H, unsubstituted —$(C_{1-9}$ alkyl), unsubstituted —$(C_{2-9}$ alkenyl), unsubstituted —$(C_{2-9}$ alkynyl), unsubstituted —$(C_{1-9}$ haloalkyl), —$(C_{1-4}$ alkylene)N$(R^{48})_2$, —$(C_{1-4}$ alkylene)OR$^{49}$, —C(=O)N$(R^{48})_2$, —$(C_{1-4}$ alkylene)$_p$heterocyclyl optionally substituted with 1-10 $R^{38}$, and -carbocyclyl optionally substituted with 1-12 $R^{39}$; wherein —$(C_{1-4}$ alkylene) is optionally substituted with one or more substituents as defined anywhere herein;

$R^{12}$, $R^{13}$, and $R^{14}$ are independently selected from the group consisting of a single bond, H, halide, unsubstituted —$(C_{1-9}$ alkyl), unsubstituted —$(C_{2-9}$ alkenyl), unsubstituted —$(C_{2-9}$ alkynyl), unsubstituted —$(C_{1-9}$ haloalkyl), —$(C_{1-4}$ alkylene)$_p$N$(R^{48})_2$, —$(C_{1-4}$ alkylene)$_p$OR$^{49}$, —C(=O)N$(R^{48})_2$, —$(C_{1-4}$ alkylene)$_p$heterocyclyl optionally substituted with 1-10 $R^{38}$, and -carbocyclyl optionally substituted with 1-12 $R^{39}$; wherein each —$(C_{1-4}$ alkylene) is, independently, optionally substituted with one or more substituents as defined anywhere herein;

alternatively, one of $R^{11}$ and $R^{12}$, $R^{12}$ and $R^{13}$, or $R^{14}$ and $R^{11}$ are taken together to form a ring which is selected from the group consisting of -heterocyclyl optionally substituted with 1-10 $R^{40}$ and -carbocyclyl optionally substituted with 1-12 $R^{41}$;

$R^{15}$ is selected from the group consisting of a single bond, H, unsubstituted —$(C_{1-9}$ alkyl), unsubstituted —$(C_{2-9}$ alkenyl), unsubstituted —$(C_{2-9}$ alkynyl), unsubstituted —$(C_{1-9}$ haloalkyl), —$(C_{1-4}$ alkylene)N$(R^{48})_2$, —$(C_{1-4}$ alkylene)OR$^{49}$, —C(=O)N$(R^{48})_2$, —$(C_{1-4}$ alkylene)$_p$heterocyclyl optionally substituted with 1-10 $R^{38}$, and -carbocyclyl optionally substituted with 1-12 $R^{39}$; wherein —$(C_{1-4}$ alkylene) is optionally substituted with one or more substituents as defined anywhere herein;

$R^{16}$ and $R^{17}$ are independently selected from the group consisting of a single bond, H, halide, unsubstituted —$(C_{1-9}$ alkyl), unsubstituted —$(C_{2-9}$ alkenyl), unsubstituted —$(C_{2-9}$ alkynyl), unsubstituted —$(C_{1-9}$ haloalkyl), —$(C_{1-4}$ alkylene)$_p$N$(R^{48})_2$, —$(C_{1-4}$ alkylene)$_p$OR$^{49}$, —C(=O)N$(R^{48})_2$, —$(C_{1-4}$ alkylene)$_p$heterocyclyl optionally substituted with 1-10 $R^{38}$, and -carbocyclyl optionally substituted with 1-12 $R^{39}$; wherein each —$(C_{1-4}$ alkylene) is, independently, optionally substituted with one or more substituents as defined anywhere herein;

alternatively, one of $R^{15}$ and $R^{16}$ or $R^{16}$ and $R^{17}$ are taken together to form a ring which is selected from the group consisting of -heterocyclyl optionally substituted with 1-10 $R^{40}$ and -carbocyclyl optionally substituted with 1-12 $R^{41}$;

$R^{18}$ is selected from the group consisting of a single bond, H, unsubstituted —$(C_{1-9}$ alkyl), unsubstituted —$(C_{2-9}$ alkenyl), unsubstituted —$(C_{2-9}$ alkynyl), unsubstituted —$(C_{1-9}$ haloalkyl), —$(C_{1-4}$ alkylene)N$(R^{48})_2$, —$(C_{1-4}$ alkylene)OR$^{49}$, —C(=O)N$(R^{48})_2$, —$(C_{1-4}$ alkylene)$_p$heterocyclyl optionally substituted with 1-10 $R^{38}$, and -carbocyclyl optionally substituted with 1-12 $R^{39}$; wherein —$(C_{1-4}$ alkylene) is optionally substituted with one or more substituents as defined anywhere herein;

$R^{19}$ and $R^{20}$ are independently selected from the group consisting of a single bond, H, halide, unsubstituted —$(C_{1-9}$ alkyl), unsubstituted —$(C_{2-9}$ alkenyl), unsubstituted —$(C_{2-9}$ alkynyl), unsubstituted —$(C_{1-9}$ haloalkyl), —$(C_{1-4}$ alkylene)$_p$N$(R^{48})_2$, —$(C_{1-4}$ alkylene)$_p$OR$^{49}$, —C(=O)N$(R^{48})_2$, —$(C_{1-4}$ alkylene)$_p$heterocyclyl optionally substituted with 1-10 $R^{38}$, and -carbocyclyl optionally substituted with 1-12 $R^{39}$; wherein each —$(C_{1-4}$ alkylene) is, independently, optionally substituted with one or more substituents as defined anywhere herein;

alternatively, one of $R^{18}$ and $R^{19}$ or $R^{18}$ and $R^{20}$ are taken together to form a heterocyclyl optionally substituted with 1-10 $R^{40}$;

$R^{21}$ is selected from the group consisting of a single bond, H, unsubstituted —$(C_{1-9}$ alkyl), unsubstituted —$(C_{2-9}$ alkenyl), unsubstituted —$(C_{2-9}$ alkynyl), unsubstituted —$(C_{1-9}$ haloalkyl), —$(C_{1-4}$ alkylene)N$(R^{48})_2$, —$(C_{1-4}$ alkylene)OR$^{49}$, —C(=O)N$(R^{48})_2$, —$(C_{1-4}$ alkylene)$_p$heterocyclyl optionally substituted with 1-10 $R^{38}$, and -carbocyclyl optionally substituted with 1-12 $R^{39}$; wherein —$(C_{1-4}$ alkylene) is optionally substituted with one or more substituents as defined anywhere herein;

$R^{22}$ and $R^{23}$ are independently selected from the group consisting of a single bond, H, halide, unsubstituted —$(C_{1-9}$ alkyl), unsubstituted —$(C_{2-9}$ alkenyl), unsubstituted —$(C_{2-9}$ alkynyl), unsubstituted —$(C_{1-9}$ haloalkyl), —$(C_{1-4}$ alkylene)$_p$N$(R^{48})_2$, —$(C_{1-4}$ alkylene)$_p$OR$^{49}$, —C(=O)N$(R^{48})_2$, —$(C_{1-4}$ alkylene)$_p$heterocyclyl optionally substituted with 1-10 $R^{38}$, and -carbocyclyl optionally substituted with 1-12

$R^{39}$; wherein each —($C_{1-4}$ alkylene) is, independently, optionally substituted with one or more substituents as defined anywhere herein;

alternatively, $R^{22}$ and $R^{23}$ are taken together to form a ring which is selected from the group consisting of -heterocyclyl optionally substituted with 1-10 $R^{40}$ and -carbocyclyl optionally substituted with 1-12 $R^{41}$;

$R_{24}$, $R_{25}$, and $R^{26}$ are independently selected from the group consisting of a single bond, H, halide, unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), —($C_{1-4}$ alkylene)$_p$N($R^{48}$)$_2$, —($C_{1-4}$ alkylene)$_p$OR$^{49}$, —C(=O)N($R^{48}$)$_2$, —($C_{1-4}$ alkylene)$_p$heterocyclyl optionally substituted with 1-10 $R^{38}$, and -carbocyclyl optionally substituted with 1-12 $R^{39}$; wherein each —($C_{1-4}$ alkylene) is, independently, optionally substituted with one or more substituents as defined anywhere herein;

alternatively, one of $R^{24}$ and $R^{25}$ or $R^{25}$ and $R^{26}$ are taken together to form a ring which is selected from the group consisting of -heterocyclyl optionally substituted with 1-10 $R^{40}$ and -carbocyclyl optionally substituted with 1-12 $R^{41}$;

$R^{27}$, $R^{28}$, and $R^{29}$ are independently selected from the group consisting of a single bond, H, halide, unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), —($C_{1-4}$ alkylene)$_p$N($R^{48}$)$_2$, —($C_{1-4}$ alkylene)$_p$OR$^{49}$, —C(=O)N($R^{48}$)$_2$, —($C_{1-4}$ alkylene)$_p$heterocyclyl optionally substituted with 1-10 $R^{38}$, and -carbocyclyl optionally substituted with 1-12 $R^{39}$; wherein each —($C_{1-4}$ alkylene) is, independently, optionally substituted with one or more substituents as defined anywhere herein;

alternatively, $R^{27}$ and $R^{28}$ are taken together to form a ring which is selected from the group consisting of -heterocyclyl optionally substituted with 1-10 $R^{40}$ and -carbocyclyl optionally substituted with 1-12 $R^{41}$;

$R^{30}$ and $R^{31}$ are independently selected from the group consisting of a single bond, H, halide, unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), —($C_{1-4}$ alkylene)$_p$N($R^{48}$)$_2$, —($C_{1-4}$ alkylene)$_p$OR$^{49}$, —C(=O)N($R^{48}$)$_2$, —($C_{1-4}$ alkylene)$_p$heterocyclyl optionally substituted with 1-10 $R^{38}$, and -carbocyclyl optionally substituted with 1-12 $R^{39}$; wherein each —($C_{1-4}$ alkylene) is, independently, optionally substituted with one or more substituents as defined anywhere herein;

alternatively, $R^{30}$ and $R^{31}$ are taken together to form a ring which is selected from the group consisting of -heterocyclyl optionally substituted with 1-10 $R^{40}$ and -carbocyclyl optionally substituted with 1-12 $R^{41}$;

$R^{32}$ and $R^{33}$ are independently selected from the group consisting of a single bond, H, halide, unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), —($C_{1-4}$ alkylene)$_p$N($R^{48}$)$_2$, —($C_{1-4}$ alkylene)$_p$OR$^{49}$, —C(=O)N($R^{48}$)$_2$, —($C_{1-4}$ alkylene)$_p$heterocyclyl optionally substituted with 1-10 $R^{38}$, and -carbocyclyl optionally substituted with 1-12 $R^{39}$; wherein each —($C_{1-4}$ alkylene) is, independently, optionally substituted with one or more substituents as defined anywhere herein;

$R^{34}$ and $R^{35}$ are independently selected from the group consisting of a single bond, H, halide, unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), —($C_{1-4}$ alkylene)$_p$N($R^{48}$)$_2$, —($C_{1-4}$ alkylene)$_p$OR$^{49}$, —C(=O)N($R^{48}$)$_2$, —($C_{1-4}$ alkylene)$_p$heterocyclyl optionally substituted with 1-10 $R^{38}$, and -carbocyclyl optionally substituted with 1-12 $R^{39}$; wherein each —($C_{1-4}$ alkylene) is, independently, optionally substituted with one or more substituents as defined anywhere herein;

alternatively, $R^{34}$ and $R^{35}$ are taken together to form a ring which is selected from the group consisting of -heterocyclyl optionally substituted with 1-10 $R^{40}$ and -carbocyclyl optionally substituted with 1-12 $R^{41}$;

each $R^{36}$ is independently selected from the group consisting of halide, unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), —XR$^{42}$, —C(=O)N($R^{47}$)$_2$, —($C_{1-4}$ alkylene)$_p$N($R^{50}$)$_2$, —($C_{1-4}$ alkylene)$_p$heterocyclyl optionally substituted with 1-10 $R^{43}$, and —($C_{1-4}$ alkylene)$_p$carbocyclyl optionally substituted with 1-12 $R^{44}$; wherein each —($C_{1-4}$ alkylene) is, independently, optionally substituted with one or more substituents as defined anywhere herein;

each $R^{37}$ is independently selected from the group consisting of halide, unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), —XR$^{42}$, —C(=O)N($R^{47}$)$_2$, —($C_{1-4}$ alkylene)$_p$N($R^{50}$)$_2$, —($C_{1-4}$ alkylene)$_p$heterocyclyl optionally substituted with 1-10 $R^{43}$, and —($C_{1-4}$ alkylene)$_p$carbocyclyl optionally substituted with 1-12 $R^{44}$; wherein each —($C_{1-4}$ alkylene) is, independently, optionally substituted with one or more substituents as defined anywhere herein;

each $R^{38}$ is independently selected from the group consisting of halide, unsubstituted —($C_{1-5}$ alkyl), unsubstituted —($C_{2-5}$ alkenyl), unsubstituted —($C_{2-5}$ alkynyl), unsubstituted —($C_{1-5}$ haloalkyl), —CN, and —($C_{1-4}$ alkylene)$_p$carbocyclyl optionally substituted with 1-12 $R^{44}$; wherein each —($C_{1-4}$ alkylene) is, independently, optionally substituted with one or more substituents as defined anywhere herein;

each $R^{39}$ is independently selected from the group consisting of halide, unsubstituted —($C_{1-5}$ alkyl), unsubstituted —($C_{2-5}$ alkenyl), unsubstituted —($C_{2-5}$ alkynyl), unsubstituted —($C_{1-5}$ haloalkyl), —CN, and —($C_{1-4}$ alkylene)$_p$carbocyclyl optionally substituted with 1-12 $R^{44}$; wherein each —($C_{1-4}$ alkylene) is, independently, optionally substituted with one or more substituents as defined anywhere herein;

each $R^{40}$ is independently selected from the group consisting of halide, unsubstituted —($C_{1-5}$ alkyl), unsubstituted —($C_{2-5}$ alkenyl), unsubstituted —($C_{2-5}$ alkynyl), unsubstituted —($C_{1-5}$ haloalkyl), —CN, and —($C_{1-4}$ alkylene)$_p$carbocyclyl optionally substituted with 1-12 $R^{44}$; wherein each —($C_{1-4}$ alkylene) is, independently, optionally substituted with one or more substituents as defined anywhere herein;

each $R^{41}$ is independently selected from the group consisting of halide, unsubstituted —($C_{1-5}$ alkyl), unsubstituted —($C_{2-5}$ alkenyl), unsubstituted —($C_{2-5}$ alkynyl), unsubstituted —($C_{1-5}$ haloalkyl), and —CN;

each $R^{42}$ is independently selected from the group consisting of H, unsubstituted —($C_{1-5}$ alkyl), unsubstituted —($C_{2-5}$ alkenyl), unsubstituted —($C_{2-5}$ alkynyl), unsubstituted —($C_{1-5}$ haloalkyl), —($C_{1-4}$ alkylene)N($R^{48}$)$_2$, —($C_{1-4}$ alkylene)$_p$aryl optionally substituted with 1-10 $R^{46}$, —($C_{1-4}$ alkylene)$_p$heterocyclyl optionally substituted with 1-12 $R^{43}$, and —($C_{1-4}$ alkylene)$_p$carbocyclyl optionally substituted with 1-12 R$^{44}$; wherein each —(C$_{1-4}$ alkylene) is, independently, optionally substituted with one or more substituents as defined anywhere herein;

each R$^{43}$ is independently selected from the group consisting of halide, unsubstituted —(C$_{1-5}$ alkyl), unsubstituted —(C$_{2-5}$ alkenyl), unsubstituted —(C$_{2-5}$ alkynyl), unsubstituted —(C$_{1-5}$ haloalkyl), —CN, —OH, —C(=O)R$^{51}$, —N(R$^{50}$)$_2$, and —(C$_{1-4}$ alkylene)$_p$carbocyclyl optionally substituted with 1-12 R$^{44}$; wherein each —(C$_{1-4}$ alkylene) is, independently, optionally substituted with one or more substituents as defined anywhere herein;

each R$^{44}$ is selected from the group consisting of halide, unsubstituted —(C$_{1-5}$ alkyl), unsubstituted —(C$_{2-5}$ alkenyl), unsubstituted —(C$_{2-5}$ alkynyl), unsubstituted —(C$_{1-5}$ haloalkyl), and —CN;

each R$^{46}$ is independently selected from the group consisting of halide, unsubstituted —(C$_{1-5}$ alkyl), unsubstituted —(C$_{2-5}$ alkenyl), unsubstituted —(C$_{2-5}$ alkynyl), unsubstituted —(C$_{1-5}$ haloalkyl), and —CN;

each R$^{47}$ is independently selected from the group consisting of H, unsubstituted —(C$_{1-5}$ alkyl), unsubstituted —(C$_{2-5}$ alkenyl), unsubstituted —(C$_{2-5}$ alkynyl), and unsubstituted —(C$_{1-5}$ haloalkyl);

each R$^{48}$ is independently selected from the group consisting of H, unsubstituted —(C$_{1-5}$ alkyl), unsubstituted —(C$_{2-5}$ alkenyl), unsubstituted —(C$_{2-5}$ alkynyl), and unsubstituted —(C$_{1-5}$ haloalkyl);

each R$^{49}$ is independently selected from the group consisting of H, unsubstituted —(C$_{1-5}$ alkyl), unsubstituted —(C$_{2-5}$ alkenyl), unsubstituted —(C$_{2-5}$ alkynyl), and unsubstituted —(C$_{1-5}$ haloalkyl);

each R$^{50}$ is independently selected from the group consisting of H, unsubstituted —(C$_{1-5}$ alkyl), unsubstituted —(C$_{2-5}$ alkenyl), unsubstituted —(C$_{2-5}$ alkynyl), unsubstituted —(C$_{1-5}$ haloalkyl), and —(C$_{1-4}$ alkylene)N(R$^{48}$)$_2$; wherein —(C$_{1-4}$ alkylene) is optionally substituted with one or more substituents as defined anywhere herein;

each R$^{51}$ is a heteroaryl optionally substituted with 1-6 R$^{52}$;

each R$^{52}$ is a -heterocyclyl optionally substituted with 1-10 R$^{46}$;

each X is selected from the group consisting of O, S, and NR$^{48}$;

each Y is selected from the group consisting of O and S;

each p is independently 0 or 1, and wherein each H atom is optionally independently replaced by $^2$H (deuterium).

2. The method of claim 1, wherein R$^1$, R$^2$, R$^4$, and R$^5$ are H.

3. The method of claim 2, wherein R$^3$ is selected from the group consisting of:

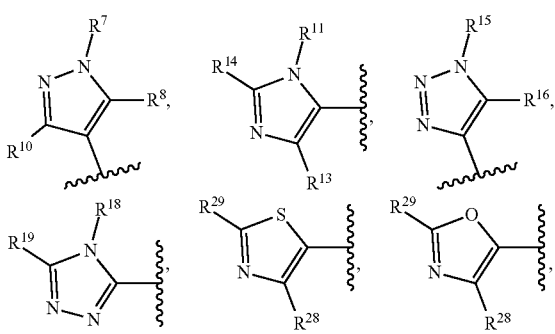

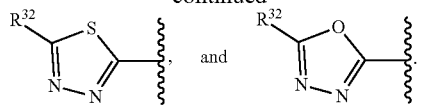

4. The method of claim 3, wherein R$^3$ is selected from the group consisting of:

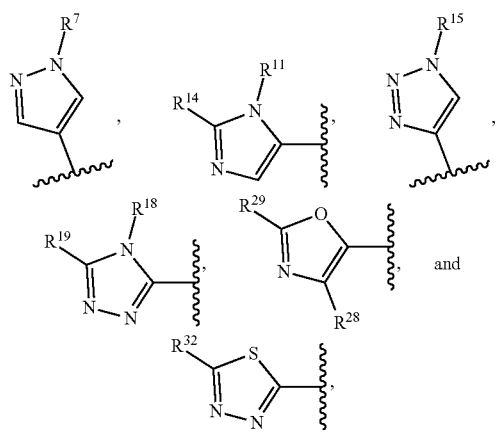

wherein R$^7$, R$^{11}$, R$^{14}$, R$^{15}$, R$^{18}$, and R$^{19}$ are independently selected from the group consisting of H and —(C$_{1-3}$ alkyl).

5. The method of claim 4, wherein R$^3$ is

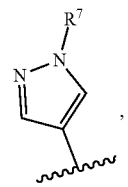

wherein R$^7$ is —(C$_{1-3}$alkyl).

6. The method of claim 1 wherein R$^6$ is -phenyl substituted with 1-5 R$^{36}$.

7. The method of claim 4 wherein R$^6$ is -phenyl substituted with 1-5 R$^{36}$.

8. The method of claim 5, wherein R$^6$ is -phenyl substituted with 1-5 R$^{36}$.

9. The method of claim 6, wherein R$^6$ is -phenyl substituted with one R$^{36}$.

10. The method of claim 7, wherein R$^6$ is -phenyl substituted with one R$^{36}$.

11. The method of claim 8, wherein R$^6$ is -phenyl substituted with one R$^{36}$.

12. The method of claim 9, wherein R$^{36}$ is selected from the group consisting of halide, -heterocyclyl optionally substituted with 1-2 R$^{43}$, —CH$_2$heterocyclyl optionally substituted with 1-2 R$^{43}$, —Oheterocyclyl optionally substituted with 1-2 R$^{43}$, —NHheterocyclyl optionally substituted with 1-2 R$^{43}$, —O(C$_{1-4}$ alkyl), and —O(C$_{1-4}$ haloalkyl).

13. The method of claim 10, wherein R$^{36}$ is selected from the group consisting of halide, -heterocyclyl optionally substituted with 1-2 R$^{43}$, —CH$_2$heterocyclyl optionally substituted with 1-2 R$^{43}$, —Oheterocyclyl optionally substituted with 1-2 R$^{43}$, —NHheterocyclyl optionally substituted with 1-2 R$^{43}$, —O(C$_{1-4}$ alkyl), and —O(C$_{1-4}$ haloalkyl).

14. The method of claim 11, wherein $R^{36}$ is selected from the group consisting of halide, -heterocyclyl optionally substituted with 1-2 $R^{43}$, —$CH_2$heterocyclyl optionally substituted with 1-2 $R^{43}$, —Oheterocyclyl optionally substituted with 1-2 $R^{43}$, —NHheterocyclyl optionally substituted with 1-2 $R^{43}$, —O($C_{1-4}$ alkyl), and —O($C_{1-4}$ haloalkyl).

15. The method of claim 1, wherein $R^6$ is a 6-membered heteroaryl optionally substituted with 1-6 $R^{37}$.

16. The method of claim 4, wherein $R^6$ is a 6-membered heteroaryl optionally substituted with 1-6 $R^{37}$.

17. The method of claim 5, wherein $R^6$ is a 6-membered heteroaryl optionally substituted with 1-6 $R^{37}$.

18. The method of claim 15, wherein $R^6$ is -pyridin-3-yl optionally substituted with one $R^{37}$.

19. The method of claim 16, wherein $R^6$ is -pyridin-3-yl optionally substituted with one $R^{37}$.

20. The method of claim 17, wherein $R^6$ is -pyridin-3-yl optionally substituted with one $R^{37}$.

21. The method of claim 15, wherein $R^6$ is -pyridin-4-yl optionally substituted with one $R^{37}$.

22. The method of claim 16, wherein $R^6$ is -pyridin-4-yl optionally substituted with one $R^{37}$.

23. The method of claim 17, wherein $R^6$ is -pyridin-4-yl optionally substituted with one $R^{37}$.

24. The method of claim 21, wherein $R^{37}$ is selected from the group consisting of halide, —($C_{1-3}$ alkyl), -heterocyclyl optionally substituted with 1-2 $R^{43}$, —$CH_2$heterocyclyl optionally substituted with 1-2 $R^{43}$, —Oheterocyclyl optionally substituted with 1-2 $R^{43}$, —NHheterocyclyl optionally substituted with 1-2 $R^{43}$, —O($C_{1-4}$ alkyl), and —O($C_{1-4}$ haloalkyl).

25. The method of claim 22, wherein $R^{37}$ is selected from the group consisting of halide, —($C_{1-3}$ alkyl), -heterocyclyl optionally substituted with 1-2 $R^{43}$, —$CH_2$heterocyclyl optionally substituted with 1-2 $R^{43}$, —Oheterocyclyl optionally substituted with 1-2 $R^{43}$, —NHheterocyclyl optionally substituted with 1-2 $R^{43}$, —O($C_{1-4}$ alkyl), and —O($C_{1-4}$ haloalkyl).

26. The method of claim 23, wherein $R^{37}$ is selected from the group consisting of halide, —($C_{1-3}$ alkyl), -heterocyclyl optionally substituted with 1-2 $R^{43}$, —$CH_2$heterocyclyl optionally substituted with 1-2 $R^{43}$, —Oheterocyclyl optionally substituted with 1-2 $R^{43}$, —NHheterocyclyl optionally substituted with 1-2 $R^{43}$, —O($C_{1-4}$ alkyl), and —O($C_{1-4}$ haloalkyl).

27. The method of claim 24, wherein $R^{43}$ is selected from the group consisting of unsubstituted —($C_{1-3}$ alkyl), unsubstituted —($C_{1-3}$ haloalkyl), and -carbocyclyl optionally substituted with 1-12 $R^{44}$.

28. The method of claim 25, wherein $R^{43}$ is selected from the group consisting of unsubstituted —($C_{1-3}$ alkyl), unsubstituted —($C_{1-3}$ haloalkyl), and -carbocyclyl optionally substituted with 1-12 $R^{44}$.

29. The method of claim 26, wherein $R^{43}$ is selected from the group consisting of unsubstituted —($C_{1-3}$ alkyl), unsubstituted —($C_{1-3}$ haloalkyl), and -carbocyclyl optionally substituted with 1-12 $R^{44}$.

30. The method of claim 1, wherein the compound of Formula I is selected from the group consisting of:

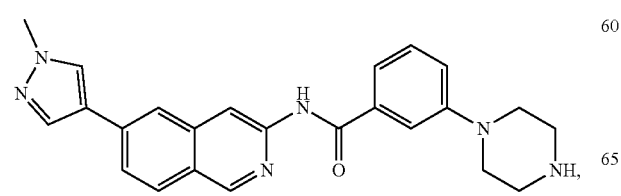

-continued

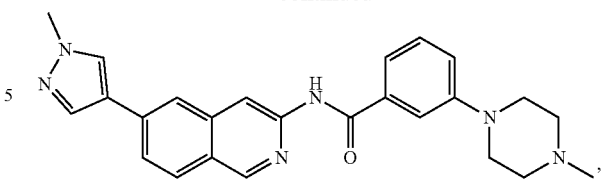

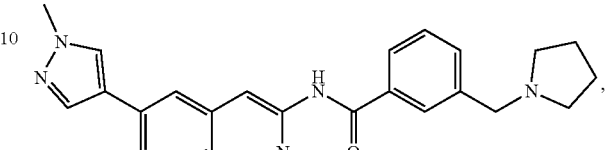

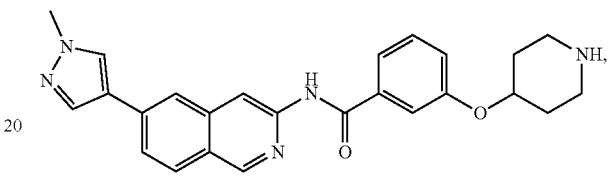

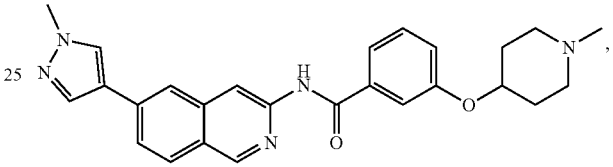

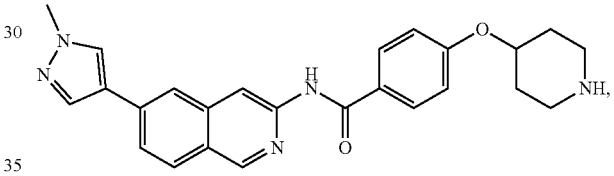

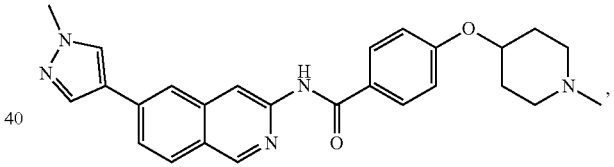

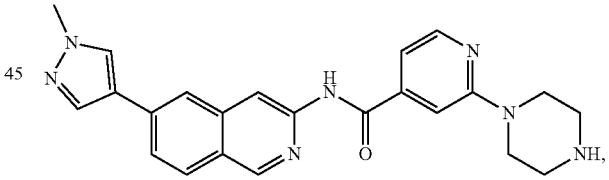

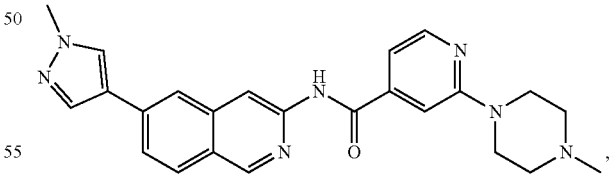

363
-continued
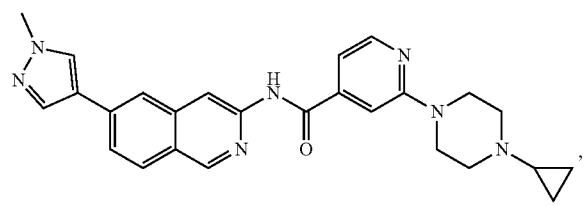
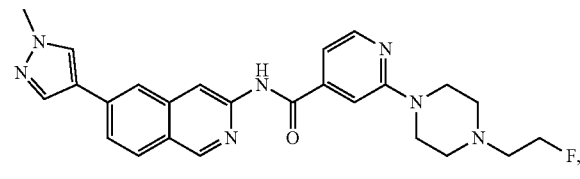
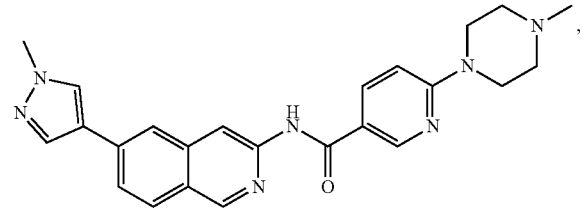
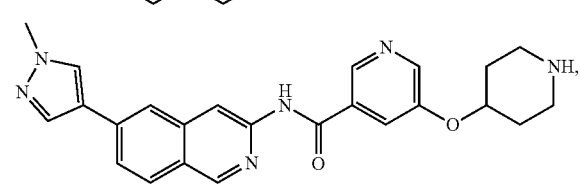
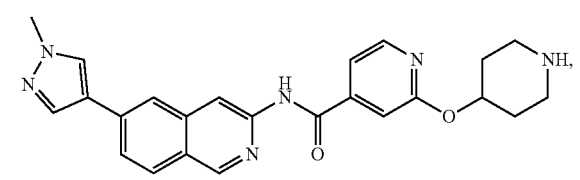
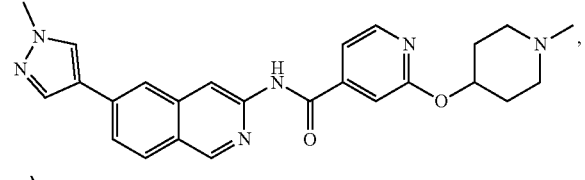
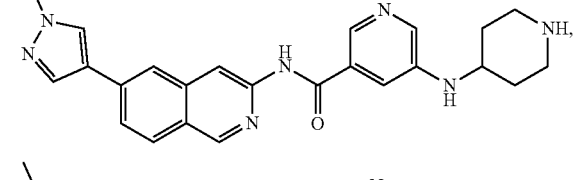
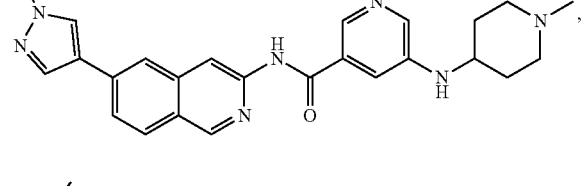
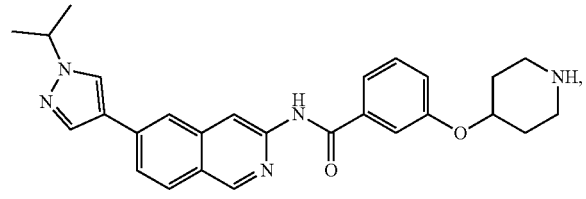
364
-continued
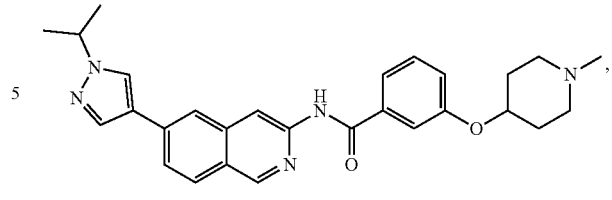
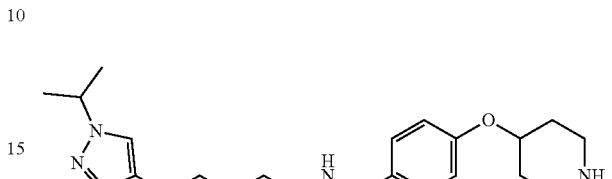
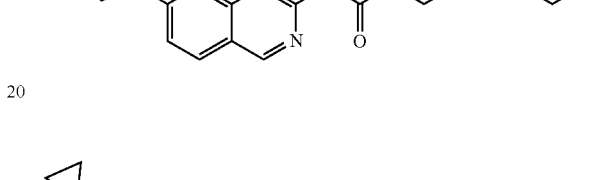
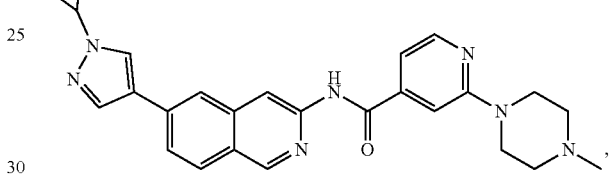
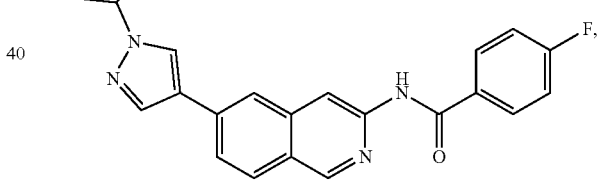
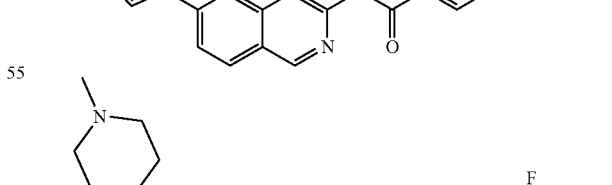
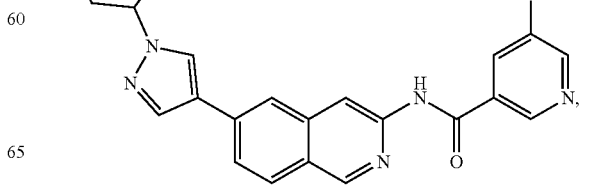

365
-continued
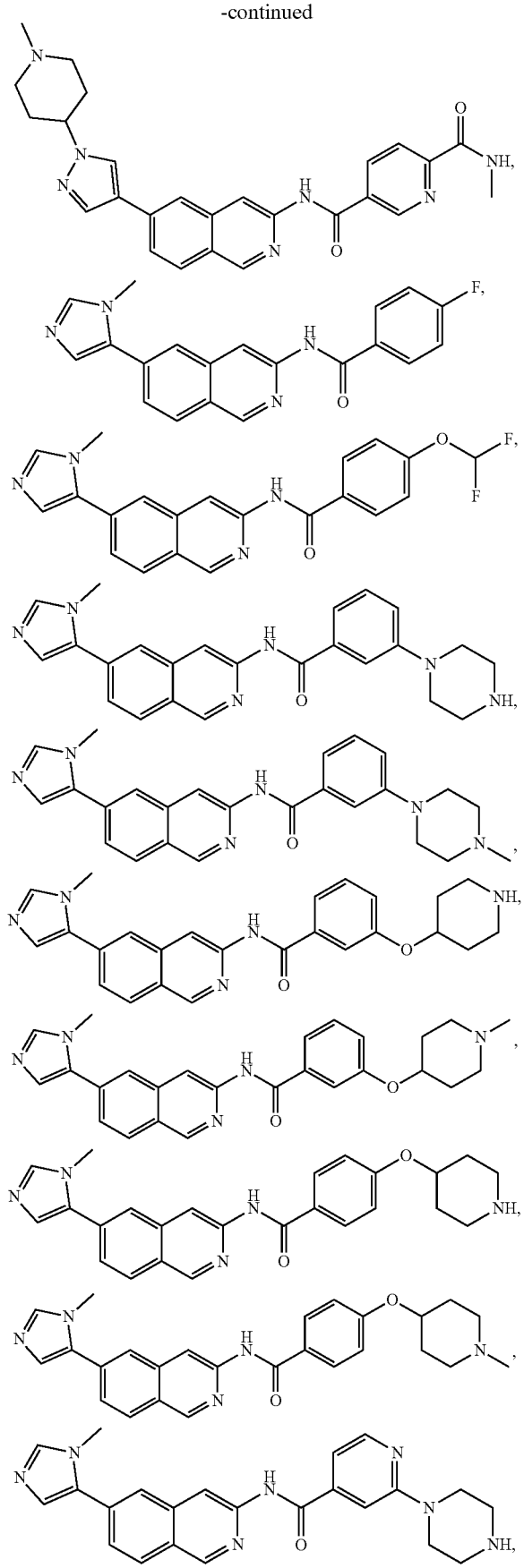
366
-continued
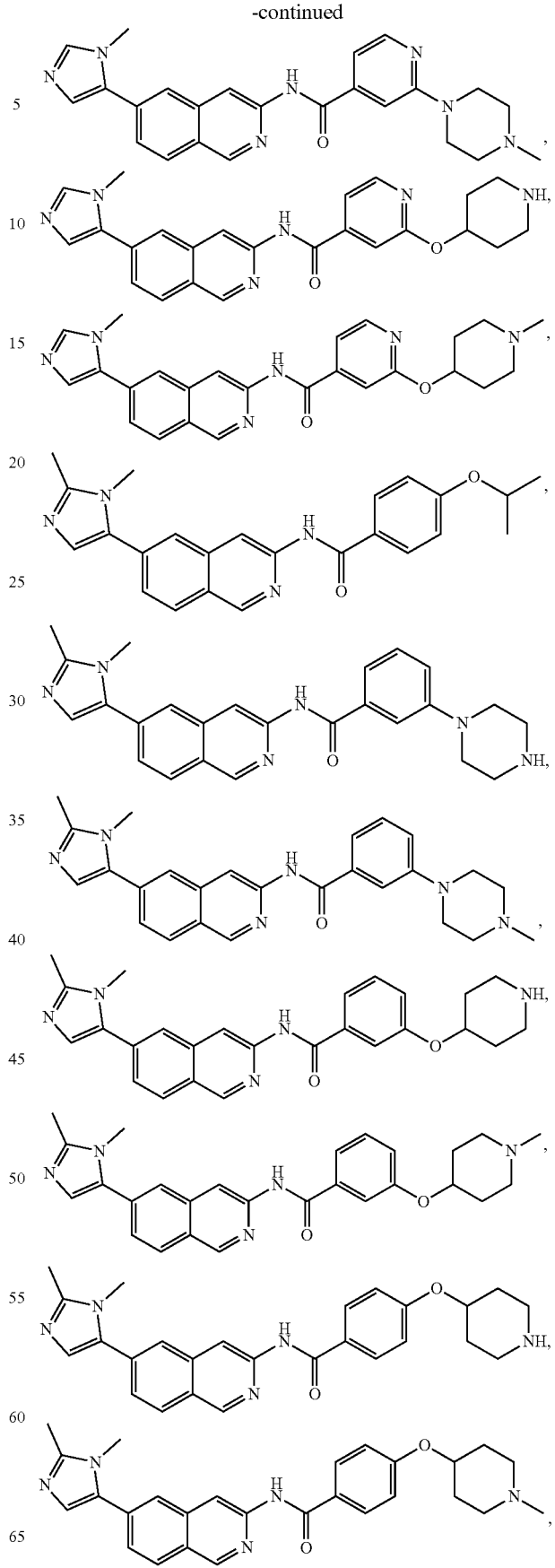

367
-continued
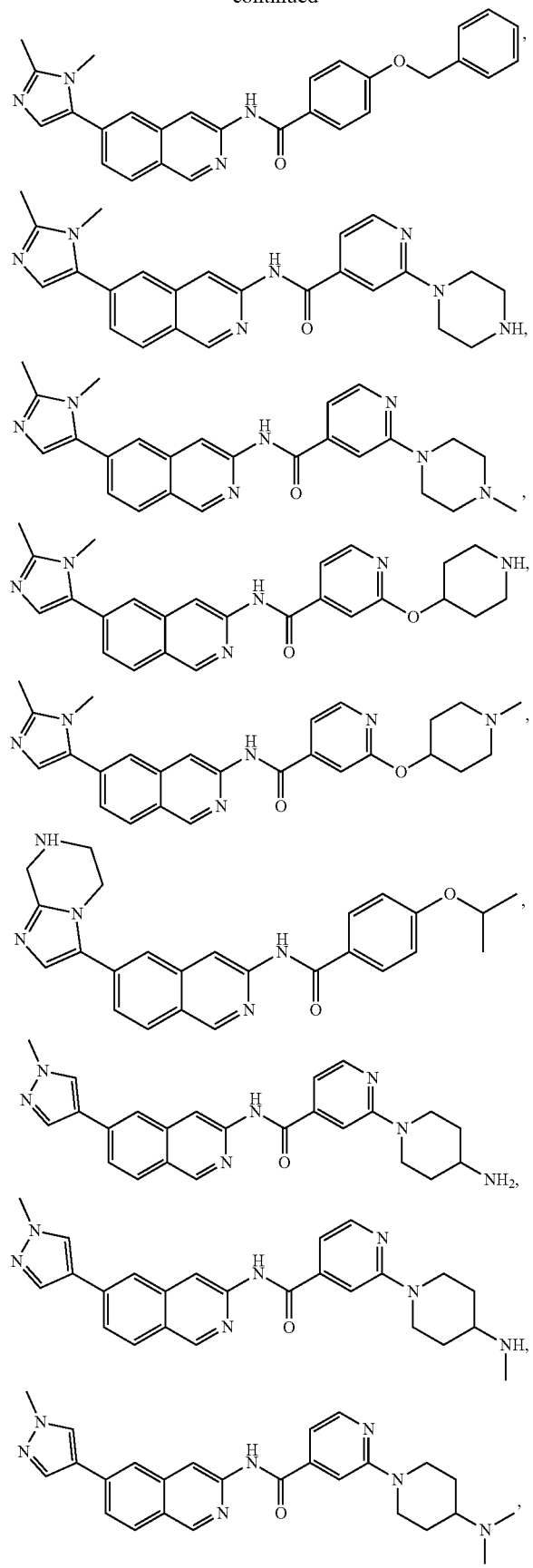
368
-continued
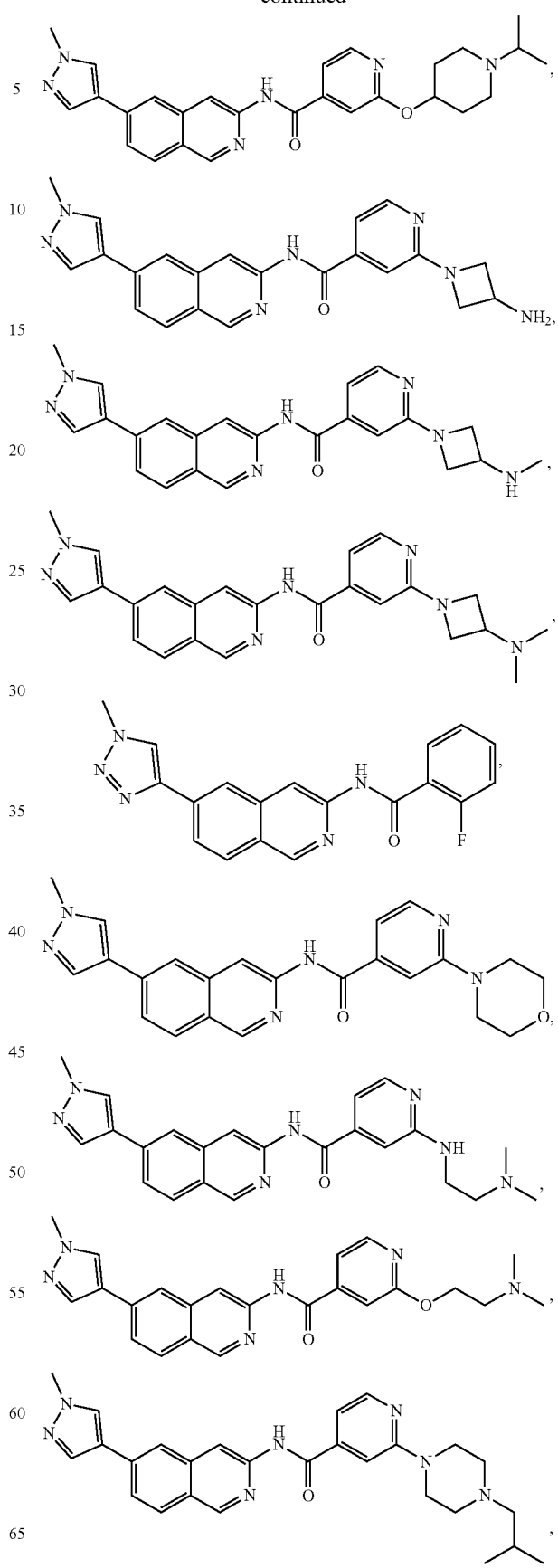

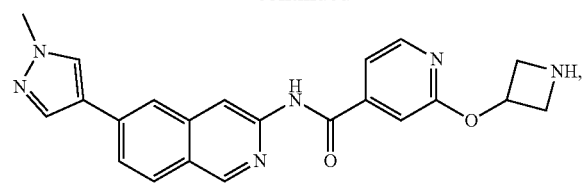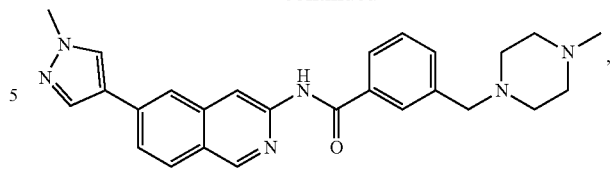

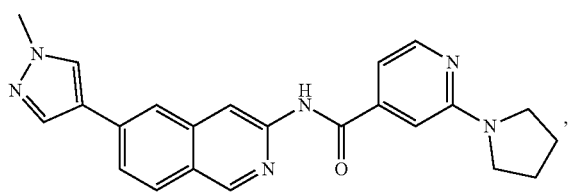
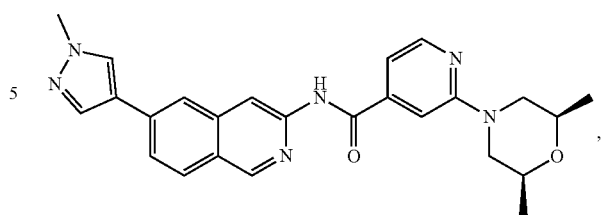
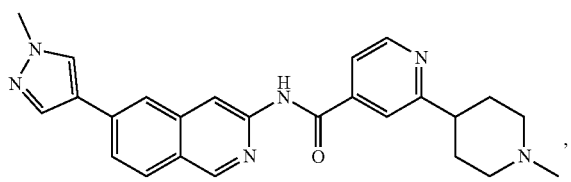
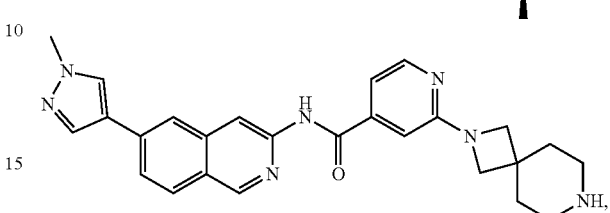
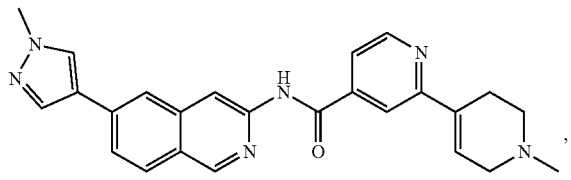
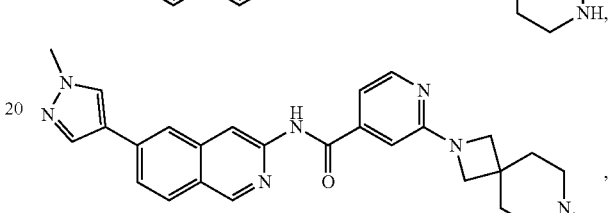
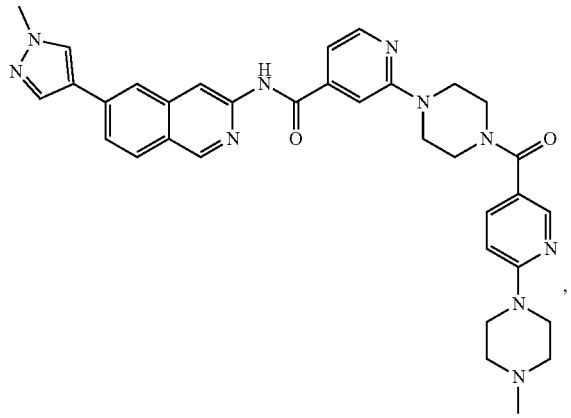
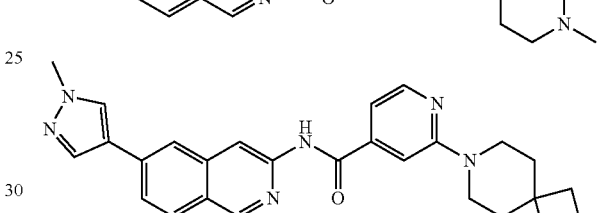
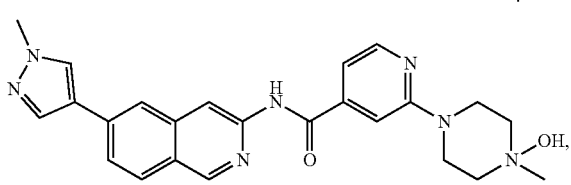
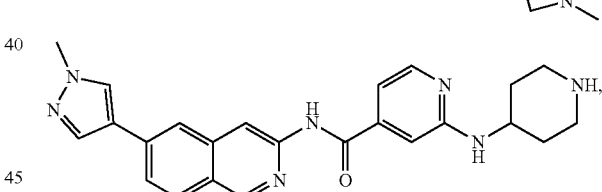
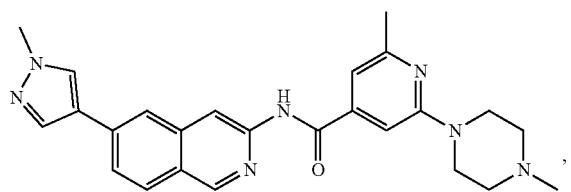
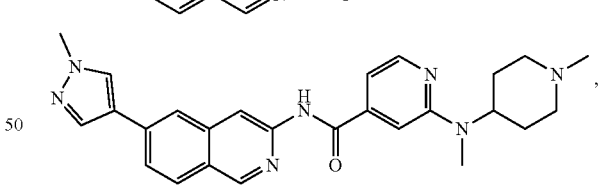
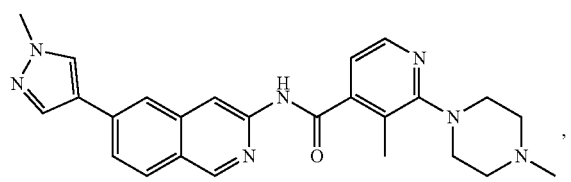
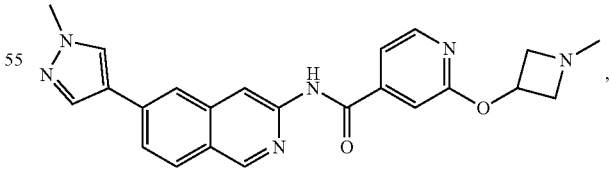
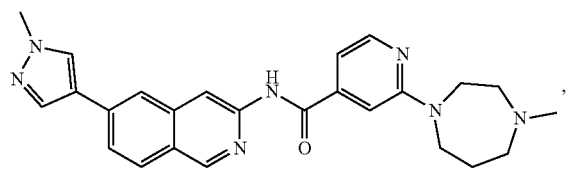

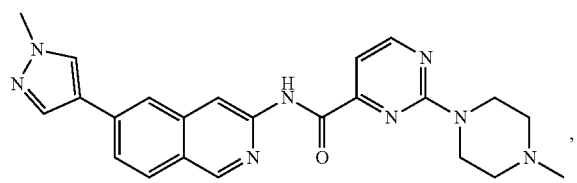
or a pharmaceutically acceptable salt thereof.
31. The method of claim 1, wherein the compound of Formula I is selected from the group consisting of:
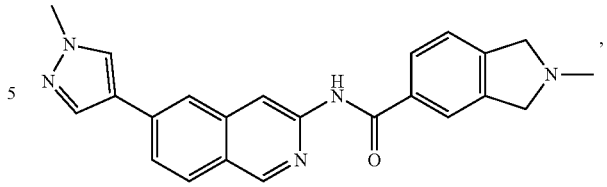
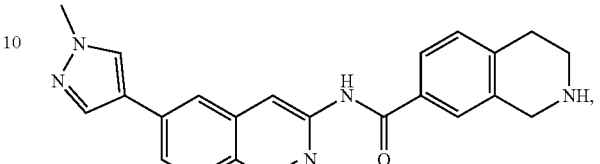
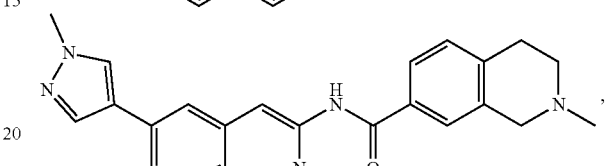
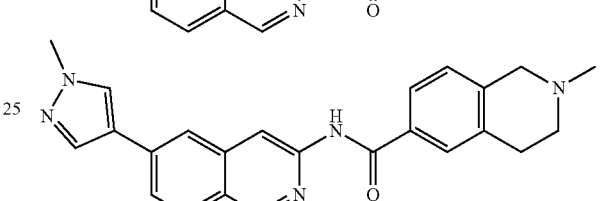
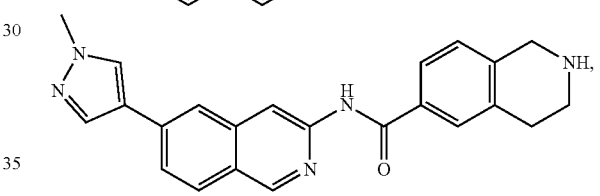
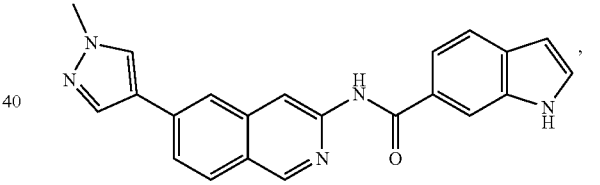
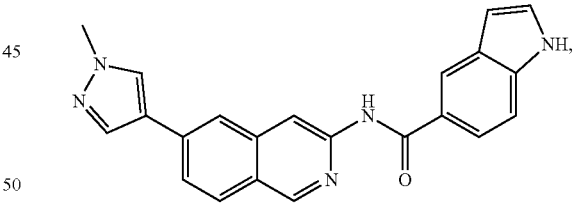
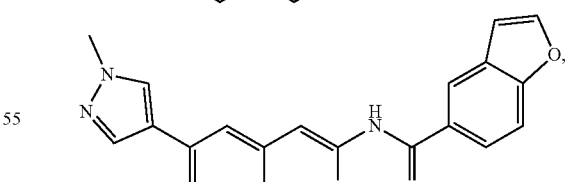
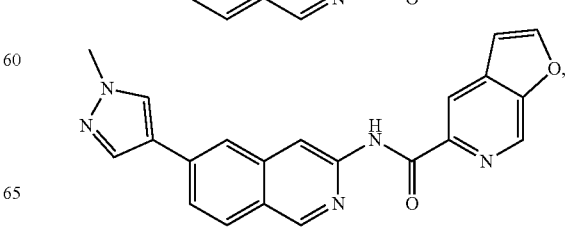

375
-continued
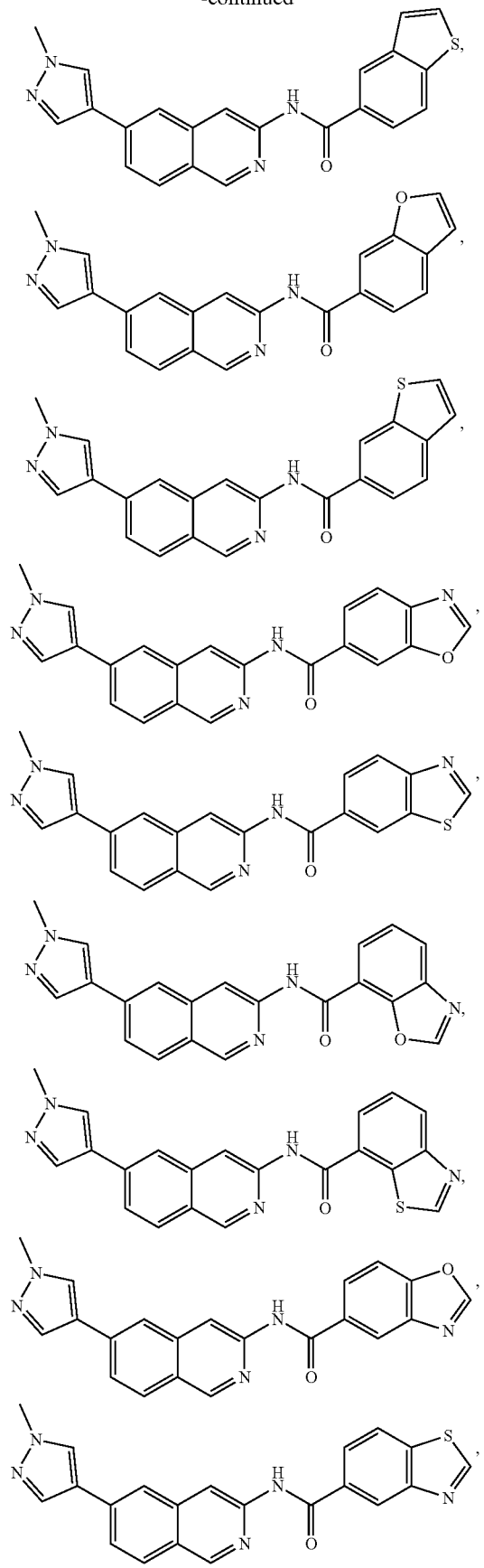
376
-continued
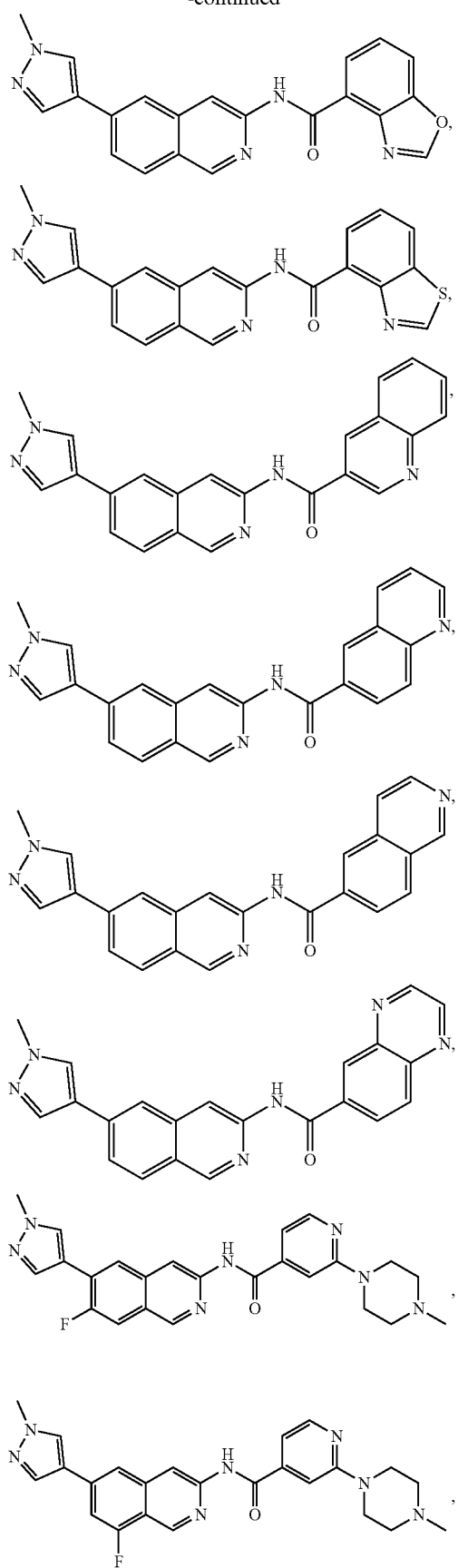

377
-continued
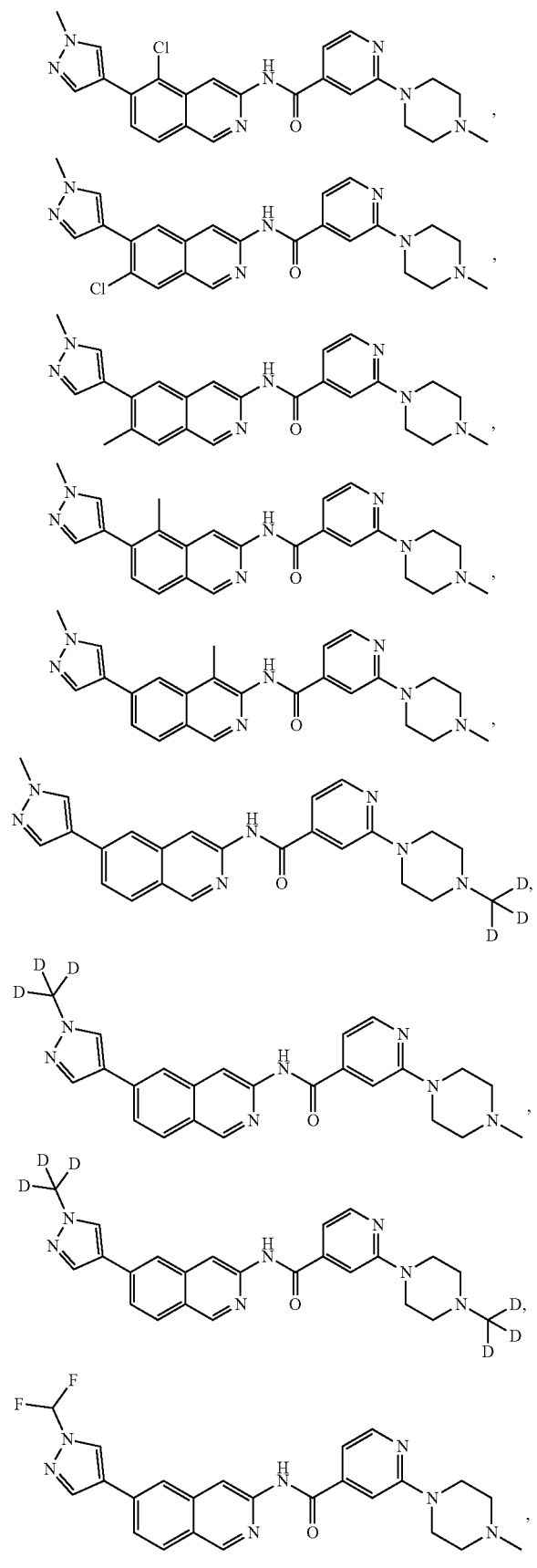
378
-continued
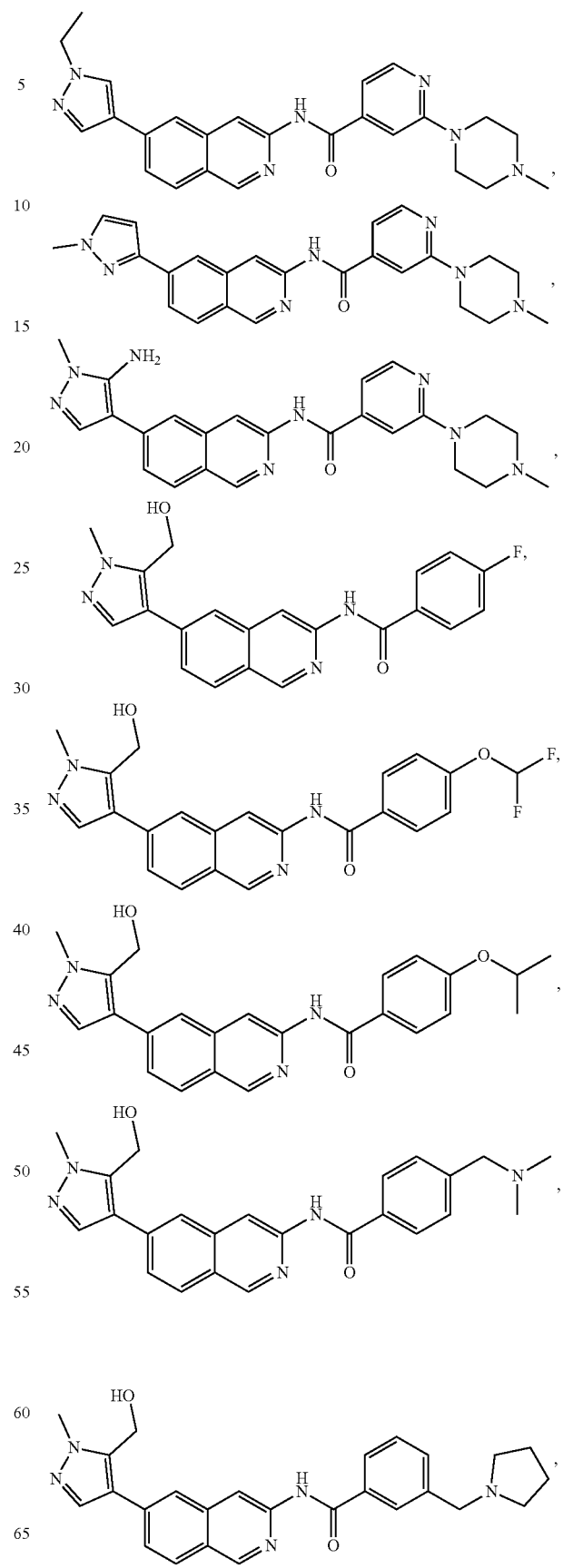

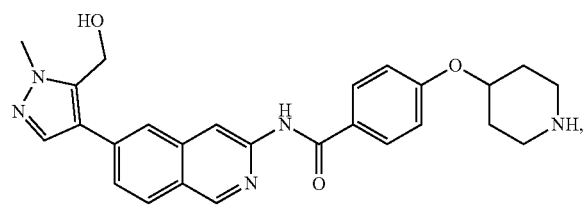
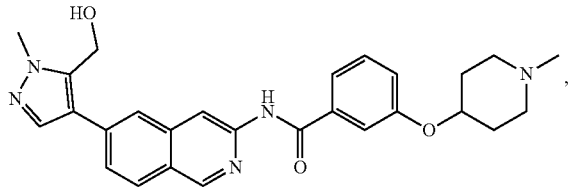
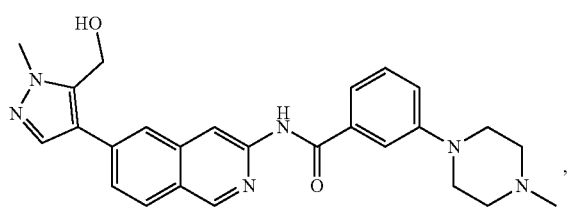
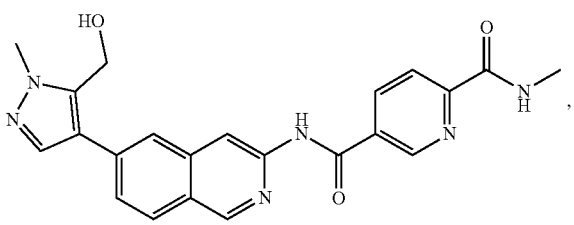
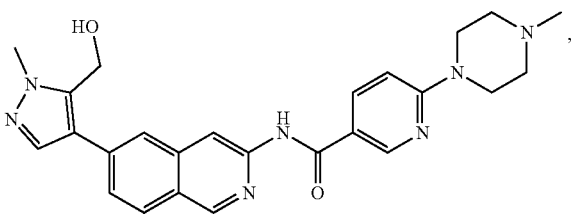
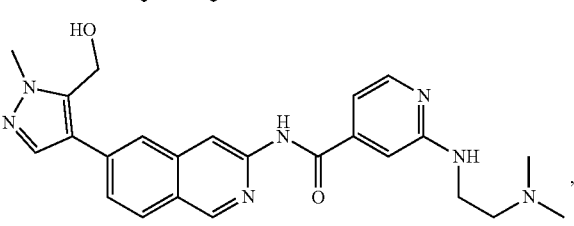
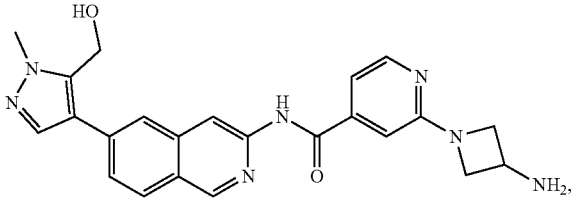
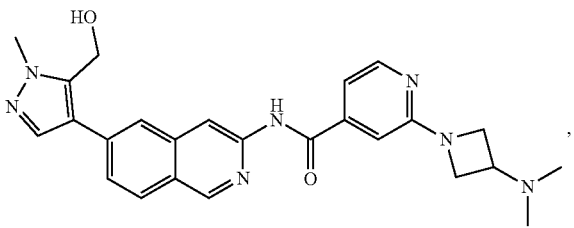
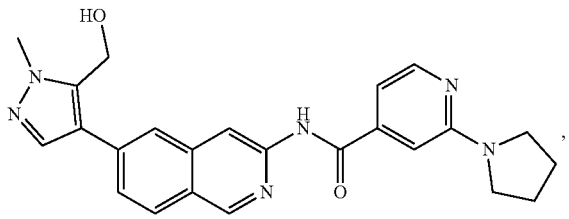
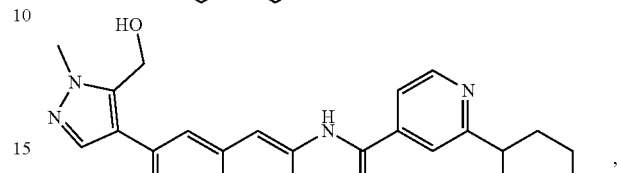
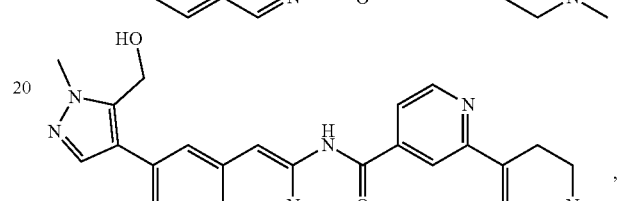
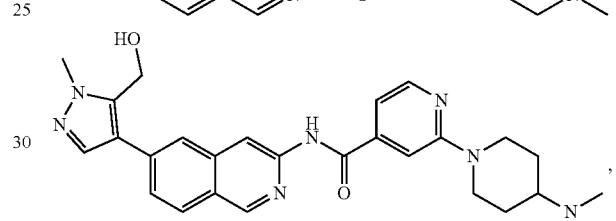
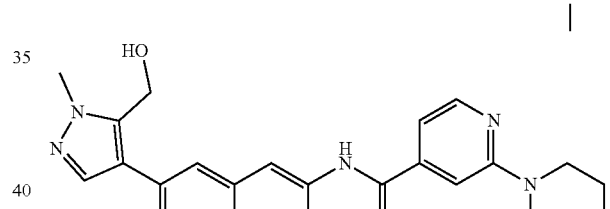
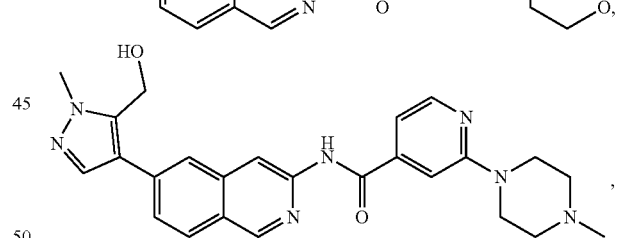
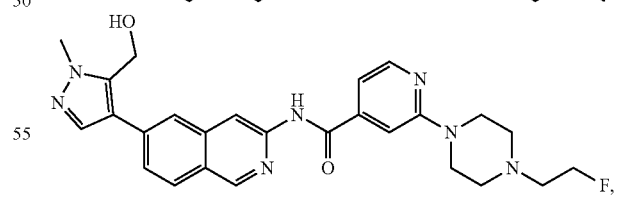
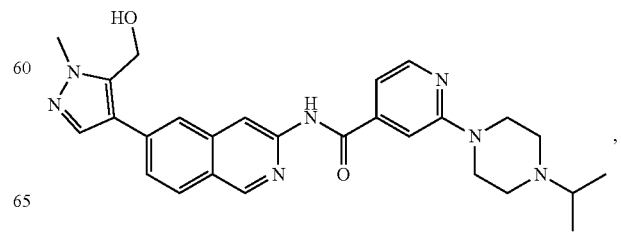

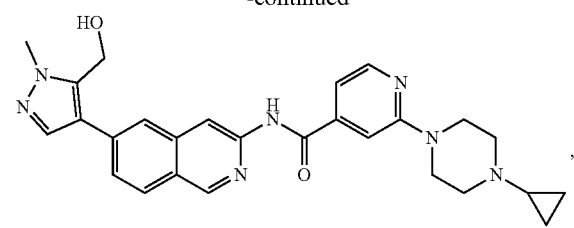
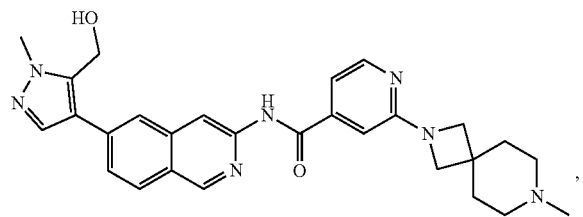
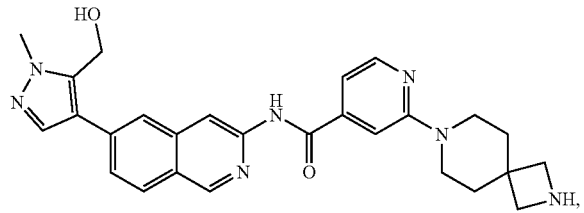
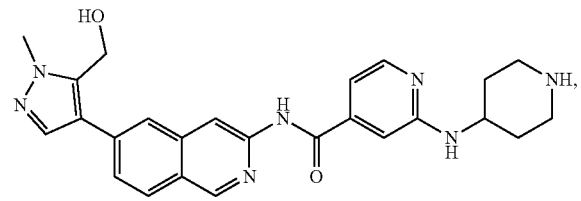
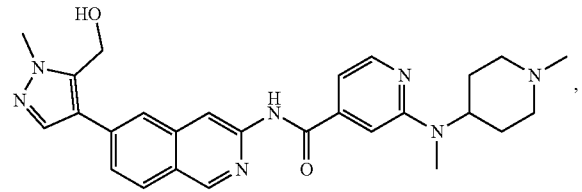
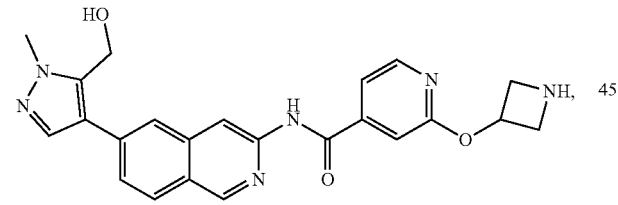
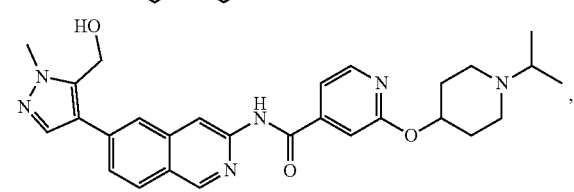
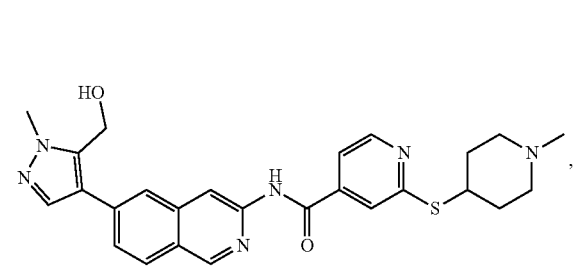
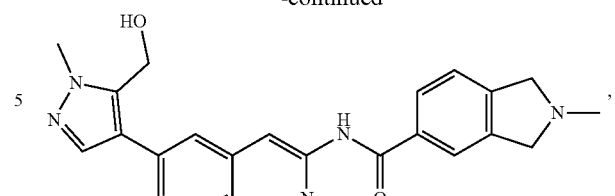
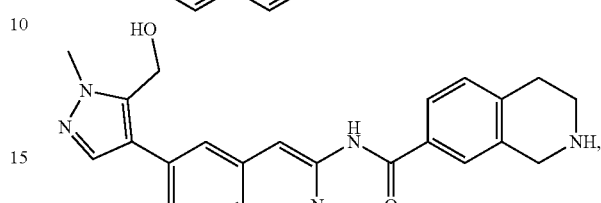
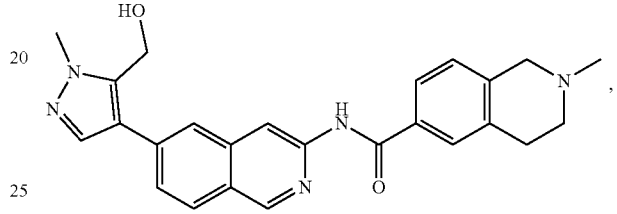
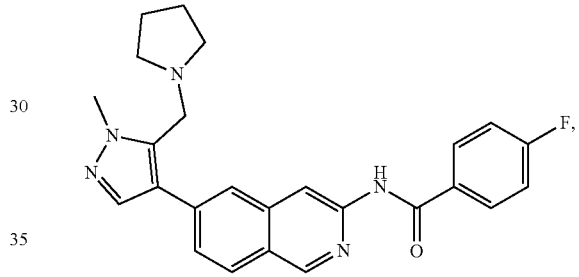

383
-continued
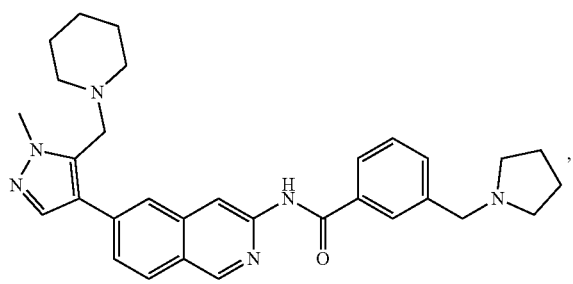
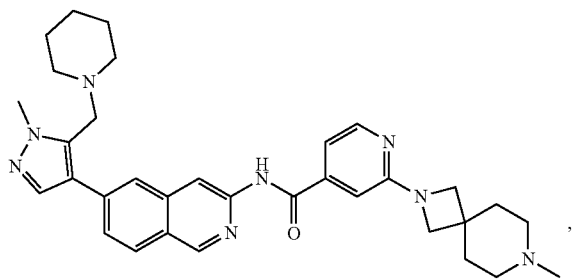
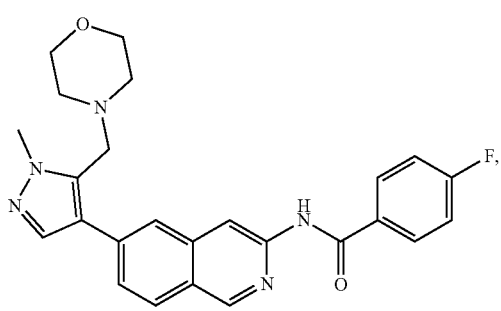
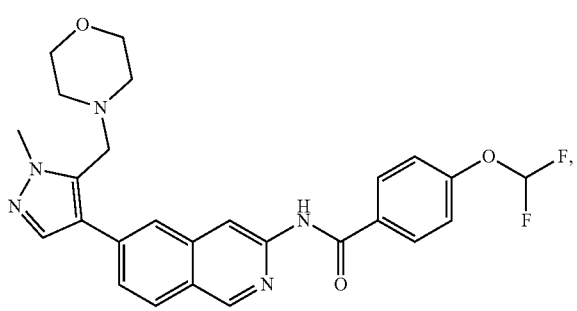
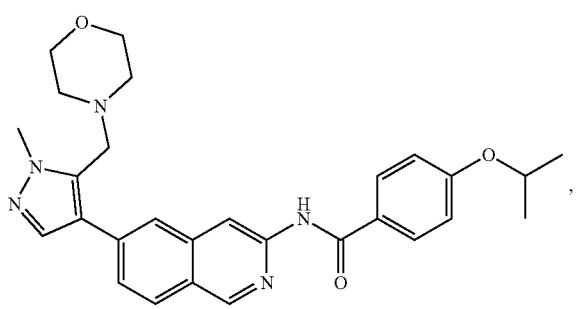
384
-continued
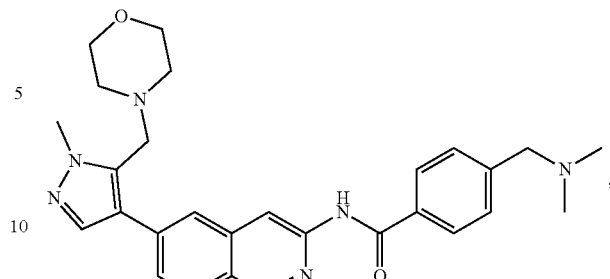
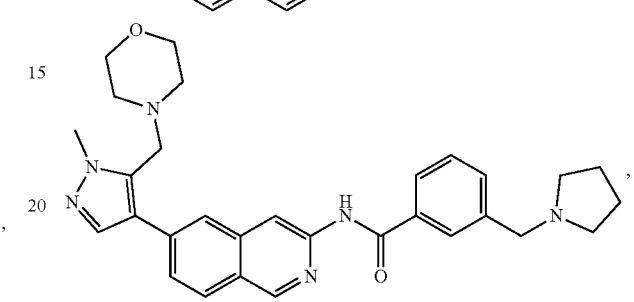
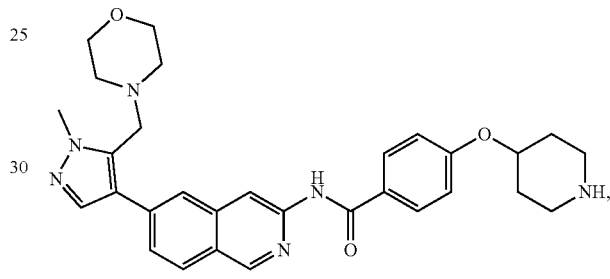
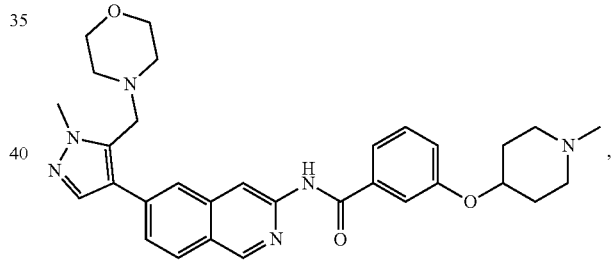
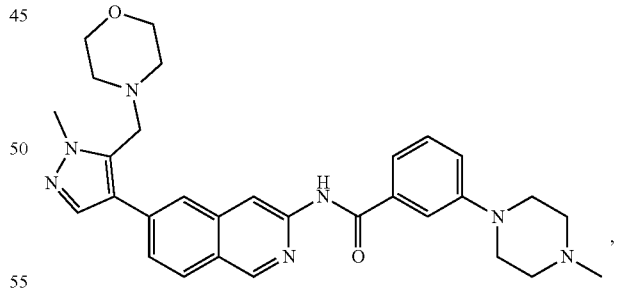
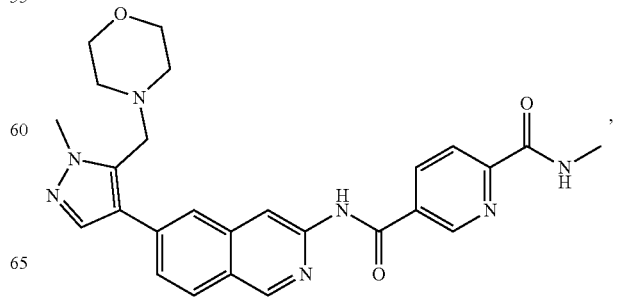

-continued
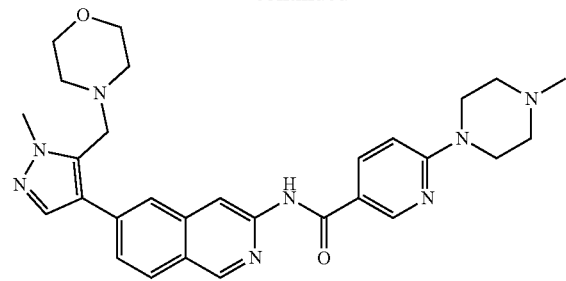
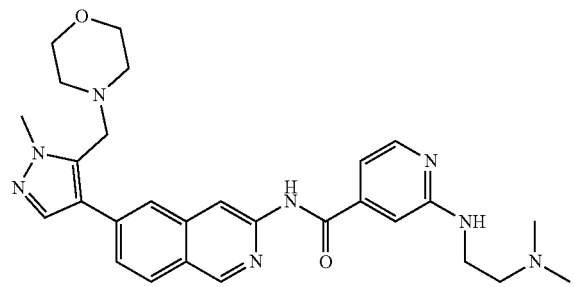
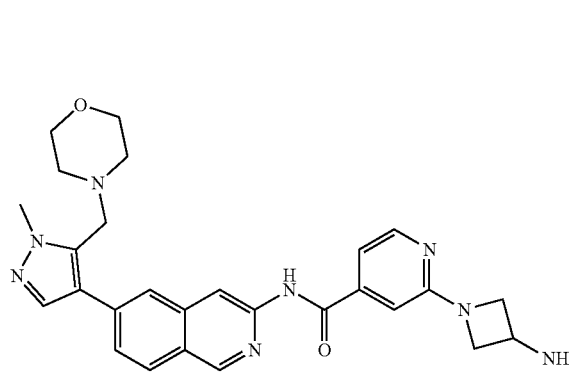
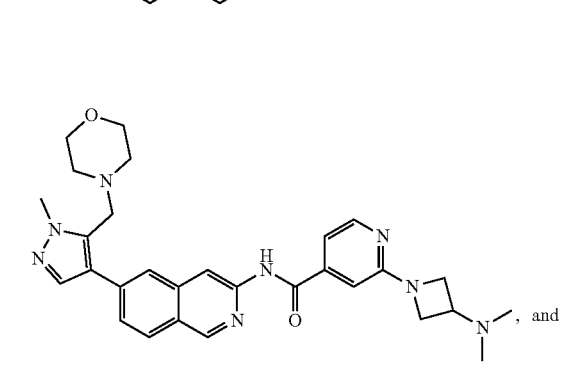
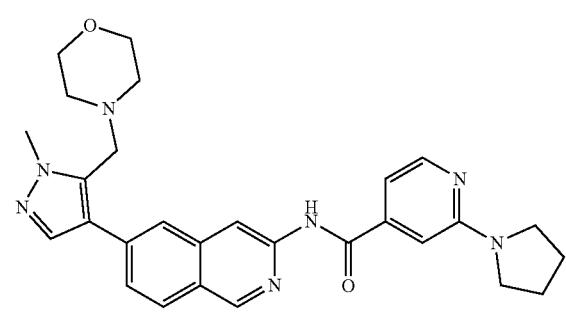
or a pharmaceutically acceptable salt thereof.
32. The method of claim 1, wherein the compound of Formula I is selected from the group consisting of:
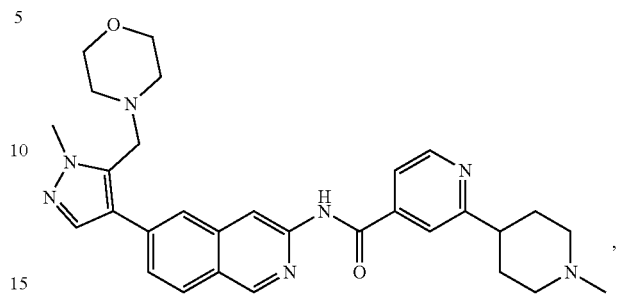
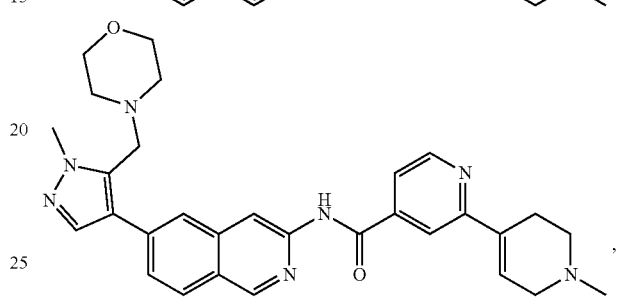
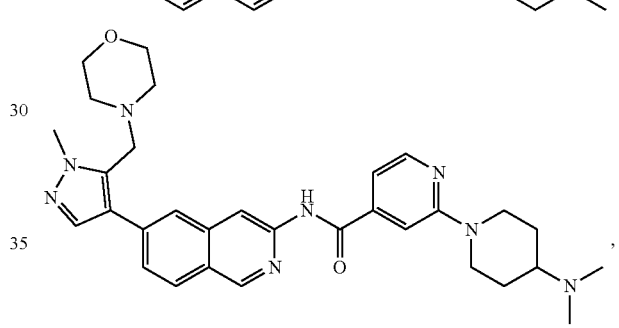
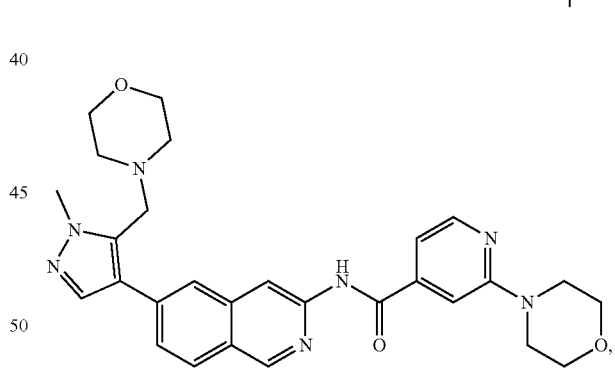
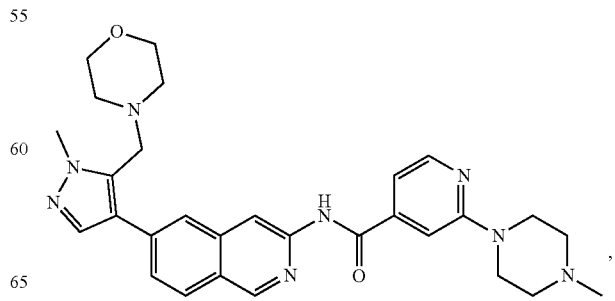

387
-continued
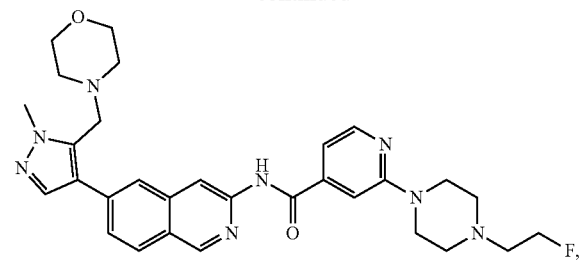
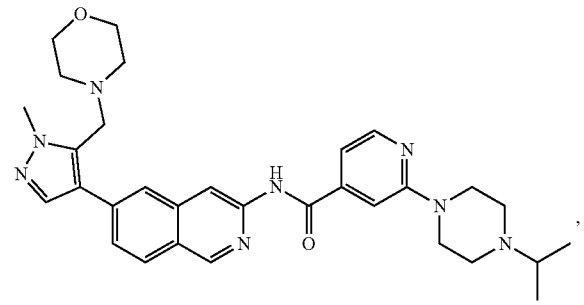
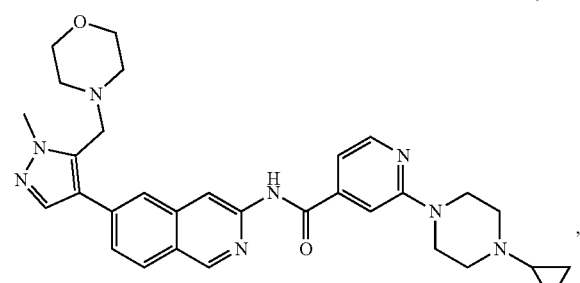
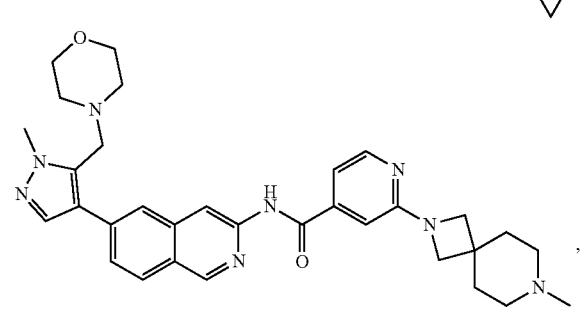
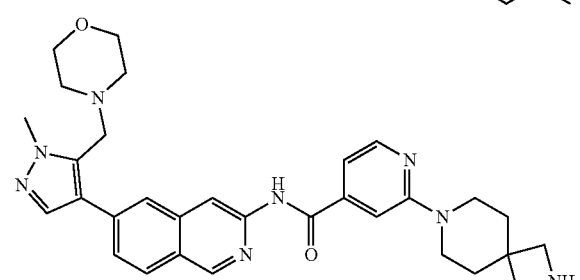
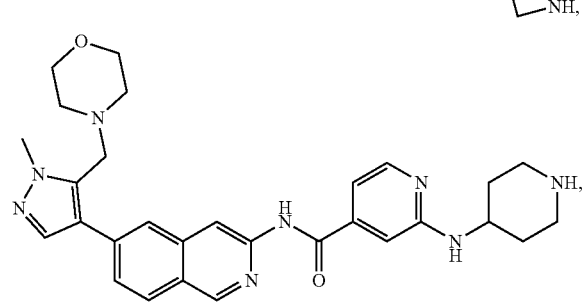
388
-continued
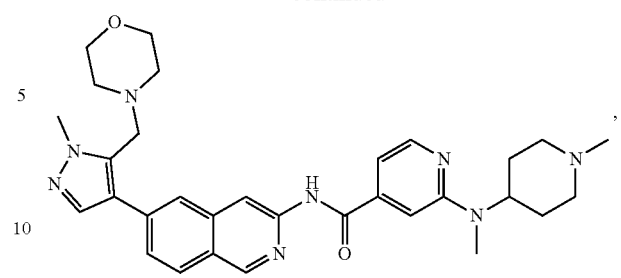
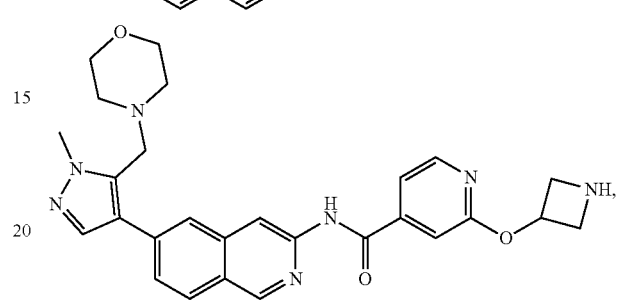
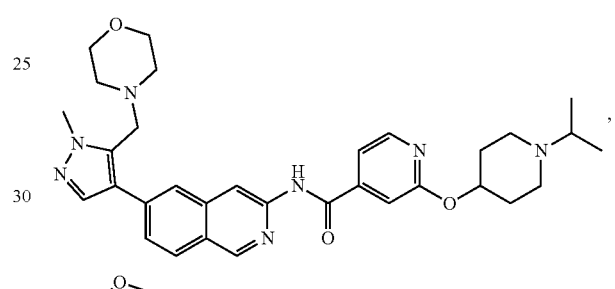
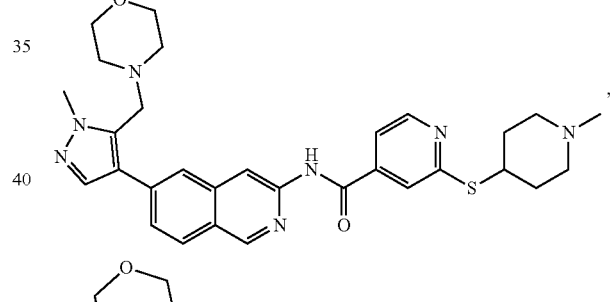
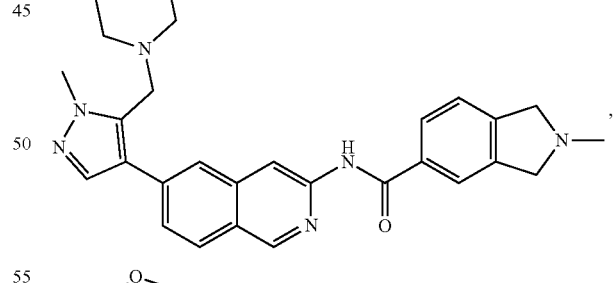
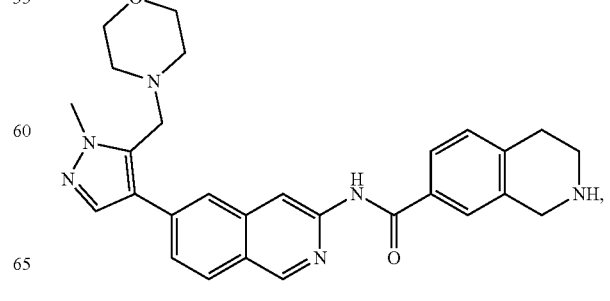

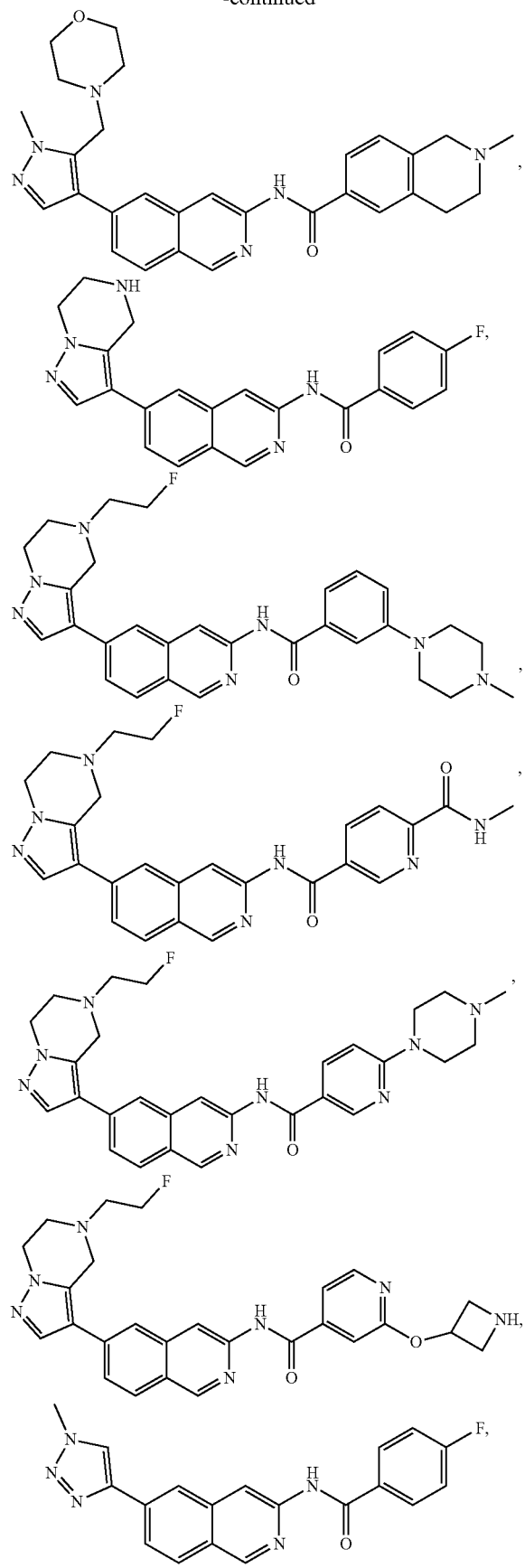
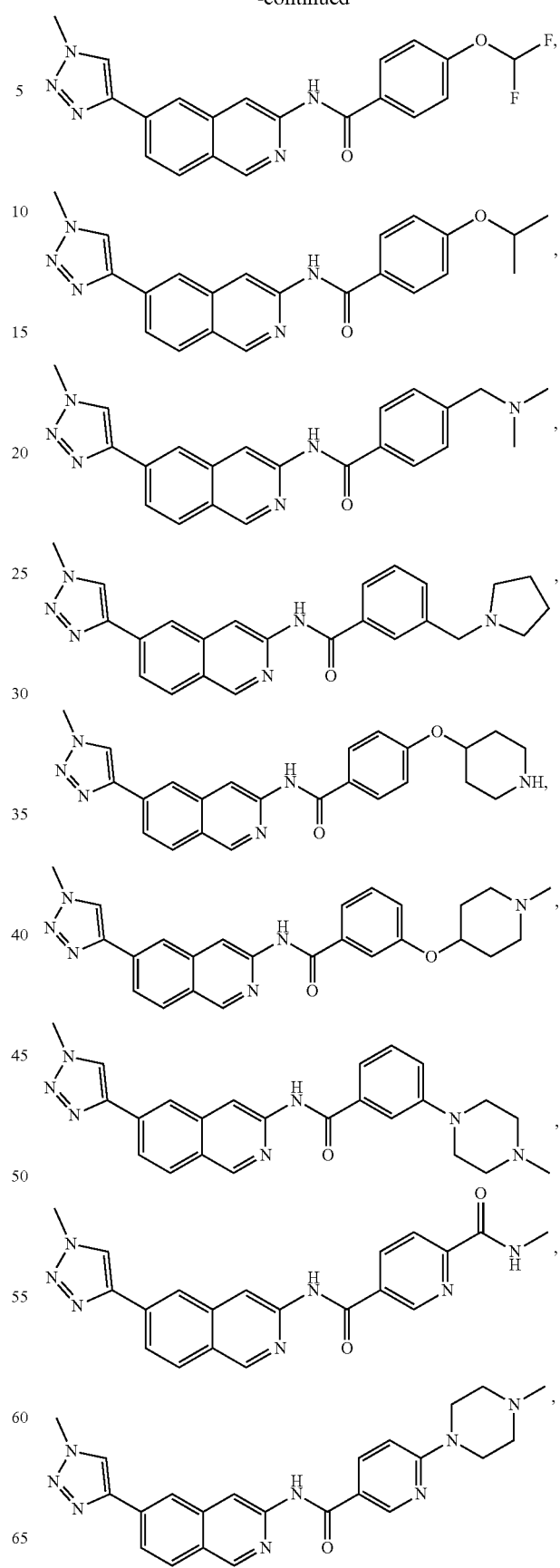

391
-continued
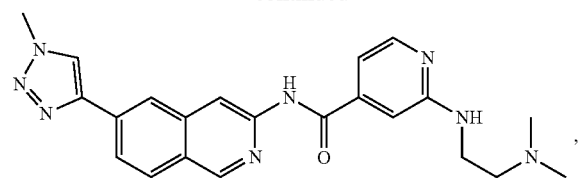,
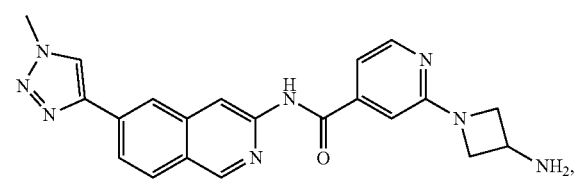,
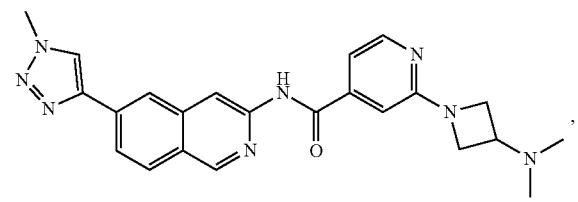,
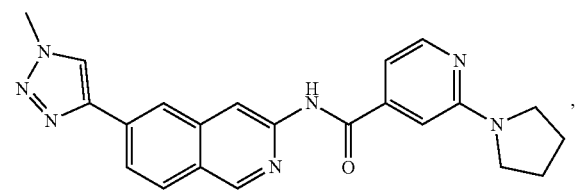,
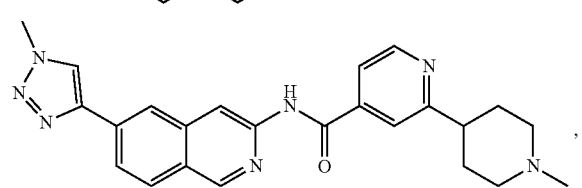,
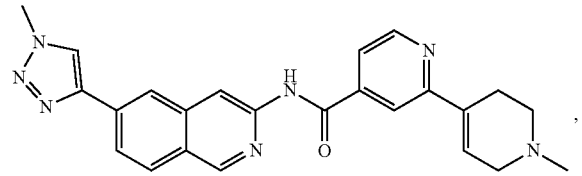,
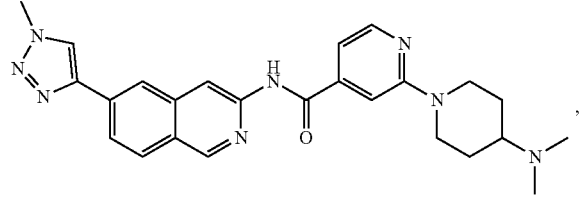,
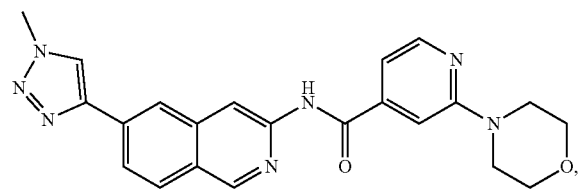,
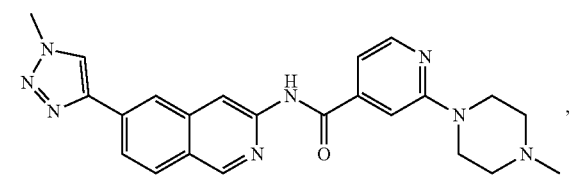,
392
-continued
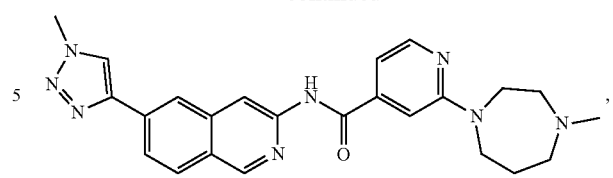,
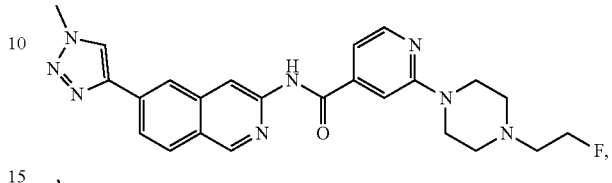,
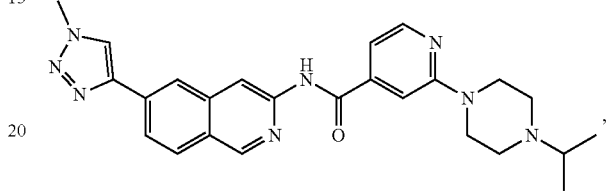,
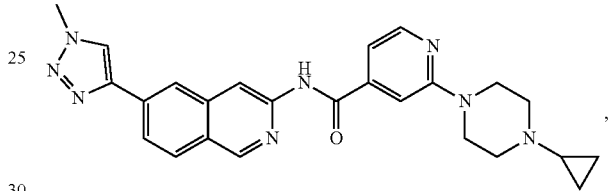,
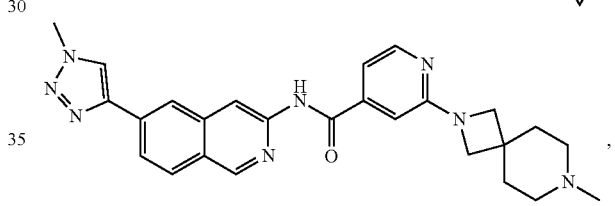,
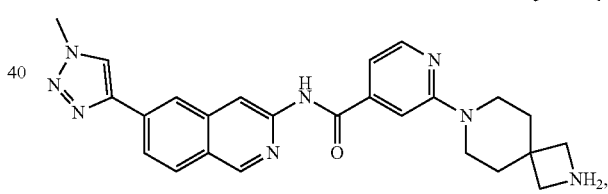,
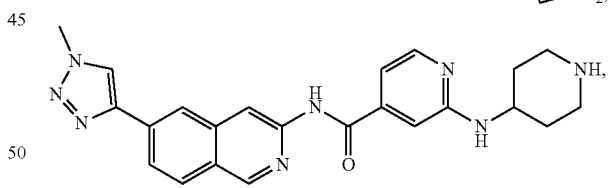,
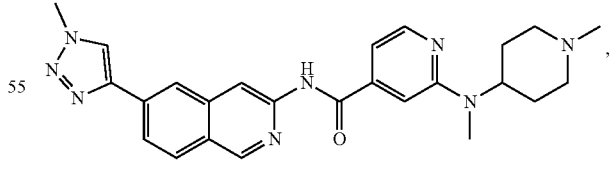,
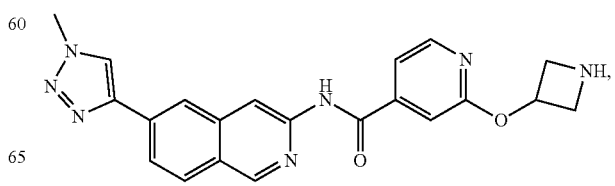, 393
-continued
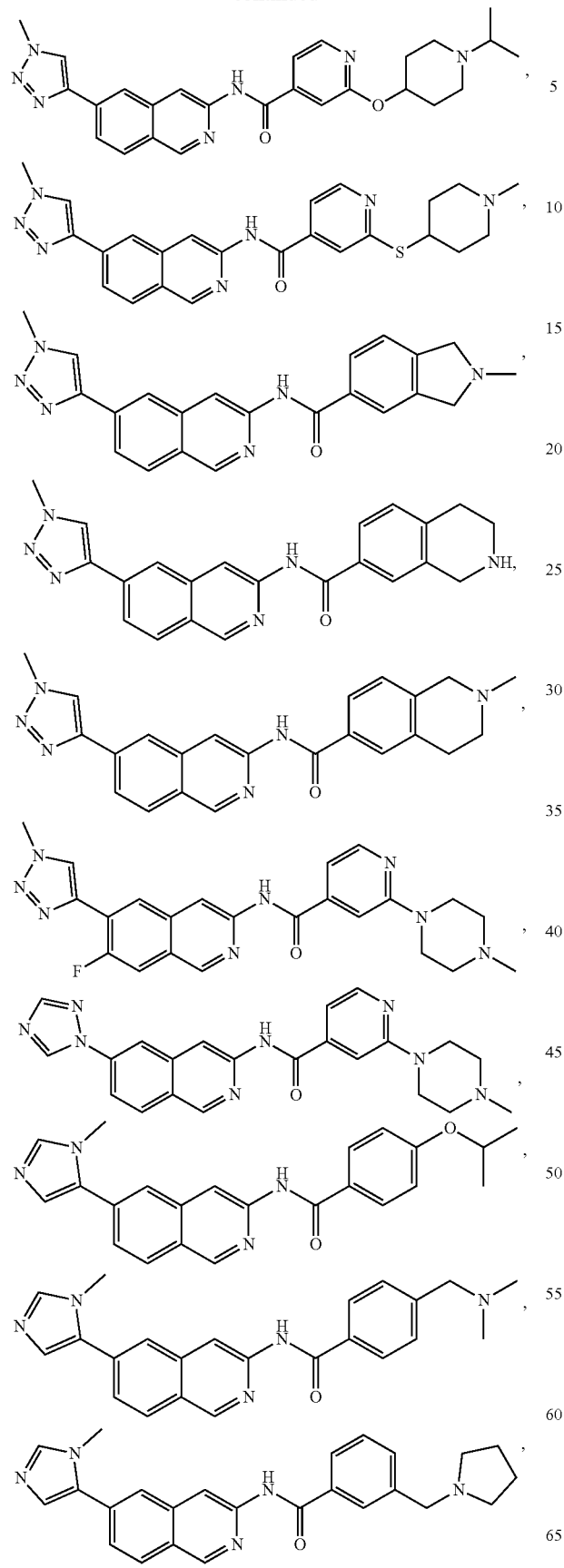
394
-continued
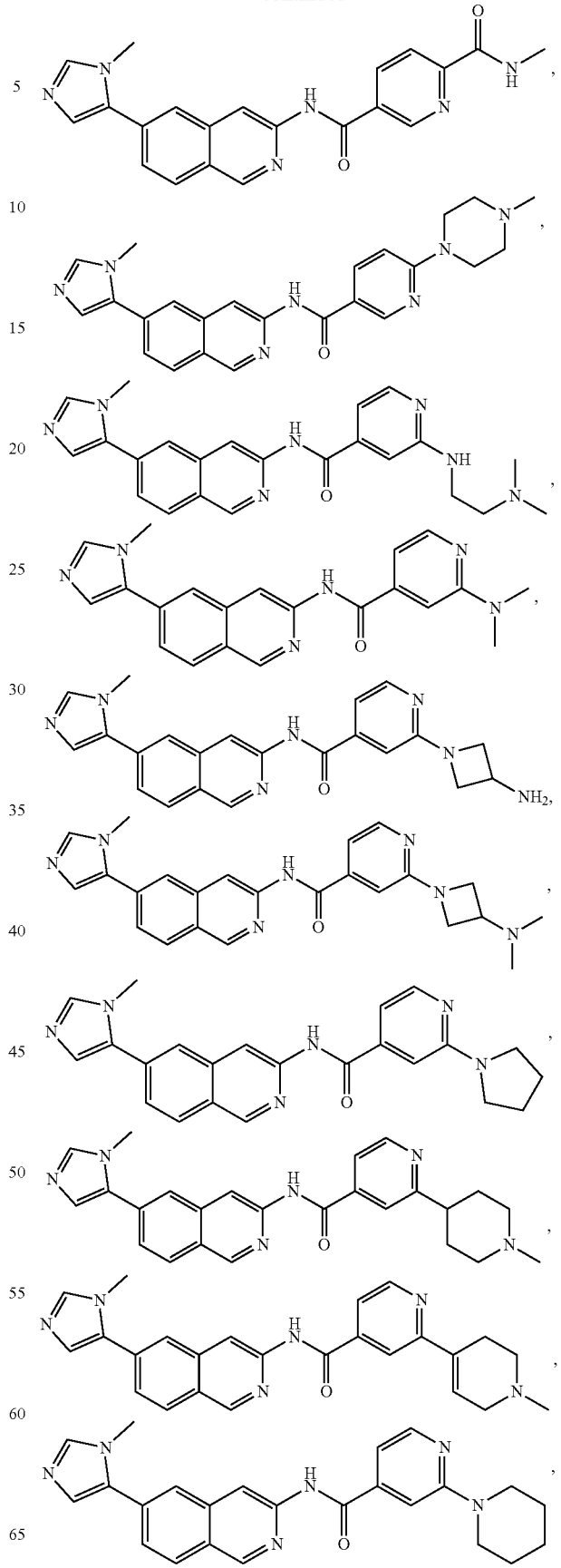

395
-continued

396
-continued

397
-continued
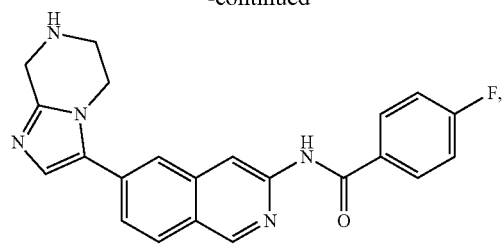
398
-continued
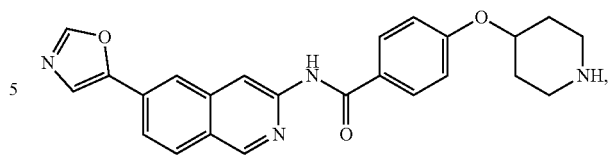
or a pharmaceutically acceptable salt thereof.
33. The method of claim 1, wherein the compound of Formula I is selected from the group consisting of:
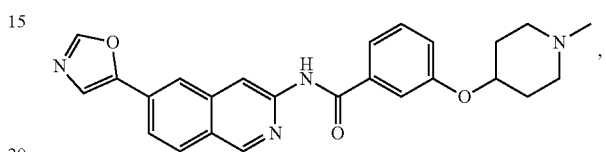
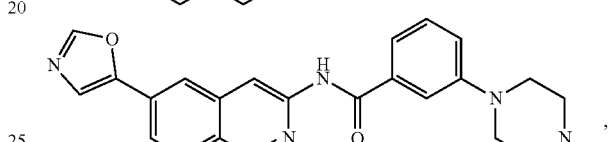
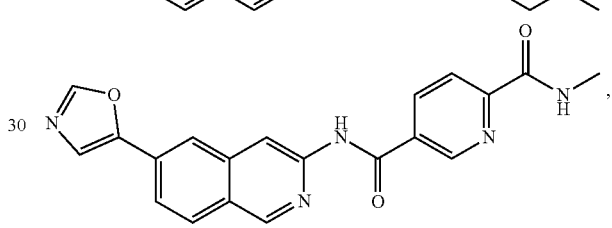
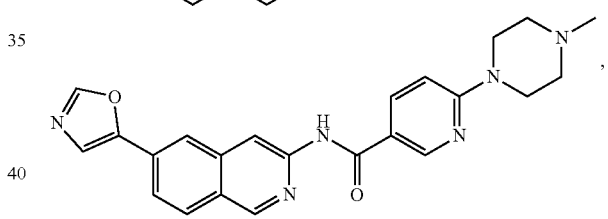
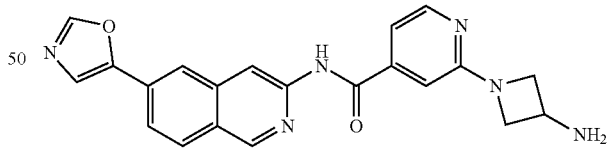
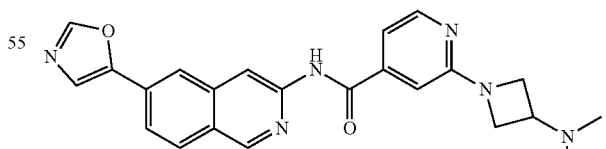
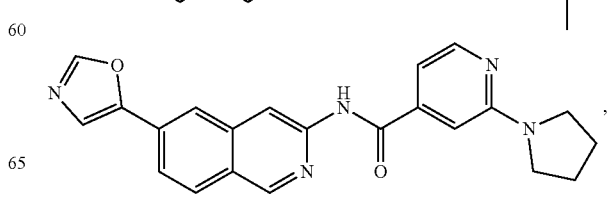

399
-continued
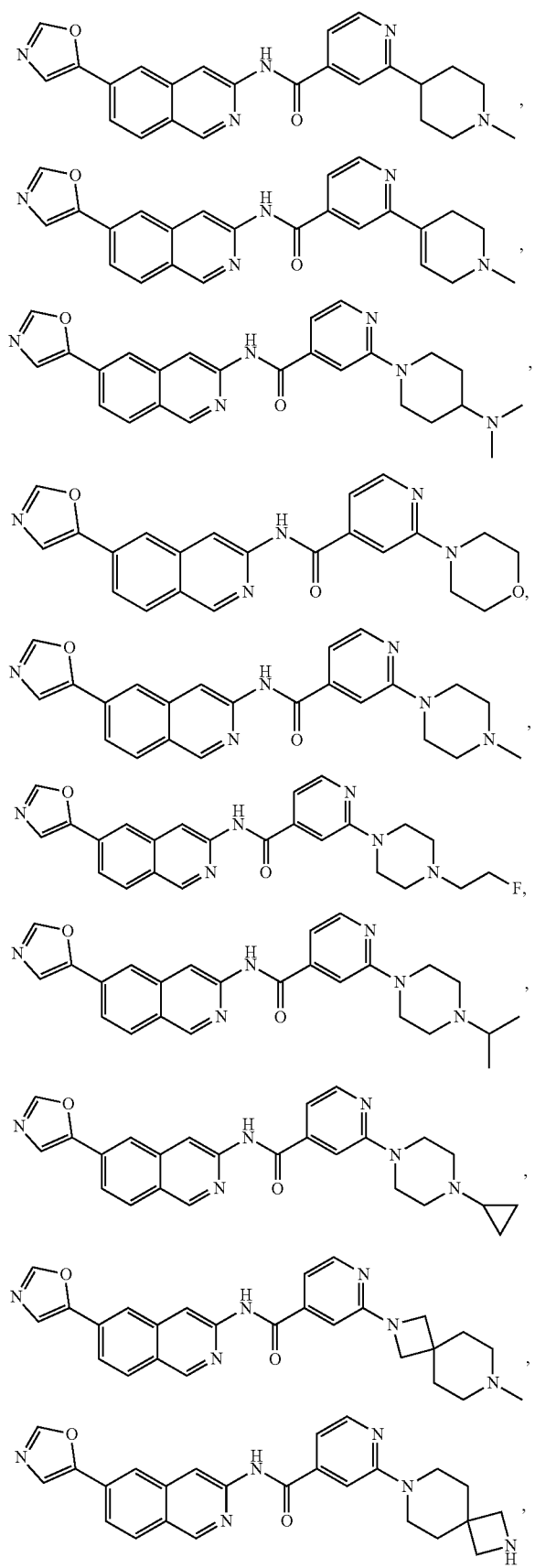
400
-continued
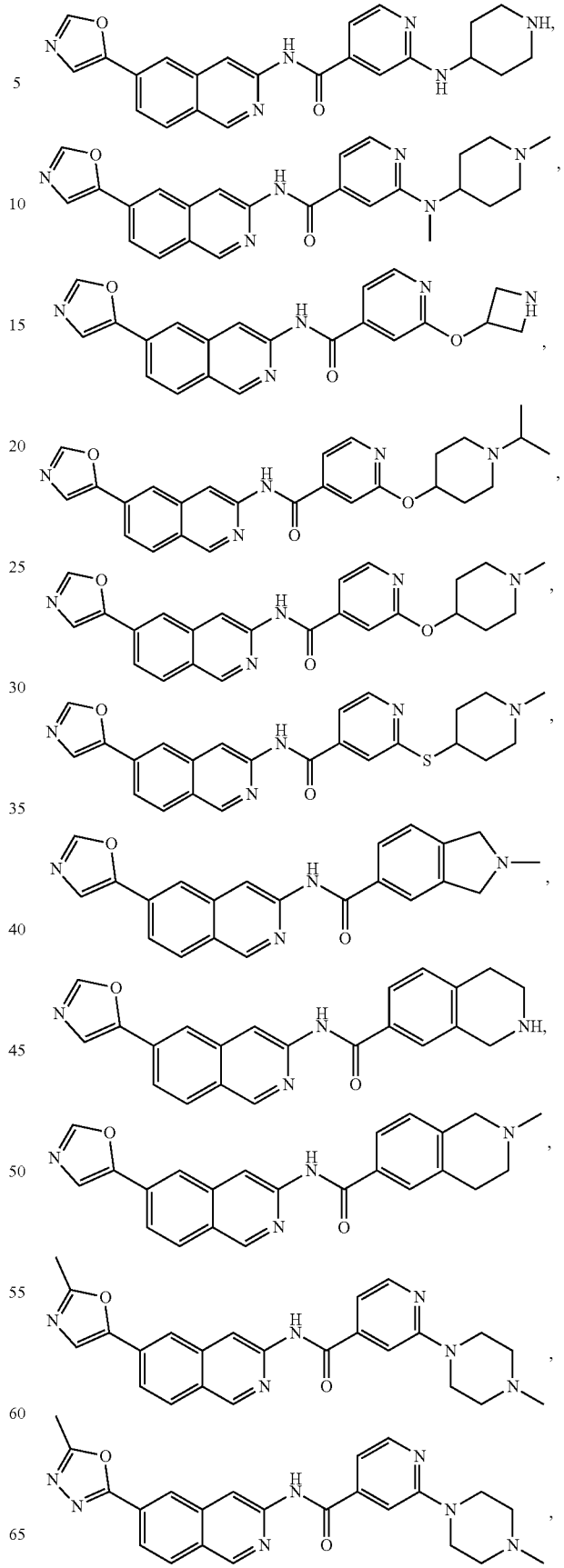

401
-continued
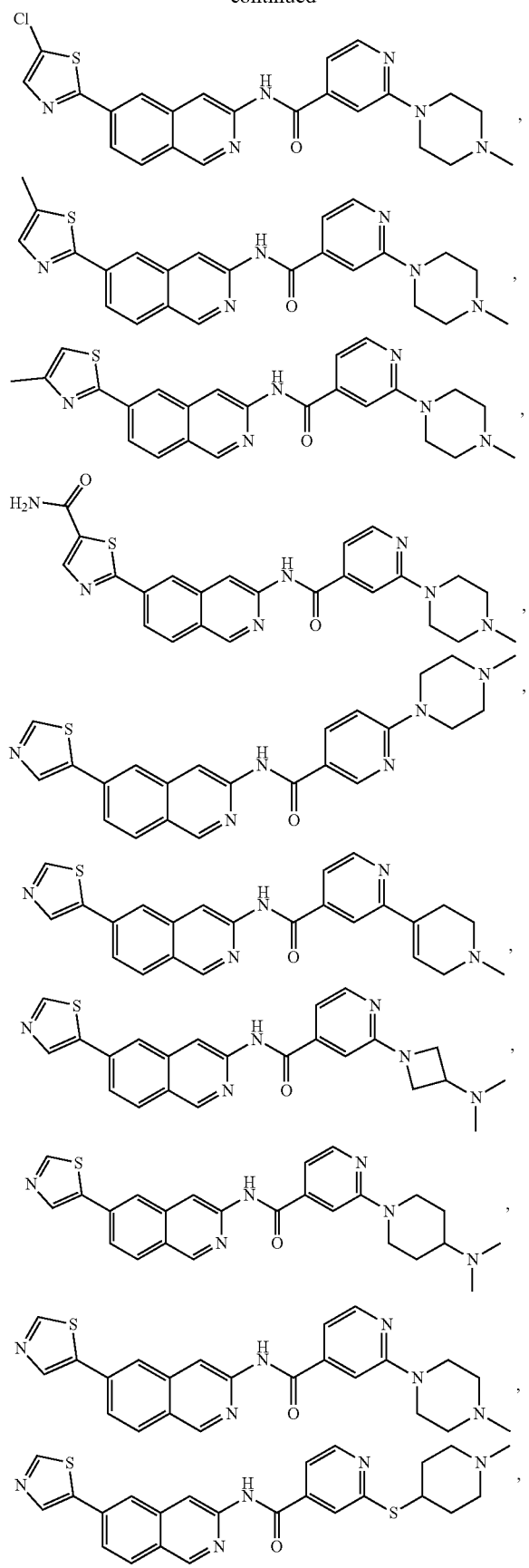
402
-continued
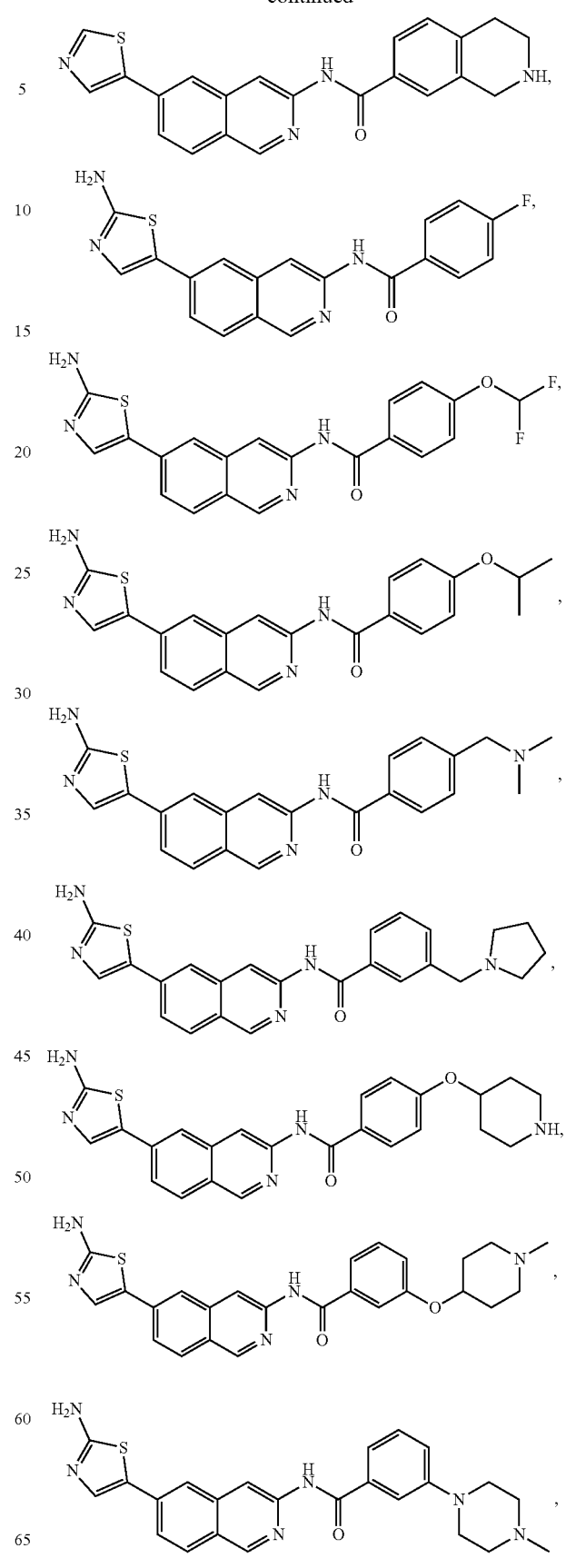

403
-continued
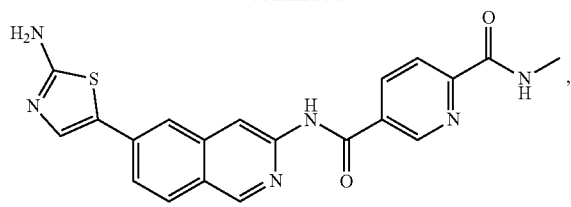,
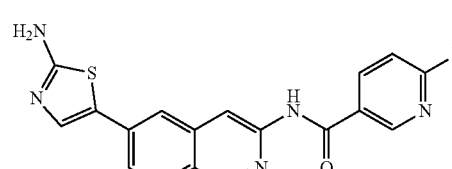,
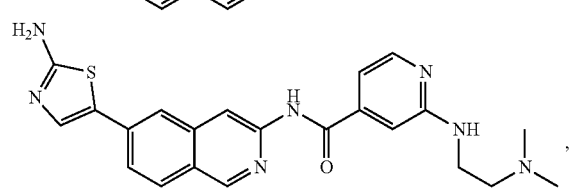,
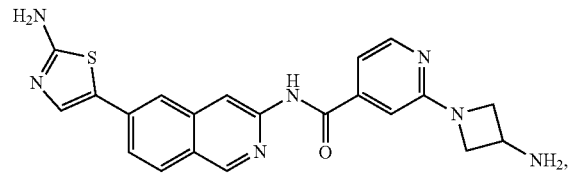,
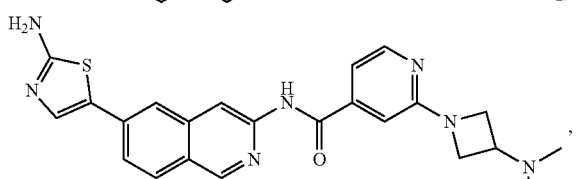,
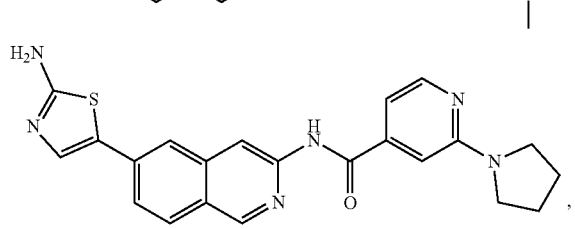,
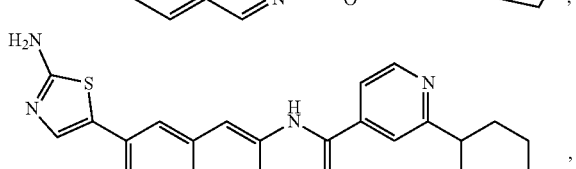,
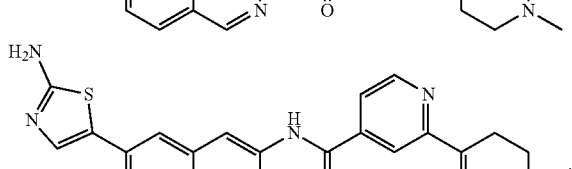,
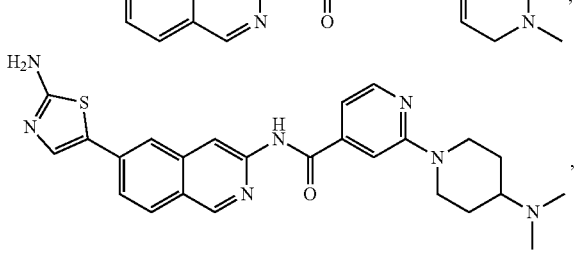,
404
-continued
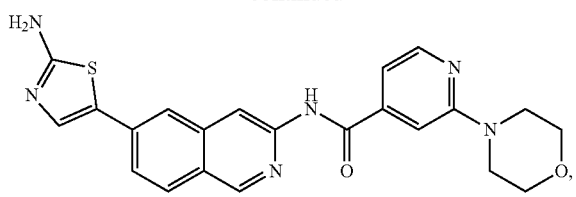,
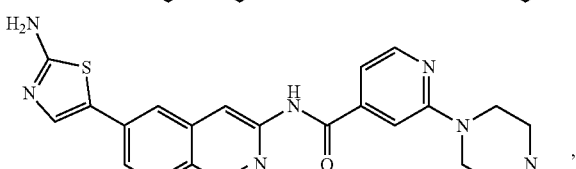,
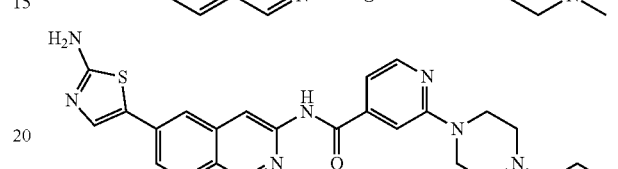,
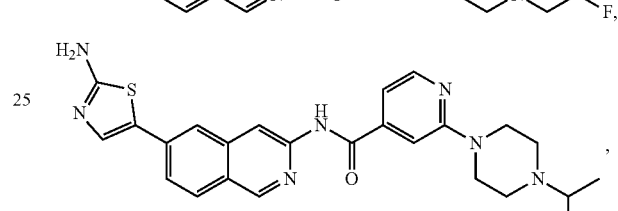,
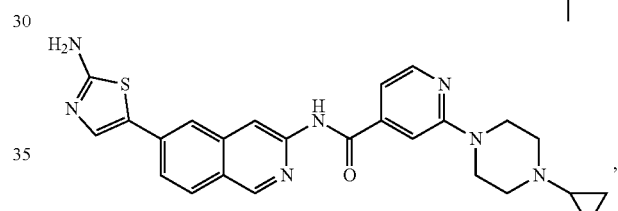,
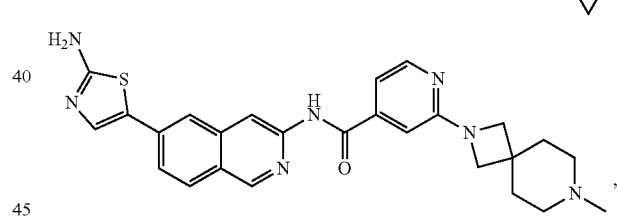,
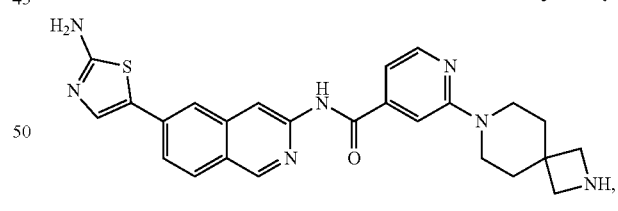,
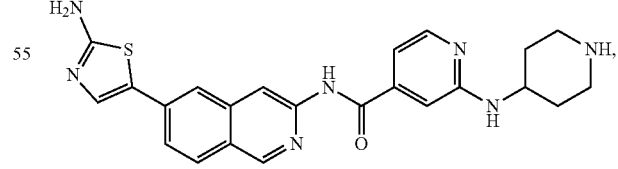,
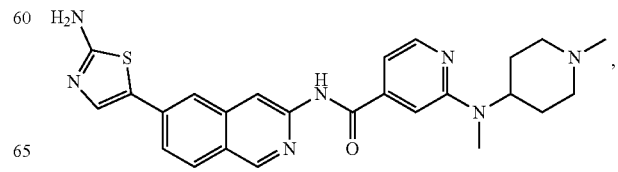,

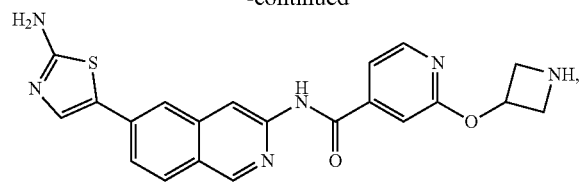
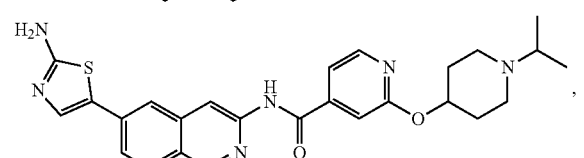
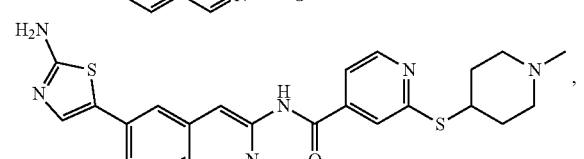
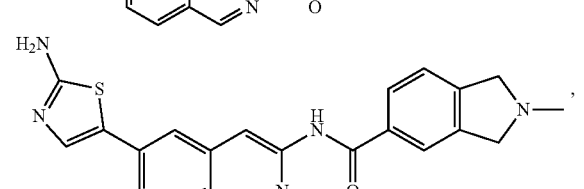
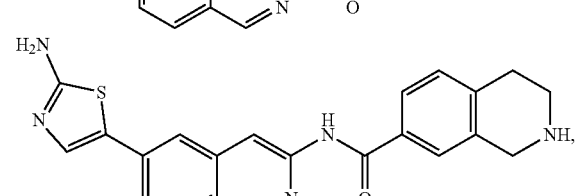
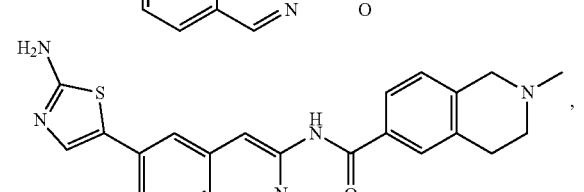
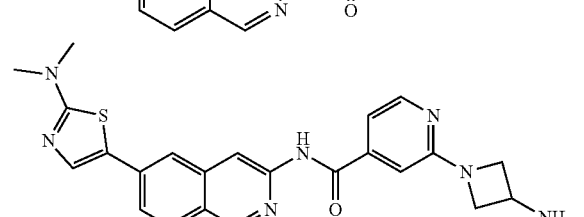
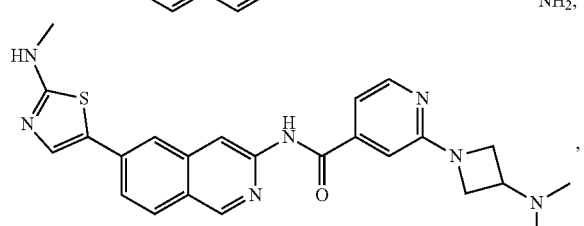
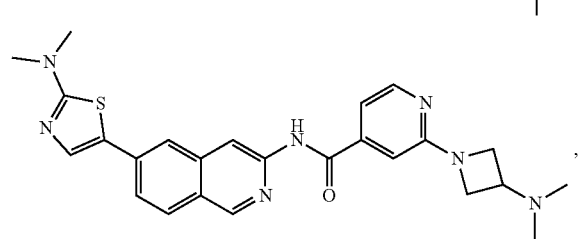
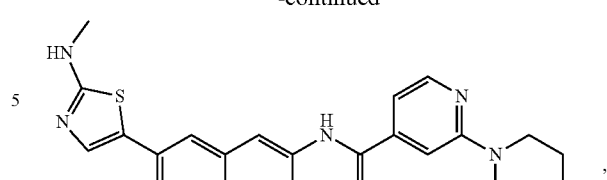
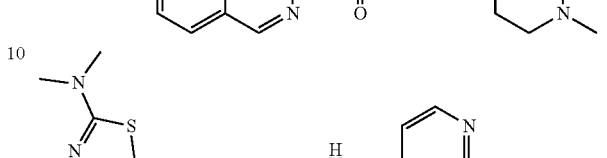
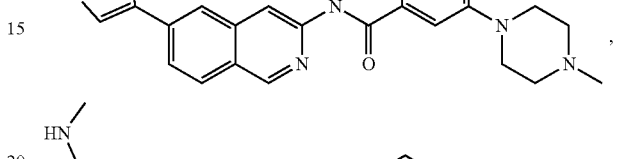
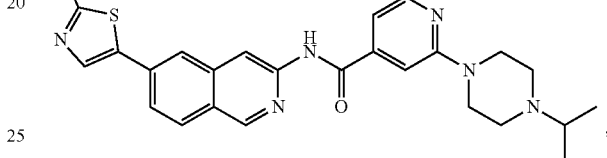
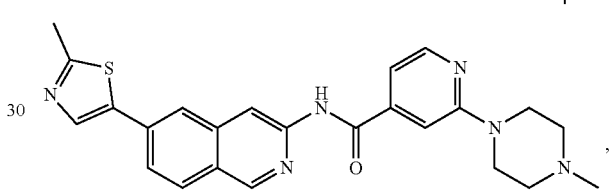
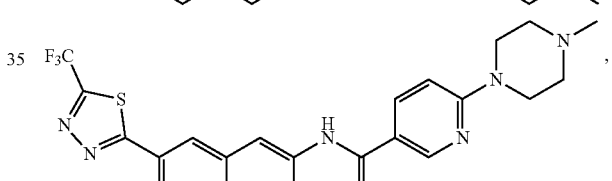
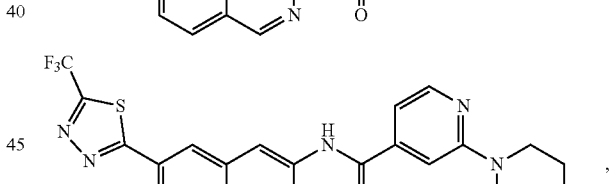
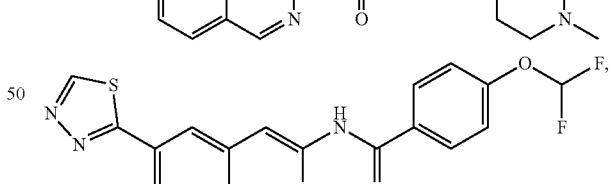
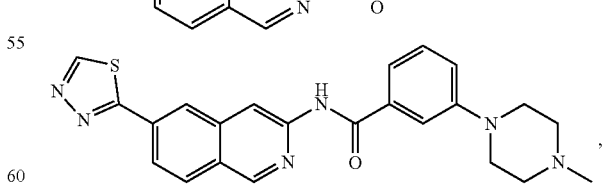
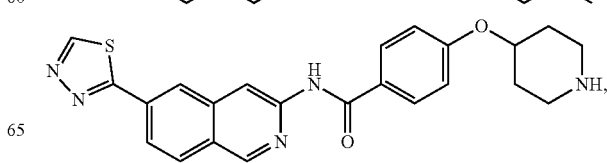

407
-continued
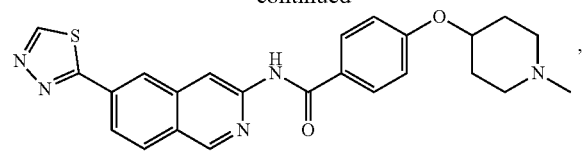
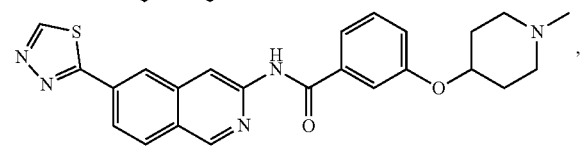
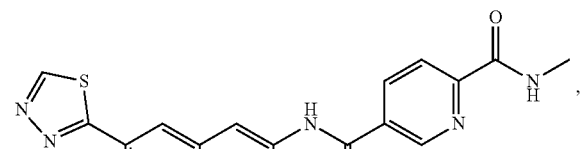
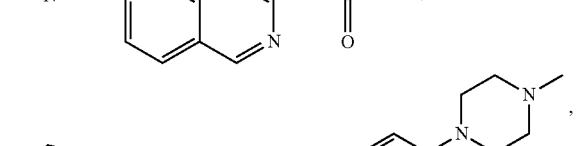
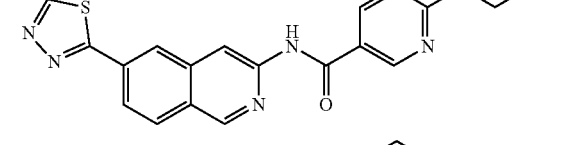
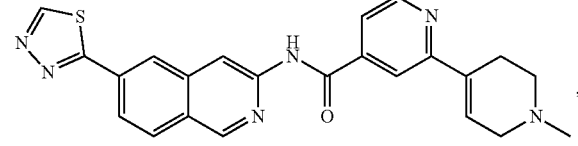
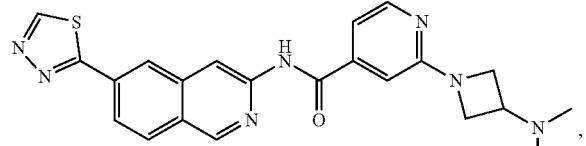
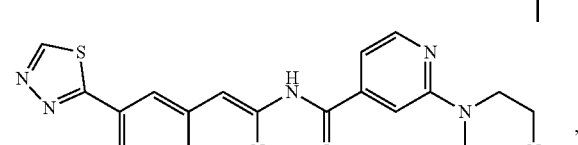
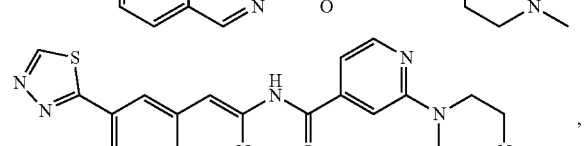
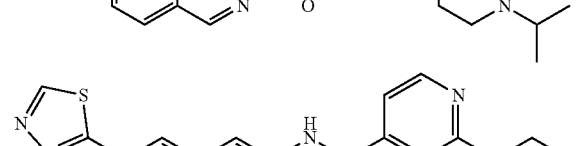
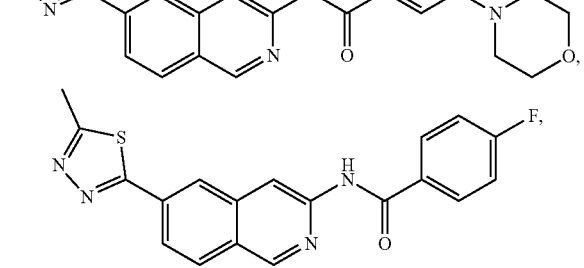
408
-continued
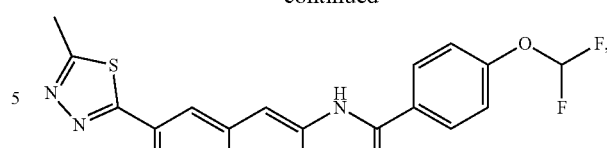
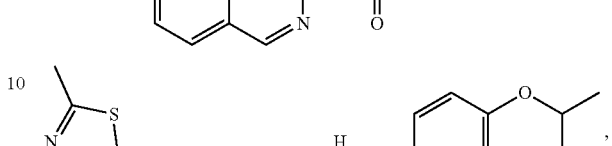
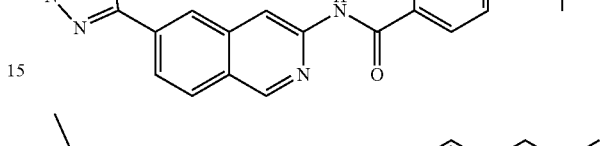
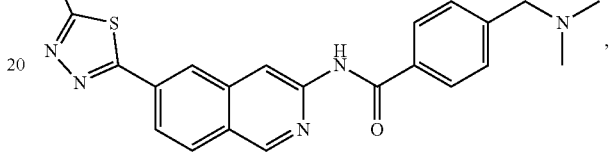
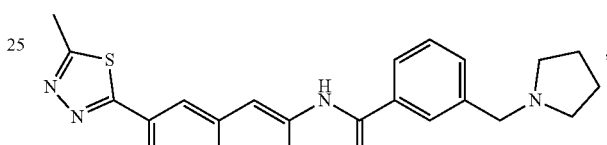
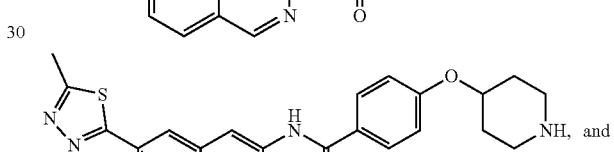
or a pharmaceutically acceptable salt thereof.
34. The method of claim 1, wherein the compound of Formula I is selected from the group consisting of:
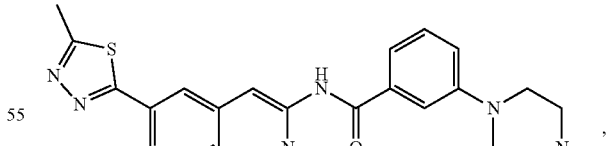
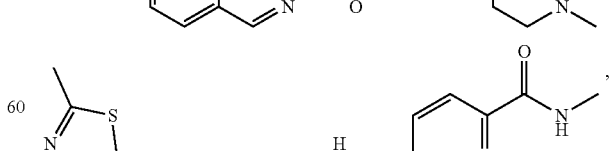

409
-continued
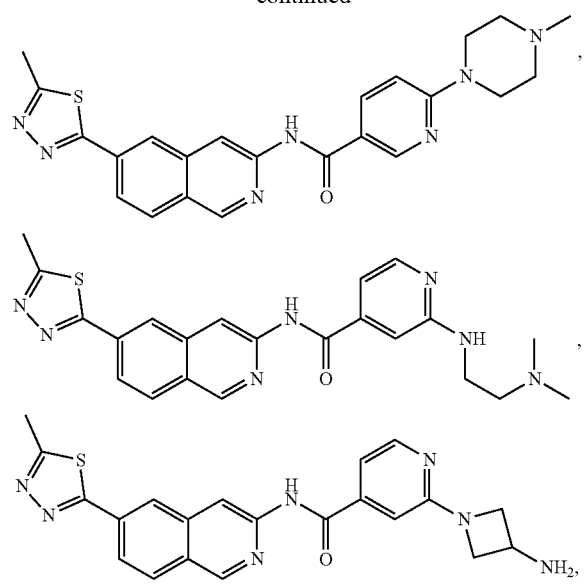
410
-continued
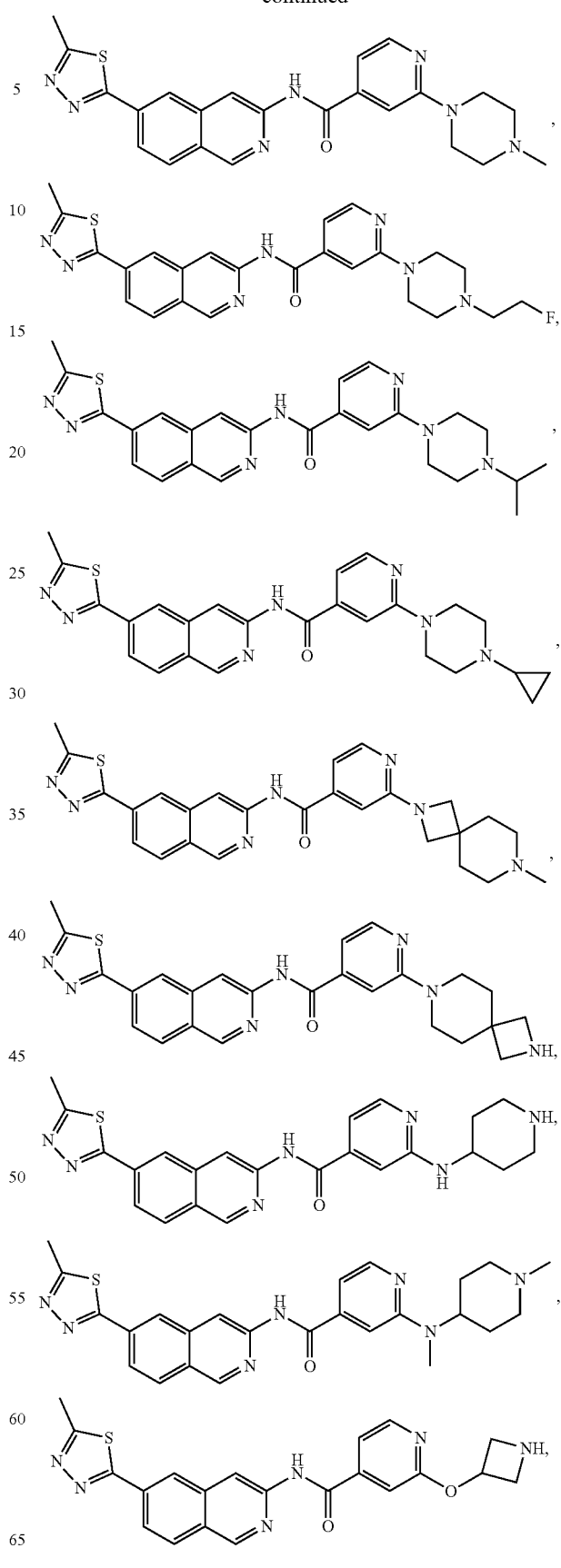

411
-continued
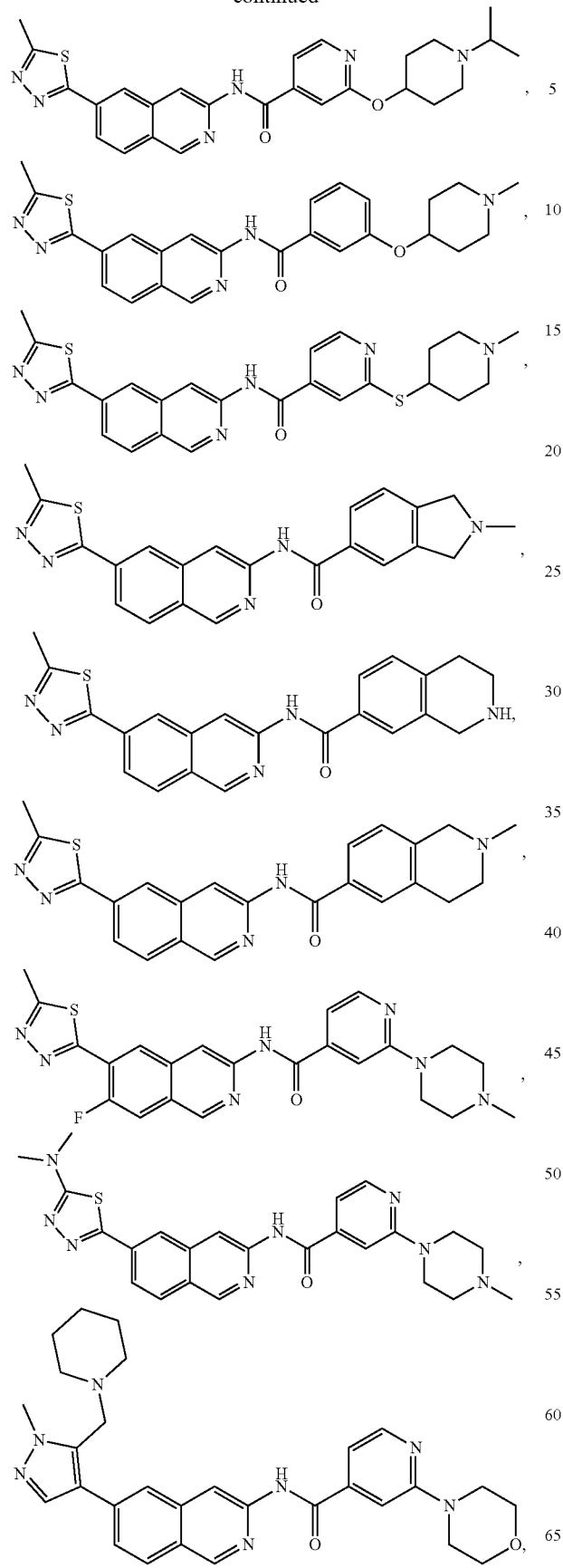
412
-continued
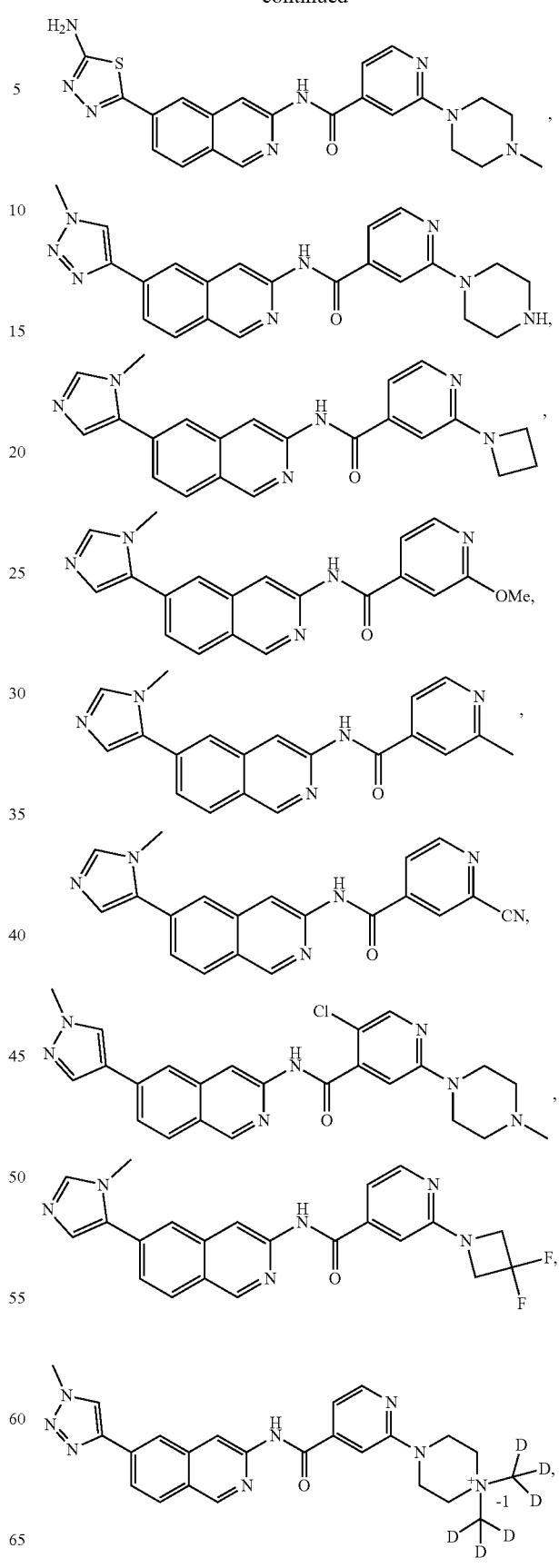

-continued
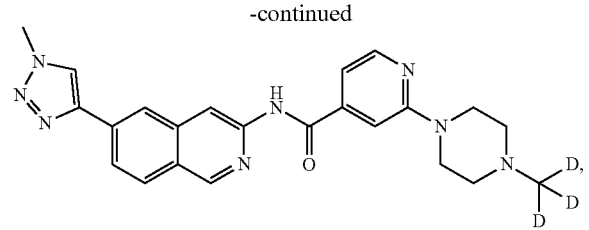
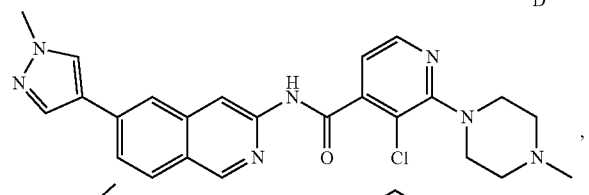
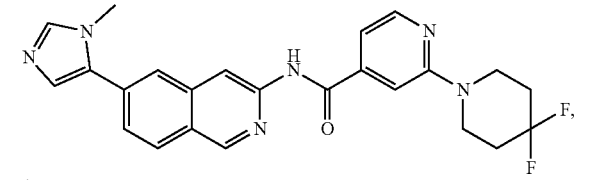
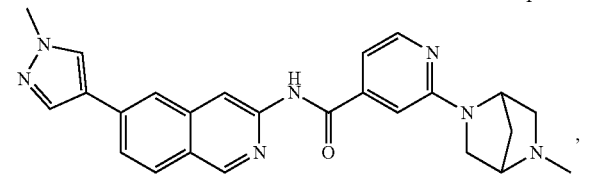
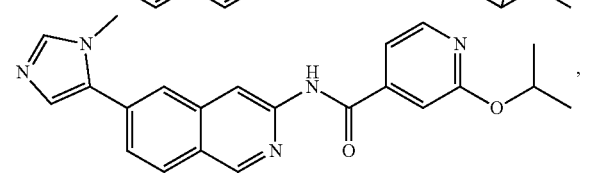
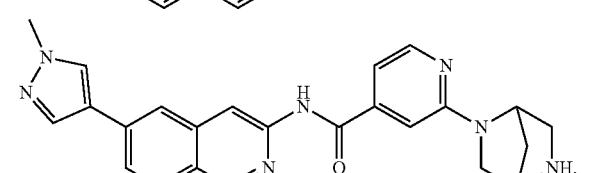
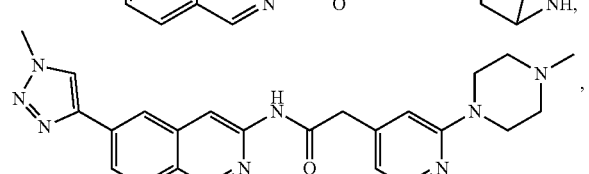
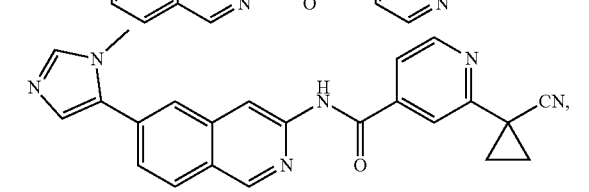
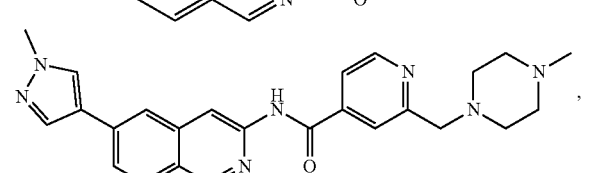
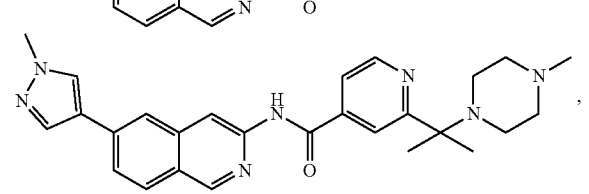
-continued
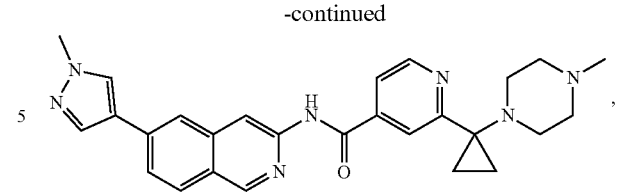
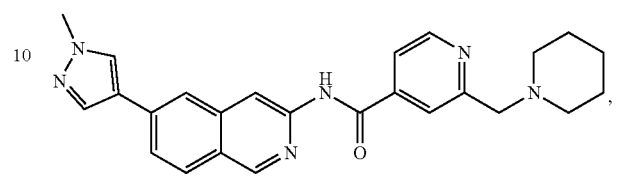
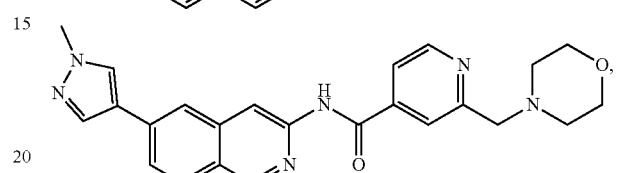
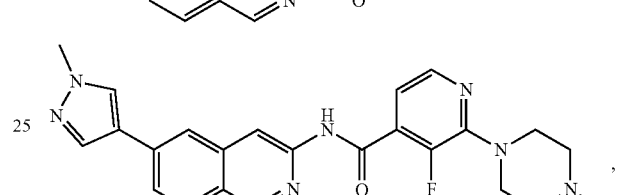
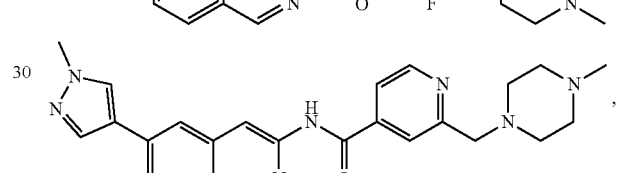
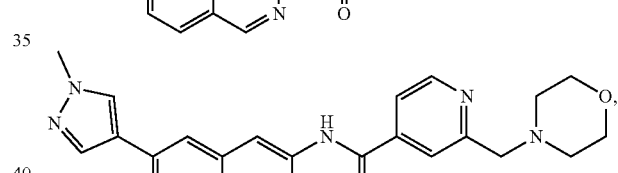
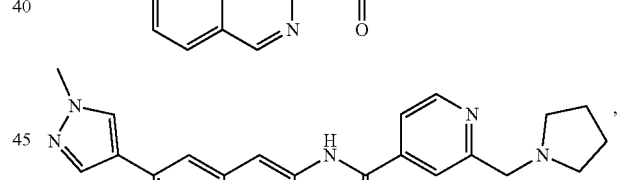
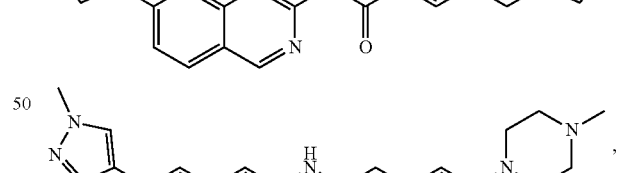
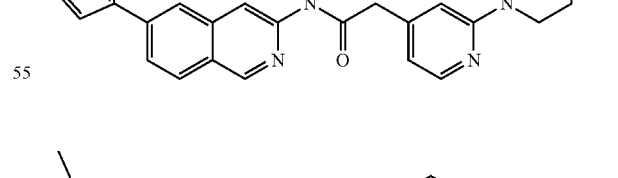
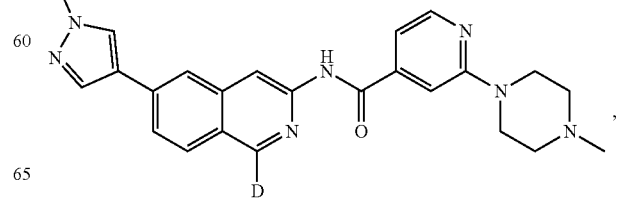

415
-continued
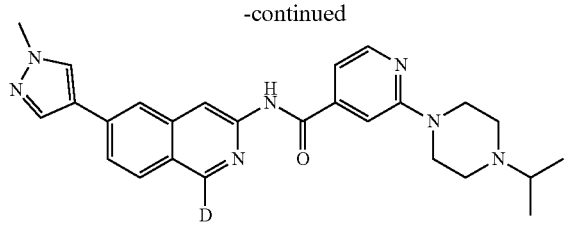
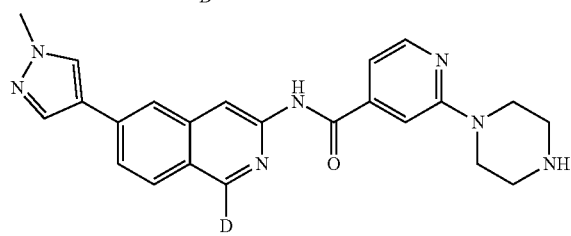
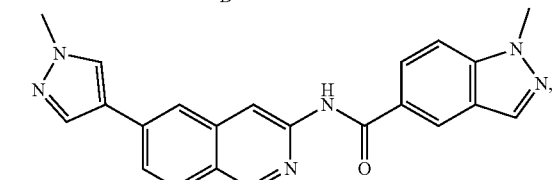
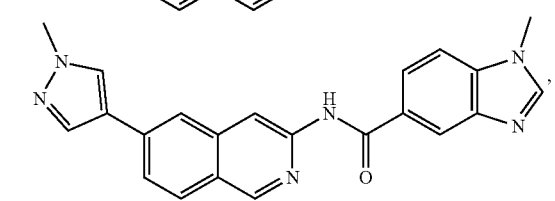
416
-continued
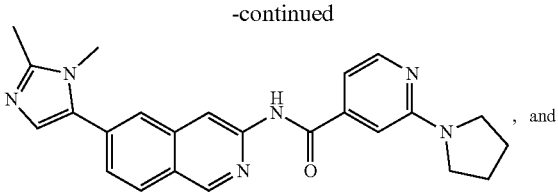
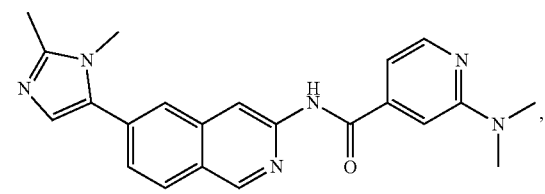
or a pharmaceutically acceptable salt thereof.
35. The method of claim 1, wherein the disorder or disease is a bone or cartilage disease.
36. The method of claim 1, wherein the disorder or disease is osteoarthritis.
37. The method of claim 1, wherein the disorder or disease is degenerative disc disease.
* * * * *

UNITED STATES PATENT AND TRADEMARK OFFICE
CERTIFICATE OF CORRECTION

PATENT NO. : 11,548,872 B2
APPLICATION NO. : 17/155577
DATED : January 10, 2023
INVENTOR(S) : Sunil Kumar KC et al.

Page 1 of 2

It is certified that error appears in the above-identified patent and that said Letters Patent is hereby corrected as shown below:

In the Claims

Column 352, Approximately Lines 47-53, in Claim 1, delete " 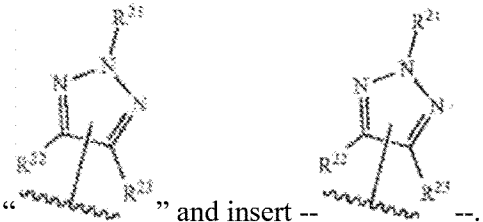 " and insert -- --.

Column 357, Line 8, in Claim 1, delete "$R_{24}, R_{25}$," and insert -- $R^{24}, R^{25}$, --.

Column 359, Line 43, in Claim 1, delete "0," and insert -- O --.

Column 359, Line 45, in Claim 1, delete "0" and insert -- O --.

Column 360, Approximately Line 42, in Claim 5, delete "—($C_{1-3}$alkyl)." and insert -- —($C_{1-3}$ alkyl). --.

Column 392, Approximately Lines 38-45, in Claim 32, delete

" 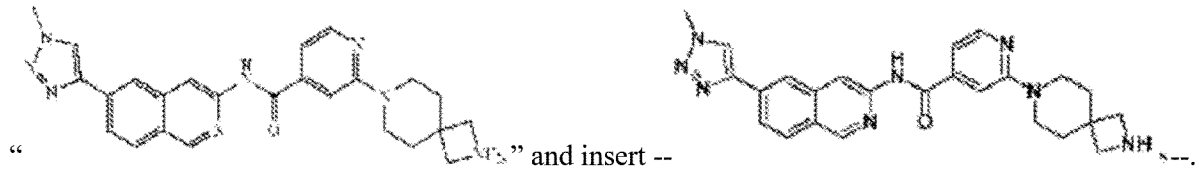 " and insert -- --.

Signed and Sealed this
Twenty-eighth Day of February, 2023

Katherine Kelly Vidal
*Director of the United States Patent and Trademark Office*

CERTIFICATE OF CORRECTION (continued)
U.S. Pat. No. 11,548,872 B2

Column 412, Approximately Line 57-66, in Claim 34, delete

" 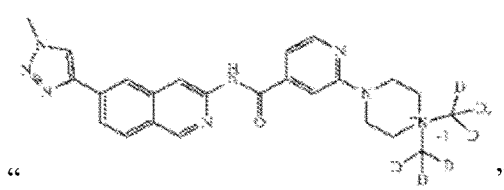 " and insert -- 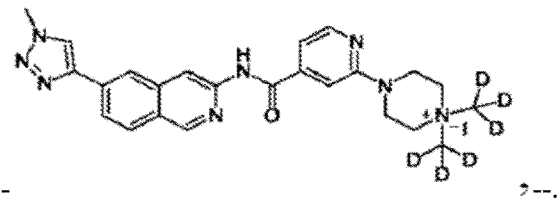 --.